United States Patent
Kobayashi et al.

(10) Patent No.: US 10,150,728 B2
(45) Date of Patent: *Dec. 11, 2018

(54) ALKYLENE DERIVATIVES

(71) Applicant: Shionogi & Co., Ltd., Osaka (JP)

(72) Inventors: Naotake Kobayashi, Osaka (JP); Kentarou Asahi, Osaka (JP); Yutaka Tomida, Osaka (JP); Masahide Ohdan, Osaka (JP); Masataka Fumoto, Osaka (JP); Yoshikazu Sasaki, Osaka (JP); Kana Kurahashi, Osaka (JP); Takatsugu Inoue, Osaka (JP); Tomomi Urabe, Osaka (JP); Yuji Nishiura, Osaka (JP); Masafumi Iwatsu, Osaka (JP); Keisuke Miyazaki, Osaka (JP); Naoki Ohyabu, Osaka (JP); Toshihiro Wada, Osaka (JP); Manabu Katou, Osaka (JP)

(73) Assignee: SHIONOGI & CO., LTD., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/029,031

(22) PCT Filed: Oct. 17, 2014

(86) PCT No.: PCT/JP2014/077700
§ 371 (c)(1),
(2) Date: Apr. 13, 2016

(87) PCT Pub. No.: WO2015/056782
PCT Pub. Date: Apr. 23, 2015

(65) Prior Publication Data
US 2016/0257641 A1    Sep. 8, 2016

(30) Foreign Application Priority Data

Oct. 17, 2013 (JP) ................. 2013-216544

(51) Int. Cl.
C07C 233/22 (2006.01)
C07C 233/18 (2006.01)
(Continued)

(52) U.S. Cl.
CPC .......... C07C 233/22 (2013.01); C07C 233/18 (2013.01); C07C 233/31 (2013.01);
(Continued)

(58) Field of Classification Search
CPC ... C07C 233/18; C07C 233/22; C07C 233/31; C07C 2601/02; C07C 275/10; C07D 213/64; C07D 213/69; C07D 231/56; C07D 239/80; C07D 241/18; C07D 261/20; C07D 263/56; C07D 267/14; C07D 277/20; C07D 277/34; C07D 277/64; C07D 277/68;
(Continued)

(56) References Cited

U.S. PATENT DOCUMENTS 5,166,153 A * 11/1992 Karrer ............... A01N 47/12
514/211.01
2006/0178400 A1* 8/2006 Beutel ............... C07D 211/68
514/317

(Continued)

FOREIGN PATENT DOCUMENTS

EP   2 351 743   8/2011
EP   2 604 595   6/2013

(Continued)

OTHER PUBLICATIONS

Richard F. Clark et al., Structure-activity relationships for a novel series of thiazolyl phenyl ether derivatives exhibiting potent and selective acetyl-CoA carboxylase 2 inhibitory activity, Bioorganic & Medicinal Chemistry Letters, vol. 16, 2006, pp. 6078-6081.

Yu Gui Gu et al., Synthesis and Structure-Activity Relationships of N-{3-[2-(4-Alkoxyphenoxy)thiazol-5-yl]-1-methlyprop-2-ynyl}carboxy Derivatives as Selective Acetyl-CoA Carboxylase 2 Inhibitors, Journal of Medicinal Chemistry, vol. 49, 2006, pp. 3770-3773.

(Continued)

Primary Examiner — Sarah Pihonak
(74) Attorney, Agent, or Firm — Wenderoth, Lind & Ponack, L.L.P.

(57) ABSTRACT

The object of the present invention is to provide novel compounds having ACC2 inhibiting activity. In addition, the object of the present invention is to provide a pharmaceutical composition comprising the compound.

A compound of formula (I):

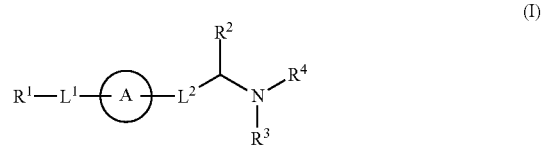

(I)

wherein $R^1$ is substituted or unsubstituted fused aromatic heterocyclyl etc., ring A is substituted or unsubstituted non-aromatic carbocycle etc., -$L^1$- is —O—$(CR^6R^7)_m$- etc., -$L^2$- is —O—$(CR^6R^7)_n$- etc., each $R^6$ and $R^7$ are independently hydrogen, halogen etc., $R^2$ is substituted or unsubstituted alkyl, $R^3$ is hydrogen or substituted or unsubstituted alkyl, $R^4$ is substituted or unsubstituted alkylcarbonyl etc.

19 Claims, No Drawings

US 10,150,728 B2

Page 2

(51) Int. Cl.
| | |
|---|---|
| C07C 233/31 | (2006.01) |
| C07C 275/10 | (2006.01) |
| C07D 403/12 | (2006.01) |
| C07D 401/14 | (2006.01) |
| C07D 231/56 | (2006.01) |
| C07D 401/12 | (2006.01) |
| C07D 403/14 | (2006.01) |
| C07D 239/80 | (2006.01) |
| C07D 413/12 | (2006.01) |
| C07D 241/18 | (2006.01) |
| C07D 417/12 | (2006.01) |
| C07D 261/20 | (2006.01) |
| C07D 267/14 | (2006.01) |
| C07D 277/20 | (2006.01) |
| C07D 277/34 | (2006.01) |
| C07D 213/64 | (2006.01) |
| C07D 213/69 | (2006.01) |
| C07D 263/56 | (2006.01) |
| C07D 277/64 | (2006.01) |
| C07D 277/68 | (2006.01) |

(52) U.S. Cl.
CPC .......... *C07C 275/10* (2013.01); *C07D 213/64* (2013.01); *C07D 213/69* (2013.01); *C07D 231/56* (2013.01); *C07D 239/80* (2013.01); *C07D 241/18* (2013.01); *C07D 261/20* (2013.01); *C07D 263/56* (2013.01); *C07D 267/14* (2013.01); *C07D 277/20* (2013.01); *C07D 277/34* (2013.01); *C07D 277/64* (2013.01); *C07D 277/68* (2013.01); *C07D 401/12* (2013.01); *C07D 401/14* (2013.01); *C07D 403/12* (2013.01); *C07D 403/14* (2013.01); *C07D 413/12* (2013.01); *C07D 417/12* (2013.01); *C07C 2601/02* (2017.05)

(58) Field of Classification Search
CPC .. C07D 401/12; C07D 401/14; C07D 403/12; C07D 403/14; C07D 413/12; C07D 417/12
See application file for complete search history.

(56) References Cited

U.S. PATENT DOCUMENTS

| | | | |
|---|---|---|---|
| 2007/0207984 A1 | 9/2007 | Huang et al. | |
| 2008/0161368 A1 | 7/2008 | Gu et al. | |
| 2009/0221616 A1 | 9/2009 | Bradbury | |
| 2010/0144741 A1 | 6/2010 | Frederiksen et al. | |
| 2010/0216767 A1 | 8/2010 | Aikawa et al. | |
| 2010/0267668 A1 | 10/2010 | Zhang et al. | |
| 2011/0166169 A1 | 7/2011 | Ruxer et al. | |
| 2011/0183998 A1 | 7/2011 | Zoller et al. | |
| 2013/0030181 A1 | 1/2013 | Bagley et al. | |
| 2013/0158004 A1* | 6/2013 | Fleck ................ | C07D 403/12 514/210.21 |
| 2013/0251787 A1* | 9/2013 | Nicolls ................ | A61K 31/222 424/450 |
| 2014/0011853 A1 | 1/2014 | Liu et al. | |
| 2014/0045696 A1 | 2/2014 | Bretschneider et al. | |
| 2014/0243310 A1 | 8/2014 | Yamashita et al. | |
| 2014/0275199 A1 | 9/2014 | Liu et al. | |
| 2015/0246938 A1 | 9/2015 | Matsumura et al. | |

FOREIGN PATENT DOCUMENTS

| | | | |
|---|---|---|---|
| WO | 2004/009784 | 1/2004 | |
| WO | 2006/117521 | 11/2006 | |
| WO | WO 2006117521 A1 * | 11/2006 | ............ C07D 401/14 |
| WO | 2007/095601 | 8/2007 | |
| WO | 2007/095602 | 8/2007 | |
| WO | 2007/095603 | 8/2007 | |
| WO | WO-2008079610 A2 * | 7/2008 | ............ C07C 233/18 |
| WO | 2010/000611 | 1/2010 | |
| WO | 2010/000612 | 1/2010 | |
| WO | 2010/000615 | 1/2010 | |
| WO | WO 2010003624 A2 * | 1/2010 | ............ C07D 213/69 |
| WO | 2012/108478 | 8/2012 | |
| WO | 2012/143813 | 10/2012 | |
| WO | 2013/071169 | 5/2013 | |
| WO | 2013/079668 | 6/2013 | |
| WO | 2013/092616 | 6/2013 | |
| WO | 2013/092976 | 6/2013 | |
| WO | 2013/098373 | 7/2013 | |
| WO | 2013/098375 | 7/2013 | |
| WO | 2013/142369 | 9/2013 | |
| WO | 2014/056771 | 4/2014 | |
| WO | 2014/061693 | 4/2014 | |
| WO | 2014/114578 | 7/2014 | |
| WO | 2014/170197 | 10/2014 | |
| WO | 2014/182943 | 11/2014 | |
| WO | 2014/182945 | 11/2014 | |
| WO | 2014/182950 | 11/2014 | |
| WO | 2014/182951 | 11/2014 | |
| WO | 2014/184104 | 11/2014 | |
| WO | 2014/206922 | 12/2014 | |

OTHER PUBLICATIONS

Xiangdong Xu et al., The synthesis and structure-activity relationship studies of selective acetyl-CoA carboxylase inhibitors containing 4(thiazol-5-yl) but-3-yn-2-amino motif: Polar region modifications, Bioorganic & Medicinal Chemistry Letters, vol. 17, 2007, pp. 1803-1807.

Richard F. Clark et al., Phenoxy thiazole derivatives as potent and selective acetyl-CoA carboxylase 2 inhibitors: Modulation of isozyme selectivity by incorporation of phenyl ring substituents, Bioorganic & Medicinal Chemistry Letters, vol. 17, 2007, pp. 1961-1965.

Yu Gui Gu et al., N-{3-[2-(4-Alkoxyphenoxy)thiazol-5-yl]-1-methylprop-2-ynyl}carboxy Derivatives as Acetyl-CoA Carboxylase Inhibitors-Improvement of Cardiovascular and Neurological Liabilities via Structural Modifications, Journal of Medicinal Chemistry, vol. 50, 2007, pp. 1078-1082.

Tasir S. Haque et al., Potent biphenyl- and 3-phenyl pyridine-based inhibitors of Acetyle-CoA carboxylase, Bioorganic & Medicinal Chemistry Letters, vol. 19, 2009, pp. 5872-5876.

Stefanie Keil et al., Identification and Synthesis of Novel Inhibitors of Acetyl-CoA Carboxylase with in Vitro and in Vivo Efficacy on Fat Oxidation, Journal of Medicinal Chemistry, vol. 53, 2010, pp. 8679-8687.

Anuseema Bhadauriya et al., Identification of dual Acetyl-CoA carboxylases 1 and 2 inhibitors by pharmacophore based virtual screening and molecular docking approach, Molecular Diversity, vol. 17, 2013, pp. 139-149.

Written Opinion of the International Searching Authority dated Nov. 18, 2014 in corresponding International Application No. PCT/JP2014/077700.

International Search Report dated Nov. 18, 2014 in corresponding International Application No. PCT/JP2014/077700.

Extended European Search Report dated Aug. 4, 2017 in European Patent Application No. 14853664.2.

Database PubChem Compound [Online] Nov. 30, 2012 (Nov. 30, 2012), retrieved from NCBI Database accession No. 69029639.

Database PubChem Compound [Online] Jun. 18, 2007 (Jun. 18, 2007), XP002769855, retrieved from NCBI Database accession No. 16097241.

Database PubChem Compound [Online] Nov. 3, 2008 (Nov. 3, 2008), XP002769856, retrieved from NCBI Database accession No. 25015932.

Database PubChem Compound [Online] Nov. 20, 2006 (Nov. 20, 2006), XP002769857, retrieved from NCBI Database accession No. 11949655.

Database PubChem Compound [Online] Oct. 26, 2006 (Oct. 26, 2006), XP002769858, retrieved from NCBI Database accession No. 11620695.

(56) References Cited

OTHER PUBLICATIONS

Database PubChem Compound [Online] Nov. 30, 2012 (Nov. 30, 2012), XP002772295, retrieved from NCBI Database accession No. 66720158.
Database PubChem Compound [Online] Nov. 30, 2012 (Nov. 30, 2012), XP002772296, retrieved from NCBI Database accession No. 69007793.
Database PubChem Compound [Online] Nov. 30, 2012 (Nov. 30, 2012), XP002772297, retrieved from NCBI Database accession No. 69004180.
Database PubChem Compound [Online] Nov. 30, 2012 (Nov. 30, 2012), XP002772298, retrieved from NCBI Database accession No. 69002617.
Database PubChem Compound [Online] Nov. 30, 2012 (Nov. 30, 2012), XP002772299 retrieved from NCBI Database accession No. 67977323.

* cited by examiner

ALKYLENE DERIVATIVES

TECHNICAL FIELD

The present invention relates to a compound having an acetyl CoA carboxylase 2 (hereinafter referred to as ACC2) inhibitory activity.

BACKGROUND

Acetyl-CoA carboxylase (hereinafter referred to as ACC) is an enzyme that converts malonyl-CoA by carboxylation of acetyl-CoA. It is involved in the metabolism of fatty acids. The ACC has two isoforms called acetyl-CoA carboxylase 1 (hereinafter referred to as ACC1) and ACC2.

ACC2 is mainly expressed in heart and skeletal muscle, and malonyl-CoA produced by ACC2 inhibits the oxidation of fatty acids by inhibiting carnitine palmitoyl transferase I (CPT-I).

ACC2 deficient mice reduce the amount of malonyl-CoA in heart and skeletal muscle. As a result, fatty acids in the mice continuously are oxidized, and the mice lose their weight regardless of the increase in food intake. In addition, it is reported that ACC2 deficient mice develop tolerance to diabetes and obesity induced by the administration of high fatty/high carbohydrate food.

In view of the above information, ACC2 relates to disorders such as diabetes, obesity and the like. It is suggested that the inhibitor is expected as an anti-diabetes and anti-obesity drug.

On the other hand, since ACC1 deficient mice are fetal in fetal life, the drug inhibiting ACC2 selectively without inhibiting ACC1 is anticipated.

ACC2 inhibitors are disclosed in Patent Document 1 to 7. For example, the following two compounds having oxy methylene structure are disclosed in Patent Document 1.

[Formula 1]

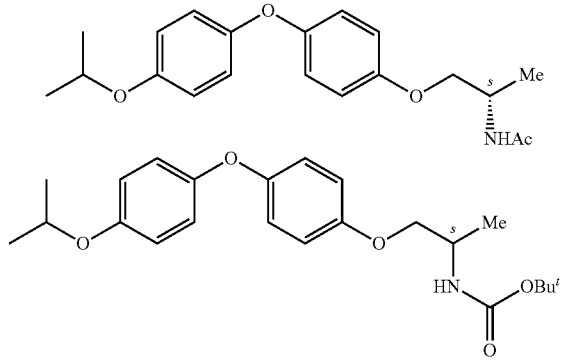

Ten compounds shown below having oxy methylene structure are disclosed in Patent Document 3.

[Formula 2]

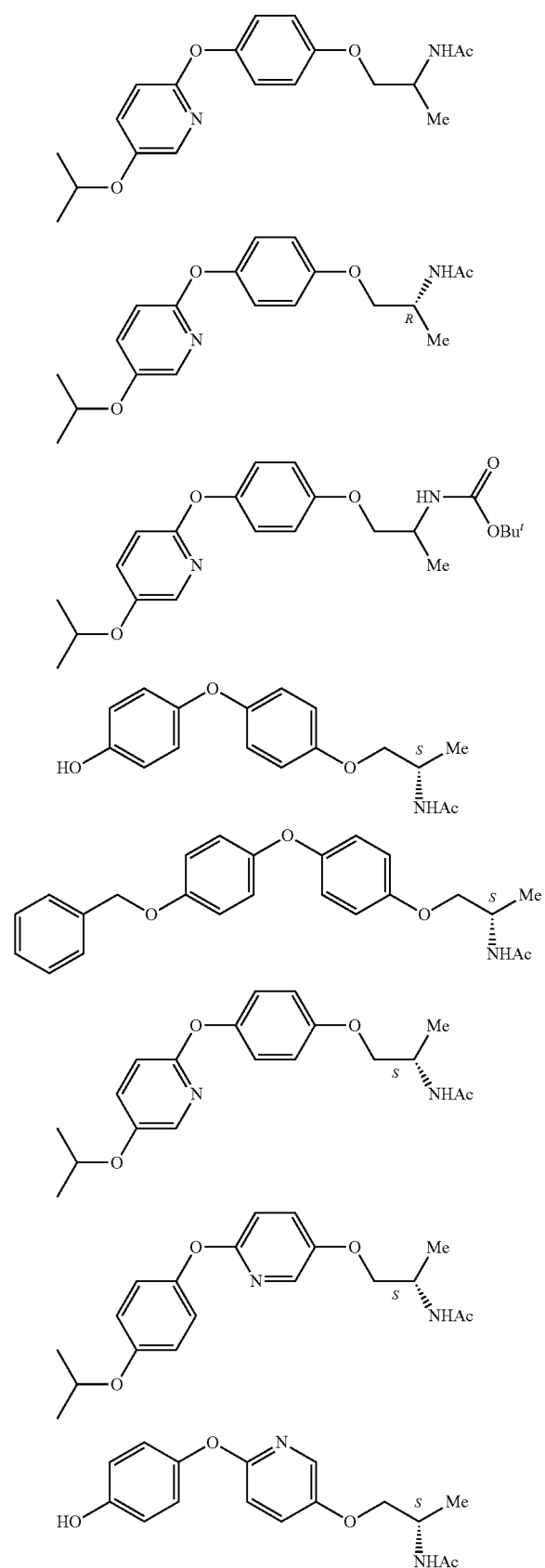

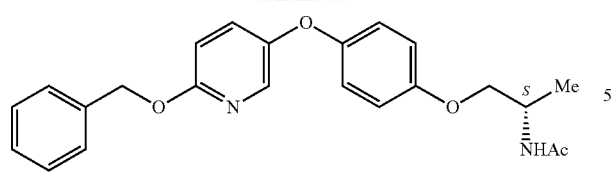

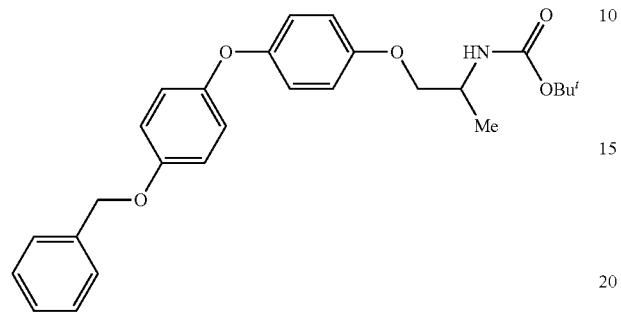

Although every these compounds has substituted or unsubstituted alkyloxy group at the para position of the terminal ring, there is no substituent at the ortho position.

The compound shown below is disclosed as a compound having olefinic structure in Patent Document 3.

[Formula 3]

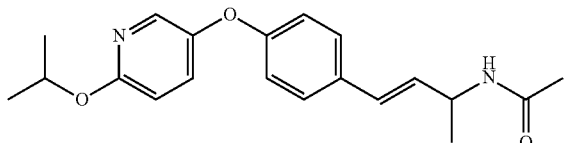

Thiazole phenyl ether derivatives specifically-inhibiting ACC2 are disclosed in non-Patent Documents 1 to 5. Biphenyl or 3-phenyl-pyridine derivatives exhibiting an ACC1 and ACC2 receptor inhibitory activity are disclosed in non-Patent Document 6. The compound shown below exhibiting an ACC2 receptor inhibitory activity and having preferable pharmacokinetic parameters is disclosed in Non-patent Document 7.

[Formula 4]

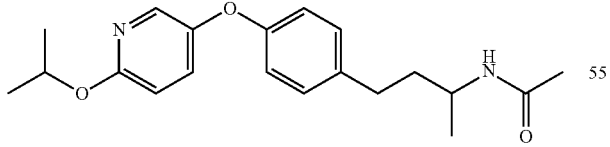

The preferable compounds having ACC1 and 2 dual inhibitory activity in the virtual screening are disclosed in non-Patent Document 8.

However, the present invention is not disclosed nor suggested in the above prior arts.

Moreover, the compounds shown below are disclosed as a compound having ACC2 receptor inhibitory activity.

[Formula 5]

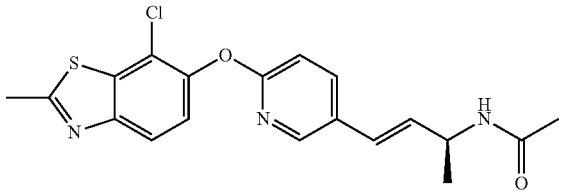

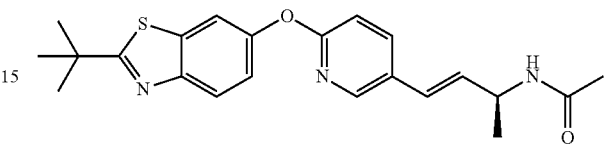

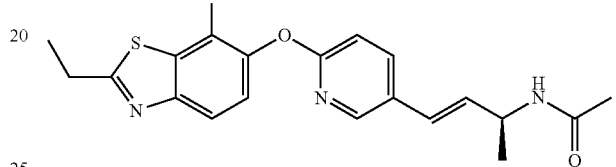

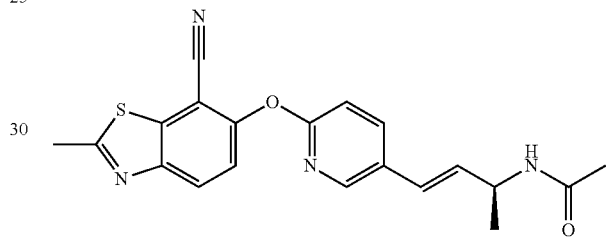

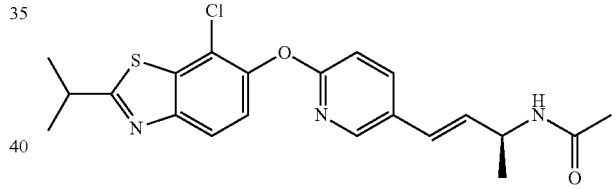

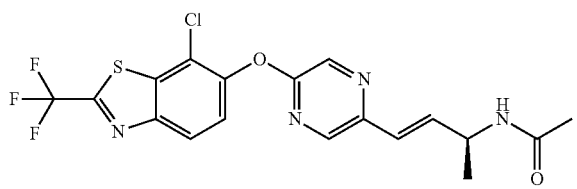

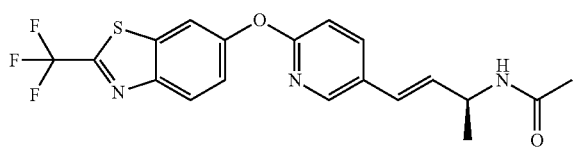

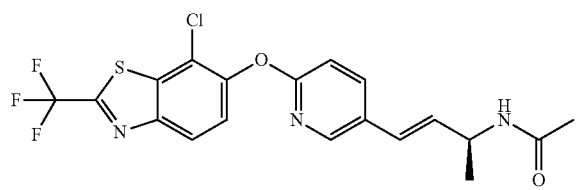
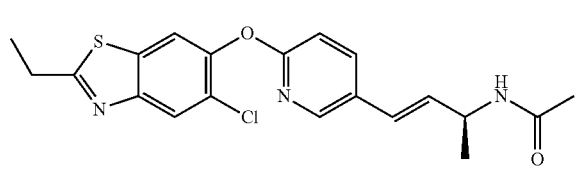
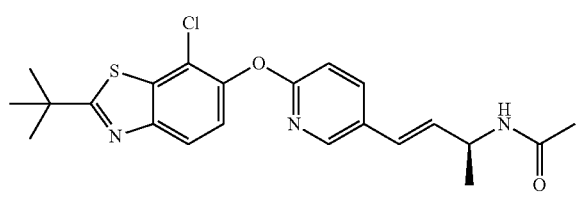
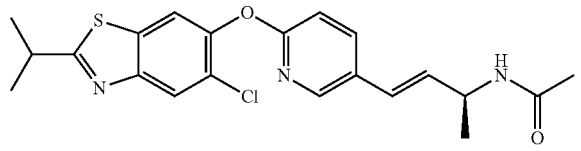
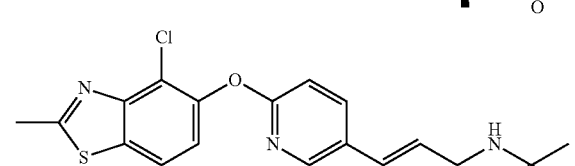
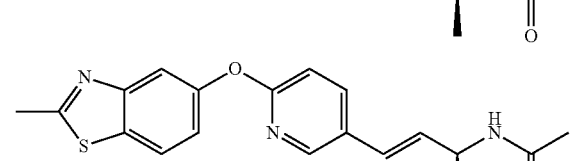
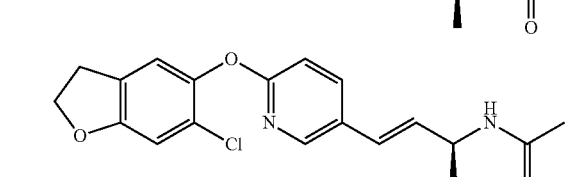
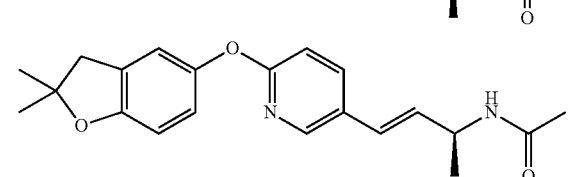
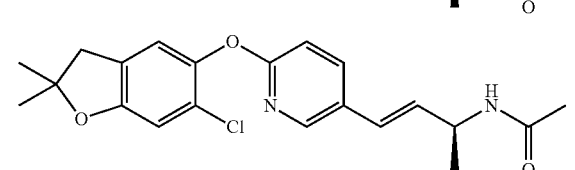
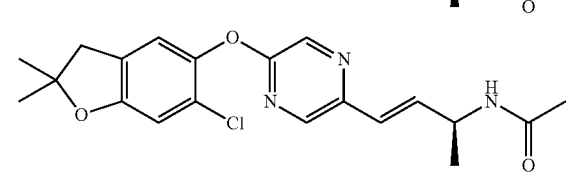
[Formula 6]
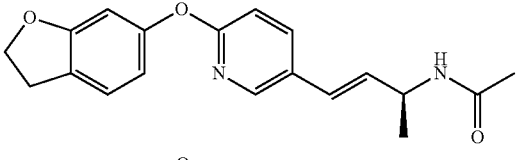
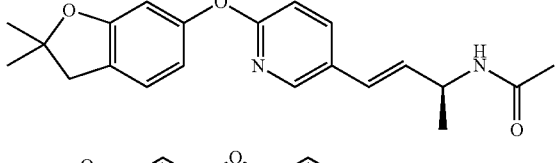
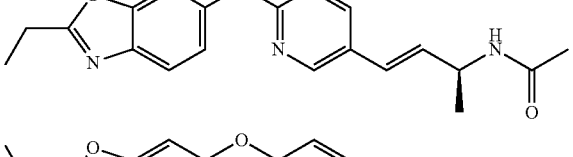
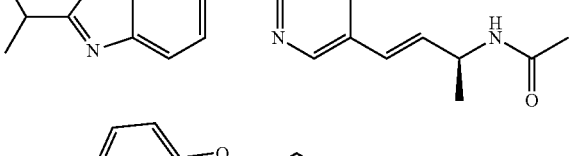
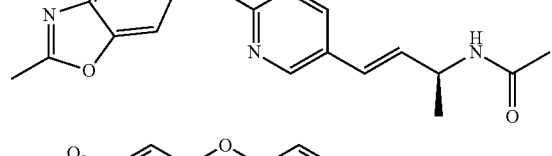
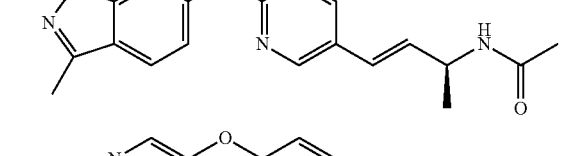
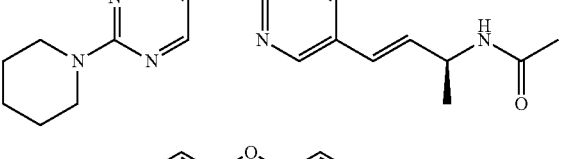
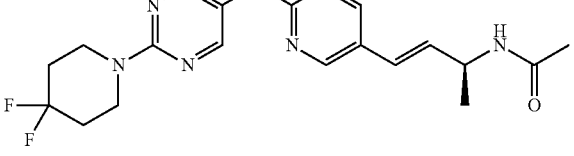
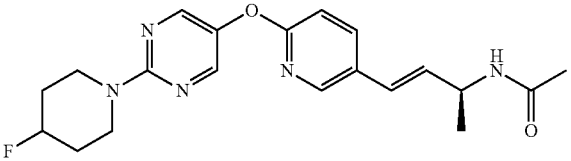
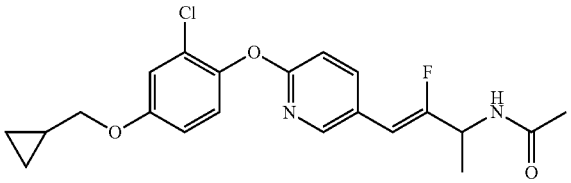

-continued

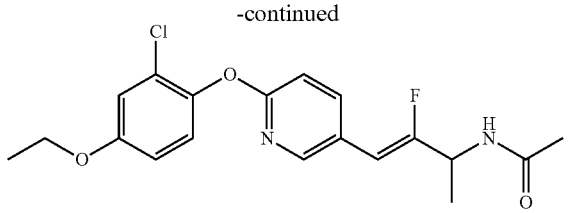

Although the compounds having alkylene group are disclosed in Patent Document 9 or 10, the present invention is not disclosed nor suggested in the prior art. Although the compounds having 9-membered fused ring are disclosed in Patent Documents 11 to 14, the present invention is not disclosed nor suggested in these prior art.

PRIOR ART

Patent Document

[Patent Document 1] International Publication No. 2008/079610 pamphlet
[Patent Document 2] International Publication No. 2010/050445 pamphlet
[Patent Document 3] International Publication No. 2010/003624 pamphlet
[Patent Document 4] International Publication No. 2007/095601 pamphlet
[Patent Document 5] International Publication No. 2007/095602 pamphlet
[Patent Document 6] International Publication No. 2007/095603 pamphlet
[Patent Document 7] United States Patent Application Publication No. 2006/178400
[Patent Document 8] International Publication No. 2013/035827 pamphlet
[Patent Document 9] International Publication No. 2009/122034 pamphlet
[Patent Document 10] United States Patent Application Publication No. 2007/0207984 pamphlet
[Patent Document 11] International Publication No. 2013/142369 pamphlet
[Patent Document 12] International Publication No. 2010/000615 pamphlet
[Patent Document 13] International Publication No. 2010/000612 pamphlet
[Patent Document 14] International Publication No. 2010/000611 pamphlet Non-Patent Document

[Non-patent Document 1] Bioorganic & Medicinal Chemistry Letters, (2006), Vol. 16, 6078-6081
[Non-patent Document 2] Journal of Medicinal Chemistry, (2006), Vol. 49, 3770-3773
[Non-patent Document 3] Bioorganic & Medicinal Chemistry Letters, (2007), Vol. 17, 1803-1807
[Non-patent Document 4] Bioorganic & Medicinal Chemistry Letters, (2007), Vol. 17, 1961-1965
[Non-patent Document 5] Journal of Medicinal Chemistry, (2007), Vol. 50, 1078-1082
[Non-patent Document 6] Bioorganic & Medicinal Chemistry Letters, (2009), Vol. 19, 5872-5876
[Non-patent Document 7] Journal of Medicinal Chemistry, (2010), Vol. 53, 8679-8687
[Non-patent Document 8] Molecular Diversity, (2013), Vol. 17, 139-149

SUMMARY OF THE INVENTION

Problems to be Solved by the Invention

The object of the present invention is to provide novel compounds having ACC2 selective inhibitory activity. In addition, the present invention provides a pharmaceutical composition comprising the compound.

Means for Solving the Problem

The present invention includes the followings.
(1) A compound of Formula (I):

[Formula 7]

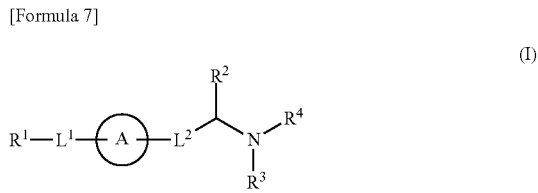

or its pharmaceutically acceptable salt,
wherein
$R^1$ is substituted or unsubstituted fused aromatic heterocyclyl, substituted or unsubstituted fused aromatic carbocyclyl, substituted or unsubstituted non-aromatic heterocyclyl, substituted or unsubstituted non-aromatic carbocyclyl, the group represented by Formula:

[Formula 8]

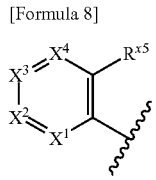

or substituted or unsubstituted 5-membered aromatic heterocyclyl,
$X^1$ is N or $C(R^{x1})$,
$X^2$ is N or $C(R^{x2})$,
$X^3$ is N or $C(R^{x3})$,
$X^4$ is N or $C(R^{x4})$,
each $R^{x1}$, $R^{x2}$, $R^{x3}$, and $R^{x4}$ is independently hydrogen, halogen, hydroxy, carboxy, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfanyl, substituted or unsubstituted alkynylsulfanyl, substituted or unsubstituted amino, substituted or unsubstituted carbamoyl, substituted or unsubstituted sulfamoyl, substituted or unsubstituted alkylcarbonyl, substituted or unsubstituted alkenylcarbonyl, substituted or unsubstituted alkynylcarbonyl, substituted or unsubstituted alkyloxycarbonyl, substituted or unsubstituted alkenyloxycarbonyl, substituted or unsubstituted alkynyloxycarbonyl, substituted or unsubstituted alkylsulfonyl, substituted or unsubstituted alkenylsulfonyl, substituted or unsubstituted alkynylsulfonyl, substituted or unsubstituted non-aromatic carbocyclylsulfonyl, substituted or unsubstituted aromatic carbocyclylsulfonyl, substituted or unsubstituted non-aromatic heterocyclylsulfonyl, substituted or unsubstituted aromatic heterocyclylsulfonyl or substituted or unsubstituted sulfamoyl, $R^{x5}$ is halogen, hydroxy, carboxy, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfanyl, substituted or unsubstituted alkynylsulfanyl, substituted or unsubstituted amino, substituted or unsubstituted carbamoyl, substituted or unsubstituted alkylcarbonyl, substituted or unsubstituted alkenylcarbonyl, substituted or unsubstituted alkynylcarbonyl, substituted or unsubstituted alkyloxycarbonyl, substituted or unsubstituted alkenyloxycarbonyl, substituted or unsubstituted alkynyloxycarbonyl, substituted or unsubstituted alkylsulfonyl, substituted or unsubstituted alkenylsulfonyl, substituted or unsubstituted alkynylsulfonyl, substituted or unsubstituted non-aromatic carbocyclylsulfonyl, substituted or unsubstituted aromatic carbocyclylsulfonyl, substituted or unsubstituted non-aromatic heterocyclylsulfonyl, substituted or unsubstituted aromatic heterocyclylsulfonyl or substituted or unsubstituted sulfamoyl, ring A is substituted or unsubstituted non-aromatic carbocycle, substituted or unsubstituted non-aromatic heterocycle, substituted or unsubstituted aromatic carbocycle or substituted or unsubstituted aromatic heterocycle, -$L^1$- is —O—(CR$^6$R$^7$)m- or —N(R$^8$)—(CR$^6$R$^7$)m-, -$L^2$- is —O—(CR$^6$R$^7$)n-, —O—CR$^6$=CR$^7$—, —(CR$^6$R$^7$)n- or —C(=O)—(CR$^6$R$^7$)n-, each $R^6$ is independently hydrogen, halogen, cyano, substituted or unsubstituted alkyl, substituted or unsubstituted alkenyl or substituted or unsubstituted alkynyl, each $R^7$ is independently hydrogen, halogen, cyano, substituted or unsubstituted alkyl, substituted or unsubstituted alkenyl or substituted or unsubstituted alkynyl, or $R^6$ and $R^7$ on the same carbon atom may be taken together with the carbon atom to form ring, or $R^2$ is taken together with either $R^6$ or $R^7$ to form ring, each m is independently an integer of 0, 1, 2 or 3,
each n is independently an integer of 1, 2 or 3,
$R^2$ is substituted or unsubstituted alkyl,
$R^3$ is hydrogen or substituted or unsubstituted alkyl,
$R^4$ is substituted or unsubstituted alkylcarbonyl, substituted or unsubstituted alkenylcarbonyl, substituted or unsubstituted alkynylcarbonyl, substituted or unsubstituted non-aromatic carbocyclylcarbonyl, substituted or unsubstituted aromatic carbocyclylcarbonyl, substituted or unsubstituted non-aromatic heterocyclylcarbonyl, substituted or unsubstituted aromatic heterocyclylcarbonyl, substituted or unsubstituted alkyloxycarbonyl, substituted or unsubstituted alkenyloxycarbonyl, substituted or unsubstituted alkynyloxycarbonyl, substituted or unsubstituted non-aromatic carbocyclyloxycarbonyl, substituted or unsubstituted aromatic carbocyclyloxycarbonyl, substituted or unsubstituted non-aromatic heterocyclyloxycarbonyl, substituted or unsubstituted aromatic heterocyclyloxycarbonyl, substituted or unsubstituted carbamoyl, substituted or unsubstituted alkylsulfonyl, substituted or unsubstituted alkenylsulfonyl, substituted or unsubstituted alkynylsulfonyl, substituted or unsubstituted non-aromatic carbocyclylsulfonyl, substituted or unsubstituted aromatic carbocyclylsulfonyl, substituted or unsubstituted non-aromatic heterocyclylsulfonyl, substituted or unsubstituted aromatic heterocyclylsulfonyl or substituted or unsubstituted sulfamoyl;

provided that the following compounds are excluded, (i) the compounds wherein $R^1$ is a substituent selected from Substituent group α (Substituent group α: unsubstituted phenyl and substituted or unsubstituted aromatic heterocyclyl) and quinolinyl substituted with two alkyloxy groups, ring A is substituted pyrrolidine, and -$L^2$- is —C(=O)—(CR$^6$R$^7$)n-, (ii) the compounds wherein ring A is nitrogen-containing non-aromatic heterocycle, -$L^2$- is —C(=O)—(CR$^6$R$^7$)n-, and the atom on ring A bonded to -$L^2$- is nitrogen, (iii) the compounds wherein $R^1$ is benzimidazolyl substituted with substituted or unsubstituted aromatic heterocyclylalkyl or substituted or unsubstituted non-aromatic heterocyclylalkyl, ring A is piperidine, -$L^1$- is —NH—, -$L^2$- is —CH$_2$—, and $R^4$ is tert-butyloxycarbonyl, (iv) the compounds wherein $R^1$ is substituted or unsubstituted fused aromatic heterocyclyl represented by Formula:

[Formula 9]

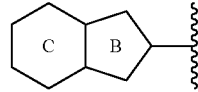

wherein
ring B is 5-membered, and ring C is 6-membered,
and -$L^2$- is —C(=O)—(CR$^6$R$^7$)n-, (v) the compounds wherein $X^1$ is C($R^{x1}$), $X^2$ is C($R^{x2}$), $X^3$ is C($R^{x3}$), $X^4$ is C($R^{x4}$), $R^{x5}$ is unsubstituted carbamoyl, ring A is unsubstituted cyclohexane, -$L^1$- is —N(H)—, -$L^2$- is —C(=O)—, and $R^4$ is alkylcarbonyl substituted with amino or unsubstituted alkyloxycarbonyl, and (vi) the following compounds:

[Formula 10]

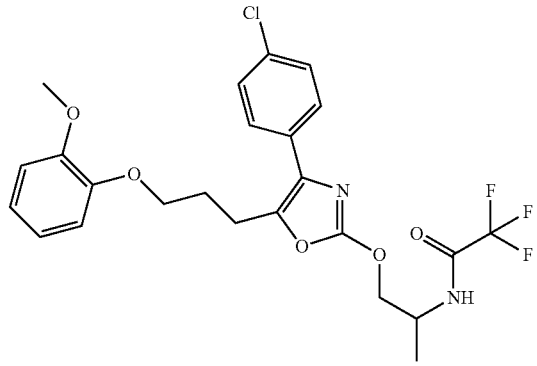
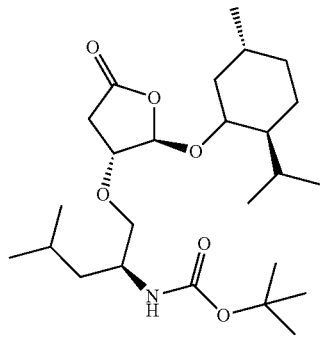

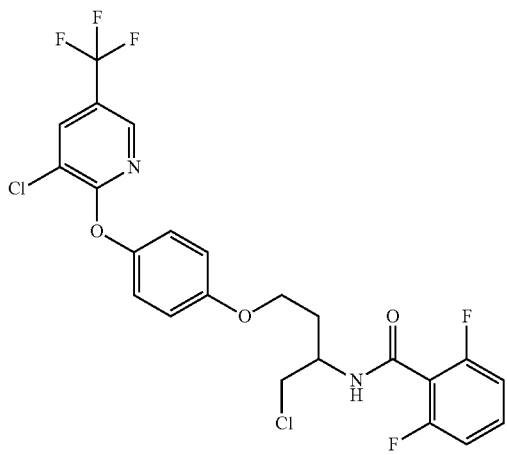
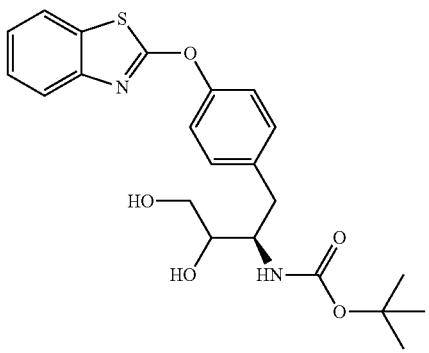
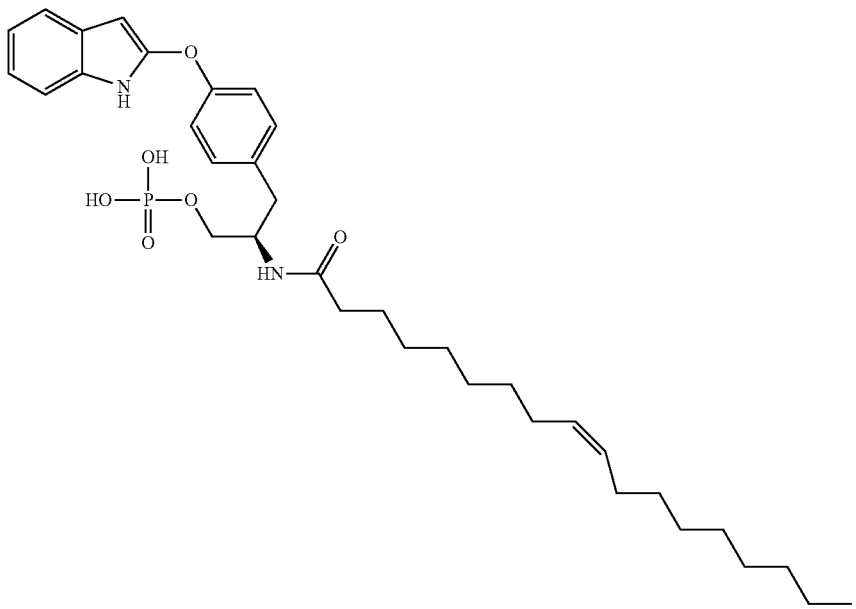
and
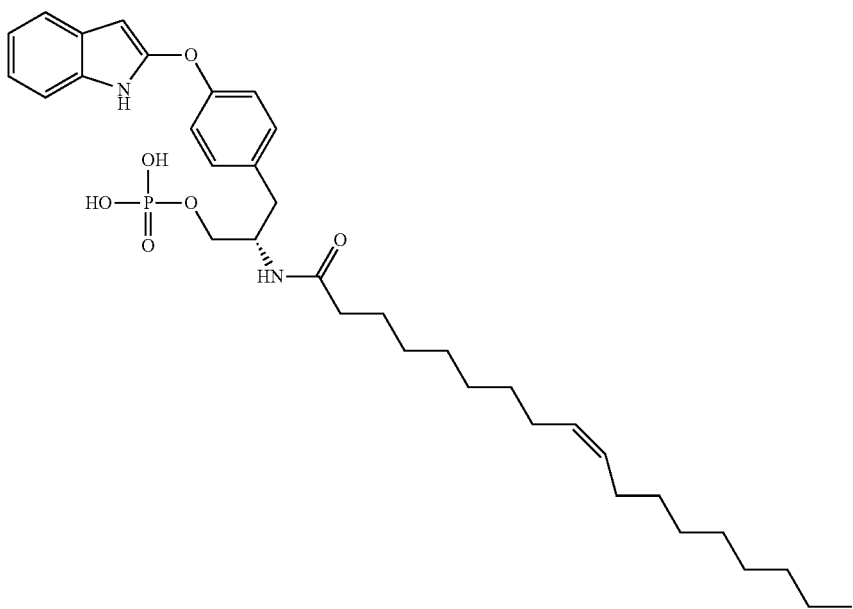 [SMILES: CCCCCCCC/C=C\CCCCCCCC(=O)N[C@H](COP(=O)(O)O)Cc1ccc(Oc2cc3ccccc3[nH]2)cc1]

(1-a) A compound of Formula (I):

[Formula 11]

$$R^1-L^1-\boxed{A}-L^2-\underset{R^3}{\overset{R^2}{\text{C}}}-N\underset{R^3}{\overset{R^4}{\diagup}}\quad (I)$$

or its pharmaceutical acceptable salt,
wherein
R¹ is substituted or unsubstituted fused aromatic heterocyclyl, substituted or unsubstituted fused aromatic carbocyclyl, substituted or unsubstituted non-aromatic heterocyclyl, substituted or unsubstituted non-aromatic carbocyclyl, the group represented by Formula:

[Formula 12]

or substituted or unsubstituted 5-membered aromatic heterocyclyl, $X^1$ is N or $C(R^{x1})$,
$X^2$ is N or $C(R^{x2})$,
$X^3$ is N or $C(R^{x3})$,
$X^4$ is N or $C(R^{x4})$,
each $R^{x1}$, $R^{x2}$, $R^{x3}$, and $R^{x4}$ is independently hydrogen, halogen, hydroxy, carboxy, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfanyl, substituted or unsubstituted alkynylsulfanyl, substituted or unsubstituted amino, substituted or unsubstituted carbamoyl, substituted or unsubstituted sulfamoyl, substituted or unsubstituted alkylcarbonyl, substituted or unsubstituted alkenylcarbonyl, substituted or unsubstituted alkynylcarbonyl, substituted or unsubstituted alkyloxycarbonyl, substituted or unsubstituted alkenyloxycarbonyl, substituted or unsubstituted alkynyloxycarbonyl, substituted or unsubstituted alkylsulfonyl, substituted or unsubstituted alkenylsulfonyl, substituted or unsubstituted alkynylsulfonyl, substituted or unsubstituted non-aromatic carbocyclylsulfonyl, substituted or unsubstituted aromatic carbocyclylsulfonyl, substituted or unsubstituted non-aromatic heterocyclylsulfonyl, substituted or unsubstituted aromatic heterocyclylsulfonyl or substituted or unsubstituted sulfamoyl, $R^{x5}$ is halogen, hydroxy, carboxy, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfanyl, substituted or unsubstituted alkynylsulfanyl, substituted or unsubstituted amino, substituted or unsubstituted carbamoyl, substituted or unsubstituted alkylcarbonyl, substituted or unsubstituted alkenylcarbonyl, substituted or unsubstituted alkynylcarbonyl, substituted or unsubstituted alkyloxycarbonyl, substituted or unsubstituted alkenyloxycarbonyl, substituted or unsubstituted alkynyloxycarbonyl, substituted or unsubstituted alkylsulfonyl, substituted or unsubstituted alkenylsulfonyl, substituted or unsubstituted alkynylsulfonyl, substituted or unsubstituted non-aromatic carbocyclylsulfonyl, substituted or unsubstituted aromatic carbocyclylsulfonyl, substituted or unsubstituted non-aromatic heterocyclylsulfonyl, substituted or unsubstituted aromatic heterocyclylsulfonyl or substituted or unsubstituted sulfamoyl, ring A is substituted or unsubstituted non-aromatic carbocycle, substituted or unsubstituted non-aromatic heterocycle, substituted or unsubstituted aromatic carbocycle or substituted or unsubstituted aromatic heterocycle, -L¹- is —O—(CR⁶R⁷)m- or —N(R⁸)—(CR⁶R⁷)m-,
-L²- is —O—(CR⁶R⁷)n-, —O—CR⁶=CR⁷—, —(CR⁶R⁷)n- or —C(=O)—(CR⁶R⁷)n-, each $R^6$ is independently hydrogen, halogen, cyano, substituted or unsubstituted alkyl, substituted or unsubstituted alkenyl or substituted or unsubstituted alkynyl, each $R^7$ is independently hydrogen, halogen, cyano, substituted or unsubstituted alkyl, substituted or unsubstituted alkenyl or substituted or unsubstituted alkynyl, or $R^6$ and $R^7$ on the same carbon atom may be taken together with the carbon atom to form ring, or $R^2$ is taken together with either $R^6$ or $R^7$ to form ring, each m is independently an integer of 0, 1, 2 or 3,
each n is independently an integer of 1, 2 or 3,
$R^2$ is substituted or unsubstituted alkyl,
$R^3$ is hydrogen or substituted or unsubstituted alkyl,
$R^4$ is substituted or unsubstituted alkylcarbonyl, substituted or unsubstituted alkenylcarbonyl, substituted or unsubstituted alkynylcarbonyl, substituted or unsubstituted non-aromatic carbocyclylcarbonyl, substituted or unsubstituted aromatic carbocyclylcarbonyl, substituted or unsubstituted non-aromatic heterocyclylcarbonyl, substituted or unsubstituted aromatic heterocyclylcarbonyl, substituted or unsubstituted alkyloxycarbonyl, substituted or unsubstituted alkenyloxycarbonyl, substituted or unsubstituted alkynyloxycarbonyl, substituted or unsubstituted non-aromatic carbocyclyloxycarbonyl, substituted or unsubstituted aromatic carbocyclyloxycarbonyl, substituted or unsubstituted non-aromatic heterocyclyloxycarbonyl, substituted or unsubstituted aromatic heterocyclyloxycarbonyl, substituted or unsubstituted carbamoyl, substituted or unsubstituted alkylsulfonyl, substituted or unsubstituted alkenylsulfonyl, substituted or unsubstituted alkynylsulfonyl, substituted or unsubstituted non-aromatic carbocyclylsulfonyl, substituted or unsubstituted aromatic carbocyclylsulfonyl, substituted or unsubstituted non-aromatic heterocyclylsulfonyl, substituted or unsubstituted aromatic heterocyclylsulfonyl or substituted or unsubstituted sulfamoyl;

provided that the following compounds are excluded,
(i) the compounds wherein R¹ is a substituent selected from Substituent group α (Substituent group α: unsubstituted phenyl and substituted or unsubstituted aromatic heterocyclyl) and quinolinyl substituted with two alkyloxy groups, ring A is substituted pyrrolidine, and -L²- is —C(=O)—(CR⁶R⁷)n-,
(ii) the compounds wherein ring A is nitrogen-containing non-aromatic heterocycle, -L²- is —C(=O)—(CR⁶R⁷)n-, and the atom on ring A bonded to -L²- is nitrogen,
(iii) the compounds wherein R¹ is benzimidazolyl or imidazopyridyl substituted with substituted or unsubstituted aromatic heterocyclylalkyl or substituted or unsubstituted non-aromatic heterocyclylalkyl, ring A is piperidine, -L¹- is —NH—, -L²- is —CH₂—, and R⁴ is tert-butyloxycarbonyl, (iv) the compounds wherein R¹ is substituted or substituted fused aromatic heterocyclyl represented by Formula:

[Formula 13]

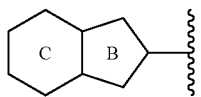

wherein
ring B is 5-membered, and ring C is 6-membered,
(iv) the compounds wherein $X^1$ is $C(R^{x1})$, $X^2$ is $C(R^{x2})$, $X^3$ is $C(R^{x3})$, $X^4$ is $C(R^{x4})$, $R^{x5}$ is unsubstituted carbamoyl, ring A is unsubstituted cyclohexane, -$L^1$- is —N(H)—, -$L^2$- is —C(=O)—, and $R^4$ is alkylcarbonyl substituted with amino or unsubstituted alkyloxycarbonyl, and (v) the following compounds:

[Formula 14]

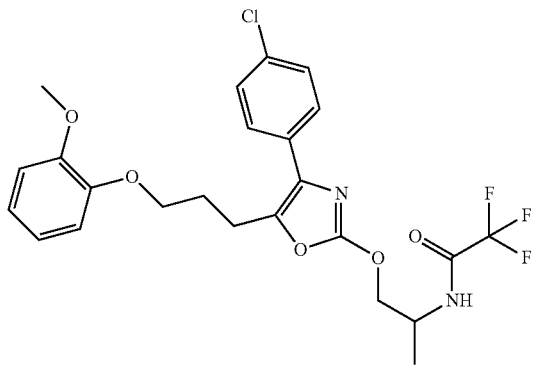

and

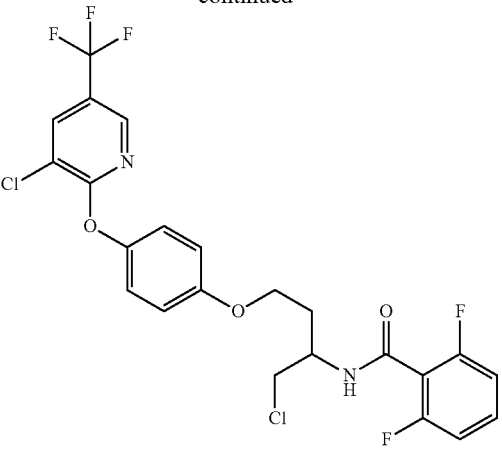

(2) The compound or its pharmaceutically acceptable salt according to the above (1) or (1-a), wherein ring A is substituted or unsubstituted cyclobutane, substituted or unsubstituted cyclopentane, substituted or unsubstituted azetidine, substituted or unsubstituted oxetane, substituted or unsubstituted thietane, substituted or unsubstituted pyrrolidine, substituted or unsubstituted tetrahydrofuran, substituted or unsubstituted thiolane, substituted or unsubstituted piperidine, substituted or unsubstituted morpholine, substituted or unsubstituted tetrahydropyran, substituted or unsubstituted tetrahydrothiopyran, substituted or unsubstituted pyrrole, substituted or unsubstituted furan, substituted or unsubstituted thiophene, substituted or unsubstituted imidazole, substituted or unsubstituted pyrazole, substituted or unsubstituted oxazole, substituted or unsubstituted isoxazole, substituted or unsubstituted thiazole, substituted or unsubstituted isothiazole, substituted or unsubstituted oxadiazole, substituted or unsubstituted thiadiazole, substituted or unsubstituted pyridine, substituted or unsubstituted pyrimidine, substituted or unsubstituted pyrazine or substituted or unsubstituted pyridazine.

(3) The compound or its pharmaceutically acceptable salt according to the above (1) or (1-a), wherein ring A is substituted or unsubstituted cyclobutane, substituted or unsubstituted cyclohexaneubstituted or unsubstituted benzene, substituted or unsubstituted piperidine, substituted or unsubstituted pyrazine, substituted or unsubstituted pyrimidine or substituted or unsubstituted thiazole.

(4) The compound or its pharmaceutically acceptable salt according to any one of the above (1) to (3) or (1-a), wherein $R^1$ is substituted or unsubstituted benzothiazolyl, substituted or unsubstituted benzoxazolyl, substituted or unsubstituted benzoimidazolyl, substituted or unsubstituted indolyl, substituted or unsubstituted indazolyl, substituted or unsubstituted isoquinolyl, substituted or unsubstituted quinoxalinyl, substituted or unsubstituted naphtalenyl, substituted or unsubstituted aziridinyl, substituted or unsubstituted oxyranyl, substituted or unsubstituted thiiranyl, substituted or unsubstituted azetidinyl, substituted or unsubstituted oxetanyl, substituted or unsubstituted thietanyl, substituted or unsubstituted pirrolidinyl, substituted or unsubstituted tetrahydrofuranyl, substituted or unsubstituted tetrahydrothiophenyl, substituted or unsubstituted piperidinyl, substituted or unsubstituted piperidino, substituted or unsubstituted tetrahydropyranyl, substituted or unsubstituted tetrahydropyranyl, substituted or unsubstituted piperazinyl, substituted or unsubstituted morpholinyl, substituted or unsubstituted morpholino, substituted or unsubstituted thiomorpholinyl, substituted or unsubstituted thiomorpholino, substituted or unsubstituted cyclobutanyl, the group represented by Formula:

[Formula 15]

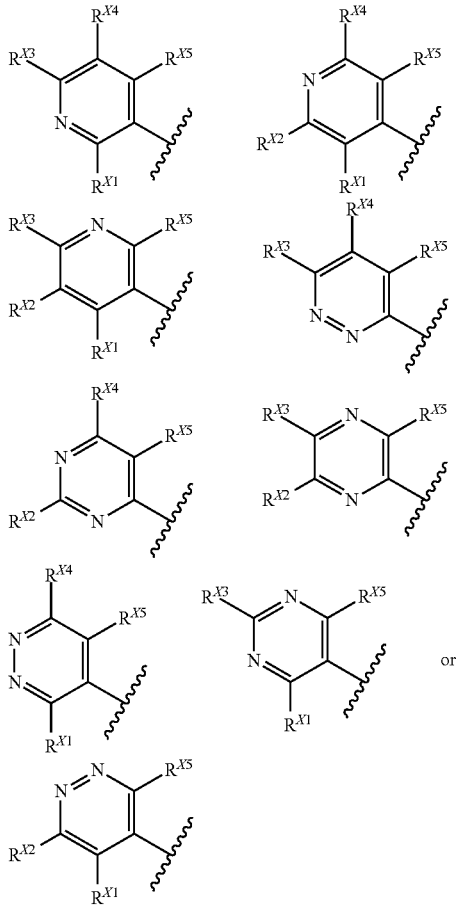

or substituted or unsubstituted 5-membered aromatic heterocyclyl.

(5) The compound or its pharmaceutically acceptable salt according to any one of claims 1 to 3, wherein $R^1$ is substituted or unsubstituted naphtalenyl, substituted or unsubstituted pyrimidinyl, substituted or unsubstituted dihydroindenyl, substituted or unsubstituted dihydrobenzofuranyl, substituted or unsubstituted indolinyl, substituted or unsubstituted tetrahydroisoquinolyl, substituted or unsubstituted benzoxazolyl, substituted or unsubstituted benzothiazolyl, substituted or unsubstituted benzopyrazolyl, substituted or unsubstituted benzoisothiazolyl or substituted or unsubstituted oxazolinyl.

(6) The compound or its pharmaceutically acceptable salt according to any one of the above (1) to (3) or (1-a), wherein $R^1$ is substituted or unsubstituted naphtalenyl, substituted or unsubstituted dihydroindenyl, substituted or unsubstituted dihydrobenzofuranyl, substituted or unsubstituted indolinyl, substituted or unsubstituted tetrahydroisoquinolinyl, substituted or unsubstituted benzoxazolyl, substituted or unsubstituted benzothiazolyl, substituted or unsubstituted benzopyrazolyl, substituted or unsubstituted benzoisothiazolyl, substituted or unsubstituted oxazolinyl, or the group represented by Formula:

[Formula 16]

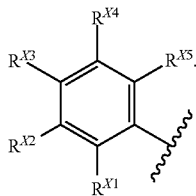

(7) The compound or its pharmaceutically acceptable salt according to any one of the above (1) to (3) or (1-a), wherein $R^1$ is substituted or unsubstituted benzothiazolyl, substituted or unsubstituted benzoxazolyl, substituted or unsubstituted benzimidazolyl, substituted or unsubstituted benzopyrazolyl, substituted or unsubstituted thiazolopyridinyl, substituted or unsubstituted indolyl, substituted or unsubstituted indazolyl, substituted or unsubstituted isoquinolyl, substituted or unsubstituted quinazolinyl, or substituted or unsubstituted quinoxalinyl.

(8) The compound or its pharmaceutically acceptable salt according to any one of the above (1) to (3) or (1-a), wherein $R^1$ is the group represented by Formula:

[Formula 17]

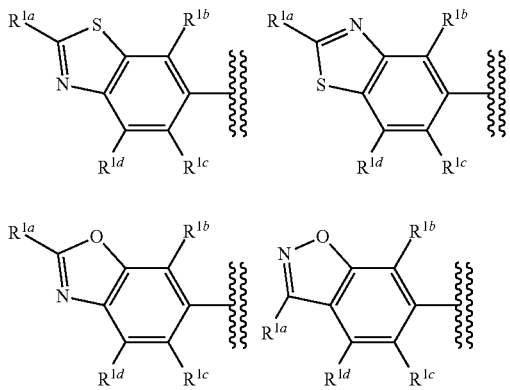

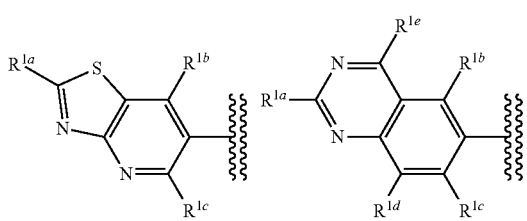

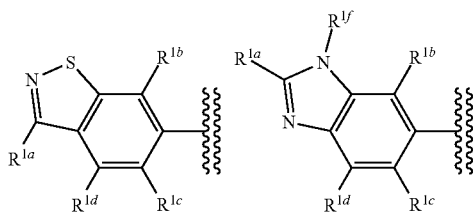

-continued

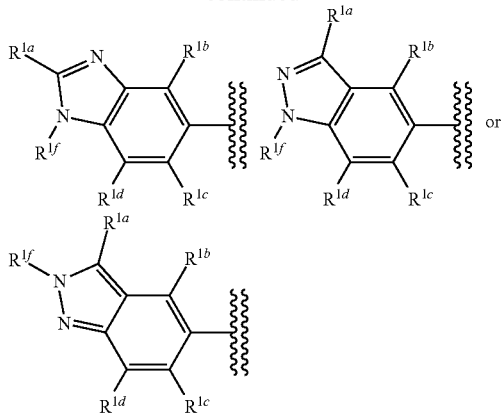

wherein
each $R^{1a}$, $R^{1b}$, $R^{1c}$, $R^{1d}$, and $R^{1e}$ is independently hydrogen, halogen, hydroxy, carboxy, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfanyl, substituted or unsubstituted alkynylsulfanyl, substituted or unsubstituted amino, substituted or unsubstituted carbamoyl, substituted or unsubstituted sulfamoyl, substituted or unsubstituted alkylcarbonyl, substituted or unsubstituted alkenylcarbonyl, substituted or unsubstituted alkynylcarbonyl, substituted or unsubstituted alkyloxycarbonyl, substituted or unsubstituted alkenyloxycarbonyl, or substituted or unsubstituted alkynyloxycarbonyl, $R^{1f}$ is hydrogen, substituted or unsubstituted alkyl, substituted or unsubstituted alkenyl, substituted or unsubstituted alkynyl, substituted or unsubstituted alkylcarbonyl, substituted or unsubstituted alkenylcarbonyl, or substituted or unsubstituted alkynylcarbonyl.

(9) The compound or its pharmaceutically acceptable salt according to the above (8), wherein $R^{1a}$ is substituted or unsubstituted alkyl, or substituted or unsubstituted alkyloxy.

(10) The compound or its pharmaceutically acceptable salt according to the above (1), wherein $R^4$ is substituted or unsubstituted alkylcarbonyl.

(11) The compound or its pharmaceutically acceptable salt according to the above (10), wherein $R^4$ is methylcarbonyl.

(12) The compound or its pharmaceutically acceptable salt according to any one of the above (1) to (9) or (1-a), wherein $R^4$ is substituted or unsubstituted non-aromatic carbocyclylcarbonyl, substituted or unsubstituted non-aromatic heterocyclylcarbonyl, or substituted or unsubstituted aromatic carbocyclylcarbonyl, or substituted or unsubstituted carbamoyl.

(13) The compound or its pharmaceutically acceptable salt according to any one of the above (1) to (12) or (1-a), wherein m is 0.

(14) The compound or its pharmaceutically acceptable salt according to any one of the above (1) to (13) or (1-a), wherein -$L^2$- is —O—$(CR^6R^7)n$-.

(15) The compound or its pharmaceutically acceptable salt according to any one of the above (1) to (14) or (1-a), wherein n is 1.

(16) The compound or its pharmaceutically acceptable salt according to any one of the above (1) to (13) or (1-a), wherein -$L^2$- is —O—$(CR^6R^7)$—, $R^2$ is taken together with either $R^6$ or $R^7$ to form ring.

(17) The compound or its pharmaceutically acceptable salt according to any one of the above (1) or (1-a), wherein $R^1$ is the group represented by Formula:

[Formula 18]

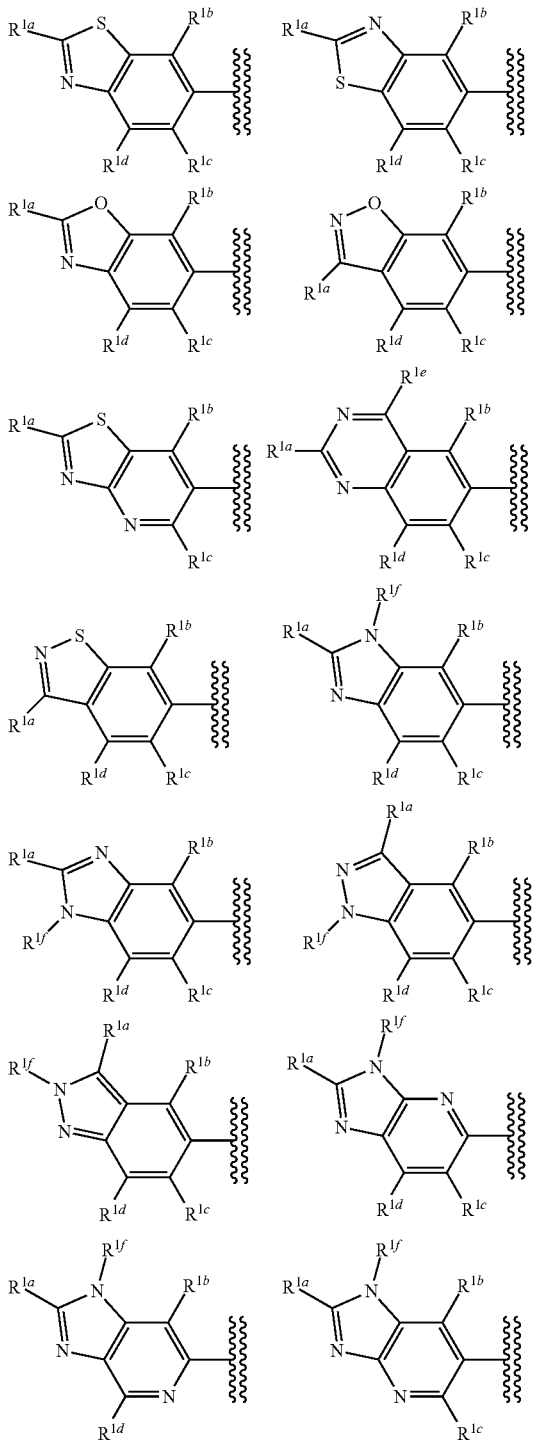

-continued

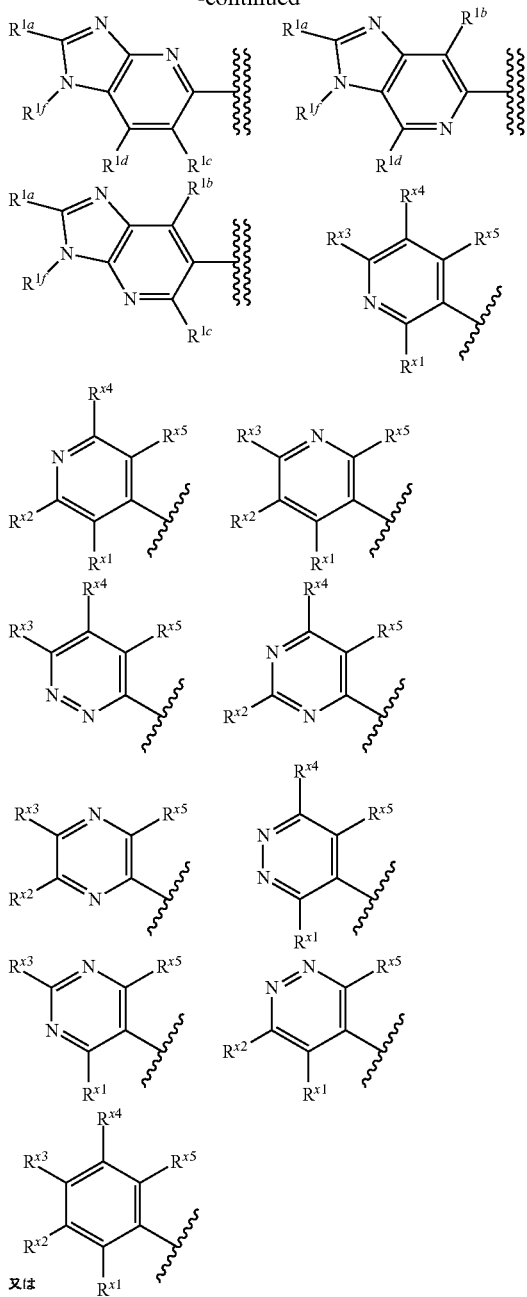

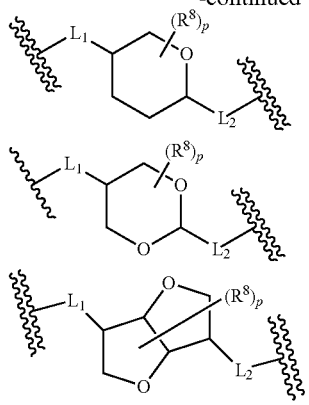

wherein each symbols is as defined above,
ring A is the group represented by Formula:

[Formula 19]

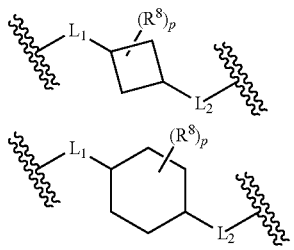

-continued

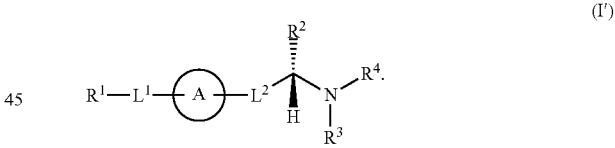

wherein $R^8$ is halogen, cyano, hydroxy, carboxy, oxo, substituted or unsubstituted alkyl, substituted or unsubstituted alkyloxy or substituted or unsubstituted amino, and p is an integer of 0 to 4, each $R^6$ is independently hydrogen, halogen, cyano, substituted or unsubstituted alkyl, substituted or unsubstituted alkenyl or substituted or unsubstituted alkynyl, each $R^7$ is independently hydrogen, halogen, cyano, substituted or unsubstituted alkyl, substituted or unsubstituted alkenyl or substituted or unsubstituted alkynyl, or $R^6$ and $R^7$ on the same carbon atom are taken together to form ring.

(18) The compound or its pharmaceutically acceptable salt according to the above (17), wherein -$L^1$- is —O—(CR$^6$R$^7$)m-, and -$L^2$- is —O—(CR$^6$R$^7$)n- or —(CR$^6$R$^7$)n-.

(19) The compound or its pharmaceutically acceptable salt according to any one of the above (1) to (18) or (1-a), wherein Formula (I) is Formula:

[Formula 20]

(I')

R$^1$—L$^1$—(A)—L$^2$—$\overset{R^2}{\underset{H}{\overset{|}{C}}}$—N$\overset{R^4}{\underset{R^3}{}}$

(20) The compound or its pharmaceutically acceptable salt according to any one of the above (1) to (19) or (1-a), wherein $R^1$ is substituted or unsubstituted fused aromatic heterocyclyl, substituted or unsubstituted fused aromatic carbocyclyl, substituted or unsubstituted non-aromatic heterocyclyl, substituted or unsubstituted non-aromatic carbocyclyl, the group represented by Formula:

[Formula 21]

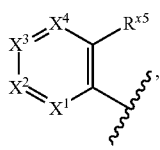

or substituted or unsubstituted 5-membered aromatic heterocyclyl, provided that R¹ is not substituted or unsubstituted fused aromatic heterocyclyl represented by Formula:

[Formula 22]

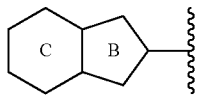

wherein ring B is 5-membered ring, and ring C is 6-membered ring.
(21) A pharmaceutical composition, which comprises a compound or its pharmaceutically acceptable salt according to any one of the above (1) to (20) or (1-a).
(22) A pharmaceutical composition according to the above (20) for treatment or prevention of a disease associated with ACC2.
(23) A method for treatment or prevention of a disease associated with ACC2 characterized by administering the compound its pharmaceutically acceptable salt according to any one of the above (1) to (20) or (1-a).
(24) Use of the compound its pharmaceutically acceptable salt according to any one of the above (1) to (20) or (1-a) for treatment or prevention of a disease associated with ACC2.
(25) The compound or its pharmaceutically acceptable salt of any one of the above (1) to (20) or (1-a) for treatment or prevention of a disease associated with ACC2.
(1') A compound of Formula (I):

[Formula 23]

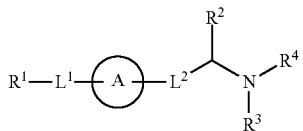

(I)

or its pharmaceutically acceptable salt,
wherein
R¹ is substituted or unsubstituted fused aromatic heterocyclyl, substituted or unsubstituted fused aromatic carbocyclyl, substituted or unsubstituted non-aromatic heterocyclyl, substituted or unsubstituted non-aromatic carbocyclyl, the group represented by Formula:

[Formula 24]

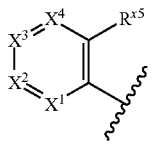

or substituted or unsubstituted 5-membered aromatic heterocyclyl,
$X^1$ is N or C($R^{x1}$),
$X^2$ is N or C($R^{x2}$),
$X^3$ is N or C($R^{x3}$),
$X^4$ is N or C($R^{x4}$),
each $R^{x1}$, $R^{x2}$, $R^{x3}$, and $R^{x4}$ is independently hydrogen, halogen, hydroxy, carboxy, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfanyl, substituted or unsubstituted alkynylsulfanyl, substituted or unsubstituted amino, substituted or unsubstituted carbamoyl, substituted or unsubstituted sulfamoyl, substituted or unsubstituted alkylcarbonyl, substituted or unsubstituted alkenylcarbonyl, substituted or unsubstituted alkynylcarbonyl, substituted or unsubstituted alkyloxycarbonyl, substituted or unsubstituted alkenyloxycarbonyl, substituted or unsubstituted alkynyloxycarbonyl, or substituted or unsubstituted sulfamoyl,
$R^{x5}$ is halogen, hydroxy, carboxy, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfanyl, substituted or unsubstituted alkynylsulfanyl, substituted or unsubstituted amino, substituted or unsubstituted carbamoyl, substituted or unsubstituted alkylcarbonyl, substituted or unsubstituted alkenylcarbonyl, substituted or unsubstituted alkynylcarbonyl, substituted or unsubstituted alkyloxycarbonyl, substituted or unsubstituted alkenyloxycarbonyl, substituted or unsubstituted alkynyloxycarbonyl, or substituted or unsubstituted sulfamoyl,
ring A is substituted or unsubstituted benzene, substituted or unsubstituted 4- to 6-membered non-aromatic carbocycle, substituted or unsubstituted 5- to 6-membered aromatic heterocycle, or substituted or unsubstituted 4- to 6-membered non-aromatic heterocycle,
-$L^1$- is —O—(CR⁶R⁷)m-,
-$L^2$- is —O—(CR⁶R⁷)n-, or —C(=O)—(CR⁶R⁷)n-,
each R⁶ is independently hydrogen, halogen, substituted or unsubstituted alkyl, substituted or unsubstituted alkenyl, or substituted or unsubstituted alkynyl,
each R⁷ is independently hydrogen, halogen, substituted or unsubstituted alkyl, substituted or unsubstituted alkenyl, or substituted or unsubstituted alkynyl, or R⁶ and R⁷ on the same carbon atom may be taken together with the carbon atom to form ring, or R² is taken together with either R⁶ or R⁷ to form ring,
each m is independently an integer of 0, 1, 2 or 3,
each n is independently an integer of 1, 2 or 3,
R² is substituted or unsubstituted alkyl,
R³ is hydrogen or substituted or unsubstituted alkyl,
R⁴ is substituted or unsubstituted alkylcarbonyl, substituted or unsubstituted alkenylcarbonyl, substituted or unsubstituted alkynylcarbonyl, substituted or unsubstituted non-aromatic carbocyclylcarbonyl, substituted or unsubstituted aromatic carbocyclylcarbonyl, substituted or unsubstituted non-aromatic heterocyclylcarbonyl, substituted or unsubstituted aromatic heterocyclylcarbonyl, substituted or unsubstituted alkyloxycarbonyl, substituted or unsubstituted alkenyloxycarbonyl, substituted or unsubstituted alkynyloxycarbonyl, substituted or unsubstituted non-aromatic carbocyclyloxycarbonyl, substituted or unsubstituted aromatic carbocyclyloxycarbonyl, substituted or unsubstituted non-aromatic heterocyclyloxycarbonyl, substituted or unsubstituted aromatic heterocyclyloxycarbonyl, non-substituted or unsubstituted carbamoyl;
provided that the following compounds are excluded,
(i) the compounds wherein R¹ is a substituent selected from Substituent group α (Substituent group α: unsubstituted phenyl and substituted or unsubstituted aromatic heterocyclyl) and quinolinyl substituted with two alkyloxy groups, ring A is substituted pyrrolidine, and -L²- is —C(=O)—(CR⁶R⁷)n-,
(ii) the compounds wherein ring A is nitrogen-containing non-aromatic heterocycle, -L²- is —C(=O)—(CR⁶R⁷)n-, and the atom on ring A bonded to -L²- is nitrogen, and
(iii) the following compounds:

[Formula 25]

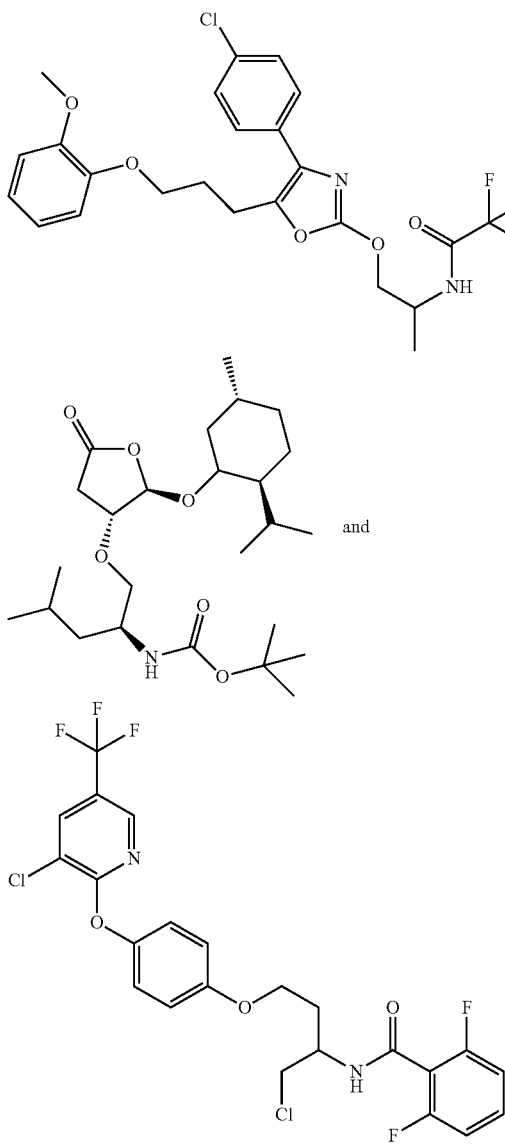

and (2') The compound or its pharmaceutically acceptable salt according to the above (1'), wherein ring A is substituted or unsubstituted cyclobutane, substituted or unsubstituted cyclopentane, substituted or unsubstituted azetidine, substituted or unsubstituted oxetane, substituted or unsubstituted thietane, substituted or unsubstituted pyrrolidine, substituted or unsubstituted tetrahydrofuran, substituted or unsubstituted thiolane, substituted or unsubstituted piperidine, substituted or unsubstituted morpholine, substituted or unsubstituted tetrahydropyran, substituted or unsubstituted tetrahydrothiopyran, substituted or unsubstituted pyrrole, substituted or unsubstituted furan, substituted or unsubstituted thiophene, substituted or unsubstituted imidazole, substituted or unsubstituted pyrazole, substituted or unsubstituted oxazole, substituted or unsubstituted isoxazole, substituted or unsubstituted thiazole, substituted or unsubstituted isothiazole, substituted or unsubstituted oxadiazole, substituted or unsubstituted thiadiazole, substituted or unsubstituted pyridine, substituted or unsubstituted pyrimidine, substituted or unsubstituted pyrazine or substituted or unsubstituted pyridazine.

(3') The compound or its pharmaceutically acceptable salt according to the above (1'), wherein ring A is substituted or unsubstituted cyclobutane, substituted or unsubstituted cyclohexane substituted or unsubstituted benzene, substituted or unsubstituted piperidine, substituted or unsubstituted pyrazine, substituted or unsubstituted pyrimidine, or substituted or unsubstituted thiazole.

(4') The compound or its pharmaceutically acceptable salt according to any one of the above (1')~(3'), wherein R¹ is substituted or unsubstituted benzothiazolyl, substituted or unsubstituted benzoxazolyl, substituted or unsubstituted benzimidazolyl, substituted or unsubstituted indolyl, substituted or unsubstituted indazolyl, substituted or unsubstituted isoquinolyl, substituted or unsubstituted quinoxalinyl, substituted or unsubstituted naphtalenyl, substituted or unsubstituted aziridinyl, substituted or unsubstituted oxyranyl, substituted or unsubstituted thiiranyl, substituted or unsubstituted azetidinyl, substituted or unsubstituted oxetanyl, substituted or unsubstituted thietanyl, substituted or unsubstituted pirrolidinyl, substituted or unsubstituted tetrahydrofuranyl, substituted or unsubstituted tetrahydrothiophenyl, substituted or unsubstituted piperidinyl, substituted or unsubstituted piperidino, substituted or unsubstituted tetrahydropyranyl, substituted or unsubstituted tetrahydropyranyl, substituted or unsubstituted piperazinyl, substituted or unsubstituted morpholinyl, substituted or unsubstituted morpholino, substituted or unsubstituted thiomorpholinyl, substituted or unsubstituted thiomorpholino, substituted or unsubstituted cyclobutanyl, the group represented by Formula:

[Formula 26]

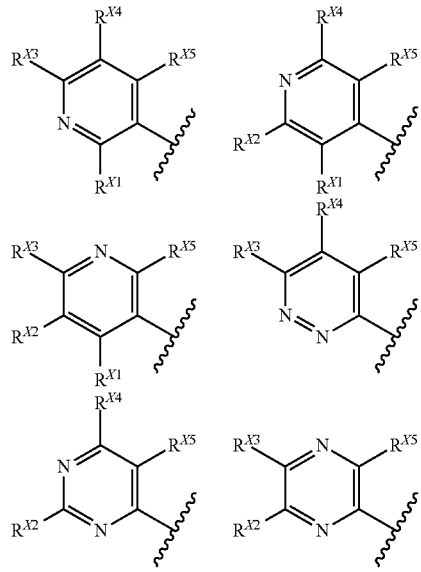

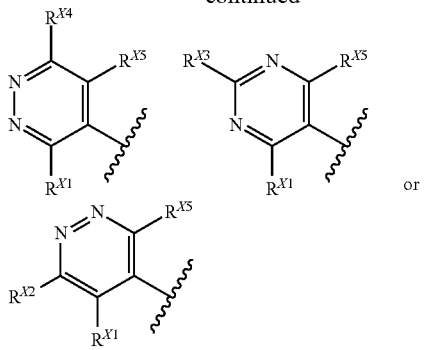

or substituted or unsubstituted 5-membered aromatic heterocyclyl.

(5') The compound or its pharmaceutically acceptable salt according to any one of the above (1')~(3'), wherein $R^1$ is substituted or unsubstituted naphtalenyl, substituted or unsubstituted pyrimidinyl, substituted or unsubstituted dihydroindenyl, substituted or unsubstituted dihydrobenzofuranyl, substituted or unsubstituted indolinyl, substituted or unsubstituted tetrahydroisoquinolinyl, substituted or unsubstituted benzoxazolyl, substituted or unsubstituted benzothiazolyl, substituted or unsubstituted benzopyrazolyl, substituted or unsubstituted benzoisothiazolyl, or substituted or unsubstituted oxazolinyl.

(6') The compound or its pharmaceutically acceptable salt according to any one of the above (1')~(3'), wherein $R^1$ is substituted or unsubstituted naphtalenyl, substituted or unsubstituted dihydroindenyl, substituted or unsubstituted dihydrobenzofuranyl, substituted or unsubstituted indolinyl, substituted or unsubstituted tetrahydroisoquinolinyl, substituted or unsubstituted benzoxazolyl, substituted or unsubstituted benzothiazolyl, substituted or unsubstituted benzopyrazolyl, substituted or unsubstituted benzoisothiazolyl, substituted or unsubstituted oxazolinyl, or the group represented by Formula:

[Formula 27]

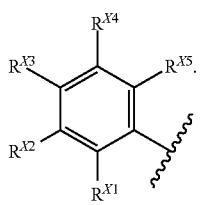

(7') The compound or its pharmaceutically acceptable salt according to any one of the above (1')~(3'), wherein $R^1$ is substituted or unsubstituted benzothiazolyl, substituted or unsubstituted benzoxazolyl, substituted or unsubstituted benzoimidazolyl, substituted or unsubstituted benzopyrazolyl, substituted or unsubstituted thiazolopyridinyl, substituted or unsubstituted indolyl, substituted or unsubstituted indazolyl, substituted or unsubstituted isoquinolyl, substituted or unsubstituted quinazolinyl, or substituted or unsubstituted quinoxalinyl.

(8') The compound or its pharmaceutically acceptable salt according to any one of the above (1')~(3'), wherein $R^1$ is the group represented by Formula:

[Formula 28]

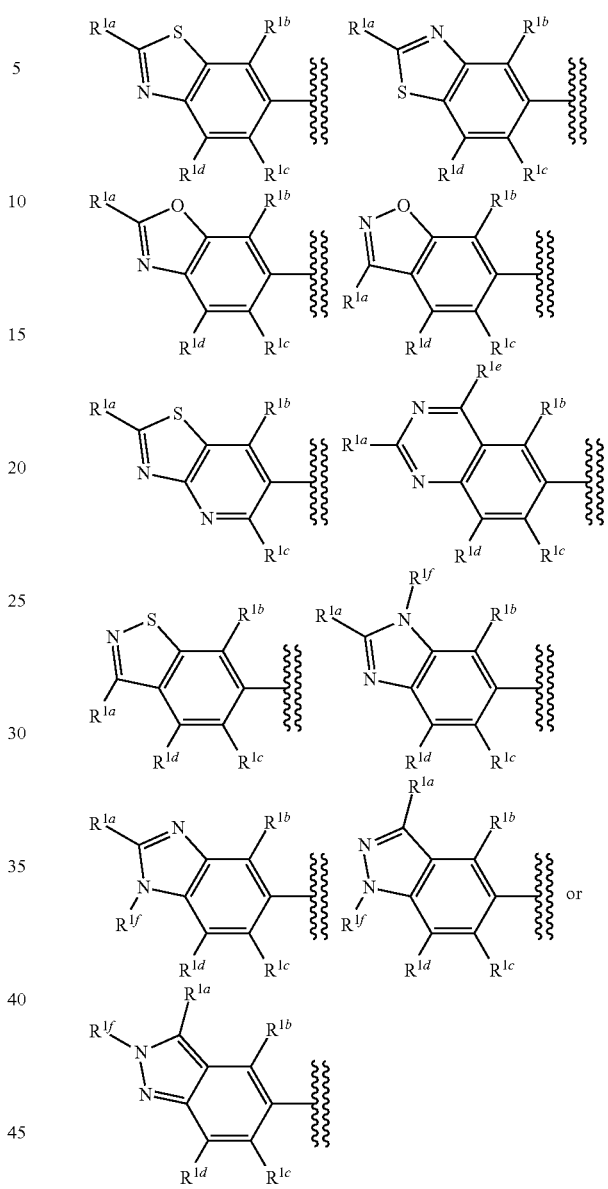

wherein
each $R^{1a}$, $R^{1b}$, $R^{1c}$, $R^{1d}$, and $R^{1e}$ is independently hydrogen, halogen, hydroxy, carboxy, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfanyl, substituted or unsubstituted alkynylsulfanyl, substituted or unsubstituted amino, substituted or unsubstituted carbamoyl, substituted or unsubstituted sulfamoyl, substituted or unsubstituted alkylcarbonyl, substituted or unsubstituted alkenylcarbonyl, substituted or unsubstituted alkynylcarbonyl, substituted or unsubstituted alkyloxycarbonyl, substituted or unsubstituted alkenyloxycarbonyl, or substituted or unsubstituted alkynyloxycarbonyl, $R^{1f}$ is hydrogen, substituted or unsubstituted alkyl, substituted or unsubstituted alkenyl, substituted or unsubstituted alkynyl, substituted or unsubstituted alkylcarbonyl, substituted or unsubstituted alkenylcarbonyl, or substituted or unsubstituted alkynylcarbonyl.

(9') The compound or its pharmaceutically acceptable salt according to any one of the above (1')~(3'), wherein $R^{1a}$ is substituted or unsubstituted alkyl, or substituted or unsubstituted alkyloxy.

(10') The compound or its pharmaceutically acceptable salt according to any one of the above (1')~(3'), wherein $R^4$ is substituted or unsubstituted alkylcarbonyl.

(11') The compound or its pharmaceutically acceptable salt according to the above (10'), $R^4$ is methylcarbonyl.

(12') The compound or its pharmaceutically acceptable salt according to any one of the above (1')~(9'), wherein $R^4$ is substituted or unsubstituted non-aromatic carbocyclylcarbonyl, substituted or unsubstituted non-aromatic heterocyclylcarbonyl, or substituted or unsubstituted aromatic carbocyclylcarbonyl, or substituted or unsubstituted carbamoyl.

(13') The compound or its pharmaceutically acceptable salt according to any one of the above (1')~(12'), wherein m is 0.

(14') The compound or its pharmaceutically acceptable salt according to any one of the above (1')~(13'), wherein -$L^2$- is —O—$(CR^6R^7)n$-.

(15') The compound or its pharmaceutically acceptable salt according to any one of the above (1')~(14'), wherein n is 1.

(16') The compound or its pharmaceutically acceptable salt according to any one of the above (1')~(14'), wherein -$L^2$- is —O—$(CR^6R^7)$—, $R^2$ is taken together with either $R^6$ or $R^7$ to form ring.

(17') The compound or its pharmaceutically acceptable salt according to any one of the above (1')~(16'), wherein formula (I) is Formula:

[Formula 29]

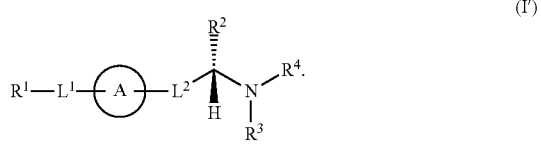

(I')

(18') The compound or its pharmaceutically acceptable salt according to any one of the above (1')~(16'), wherein $R^1$ is substituted or unsubstituted fused aromatic heterocyclyl, substituted or unsubstituted fused aromatic carbocyclyl, substituted or unsubstituted non-aromatic heterocyclyl, substituted or unsubstituted non-aromatic carbocyclyl, the group represented by Formula:

[Formula 30]

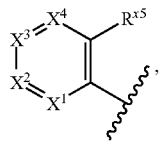

or substituted or unsubstituted 5-membered aromatic heterocyclyl, provided that $R^1$ is not substituted or unsubstituted fused aromatic heterocyclyl represented by Formula:

[Formula 31]

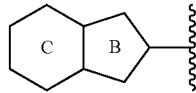

wherein ring B is 5-membered ring, and ring C is 6-membered ring.

(19') A pharmaceutical composition, which comprises a compound or its pharmaceutically acceptable salt according to any one of the above (1') to (18').

(20') A pharmaceutical composition according to the above (19') for treatment or prevention of a disease associated with ACC2.

(21') A method for treatment or prevention of a disease associated with ACC2 characterized by administering the compound its pharmaceutically acceptable salt according to any one of the above (1') to (18').

(22') Use of the compound its pharmaceutically acceptable salt according to any one of the above (1') to (18') for treatment or prevention of a disease associated with ACC2.

(23') The compound or its pharmaceutically acceptable salt of any one of the above (1')~(18') for treatment or prevention of a disease associated with ACC2.

Effect of the Invention

The compound of this invention has ACC2 inhibitory activity. A pharmaceutical composition comprising the compound of this invention is very useful as a medicine for preventing or treating disease associated with ACC2, e.g. metabolic syndrome, obesity, diabetes, insulin resistance, abnormal glucose tolerance, diabetic peripheral neuropathy, diabetic nephrophathy, diabetic retinal disease, diabetic macroangiopathy, hyperlipidemia, hypertension, cardiovascular illness, arterial sclerosis, atherosclerotic cardiovascular disease, cardiac arrest, cardiac infarction, infectious disease, neoplasm and the like (Journal of Cellular Biochemistry, (2006), vol. 99, 1476-1488, EXPERT OPINION ON THERAPEUTIC TARGETS, (2005), Vol. 9, 267-281, International publication No. 2005/108370, Japanese Patent Application publication No. 2009-196966, Japanese Patent Application Publication No. 2010-081894, Japanese Patent Application Publication No. 2009-502785).

MODE FOR CARRYING OUT THE INVENTION

Terms used in the present description are explained below. Each term has the same meaning alone or together with other terms in this description.

"Halogen" includes fluorine atom, chlorine atom, bromine atom, and iodine atom. Especially preferred is fluorine atom, or chlorine atom.

"Alkyl" includes C1 to C15, preferably C1 to C10, more preferably C1 to C6, even more preferably C1 to C4 linear or branched alkyl group. Examples include methyl, ethyl, n-propyl, isopropyl, n-butyl, isobutyl, sec-butyl, tert-butyl, n-pentyl, isopentyl, neopentyl, n-hexyl, isohexyl, n-heptyl, isoheptyl, n-octyl, isooctyl, n-nonyl, n-decyl and the like.

A preferable embodiment of "alkyl" includes methyl, ethyl, n-propyl, isopropyl, n-butyl, isobutyl, sec-butyl, tert-butyl, n-pentyl and the like. More preferably is methyl, ethyl, n-propyl, isopropyl, tert-butyl and the like.

A preferable embodiment of "alkyl" of $R^2$ includes methyl and the like.

"Alkyloxy" means the above "alkyl" bonded to the oxygen atom. Examples are methyloxy, ethyloxy, n-propyloxy, isopropyloxy, n-butyloxy, tert-butyloxy, isobutyloxy, sec-butyloxy, pentyloxy, isopentyloxy, hexyloxy and the like. A preferable embodiment of "alkyloxy" includes methyloxy, ethyloxy, n-propyloxy, isopropyloxy, tert-butyloxy and the like.

"Alkyloxycarbonyl" means a carbonyl group to which the above "alkyloxy" is bonded. Examples are methyloxycarbonyl, ethyloxycarbonyl, propyloxycarbonyl, isopropyloxycarbonyl, tert-butyloxycarbonyl, isobutyloxycarbonyl, sec-butyloxycarbonyl, pentyloxycarbonyl, isopentyloxycarbonyl, hexyloxycarbonyl and the like. A more preferable embodiment of "alkyloxycarbonyl" includes methyloxycarbonyl, ethyloxycarbonyl, propyloxycarbonyl and the like.

Especially preferable embodiment of "alkyloxycarbonyl" of $R^4$ includes tert-butyloxycarbonyl and the like.

"Alkenyl" includes linear or branched alkenyl containing one or more double bond at any position having C2 to C15, preferable C2 to C10, more preferably C2 to C6, even more preferably C2 to C4. Examples include vinyl, allyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl, decenyl, undecenyl, dodecenyl, toridecenyl, tetradecenyl, pentadecenyl and the like.

A preferable embodiment of "alkenyl" includes vinyl, allyl, propenyl, isopropenyl, butenyl.

"Alkynyl" includes linear or branched alkynyl containing one or more triple bond at any position having C2 to C15, preferably C2 to C10, more preferably C2 to C6, even more preferably C2 to C4. Examples include ethynyl, propynyl, buthynyl, pentynyl, hexynyl, heptynyl, octynyl, nonynyl, decynyl and the like. Alkynyl can have double bond(s) at any arbitrary position(s).

A preferable embodiment of "alkynyl" includes ethynyl, propynyl, butynyl, pentynyl and the like.

"Alkenyloxy" means the above "alkenyl" bonded to the oxygen atom. Examples include vinyloxy, allyloxy, 1-propenyloxy, 2-butenyloxy, 2-pentenyloxy, 2-hexenyloxy, 2-heptenyloxy, 2-octenyloxy and the like.

"Alkynyloxy" means the above "alkynyl" bonded to the oxygen atom. Examples include ethynyloxy, 1-propynyloxy, 2-propynyloxy, 2-buthynyloxy, 2-pentynyloxy, 2-hexynyloxy, 2-heptynyloxy, 2-octynyloxy and the like.

"Alkylsulfanyl" means a sulfanyl group the hydrogen atom of which is replaced by the above "alkyl". Examples are methylsulfanyl, ethylsulfanyl, n-propylsulfanyl, isopropylsulfanyl, n-butylsulfanyl, tert-butylsulfanyl, isobutylsulfanyl, sec-butylsulfanyl, pentylsulfanyl, isopentylsulfanyl, hexylsulfanyl and the like. A preferable embodiment of "alkylsulfanyl" includes methylsulfanyl, ethylsulfanyl, n-propylsulfanyl, isopropylsulfanyl, tert-butylsulfanyl.

"Alkenylsulfanyl" means a sulfanyl group the hydrogen atom of which is replaced by the above "alkenyl". Examples include vinylsulfanyl, allylsulfanyl, 1-propenylsulfanyl, 2-butenylsulfanyl, 2-pentenylsulfanyl, 2-hexenylsulfanyl, 2-heptenylsulfanyl, 2-octenylsulfanyl and the like.

"Alkynylsulfanyl" means a sulfanyl group the hydrogen atom of which is replaced by the above "alkynyl". Examples include ethynylsulfanyl, 1-propynylsulfanyl, 2-propynylsulfanyl, 2-butynylsulfanyl, 2-pentynylsulfanyl, 2-hexynylsulfanyl, 2-heptynylsulfanyl, 2-octynylsulfanyl and the like.

"Alkylcarbonyl" means a carbonyl group to which above "alkyl" is bonded. Examples include acetyl, ethylcarbonyl, propylcarbonyl, isopropylcarbonyl, tert-butylcarbonyl, isobutylcarbonyl, sec-butylcarbonyl, pentylcarbonyl, isopentylcarbonyl, hexylcarbonyl and the like. A preferable embodiment of "alkylcarbonyl" includes methylcarbonyl, ethylcarbonyl, n-propylcarbonyl and the like.

Especially preferable embodiment of "alkylcarbonyl" of $R^4$ includes methyl carbonyl and the like.

"Alkenylcarbonyl" means a carbonyl group to which above "alkenyl" is bonded. Examples include ethylenylcarbonyl, propenylcarbonyl and the like.

"Alkynylcarbonyl" means a carbonyl group to which above "alkynyl" is bonded. Examples include ethynylcarbonyl, propynylcarbonyl and the like.

"Cycloalkyl" means C3 to C8 cyclic saturated hydrocarbon group and the cyclic saturated hydrocarbon group fused with one or two C3 to C8 cyclic group(s). Examples of C3 to C8 cyclic saturated carbocyclyl include cyclopropyl, cyclobutyl, cyclopentyl, cyclohexyl, cycloheptyl, cyclooctyl and the like. Especially preferable examples include C3 to C6 cycloalkyl, or C5 to C6 cycloalkyl. Furthermore, C3 cycloalkyl is preferable.

The 3- to 8-membered ring fused with C3 to C8 cyclic saturated hydrocarbons group includes cycloalkane ring (e.g.: cyclohexane ring, cyclopentane ring etc.), cycloalkene ring (e.g.: cyclohexene ring, cyclopentene ring etc.), non-aromatic heterocycle (e.g.: piperidine ring, piperazine ring, morpholine ring etc.). At the above ring, the bond(s) can be attached to C3 to C8 cyclic saturated hydrocarbon group.

For example, the following groups are also exemplified as a cycloalkyl, and included in cycloalkyl. These groups can be substituted at any arbitrary position(s). When cycloalkyl is substituted, the substituent(s) on the cycloalkyl can be substituted on either C3 to C8 cyclic saturated hydrocarbon group or 3- to 8-membered ring fused C3 to C8 cyclic saturated hydrocarbon group.

[Formula 32]

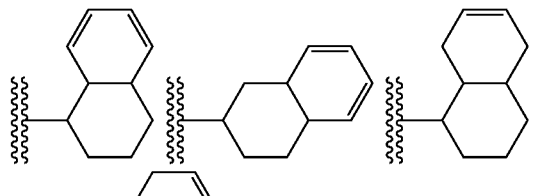

[Formula 33]

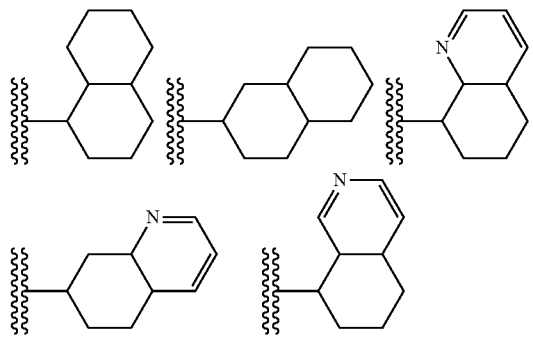

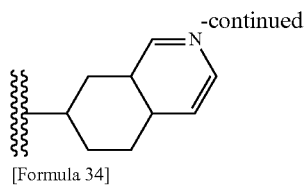

[Formula 34]

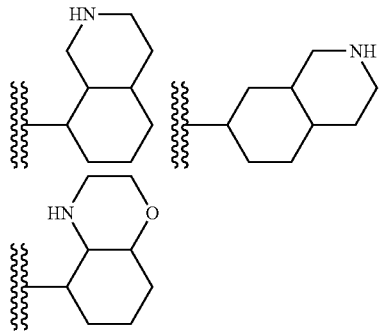

Furthermore, "cycloalkyl" includes a bridged group or a group formed Spiro ring as follows.

[Formula 35]

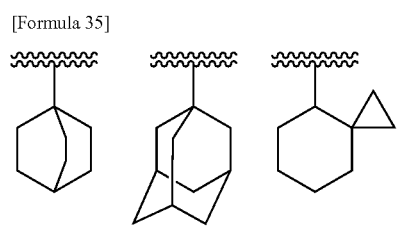

"Cycloalkyl substituted with carboxy" means the above "cycloalkyl" substituted with one or more carboxy.

"Cycloalkenyl" means C3 to C8 cyclic unsaturated aliphatic hydrocarbon group and the cyclic unsaturated aliphatic hydrocarbon group fused with one or two 3- or 8-membered cycle(s). "C3 to C8 cyclic unsaturated aliphatic hydrocarbon group" preferably means that C3 to C8 cyclic unsaturated aliphatic hydrocarbon group has 1 to 3 double bond(s) between carbon atom and carbon atom in the ring. Specifically, preferred is cyclopropenyl, cyclobutenyl, cyclopentenyl, cyclohexenyl, cycloheptenyl, cyclohexadienyl and the like. Especially preferred is C3 to C6 cycloalkenyl or C5 or C6 cycloalkenyl.

The ring fused with C3 to C8 cyclic unsaturated aliphatic hydrocarbon group includes carbocycle (aromatic carbocycle (e.g.: benzene ring, naphthalene ring etc.), cycloalkane ring (e.g.: cyclohexane ring, cyclopentane ring etc.), cycloalkene ring (e.g.: cyclohexene ring, cyclopentene ring etc.) and the like), heterocycle (aromatic heterocycle (pyridine ring, pyrimidine ring, pyrrole ring, imidazole ring etc.), non-aromatic heterocycle (e.g.: piperidine ring, piperazine ring, morpholine ring etc.)).

At the above ring, the bond(s) can be attached to C3 to C8 cyclic unsaturated aliphatic hydrocarbon group.

For example, the following groups are also exemplified as a cycloalkenyl and include in cycloalkenyl. These groups can be substituted at any arbitrary position(s). When cycloalkenyl is substituted, the substituent(s) on the cycloalkenyl can be substituted on either C3 to C8 cyclic unsaturated aliphatic hydrocarbon group or 3- to 8-membered ring fused C3 to C8 cyclic unsaturated aliphatic hydrocarbon group.

[Formula 36]

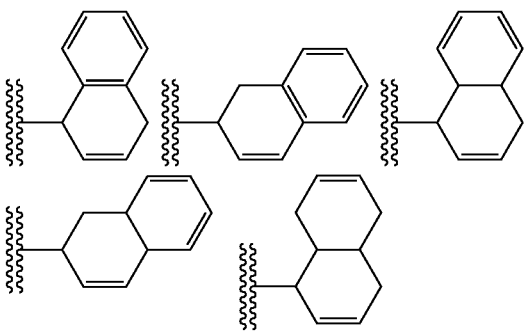

[Formula 37]

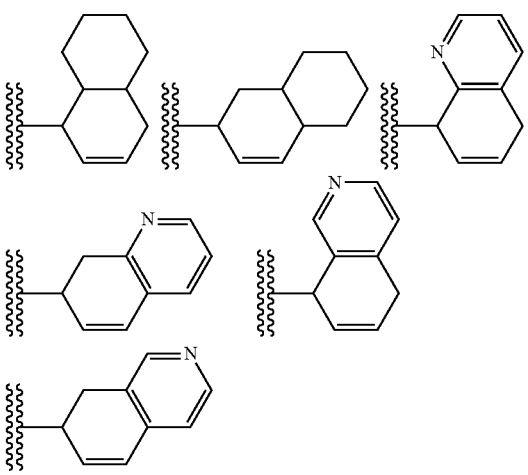

[Formula 38]

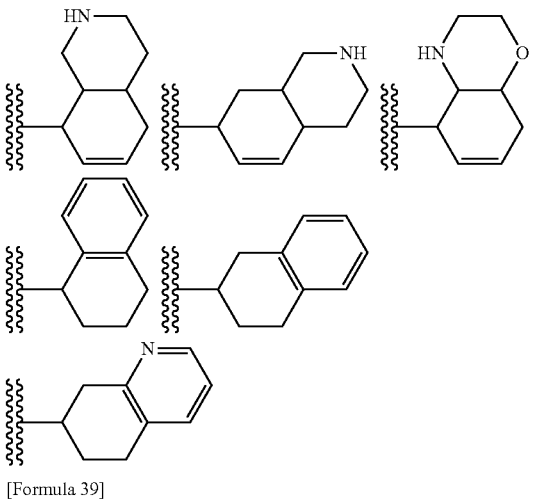

[Formula 39]

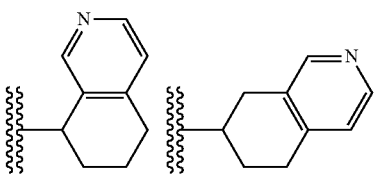

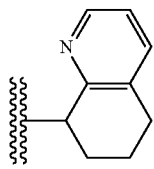

In addition, the "cycloalkenyl" also includes a group to form a spiro ring as follows:

[Formula 40]

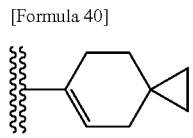

"Non-aromatic carbocyclyl" includes above "cycloalkyl" and "cycloalkenyl".

"Aromatic carbocyclyl" means monocyclic or polycyclic aromatic carbocyclyl and the monocyclic or polycyclic aromatic carbocyclyl fused with one or two 3- to 8-membered ring. Examples of "monocyclic or polycyclic aromatic carbocyclyl include phenyl, naphthyl, anthryl, phenanthryl. Especially phenyl is preferred.

The ring fused with monocyclic or polycyclic includes non-aromatic carbocycle (e.g.: cycloalkane ring (e.g.: cyclohexane ring, cyclopentane ring etc.), cycloalkene ring (e.g.: cyclohexene ring, cyclopentene ring etc.) and the like), non-aromatic heterocycle (e.g.: piperidine ring, piperazine ring, morpholine ring etc.).

At the above ring, the bond(s) can be attached to monocyclic or polycyclic aromatic carbocycle.

For example, the following groups are also exemplified as an aromatic carbocyclyl and included in aromatic carbocyclyl. These groups can be substituted at any arbitrary position(s). When aromatic carbocyclyl is substituted, the substituent(s) on the aromatic carbocyclyl group can be substituted on either monocyclic or polycyclic aromatic carbocyclyl or 3- to 8-membered ring fused monocyclic or polycyclic aromatic carbocyclyl group.

[Formula 41]

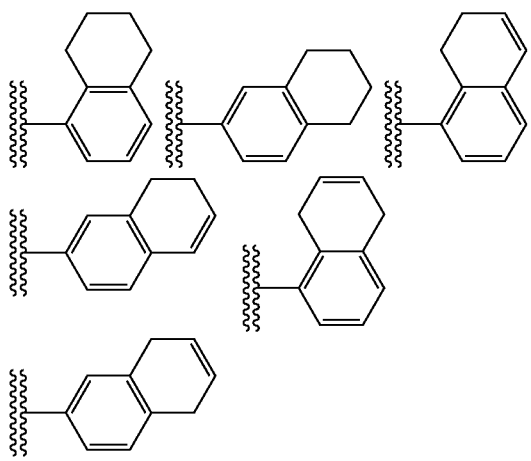

[Formula 42]

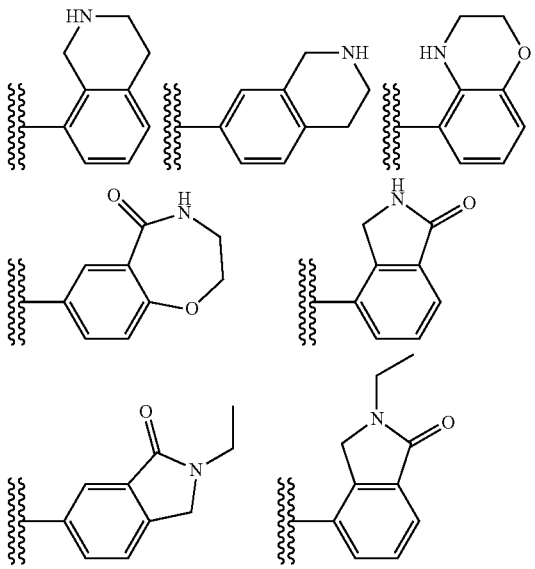

"Fused aromatic carbocyclyl" means polycyclic aromatic carbocyclyl, monocyclic or polycyclic aromatic carbocyclyl fused with one or two 3- to 8-membered ring. Examples of monocyclic or polycyclic aromatic carbocyclyl include phenyl, naphthyl, anthryl, phenanthryl. Especially, preferable example is phenyl.

The ring fused with monocyclic or polycyclic includes non-aromatic carbocycle (e.g.: cycloalkane ring (e.g.: cyclohexane ring, cyclopentane ring etc.), cycloalkene ring (e.g.: cyclohexene ring, cyclopentene ring etc.) and the like), non-aromatic heterocycle (e.g.: piperidine ring, piperazine ring, morpholine ring etc.).

At the above ring, the bond(s) can be attached to monocyclic or polycyclic aromatic carbocycle.

For example, the following groups are also exemplified as an aromatic carbocyclyl and included in aromatic carbocyclyl. These groups can be substituted at any arbitrary position(s). When aromatic carbocyclyl is substituted, the substituent(s) on the aromatic carbocyclyl group can be substituted on either monocyclic or polycyclic aromatic carbocyclyl or 3- to 8-membered ring fused monocyclic or polycyclic aromatic carbocyclyl group.

For example, the following groups are exemplified as an aromatic carbocyclyl or fused aromatic carbocyclyl, and included in aromatic carbocyclyl or fused aromatic carbocyclyl. These groups are optionally substituted at any arbitrary replaceable position. When aromatic carbocyclyl or fused aromatic carbocyclyl is substituted, the substituent(s) on the aromatic carbocyclyl or the fused aromatic carbocyclyl may be substituted on either monocyclic or fused aromatic carbocyclyl or 3- to 8-membered ring fused monocyclic or fused aromatic carbocyclyl.

[Formula 43]

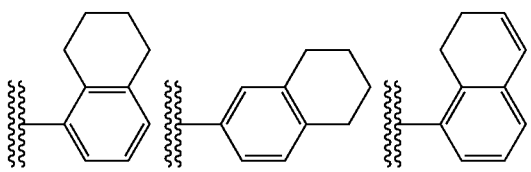

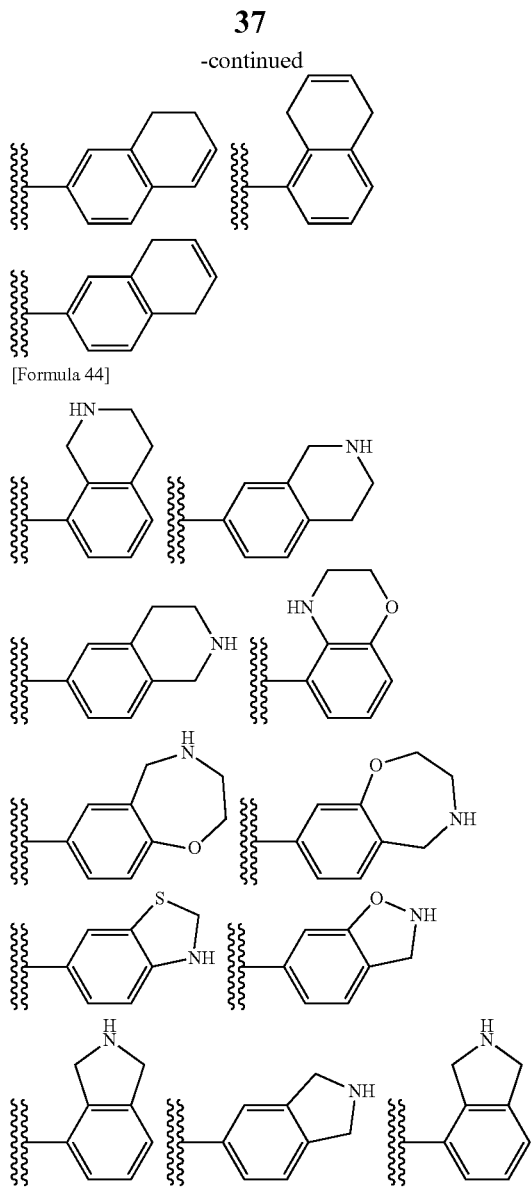

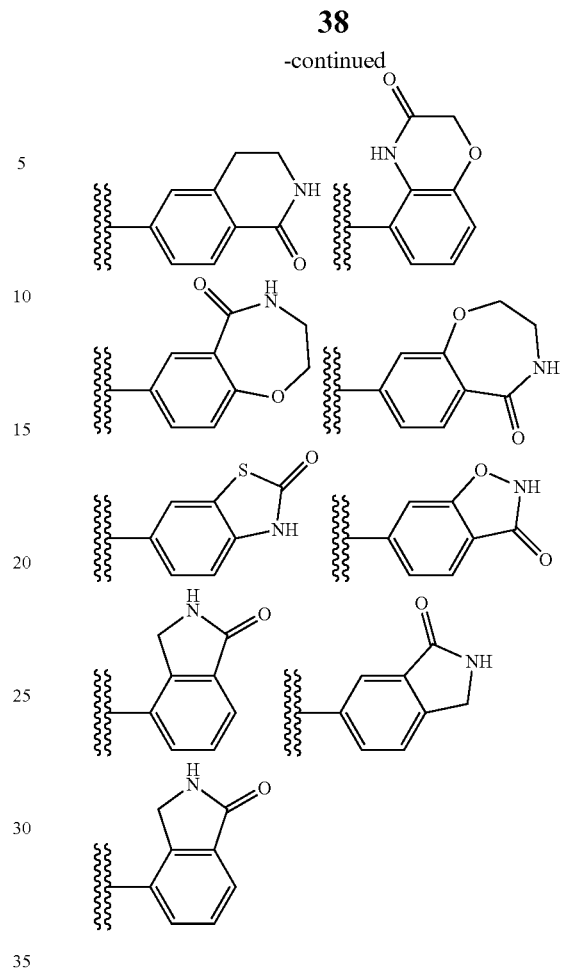

"Substituted aromatic carbocyclyl" includes an aromatic carbocyclyl substituted with oxo. "Substituted fused aromatic carbocyclyl" include a fused aromatic carbocyclyl substituted with oxo. "Aromatic carbocyclyl substituted with oxo" and "fused aromatic carbocyclyl substituted with oxo" means that two hydrogen atom on 3- to 8-membered ring fused monocyclic or polycyclic aromatic carbocyclyl constituting aromatic carbocyclyl are substituted with =O group. As a "aromatic carbocyclyl substituted with oxo" and "fused aromatic carbocyclyl substituted with oxo", the following formula:

[Formula 45]

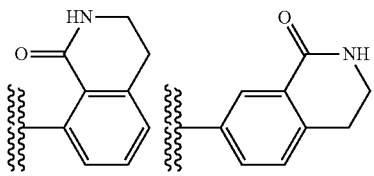

are exemplified.

"Aromatic heterocyclyl" means monocyclic or polycyclic aromatic heterocyclyl containing one or more heteroatom(s) arbitrarily selected from O, S and N on the ring or the monocyclic or polycyclic aromatic heterocyclyl with one or two 3- to 8-membered ring, and includes "monocyclic aromatic heterocyclyl" and "fused aromatic heterocyclyl".

Especially preferable examples of "monocyclic aromatic heterocyclyl" are 5- or 6-membered aromatic heterocyclyl. For example, pyrrolyl, imidazolyl, pyrazolyl, pyridyl, pyridadinyl, pyrimidinyl, pyrazinyl, triazoryl, triazinyl, tetrazolyl, isooxazolyl, oxazolyl, oxadiazolyl, isothiazolyl, thiazolyl, thiadiazolyl, furyl, thienyl and the like are exemplified.

Especially preferable examples of "fused aromatic heterocyclyl" are aromatic heterocyclyl fused with 5- or 6-membered ring. Examples include bicyclic aromatic heterocyclyl: e.g., indolyl, isoindolyl, indazolyl, indolizinyl, quinolinyl, isoquinolinyl, cinnolinyl, phthalazinyl, quinazolinyl, naphthylidinyl, quinoxalinyl, purinyl, pteridinyl, benzimidazolyl, benzisooxazolyl, benzoxazolyl, benzoxadiazoryl, benzisothiazolyl, benzothiazolyl, benzothiadiazolyl, benzofuryl, isobenzofuryl, benzothienyl, benzotriazoryl, imidazopyridyl, triazolopyridyl, imidazothiazolyl, pyrazinopyridazinyl, oxazolopyridyl, thiazolopyridyl; and tricyclic aromatic heterocyclyl: carbazolyl, acridinyl, xanthenyl, phenothiadinyl, phenoxathiinyl, phenoxadinyl, dibenzofuryl. When "aromatic heterocyclyl" is fused aromatic heterocyclyl, the bond(s) may be attached to any ring.

As a ring fused with monocyclic or fused aromatic heterocyclyl, for example, cycloalkane ring (e.g.: cyclohexane ring, cyclopentane ring etc.), cycloalkene ring (e.g.:

cyclohexene ring, cyclopentene ring etc.), non-aromatic heterocycle (e.g.: piperidine ring, piperazine ring, morpholine ring etc.) and the like are exemplified. The bond(s) can be attached to monocyclic or fused aromatic heterocyclyl containing one or more heteroatom(s) arbitrarily selected from O, S and N on the ring.

For example, the following groups include also aromatic heterocyclyl. These groups can be substituted at any arbitrary replaceable position(s). When aromatic heterocyclyl is substituted, the substituent(s) on the aromatic heterocyclyl may be substituted on either monocyclic or fused aromatic heterocyclyl or 3- to 8-membered ring fused with monocyclic or fused aromatic heterocyclyl group.

[Formula 46]

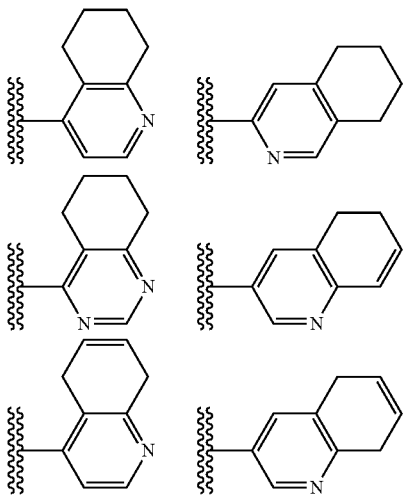

[Formula 47]

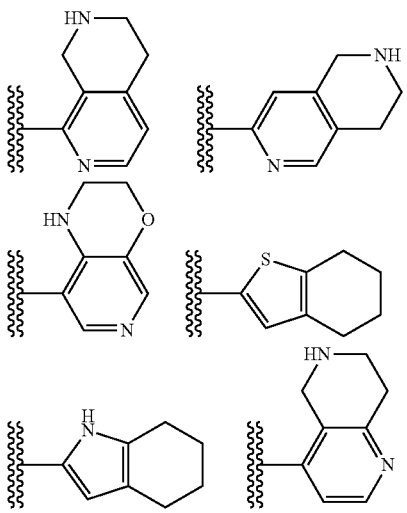

Substituted aromatic heterocyclyl includes aromatic heterocyclyl substituted with oxo. "Aromatic heterocyclyl substituted with oxo" means that two hydrogen atoms bonded to the carbon atom on 3- to 8-membered ring fused monocyclic or polycyclic aromatic heterocycle constituting aromatic heterocyclyl are substituted with =O group. As a "aromatic heterocyclyl substituted with oxo" and "fused aromatic heterocyclyl substituted with oxo", the following formula:

[Formula 48]

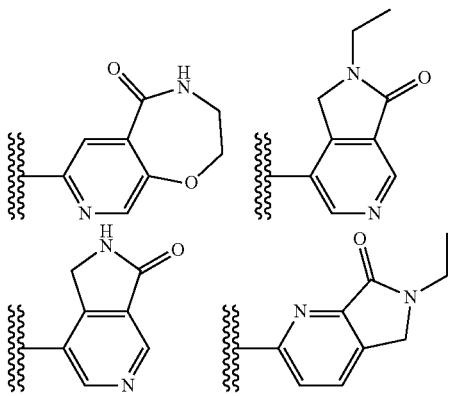

are exemplified.

Especially preferable embodiments of "fused aromatic carbocycly" of $R^1$ include tetrabenzooxazepinyl, tetrahydroisoquinolinyl, benzothiazolyl, dihydrobenzothiazolyl, dihydrobenzoisoxazolyl and the like.

"Non-aromatic heterocyclyl" means a monocyclic non-aromatic heterocyclyl containing one or more heteroatom(s) arbitrarily selected from O, S and N on the ring and the monocyclic non-aromatic heterocyclyl fused with one or two 3- to 8-membered cyclic group(s) (polycyclic non-aromatic heterocyclyl group(s)).

Preferable examples of "monocyclic non-aromatic heterocyclyl" are a monocyclic non-aromatic heterocyclyl group containing 1 to 4 heteroatom(s) arbitrarily selected from O, S and N on the ring. Specifically, dioxanyl, thiiranyl, oxiranyl, oxathiolanyl, azetidinyl, thianyl, pyrrolidinyl, pyrrolinyl, imidazolidinyl, imidazolinyl, pyrazolidinyl, pyrazolinyl, piperidyl, piperidino, piperazinyl, piperadino, morpholinyl, morpholino, oxadiazinyl, dihydropyridyl, thiomorpholinyl, thiomorpholino, tetrahydrofuryl, tetrahydropyranyl, tetrahydrothiazolyl, tetrahydroisothiazolyl, oxazolidyl, thiazolidyl, oxetanyl, thiazolidinyl, tetrahydropyridyl, dihydrothiazolyl, dihydrooxazinyl, hexahydroazepinyl, tetrahydrodiazepinyl, tetrahydropyridazinyl, hexahydropyrimidinyl, dioxolanyl, dioxazinyl, aziridinyl, dioxolinyl, oxepanyl, thiolanyl, thiazinyl, thiazinyl and the like are exemplified.

As a ring fused with monocyclic non-aromatic heterocyclyl containing one or more heteroatom(s) arbitrarily selected from O, S and N on the ring, for example, carbocycle (aromatic hydrocarbon ring (e.g.: benzene ring, naphthalene ring etc.), cycloalkane ring (e.g.: cyclohexane ring, cyclopentane ring etc.), cycloalkene ring (e.g.: cyclohexene ring, cyclopenten ring etc.) and the like), heterocycle (aromatic heterocycle (pyridine ring, pyrimidine ring, pyrrole ring, imidazole ring etc), non-aromatic heterocycle (e.g.: piperidine ring, piperazine ring, morpholine ring etc.).

As a polycyclic non-aromatic heterocyclyl, for example, indolinyl, isoindolinyl, chromanyl, isochromanyl and the like are exemplified.

When "non-aromatic heterocyclyl" is polycyclic non-aromatic heterocyclyl, the bond(s) can be attached to non-aromatic heterocyclyl containing one or more heteroatom(s) arbitrarily selected from O, S and N on the ring. For example, the following groups include also non-aromatic heterocyclyl. These groups can be substituted at any arbitrary position(s). When non-aromatic heterocyclyl is substituted, the substituent(s) on the non-aromatic heterocyclyl can be substituted on either monocyclic or polycyclic non-aromatic heterocyclyl or 3- to 8-membered fused monocyclic or polycyclic non-aromatic heterocyclyl group.

[Formula 49]

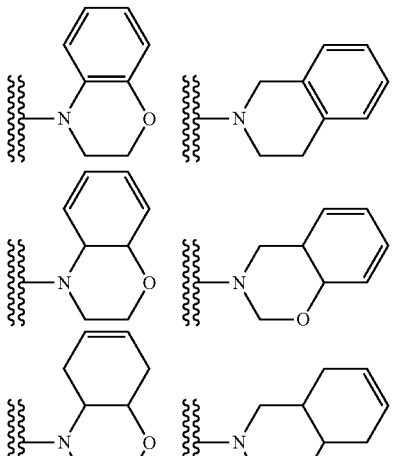

[Formula 50]

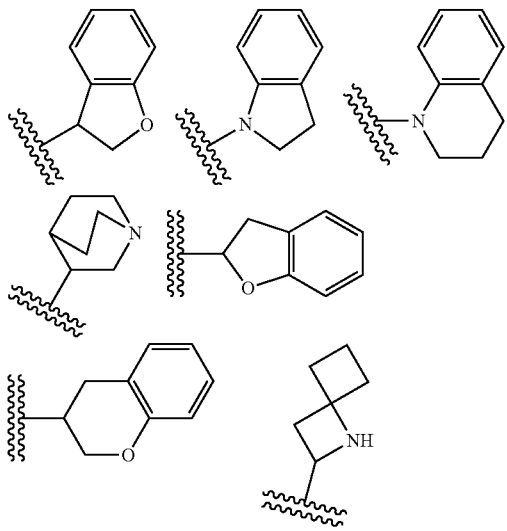

[Formula 51]

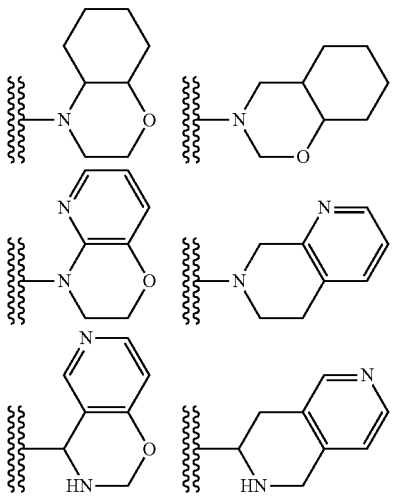

[Formula 52]

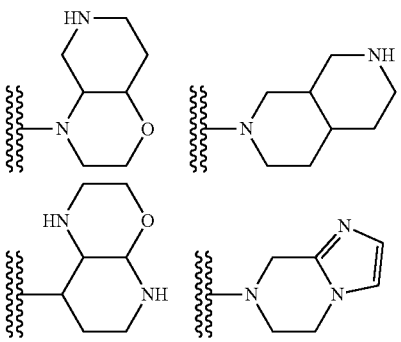

"Non-aromatic heterocyclyl" include a ring having a bridge or a ring to form a spiro ring.

[Formula 53]

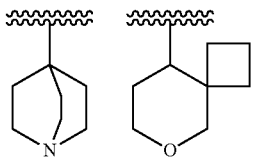

Regarding the above "cycloalkyl", "cycloalkenyl", "non-aromatic carbocyclyl", "aromatic carbocyclyl", "aromatic heterocyclyl" and "non-aromatic heterocyclyl", "non-aromatic carbocycle", "non-aromatic carbocycle", "non-aromatic heterocycle", "aromatic carbocycle", "aromatic heterocycle", "carbocycle" and "heterocycle" which is defined as "fused ring" mean as follows. When the ring is substituted, the ring may have the substitutent on the fused ring. "Non-aromatic carbocycle" and "non-aromatic heterocycle" may be substituted with oxo.

"Non-aromatic carbocycle" means C3 to C8 cyclic saturated hydrocarbon ring and C3 to C8 cyclic unsaturated aliphatic hydrocarbon ring. For example, cyclohexane ring, cyclopentane ring, cyclohexene ring, cyclopentene ring and the like are exemplified.

"Non-aromatic heterocycle" means 3- to 8-membered non-aromatic heterocycle containing one to four heteroatom(s) arbitrarily selected from O, S and N on the ring. For example, piperidine ring, piperazine ring, morpholine ring and the like are exemplified.

"Aromatic carbocycle" means monocyclic or polycyclic aromatic carbocycle. For example, benzene ring, naphthalene ring and the like are exemplified.

"Aromatic heterocycle" means monocyclic or polycyclic aromatic heterocycle containing one or more heteroatom(s) arbitrarily selected from O, S and N on the ring. For example, pyridine ring, pyrimidine ring, pyrrole ring, imidazole ring and the like are exemplified.

"Carbocycle" includes the above "non-aromatic carbocycle" and "aromatic carbocycle".

"Heterocycle" includes the above "non-aromatic heterocycle" and "aromatic heterocycle".

"Non-aromatic carbocyclyloxy" means the above "non-aromatic carbocyclyl" bonded to an oxygen atom. For example, cyclopropyloxy, cyclohexyloxy, cyclohexenyloxy, cyclopropenyloxy, cyclobutenyloxy, cyclopentenyloxy, cyclohexenyloxy, cycloheptenyloxy, cyclohexadienyloxy and the like are exemplified.

"Aromatic carbocyclyloxy" means the above "aromatic carbocyclyl" bonded to an oxygen atom. For example, phenyloxy, naphthyloxy and the like are exemplified.

"Aromatic heterocyclyloxy" means the above "aromatic heterocyclyl" bonded to an oxygen atom. For example, pyridyloxy, oxazolyloxy and the like are exemplified.

"Non-aromatic heterocyclyloxy" means the above "non-aromatic heterocyclyl" bonded to an oxygen atom. For example, piperidinyloxy, tetrahydro furyloxy and the like are exemplified.

"Non-aromatic carbocyclylcarbonyl" means the above "cycloalkyl" or "cycloalkenyl" bonded to a carbonyl group. For example, cyclopropylcarbonyl, cyclohexylcarbonyl, cyclohexenylcarbonyl, cyclohexenylcarbonyl and the like are exemplified.

"Aromatic carbocyclylcarbonyl" means the above "aromatic carbocyclyl" bonded to a carbonyl group. For example, phenylcarbonyl, naphthylcarbonyl and the like are exemplified.

"Aromatic heterocyclylcarbonyl" means the above "aromatic heterocyclyl" bonded to a carbonyl group. For example, pyridylcarbonyl, oxazolylcarbonyl, isoxazolylcarbonyl, pyrazolylcarbonyl, thiazolylcarbonyl, isothiazolylcarbonyl, thienylcarbonyl, pyrrolylcarbonyl, furylcarbonyl and the like are exemplified.

Examples of "aromatic heterocyclylcarbonyl" of $R^4$ include pyrrolylcarbonyl and the like.

"Non-aromatic heterocyclylcarbonyl" means the above "non-aromatic heterocyclyl" bonded to a carbonyl group. For example, oxetanylcarbonyl, piperidinylcarbonyl, tetrahydrofurylcarbonyl and the like are exemplified.

Examples of "non-aromatic heterocyclylcarbonyl" of $R^4$ include oxetanylcarbonyl and the like.

"Alkylsulfonyl" means the above "alkyl" bonded to a sulfonyl group. For example, methylsulfonyl, ethylsulfonyl, propylsulfonyl, isopropylsulfonyl, tert-butylsulfonyl, isobutylsulfonyl, sec-butylsulfonyl and the like are exemplified.

A preferable embodiment of "alkylsulfonyl" includes methylsulfonyl, ethylsulfonyl.

Examples of "alkylsulfonyl" of $R^4$ include methylsulfonyl, ethylsulfonyl and the like.

"Alkenylsulfonyl" means the above "alkenyl" bonded to a sulfonyl group. For example, ethylenylsulfonyl, propenylsulfonyl and the like are exemplified.

"Alkynylsulfonyl" means the above "alkynyl" bonded to a sulfonyl group. For example, ethynylsulfonyl, propynylsulfonyl and the like are exemplified.

"Non-aromatic carbocyclylsulfonyl" means the above "non-aromatic carbocyclyl" bonded to a sulfonyl group. For example, cyclopropylsulfonyl, cyclopentanylsulfonyl, cyclohexylsulfonyl, cyclopropenylsulfonyl, cyclopentenylsulfonyl, cyclohexenylsulfonyl and the like are exemplified.

"Aromatic carbocyclylsulfonyl" means the above "aromatic carbocyclyl" bonded to a sulfonyl group. For example, phenylsulfonyl, naphthylsulfonyl and the like are exemplified.

"Aromatic heterocyclylsulfonyl" means the above "aromatic heterocyclyl" bonded to a sulfonyl group. For example, pyridylsulfonyl, oxazolylsulfonyl and the like are exemplified.

"Non-aromatic heterocyclylsulfonyl" means the above "non-aromatic heterocyclyl" bonded to a sulfonyl group. For example, piperidinylsulfonyl, tetrahydrofurylsulfonyl and the like are exemplified.

"Alkenyloxycarbonyl" means the above "alkenyloxy" bonded to a carbonyl group. For example, ethylenyloxycarbonyl, propenyloxycarbonyl and the like are exemplified.

"Alkynyloxycarbonyl" means the above "alkynyloxy" bonded to a carbonyl group. For example, ethynyloxycarbonyl, propynyloxycarbonyl and the like are exemplified.

"Aromatic carbocyclyloxycarbonyl" means the above "aromatic carbocyclyloxy" bonded to a carbonyl group. For example, phenyloxycarbonyl, naphthyloxycarbonyl and the like are exemplified.

"Non-aromatic carbocyclyloxycarbonyl" means the above "non-aromatic carbocyclyloxy" bonded to a carbonyl group. For example, cyclopropyloxycarbonyl, cyclohexyloxycarbonyl, cyclohexenyloxycarbonyl, cyclopropenyloxycarbonyl and the like are exemplified.

"Aromatic heterocyclyloxycarbonyl" means the above "aromatic heterocyclyloxy" bonded to a carbonyl group. For example, pyridyloxycarbonyl, oxazolyloxycarbonyl and the like are exemplified.

"Non-aromatic heterocyclyloxycarbonyl" means the above "non-aromatic heterocyclyloxy" bonded to a carbonyl group. For example, piperidinyloxycarbonyl, tetrahydrofuryloxycarbonyl and the like are exemplified.

"Non-aromatic carbocyclylsulfanyl" means a sulfanyl group the hydrogen atom of which is replaced by the above "non-aromatic carbocyclyl". For example, cyclopropylsulfanyl, cyclohexylsulfanyl, cyclohexenylsulfanyl, cyclopropenylsulfanyl, cyclobutenylsulfanyl, cyclohexenylsulfanyl, cyclopentenylsulfanyl, cycloheptenylsulfanyl, cyclohexadienylsulfanyl and the like are exemplified.

"Aromatic carbocyclylsulfanyl" means a sulfanyl group the hydrogen atom of which is replace by the above "aromatic carbocyclyl". For example, phenylsulfanyl, naphthylsulfanyl and the like are exemplified.

"Aromatic heterocyclylsulfanyl" means a sulfanyl group the hydrogen atom of which is replaced by the above "aromatic heterocyclyl". For example, pyridylsulfanyl, oxazolylsulfanyl and the like are exemplified.

"Non-aromatic heterocyclylsulfanyl" means a sulfanyl group the hydrogen atom of which is replaced by the above "non-aromatic heterocyclyl". For example, piperidinylsulfanyl, tetrahydrofurylsulfanyl and the like are exemplified.

"Alkylsulfinyl" means the above "alkyl" bonded to a sulfinyl group. For example, methylsulfinyl, ethylsulfinyl, n-propylsulfinyl, isopropylsulfinyl and the like are exemplified.

"Alkenylsulfinyl" means the above "alkenyl" bonded to a sulfinyl group. For example, ethylenylsulfinyl, propenylsulfinyl and the like are exemplified.

"Alkynylsulfinyl" means the above "alkynyl" bonded to a sulfinyl group. For example, ethynylsulfinyl, propynylsulfinyl and the like are exemplified.

"Non-aromatic carbocyclylsulfinyl" means the above "non-aromatic carbocyclyl" bonded to a sulfinyl group. For example, cyclopropylsulfinyl, cyclohexylsulfinyl, cyclohexenylsulfinyl, cyclopropenylsulfinyl, cyclobutenylsulfinyl, cyclohexenylsulfinyl, cyclopentenylsulfinyl, cycloheptenylsulfinyl, cyclohexadienylsulfinyl and the like are exemplified.

"Aromatic carbocyclylsulfinyl" means the above "aromatic carbocyclyl" bonded to a sulfinyl group. For example, phenylsulfinyl, naphthylsulfinyl and the like are exemplified.

"Aromatic heterocyclyl sulfinyl" means the above "aromatic heterocyclyl" bonded to a sulfinyl group. For example, pyridylsulfinyl, oxazolylsulfinyl and the like are exemplified.

"Non-aromatic heterocyclyl sulfinyl" means the above "non-aromatic heterocyclyl" bonded to a sulfinyl group. For example, piperidinylsulfinyl, tetrahydrofurylsulfinyl and the like are exemplified.

"Aminosulfinyl" means an amino group bonded to a sulfinyl group.

"Alkylsulfonyloxy" means the above "alkylsulfonyl" bonded to an oxygen atom. For example, methylsulfonyloxy, ethylsulfonyloxy, propylsulfonyloxy, isopropylsulfonyloxy, tert-butylsulfonyloxy, isobutylsulfonyloxy, sec-butylsulfonyloxy and the like are exemplified.

A preferable embodiment of "alkylsulfonyloxy" includes methylsulfonyloxy, ethylsulfonyloxy and the like.

"Alkenylsulfonyloxy" means the above "alkenylsulfonyl" bonded to an oxygen atom. For example, ethylenylsulfonyloxy, propenylsulfonyloxy and the like are exemplified.

"Alkynylsulfonyloxy" means the above "alkynylsulfonyl" bonded to an oxygen atom. For example, ethynylsulfonyloxy, propynylsulfonyloxy and the like are exemplified.

"Non-aromatic carbocyclylsulfonyloxy" means the above "non-aromatic carbocyclylsulfonyl" bonded to an oxygen atom. For example, cyclopropylsulfonyloxy, cyclohexylsulfonyloxy, cyclohexenylsulfonyloxy, cyclopropenylsulfonyloxy, cyclohexenylsulfonyloxy and the like are exemplified.

"Aromatic carbocyclylsulfonyloxy" means the above "aromatic carbocyclylsulfonyl" bonded to an oxygen atom. For example, phenylsulfonyloxy, naphthylsulfonyloxy and the like are exemplified.

"Aromatic heterocyclylsulfonyloxy" means the above "aromatic heterocyclylsulfonyl" bonded to an oxygen atom. For example, pyridylsulfonyloxy, oxazolylsulfonyloxy and the like are exemplified.

"Non-aromatic heterocyclylsulfonyloxy" means the above "non-aromatic heterocyclylsulfonyl" bonded to an oxygen atom. For example, piperidinylsulfonyloxy, tetrahydrofurylsulfonyloxy and the like are exemplified.

"Alkylcarbonyloxy" means the above "alkylcarbonyl" bonded to an oxygen atom. Examples of "alkylcarbonyloxy" include methylcarbonyloxy, ethylcarbonyloxy, propylcarbonyloxy, isopropylcarbonyloxy, tert-butylcarbonyloxy, isobutylcarbonyloxy, sec-butylcarbonyloxy and the like.

A preferable embodiment of "alkylcarbonyloxy" includes methylcarbonyloxy, ethylcarbonyloxy and the like.

"Alkenylcarbonyloxy" means the above "alkenylcarbonyl" bonded to an oxygen atom. For example, ethylenylcarbonyloxy, propenylcarbonyloxy and the like are exemplified.

"Alkynylcarbonyloxy" means the above "alkynylcarbonyl" bonded to an oxygen atom. For example, ethynylcarbonyloxy, propynylcarbonyloxy and the like are exemplified.

"Non-aromatic carbocyclylcarbonyloxy" means the above "non-aromatic carbocyclylcarbonyl" bonded to an oxygen atom. Examples of "cycloalkylcarbonyloxy" include cyclopropylcarbonyloxy, cyclohexylcarbonyloxy, cyclohexenylcarbonyloxy and the like.

"Aromatic carbocyclylcarbonyloxy" means the above "aromatic carbocyclylcarbonyl" bonded to an oxygen atom. Examples of "aromatic carbocyclylcarbonyloxy" include phenylcarbonyloxy, naphthylcarbonyloxy and the like.

"Aromatic heterocyclylcarbonyloxy" means the above "aromatic heterocyclylcarbonyl" bonded to an oxygen atom. Example of "aromatic heterocyclylcarbonyloxy" include pyridylcarbonyloxy, oxazolylcarbonyloxy and the like are exemplified.

"Non-aromatic heterocyclylcarbonyloxy" means the above "non-aromatic heterocyclylcarbonyl" bonded to an oxygen atom. Examples of "non-aromatic heterocyclylcarbonyloxy" include piperidinylcarbonyloxy, tetrahydrofurylcarbonyloxy and the like are exemplified.

"Alkyloxycarbonyl" means the above "alkyloxy" bonded to a carbonyl group. Examples of "alkyloxycarbonyl" include methyloxycarbonyl, ethyloxycarbonyl, propyloxycarbonyl, isopropyloxycarbonyl, tert-butyloxycarbonyl, isobutyloxycarbonyl, sec-butyloxycarbonyl, pentyloxycarbonyl, isopentyloxycarbonyl, hexyloxycarbonyl and the like are exemplified. A preferable embodiment of "alkyloxycarbonyl" includes methyloxycarbonyl, ethyloxycarbonyl, propyloxycarbonyl and the like.

A preferable embodiment of "alkyloxycarbonyl" of $R^4$ includes methyloxycarbonyl, ethyloxycarbonyl.

"Alkenyloxycarbonyl" means the above "alkenyloxy" bonded to a carbonyl group. Examples of "alkenyloxycarbonyl" include ethylenyloxycarbonyl, propenyloxycarbonyl and the like.

"Alkynyloxycarbonyl" means the above "alkynyloxy" bonded to a carbonyl group. Examples of "alkynyloxycarbonyl" include ethynyloxycarbonyl, propynyloxycarbonyl and the like.

"Non-aromatic carbocyclyloxycarbonyl" means the above "non-aromatic carbocyclyloxy" bonded to a carbonyl group. For example, cyclopropyloxycarbonyl, cyclopentynyloxycarbonyl, cyclohexyloxycarbonyl, cyclopropenyloxycarbonyl, cyclopentenyloxycarbonyl, cyclohexenyloxycarbonyl and the like are exemplified.

"Aromatic carbocyclyloxycarbonyl" means the above "aromatic carbocyclyloxy" bonded to a carbonyl group. For example, phenyloxycarbonyl, naphthyloxycarbonyl and the like are exemplified.

"Aromatic heterocyclyloxycarbonyl" means the above "aromatic heterocyclyloxy" bonded to a carbonyl group. For example, pyridyloxycarbonyl, oxazolyloxycarbonyl and the like are exemplified.

"Non-aromatic heterocyclyloxycarbonyl" means the above "non-aromatic heterocyclyloxy" bonded to a carbonyl group. For example, piperidinyloxycarbonyl, tetrahydrofuryloxycarbonyl and the like are exemplified.

Substituents on the nitrogen atom in "substituted or unsubstituted amino", "substituted or unsubstituted carbamoyl", "substituted or unsubstituted sulfamoyl", "substituted or unsubstituted amidino" and "substituted or unsubstituted amino sulfinyl" include the following substituents. Hydrogen on the nitrogen atom can be replaced with one or two substituents selected from the following substituents.
Substituents:
alkyl, alkenyl, alkynyl, haloalkyl, haloalkenyl, halogen, hydroxy, carboxy, formyl, formyloxy, carbamoyl, sulfamoyl, sulfanyl, sulfino, sulfo, thioformyl, thiocarboxy, dithiocarboxy, thiocarbamoyl, cyano, nitro, nitroso, azido, hydradino, ureido, amidino, guanidino, trialkylsilyl, alkyloxy, alkyloxyalkyloxy, alkenyloxy, alkynyloxy, haloalkyloxy, trialkylsilyloxy, cyanoalkyloxy, alkylcarbonyl, haloalkylcarbonyl, carbamoylalkylcarbonyl, alkenylcarbonyl, alkynylcarbonyl, monoalkylamino, dialkylamino, alkylsulfonyl, alkenylsulfonyl, alkynylsulfonyl, monoalkylcarbonylamino, dialkylcarbonylamino, monoalkylsulfonylamino, dialkylsulfonylamino, alkylimino, alkenylimino, alkynylimino, alkylcarbonylimino, alkenylcarbonylimino, alkynylcarbonylimino, alkyloxyimino, alkenyloxyimino, alkynyloxyimino, alkylcarbonyloxy, alkenylcarbonyloxy, alkynylcarbonyloxy, alkyloxycarbonyl, monoalkyoxycarbonylamino, dialkyloxycarbonylamino, alkenyloxycarbonyl, alkynyloxycarbonyl, alkylsulfanyl, alkylcarbonylsulfanyl, alkenylsulfanyl, alkynylsulfanyl, alkylsulfinyl, alkenylsulfinyl, alkynylsulfinyl, monoalkylcarbamoyl, mono(hydroxyalkyl)carbamoyl, dialkylcarbamoyl, hydroxycarbamoyl, cyanocarbamoyl, carboxyalkylcarbamoyl, mono(dialkylaminoalkyl)carbamoyl di(dialkylaminoalkyl)carbamoyl, non-aromatic carbocyclylalkylcarbamoyl, non-aromatic carbocyclylcarbamoyl, non-aromatic heterocyclylalkylcarbamoyl, non-aromatic heterocyclylcarbamoyl, monoalkyloxycarbamoyl, dialkyloxycarbamoyl, monoalkyloxycarbonylalkylcarbamoyl, dialkyloxycarbonylalkylcarbamoyl, monoalkylsulfamoyl, dialkylsulfamoyl, aromatic carbocyclyl, non-aromatic carbocyclyl, aromatic heterocyclyl, non-aromatic heterocyclyl, aromatic carbocyclyloxy, non-aromatic carbocyclyloxy, non-aromatic heterocyclyloxy, non-aromatic heterocyclyloxy, aromatic carbocyclylcarbonyl, non-aromatic carbocyclylcarbonyl, aromatic heterocyclylcarbonyl, non-aromatic heterocyclylcarbonyl, non-aromatic carbocyclylcarbonyloxy, aromatic carbocyclylcarbonyloxy, aromatic heterocyclylcarbonyloxy, non-aromatic heterocyclylcarbonyloxy, aromatic carbocyclyloxycarbonyl, non-aromatic carbocyclyloxycarbonyl, aromatic heterocyclyloxycarbonyl, non-aromatic heterocyclyloxycarbonyl, aromatic carbocyclylalkyl, non-aromatic carbocyclylalkyl, aromatic heterocyclylalkyl, non-aromatic heterocyclylalkyl, aromatic carbocyclylalkyloxy, non-aromatic carbocyclylalkyloxy, aromatic heterocyclylalkyloxy, non-aromatic heterocyclylalkyloxy, aromatic carbocyclylalkyloxycarbonyl, non-aromatic carbocyclylalkyloxycarbonyl, aromatic heterocyclylalkyloxycarbonyl, non-aromatic heterocyclylalkyloxycarbonyl, aromatic carbocyclylalkylamino, non-aromatic carbocyclylalkylamino, aromatic heterocyclylalkylamino, non-aromatic heterocyclylalkylamino, aromatic carbocyclylsulfanyl, non-aromatic carbocyclylsulfanyl, aromatic heterocyclylsulfanyl, non-aromatic heterocyclylsulfanyl, aromatic carbocyclylsulfonyl, non-aromatic carbocyclylsulfonyl, aromatic heterocyclylsulfonyl, non-aromatic heterocyclylsulfonyl, alkylsulfonyloxy, alkenylsulfonyloxy, alkynylsulfonyloxy, non-aromatic carbocyclylsulfonyloxy, aromatic carbocyclylsulfonyloxy, aromatic heterocyclylsulfonyloxy, non-aromatic heterocyclylsulfonyloxy, alkyloxycarbonylalkyl, carboxyalkyl, hydroxyalkyl, dialkylaminoalkyl, hydroxyalkyl, alkyloxyalkyl, aromatic carbocyclylalkyloxyalkyl, non-aromatic carbocyclylalkyloxyalkyl, aromatic heterocyclylalkyloxyalkyl and non-aromatic heterocyclylalkyloxyalkyl.

Substituents of the above "substituted or unsubstituted alkyl", "substituted or unsubstituted alkenyl", "substituted or unsubstituted alkynyl", "substituted or unsubstituted alkyloxy", "substituted or unsubstituted alkenyloxy", "substituted or unsubstituted alkynyloxy", "substituted or unsubstituted alkyl sulfanyl", "substituted or unsubstituted alkenylsulfanyl", "substituted or unsubstituted alkynylsulfanyl", "substituted or unsubstituted alkylcarbonyl", "substituted or unsubstituted alkenylcarbonyl", "substituted or unsubstituted alkynylcarbonyl", "substituted or unsubstituted alkylsulfonyl", "substituted or unsubstituted alkenylsulfonyl", "substituted or unsubstituted alkynylsulfonyl", "substituted or unsubstituted alkyloxycarbonyl", "substituted or unsubstituted alkenyloxycarbonyl", "substituted or unsubstituted alkynyloxycarbonyl", "substituted or unsubstituted alkylsulfinyl", "substituted or unsubstituted alkenylsulfinyl", "substituted or unsubstituted alkynylsulfinyl", "substituted or unsubstituted alkyl sulfonyloxy", "substituted or unsubstituted alkenylsulfonyloxy", "substituted or unsubstituted alkynylsulfonyloxy", "substituted or unsubstituted alkylcarbonyloxy", "substituted or unsubstituted alkenylcarbonyloxy" and "substituted or unsubstituted alkynylcarbonyloxy" include the following substituents. Hydrogen atom on the carbon atom at arbitrary position(s) can be replaced with one or more substituents selected from the following substituents.

Substituents:

halogen, hydroxy, carboxy, amino, imino, hydroxyamino, hydroxyimino, formyl, formyloxy, carbamoyl, sulfamoyl, sulfanyl, sulfino, sulfo, thioformyl, thiocarboxy, dithiocarboxy, thiocarbamoyl, cyano, nitro, nitroso, azido, hydradino, ureido, amidino, guadinino, trialkylsilyl, alkyloxy, alkyloxyalkyloxy, alkenyloxy, alkynyloxy, haloalkyloxy, trialkylsilyloxy, cyanoalkyloxy, alkylcarbonyl, haloalkylcarbonyl, carbamoylalkylcarbonyl, alkenylcarbonyl, alkynylcarbonyl, monoalkylamino, dialkylamino, alkylsulfonyl, alkenylsulfonyl, alkynylsulfonyl, monoalkylcarbonylamino, dialkylcarbonylamino, monoalkylsulfonylamino, dialkylsulfonylamino, alkylimino, alkenylimino, alkynylimino, alkylcarbonylimino, alkenylcarbonylimino, alkynylcarbonylimino, alkyloxyimino, alkenyloxyimino, alkynyloxyimino, alkylcarbonyloxy, alkenylcarbonyloxy, alkynylcarbonyloxy, alkyloxycarbonyl, monoalkyloxycarbonylamino, dialkyloxycarbonylamino, alkenyloxycarbonyl, alkynyloxycarbonyl, alkylsulfanyl, alkylcarbonylsulfanyl, alkenylsulfanyl, alkynylsulfanyl, alkylsulfinyl, alkenylsulfinyl, alkynylsulfinyl, monoalkylcarbamoyl, mono(hydroxyalkyl)carbamoyl, dialkylcarbamoyl, hydroxycarbamoyl, cyanocarbamoyl, carboxyalkylcarbamoyl, mono(dialkylaminoalkyl)carbamoyl di(dialkylaminoalkyl)carbamoyl, non-aromatic carbocyclylcarbamoyl, non-aromatic heterocyclylalkylcarbamoyl, non-aromatic heterocyclylcarbamoyl, monoalkyloxycarbamoyl, dialkyloxycarbamoyl, monoalkyloxycarbonylalkylcarbamoyl, dialkyloxycarbonylalkylcarbamoyl, monoalkylsulfamoyl, dialkylsulfamoyl, aromatic carbocyclyl, non-aromatic carbocyclyl, aromatic heterocyclyl, non-aromatic heterocyclyl, aromatic carbocyclyloxy, non-aromatic carbocyclyloxy, aromatic heterocyclyloxy, non-aromatic heterocyclyloxy, aromatic carbocyclylcarbonyl, non-aromatic carbocyclylcarbonyl, aromatic heterocyclylcarbonyl, non-aromatic heterocyclylcarbonyl, non-aromatic carbocyclylcarbonyloxy, aromatic carbocyclylcarbonyloxy, aromatic heterocyclylcarbonyloxy, non-aromatic heterocyclylcarbonyloxy, aromatic carbocyclyloxycarbonyl, non-aromatic carbocyclyloxycarbonyl, aromatic heterocyclyloxycarbonyl, non-aromatic heterocyclyloxycarbonyl, aromatic carbocyclylalkyloxy, non-aromatic carbocyclylalkyloxy, aromatic heterocyclylalkyloxy, non-aromatic heterocyclylalkyloxy, aromatic carbocyclylalkyloxycarbonyl, non-aromatic carbocyclylalkyloxycarbonyl, aromatic heterocyclylalkyloxycarbonyl, non-aromatic heterocyclylalkyloxycarbonyl, aromatic carbocyclylalkylamino, non-aromatic carbocyclylalkylamino, aromatic heterocyclylalkylamino, non-aromatic heterocyclylalkylamino, aromatic carbocyclylsulfanyl, non-aromatic carbocyclylsulfanyl, aromatic heterocyclylsulfanyl, non-aromatic heterocyclylsulfanyl, non-aromatic carbocyclylsulfonyl, aromatic carbocyclylsulfonyl, aromatic heterocyclylsulfonyl, non-aromatic heterocyclylsulfonyl, alkylsulfonyloxy, alkenylsulfonyloxy, alkynylsulfonyloxy, non-aromatic carbocyclylsulfonyloxy, aromatic carbocyclylsulfonyloxy, aromatic heterocyclyl sulfonyloxy and non-aromatic heterocyclylsulfonyloxy.

Substituents in the ring of the above "substituted or unsubstituted fused aromatic heterocyclyl", "substituted or unsubstituted fused aromatic carbocyclyl", "substituted or unsubstituted non-aromatic carbocyclyl", "substituted or unsubstituted aromatic carbocyclyl", "substituted or unsubstituted non-aromatic heterocyclyl", "substituted or unsubstituted non-aromatic heterocyclyl", "substituted or unsubstituted non-aromatic carbocyclylcarbonyl", "substituted or unsubstituted aromatic carbocyclylcarbonyl", "substituted or unsubstituted aromatic heterocyclylcarbonyl", "substituted or unsubstituted non-aromatic heterocyclylcarbonyl", "substituted or unsubstituted non-aromatic carbocyclylsulfonyl", "substituted or unsubstituted aromatic carbocyclylsulfonyl", "substituted or unsubstituted aromatic heterocyclylsulfonyl", "substituted or unsubstituted non-aromatic heterocyclylsulfonyl", "substituted or unsubstituted non-aromatic carbocyclyl", "substituted or unsubstituted aromatic carbocyclyl", "substituted or unsubstituted aromatic heterocyclyl", "substituted or unsubstituted fused aromatic carbocyclyl", "substituted or unsubstituted fused aromatic heterocyclyl", "substituted or unsubstituted non-aromatic heterocyclyl", "substituted or unsubstituted aromatic carbocyclyloxycarbonyl", "substituted or unsubstituted non-aromatic carbocyclyloxycarbonyl", "substituted or unsubstituted aromatic heterocyclyloxycarbonyl", "substituted or unsubstituted non-aromatic heterocyclyloxycarbonyl", "substituted or unsubstituted non-aromatic carbocyclyloxy", "substituted or unsubstituted aromatic carbocyclyloxy", "substituted or unsubstituted aromatic heterocyclyloxy", "substituted or unsubstituted non-aromatic heterocyclyloxy", "substituted or unsubstituted non-aromatic carbocyclylsulfanyl", "substituted or unsubstituted aromatic carbocyclylsulfanyl", "substituted or unsubstituted aromatic heterocyclylsulfanyl", "substituted or unsubstituted non-aromatic heterocyclylsulfanyl", "substituted or unsubstituted non-aromatic carbocyclylsulfinyl", "substituted or unsubstituted aromatic carbocyclylsulfinyl", "substituted or unsubstituted aromatic heterocyclyl sulfinyl", "substituted or unsubstituted non-aromatic heterocyclyl sulfinyl", "substituted or unsubstituted non-aromatic carbocyclylsulfonyloxy", "substituted or unsubstituted aromatic carbocyclylsulfonyloxy", "substituted or unsubstituted aromatic heterocyclylsulfonyloxy", "substituted or unsubstituted non-aromatic heterocyclylsulfonyloxy", "substituted or unsubstituted non-aromatic carbocyclylcarbonyloxy", "substituted or unsubstituted aromatic carbocyclylcarbonyloxy", "substituted or unsubstituted aromatic heterocyclylcarbonyloxy" and "substituted or unsubstituted non-aromatic heterocyclylcarbonyloxy" include the following substituents. Hydrogen atom on the ring at arbitrary position(s) can be substituted with one or more group(s) selected from the following substituents.
Substituent:
alkyl, alkenyl, alkynyl, haloalkyl, haloalkenyl, halogen, hydroxy, carboxy, formyl, formyloxy, carbamoyl, sulfamoyl, sulfanyl, sulfino, sulfo, thioformyl, thiocarboxy, dithiocarboxy, thiocarbamoyl, cyano, nitro, nitroso, azido, hydradiono, ureido, amidino, guanidino, trialkylsilyl, alkyloxy, alkyloxy alkyloxy, alkenyloxy, alkynyloxy, haloalkyloxy, trialkylsilyloxy, cyanoalkyloxy, alkylcarbonyl, haloalkylcarbonyl, carbamoylalkylcarbonyl, alkenylcarbonyl, alkynylcarbonyl, monoalkylamino, dialkylamino, alkylsulfonyl, alkenylsulfonyl, alkynylsulfonyl, monoalkylcarbonylamino, dialkylcarbonylamino, monoalkylsulfonylamino, dialkylsulfonylamino, alkylimino, alkenylimino, alkynylimino, alkylcarbonylimino, alkenylcarbonylimino, alkynylcarbonylimino, alkyloxyimino, alkenyloxyimino, alkynyloxyimino, alkylcarbonyloxy, alkenylcarbonyloxy, alkynylcarbonyloxy, alkyloxycarbonyl, monoalkyloxycarbonylamino, dialkyloxycarbonylamino, alkenyloxycarbonyl, alkynyloxycarbonyl, alkylsulfanyl, alkylcarbonylsulfanyl, alkenylsulfanyl, alkynylsulfanyl, alkylsulfinyl, alkenylsulfinyl, alkynylsulfinyl, monoalkylcarbamoyl, mono(hydroxyalkyl)carbamoyl, dialkylcarbamoyl, hydroxycarbamoyl, cyanocarbamoyl, carboxyalkylcarbamoyl, mono(dialkylaminoalkyl)carbamoyl di(dialkylaminoalkyl)carbamoyl, non-aromatic carbocyclylalkylcarbamoyl, non-aromatic carbocyclylcarbamoyl, non-aromatic heterocyclylalkylcarbamoyl, non-aromatic heterocyclylcarbamoyl, monoalkyloxycarbamoyl, dialkyloxycarbamoyl, monoalkyloxycarbonylalkylcarbamoyl, dialkyloxycarbonylalkylcarbamoyl, monoalkylsulfamoyl, dialkylsulfamoyl, aromatic carbocyclyl, non-aromatic carbocyclyl, aromatic heterocyclyl, non-aromatic heterocyclyl, aromatic carbocyclyloxy, non-aromatic carbocyclyloxy, non-aromatic heterocyclyloxy, non-aromatic heterocyclyloxy, aromatic carbocyclylcarbonyl, non-aromatic carbocyclylcarbonyl, aromatic heterocyclylcarbonyl, non-aromatic heterocyclylcarbonyl, non-aromatic carbocyclylcarbonyloxy, aromatic carbocyclylcarbonyloxy, aromatic heterocyclylcarbonyloxy, non-aromatic heterocyclylcarbonyloxy, aromatic carbocyclyloxycarbonyl, non-aromatic carbocyclyloxycarbonyl, aromatic heterocyclyloxycarbonyl, non-aromatic heterocyclyloxycarbonyl, aromatic carbocyclylalkyl, non-aromatic carbocyclylalkyl, aromatic heterocyclylalkyl, non-aromatic heterocyclylalkyl, aromatic carbocyclylalkyloxy, non-aromatic carbocyclylalkyloxy, aromatic heterocyclylalkyloxy, non-aromatic heterocyclylalkyloxy, aromatic carbocyclylalkyloxycarbonyl, non-aromatic carbocyclylalkyloxycarbonyl, aromatic heterocyclylalkyloxycarbonyl, non-aromatic heterocyclylalkyloxycarbonyl, aromatic carbocyclylalkylamino, non-aromatic carbocyclylalkylamino, aromatic heterocyclylalkylamino, non-aromatic heterocyclylalkylamino, aromatic carbocyclylsulfanyl, non-aromatic carbocyclylsulfanyl, aromatic heterocyclylsulfanyl, non-aromatic heterocyclylsulfanyl, aromatic carbocyclylsulfonyl, non-aromatic carbocyclylsulfonyl, aromatic heterocyclylsulfonyl, non-aromatic heterocyclylsulfonyl, alkylsulfonyloxy, alkenylsulfonyloxy, alkynylsulfonyloxy, non-aromatic carbocyclylsulfonyloxy, aromatic carbocyclylsulfonyloxy, aromatic heterocyclylsulfonyloxy, non-aromatic heterocyclylsulfonyloxy, alkyloxycarbonylalkyl, carboxyalkyl, hydroxyalkyl, dialkylaminoalkyl, hydroxyalkyl, alkyloxyalkyl, aromatic carbocyclylalkyloxyalkyl, non-aromatic carbocyclylalkyloxyalkyl, aromatic heterocyclylalkyloxyalkyl and non-aromatic heterocyclylalkyloxyalkyl.

Preferably, halogen, substituted or unsubstituted alkyl (a substituent group: halogen, hydroxy), substituted or unsubstituted alkenyl (a substituent group: halogen, hydroxy), substituted or unsubstituted alkynyl (a substituent group: halogen, hydroxy), substituted or unsubstituted non-aromatic carbocyclyl (a substituent group: halogen, hydroxy, cyano, alkyl, haloalkyl, aromatic carbocyclyl), substituted or unsubstituted aromatic carbocyclyl (a substituent group: halogen, hydroxy, cyano, alkyl, haloalkyl, aromatic carbocyclyl), substituted or unsubstituted non-aromatic heterocyclyl (a substituent group: halogen, hydroxy, cyano, alkyl, haloalkyl, aromatic carbocyclyl), substituted or unsubstituted aromatic heterocyclyl (a substituent group: halogen, hydroxy, cyano, alkyl, haloalkyl, aromatic carbocyclyl), substituted or unsubstituted alkyloxy (a substituent group: halogen, cyano, non-aromatic carbocyclyl, halo non-aromatic carbocyclyl, cyano non-aromatic carbocyclyl, halo aromatic carbocyclyl, non-aromatic heterocyclyl), substituted or unsubstituted alkenyloxy (a substituent group: halogen, cyano, non-aromatic carbocyclyl, halo non-aromatic carbocyclyl, cyano non-aromatic carbocyclyl, halo aromatic carbocyclyl, non-aromatic heterocyclyl), substituted or unsubstituted alkynyloxy (a substituent group: halogen, cyano, non-aromatic carbocyclyl, halo non-aromatic carbocyclyl, cyano non-aromatic carbocyclyl, halo aromatic carbocyclyl, non-aromatic heterocyclyl), substituted or unsubstituted non-aromatic carbocyclyloxy (a substituent group: cyano, halogen, hydroxy, alkyl, alkyloxy), substituted or unsubstituted aromatic carbocyclyloxy (a substituent group: cyano, halogen, hydroxy, alkyl, alkyloxy), substituted or unsubstituted non-aromatic heterocyclyloxy (a substituent group: cyano, halogen, hydroxy, alkyl, alkyloxy), substituted or unsubstituted aromatic heterocyclyloxy (a substituent group: cyano, halogen, hydroxy, alkyl, alkyloxy), substituted or unsubstituted amino (a substituent group: cyano, alkyl, cyanoalkyl) are exemplified.

More preferably, halogen, alkyl, dihaloalkyl, hydroxyalkyl, halo non-aromatic carbocyclyl, non-aromatic heterocyclyl, halo non-aromatic heterocyclyl, dihalo non-aromatic heterocyclyl, tetrahalo non-aromatic heterocyclyl, hydroxy non-aromatic heterocyclyl, alkyl non-aromatic heterocyclyl, dialkyl non-aromatic heterocyclyl, cyano non-aromatic heterocyclyl, aromatic carbocycle non-aromatic heterocyclyl, alkyloxy, haloalkyloxy, dihaloalkyloxy, trihaloalkyloxy, cyanoalkyloxy, non-aromatic carbocyclylalkyloxy, dihalo non-aromatic carbocyclylalkyloxy, cyano non-aromatic carbocyclylalkyloxy, halo aromatic carbocyclylalkyloxy, non-aromatic heterocyclylalkyloxy, halo non-aromatic heterocyclylalkyloxy, non-aromatic heterocyclyloxyalkyloxy, non-aromatic carbocyclyloxy, cyano non-aromatic carbocyclyloxy, halo non-aromatic carbocyclyloxy, dihalo non-aromatic carbocyclyloxy, methyl non-aromatic carbocyclyloxy, hydroxy non-aromatic carbocyclyloxy, alkyloxy non-aromatic carbocyclyloxy, aromatic carbocyclyloxy, non-aromatic heterocyclyloxy, halo non-aromatic heterocyclyloxy, halo aromatic heterocyclyloxy, dialkylamino, cyanoalkyl, alkyl (cyanoalkyl)amino are exemplified.

The above "substituted or unsubstituted non-aromatic carbocyclyl", "substituted or unsubstituted non-aromatic heterocyclyl", "substituted or unsubstituted fused aromatic carbocyclyl" and "substituted or unsubstituted fused aromatic heterocyclyl" can be substituted with "oxo". In this case, two hydrogen atoms on the carbon atom are replaced with =O group as follows:

[Formula 54]

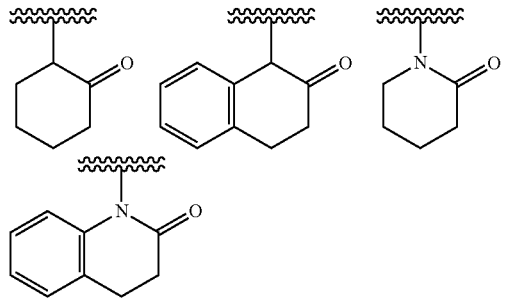

The non-aromatic carbocycle part and non-aromatic heterocycle part in the above "substituted or unsubstituted non-aromatic heterocyclyl", "substituted or unsubstituted aromatic carbocyclyloxy", "substituted or unsubstituted non-aromatic heterocyclyloxy", "substituted or unsubstituted non-aromatic carbocyclylsulfanyl", "substituted or unsubstituted non-aromatic heterocyclylsulfanyl", "substituted or unsubstituted non-aromatic carbocyclylsulfinyl", "substituted or unsubstituted non-aromatic heterocyclyl sulfinyl", "substituted or unsubstituted non-aromatic carbocyclylsulfonyl", "substituted or unsubstituted non-aromatic heterocyclylsulfonyl", "substituted or unsubstituted non-aromatic carbocyclylsulfonyloxy", "substituted or unsubstituted non-aromatic heterocyclylsulfonyloxy", "substituted or unsubstituted non-aromatic carbocyclylcarbonyl", "substituted or unsubstituted non-aromatic heterocyclylcarbonyl", "substituted or unsubstituted non-aromatic carbocyclylcarbonyloxy", "substituted or unsubstituted non-aromatic heterocyclylcarbonyloxy", "substituted or unsubstituted non-aromatic carbocyclyloxycarbonyl" and "substituted or unsubstituted non-aromatic heterocyclyloxycarbonyl" can be substituted with "oxo".

"Alkylcarbonylsulfanyl" means the above "alkylcarbonyl" bonded to a sulfur atom. For example, methylcarbonylsulfanyl, ethylcarbonylsulfanyl, n-propylcarbonylsulfanyl, isopropylcarbonylsulfanyl, n-butylcarbonylsulfanyl, tert-butylcarbonylsulfanyl, isobutylcarbonylsulfanyl, sec-butylcarbonylsulfanyl, pentylcarbonylsulfanyl, isopentylcarbonylsulfanyl, hexylcarbonylsulfanyl and the like are exemplified. A preferable embodiment of "alkylcarbonylsulfanyl" includes methylcarbonylsulfanyl, ethylcarbonylsulfanyl, propylcarbonylsulfanyl, isopropylcarbonylsulfanyl, n-butylcarbonylsulfanyl, tert-butylcarbonylsulfanyl, isobutylcarbonylsulfanyl, sec-butylcarbonylsulfanyl and the like.

"Haloalkyl" means the above "alkyl" the one or more arbitrary hydrogen(s) of which is (are) substituted with the above "halogen". For example, monofluoromethyl, monofluoroethyl, monofluoropropyl, 2,2,3,3,3-pentafluoropropyl, monochloromethyl, trifluoromethyl, trichloromethyl, 2,2,2-trifluoroethyl, 2,2,2-trichloroethyl, 1,2-dibromoethyl, 1,1,1-trifluoropropane-2-yl and the like are exemplified.

"Haloalkylcarbonyl" means the above "haloalkyl" bonded to a carbonyl group. For example, monofluoromethylcarbonyl, difluoromethylcarbonyl, monofluoroethylcarbonyl, monofluoropropylcarbonyl, 2,2,3,3,3-pentafluoropropylcarbonyl, monochloromethylcarbonyl, trifluoromethylcarbonyl, trichloromethylcarbonyl, 2,2,2-trifluoroethylcarbonyl, 2,2,2-trichloroethylcarbonyl, 1,2-dibromoethylcarbonyl, 1,1,1-trifluoropropane-2-ylcarbonyl and the like are exemplified.

"Haloalkenyl" means the above "alkenyl" the one or more arbitrary hydrogen(s) of which is (are) substituted the above "halogen".

"Hydroxyalkyl" means the above "alkyl" the one or more arbitrary hydrogen(s) of which is (are) substituted with "hydroxyl".

"Trialkylsilyl" means silicon atom bonded to above tree "alkyl" group. Three alkyl groups may be same or different. For example, trimethylsilyl, triethylsilyl, tert-butyldimethylsilyl, triisopropylsilyl and the like are exemplified.

"Trialkylsilyloxy" means the above "trialkylsilyl" bonded to an oxygen atom. For example, trimethylsilyloxy, triethylsilyloxy, tert-butyldimethylsilyloxy, triisopropylsilyloxy and the like are exemplified.

"Cyanoalkyl" means the above "alkyl" the one or more arbitrary hydrogen(s) of which is (are) substituted with cyano. For example, cyanomethyl and the like is exemplified.

"Cyanoalkyloxy" means the above "cyanoalkyl" bonded to an oxygen atom. For example, cyanomethyloxy and the like are exemplified.

"Haloalkyloxy" means the above "haloalkyl" bonded to an oxygen atom. For example, monofluoromethyloxy, monofluoroethyloxy, trifluoromethyloxy, trichloromethyloxy, trifluoroethyloxy, trichloroethyloxy and the like are exemplified. A preferable embodiment of "haloalkyloxy" includes trifluoromethyloxy, trichloromethyloxy and the like.

"Carbamoylalkylcarbonyl" means the above "alkylcarbonyl" substituted with carbamoyl. For example, carbamoylmethylcarbonyl, carbamoylethylcarbonyl and the like are exemplified.

"Monoalkylamino" means an amino group one hydrogen atom bonded to the nitrogen atom of which is substituted with the above "alkyl". Examples of "monoalkylamino" include methylamino, ethylamino and the like.

"Dialkylamino" means an amino group two hydrogen atoms bonded to the nitrogen atom of which are substituted with the above "alkyl". Two alkyl groups may be same or different. For example, dimethylamino, diethylamino, N,N-diisopropylamino, N-methyl-N-ethylamino, N-isopropyl-N-ethylamino and the like are exemplified.

A preferable embodiment of "dialkylamino" includes dimethylamino, diethylamino and the like.

"Monoalkylcarbonylamino" means an amino group one hydrogen atom bonded to the nitrogen atom of which is replaced with the above "alkylcarbonyl". For example, methylcarbonylamino, ethylcarbonylamino, propylcarbonylamino, isopropylcarbonylamino, tert-butylcarbonylamino, isobutylcarbonylamino, sec-butylcarbonylamino and the like are exemplified.

A preferable embodiment of "monoalkylcarbonylamino" includes methylcarbonylamino, ethylcarbonylamino and the like.

"Dialkylcarbonylamino" means an amino group two hydrogen atoms bonded to the nitrogen atom of which are replaced with the above "alkylcarbonyl". Two alkylcarbonyl groups may be same or different. For example, dimethylcarbonylamino, diethylcarbonylamino, N,N-diisopropylcarbonylamino and the like are exemplified. A preferable embodiment of "dialkylcarbonylamino" includes dimethylcarbonylamino, diethylcarbonylamino and the like.

"Monoalkyloxycarbonylamino" means an amino group one hydrogen atom bonded to the nitrogen atom of which is replaced with the above "alkyloxycarbonyl". A preferable embodiment of "monoalkyloxycarbonylamino" includes methyloxycarbonylamino, ethyloxycarbonylamino and the like.

"Dialkyloxycarbonylamino" means an amino group two hydrogen atoms bonded to the nitrogen atom of which are replaced with the above "alkyloxycarbonyl". Two alkyloxycarbonyl groups may be same or different.

"Monoalkylsulfonylamino" means an amino group one hydrogen atom bonded to the nitrogen atom of which is replaced with the above "alkylsulfonyl". For example, methylsulfonylamino, ethylsulfonylamino, propylsulfonylamino, isopropylsulfonylamino, tert-butylsulfonylamino, isobutylsulfonylamino, sec-butylsulfonylamino and the like are exemplified.

A preferable embodiment of "monoalkylsulfonylamino" includes methylsulfonylamino, ethylsulfonylamino and the like.

"Dialkylsulfonylamino" means an amino group two hydrogen atoms bonded to the nitrogen atom of which are replaced with the above "alkylsulfonyl". Two alkylsulfonyl groups may be same or different. For example, dimethylsulfonylamino, diethylsulfonylamino, N,N-diisopropylsulfonylamino and the like are exemplified. A preferable embodiment of "dialkylsulfonylamino" includes dimethylsulfonylamino, diethylsulfonylamino and the like.

"Alkylimino" means an imino group a hydrogen atom bonded to the nitrogen atom of which is replaced with the above "alkyl". For example, methylimino, ethylimino, n-propylimino, isopropylimino and the like are exemplified.

"Alkenylimino" means an imino group a hydrogen atom bonded to the nitrogen atom of which is replaced with the above "alkenyl". For example, ethylenylimino, propenylimino and the like are exemplified.

"Alkynylimino" means an imino group a hydrogen atom bonded to the nitrogen atom of which is replaced with the above "alkynyl". For example, ethynylimino, propynylimino and the like are exemplified.

"Alkylcarbonylimino" means an imino group a hydrogen atom bonded to the nitrogen atom of which is replaced with the above "alkylcarbonyl". For example, methylcarbonylimino, ethylcarbonylimino, n-propylcarbonylimino, isopropylcarbonylimino and the like are exemplified.

"Alkenylcarbonylimino" means an imino group a hydrogen atom bonded to the nitrogen atom of which is replaced with the above "alkenylcarbonyl". For example, ethylenylcarbonylimino, propenylcarbonylimino and the like are exemplified.

"Alkynylcarbonylimino" means an imino group a hydrogen atom bonded to the nitrogen atom of which is replaced with the above "alkynylcarbonyl". For example, ethynylcarbonylimino, propynylcarbonylimino and the like are exemplified.

"Alkyloxyimino" means an imino group a hydrogen atom bonded to the nitrogen atom of which is replaced with the above "alkyloxy". For example, methyloxyimino, ethyloxyimino, n-propyloxyimino, isopropyloxyimino and the like are exemplified.

"Alkenyloxyimino" means an imino group a hydrogen atom bonded to the nitrogen atom of which is replaced with the above "alkenyloxy". For example, ethylenyloxyimino, propenyloxyimino and the like are exemplified.

"Alkynyloxyimino" means an imino group a hydrogen atom bonded to the nitrogen atom of which is replaced with the above "alkynyloxy". For example, ethynyloxyimino, propynyloxyimino and the like are exemplified.

"Monoalkylcarbamoyl" means a carbomoyl group a hydrogen atom bonded to the nitrogen atom of which is replaced with the above "alkyl". For example, methylcarbamoyl, ethylcarbamoyl and the like are exemplified.

"Monoalkylcarbamoylalkyloxy" means the above "alkyloxy" substituted with one or more the above "monoalkylcarbamoyl". For example, methylcarbamoylmethyloxy and the like are exemplified.

"Mono(hydroxyalkyl)carbamoyl" means the above "monoalkylcarbamoyl" the arbitrary hydrogen atoms of which is replaced with a hydroxyl group. For example, hydroxymethylcarbamoyl, hydroxyethylcarbamoyla and the like are exemplified.

"Dialkylcarbamoyl" means a carbamoyl group two hydrogen atoms bonded to the nitrogen atom of which are replaced with the above "alkyl". Two alkyl groups may be same or different. For example, dimethylcarbamoyl, diethylcarbamoyl and the like are exemplified.

"Alkyloxycarbonylalkyl" means the above "alkyl" substituted with one or more the above "alkyloxycarbonyl".

"Monoalkyloxycarbonylalkylcarbamoyl" means a carbamoyl group one hydrogen atom bonded to nitrogen atom of which is replaced with the above "alkyloxycarbonylalkyl". For example, methyloxycarbonylmethylcarbamoyl, ethyloxycarbonylmethylcarbamoyl and the like are exemplified.

"Dialkyloxycarbonylalkylcarbamoyl" means a carbamoyl group two hydrogen atoms bonded to the nitrogen atom of which is replaced with the above "alkyloxycarbonylalkyl".

"Carboxyalkyl" means the above "alkyl" substituted with one or more above "carboxy".

"Carboxyalkylcarbamoyl" means a carbamoyl group one or more two hydrogen atom(s) bonded to the nitrogen atom of which is (are) replaced with one or more above "carboxyalkyl". For example, carboxymethylcarbamoyl and the like are exemplified.

"Dialkylaminoalkyl" means the above "alkyl" substituted with one or more above "dialkylamino". For example, dimethylaminomethyl, dimethylaminoethyl and the like are exemplified.

"Mono(dialkylaminoalkyl)carbamoyl" means a carbamoyl group one hydrogen atom bonded to the nitrogen atom of which is replaced with the above "dialkylaminoalkyl". For example, dimethylaminomethylcarbamoyl, dimethylaminoethylcarbamoyl and the like are exemplified.

"Di(dialkylaminoalkyl)carbamoyl" means a carbamoyl group two hydrogen atoms bonded to the nitrogen atom of which are replaced with the above "dialkylaminoalkyl". For example, di(methyloxycarbonylmethyl)carbamoyl, di(ethyloxycarbonylmethyl)carbamoyl and the like are exemplified.

"Non-aromatic carbocyclylcarbamoyl" means a carbamoyl group the hydrogen atom bonded to nitrogen atom of which is replaced with one or more above "non-aromatic carbocyclyl". For example, cyclopropylcarbamoyl and the like are exemplified.

"Non-aromatic heterocyclylcarbamoyl" means a carbamoyl group the hydrogen atom bonded to nitrogen atom of which is replaced with one or more above "non-aromatic heterocyclyl". Examples include a group represented by the following Formula:

[Formula 55]

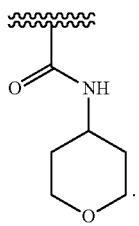

"Monoalkyloxycarbamoyl" means a carbamoyl group one hydrogen atom bonded to the nitrogen atom of which is replaced with the above "alkyloxy". For example, methyloxycarbamoyl and the like are exemplified.

"Dialkyloxycarbamoyl" means a carbomoyl group two hydrogen atoms bonded to the nitrogen of which are replaced with the above "alkyloxy". For example, di(methyloxy)carbamoyl and the like are exemplified.

"Monoalkylsulfamoyl" means a sulfamoyl group one hydrogen atom bonded to nitrogen atom of which is replaced with the above "alkyl". For example, methylsulfamoyl, dimethylsulfamoyl and the like are exemplified.

"Dialkylsulfamoyl" means a sulfamoyl group two hydrogen atoms bonded to the nitrogen atom of which are replaced with the above "alkyl". Two alkyl groups may be same or different. For example, dimethylsulfamoyl, diethylsulfamoyl and the like are exemplified.

"Aromatic carbocyclylalkyl" means the above "alkyl" substituted with one or more above "aromatic carbocyclyl". For example, benzyl, phenethyl, phenylpropyl, benzhydryl, trityl, naphthylmethyl, a group represented by the following formula:

[Formula 56]

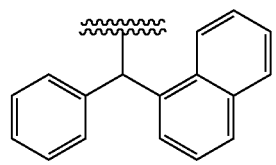

and the like are exemplified.

A preferable embodiment of "aromatic carbocyclylalkyl" includes benzyl, phenethyl, benzhydryl and the like.

"Cycloalkylalkyl" means the above "alkyl" substituted with one or more above "cycloalkyl". "Cycloalkylalkyl" includes "cycloalkylalkyl" which the alkyl part is further substituted with the above "aromatic carbocyclyl". For example, cyclopentylmethyl, cyclohexylmethyl, a group represented by the following formula:

[Formula 57]

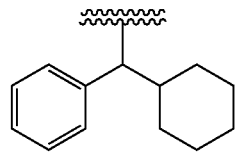

and the like are exemplified.

"Cycloalkenylalkyl" means the above "alkyl" substituted with one or more above "cycloalkenyl". "Cycloalkenylalkyl" includes "Cycloalkenylalkyl" which the alkyl part is further substituted with the above "aromatic carbocyclyl". For example, cyclopropenylmethyl, cyclobutenylmethyl, cyclopentenylmethyl, cyclohexenylmethyl, and the like are exemplified.

"Aromatic heterocyclylalkyl" means the above "alkyl" substituted with one or more above "aromatic carbocyclyl". "Aromatic heterocyclylalkyl" includes "Aromatic heterocyclylalkyl" which the alkyl part is further substituted with the above "aromatic carbocyclyl" and/or "non-aromatic carbocyclyl". For example, pyridylmethyl, furanylmethyl, imidazolylmethyl, indolylmethyl, benzothiophenylmethyl, oxazolylmethyl, isoxazolylmethyl, thiazolylmethyl, isothiazolylmethyl, pyrazolylmethyl, isopyrazolylmethyl, pyrrolidinylmethyl, benzoxazolylmethyl, a group represented by the following formula:

[Formula 58]

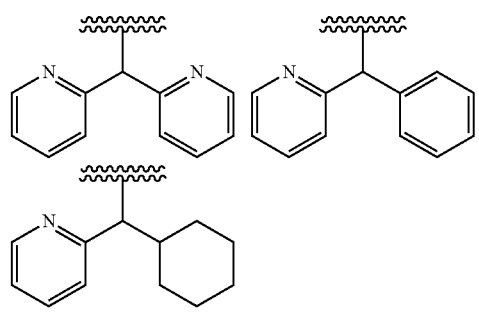

and the like are exemplified.

"Non-aromatic heterocyclylalkyl" means the above "alkyl" substituted with one or more above "non-aromatic heterocyclyl". "Non-aromatic heterocyclylalkyl" includes "non-aromatic heterocyclylalkyl" which the alkyl part is further substituted with the above "aromatic carbocyclyl", "non-aromatic carbocyclyl" and/or "aromatic heterocyclyl". For example, tetrahydropyranylmethyl, morpholinylethyl, piperidinylmethyl, piperazinylmethyl, a group represented by the following formula:

[Formula 59]

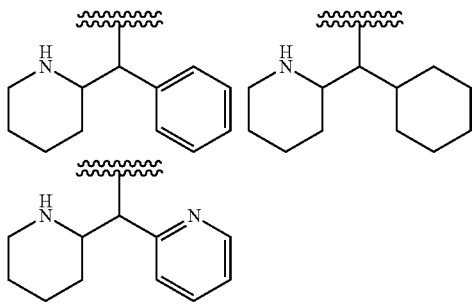

and the like are exemplified.

"Non-aromatic heterocyclylalkylcarbamoyl" means a carbamoyl group one or two hydrogen atom(s) bonded to nitrogen atom of which is replaced with one or two above "non-aromatic heterocyclylalkyl". For example, a group represented by the following formula is exemplified:

[Formula 60]

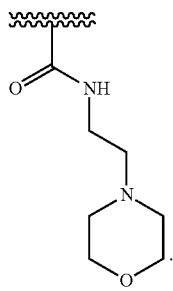

"Aromatic carbocyclylalkyloxy" means the above "alkyloxy" substituted with one or more above "aromatic carbocycle". For example, benzyloxy, phenethyloxy, phenylpropynyloxy, benzhydryloxy, trityloxy, naphthylmethyloxy, a group represented by the following formula:

[Formula 61]

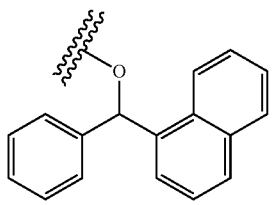

and the like are exemplified.

"Non-aromatic carbocyclylalkyloxy" means the above "alkyloxy" substituted with one or more above "non-aromatic carbocyclyl". "Non-aromatic carbocyclylalkyloxy" includes "non-aromatic carbocyclylalkyloxy" which the alkyl part are further substituted with the above "aromatic carbocyclyl". For example, cyclopeopylmethyloxy, cyclobutylmethyloxy, cyclopenthylmethyloxy, cyclohexylmethyloxy, cyclopropylmethyloxy, cyclobutylmethyloxy, cyclopenthylmethyloxy, cyclohexylmethyloxy, a group represented by the following formula:

[Formula 62]

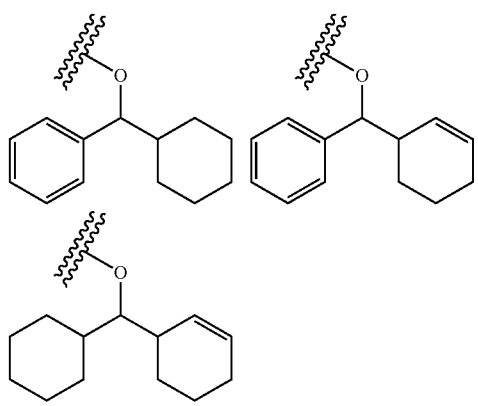

and the like are exemplified.

"Aromatic heterocyclylalkyloxy" means the above "alkyloxy" substituted with one or more above "aromatic heterocyclyl". "Aromatic heterocyclylalkyloxy" includes "aromatic heterocyclylalkyloxy" which the alkyl part is further substituted with the above "aromatic carbocyclyl" and/or "non-aromatic carbocyclyl". For example, pyridylmethyloxy, furanylmethyloxy, imidazolylmethyloxy, indolylmethyloxy, benzothiophenylmethyloxy, oxazolylmethyloxy, isoxazolylmethyloxy, thiazolylmethyloxy, isothiazolylmethyloxy, pyrazolylmethyloxy, isopyrazolylmethyloxy, pyrrolidinylmethyloxy, benzoxazolylmethyloxy, a group represented by the following formula:

[Formula 63]

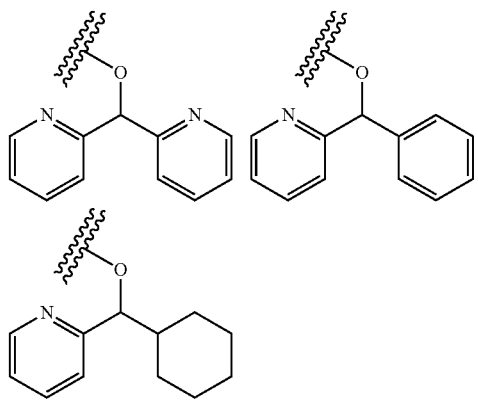

and the like are exemplified.

"Non-aromatic heterocyclylalkyloxy" means the above "alkyloxy" substituted with one or more above "non-aromatic heterocyclyl". "Non-aromatic heterocyclylalkyloxy" includes "non-aromatic heterocyclylalkyloxy" which the alkyl part is further substituted with the above "aromatic carbocyclyl", "non-aromatic carbocyclyl" and/or "aromatic heterocyclyl". For example, tetrahydropyranylmethyloxy, morpholinylethyloxy, piperidinylmethyloxy, piperazinylmethyloxy, a group represented by the following formula:

[Formula 64]

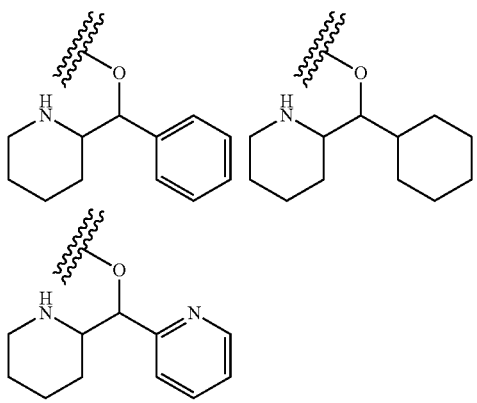

and the like are exemplified.

"Aromatic carbocyclylalkyloxycarbonyl" means the above "alkyloxycarbonyl" substituted with one or more above "aromatic carbocyclyl". For example, benzyloxycarbonyl, phenethyloxycarbonyl, phenylpropynyloxycarbonyl, benzhydryloxycarbonyl, trityloxycarbonyl, naphthylmethyloxycarbonyl, a group represented by the following formula:

[Formula 65]

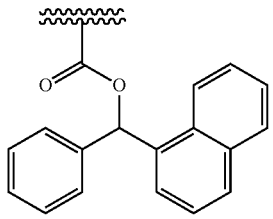

and the like are exemplified.

"Non-aromatic carbocyclylalkyloxycarbonyl" means the above "alkyloxycarbonyl" substituted with one or more above "non-aromatic carbocyclyl". "Non-aromatic carbocyclylalkyloxycarbonyl" includes "non-aromatic carbocyclylalkyloxycarbonyl" which the alkyl part is further substituted with the above "aromatic carbocyclyl". For example, cyclopropylmethyloxycarbonyl, cyclobutylmethyloxycarbonyl, cyclopentylmethyloxycarbonyl, cyclohexylmethyloxycarbonyl, cyclopropenylmethyloxycarbonyl, cyclobutenylmethyloxycarbonyl, cyclopentenylmethyloxycarbonyl, cyclohexenylmethyloxycarbonyl, a group represented by the following formula:

[Formula 66]

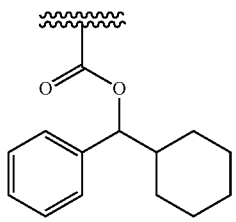

and the like are exemplified.

"Aromatic heterocyclylalkyloxycarbonyl" means the above "alkyloxycarbonyl" substituted with one or more above "aromatic heterocyclyl". "Aromatic heterocyclylalkyloxycarbonyl" includes "aromatic heterocyclylalkyloxycarbonyl" which the alkyl part is further substituted with the above "aromatic carbocyclyl" and/or "non-aromatic carbocyclyl". For example, pyridylmethyloxycarbonyl, furanylmethyloxycarbonyl, imidazolylmethyloxycarbonyl, indolylmethyloxycarbonyl, benzothiophenylmethyloxycarbonyl, oxazolylmethyloxycarbonyl, isoxazolylmethyloxycarbonyl, thiazolylmethyloxycarbonyl, isothiazolylmethyloxycarbonyl, pyrazolylmethyloxycarbonyl, isopyrazolylmethyloxycarbonyl, pyrrolidinylmethyloxycarbonyl, benzoxazolylmethyloxycarbonyl, a group represented by the following formula:

[Formula 67]

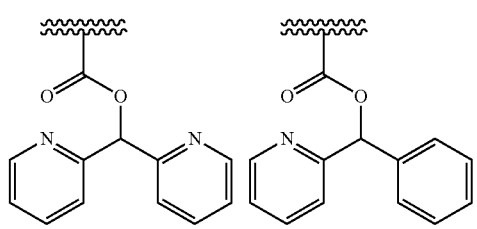

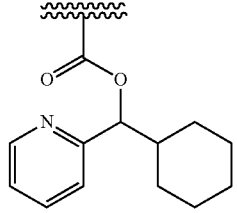

and the like are exemplified.

"Non-aromatic heterocyclylalkyloxycarbonyl" means the above "alkyloxycarbonyl" substituted with one or more above "non-aromatic heterocyclyl". "Non-aromatic heterocyclylalkyloxycarbonyl" includes "non-aromatic heterocyclylalkyloxycarbonyl" which the alkyl part is further substituted with the above "aromatic carbocyclyl", "non-aromatic carbocyclyl" and/or "aromatic heterocycle". For example, tetrahydropyranylmethyloxy, morpholinylethyloxy, piperidinylmethyloxy, piperazinylmethyloxy, a group represented by the following formula:

[Formula 68]

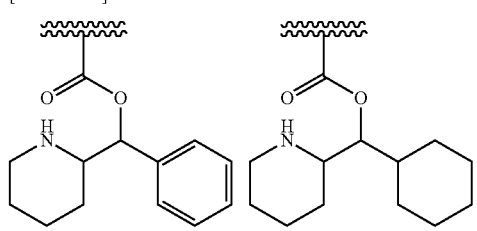

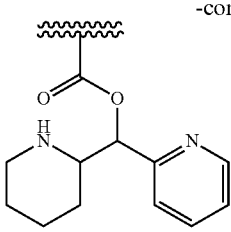

and the like are exemplified.

"Aromatic carbocyclylalkylamino" means an amino group one or two hydrogen atom(s) bonded to the nitrogen atom of which is (are) replaced with the above "aromatic carbocyclylalkyl". For example, benzylamino, phenethylamino, phenylpropynylamino, benzhydrylamino, tritylamino, naphthylmethylamino, dibenzylamino and the like are exemplified.

"Non-aromatic carbocyclylalkylamino" means an amino group one or two hydrogen atom(s) bonded to the nitrogen atom of which is (are) replaced with the above "non-aromatic carbocyclylalkyl". For example, cyclopropylmethylamino, cyclobutylmethylamino, cyclopentylmethylamino, cyclohexylmethylamino, cyclopropenylmethylamino, cyclobutenylmethylamino, cyclopentenylmethylamino, cyclohexenylmethylamino and the like are exemplified.

"Aromatic heterocyclylalkylamino" means an amino group one or two hydrogen atom(s) bonded to the nitrogen atom of which is (are) replaced with the above "aromatic heterocyclylalkyl". For example, pyridylmethylamino, franylmethylamino, imidazolylmethylamino, indolylmethylamino, benzothiophenylmethylamino, oxazolylmethylamino, isoxazolylmethylamino, thiazolylmethylamino, isothiazolylmethylamino, pyrazolylmethylamino, isopyrazolylmethylamino, pyrrolidinylmethylamino, benzoxazolylmethylamino and the like are exemplified.

"Non-aromatic heterocyclylalkylamino" means an amino group one or two hydrogen atom(s) bonded to the nitrogen atom of which is (are) replaced with the above "non-aromatic heterocyclylalkyl". For example, tetrahydropyranylmethylamino, morpholinylethylamino, piperidinylmethylamino, piperazinylmethylamino and the like are exemplified.

"Alkyloxyalkyl" means the above "alkyl" substituted with one or two above "alkyloxy". For example, methyloxymethyl, methyloxyethyl, ethyloxymethyl and the like are exemplified.

"Aromatic carbocyclylalkyloxyalkyl" means the above "alkyloxyalkyl" substituted with one or more above "aromatic carbocyclyl". For example, benzyloxymethyl, phenethyloxymethyl, phenylpropynyloxymethyl, benzhydryloxymethyl, trityloxymethyl, naphthylmethyloxymethyl, a group represented by the following formula:

[Formula 69]

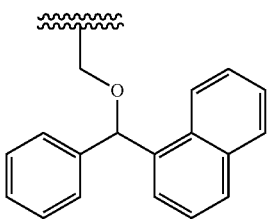

and the like are exemplified.

"Non-aromatic carbocyclylalkyloxyalkyl" means the above "alkyloxyalkyl" substituted with one or more above "non-aromatic carbocyclyl". "Non-aromatic carbocyclylalkyloxyalkyl" includes "non-aromatic carbocyclylalkyloxyalkyl" which the alkyl part bonded to the non-aromatic heterocycle is further substituted with the above "aromatic carbocyclyl". For example, cyclopropylmethyloxymethyl, cyclobutylmethyloxymethyl, cyclopentylmethyloxymethyl, cyclohexylmethyloxymethyl, cyclopropenylmethyloxymethyl, cyclobutenylmethyloxymethyl, cyclopentenylmethyloxymethyl, cyclohexenylmethyloxymethyl, groups represented by the following formula:

[Formula 70]

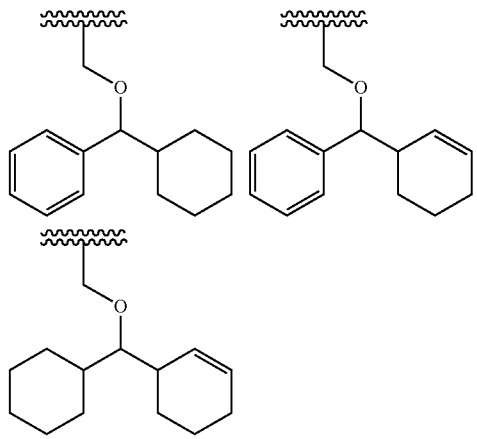

and the like are exemplified.

"Aromatic heterocyclylalkyloxyalkyl" means the above "alkyloxyalkyl" substituted with one or more above "aromatic heterocyclyl". "Aromatic heterocyclylalkyloxyalkyl" includes "aromatic heterocyclylalkyloxyalkyl" which the alkyl part bonded to the aromatic heterocycle is further substituted with the above "aromatic carbocyclyl" and/or "non-aromatic carbocyclyl". For example, pyridylmethyloxymethyl, franylmethyloxymethyl, imidazolylmethyloxymethyl, indolylmethyloxymethyl, benzothiophenylmethyloxymethyl, oxazolylmethyloxymethyl, isoxazolylmethyloxymethyl, thiazolylmethyloxymethyl, isothiazolylmethyloxymethyl, pyrazolylmethyloxymethyl, isopyrazolylmethyloxymethyl, pyrrolidinylmethyloxymethyl, benzoxazolylmethyloxymethyl, groups represented by the following formula:

[Formula 71]

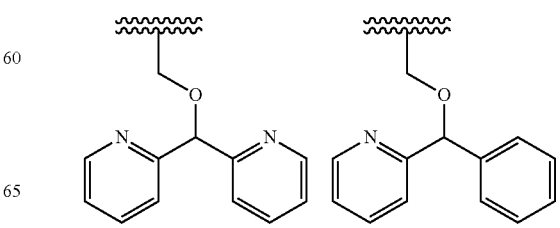

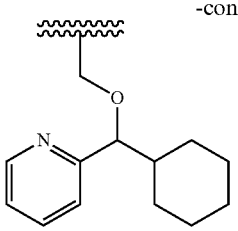

and the like are exemplified.

"Non-aromatic heterocyclylalkyloxyalkyl" means the above "alkyloxyalkyl" substituted with one or more above "non-aromatic heterocyclyl". "Non-aromatic heterocyclylalkyloxyalkyl" includes "non-aromatic heterocyclylalkyloxyalkyl" which the alkyl part bonded to the non-aromatic heterocycle is further substituted with the above "aromatic carbocyclyl", "non-aromatic carbocyclyl" and/or "aromatic heterocyclyl". For example, tetrahydropyranylmethyloxymethyl, morpholinylethyloxymethyl, piperidinylmethyloxymethyl, piperazinylmethyloxymethyl, groups represented by the following formula:

[Formula 72]

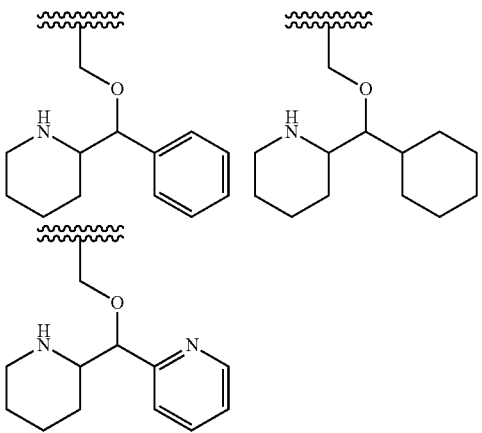

and the like are exemplified.

"Alkyloxyalkyloxy" means the above "alkyloxyalkyl" bonded to an oxygen atom.

Preferable embodiments of $R^1$, $R^2$, $R^3$, $R^4$, -$L^1$-, -$L^2$- and ring A in the compounds of formula (I) are described below.

[Formula 73]

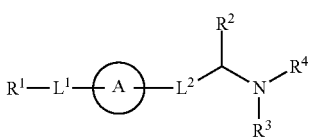

(I)

The following possible combinatorial compounds are preferable.

$R^1$ includes substituted or unsubstituted fused aromatic heterocyclyl, substituted or unsubstituted fused aromatic carbocyclyl, substituted or unsubstituted non-aromatic heterocyclyl, substituted or unsubstituted non-aromatic carbocyclyl, a group represented by Formula:

[Formula 74]

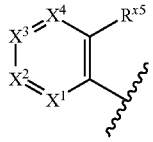

or substituted or unsubstituted 5-membered aromatic heterocyclyl,
$X^1$ is N or $C(R^{x1})$,
$X^2$ is N or $C(R^{x2})$,
$X^3$ is N or $C(R^{x3})$,
$X^4$ is N or $C(R^{x4})$,
$R^{x1}$, $R^{x2}$, $R^{x3}$, and $R^{x4}$ include each independently hydrogen, halogen, hydroxy, carboxy, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfanyl, substituted or unsubstituted alkynylsulfanyl, substituted or unsubstituted amino, substituted or unsubstituted carbamoyl, substituted or unsubstituted sulfamoyl, substituted or unsubstituted alkylcarbonyl, substituted or unsubstituted alkenylcarbonyl, substituted or unsubstituted alkynylcarbonyl, substituted or unsubstituted alkyloxycarbonyl, substituted or unsubstituted alkenyloxycarbonyl, substituted or unsubstituted alkynyloxycarbonyl or substituted or unsubstituted sulfamoyl,
$R^{x5}$ includes halogen, hydroxy, carboxy, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfanyl, substituted or unsubstituted alkynylsulfanyl, substituted or unsubstituted amino, substituted or unsubstituted carbamoyl, substituted or unsubstituted alkylcarbonyl, substituted or unsubstituted alkenylcarbonyl, substituted or unsubstituted alkynylcarbonyl, substituted or unsubstituted alkyloxycarbonyl, substituted or unsubstituted alkenyloxycarbonyl, substituted or unsubstituted alkynyloxycarbonyl or substituted or unsubstituted sulfamoyl.

A preferable embodiment of $R^1$ includes substituted or unsubstituted benzothiazolyl, substituted or unsubstituted benzoxazolyl, substituted or unsubstituted benzimidazolyl, substituted or unsubstituted indolyl, substituted or unsubstituted indazolyl, substituted or unsubstituted isoquinolyl, substituted or unsubstituted quinoxalinyl, substituted or unsubstituted naphtalenyl, substituted or unsubstituted aziridinyl, substituted or unsubstituted oxyranyl, substituted or unsubstituted thiiranyl, substituted or unsubstituted azetidinyl, substituted or unsubstituted oxetanyl, substituted or unsubstituted thietanyl, substituted or unsubstituted pyrrolidinyl, substituted or unsubstituted tetrahydrofuranyl, substituted or unsubstituted tetrahydrothiophenyl, substituted or unsubstituted piperidinyl, substituted or unsubstituted piperidino, substituted or unsubstituted tetrahydropyranyl, substituted or unsubstituted tetrahydropyranyl, substituted or unsubstituted piperazinyl, substituted or unsubstituted morpholinyl, substituted or unsubstituted morpholino, substituted or unsubstituted thiomorpholinyl, substituted or unsubstituted thiomorpholino, substituted or unsubstituted cyclobutanyl, the groups represented by Formula:

[Formula 75]

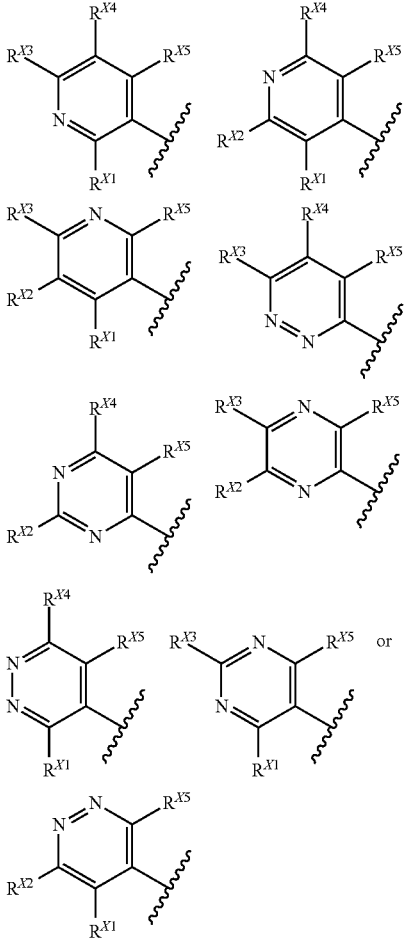

or substituted or unsubstituted 5-membered aromatic heterocyclyl.

Another preferable embodiment of $R^1$ includes substituted or unsubstituted naphtalenyl, substituted or unsubstituted pyrimidinyl, substituted or unsubstituted dihydroindenyl, substituted or unsubstituted dihydrobenzofuranyl, substituted or unsubstituted indolinyl, substituted or unsubstituted tetrahydroisoquinolinyl, substituted or unsubstituted benzoxazolyl, substituted or unsubstituted benzothiazolyl, substituted or unsubstituted benzopyrazolyl, substituted or unsubstituted benzoisothiazolyl or substituted or unsubstituted oxazolinyl and the like.

Furthermore, another preferable embodiment of $R^1$ includes substituted or unsubstituted naphtalenyl, substituted or unsubstituted dihydroindenyl, substituted or unsubstituted dihydrobenzofuranyl, substituted or unsubstituted indolinyl, substituted or unsubstituted tetrahydroisoquinolinyl, substituted or unsubstituted benzoxazolyl, substituted or unsubstituted benzothiazolyl, substituted or unsubstituted benzopyrazolyl, substituted or unsubstituted benzoisothiazolyl, substituted or unsubstituted oxazolinyl or the group represented by Formula:

[Formula 76]

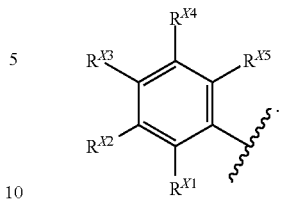

Furthermore, another preferable embodiment of $R^1$ includes substituted or unsubstituted benzothiazolyl, substituted or unsubstituted benzoxazolyl, substituted or unsubstituted benzoimidazolyl, substituted or unsubstituted benzopyrazolyl, substituted or unsubstituted thiazolopyridinyl, substituted or unsubstituted indolyl, substituted or unsubstituted indazolyl, substituted or unsubstituted isoquinolyl, substituted or unsubstituted quinazolinyl or substituted or unsubstituted quinoxalinyl.

In the above formula, $R^{x1}$, $R^{x2}$, $R^{x3}$, and $R^{x4}$ include each independently hydrogen, halogen, hydroxy, carboxy, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkyl sulfanyl, substituted or unsubstituted alkenylsulfanyl, substituted or unsubstituted alkynylsulfanyl, substituted or unsubstituted amino, substituted or unsubstituted carbamoyl, substituted or unsubstituted sulfamoyl, substituted or unsubstituted alkylcarbonyl, substituted or unsubstituted alkenylcarbonyl, substituted or unsubstituted alkynylcarbonyl, substituted or unsubstituted alkyloxycarbonyl, substituted or unsubstituted alkenyloxycarbonyl, substituted or unsubstituted alkynyloxycarbonyl or substituted or unsubstituted sulfamoyl.

A preferable embodiment of $R^{x1}$, $R^{x2}$, $R^{x3}$, and $R^{x4}$ include each independently hydrogen, halogen, hydroxy, carboxy, cyano, substituted or unsubstituted alkyl, substituted or unsubstituted alkyloxy, substituted or unsubstituted alkylsulfanyl, substituted or unsubstituted amino, substituted or unsubstituted carbamoyl, substituted or unsubstituted alkylcarbonyl, substituted or unsubstituted alkyloxycarbonyl or substituted or unsubstituted sulfamoyl.

Another preferable embodiment of $R^{x1}$, $R^{x2}$, $R^{x3}$, and $R^{x4}$ include hydrogen, halogen, cyano or substituted or unsubstituted alkyl.

$R^{x5}$ includes halogen, hydroxy, carboxy, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfanyl, substituted or unsubstituted alkynylsulfanyl, substituted or unsubstituted amino, substituted or unsubstituted carbamoyl, substituted or unsubstituted alkylcarbonyl, substituted or unsubstituted alkenylcarbonyl, substituted or unsubstituted alkynylcarbonyl, substituted or unsubstituted alkyloxycarbonyl, substituted or unsubstituted alkenyloxycarbonyl, substituted or unsubstituted alkynyloxycarbonyl or substituted or unsubstituted sulfamoyl.

Another preferable embodiment of $R^{x5}$ includes halogen, cyano, substituted or unsubstituted alkyl, substituted or unsubstituted alkyloxy, substituted or unsubstituted alkylsulfanyl, substituted or unsubstituted amino, substituted or unsubstituted carbamoyl, substituted or unsubstituted alkylcarbonyl, substituted or unsubstituted alkyloxycarbonyl or substituted or unsubstituted sulfamoyl.

Another preferable embodiment of $R^{x5}$ includes halogen, cyano, substituted or unsubstituted alkyl, substituted or unsubstituted alkyloxy, substituted or unsubstituted alkylsulfanyl, substituted or unsubstituted amino, substituted or unsubstituted carbamoyl or substituted or unsubstituted alkylcarbonyl.

Furthermore, another preferable embodiment of $R^1$ includes the groups represented by Formula:

[Formula 77]

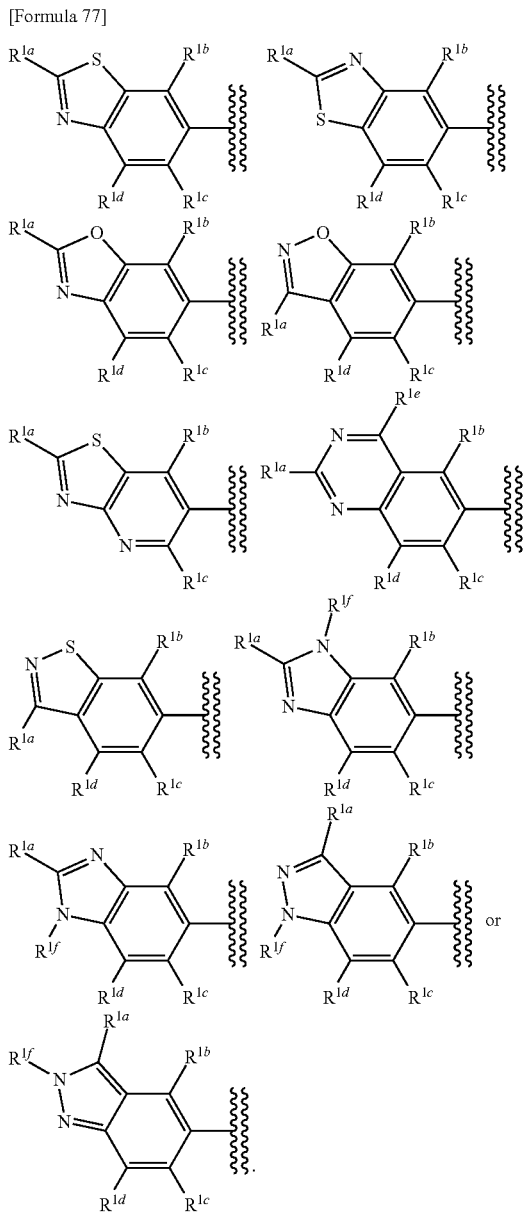

In the above formula, a preferable embodiment of $R^{1a}$, $R^{1b}$, $R^{1c}$, $R^{1d}$ and $R^{1e}$ includes each independently hydrogen, halogen, hydroxy, carboxy, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfanyl, substituted or unsubstituted alkynylsulfanyl, substituted or unsubstituted amino, substituted or unsubstituted carbamoyl, substituted or unsubstituted sulfamoyl, substituted or unsubstituted alkylcarbonyl, substituted or unsubstituted alkenylcarbonyl, substituted or unsubstituted alkynylcarbonyl, substituted or unsubstituted alkyloxycarbonyl, substituted or unsubstituted alkenyloxycarbonyl or substituted or unsubstituted alkynyloxycarbonyl.

More preferably, $R^{1a}$, $R^{1b}$, $R^{1c}$, $R^{1d}$ and $R^{1e}$ include each independently hydrogen, halogen, cyano, substituted or unsubstituted alkyl, substituted or unsubstituted alkyloxy, substituted or unsubstituted alkylsulfanyl, substituted or unsubstituted amino, substituted or unsubstituted carbamoyl, substituted or unsubstituted sulfamoyl, substituted or unsubstituted alkylcarbonyl or substituted or unsubstituted alkyloxycarbonyl.

Especially, preferable examples include each independently hydrogen, halogen, cyano, substituted or unsubstituted alkyl or substituted or unsubstituted alkyoxy.

A preferable embodiment of $R^{1a}$ includes substituted or unsubstituted alkyl or substituted or unsubstituted alkyloxy.

In the above formula, a preferable embodiment of $R^{1f}$ includes hydrogen, substituted or unsubstituted alkyl, substituted or unsubstituted alkenyl, substituted or unsubstituted alkynyl, substituted or unsubstituted alkylcarbonyl, substituted or unsubstituted alkenylcarbonyl or substituted or unsubstituted alkynylcarbonyl, more preferably hydrogen, substituted or unsubstituted alkyl, substituted or unsubstituted alkylcarbonyl.

$R^2$ includes substituted or unsubstituted alkyl.

A preferable embodiment of $R^2$ includes methyl or hydroxymethyl.

$R^3$ includes hydrogen or substituted or unsubstituted alkyl.

A preferable embodiment of $R^3$ includes hydrogen.

$R^4$ includes substituted or unsubstituted alkylcarbonyl, substituted or unsubstituted alkenylcarbonyl, substituted or unsubstituted alkynylcarbonyl, substituted or unsubstituted non-aromatic carbocyclylcarbonyl, substituted or unsubstituted aromatic carbocyclylcarbonyl, substituted or unsubstituted non-aromatic heterocyclylcarbonyl, substituted or unsubstituted aromatic heterocyclylcarbonyl, substituted or unsubstituted alkyloxycarbonyl, substituted or unsubstituted alkenyloxycarbonyl, substituted or unsubstituted alkynyloxycarbonyl, substituted or unsubstituted non-aromatic carbocyclyloxycarbonyl, substituted or unsubstituted aromatic carbocyclyloxycarbonyl, substituted or unsubstituted non-aromatic heterocyclyloxycarbonyl, substituted or unsubstituted aromatic heterocyclyloxycarbonyl or substituted or unsubstituted carbamoyl.

A preferable embodiment of $R^4$ includes substituted or unsubstituted alkylcarbonyl, substituted or unsubstituted alkenylcarbonyl, substituted or unsubstituted alkynylcarbonyl, substituted or unsubstituted alkyloxycarbonyl, substituted or unsubstituted alkenyloxycarbonyl, substituted or unsubstituted alkynyloxycarbonyl or substituted or unsubstituted carbamoyl.

Another preferable embodiment of $R^4$ includes substituted or unsubstituted alkylcarbonyl, substituted or unsubstituted alkyloxycarbonyl or substituted or unsubstituted carbamoyl.

-$L^1$- includes —O—$(CR^6R^7)$m-.

A preferable embodiment of -$L^1$- includes —O— or —O—$CH_2$—.

Another preferable embodiment of -$L^1$- includes —O—.

-$L^2$- includes —O—$(CR^6R^7)$n- or —C(=O)—$(CR^6R^7)$n-.

A preferable embodiment of -L²- includes —O—CH₂—, —O—CH(CH₃)—, —O—CH₂—CH₂— or —C(=O)—(CH₂)—.

Another preferable embodiment of -L²- includes —O—CH₂—, —O—CH(CH₃)— or —O—CH₂—CH₂—.

Another preferable embodiment of -L²- includes —O—CH₂— or —O—CH(CH₃)—.

Each R⁶ is independently hydrogen, halogen, substituted or unsubstituted alkyl, substituted or unsubstituted alkenyl or substituted or unsubstituted alkynyl.

A preferable embodiment of R⁶ includes hydrogen, halogen or substituted or unsubstituted alkyl.

Another preferable embodiment of R⁶ includes hydrogen or substituted or unsubstituted alkyl.

Each R⁷ is independently hydrogen, halogen, substituted or unsubstituted alkyl, substituted or unsubstituted alkenyl or substituted or unsubstituted alkynyl.

A preferable embodiment of R⁷ includes hydrogen, halogen or substituted or unsubstituted alkyl.

Another preferable embodiment of R⁷ includes hydrogen or substituted or unsubstituted alkyl.

A preferable embodiment of the ring which is formed by R² taken together with either R⁶ or R⁷ includes cyclobutane, cyclopentane, cyclohexane, oxetane, tetrahydrofuran, tetrahydropyran, azetidine, piperidine, piperazine or morpholine.

Another preferable embodiment of the ring which is formed by R² taken together with either R⁶ or R⁷ includes cyclobutane, cyclopentane or cyclohexane.

A preferable embodiment of n includes 1.

A preferable embodiment of m includes 0 or 1.

Another preferable embodiment of m includes 0.

A preferable embodiment of the group represented by Formula:

[Formula 78]

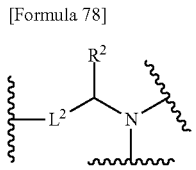

includes the group represented by Formula:

[Formula 79]

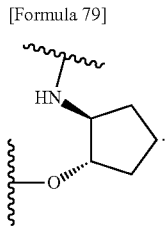

Ring A includes substituted or unsubstituted benzene, substituted or unsubstituted 4- to 6-membered non-aromatic carbocycle, substituted or unsubstituted 5- to 6-membered aromatic heterocycle or substituted or unsubstituted 4- to 6-membered non-aromatic heterocycle.

A preferable embodiment of ring A includes substituted or unsubstituted cyclobutane, substituted or unsubstituted cyclopentane, substituted or unsubstituted azetidine, substituted or unsubstituted oxetane, substituted or unsubstituted thietane, substituted or unsubstituted pyrrolidine, substituted or unsubstituted tetrahydrofuran, substituted or unsubstituted thiorane, substituted or unsubstituted piperidine, substituted or unsubstituted molpholine, substituted or unsubstituted tetrahydropyran, substituted or unsubstituted tetrahydrothiopyran, substituted or unsubstituted pyrrole, substituted or unsubstituted furan, substituted or unsubstituted thiophene, substituted or unsubstituted imidazole, substituted or unsubstituted pyrazole, substituted or unsubstituted oxazole, substituted or unsubstituted isoxazole, substituted or unsubstituted thiazole, substituted or unsubstituted isothiazole, substituted or unsubstituted oxadiazole, substituted or unsubstituted thiadiazole, substituted or unsubstituted pyridine, substituted or unsubstituted pyrimidine, substituted or unsubstituted pyrazine or substituted or unsubstituted pyridazine.

Another preferable embodiment of ring A includes substituted or unsubstituted cyclobutane, substituted or unsubstituted cyclopentane, substituted or unsubstituted cyclohexaneubstituted or unsubstituted benzene, substituted or unsubstituted piperidine, substituted or unsubstituted pyridine, substituted or unsubstituted pyrazine, substituted or unsubstituted pyrimidine or substituted or unsubstituted thiazole.

Another preferable embodiment of ring A includes cyclobutane, cyclohexane, benzene, piperidine, pyrazine, pyrimidine or thiazole.

"A disease associated with ACC2" includes metabolic syndrome, obesity, diabetes, insulin resistance, abnormal glucose tolerance, diabetic peripheral neuropathy, diabetic nephropathy, diabetic retinal disease, diabetic macroangiopathy, hyperlipidemia, hypertension, cardiovascular illness, arterial sclerosis, atherosclerotic cardiovascular disease, cardiac arrest, cardiac infarction, infectious disease, neoplasm and the like.

The compound of formula (I) and (I') are not limited to the specific isomer, include all possible isomers (for example, keto-enol isomer, imine-enamine isomer, diastereo isomer, enantiomer, rotamer and the like) and racemates or thereof, with the exception of a part represented by the chemical structure.

One or more hydrogen, carbon and/or other atoms of the compounds of formula (I) and (I') can be replaced by an isotope of the hydrogen, carbon, and/or other atoms. The examples of isotopes include isotopes of hydrogen, carbon, nitrogen, oxygen, phosphorous, sulfur, fluorine and chloride, such as ²H, ³H, ¹¹C, ¹³C, ¹⁴C, ¹⁵N, ¹⁸O, ¹⁷O, ³¹P, ³²P, ³⁵S, ¹⁸F, ¹²³I and ³⁶Cl, respectively. The compounds of formula (I) and (I') include compounds that substituted with the isotopes. And the compounds substituted with the isotopes are useful as medicine, and include radiolabeled forms of the compounds of formula (I) and (I') "radiolabeled", "radiolabeled form". The process for radiolabeling the compounds thereof to prepare the "radiolabeled form" is encompassed by the invention, is useful as a research and/or diagnostic tool in metabolism pharmacokinetic studies and in binding assays.

Radiolabeled compounds of formula (I) and (I') can be prepared by methods known in the art. For example, tritiated compounds of formula (I) and (I') can be prepared by introducing tritium into the particular compound of formula ((I) and (I'), for example, by catalytic dehalogenation with tritium. This method may include reacting a suitably halogen-substituted precursor of a compound of formula (I) and (I') with tritium gas in the presence of a suitable catalyst such as Pd/C, in the presence or absence of a base. Other suitable methods for preparing tritiated compounds can be found in Filer, Isotopes in the Physical and Biomedical Sciences, Vol.

1, Labeled Compounds (Part A), Chapter 6 (1987). $^{14}$C-labeled compounds can be prepared by employing materials having a $^{14}$C carbon.

Examples of "pharmaceutically acceptable salts" include salt such as a compound of formula (I) and (I') with alkaline metals (e.g.: lithium, sodium, potassium etc.), alkaline earth metals (e.g., calcium, barium etc.), magnesium, transition metals (e.g. zinc, iron etc.), ammonium, organic bases (e.g. trimethylamine, triethylamine, dicyclohexylamine, ethanolamine, diethanolamine, triethanolamine, meglumine, diethanolamine, ethylenediamine, pyridine, picoline, quinolone etc.) and amino acids, and salts with inorganic acids (e.g. hydrocholoric, sulfuric acid, nitric acid, carbonic acids, hydrobromic acid, phosphoric acid, hydroiodic acid etc.), or organic acids (e.g. formic acid, acetic acid, propionic acid, trifluoroacetic acid, citric acid, lactic acid, tartaric acid, oxalic acid, maleic acid, fumaric acid, maldelic acid, glutaric acid, malic acid, benzoic acid, phthalic acid, ascorbic acid, benzenesulfonic acid, p-toluenesulfonic acid, methanesulfonic acid, ethanesulfonic acid etc.). Especially, preferable examples are salts with hydrochloric acid, sulfuric acid, phosphoric acid, tartaric acid, or methanesulfonic acid. These salts may be formed by a routine method.

The compounds of the invention of formula (I) and (I') or its pharmaceutically acceptable salts can be prepared in a form of solvate thereof (for example, hydrate etc.) and/or its crystal polymorph, the present invention includes such solvate and polymorph. Any number of solvent molecules can be coordinated to form such solvate to the compounds of formula (I) and (I'). When the compounds of formula (I) and (I') or its pharmaceutically acceptable salt are left in the atmosphere, its can absorb moisture to attach the absorbed water or to form the hydrate. Also, the compounds of formula (I) and (I') or its pharmaceutically acceptable salt can be recrystallized to form the crystal polymorph.

The compounds of the invention of formula (I) and (I') or its pharmaceutically acceptable salts can be formed the prodrug, the present invention includes the various prodrug. The prodrug is the derivatives of the compounds for this invention having the group decomposed by chemical or metabolic method, and are compounds that prepared by solvolysis or under condition, and are compounds having an activity in vivo. The prodrug includes compounds converted to the compounds for this invention of formula (I) and (I') by oxidation, reduction or hydrolysis under physiological conditions in vivo and compounds hydrolyzed to the compounds for this invention of formula (I) and (I') by gastric acid and the like. The methods for selecting suitable prodrug derivatives and preparing thereof can be found in filer, for example, Design of Prodrugs, Elsevier, Amsterdam 1985. The prodrug may have an activity in its own.

When the compounds of the invention of formula (I) and (I') or its pharmaceutically acceptable salt has hydroxy, for example, it is reacted with the suitable acyl halide, the suitable acid anhydride, the suitable sulfonyl chloride, the suitable sulfonyl anhydride and mixed anhydride or with condensation agent to afford the prodrug such as the acyloxy derivatives or sulfonyloxy derivatives.

Examples of the prodrug are $CH_3COO-$, $C_2H_5COO-$, t-BuCOO—, $C_{15}H_{31}COO-$, PhCOO—, (m-NaOOCPh)COO—, $NaOOCCH_2CH_2COO-$, $CH_3CH(NH_2)COO-$, $CH_2N(CH_3)_2COO-$, $CH_3SO_3-$, $CH_3CH_2SO_3-$, $CF_3SO_3-$, $CH_2FSO_3-$, $CF_3CH_2SO_3-$, p-$CH_3$—O-$PhSO_3-$, $PhSO_3-$, p-$CH_3PhSO_3-$ and the like.

The general procedures for the compounds of the present invention are described as follows. Any starting materials are readily available ar are prepared by techniques and procedures readily available to one skilled in the art.

For example, the compound of the present invention represented by formula (I) and (I') can be prepared by the following synthetic route.

A Method for Preparing the Formula b5

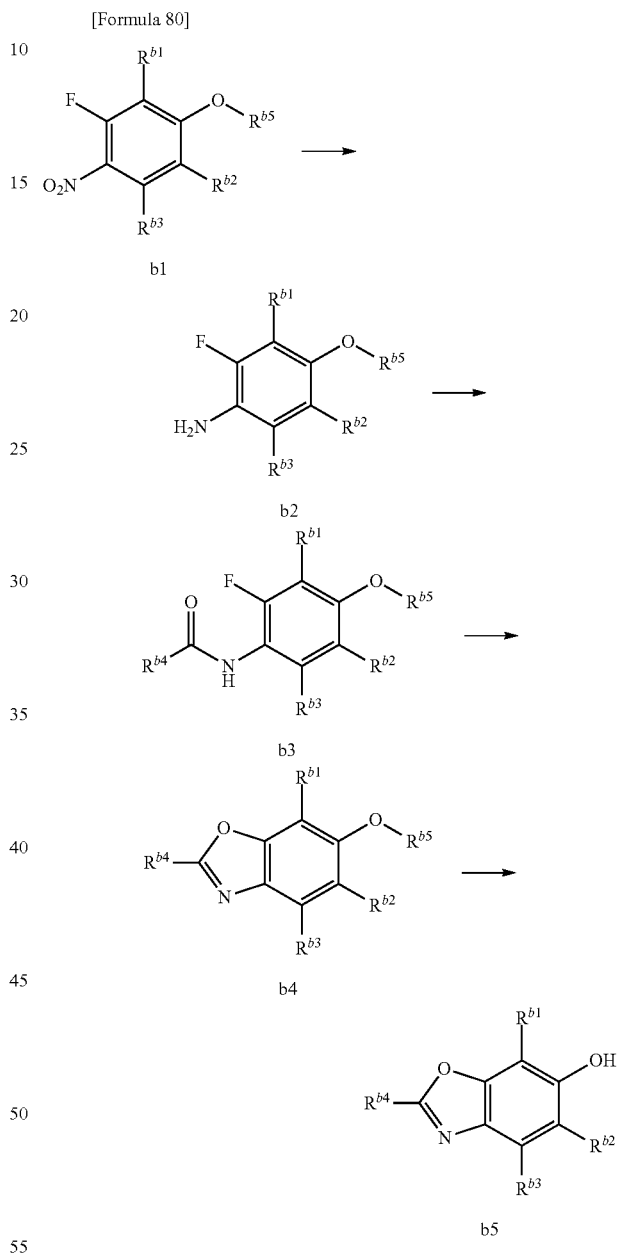

wherein $R^{b1}$, $R^{b2}$, $R^{b3}$ and $R^{b4}$ are each independently hydrogen, halogen, hydroxy, carboxy, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfanyl, substituted or unsubstituted alkynylsulfanyl, substituted or unsubstituted amino, substituted or unsubstituted carbamoyl, substituted or unsubstituted sulfamoyl, substituted or unsubstituted alkylcarbonyl, substituted or unsubstituted alkenylcarbonyl, substituted or unsubstituted alkynylcarbonyl, substituted or unsubstituted alkyloxycarbonyl, substituted or unsubstituted alkenyloxycarbonyl substituted or unsubstituted alkynyloxycarbonyl or substituted or unsubstituted sulfamoyl; $R^{65}$ is substituted or unsubstituted alkyl.

Step 1 Preparation of the Compound b2

The compound b2 can be obtained by reacting a solution of the compound b1 in the presence of iron.

Examples of the reaction solvent include water, ethanol, methanol, THF, toluene and the like, and their mixed solvents can be used as well as the single solvent.

Examples of the additive include ammonium chloride, hydrochloric acid and the like. The amount thereof may be 1 to 10 mole equivalent(s), preferably 1 to 3 mole equivalent(s), for 1 mole equivalent of the compound b1.

The reaction temperature may be room temperature to heating under reflux, preferably room temperature to 100° C.

The reaction time may be 1 to 48 hour(s), preferably 1 to 5 hour(s).

Step 2 Preparation of the Compound b3

The compound b3 can be obtained by reacting a solution of the compound b2 with a calboxylic acid in presence of a condensing agent.

Examples of the reaction solvent include DMF, NMP, THF and the like, their mixed solvent can be used as well as the single solvent.

Examples of the condensing agent include HATU, dicyclohexylcarbodiimide, carbonyl diimidazole, dicyclohexyl-carbodiimido-N-hydroxy benzotriazole, EDC, 4-(4,6-dimethyloxy-1,3,5,-triazine-2-yl)-4-methyl morpholinium chloride and the like. The amount thereof may be 1 to 10 mole equivalent(s), preferably 1 to 3 mole equivalent(s), for 1 mole equivalent of the compound b2.

The reaction temperature may be room temperature to heating under reflux, preferably room temperature to 50° C.

The reaction time may be 1 to 48 hour(s), preferably 1 to 5 hour(s).

Step 3 Preparation of the Compound b4

The compound b4 can be obtained by reacting a solution of the compound b3 in presence of a base.

Examples of the reaction solvent include NMP, DMF, THF and the like, their mixed solvent can be used as well as the single solvent.

Examples of the base include cesium carbonate, potassium carbonate, sodium carbonate and the like. The amount thereof may be 1 to 10 mole equivalent(s), preferably 1 to 3 mole equivalent(s), for 1 mole equivalent of the compound b3.

The reaction temperature may be room temperature to heating under reflux, preferably room temperature to 120° C.

The reaction time may be 0.5 to 48 hour(s), preferably 1 to 5 hour(s).

Step 4 Preparation of the Compound b5

The compound b5 can be obtained by reacting a solution of the compound b4 in presence of a Lewis acid.

Examples of the reaction solvent include toluene, methylene chloride, THF and the like, their mixed solvent can be used as well as the single solvent.

Examples of the Lewis acid include aluminum chloride, include trifluoroborane-ether complex and the like. The amount thereof may be 1 to 10 mole equivalent(s), preferably 1 to 3 mole equivalent(s), for 1 mole equivalent of the compound b4.

The reaction temperature may be room temperature to heating under reflux, preferably room temperature to 120° C.

The reaction time may be 1 to 48 hour(s), preferably 1 to 5 hour(s).

A Method for Preparing the Formula (Ia)

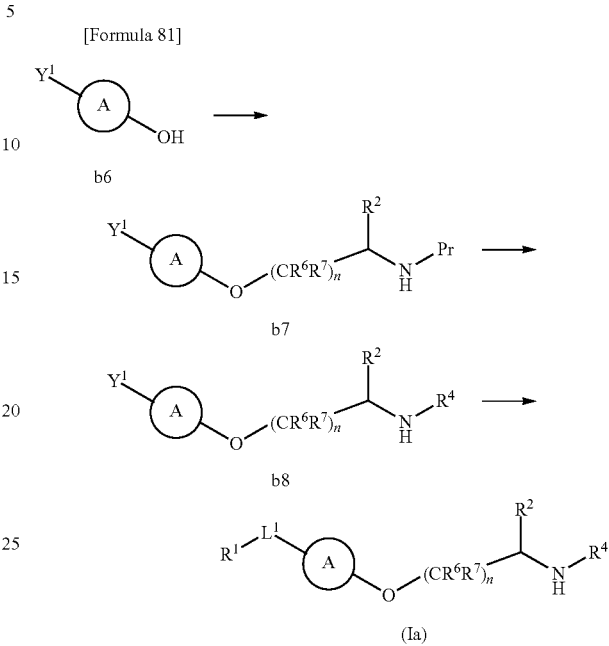

wherein $R^2$ is substituted or unsubstituted alkyl; $R^4$ is substituted or unsubstituted alkylcarbonyl, substituted or unsubstituted alkenylcarbonyl, substituted or unsubstituted alkynylcarbonyl, substituted or unsubstituted non-aromatic carbocyclylcarbonyl, substituted or unsubstituted aromatic carbocyclylcarbonyl, substituted or unsubstituted non-aromatic heterocyclylcarbonyl, substituted or unsubstituted aromatic heterocyclylcarbonyl, substituted or unsubstituted alkyloxycarbonyl, substituted or unsubstituted alkenyloxycarbonyl, substituted or unsubstituted alkynyloxycarbonyl, substituted or unsubstituted non-aromatic carbocyclyloxycarbonyl, substituted or unsubstituted aromatic carbocyclyloxycarbonyl, substituted or unsubstituted non-aromatic heterocyclyloxycarbonyl, substituted or unsubstituted aromatic heterocyclyloxycarbonyl or substituted or unsubstituted carbamoyl; each $R^6$ is independently hydrogen, halogen, substituted or unsubstituted alkyl, substituted or unsubstituted alkenyl or substituted or unsubstituted alkynyl; each $R^7$ is independently hydrogen, halogen, substituted or unsubstituted alkyl, substituted or unsubstituted alkenyl or substituted or unsubstituted alkynyl, or $R^6$ and $R^7$ on the same carbon atom may be taken together to form a ring, or $R^2$ may be taken together with either $R^6$ or $R^7$ to form a ring; each n is independently an integer of 1, 2 or 3; ring A is substituted or unsubstituted benzene, substituted or unsubstituted 4- to 6-membered non-aromatic carbocycle, substituted or unsubstituted 5- to 6-membered aromatic heterocycle or substituted or unsubstituted 4- to 6-membered non-aromatic heterocycle, $Y^1$ is a leaving group; Pr is an protecting group of amino.

Step 1 Preparation of the Compound b7

The compound b7 can be obtained by reacting a solution of the compound b6 with an alcohol in the presence of a phosphine reagent and a condensing agent.

Examples of the reaction solvent include 1,4-dioxane, THF, diethylether and the like, their mixed solvent can be obtained as well as the single solvent.

Examples of the condensing agent include dimethyl oxyethyl azodicarboxylate, diethyl azodicarboxylate and the like. The amount thereof may be 1 to 10 mole equivalent(s), preferably 1 to 3 mole equivalent(s), for 1 mole equivalent of the compound b7.

Examples of the alcohol include a primary alcohol such as (S)-t-butyl-1-hydroxy propy-2-yl carbamate etc., a secondary alcohol and the like. The amount thereof may be 1 to 10 mole equivalent(s), preferably 1 to 3 mole equivalent(s), for 1 mole equivalent of the compound b7.

Examples of the phosphine reagent include triphenylphosphine and the like. The amount thereof may be 1 to 1-mole equivalent(s), preferably 1 to 3 mole equivalent(s), for 1 mole equivalent of the compound b7.

The reaction temperature may be 0° C. to heating under reflux, preferably 0° C. to room temperature.

The reaction time may be 0.5 to 48 hour(s), preferably 1 to 5 hour(s).

Step 2 Preparation of the Compound b8

The compound b8 can be obtained by reacting with an acid anhydride in presence of a base after deprotecting the compound b7.

Examples of the deprotecting agent include hydrochloric acid-1,4-dioxane, hydrochloride-ethyl acetate, hydrochloric acid-methanol, TFA, toluene sulfonic acid and the like. The amount thereof may be 1 mole equivalent excess quantity, preferably 1 to 10 mole equivalent(s), for 1 mole equivalent of the compound b7.

Examples of the reaction solvent include 1,4-dioxane, methylene chloride, ethyl acetate, methanol and the like, their mixed solvent can be used as well as the single solvent.

Examples of the acid anhydride include acetic acid anhydride, trifluoroacetic acid anhydride and the like. The amount thereof may be 1 to 10 mole equivalent(s), preferably 1 to 3 equivalent(s), for 1 mole equivalent of the compound b7.

Examples of the base include pyridine, triethylamine, diisopropylethylamine and the like. The amount thereof may be 1 to 10 mole equivalent(s), preferably 1 to 3 mole equivalent(s), for 1 mole equivalent of the compound b7.

The reaction temperature may be 0° C. to heating under reflux, preferably 0° C. to room temperature.

The reaction time may be 0.1 to 48 hour(s), preferably 1 to 5 hour(s).

Step 3 Preparation of the Compound (Ia)

The compound (Ia) can be obtained by reacting a solution of the compound b8 with an alcohol in presence of a ligand, a base and a metal catalyst.

Examples of the ligand include N,N-dimethylglycine, glycine, methylglycine and the like. The amount thereof may be 1 to 10 mole equivalent(s), preferably 1 to 3 mole equivalent(s), for 1 mole equivalent of the compound b8.

Examples of the reaction solvent may be 1,4-dioxane, THF, DMF and the like, their mixed solvent can be used as well as the single solvent.

Examples of the metal catalyst include copper iodide, copper chloride, copper bromide and the like. The amount thereof may be 0.001 to 2 mole equivalent(s), preferably 0.01 to 0.5 mole equivalent(s), for 1 mole equivalent of the compound b8.

Examples of the base include cesium carbonate, potassium carbonate, sodium carbonate and the like. The amount thereof may be 1 to 10 mole equivalent(s), preferably 1 to 3 mole equivalent(s), for 1 mole equivalent of the compound b8.

The reaction temperature may be room temperature to heating under reflux, preferably 50° C. to heating under reflux.

The reaction time may be 1 to 48 hour(s), preferably 1 to 5 hour(s).

A Method for Preparing the Compound b12

[Formula 82]

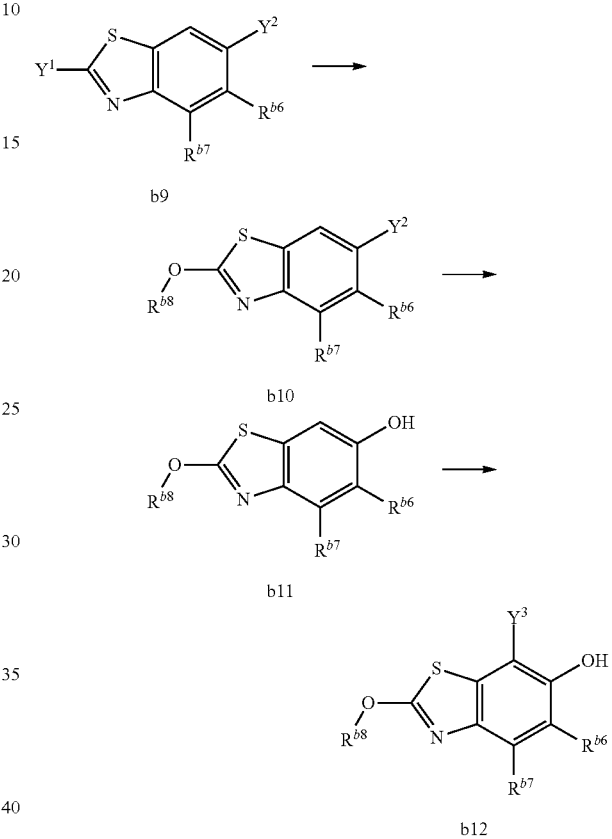

wherein each $R^{b6}$ and $R^{b7}$ is independently hydrogen, halogen, hydroxy, carboxy, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfanyl, substituted or unsubstituted alkynylsulfanyl, substituted or unsubstituted amino, substituted or unsubstituted carbamoyl, substituted or unsubstituted sulfamoyl, substituted or unsubstituted alkylcarbonyl, substituted or unsubstituted alkenylcarbonyl, substituted or unsubstituted alkynylcarbonyl, substituted or unsubstituted alkyloxycarbonyl, substituted or unsubstituted alkenyloxycarbonyl, substituted or unsubstituted alkynyloxycarbonyl or substituted or unsubstituted sulfamoyl; $R^{b8}$ is substituted or unsubstituted alkyl; $Y^1$ is a leaving group; $Y^2$ is halogen; $Y^3$ is halogen.

Step 1 Preparation of the Compound b10

The compound b10 can be obtained by reacting an alcohol solution of the compound b9 in presence of a base.

Examples of the alcohol include methanol, ethanol, isopropanol and the like.

Examples of the base include sodium hydride, potassium hydride, sodium hydroxide, potassium hydroxide, potassium carbonate, cesium carbonate and the like. The amount thereof may be 1 to 5 mole equivalent(s), preferably 1 to 3 mole equivalent(s), for 1 mole equivalent of the compound b9.

The reaction temperature may be 0° C. to heating under reflux, preferably room temperature to 100° C.

The reaction time may be 0.1 to 24 hour(s), preferably 0.1 to 3 hour(s).

Step 2 Preparation of the Compound b11

The compound b11 can be obtained by reacting a solution of the compound b10 with a borane reagent in presence of, a base and a palladium catalyst then oxidizing them.

Examples of the borane reagent include 4,4,4',4',5,5,5',5'-octamethyl-2,2'-bis(1,3,2-dioxaborane), triethylborane, trimethyl borane and the like. The amount thereof may be 1 to 10 mole equivalent(s), preferably 1 to 3 mole equivalent(s), for 1 mole equivalent of the compound b10.

Examples of the reaction solvent include methylene chloride, 1,4-dioxane, THF and the like, their mixed solvent can be used as well as the single solvent.

Examples of the base include sodium acetate, potassium acetate, sodium carbonate, potassium carbonate and the like. The amount thereof may be 1 to 10 mole equivalent(s), preferably 1 to 3 mole equivalent(s), for 1 mole equivalent of the compound b10.

Examples of the palladium catalyst include chloride (diphenylphosphino ferrocene) palladium dichloromethane complex, palladium acetate, bis(dibenzylideneacetone)palladium, tetrakis(triphenylphosphine)palladium, bis(triphenylphosphine)palladium(II)dichloride, bis(tri-tert-butylphosphine)palladium and the like. The amount thereof may be 0.001 to 1 mole equivalent, preferably 0.01 to 0.5 mole equivalents, for 1 mole equivalent of the compound b10.

Examples of the oxidant include hydrogen peroxide, m-chloroperbenzoic acid and the like. The amount thereof may be 1 to 10 mole equivalent(s), preferably 5 to 10 mole equivalent(s), for 1 mole equivalent of the compound b10.

The reaction temperature may be 0° C. to heating under reflux, preferably room temperature to 130° C.

The reaction time may be 0.1 to 48 hour(s), preferably 0.5 to 5 hour(s).

Step 3 Preparation of the Compound b12

The compound b12 can be obtained by reacting a solution of the compound b11 in presence of a metal catalyst and a halogenating agent.

Examples of the reaction solvent include DMF, NMP, THF and the like, their mixed solvent can be used as well as the single solvent.

Examples of the metal catalyst include zirconium chloride, bis(cyclopentadienyl)zirconium chloride hydride and the like. The amount thereof may be 0.01 to 1 mole equivalent, preferably 0.1 to 0.5 mole equivalents, for 1 mole equivalent of the compound b11.

Examples of the halogenating agent include N-chlorosuccinimide, N-bromosuccinimide and the like. The amount thereof may be 1 to 10 mole equivalent(s), preferably 1 to 3 mole equivalent(s), for 1 mole equivalent of the compound b11.

The reaction temperature may be 0° C. to heating under reflux, preferably room temperature to 100° C.

The reaction time may be 0.5 to 48 hour(s), preferably 0.5 to 5 hour(s).

Preparation of the Compound b15

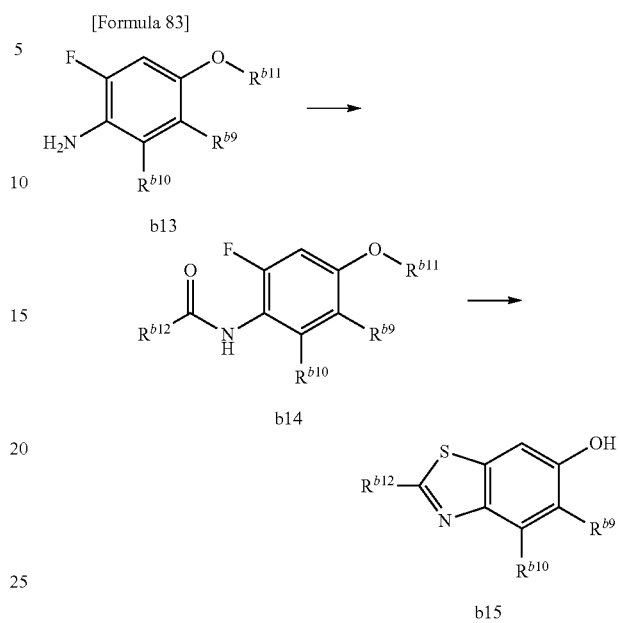

wherein each $R^{b9}$ and $R^{b10}$ is independently hydrogen, halogen, hydroxy, carboxy, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfanyl, substituted or unsubstituted alkynylsulfanyl, substituted or unsubstituted amino, substituted or unsubstituted carbamoyl, substituted or unsubstituted sulfamoyl, substituted or unsubstituted alkylcarbonyl, substituted or unsubstituted alkenylcarbonyl, substituted or unsubstituted alkynylcarbonyl, substituted or unsubstituted alkyloxycarbonyl, substituted or unsubstituted alkenyloxycarbonyl, substituted or unsubstituted alkynyloxycarbonyl or substituted or unsubstituted sulfamoyl; $R^{b11}$ is substituted or unsubstituted alkyl; $R^{b12}$ is substituted or unsubstituted alkyl, substituted or unsubstituted alkenyl or substituted or unsubstituted alkynyl.

Step 1 Preparation of the Compound b14

The compound b14 can be obtained by reacting a solution of the compound b13 with an acid chloride in presence of a base.

Examples of the base include pyridine, tirethylamine, diisopropylethylamine, potassium carbonate ad the like, it is also possible to use as a solvent.

Examples of the acid chloride include chloride isobutyl acid, acetyl chloride, trifluoroacetyl chloride and the like. The amount thereof can be 1 to 10 mole equivalent(s), preferably 1 to 3 mole equivalent(s), for 1 mole equivalent of the compound b13.

The reaction temperature may be 0° C. to heating under reflux, preferably 0° C. to 50° C.

The reaction time may be 0.1 to 48 hour(s), preferably 0.1 to 3 hour(s).

Step 2 Preparation of the Compound b15

The compound b15 can be obtained by reacting a solution of the compound b14 with Lawesson's reagent, with a base, then with a Lewis acid.

Examples of the solvent include toluene, methylene chloride and the like, their mixed solvent can be used as well as the single solvent.

The amount of Lawesson's reagent may be 0.5 to 10 mole equivalent(s), preferably 0.5 to 3 mole equivalent(s), for 1 mole equivalent of the compound b14.

The reaction temperature may be room temperature to heating under reflux, preferably room temperature to 120° C.

The reaction time may be 0.5 to 48 hour(s), preferably 1 to 5 hour(s).

Examples of the base include cesium carbonate, potassium carbonate, sodium carbonate and the like. The amount thereof can be 1 to 10 mole equivalent(s), preferably 1 to 3 mole equivalent(s) for 1 mole equivalent of the compound b14.

Examples of the solvent include DMF, NMP and the like, their mixed solvent can be used as well as the single solvent.

The reaction temperature may be room temperature to heating under reflux, preferably room temperature to 120° C.

The reaction time may be 1 to 48 hour(s), preferably 1 to 5 hour(s).

Examples of the Lewis acid include tribromoborane, trichloroborane, aluminum chloride. The amount thereof can be 1 to 10 mole equivalent(s), preferably 1 to 5 mole equivalent(s).

Preparing of the Compound b19

[Formula 84]

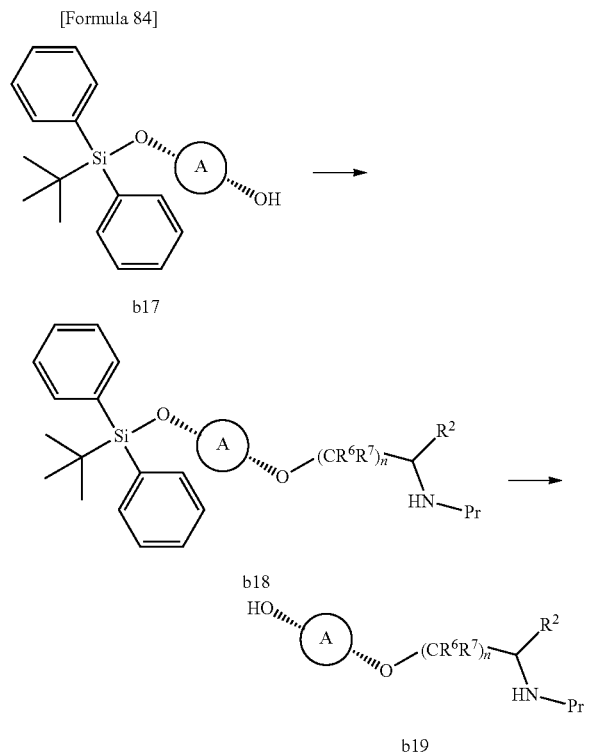

wherein $R^2$ is substituted or unsubstituted alkyl; $R^4$ is substituted or unsubstituted alkylcarbonyl, substituted or unsubstituted alkenylcarbonyl, substituted or unsubstituted alkynylcarbonyl, substituted or unsubstituted non-aromatic carbocyclylcarbonyl, substituted or unsubstituted aromatic carbocyclylcarbonyl, substituted or unsubstituted non-aromatic heterocyclylcarbonyl, substituted or unsubstituted aromatic heterocyclylcarbonyl, substituted or unsubstituted alkyloxycarbonyl, substituted or unsubstituted alkenyloxycarbonyl, substituted or unsubstituted alkynyloxycarbonyl, substituted or unsubstituted non-aromatic carbocyclyloxycarbonyl, substituted or unsubstituted aromatic carbocycly- loxycarbonyl, substituted or unsubstituted non-aromatic heterocyclyloxycarbonyl, substituted or unsubstituted aromatic heterocyclyloxycarbonyl or substituted or unsubstituted carbamoyl; each $R^6$ is independently hydrogen, halogen, substituted or unsubstituted alkyl, substituted or unsubstituted alkenyl or substituted or unsubstituted alkynyl; each $R^7$ is independently hydrogen, halogen, substituted or unsubstituted alkyl, substituted or unsubstituted alkenyl or substituted or unsubstituted alkynyl, or $R^6$ and $R^7$ bonded to the same carbon atom may be taken together to form a ring, or $R^2$ may be taken together with either $R^6$ or $R^7$ to form a ring; each n is independently an integer of 1, 2 or 3; ring A substituted or unsubstituted benzene, substituted or unsubstituted 4- to 6-membered non-aromatic carbocycle, substituted or unsubstituted 5- to 6-membered aromatic heterocycle or substituted or unsubstituted 4- to 6-membered non-aromatic heterocycle, $Y^1$ is a leaving group; Pr is a protecting group of amino.

Step 1 Preparation of the Compound b18

The compound b18 can be obtained by reacting a solution of the compound b17 with oxathiazolidine dioxide in presence of a base.

Examples of the solvent include DMF, NMP, THF, methylene chloride and the like, their mixed solvent can be obtained as well as the single solvent.

Examples of the base include sodium hydride, potassium hydride and the like. The amount thereof may be 1 to 10 mole equivalent(s), preferably 1 to 3 mole equivalent(s), for 1 mole equivalent of the compound b17.

Examples of oxathiazolidine dioxide include (S)-3-benzyl-4-methyl-1,2,3-oxathiazolidine-2,2-dioxide and the like. The amount thereof may be 1 to 10 mole equivalent(s), preferably 1 to 3 mole equivalent(s), for 1 mole equivalent of the compound b17.

The reaction temperature may be 0° C. to heating under reflux, preferably 0° C. to 50° C.

The reaction time may be 0.1 to 48 hour(s), preferably 0.1 to 3 hour(s).

Step 2 Preparation of the Compound b19

The compound b19 can be obtained by reacting with a deprotecting agent, after reacting a solution of the compound b18 with an acid anhydrate in presence of a additive and a palladium catalyst.

Examples of the solvent include methanol, ethanol, THF, ethyl acetate, water and the like, their mixed solvent can be used as well as the single solvent.

Examples of the metallic catalyst include palladium hydroxide, palladium chloride, palladium on carbon, platinum oxide and the like. The amount thereof may be 0.001 to 1 mole equivalent, preferably 0.01 to 0.5 mole equivalents, for 1 mole equivalent of the compound b18.

Examples of the additive include ammonium formate, triethylamine formic acid and the like. The amount thereof can be 1 to 10 mole equivalent(s), preferably 1 to 3 mole equivalent(s), for 1 mole equivalent of the compound b17.

The reaction temperature may be 0° C. to heating under reflux, preferably room temperature to 80° C.

The reaction time may be 0.1 to 48 hour(s), preferably 1 to 5 hour(s).

Examples of the acid anhydride include acetic anhydride, include trifluoroacetic anhydride and the like. The amount thereof may be 1 to 10 mole equivalent(s), preferably 1 to 3 mole equivalent(s) for 1 mole equivalent of the compound b18.

Examples of the base include pyridine, triethylamine diisopropylethylamine and the like. The amount thereof can be 1 to 10 mole equivalent(s), preferably 1 to 3 mole equivalent(s) for 1 mole equivalent of the compound b18.

The reaction temperature may be 0° C. to heating under reflux, preferably 0° C. to 100° C.

The reaction time may be 0.1 to 48 hour(s), preferably 1 to 24 hour(s).

Examples of the deprotecting agent include tetrabutylammonium fluoride, hydrogen fluoride, hydrogen fluoride-pyridine and the like. The amount thereof may be 1 to 10 mole equivalent(s), preferably 1 to 3 mole equivalent(s) for 1 mole equivalent of the compound b18.

The reaction temperature may be 0° C. to heating under reflux, preferably 0° C. to 100° C.

The reaction time may be 0.1 to 48 hour(s), preferably 1 to 24 hour(s).

Preparing of the Compound b26

[Formula 85]

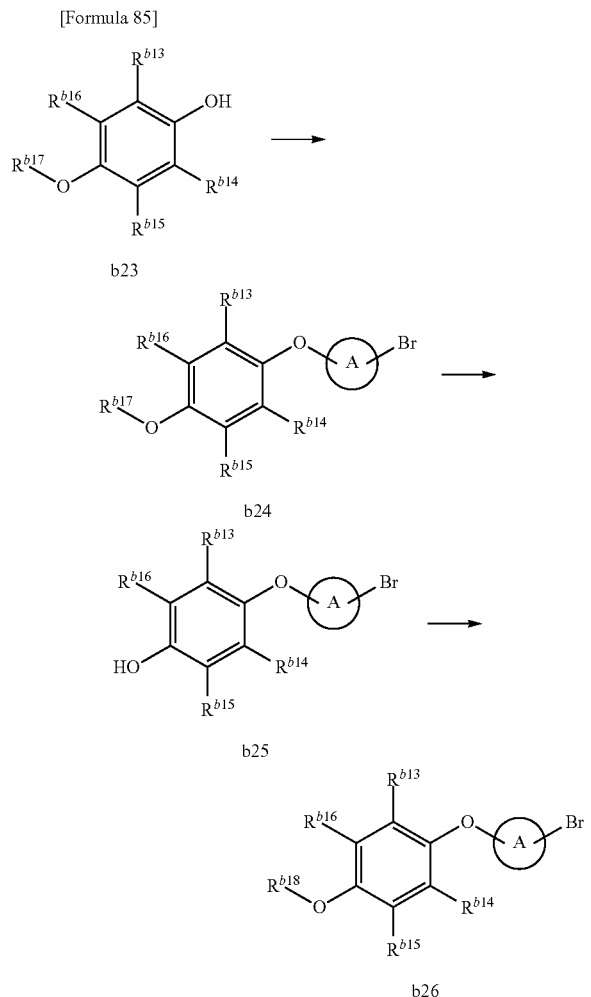

wherein $R^{b13}$, $R^{b14}$, $R^{b15}$ and $R^{b16}$ are each independently hydrogen, halogen, hydroxy, carboxy, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfanyl, substituted or unsubstituted alkynylsulfanyl, substituted or unsubstituted amino, substituted or unsubstituted carbamoyl, substituted or unsubstituted sulfamoyl, substituted or unsubstituted alkylcarbonyl, substituted or unsubstituted alkenylcarbonyl, substituted or unsubstituted alkynylcarbonyl, substituted or unsubstituted alkyloxycarbonyl, substituted or unsubstituted alkenyloxycarbonyl, substituted or unsubstituted alkynyloxycarbonyl or substituted or unsubstituted sulfamoyl; $R^{b17}$ is substituted or unsubstituted alkyl; $R^{b18}$ is substituted or unsubstituted alkyl; ring A is substituted or unsubstituted benzene, substituted or unsubstituted 4- to 6-membered non-aromatic carbocycle, substituted or unsubstituted 5- to 6-membered aromatic heterocycle or substituted or unsubstituted 4- to 6-membered non-aromatic heterocycle.

Step 1 Preparation of the Compound b24

The compound b24 can be obtained by reacting a solution of the compound b23 with a halide in presence of a base.

Examples of the solvent include DMF, NMP, THF and the like, their mixed solvent can be used as well as the single solvent.

Examples of the base include potassium carbonate, sodium carbonate, cesium carbonate and the like. The amount thereof may be 1 to 10 mole equivalent(s), preferably 1 to 3 mole equivalent(s), for 1 mole equivalent of the compound b23.

The reaction temperature may be 0° C. to heating under reflux, preferably room temperature to heating under reflux.

The reaction time may be 1 to 24 hour(s), preferably 1 to 5 hour(s).

Step 2 Preparation of the Compound b25

The compound b25 can be obtained by reacting a solution of the compound b24 with a Lewis acid.

Examples of the solvent include methylene chloride and the like, their mixed solvent can be used as well as the single solvent.

Examples of the Lewis acid include aluminum chloride, include trifluoroborane-ether complex and the like. The amount thereof may be 1 to 10 mole equivalent(s), preferably 1 to 3 mole equivalent(s), for 1 mole equivalent of the compound b24.

The reaction temperature may be −78° C. to 50° C., preferable −78° C. to room temperature.

The reaction time may be 1 to 24 hour(s), preferably 1 to 5 hour(s).

Step 3 Preparation of the Compound b26

The compound b26 can be obtained by reacting a solution of the compound b25 with a halide in presence of a base.

Examples of the solvent include DMF, NMP, THF and the like, their mixed solvent can be used as well as the single solvent.

Examples of the base include potassium carbonate, sodium carbonate, cesium carbonate and the like. The amount thereof can be 1 to 10 mole equivalent(s), preferably 1 to 3 mole equivalent(s), for 1 mole equivalent of the compound b25.

Examples of the halide include alkyl bromide, alkyl chlorides and the like. The amount thereof can be 1 to 10 mole equivalent(s), preferably 1 to 3 mole equivalent(s), for 1 mole equivalent of the compound b25.

The reaction temperature may be 0° C. to heating under reflux, preferable room temperature to 100° C.

The reaction time may be 1 to 24 hour(s), preferably 1 to 5 hour(s).

Preparing of the Compound b29

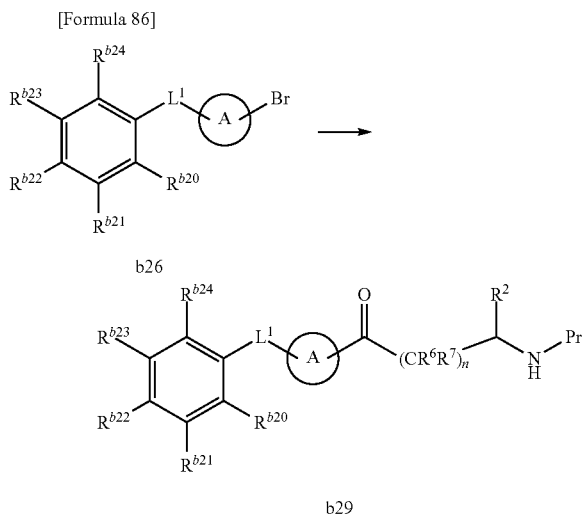

b29 wherein $R^2$ is substituted or unsubstituted alkyl; $R^{b20}$, $R^{b21}$, $R^{b22}$, $R^{b23}$ and $R^{b24}$ are each independently hydrogen, halogen, hydroxy, carboxy, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfanyl, substituted or unsubstituted alkynylsulfanyl, substituted or unsubstituted amino, substituted or unsubstituted carbamoyl, substituted or unsubstituted sulfamoyl, substituted or unsubstituted alkylcarbonyl, substituted or unsubstituted alkenylcarbonyl, substituted or unsubstituted alkynylcarbonyl, substituted or unsubstituted alkyloxycarbonyl, substituted or unsubstituted alkenyloxycarbonyl, substituted or unsubstituted alkynyloxycarbonyl or substituted or unsubstituted sulfamoyl; $-L^1-$ is $-O-(CR^6R^7)m-$; each $R^6$ is independently hydrogen, halogen, substituted or unsubstituted alkyl, substituted or unsubstituted alkenyl or substituted or unsubstituted alkynyl; each $R^7$ is independently hydrogen, halogen, substituted or unsubstituted alkyl, substituted or unsubstituted alkenyl or substituted or unsubstituted alkynyl; or $R^6$ and $R^7$ bonded to the same carbon atom may be taken together to form a ring, or $R^2$ may be taken together with either $R^6$ or $R^7$ to form a ring; each m is independently an integer of 0, 1, 2 or 3; ring A is substituted or unsubstituted benzene, substituted or unsubstituted 4- to 6-membered non-aromatic carbocycle, substituted or unsubstituted 5- to 6-membered aromatic heterocycle or substituted or unsubstituted 4- to 6-membered non-aromatic heterocycle; Pr is a protecting group of amino.

Step 1 Preparation of the Compound b29

The compound b26 can be obtained by reacting a solution of the compound b26 with Weinreb amides in presence of a base.

Examples of the solvent include THF, diethylether and the like, their mixed solvent can be used as well as the single solvent.

Examples of the base include n-butyllithium, sec-butyl lithium, t-butyl lithium, lithium hexamethyl distill amide and the like. The amount thereof may be 1 to 10 mole equivalent(s), preferably 1 to 3 mole equivalent(s), for 1 mole equivalent of the compound b25.

The amount of the Weinreb amide may be 1 to 10 mole equivalent(s), preferably 1 to 3 mole equivalent(s), for 1 mole equivalent of the compound b26.

The reaction temperature may be −78° C. to 50° C., preferably −78° C. to room temperature.

The reaction time may be 0.1 to 24 hour(s), preferably 0.5 to 5 hour(s).

The compound of the present invention has ACC2 inhibitory activity. Moreover, the compound of the present invention can be a medicine which is reduced the side effect, because of having high ACC2 selectivity as against ACC1. Additionally, the compound of the present invention can be a medicine which is rescued the side effect, because of low cardiovascular or MBI risks. A pharmaceutical composition comprising the compound of the present invention is very useful for preventing or treating a disease associated with ACC2. Examples of the diseases associated with ACC2 means a disease induced by malonyl-CoA produced by ACC2 are metabolic syndrome, obesity, diabetes, insulin resistance, abnormal glucose tolerance, diabetic peripheral neutopathy, diabetic nephropathy, diabetic retinal disease, diabetic macroangiopathy, hyperlipidemia, hypertension, cardiovascular illness, arterioscerosis, atherosclerosis, cardiac arrest, cardiac infarction, infectious disease, neoplasm and the like. A pharmaceutical composition comprising the compound of the present invention is very useful as a medicine for preventing or treating these disease.

A compound of the present invention has not only ACC2 inhibitory activity but also usefulness as a medicine and any or all good characters selected from the followings:

a) weak CYP enzyme (e.g., CYP1A2, CYP2C9, CYP2C19, CYP2D6, CYP3A4 etc.) inhibition.
b) good drug disposition such as high bioavailavility, appropriate clearance and the like.
c) high metabolic stability.
d) no irreversible CYP enzyme (e.g., CYP3A4) inhibition in the range of the concentration as a measuring condition described in the specification.
e) no mutagenicity.
f) low cardiovascular risk.
g) high water solubility.

The pharmaceutical composition of the invention can be administered orally or parenterally as an anti-obesity agent or anorectic agent. In the case of oral administration, it may be in any usual form such as tablets, granules, powders, capsules and the like. When the compound is parenterally administered, any usual form is preferable injections and the like. Oral administration is especially preferable because the compounds of the present invention show a high oral absorbability.

The pharmaceutical composition may be manufactured by mixing an effective amount of the compound of the present invention with various pharmaceutical additives suitable for the administration form, such as excipients, binders, moistening agents, disintegrants, lubricants and the like.

Although the dosage of the pharmaceutical composition of the invention as an anti-obesity agent or anorectic agent should be determined in consideration of the patient's age and body weight, the type and degree of diseases, the administration route and the like, a usual oral dosage for an adult is 0.05 to 100 mg/kg/day, preferable is 0.1 to 10 mg/kg/day. For parenteral administration, although the dosage highly varies with administration routes, a usual dosage is 0.005 to 10 mg/kg/day, preferably 0.01 to 1 mg/kg/day. The dosage may be administered in one to several divisions per day.

EXAMPLES

The present invention is further explained by the following Examples and references, which are not intended to limit the scope of this invention.

The abbreviations used in the present description stand for the following meanings.

Ac: acetyl
Bu: butyl
dba: dibenzylideneacetone
DMF: N,N-dimethylformamide
Et: ethyl
HATU: O-(7-azabenzotriazole-1-yl)-1,1,3,3-tetramethyl uranium hexafluorophosphate
Me: methyl
NMP: N-methyl-2-pyrrolidone
$Pd_2(dba)_3$: tris(dibenzylideneacetone)bispalladium
Ph: phenyl
Tf: trifluoromethanesulfonyl
THF: tetrahydrofuran $^1$H NMR spectra of the examples were measured on 300 MHz in $d_6$-DMSO or $CDCl_3$.

"RT" in the examples or the tables represents "Retention Time" by LC/MS: Liquid Chromatography/Mass Spectrometry. LC/MS data of the compounds were measured under the following condition.

Method 1: Column: Gemini-NX (5 μm, i.d. 4.6×50 mm (Phenomenex)
Flow rate: 3.0 mL/min
UV detection wavelength: 254 nm
Mobile phase: [A] is 0.1% formic acid-containing aqueous solution, [B] is 0.1% formic acid-containing acetonitrile solution
Gradient: Linear gradient of 5% to 100% solvent [B] for 3.5 minutes was performed, and 100% solvent [B] was maintained for 0.5 minutes.

Method 2: Column: Shim-pack XR-ODS (2.2 μm, i.d. 50×3.0 mm (Shimadzu)
Flow late: 1.6 mL/min
UV detection wavelength: 254 nm
Mobile phase: [A] is 0.1% formic acid-containing aqueous solution, [B] is 0.1% formic acid-containing acetonitrile solution
Gradient: Linear gradient of 10% to 100% solvent [B] for 3 minutes was performed, and 100% solvent [B] was maintained for 1 minute.

Method 3: Column: ACQUITY UPLC(R) BEH C18 (1.7 μm, i.d. 2.1×50 mm (Waters)
Flow rate: 0.55 mL/min
UV detection wavelength: 254 nm
Mobile phase: [A] is 0.1% formic acid-containing aqueous solution, and [B] is 0.1% formic acid-containing acetonitrile solution
Gradient: Linear gradient of 5% to 100% solvent [B] for 3 minutes was performed, and 100% solvent [B] was maintained for 0.5 minutes.

Method 4: Column: ACQUITY UPLC(R)BEH C18 (1.7 μm i.d. 2.1×50 mm (Waters) Flow rate: 0.8 mL/min
UV detection wavelength: 254 nm
Mobile phase: [A] is 0.1% formic acid-containing aqueous solution, and [B] is 0.1% formic acid-containing acetonitrile solution
Gradient: Linear gradient of 5% to 100% solvent [B] for 3.5 minutes was performed, and 100% solvent [B] was maintained for 0.5 minutes.

Method 5: Column: Shim-pack XR-ODS (2.2 μm, i.d. 50×3.0 mm (Shimadzu)
Flow rate: 1.6 mL/min
UV detection wavelength: 254 nm
Mobile phase: [A] is 0.1% formic acid-containing aqueous solution, and [B] is 0.1% formic acid-containing acetonitrile solution
Gradient: Linear gradient of 10% to 100% solvent [B] for 8 minutes was performed, and 100% solvent [B] was maintained for 0.5 minutes.

Example 1

Preparation of Compound a2

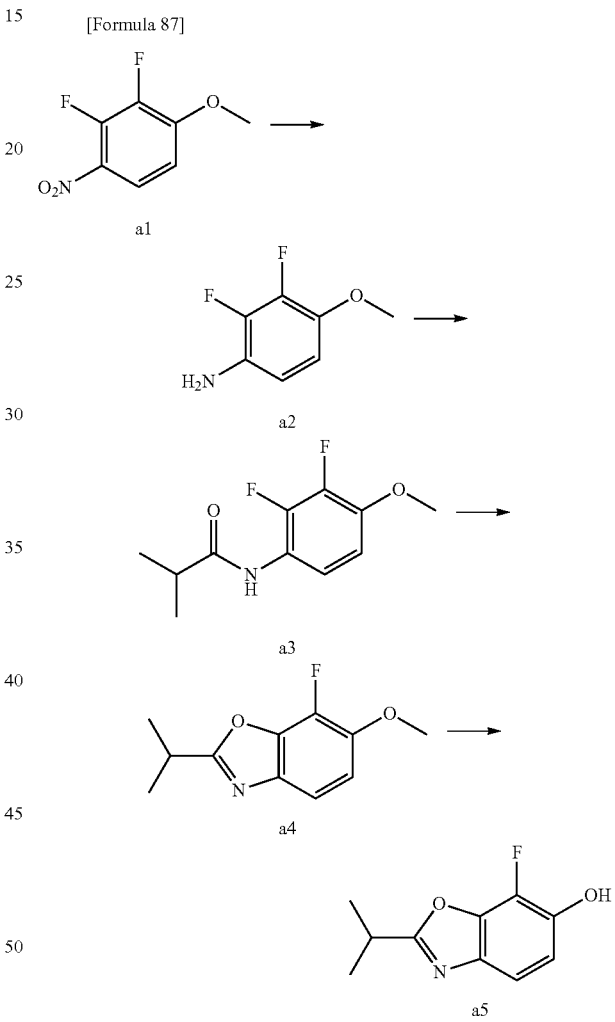

[Formula 87]

Step 1 Preparation of Compound a2

Compound a1 (3.0 g, 16 mmol) was dissolved in ethanol (30 mL) and water (10 mL), and iron (2.7 g, 48 mmol) and ammonium chloride (2.6 g, 48 mmol) were added into the reaction mixture, the reaction mixture was stirred at 80° C. for 4 hours. The mixtures are filtered, and water was added into the mother liquor. The reaction mixture was extracted with ethyl acetate. The organic layer was washed with saturated brine, and dried over magnesium sulfate. The organic layer was condensed under reduced pressure to afford Compound a2 (2.5 g) as crude.

M+H=159.6, Method Condition 4: retention time 1.07 min

Step 2 Preparation of Compound a3

Compound a2 (2.5 g, 16 mmol) was dissolved in DMF (30 mL), and isobutyric acid (1.7 g, 19 mmol) and O-(7-Azabenzotriazol-1-yl)-1,1,3,-tetramethyluronium hexafluorophosphate (7.8 g, 21 mmol) and triethyl amine (3.1 g, 32 mmol) was added to the reaction mixture while cooling in ice. The reaction mixture was stirred at room temperature overnight. Water was added into the mixture and the mixture was extracted with diethyl ether. The organic layer was washed with saturated brine, and dried over magnesium sulfate. The solvent was condensed under reduced pressure to afford Compound a3 (5.1 g) as crude.

M+H=229.8, Method Condition 4: retention time 1.54 min

Step 3 Preparation of Compound a4

Compound a3 (2.0 g, 8.7 mmol) was dissolved in NMP (1.0 mL), and cesium carbonate (5.7 g, 17 mmol) was added to the mixture. The mixture was stirred at 160° C. for 12 hours. DMF (13 mL) was added to the mixture, and the mixture was stirred at 100° C. for 1 hour. Water was added to the mixture, and the mixture was extracted with ethyl acetate. The organic layer was washed with hydrochloric acid and saturated brine, and dried over magnesium sulfate. The solvent was condensed under reduced pressure. The residue was purified by silica gel chromatography (hexane-ethyl acetate) to afford Compound a4 (0.46 g, yield 25%).

$^1$H NMR (CDCl3) δ: 1.46 (d, J=7.0 Hz, 6H), 3.31-3.17 (m, 1H), 3.95 (s, 3H), 6.97 (dd, J=8.0, 4.0 Hz, 1H), 7.36 (d, J=8.8 Hz, 1H).

M+H=209.8, Method Condition 4: retention time 2.04 min

Step 4 Preparation of Compound a5

Compound a4 (0.36 g, 1.7 mmol) was dissolved in toluene (8.0 mL), and aluminum chloride (0.57 g, 4.3 mmol) was added to the mixture. The mixture was stirred at 100° C. for 2 hours. The sodium acetate solution was added to the mixture while cooling in ice, and the mixture was extracted with diethyl ether. The organic layer was washed with saturated brine, and dried over magnesium sulfate. The solvent was condensed under reduced pressure. The solid was filtrated to afford Compound a5 (0.28 g, yield 83%).

$^1$H NMR (CDCl3) δ: 1.46 (d, J=6.9 Hz, 6H), 3.21-3.28 (m, 1H), 5.54 (s, 1H), 6.98 (dd, J=8.1 Hz, 1H), 7.32 (d, J=8.5 Hz, 1H).

[M+H]=195.7, Method Condition 2: retention time 1.55 min

Example 2

Preparation of Compound I-031

[Formula 88]

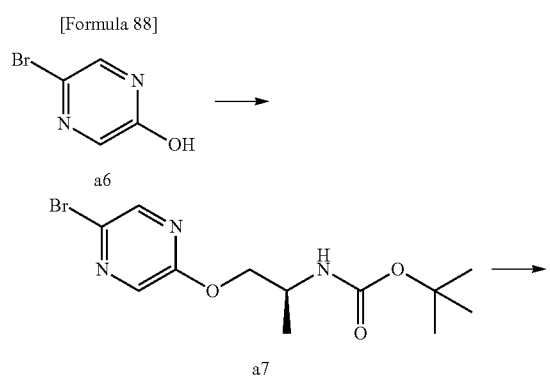

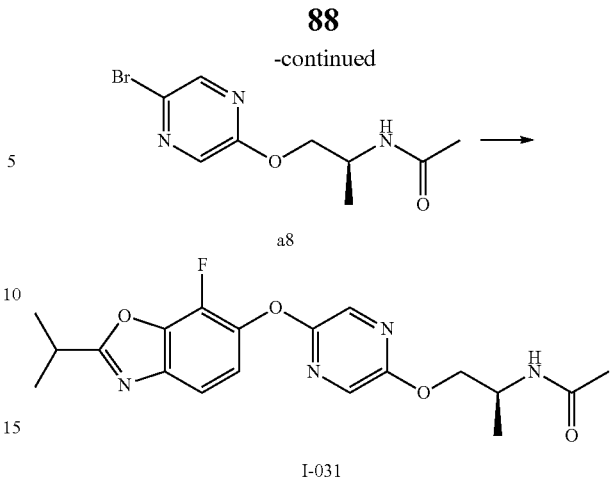

Step 1 Preparation of Compound a7

Compound a6 (1.0 g, 5.7 mmol) was dissolved in 1,4-dioxane (10 mL), and (s)-t-butyl-1-hydroxypurop-2-yl carbamate (1.2 g, 6.9 mmol), triphenylphosphine (1.8 g, 6.9 mmol) and dimethyloxyethylazodicarboxylate (1.6 g, 6.9 mmol) was added to the mixture while cooling in ice. The mixture was stirred at room temperature for I hour. Water was added to the mixture, and the mixture was extracted with ethyl acetate. The organic layer was washed with saturated brine, and dried over magnesium sulfate. The solvent was condensed under reduced pressure. The residue was purified by silica gel chromatography (hexane-ethyl acetate) to afford Compound a7 (1.3 g, yield 67%).

[M+H]=332.0, Method Condition 4: retention time 2.16 min

Step 2 Preparation of Compound a8

Compound a7 (0.70 g, 2.1 mmol) was added to 4 mol/L hydrochloric acid-1,4-dioxane (5.3 mL), and the mixture was stirred at room temperature for 1 hour. The reaction solution was distilled off under reduced pressure, and the obtained residue was dissolved in methylene chloride (6.0 mL), pyridine (0.83 g, 11 mmol) and acetic anhydride (3.2 mg, 3.2 mmol) were added, and the mixture was stirred at room temperature for 1 hour. A saturated aqueous sodium hydrogen carbonate solution was added to the reaction mixture, and the mixture was extracted with ethyl acetate. The organic layer was washed with saturated brine, and dried over anhydrous magnesium sulfate. The solvent was distilled off under reduced pressure, and the precipitated solid was collected by filtration to give Compound a8 (0.54 g, 93% yield).

$^1$H NMR (CDCl$_3$) δ: 1.28 (d, J=6.8 Hz, 3H), 1.99 (s, 3H), 4.29 (d, J=4.4 Hz, 2H), 4.38-4 51 (m, 1H), 5.58-5.73 (m, 1H), 8.05 (s, 1H), 8.18 (s, 1H).

[M+H]=274.0, Method Condition 4: retention time 1.18 minutes

Step 3 Preparation of Compound I-031

Compounds a8 (30 mg, 0.11 mmol) was dissolved in 1,4-dioxane (1.0 mL) then, Compound a5 (47 mg, 0.22 mmol), copper iodide (6.3 mg, 0.033 mmol), N,N-dimethyl glycine (10 mg, 0.098 mmol) and cesium carbonate (0.11 g, 0.33 mmol) were added and the mixture was stirred at 130° C. under microwave irradiation for 4 hours. Water was added and the mixture was extracted with chloroform. The solvent was distilled off under reduced pressure, and the obtained residue was purified by silica gel column chromatography (chloroform-methanol) to give Compound I-031 (27 mg, 64% yield).

¹H NMR (CDCl₃) δ: 1.29 (d, J=6.7 Hz, 3H), 1.48 (d, J=6.9 Hz, 6H), 1.99 (s, 3H), 3.21-3.36 (m, 1H), 4.29 (d, J=4.0 Hz, 2H), 4.36-4.49 (m, 1H), 5.67-5.81 (m, 1H), 7.15 (dd, J=7.7 Hz, 1H), 7.46 (d, J=8.5 Hz, 1H), 7.76 (s, 1H), 8.03 (s, 1H).

[M+H]=389.2, Method Condition 4: retention time 1.97 minutes

Example 3

Preparation of Compound I-039

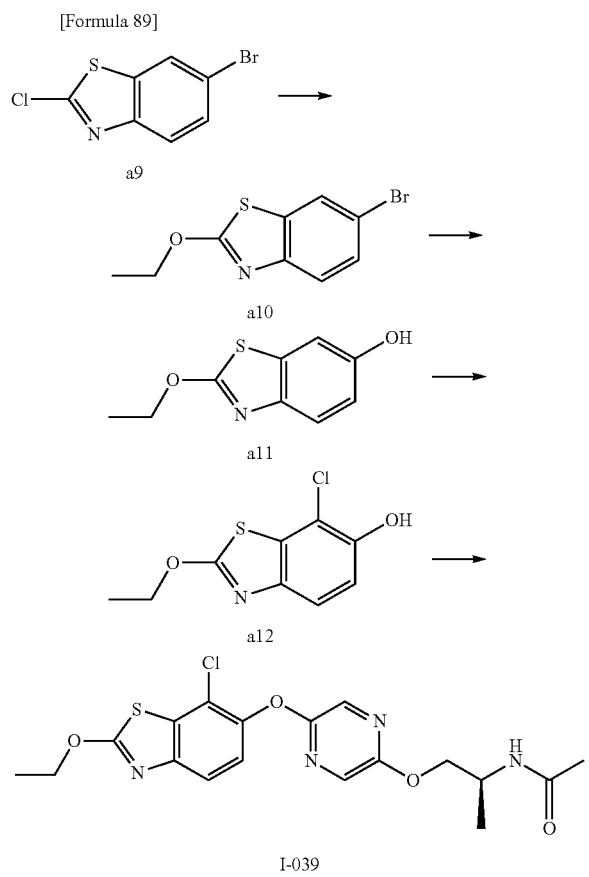

Step 1 Preparation of Compound a10

Compound a9 (20 g, 82 mmol) was dissolved in ethanol (0.16 L) and, 2 mol/L aqueous sodium hydroxide solution (45 mL, and 90 mmol) was added, and the mixture was stirred at 100° C. for 30 minutes. Water was added to the mixture, the precipitate was filtered and the filtrate was extracted with ethyl acetate. The organic layer was washed with saturated brine and dried with anhydrous magnesium sulfate. The solvent was distilled off under reduced pressure to give Compound a10 (20 g, 95% yield).

[M+H]=257.9, Method Condition 4: retention time 2.59 minutes

Step 2 Preparation of Compound a11

Compound a11 (20 g, 82 mmol) was dissolved in 1,4-dioxane (0.15 L) and 4,4,4',4',5,5,5',5'-octamethyl-2,2'-bis (1,3,2-dioxaborolan) (18 g, 70 mmol), sodium acetate (17 g, 0.17 mol) and chloride (diphenylphosphino ferrocene) palladium dichloromethane complex (4.8 g, 5.8 mmol) were added and the mixture was stirred at 110° C. for 2 hours. Water was added to the mixture, the precipitate was filtered and the filtrate was extracted with ethyl acetate. The organic layer was washed with saturated brine, and dried over anhydrous magnesium sulfate. The obtained residue was dissolved in dichloromethane (0.15 L), 30% aqueous hydrogen peroxide (59 mL, 0.58 mol) was added under ice-cooling, and the mixture was stirred at room temperature for 1 hour. Water was added to the reaction mixture, and the mixture was extracted with ethyl acetate. The organic layer was washed with water and brine, and dried over anhydrous magnesium sulfate. The solvent was distilled off under reduced pressure, and the obtained residue was purified by silica gel column chromatography (hexane-ethyl acetate) to give compound a11 (13 g, 87% yield).

[M+H]=196.1, Method Condition 4: retention time 1.54 minutes

Step 3 Preparation of Compound a12

Compound a11 (9.5 g, 49 mmol) was dissolved in DMF (0.20 L), zirconium chloride (2.3 g, 9.7 mmol) and N-chlorosuccinimide (6.8 g, 51 mmol) was added and the mixture was stirred at 50° C. for 1 hour. Hydrochloric acid aqueous solution was added to the reaction mixture, and the mixture was extracted with ethyl acetate. The organic layer was washed with water and brine, and dried over anhydrous magnesium sulfate. The solvent was distilled off under reduced pressure, and the obtained residue was purified by silica gel column chromatography (hexane-ethyl acetate) to give Compound a12 (8.4 g, 62% yield).

¹H NMR (CDCl₃) δ: 1.47 (t, J=8.0 Hz, 3H), 4.58 (q, J=8.0 Hz, 2H), 5.44 (s, 1H), 7.04 (d, J=8.8 Hz, 1H), 7.47 (d, J=8.8 Hz, 1H).

[M+H]=230.0, Method Condition 4: retention time 1.96 minutes

Step 4 Preparation of Compound I-039

Compound a8 (3.1 g, 10 mmol) was dissolved in 1,4-dioxane (40 mL), Compound a12 (2.0 g, 8.7 mmol), copper iodide (0.83 g, 4.4 mmol), N,N-dimethyl glycine (0.81 g, 7.8 mmol) and cesium carbonate (8.5 g, 26 mmol) were added and the mixture was stirred for 2 hours at 130° C. under microwave irradiation. Water was added to the reaction mixture, and the mixture was extracted with ethyl acetate. The solvent was distilled off under reduced pressure, and the obtained residue was purified by silica gel column chromatography (chloroform-ethyl acetate) to afford Compound I-039 (3.6 g, 64% yield).

¹H NMR (CDCl₃) δ: 1.28 (d, J=6.8 Hz, 3H), 1.49 (t, J=7.2 Hz, 3H), 1.98 (s, 3H), 4.28 (d, J=4.0 Hz, 1H), 4.37-4.46 (m, 1H), 4.62 (q, J=7.2 Hz, 2H), 5.72 (bd, J=7.2 Hz, 1H), 7.18 (d, J=8.4 Hz, 1H), 7.58 (d, J=8.4 Hz, 1H), 7.77 (d, J=1.6 Hz, 1H), 7.98 (d, J=1.6 Hz, 1H).

[M+H]=423.2, Method Condition 4: retention time 2.30 minutes

Example 4

Preparation of Compound I-038

[Formula 90]

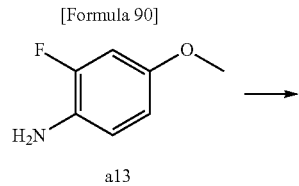

a13

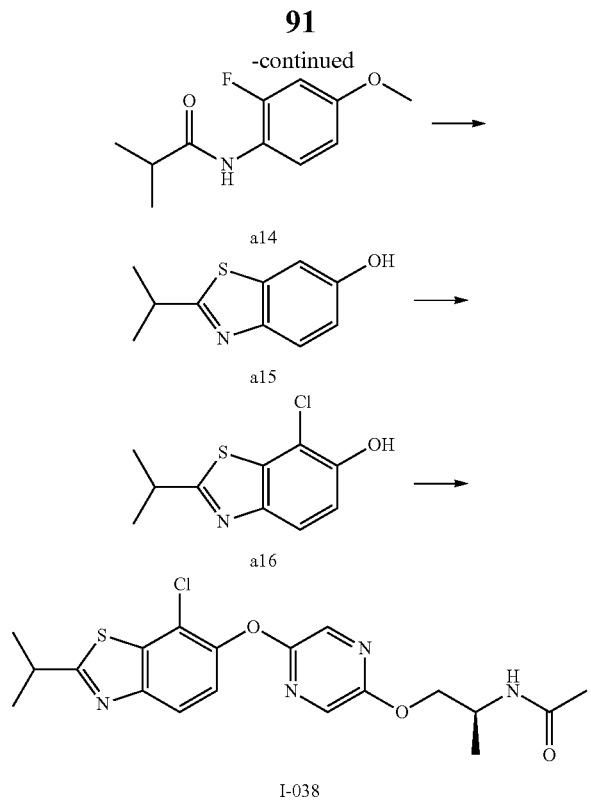

Step 1 Preparation of Compound a14

Compound a13 (3.3 g, 23 mmol) was dissolved in pyridine (16 mL), isobutyric acid chloride (3.0 g, 28 mmol) was added and the mixture was stirred at room temperature for 30 minutes. Water was added to the reaction mixture and the mixture was extracted with ethyl acetate. The organic layer was washed with hydrochloric acid and saturated brine, and dried over anhydrous sodium sulfate. The solvent was distilled off under reduced pressure, and then filtered and the obtained solid was filtrated to afford Compound a14 (4.1 g, 83% yield).

$^1$H NMR (CDCl$_3$) δ: 1.27 (d, J=8.0 Hz, 6H), 2.54 (m, 1H), 3.78 (s, 3H), 6.60-6.70 (m, 2H), 7.17 (bs, 1H), 8.10-8.20 (m, 1H).

[M+H]=212.5, Method Condition 2: retention time 1.45 minutes

Step 2 Preparation of Compound a15

Compound a14 (1.7 g, 23 mmol) was dissolved in toluene (18 mL), Lawesson's reagent (1.9 g, 4.7 mmol) was added and the mixture was stirred at 110° C. for 2 hours. DMF (9.0 mL) and cesium carbonate (6.4 g, 20 mmol) was added to the reaction solution and the mixture was stirred at 100° C. for 2 hours. Water was added to the reaction mixture and the mixture was extracted with ethyl acetate. The organic layer was washed with saturated brine and sodium bicarbonate solution, and dried over anhydrous magnesium sulfate. The solvent was distilled off under reduced pressure, and the obtained residue was dissolved in methylene chloride (25 mL), 1 mol/L tribromoborane dichloromethane solution (69 mL, 69 mmol) was added under ice cooling, and the mixture was stirred at room temperature for 1 hour. Water was added to the reaction mixture and the mixture was extracted with ethyl acetate. The organic layer was washed with saturated brine, and then dried over anhydrous sodium sulfate. The solvent was distilled off under reduced pressure, and the obtained residue was washed with hexane to give compound a15 (1.4 g, 94% yield).

$^1$H NMR (CDCl$_3$) δ: 1.46 (d, J=8.0 Hz, 6H), 3.39 (m, 1H), 6.30 (bs, 1H), 6.96 (dd, J=8.0, 4.0 Hz, 1H), 7.30 (d, J=4.0 Hz, 1H), 7.79 (d, J=8.0 Hz, 1H).

[M+H]=194.2, Method Condition 2: retention time 1.52 minutes

Step 3 Preparation of Compound a16

Compound a15 was dissolved in DMF (30 mL) and, N-chlorosuccinimide (2.3 g, 17 mmol) was added, and the mixture was stirred at 50° C. for 4 hours. Water was added to the reaction mixture, and the mixture was extracted with ethyl acetate. The organic layer was washed with aqueous ammonium chloride and brine, and dried over anhydrous magnesium sulfate. The solvent was distilled off under reduced pressure, and the obtained residue was purified by silica gel column chromatography (hexane-ethyl acetate) to give compound a16 (3.5 g, 88% yield).

$^1$H NMR (CDCl$_3$) δ: 1.47 (d, J=8.0 Hz, 6H), 3.39 (m, 1H), 5.67 (s, 1H), 7.15 (d, J=8.0 Hz, 1H), 7.77 (d, J=8.0 Hz, 1H).

[M+H]=228.9, Method Condition 2: retention time 1.91 minutes

Step 4 Preparation of Compound I-038

Compounds a8 (30 mg, 0.11 mmol) was dissolved in 1,4-dioxane (1.0 mL) then, the compound 16 (37 mg, 0.16 mmol), copper iodide (6.3 mg, 0.033 mmol), N,N-dimethyl glycine (10 mg, 0.098 mmol) and cesium carbonate (0.11 g, 0.33 mmol) were added and the mixture was stirred at 130° C. for 1 hour Water was added and the mixture was extracted with chloroform. The solvent was distilled off under reduced pressure, and the obtained residue was purified by silica gel column chromatography (hexane-ethyl acetate) to afford Compound I-038 (26 mg, 57% yield).

$^1$H-NMR (CDCl$_3$) δ: 1.29 (d, J=6.8 Hz, 3H) 1.49 (d, J=6.8 Hz, 6H) 1.99 (s, 3H) 3.36-3.49 (m, 1H) 4.24-4.33 (m, 2H), 4.36-4.48 (m, 1H), 5.69-5.80 (m, 1H), 7.24-7.31 (m, 1H), 7.77 (s, 1H), 7.89 (d, J=8.7 Hz, 1H), 8.01 (s, 1H).

[M+H]=421.1, Method Condition 4: retention time 2.62 minutes

Example 5

Preparation of Compound I-046

[Formula 91]

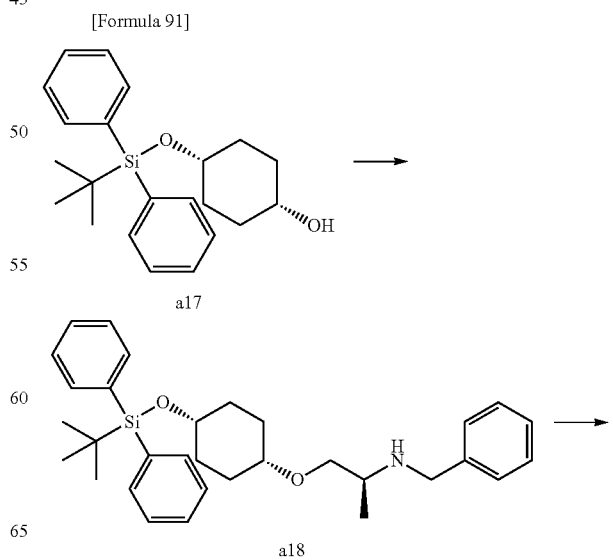

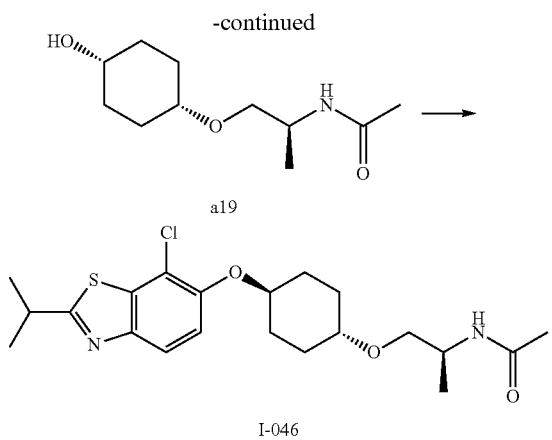

Step 1 Preparation of Compound a18

Compound a17 (1.0 g, 4.4 mmol; J. Org. Chem. 2004, 69, 7694) was dissolved in DMF (15 mL) and sodium hydride (0.26 g, 6.6 mmol) was added under ice-cooling and the mixture was stirred at room temperature for 30 minutes. THF (3.5 mL) solution of (S)-3-benzyl-4-methyl-1,2,3-oxathiazolidine-2,2-dioxide (1.6 g, 4.4 mmol) was to the reaction solution under ice-cooling, and the mixture was stirred at room temperature for 2 hours. 2 mol/L hydrochloric acid aqueous solution (8.8 mL) was added to the reaction solution under ice-cooling, and the mixture was stirred at room temperature for 1 hour. 2 mol/L sodium hydroxide solution (18 mL) was added to the reaction mixture, and the mixture was extracted with ethyl acetate. The solvent was distilled off under reduced pressure, and the obtained residue was purified by amino silica gel column chromatography (hexane-ethyl acetate) to give Compound a18 (1.6 g, 71% yield).

$^1$H NMR (CDCl$_3$) δ: 1.06 (m, 12H), 1.37 (m, 2H), 1.51 (m, 2H), 1.67 (m, 2H), 1.79 (m, 2H), 2.94 (m, 1H), 3.22 (m, 1H), 3.28 (t, J=8.5 Hz, 1H), 3.41 (dd, J=9.3, 4.3 Hz, 1H), 3.77 (d, J=12.8 Hz, 1H), 3.78 (m, 1H), 3.90 (d, J=12.8 Hz, 1H), 7.30-7.41 (m, 11H), 7.66 (d, J=7.9 Hz, 4H).

[M+H]=502.2, Method Condition 2: retention time 2.15 minutes

Step 2 Preparation of Compound a19

Compounds a18 (0.65 g, 1.3 mmol) was dissolved in methanol (6.5 mL), palladium hydroxide (0.16 g, 1.2 mmol) and ammonium formate (0.24 g, 3.9 mmol) were added and the mixture was refluxed for 4 hours. A sodium hydroxide solution was added to the reaction solution and the mixture was extracted with ethyl acetate. The organic layer was washed with brine and dried over anhydrous sodium sulfate. The solvent was distilled off under reduced pressure, and the obtained residue was dissolved in methylene chloride (3.2 mL). Acetic anhydride (0.13 mL, 1.4 mmol) and triethylamine (0.18 mL, 1.3 mmol) were added and the mixture was stirred at room temperature for 30 minutes. Water was added to the reaction mixture and the mixture was extracted with ethyl acetate. The organic layer was washed with brine and dried over anhydrous magnesium sulfate. The solvent was evaporated under reduced pressure, 1 mol/L tetrabutylammonium fluoride (1.9 mL, 1.9 mmol) was added to the obtained residue and the mixture was stirred at 70° C. for 10 hours. The reaction mixture was distilled off under reduced pressure, and the obtained residue was purified by silica gel column chromatography (chloroform-methanol) to give Compound a19 (0.27 g, 98% yield).

$^1$H NMR (CDCl$_3$) δ: 1.19 (d, J=6.7 Hz, 3H), 1.44-1.60 (m, 2H), 1.60-1.72 (m, 4H), 1.76-1.90 (m, 2H), 1.97 (s, 3H), 3.37-3.40 (m, 1H), 3.31-3.46 (m, 2H), 3.68-3.80 (m, 1H), 4.14 (bs, 1H), 5.94 (bs, 1H).

[M+H]=216.2, Method Condition 2: retention time 0.79 minutes

Step 3 Preparation of Compound I-046

Compound a19 (22 mg, 0.10 mmol) was dissolved in THF (1.0 mL) and Compound 15 (27 mg, 0.12 mmol), triphenylphosphine (34 mg, 0.13 mmol) and dimethyloxyethylazodicarboxylate (30 mg, 0.13 mmol) was added and the mixture was with stirred at room temperature for 3 hours. Water was added to the reaction mixture and the mixture was extracted with ethyl acetate. The organic layer was washed with brine and dried over anhydrous magnesium sulfate. The solvent was distilling off under reduced pressure and the obtained residue was purified by silica gel column chromatography (chloroform-methanol) to give Compound I-046 (15 mg, 35% yield).

$^1$H-NMR (CDCl$_3$) δ: 1.19 (d, J=6.8 Hz, 3H), 1.42-1.54 (m, 8H), 1.61-1.75 (m, 2H) 1.98 (s, 3H), 2.01-2.11 (m, 4H), 3.32-3.50 (m, 4H), 4.08-4.20 (m, 1H), 4.34-4.47 (m, 1H), 5.60-5.71 (m, 1H), 7.13 (d, J=9.0 Hz, 1H), 7.78 (d, J=9.0 Hz, 1H).

[M+H]=399.5, Method Condition 4: retention time 2.28 minutes

Example 6

Preparation of Compound I-075

[Formula 92]

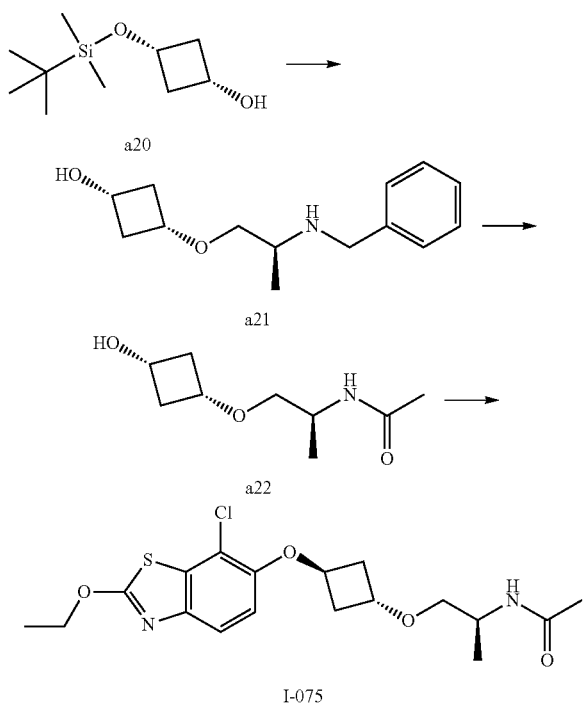

Step 1 Preparation of Compound a21

Compounds a20 (0.53 g, 2.6 mmol) was dissolved in DMF (5.0 mL) and THF (2.5 mL), sodium hydride (0.13 g, 3.3 mmol) was added under ice-cooling and the mixture was stirred for 30 minutes under ice-cooling. THF (2.5 mL) solution of (S)-3-benzyl-4-methyl-1,2,3-oxathiazolidine-2,2-dioxide (0.50 g, 2.2 mmol) was to the reaction solution under ice-cooling, and the mixture was stirred at room temperature for 2 hours. 2 mol/L hydrochloric acid aqueous solution (10 mL) was added to the reaction solution under ice-cooling, and the mixture was stirred at room temperature for 1 hour. 2 mol/L sodium hydroxide solution (10 mL) was added to the reaction mixture, and the mixture was extracted with ethyl acetate. The reaction solvent was distilled off under reduced pressure, and the obtained residue was purified by amino silica gel column chromatography (chloroform-methanol) to give Compound a21 (0.53 g, 95% yield).

$^1$H-NMR (CDCl$_3$) δ: 1.06 (d, J=6.3 Hz, 3H), 1.91-1.78 (m, 2H), 2.76-2.62 (m, 2H), 2.95-2.85 (m, 1H) 3.32-3.17 (m, 2H), 3.56-3.46 (m, 1H), 3.78-3.67 (m, 1H), 3.96-3.83 (m, 2H), 7.37-7.21 (m, 5H).

[M+H]=236.5, Method Condition 4: retention time 0.66 minutes

Step 2 Preparation of Compound a22

Compounds a19 (0.51 g, 2.1 mmol) was dissolved in methanol (2.5 mL), palladium hydroxide (0.30 g, 2.2 mmol) was added and the mixture was stirred for 1 hour under a hydrogen stream. Acetic anhydride (0.60 mL, 4.6 mmol) was added to the reaction solution and the mixture was stirred at room temperature overnight. 2 mol/L hydrochloric acid aqueous solution (10 mL) was added to the reaction solution under ice-cooling, and the mixture was stirred at room temperature for 1 hour. A saturated sodium bicarbonate solution was added to the mixture and the mixture was extracted with chloroform. The organic layer was washed with brine and dried over anhydrous magnesium sulfate. The reaction solvent was distilled off under reduced pressure, and the obtained residue was purified by silica gel column chromatography (chloroform-methanol) to give Compound a22 (0.24 g, 61% yield).

1H-NMR (CDCl$_3$) δ: 1.18 (d, J=6.8 Hz, 3H), 1.82-1.92 (m, 2H), 1.97 (s, 3H), 2.66-2.76 (m, 2H), 3.27 (dd, J=9.4, 3.9 Hz, 1H), 3.33 (dd, J=9.4, 4.1 Hz, 1H), 3.50-3.59 (m, 1H), 3.89-4.00 (m, 1H), 4.08-4.17 (m, 1H), 5.62-5.77 (m, 1H)

[M+H]=188.4, Method Condition 4: retention time 0.51 minutes

Step 3 Preparation of Compound I-075

Compounds a22 (30 mg, 0.16 mmol) was dissolved in THF (1 mL), Compound a11 (55 mg, 0.24 mmol), triphenylphosphine (84 mg, 0.32 mmol) and diisopropyl azodicarboxylate (0.17 mL, 0.32 mmol) were added, and the mixture was stirred at room temperature. Water was added to the reaction mixture and the mixture was extracted with ethyl acetate. The organic layer was washed with brine and dried over anhydrous magnesium sulfate. The solvent was distilled off under reduced pressure, and the obtained residue was purified by reverse phase column chromatography to give Compound I-075 (30 mg, 47% yield).

$^1$H-NMR (CDCl$_3$) δ: 1.20 (d, J=6.8 Hz, 3H), 1.48 (t, J=7.2 Hz, 3H), 1.99 (s, 3H), 2.38-2.59 (m, 4H), 3.27-3.42 (m, 2H), 4.09-4.21 (m, 1H), 4.22-4.33 (m, 1H), 4.58 (q, J=7.1 Hz, 2H), 4.84-4.96 (m, 1H), 5.55-5.72 (m, 1H), 6.80 (d, J=8.8 Hz, 1H), 7.47 (d, J=8.8 Hz, 1H).

[M+H]=399.5, Method Condition 4: retention time 2.28 minutes

Example 7

Preparation of Compound a26

[Formula 93]

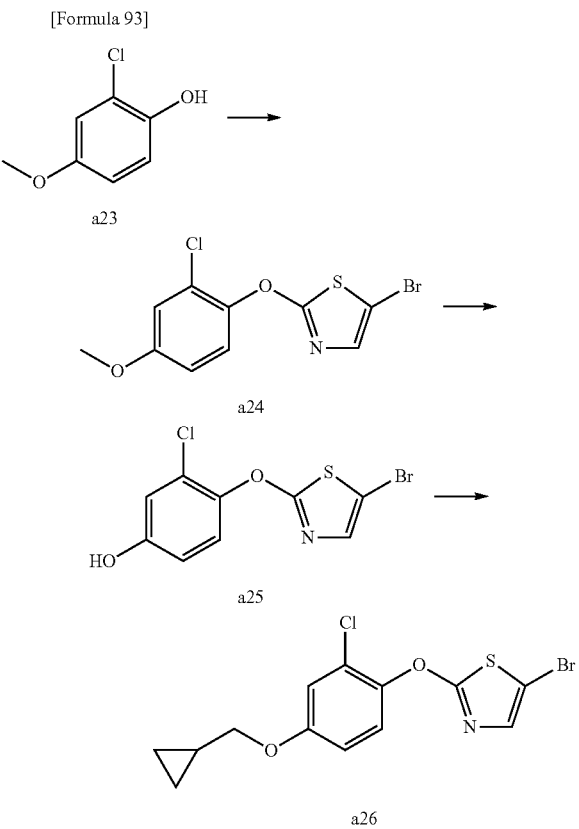

Step 1 Preparation of Compound a24

2,5-Dibromo-thiazole (8.6 g, 35 mmol) and Compound a23 (6.0 g, 38 mmol) were dissolved in DMF (90 mL), and potassium carbonate (9.8 g, 71 mmol) was added, and the mixture was stirred at 105° C. for 3 hours. Water was added to the reaction mixture, and the mixture was extracted with ethyl acetate. The organic layer was washed with saturated brine, and then dried with anhydrous magnesium sulfate. The solvent was evaporated under reduced pressure to give compound a24 (12 g, 100% yield).

$^1$H NMR (CDCl$_3$) δ: 3.81 (s, 3H), 6.84 (dd, J=8.9, 3.0 Hz, 1H), 7.00 (d, J=3.0 Hz, 1H), 7.11 (s, 1H), 7.23 (d, J=8.9 Hz, 1H).

Step 2 Preparation of Compound a25

Under a nitrogen atmosphere dichloromethane (240 mL) solution of Compound a22 (12 g, 37 mmol) was cooled to −78° C. with dry ice-acetone. 1.0 mol/L boron tribromide (150 mL, 150 mmol) was added dropwise in a reaction solution, and the mixture was raised to room temperature over 3 hours. The reaction mixture was poured into saturated sodium bicarbonate solution, the mixture was stirred, and extracted with ethyl acetate. The organic layer was washed with saturated brine, and then dried with anhydrous magnesium sulfate. The solvent was evaporated under reduced pressure to give compound a25 (12 g, 100% yield).

$^1$H NMR (DMSO-d6) δ: 6.82 (dd, J=8.9, 2.9 Hz, 1H), 6.97 (d, J=2.9 Hz, 1H), 7.37 (d, J=8.9 Hz, 1H), 7.40 (s, 1H), 10.17 (s, 1H).

Step 3 Preparation of Compound a26

Compound a25 (6.0 g, 20 mmol) was dissolved in DMF (15 mL) and potassium carbonate (4.1 g, 29 mmol) and (bromomethyl) cyclopropane (2.9 mL, 29 mmol) were added, and the mixture was stirred at 80° C. for 7 hours. Water was added to the reaction mixture, and the mixture was extracted with diethyl ether. The organic layer was washed with saturated brine, and then dried with anhydrous magnesium sulfate. The solvent was distilled off under reduced pressure, and the obtained residue was purified by silica gel column chromatography (hexane-ethyl acetate) to give compound a26 (6.4 g, 96% yield).

$^1$H NMR (CDCl$_3$) δ: 0.38-0.32 (m, 2H), 0.70-0.63 (m, 2H), 1.33-1.20 (m, 1H), 3.78 (d, J=7.0 Hz, 2H), 6.84 (dd, J=9.0, 2.9 Hz, 1H), 6.99 (d, J=2.9 Hz, 1H), 7.11 (s, 1H), 7.22 (d, J=9.0 Hz, 1H).

Example 8

Preparation of Compound a28

[Formula 94]

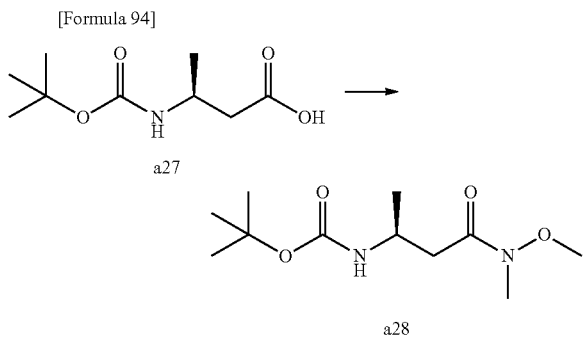

Compound a27 (40 g, 0.20 mol), N,O-dimethylhydroxylamine hydrochloride (23 g, 0.24 mol), HATU (112 g, 0.30 mol) were dissolved in DMF (0.60 L) and triethylamine (60 g, 0.60 mol) was added and the mixture was stirred at room temperature overnight. Water was added to the reaction mixture, and the mixture was extracted with ethyl acetate. The organic layer was washed with saturated brine, and then dried with anhydrous magnesium sulfate. The solvent was distilled off under reduced pressure, and the obtained residue was purified by silica gel column chromatography (hexane-ethyl acetate) to give compound a28 (34 g, 69% yield).

$^1$H NMR (CDCl$_3$) δ: 1.24 (d, J=6.4 Hz, 3H), 1.43 (s, 9H), 2.53-2.74 (m, 2H), 3.18 (s, 3H), 3.69 (s, 3H), 4.06-4.11 (m, 1H), 5.32 (bs, 1H).

Example 9

Preparation of Compound I-002

[Formula 95]

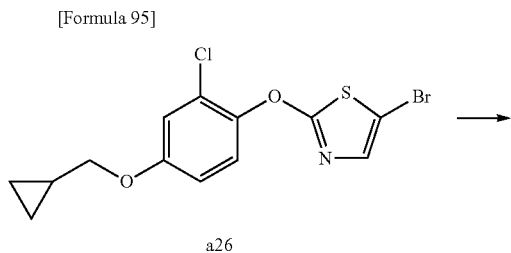

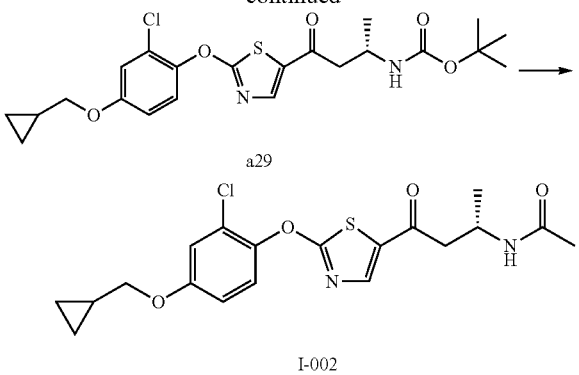

Step 1 Preparation of Compound a29

Compounds of a26 (1.0 g, 2.8 mmol) was dissolved in THF (20 mL) and cooled to −78° C. 2.6 mol/L butyl lithium solution in hexane (2.2 mL, 5.6 mmol) was added to the mixture and the mixture was stirred for 30 minutes at −78° C. THF (5.0 mL) solution of Compound a28 (0.75 g, 3.1 mmol) was added to the reaction mixture, and the mixture was stirred at −78° C. for 5 minutes. The mixture was further gradually warmed to room temperature, and stirred for 1 hour. A saturated aqueous ammonium chloride solution and saturated brine was added to the reaction solution the mixture was extracted with ethyl acetate, and the organic layer was dried over anhydrous magnesium sulfate. The solvent was distilled off under reduced pressure, the obtained residue was purified by silica gel column chromatography (hexane-ethyl acetate) to give compound a29 (0.30 g, 23% yield).

$^1$H NMR (CDCl$_3$) δ: 0.36 (m, 2H), 0.67 (m, 2H), 1.25 (d, J=6.7 Hz, 3H), 1.42 (s, 9H), 2.86 (dd, J=15.1, 6.8 Hz, 1H), 3.16 (dd, J=15.1, 3.3 Hz, 1H), 3.80 (d, J=7.0 Hz, 2H), 4.10 (m, 1H), 4.88 (bs, 1H), 6.87 (dd, J=9.0, 3.0 Hz, 1H), 7.01 (d, J=3.0 Hz, 1H), 7.22 (d, J=9.0 Hz, 1H), 7.89 (s, 1H).

Step 2 Preparation of Compound I-002

Compound a29 (0.30 g, 0.64 mmol) was dissolved in 1,4-dioxane (3.0 mL), 4 mol/L hydrochloric acid in 1,4-dioxane (1.6 mL, 6.4 mmol) was added and the mixture was stirred at room temperature for 2 hours. The solvent was distilled off under reduced pressure, the obtained reaction product was dissolved in chloroform (3.0 mL), pyridine (0.16 mL, 1.9 mmol) and acetic anhydride (0.24 mL, 2.6 mmol) was added, and the mixture was stirred at 60° C. for 1 hour. A saturated aqueous sodium hydrogen carbonate solution was added, and the mixture was extracted with chloroform, and then dried with anhydrous magnesium sulfate. The solvent was distilled off under reduced pressure, the obtained residue was purified by silica gel column chromatography (hexane-ethyl acetate) to afford Compound I-002 (0.21 g, 81% yield).

$^1$H NMR (CDCl$_3$) δ: 0.36 (m, 2H), 0.66 (m, 2H), 1.27 (d, J=6.8 Hz, 3H), 1.95 (s, 3H), 2.93 (dd, J=15.8, 6.0 Hz, 1H), 3.16 (dd, J=15.8, 4.5 Hz, 1H), 3.80 (d, J=7.0 Hz, 2H), 4.40 (m, 1H), 6.04 (bd, J=7.8 Hz, 1H), 6.87 (dd, J=8.8, 2.8 Hz, 1H), 7.02 (d, J=2.8 Hz, 1H), 7.22 (d, J=8.8 Hz, 1H), 7.86 (s, 1H).

[M+H]=409.3, Method Condition 2: retention time 2.15 minutes

Example 10

Preparation of Compound I-004

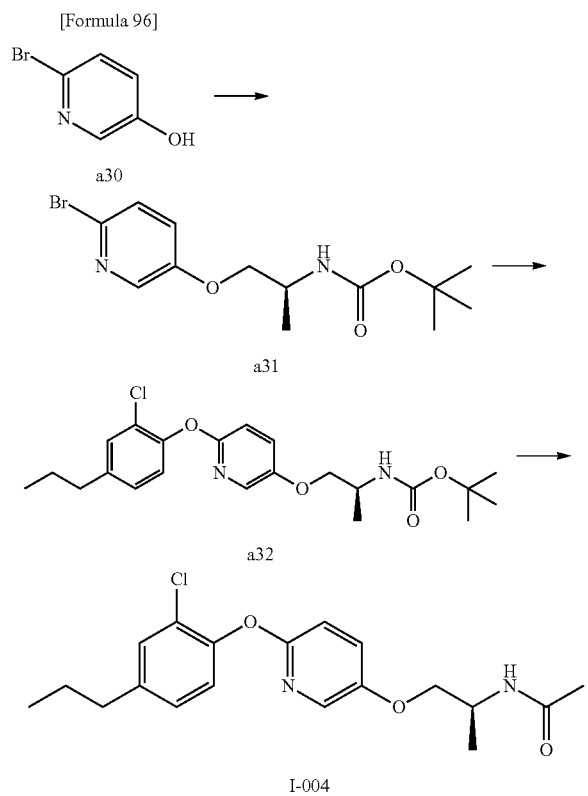

Step 1 Preparation of Compound a31

Compound a30 (0.5 g, 2.9 mmol) was dissolved in 1,4-dioxane (10 mL), Boc-L-alaninol (0.76 g, 4.3 mmol), triphenylphosphine (1.1 g, 4.3 mmol) and dimethyloxyethylazodicarboxylate (1.0 g, 4.3 mmol) were added, and, the mixture was stirred at 60° C. for 1 hour. Water was added to the reaction mixture, and the mixture was extracted with ethyl acetate. The organic layer was washed with saturated brine and dried over anhydrous magnesium sulfate. The solvent was distilled off under reduced pressure, and the obtained residue was purified by silica gel column chromatography (hexane-ethyl acetate) to give compound a31 (0.82 g, 86% yield).

$^1$H NMR (CDCl$_3$) δ: 1.29 (d, J=6.8 Hz, 3H), 1.45 (s, 9H), 3.96 (bs, 2H), 4.06 (bs, 1H), 4.68 (bs, 1H), 7.13 (dd, J=8.7, 2.6 Hz, 1H), 7.37 (d, J=8.7 Hz, 1H), 8.07 (d, J=2.6 Hz, 1H).

[M+H]=333.1, Method Condition 2: retention time 2.10 minutes

Step 2 Preparation of Compound a32

Compound a31 (0.11 g, 0.34 mmol) was dissolved in 1,4-dioxane (2.0 mL), 2-chloro-4-propyl phenol (87 mg, 0.51 mmol), 2-dimethyl-amino-acetic acid (32 mg, 0.31 mmol), copper iodide (20 mg, 0.10 mmol) and cesium carbonate (0.33 g, 1.0 mmol) were added, and, the mixture was stirred under microwave irradiation at 150° C. for 75 minutes. Water was added to the reaction mixture, and the mixture was extracted with ethyl acetate. The organic layer was washed with brine and dried over anhydrous magnesium sulfate. The solvent was distilled off under reduced pressure, and the obtained residue was purified by silica gel column chromatography (hexane-ethyl acetate) to give compound a32 (81 mg, 56% yield).

$^1$H NMR (CDCl$_3$) δ: 0.96 (t, J=7.3 Hz, 3H), 1.30 (d, J=6.8 Hz, 3H), 1.61-1.70 (m, 2H), 1.99 (s, 3H), 2.57 (t, J=7.5 Hz, 2H), 3.89-3.98 (m, 2H), 4.37 (m, 1H), 5.71 (bd, J=7.3 Hz, 1H), 6.89 (d, J=9.0 Hz, 1H), 7.05-7.13 (m, 2H), 7.31 (dd, J=9.0, 3.0 Hz, 1H), 7.80 (bd, J=2.8 Hz, 1H).

[M+H]=422.0, Method Condition 2: retention time 2.88 minutes

Step 3 Preparation of Compound I-004

Compound a32 (78 mg, 0.19 mmol) was dissolved in 1,4-dioxane (10 mL) and then, 4 mol/L hydrochloric acid in 1,4-dioxane (0.93 mL, 3.7 mmol) was added, and the mixture was stirred at room temperature for 1 hour. A saturated aqueous sodium hydrogen carbonate solution and water were added to the reaction mixture, and the mixture was extracted with ethyl acetate, and dried with anhydrous magnesium sulfate. The solvent was distilled off under reduced pressure, the obtained reaction product was dissolved in chloroform (3.0 mL), pyridine (0.045 mL, 0.56 mmol) and acetic anhydride (0.053 mL, 0.56 mmol) were added, and the mixture was stirred at room temperature for 1 hour. The solvent was distilled off under reduced pressure, and the obtained residue was purified by silica gel column chromatography (hexane-ethyl acetate) to afford Compound I-004 (37 mg, 56% yield).

$^1$H NMR (CDCl$_3$) δ: 0.96 (t, J=7.3 Hz, 3H), 1.30 (d, J=6.8 Hz, 3H), 1.61-1.70 (m, 2H), 1.99 (s, 3H), 2.57 (t, J=7.5 Hz, 2H), 3.89-3.98 (m, 2H), 4.37 (m, 1H), 5.71 (bd, J=7.3 Hz, 1H), 6.89 (d, J=9.0 Hz, 1H), 7.05-7.13 (m, 2H), 7.31 (dd, J=9.0, 3.0 Hz, 1H), 7.80 (bd, J=2.8 Hz, 1H).

[M+H]=364.2, Method Condition 2: retention time 2.32 minutes

Example 11

Preparation of Compound I-005

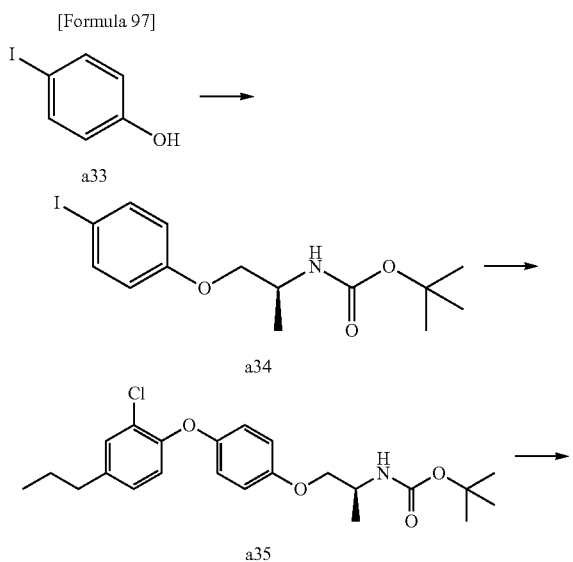

101

-continued

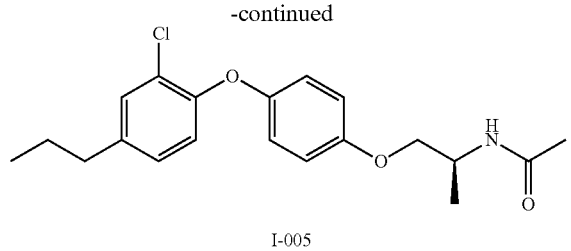

I-005

Step 1 Preparation of Compound a34

Compound a33 (0.50 g, 2.3 mmol) was dissolved in 1,4-dioxane (10 mL), Boc-L-alaninol (0.60 g, 3.4 mmol), triphenylphosphine (0.89 g, 3.4 mmol) and dimethyloxyethylazodicarboxylate (0.80 g, 3.4 mmol) were added, and, the mixture was stirred at room temperature. Water was added to the reaction mixture, and the mixture was extracted with ethyl acetate. The organic layer was washed with saturated brine and dried over anhydrous magnesium sulfate. The solvent was distilled off under reduced pressure, and the obtained residue was purified by silica gel column chromatography (hexane-ethyl acetate) to give compound a34 (0.42 g, 49% yield).

$^1$H NMR (CDCl$_3$) δ: 1.27 (d, J=7.0 Hz, 3H), 1.45 (s, 9H), 3.88-3.89 (m, 2H), 4.11 (bs, 1H), 4.71 (bs, 1H), 6.68 (d, J=7.3 Hz, 2H), 7.55 (d, J=7.3 Hz, 2H).

Step 2 Preparation of Compound a35

Compound a34 (0.20 g, 0.53 mmol) was dissolved in 1,4-dioxane (2.0 mL), 2-chloro-4-propyl phenol (0.14 g, 0.80 mmol), 2-dimethyl-amino-acetic acid (49 mg, 0.48 mmol), copper iodide (30 mg, 0.16 mmol) and cesium carbonate (0.52 g, 1.6 mmol) were added, and, the mixture was stirred under microwave irradiation at 150° C. for 75 minutes. Water was added to the reaction mixture, and the mixture was extracted with ethyl acetate. The organic layer was washed with brine and dried over anhydrous magnesium sulfate. The solvent was distilled off under reduced pressure, and the obtained residue was purified by silica gel column chromatography (hexane-ethyl acetate) to give compound a35 (0.14 g, 63% yield).

$^1$H NMR (CDCl$_3$) δ: 0.94 (t, J=7.5 Hz, 3H), 1.29 (d, J=6.8 Hz, 3H), 1.45 (s, 9H), 1.62 (m, 2H), 2.54 (t, J=7.5 Hz, 2H), 3.90-3.93 (m, 2H), 4.05 (bs, 1H), 4.79 (bs, 1H), 6.74-7.05 (m, 6H), 7.25-7.31 (m, 2H).

Step 3 Preparation of Compound I-005

Compound a35 (70 mg, 0.34 mmol) was dissolved in 1,4-dioxane (0.50 mL), 4 mol/L hydrochloric acid in 1,4-dioxane (2.5 mL, 10 mmol), and the mixture was stirred at room temperature for 3 hours. The solvent was evaporated under reduced pressure. The obtained residue was dissolved in chloroform (2.0 mL), pyridine (0.045 mL, 0.56 mmol) and acetic anhydride (0.053 mL, 0.56 mmol) were added, and the mixture was stirred at room temperature for 1 hour. The solvent was distilled off under reduced pressure, and the obtained residue was purified by preparative HPLC (0.1% formic acid-containing acetonitrile-water) to give Compound I-005 (19 mg, 46% yield).

$^1$H NMR (CDCl$_3$) δ: 0.94 (t, J=7.3 Hz, 3H), 1.31 (d, J=6.9 Hz, 3H), 1.62 (m, 2H), 2.00 (s, 3H), 2.54 (t, J=7.6 Hz, 2H), 3.88-3.97 (m, 2H), 4.38 (m, 1H), 5.80 (bd, J=7.5 Hz, 1H), 6.79-7.05 (m, 6H), 7.25-7.27 (m, 2H).

[M+H]=362.3, Method Condition 3: retention time 2.56 minutes

102

Example 12

Preparation of Compound I-011

[Formula 98]

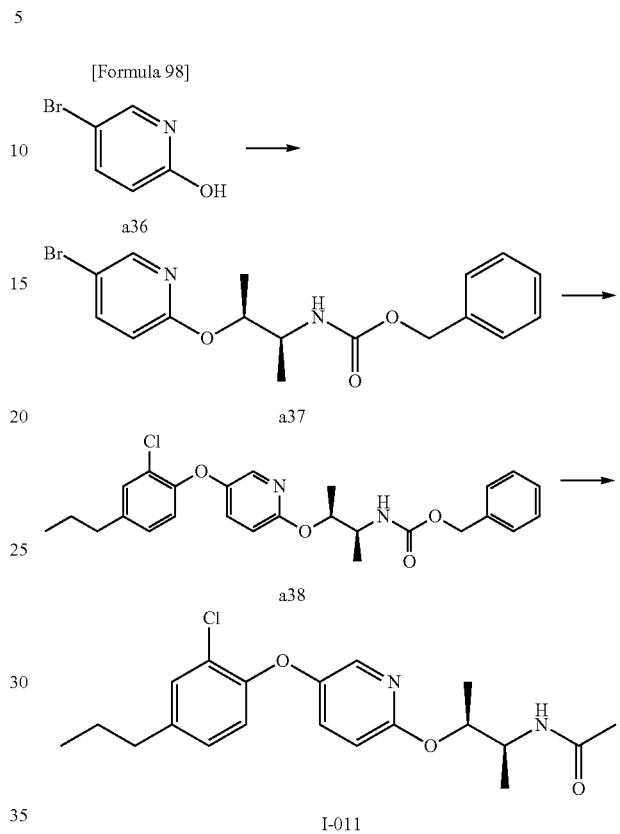

Step 1 Preparation of Compound a37

Compound a36 (0.34 g, 2.0 mmol) was dissolved in 1,4-dioxane (8.0 mL), benzyl ((2S,3R)-3-hydroxy-butan-2-yl) carbamate (0.40 g, 1.8 mmol; Tetrahedron Letters, 1998, 39, 5195-5198), triphenylphosphine (0.66 g, 2.3 mmol) and dimethyloxyethylazodicarboxylate (0.55 g, 2.3 mol) were added, and the mixture was stirred at 50° C. for 30 minutes. Water was added to the reaction mixture, and the mixture was extracted with ethyl acetate. The organic layer was washed with saturated brine, and dried over anhydrous magnesium sulfate. The solvent was distilled off under reduced pressure, the obtained residue was purified by silica gel column chromatography (hexane-ethyl acetate) to give compound a37 (0.26 g, 39% yield).

$^1$H NMR (CDCl$_3$) δ: 1.19 (d, J=6.9 Hz, 3H), 1.29 (d, J=6.2 Hz, 3H), 3.95 (bs, 2H), 5.07-5.21 (m, 4H), 6.58 (d, J=8.4 Hz, 1H), 7.34 (m, 5H), 7.60 (d, J=8.4 Hz, 1H), 8.14 (s, 1H).

[M+H]=380.7, Method Condition 2: retention time 2.50 minutes

Step 2 Preparation of Compound a38

Compound a37 (0.13 g, 0.34 mmol) was dissolved in 1,4-dioxane (2.0 mL), 2-chloro-4-propyl phenol (86 mg, 0.51 mmol), 2-dimethyl amino acetic acid (31 mg, 0.30 mmol), copper iodide (19 mg, 0.10 mmol) and cesium carbonate (0.33 g, 1.0 mmol) were added, and, the mixture was stirred under microwave irradiation at 150° C. for 75 minutes. Water and 28% aqueous ammonia were added to the reaction mixture, and the mixture was extracted with ethyl acetate. The organic layer was washed with brine and dried over anhydrous magnesium sulfate. The solvent was distilled off under reduced pressure, and the obtained residue was purified by silica gel column chromatography (hexane-ethyl acetate) to give compound a38 (28 mg, 18% yield).

[M+H]=469.2, Method Condition 3: retention time 3.23 minutes

Step 3 Preparation of Compound I-011

Compound a38 (27 mg, 0.058 mmol) was dissolved in methanol (10 mL), 10% palladium on carbon (50% water) (27 mg) was added, and the mixture was stirred at room temperature under hydrogen atmosphere of 1 atm for 1 hour. Triethylamine (1.0 mL) was added to the reaction mixture, and the mixture was filtered through Celite. The solvent was distilled off under reduced pressure, and the obtained residue was dissolved in DMF (1 mL). Pyridine (0.023 mL, 0.29 mmol) and acetic anhydride (0.027 mL, 0.29 mmol) were added and the mixture was stirred overnight at room temperature. The obtained reaction solution was purified by preparative HPLC (0.1% formic acid-containing acetonitrile-water) to give Compound I-011 (4.0 mg, 18% yield).

1H NMR (CDCl$_3$) δ: 0.94 (t, J=7.0 Hz, 3H), 1.20 (d, J=6.8 Hz, 3H), 1.30 (d, J=6.2 Hz, 3H), 1.59-1.68 (m, 2H), 1.99 (s, 3H), 2.57 (t, J=7.5 Hz, 2H), 4.20 (m, 1H), 5.14 (m, 1H), 5.94 (bd, J=8.5 Hz, 1H), 6.70 (d, J=9.3 Hz, 1H), 6.85 (d, J=8.2 Hz, 2H), 7.01 (d, J=8.2 Hz, 2H), 7.27 (m, 2H), 7.85 (s, 1H).

[M+H]=377.4, Method Condition 3: retention time 2.60 minutes

Example 13

Preparation of Compound I-0126

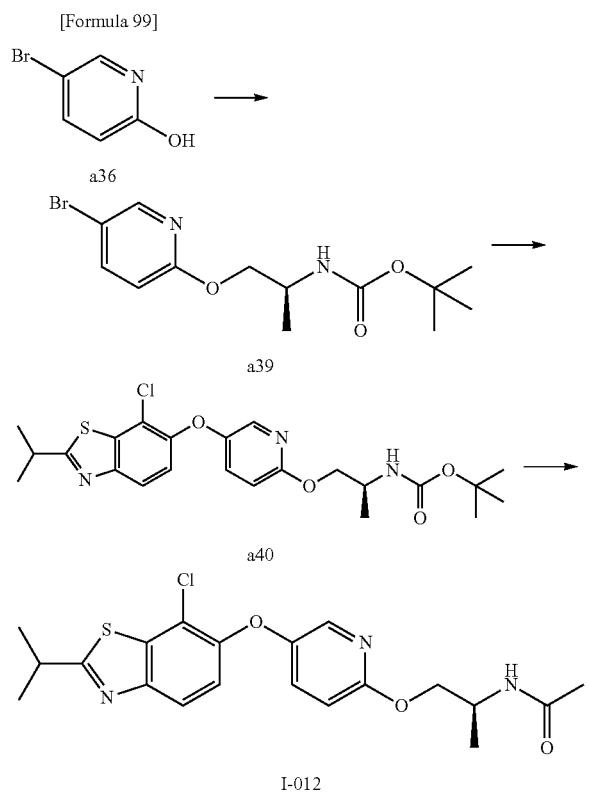

[Formula 99]

Step 1 Preparation of Compound a39

Compound a36 (1.5 g, 8.6 mmol) was dissolved in 1,4-dioxane (15 mL), Boc-L-alaninol (1.8 g, 10 mmol), triphenylphosphine (2.9 g, 11 mmol) and dimethyloxyethylazodicarboxylate (2.6 g, 11 mmol) were added and the mixture was stirred at room temperature for 1 hour. Water was added to the reaction mixture, and the mixture was extracted with ethyl acetate. The organic layer was washed with saturated brine, and dried over anhydrous magnesium sulfate. The solvent was distilled off under reduced pressure, the obtained residue was purified by silica gel column chromatography (hexane-ethyl acetate) to give compound a39 (2.2 g, 76% yield).

$^1$H NMR (CDCl$_3$) δ: 1.24 (d, J=6.8 Hz, 3H), 1.44 (s, 9H), 4.07 (bs, 1H), 4.22-4.23 (m, 2H), 4.76 (bs, 1H), 6.68 (d, J=8.5 Hz, 1H), 7.65 (d, J=8.5 Hz, 1H), 8.17 (s, 1H).

[M+H]=333.1, Method Condition 2: retention time 2.35 minutes

Step 2 Preparation of Compound a40

Compound a39 was dissolved in 1,4-dioxane (4.0 mL), Compound 16 (0.21 g, 0.91 mmol), 2-dimethyl amino acetic acid (56 mg, 0.54 mmol), copper iodide (35 mg, 0.18 mmol) and cesium carbonate (0.59 g, 1.8 mmol) were added, and the mixture was stirred under microwave irradiation at 150° C. for 1 hour. Water and 28% aqueous ammonia were added to the reaction mixture, and the mixture was extracted with ethyl acetate. The organic layer was washed with brine and dried over anhydrous magnesium sulfate. The solvent was distilled off under reduced pressure, and the obtained residue was purified by silica gel column chromatography (hexane-ethyl acetate) to give compound a40 (46 mg, 16% yield).

[M+H]=478.1, Method Condition 2: retention time 2.95 minutes

Step 3 Preparation of Compound I-012

Compound a40 (46 mg, 0.096 mmol) and 1,4-dioxane (1.0 mL) and then 4 mol/L hydrochloric acid in 1,4-dioxane (0.48 mL, 1.9 mmol) was added and the mixture was stirred at room temperature for 30 minutes. The solvent was evaporated under reduced pressure. The residue was dissolved in DMF (1.0 mL) and pyridine (0.039 mL, 0.48 mmol) and acetic anhydride (0.045 mL, 0.48 mmol) were added and the mixture was stirred at room temperature for 1 hour. The residue was purified by preparative HPLC (0.1% formic acid-containing acetonitrile-water) to give Compound I-012 (25 mg, 62% yield).

$^1$H NMR (CDCl$_3$) δ: 1.27 (d, J=7.0 Hz, 3H), 1.50 (d, J=7.3 Hz, 3H), 1.97 (s, 3H), 3.42 m, J=6.8 Hz, 2H), 4.24-4.38 (m, 3H), 5.93 (bd, J=6.0 Hz, 1H), 6.76 (d, J=8.8 Hz, 1H), 7.08 (d, J=8.8 Hz, 1H), 7.28-7.31 (m, 1H), 7.80 (d, J=8.8 Hz, 1H), 7.89 (bd, J=2.3 Hz, 1H).

[M+H]=420.3, Method Condition 3: retention time 2.39 minutes

Example 14

Preparation of Compound I-106

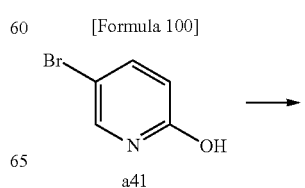

[Formula 100]

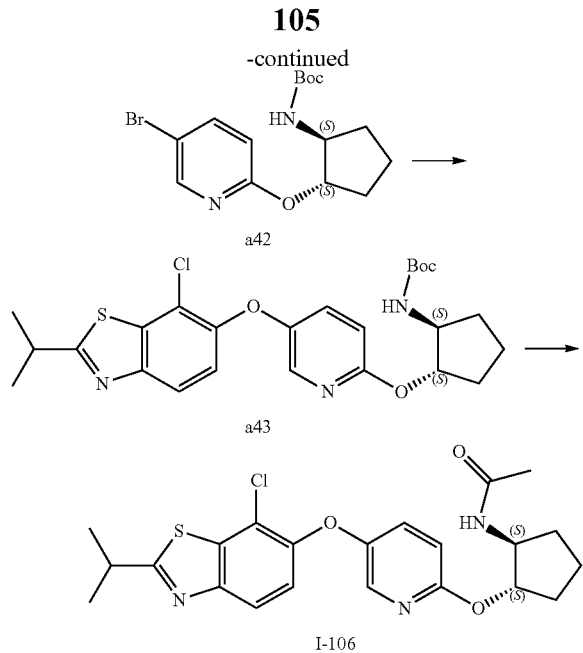

Step 1 Preparation of Compound a42

Compound a41 (1.12 g, 6.5 mmol) was dissolved in 1,4-dioxane (15 mL), t-butyl ((1S,2R)-2-hydroxy-cyclopentyl) carbamate (1.0 g, 5.0 mmol), triphenylphosphine (1.7 g, 6.5 mmol) and dimethyl oxyethyl azodicarboxylate (1.5 g, 6.5 mmol) were added and the mixture was stirred at 65° C. for 1 hour. Water was added to the reaction mixture, and the mixture was extracted with ethyl acetate. The organic layer was washed with saturated brine, and dried over anhydrous magnesium sulfate. The solvent was distilled off under reduced pressure, and the contained residue was purified by silica gel column chromatography (hexane-ethyl acetate) to give compound a42 (1.4 g, 77% yield).

$^1$H NMR (CDCl$_3$) δ: 1.41 (s, 9H), 1.45-1.54 (m, 1H), 1.71-1.85 (m, 3H), 2.10-2.15 (m, 1H), 2.23-2.26 (m, 1H), 3.97 (m, 1H), 4.91 (m, 1H), 5.13-5.14 (m, 1H), 6.67 (d, J=8.7 Hz, 1H), 7.63 (d, J=8.7 Hz, 1H), 8.15 (s, 1H).

[M+H]=358.3, Method Condition 4: retention time 2.57 minutes

Step 2 Preparation of Compound a43

Compound a42 was dissolved in 1,4-dioxane (8.0 mL), Compound a16 (0.38 g, 1.68 mmol), 2-dimethyl amino acetic acid (104 mg, 1.01 mmol), copper iodide (64 mg, 0.34 mmol) and cesium carbonate (1.09 g, 3.36 mmol) were added, and the mixture was stirred under microwave irradiation at 150° C. for 70 minutes. Water and 28% aqueous ammonia were added to the reaction mixture, and the mixture was extracted with ethyl acetate. The organic layer was washed with brine and dried over anhydrous magnesium sulfate. The solvent was distilled off under reduced pressure, and the obtained residue was purified by silica gel column chromatography (hexane-ethyl acetate) to give compound a43 (135 mg, 24% yield).

[M+H]=504.1, Method Condition 2: retention time 3.08 minutes

Step 3 Preparation of Compound I-106

Compound a43 was dissolved in 1,4-dioxane (1.0 mL) and 4 mol/L hydrochloric acid in 1,4-dioxane (1.34 mL, 5.36 mmol) was added and the mixture was stirred at room temperature for 30 minutes. The solvent was evaporated under reduced pressure. The residue was dissolved in DMF (1.0 mL) and pyridine (0.108 mL, 1.34 mmol) and acetic anhydride (0.127 mL, 1.34 mmol) was added and the mixture was stirred at room temperature for 1 hour. The residue was purified by preparative HPLC (0.1% formic acid-containing acetonitrile-water) to afford Compound I-106 (34 mg, 29% yield).

$^1$H NMR (CDCl$_3$) δ 1.46 (m, 1H), 1.50 (d, J=7.0 Hz, 6H), 1.70-1.85 (m, 3H), 1.93 (s, 3H), 2.09-2.20 (m, 1H), 2.33-2.39 (m, 3H), 3.37-3.47 (m, 1H), 4.12-4.19 (m, 1H), 5.15-5.22 (m, 1H), 6.40 (m, 1H), 6.77 (d, J=9.0 Hz, 1H), 7.07 (d, J=8.8 Hz, 1H), 7.28-7.29 (m, 1H), 7.80 (d, J=8.8 Hz, 1H), 7.86-7.87 (m, 1H).

[M+H]=446.0, Method Condition 4: retention time 2.58 minutes

Example 15

Preparation of Compound c7

Step 1 Preparation of Compound c1

[Formula 101]

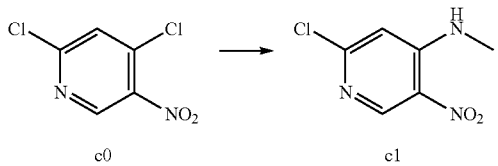

Compound c0 (4.0 g, 20.7 mmol) was dissolved in THF (20 mL), and triethylamine (3.74 mL, 26.9 mmol) and 1.0 mol/L methyl amine THF solution (11.4 mL, 22.8 mmol) were added to the mixture while cooling in ice, and the mixture was stirred at room temperature for 1 hour. 1.0 mol/L methyl amine THF solution (34.2 mL, 68.4 mmol) was further added to the mixture, and the mixture was stirred for one and half hours. In addition, 1.0 mol/L methyl amine THF solution (18.0 mL, 36.0 mmol) was added to the mixture, and the mixture was stirred for 15 hours. Water was added to the mixture while cooling in ice, and the mixture was extracted with ethyl acetate. The organic layer was washed with saturated brine, and dried over anhydrous magnesium sulfate. The solvent was condensed under reduced pressure to afford a crude compound c1 (3.50 g, yield 90%).

$^1$H-NMR (CDCl$_3$) δ: 3.06 (d, J=4.8 Hz, 3H), 6.75 (s, 1H), 8.17 (brs, 1H), 9.02 (s, 1H).

[M+H]=187.95, Method Condition 3: retention time 1.45 min

Step 2 Preparation of Compound c2

[Formula 102]

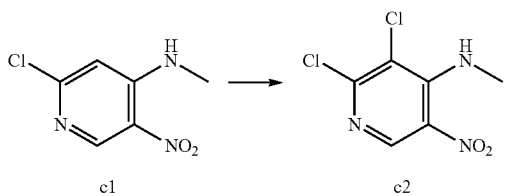

N-chlorosuccinimide (615 mg, 4.61 mmol) was added to the DMF solution (10 mL) of Compound c1 (786 mg, 4.19 mmol), and the mixture was stirred for 2.5 hours at room temperature. Distilled water (50 mL) was added to the mixture, and the mixture was extracted with ethyl acetate twice. The organic layer was washed with 50 mL of distilled water five times and 50 mL of saturated brine once. The organic layer was dried over anhydrous sodium sulfate. The solvent was condensed under reduced pressure to afford a compound c2 (960 mg, quant).

$^1$H-NMR (CDCl$_3$) δ: 3.29 (d, J=5.5 Hz, 3H), 7.62 (br s, 1H), 8.78 (s, 1H).

Step 3 Preparation of Compound c3

[Formula 103]

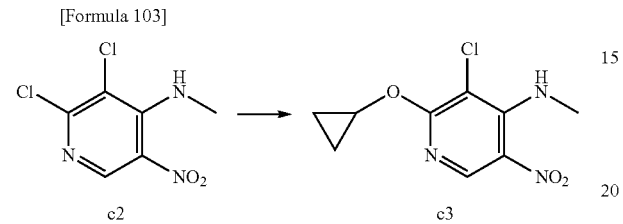

Cyclopropanol (157 mg, 2.70 mmol), 18-crown-6 (714 mg, 2.70 mmol) and cesium carbonate (1.761 g, 5.40 mmol) were added to the THF solution (4 mL) of Compound c2 (400 mg, 1.802 mmol), and the mixture was refluxed for 7 hours. The mixture was diluted with ethyl acetate (20 mL) and filtered through celite. The filtrate was condensed under reduced pressure, and the residue was purified by silica gel chromatography (hexane:ethyl acetate=5:1) to afford Compound c3 (140 mg, yield 32%) as yellow solid.

$^1$H-NMR (CDCl$_3$) δ: 0.82-0.85 (m, 4H), 3.33 (d, J=5.5 Hz, 3H), 4.40-4.45 (m, 1H), 7.84 (br s, 1H), 8.86 (s, 1H).

Step 4 Preparation of Compound c4

[Formula 104]

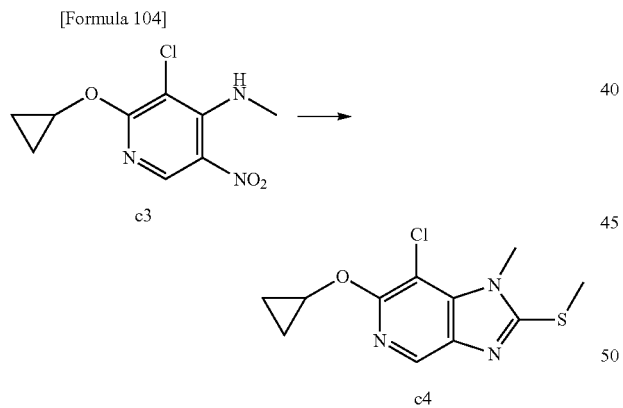

Diluted water (0.5 mL), reduced iron (128 mg, 2.298 mmol) and ammonium chloride (123 mg, 2.298 mmol) were added to the ethanol solution (2 mL) of Compound a3, and the mixture was stirred at 60° C. for 4 hours. The mixture was filtered through celite and the filtrate was condensed under reduced pressure. 1,1'-thiocarbonyl diimidazole (123 mg, 0.690 mmol) was added to THF solution (2 mL) of the obtained residue, the mixture was stirred at room temperature for 1.5 hours. Potassium carbonate (318 mg, 2.298 mmol) and methyl iodide (0.072 ml, 1.149 mmol) were added to the mixture, the mixture was stirred at room temperature for further 12 hours. The mixture was filtered through celite. The filtrate was condensed under reduced pressure, and the residue was purified by silica gel chromatography (hexane:ethyl acetate=2:1) to afford Compound c4 (68 mg, yield 44%) as white solid.

$^1$H-NMR (d6-DMSO) δ: 0.65-0.81 (m, 4H), 2.73 (s, 3H), 3.88 (s, 3H), 4.32-4.36 (m, 1H), 8.40 (s, 1H).

Step 5 Preparation of Compound c5

[Formula 105]

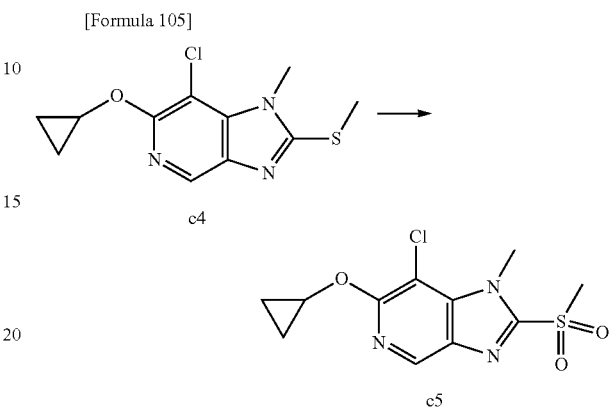

m-CPBA (131 mg, 0.530 mmol) was added to the dichloromethane (1 mL) solution of Compound c4 (65 mg, 0.241 mmol), and the mixture was stirred at room temperature for 2 hours. A saturated sodium bicarbonate aqueous solution (10 mL) was added to the mixture, and the mixture was extracted with ethyl acetate (10 mL) twice. The organic layer was washed with saturated sodium bicarbonate aqueous solution (10 mL) three times, and saturated brine (10 mL) once. The organic layer was dried over anhydrous sodium sulfate. The solvent was condensed under reduced pressure, and the residue was purified by silica gel chromatography (hexane:ethyl acetate=1:1) to afford Compound c5 (65 mg, yield 89%) as white solid.

$^1$H-NMR (CDCl$_3$) δ: 0.83-0.87 (m, 4H), 3.56 (s, 3H), 4.39 (s, 3H), 4.41-4.45 (m, 1H), 8.68 (s, 1H).

Step 6 Preparation of Compound c7

[Formula 106]

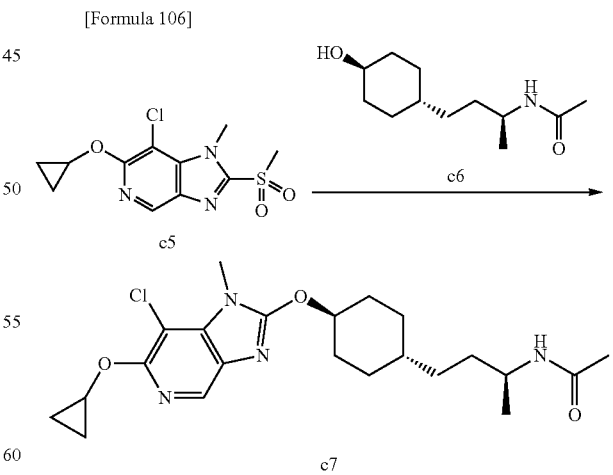

Compound c6 (57.9 mg, 0.271 mmol) and tert-butoxy potassium (60.9 mg, 0.543 mmol) were successively added to the THF (1 mL) solution of Compound c5 (63 mg, 0.209 mmol) under ice-cooling. The reaction solution was stirred at 0° C. for 30 minutes A saturated ammonium chloride solution (10 ml) was added to the reaction mixture, and the mixture was extracted with ethyl acetate (10 ml) twice. The organic layers washed with distilled water (10 ml) twice once with saturated brine (10 ml), and dried over sodium sulfate. The solvent was evaporated under reduced pressure, and the residue was sequentially purified by DNH column chromatography (hexane:ethyl acetate=1:2) and silica gel column chromatography (chloroform:methanol=10:1) to give compound c7 to (30 mg, 33%) by solidifying with ethyl acetate.

Example 16

Preparation of Compound c18

Step 1 Preparation of Compound c9

[Formula 107]

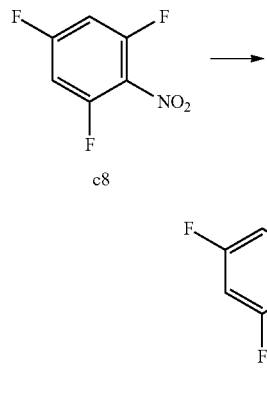

To the THF (20 ml) solution of Compound c8 (2 g, 11.29 mmol), trimethylamine (3.44 ml, 24.85 mmol) and methylamine (33% ethanol solution, 1.547 ml, 12.42 mmol) were added sequentially while cooling in ice. The reaction mixture was stirred at 0° C. for 10 hours. A saturated brine was added to the reaction mixture, and the reaction mixture was extracted with ethyl acetate (100 ml) twice. The organic layer was dried over sodium sulfate. The solvent was condensed under reduced pressure to afford Compound c9 (2.2 g, 90% purity, 93%) as a mixture with Compound c10.

$^1$H-NMR (CDCl$_3$) δ: 2.97 (d, J=5.0 Hz, 3H), 6.18-6.28 (m, 2H), 7.64 (s, 1H).

Step 2 Preparation of Compound c11

[Formula 108]

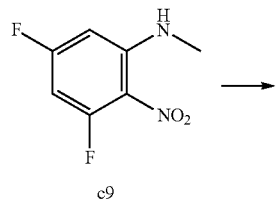

-continued

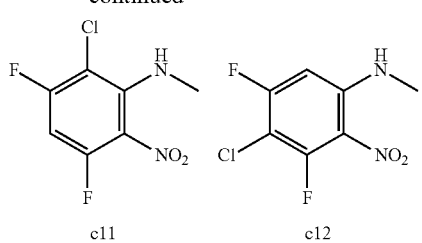

N-chlorosuccinimide (4.62 g, 34.6 mmol) was added to the acetonitrile (40 ml) solution of Compound c9 (5.92 g, 90% purity, 28.35 mmol), and the mixture was stirred at 90° C. for 1 hour. The reaction mixture was condensed under reduced pressure, and the insoluble matter was filtered. The residue was purified by silica gel column chromatography (hexane:ethyl acetate=5:1) to afford the mixture of Compounds c11 and c12 (2.25 g, 32%) as a yellow solid.

$^1$H-NMR (CDCl$_3$) δ: 2.94 (d, J=5.5 Hz, 3H), 5.23 (s, 1H), 6.43 (dd, J=9.9, 8.5 Hz, 1H).

Step 3 Preparation of Compound c13

[Formula 109]

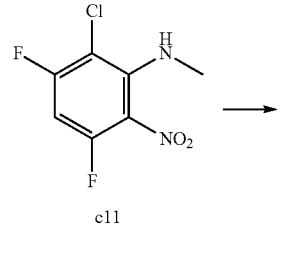

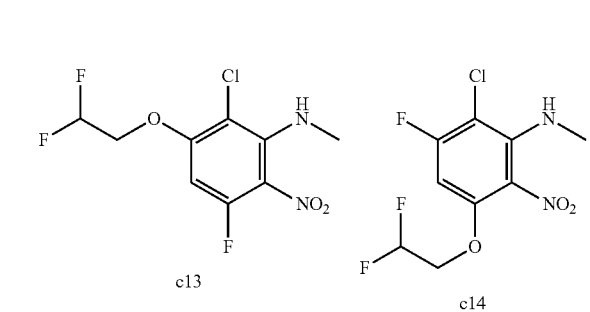

To the THF (20 mL) solution of Compound c11 (2.25 g, 10.11 mmol), 2,2-difluoroethanol (0.704 ml, 11.12 mmol), potassium carbonate (3.07 g, 22.24 mmol) and 18-crown-6 (8.02 g, 30.3 mmol) were added, and then the mixture was refluxed for 1 hour. Distilled water (30 ml) was added to the reaction mixture, and the reaction mixture was extracted with ethyl acetate (30 ml) twice. The organic layer was washed with distilled water (30 ml) twice, and saturated brine (30 ml) once. The organic layer was dried over sodium sulfate, and the solvent was concentrated under reduced pressure. The residue was purified by silica gel column chromatography (hexane:ethyl acetate=5:1) to afford Compound c13 as the mixture with Compound c14 (1.33 g, c13:c14=2:1, 31%).

Step 4 Preparation of Compound c15

[Formula 110]

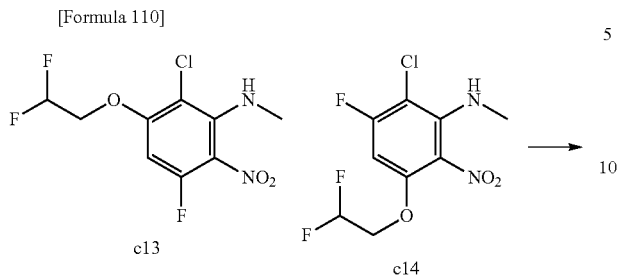

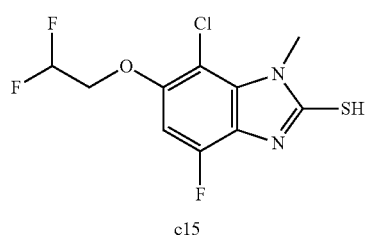

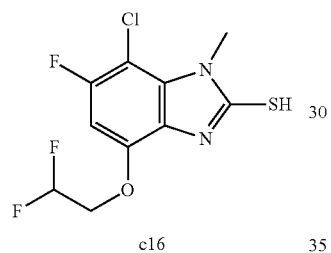

To the THF (20 ml) solution of the mixture of Compound c13 and Compound c14 (1.33 g, 4.67 mmol, c13:c14=2:1), 5% Pt/C (50% wet, 300 mg, 0.038 mmol) was added, and the mixture was stirred for 14 hours under hydrogen atmosphere. After filtered by celite, the solvent was concentrated under reduced pressure. Imidazole (0.636 g, 9.35 mmol) and 1,1'-thiocarbonyl diimidazole (0.999 g, 5.61 mmol) were added to the THF (20 ml) solution of the residue, and the mixture was refluxed for 2 hours. Distilled water was added to the reaction mixture, and the reaction mixture was extracted with ethyl acetate. The organic layer was washed with brine twice, and dried over sodium sulfate. The solvent was concentrated under reduced pressure. The residue was suspended with ethyl acetate, and filtered to afford Compound c15 as a mixture with Compound c16 (1.05 g, c15:c16=2:1, 50%).

Step 5 Preparation of Compound c17

[Formula 111]

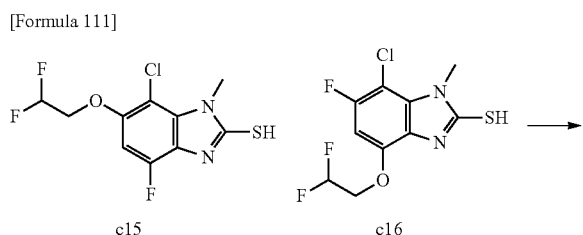

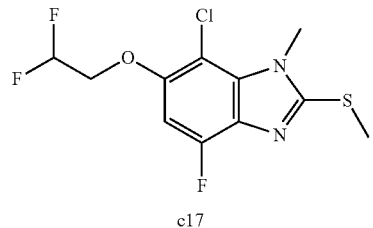

To the THF (10 ml) solution of the mixture of Compound c15 and Compound c16 (988 mg, 3.33 mmol, c15:c16=2:1), potassium carbonate (1013 mg, 7.33 mmol) and methyl iodide (0.229 ml, 3.66 mmol) were added, and the mixture was stirred at room temperature for 3 hours. After filtered by celite, the solvent was concentrated under reduced pressure. The residue was purified by silica gel column chromatography (hexane:ethyl acetate=3:1) to afford Compound c17 (581 mg, 56%) as a white solid.

$^{1}$H-NMR (CDCl$_3$) δ: 2.80 (s, 3H), 4.00 (s, 3H), 4.23 (td, J=13.0, 4.1 Hz, 2H), 6.14 (tt, J=55.0, 4.1 Hz, 1H), 6.68 (d, J=10.7 Hz, 1H).

Step 6 Preparation of Compound c18

[Formula 112]

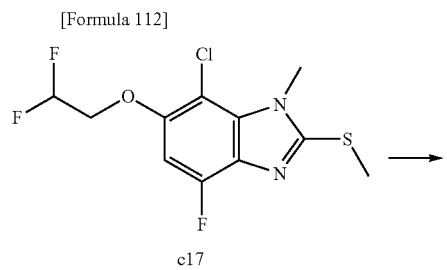

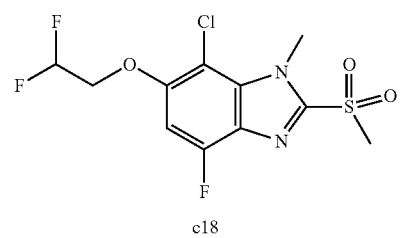

To the dichloromethane (10 ml) solution of Compound c17 (580 mg, 1.867 mmol), m-chloroperbenzoic acid (1012 mg, 4.11 mmol) was added at room temperature for 5 hours. Distilled water (50 ml) was added to the reaction mixture, and the reaction mixture was extracted with ethyl acetate (50 ml) twice. The organic layer was washed with 1 mol/L sodium hydrate aqueous solution (50 ml) five times and saturated brine (50 ml) once. The organic layer dried over sodium sulfate, and then the solvent was concentrated under reduced pressure. The residue was suspended with ethyl acetate, and filtered to afford Compound c18 (640 mg, 100%) as a white solid.

$^{1}$H-NMR (CDCl$_3$) δ: 3.59 (s, 3H), 4.29 (td, J=12.8, 4.1 Hz, 2H), 4.45 (s, 3H), 6.16 (tt, J=54.8, 4.1 Hz, 1H), 6.85 (d, J=10.5 Hz, 1H).

Example 17

Preparation of Compound c26

Step 1 Preparation of Compound c20

[Formula 113]

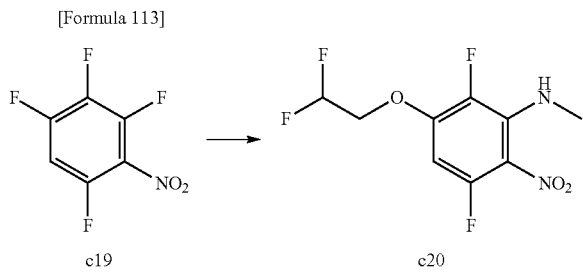

To the THF (50 ml) solution of Compound c19 (21.63 g, 111 mmol), potassium carbonate (33.7 g, 244 mmol) and methylamine (33% ethanol solution, 14.49 ml, 116 mmol) were sequentially added while cooling in ice, and the mixture was stirred at 0° C. for 20 minutes. After filtered by celite, the solvent was concentrated under reduced pressure. The residue was diluted with ethyl acetate (200 ml). The organic layer was washed with saturated brine (200 ml) three times, and dried with sodium sulfate. The solvent was concentrated under reduced pressure. To the THF (150 ml) solution of the obtained solid residue, potassium carbonate (30.6 g, 222 mmol), 2,2-difluoroethanol (7.02 ml, 111 mmol) and 18-crown-6 (35.2 g, 133 mmol) were added, and then the mixture was refluxed for 1 hour. After filtered by celite, the solvent was concentrated under reduced pressure. The residue was purified by silica gel chromatography (hexane:ethyl acetate=5:1) to afford Compound c20 (21.1 g, 71%) as a yellow solid.

$^1$H-NMR (CDCl$_3$) δ: 3.18 (dd, J=6.9, 5.4 Hz, 3H), 4.26 (td, J=12.7, 4.0 Hz, 2H), 5.93-6.28 (m, 2H), 6.83 (s, 1H).

Step 2 Preparation of Compound c21

[Formula 114]

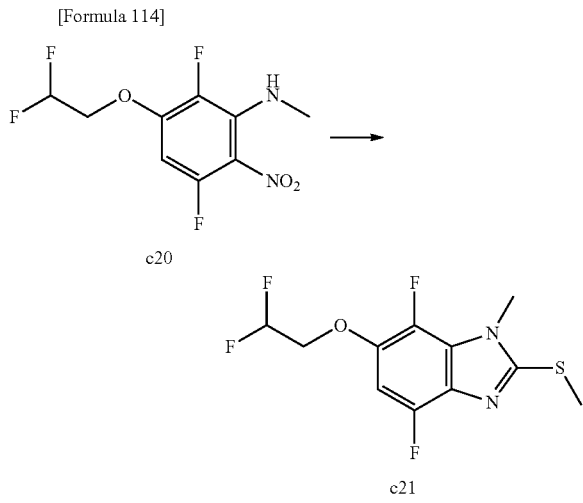

To the ethanol (10 ml) suspension of Compound c21 (2.03 g, 7.57 mmol), THF (10 mL), zinc (2.475 g, 37.8 mmol) and ammonium chloride (2.025 g, 37.8 mmol) were added, and the mixture was stirred at room temperature for 2 hours. The reaction mixture was filtered by celite, and the solvent was concentrated under reduced pressure. To the THF (20 ml) solution of the obtained residue, imidazole (1.546 g, 22.71 mmol) and 1,1'-thiocarbonyl diimidazole (1.619 g, 9.08 mmol) were added, and the mixture was stirred for 1 hour while refluxing. Potassium carbonate (2.092 g, 15.14 mmol) and methyl iodide (0.568 ml, 9.08 mmol) were added to the reaction solution, and the mixture was further stirred at room temperature for 3 hours. The reaction mixture was filtered by celite, and the solvent was concentrated under reduced pressure. The residue was purified by silica gel column chromatography (hexane:ethyl acetate=2:1) to afford Compound c21 (1.83 g, 82%) as a white solid.

$^1$H-NMR (CDCl$_3$) δ: 2.80 (s, 3H), 3.84 (s, 3H), 4.25 (td, J=13.1, 4.1 Hz, 2H), 6.10 (tt, J=55.0, 4.1 Hz, 1H), 6.66 (dd, J=10.5, 6.0 Hz, 1H).

Step 3 Preparation of Compound c22

[Formula 115]

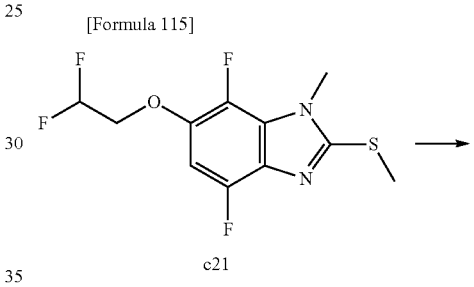

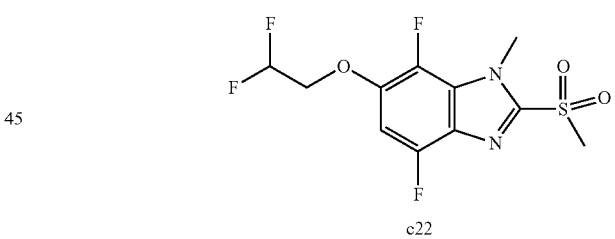

To the dichloromethane (30 ml) solution of Compound c21 (1.8 g, 6.12 mmol), m-chloroperbenzoic acid (3.32 g, 13.46 mmol) was added, and the mixture was stirred at room temperature for 3 hours. Distilled water (200 ml) was added to the reaction mixture, and the reaction mixture was extracted with ethyl acetate (200 ml) twice. The organic layer was washed with 0.1 mol/L sodium hydrate aqueous solution (200 ml) five times, and brine (200 ml) once. The organic layer was dried over sodium sulfate, and the solvent was concentrated under reduced pressure. The residue was suspended with ethyl acetate and filtered to afford Compound c22 (2 g, 100%) as a white solid.

$^1$H-NMR (CDCl$_3$) δ: 3.58 (s, 3H), 4.29 (s, 3H), 4.32 (dt, J=4.0, 12.9 Hz, 2H), 6.12 (tt, J=54.8, 4.0 Hz, 1H), 6.84 (dd, J=10.3, 5.9 Hz, 1H).

Step 4 Preparation of Compound c24

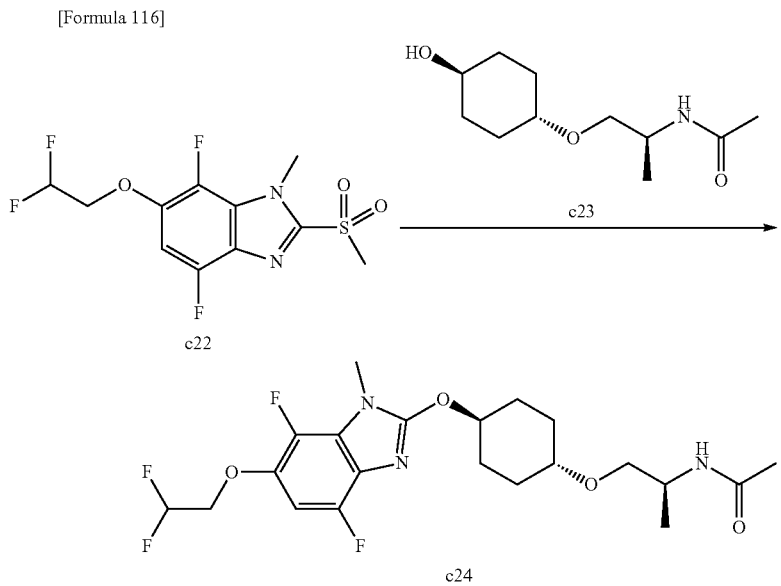

[Formula 116]

The compound c23 (145 mg, 0.674 mmol) was added to the THF (2 ml) suspension of tert-butoxy potassium (151 mg, 1.349 mmol) under ice-cooling. After the reaction mixture was stirred at 0° C. for 10 minutes, the THF (3 ml) solution of Compounds c22 (200 mg, 0.613 mmol) was added dropwise under ice-cooling. The mixture was stirred for a further 1 hour at 0° C. A saturated aqueous ammonium chloride solution (30 ml) was added to the mixture under ice-cooling. The reaction solution was extracted with ethyl acetate (30 ml) twice, with a saturated aqueous ammonium chloride solution (30 ml) once, and washed with saturated brine (30 ml) twice. The organic layer was dried with sodium sulfate, and the solvent was evaporated under reduced pressure.

The residue was purified by DNH column chromatography (chloroform:methanol=10:1) and purified sequentially silica gel column chromatography (chloroform:methanol=10:1) to give Compound c24 (250 mg, 88%) as a white solid by solidifying with ethyl acetate.

$^1$H-NMR (CDCl$_3$) δ 1.19 (d, J=6.7 Hz, 3H), 1.49-1.61 (m, 2H), 1.63-1.72 (m, 2H), 1.94-2.05 (m, 5H), 2.14-2.25 (m, 2H), 3.36-3.50 (m, 3H), 3.70 (d, J=0.9 Hz, 3H), 4.09-4.28 (m, 3H), 5.17-5.23 (m, 1H), 5.66 (d, J=7.0 Hz, 1H), 6.09 (tt, J=55.1, 4.1 Hz, 1H), 6.61 (dd, J=10.7, 6.1 Hz, 1H).

Step 5 Preparation of Compound c25

[Formula 117]

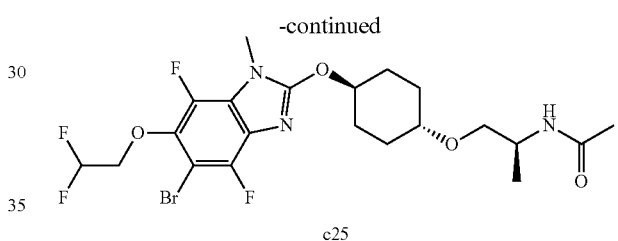

-continued

N-bromosuccinimide (106 mg, 0.596 mmol) was added to the acetonitrile (0.5 ml) solution of Compound c24 (250 mg, 0.541 mmol), and the mixture was stirred for 2 hours at 45° C. The solvent was evaporated under reduced pressure, and the residue was purified by silica gel column chromatography (chloroform:methanol=10:1) to give compound c25 (299 mg, quant) as a white solid.

$^1$H-NMR (CDCl$_3$) δ: 1.19 (d, J=6.8 Hz, 3H), 1.51-1.61 (m, 2H), 1.63-1.72 (m, 2H), 1.95-2.04 (m, 5H), 2.15-2.24 (m, 2H), 3.38-3.49 (m, 3H), 3.71 (d, J=0.8 Hz, 3H), 4.10-4.20 (m, 1H), 4.26 (td, J=13.1, 4.2 Hz, 2H), 5.18-5.24 (m, 1H), 5.65 (d, J=7.7 Hz, 1H), 6.17 (tt, J=55.1, 4.2 Hz, 1H).

Step 6 Preparation of Compound c26

[Formula 118]

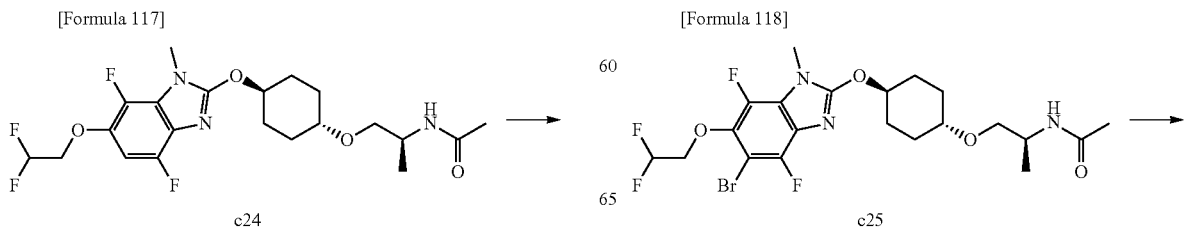

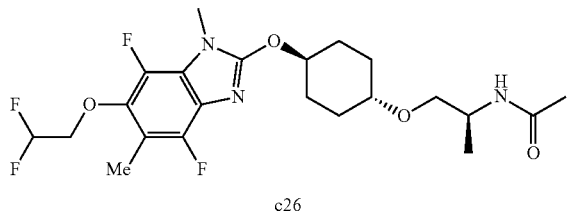

Trimethylboroxine (0.019 ml, 0.139 mmol), PdCl$_2$ (dppf) CH$_2$Cl$_2$ complex (3.78 mg, 0.00463 mmol), and 2 mol/L aqueous solution of potassium carbonate (0.116 ml, 0.231 mmol) were sequentially added to the 1,4-dioxane (0.5 ml) of solution Compound c25 (50 mg, 0.093 mmol), and the mixture was stirred for 30 minutes at 130° C. under microwave irradiation. Distilled water (10 ml) was added to the reaction mixture, and the mixture was extracted twice with ethyl acetate (10 ml). The organic layer was washed with diluted water (10 ml) and saturated brine (10 ml) each once. The organic layer was dried over sodium sulfate, and the solvent was evaporated under reduced pressure. The residue was purified by reverse phase chromatography (H$_2$O-acetonitrile) to give the compound c26 (25 mg, 57%) as a white solid.

$^1$H-NMR (CDCl$_3$) δ: 1.19 (d, J=6.8 Hz, 3H), 1.49-1.61 (m, 2H), 1.61-1.72 (m, 2H), 1.95-2.04 (m, 5H), 2.15-2.24 (m, 2H), 2.27 (d, J=2.3 Hz, 3H), 3.37-3.49 (m, 3H), 3.68 (d, J=0.8 Hz, 3H), 4.09-4.26 (m, 3H), 5.18-5.24 (m, 1H), 5.66 (d, J=7.3 Hz, 1H), 6.09 (tt, J=55.1, 4.1 H).

Example 18

Preparation of Compound c34

[Formula 119]

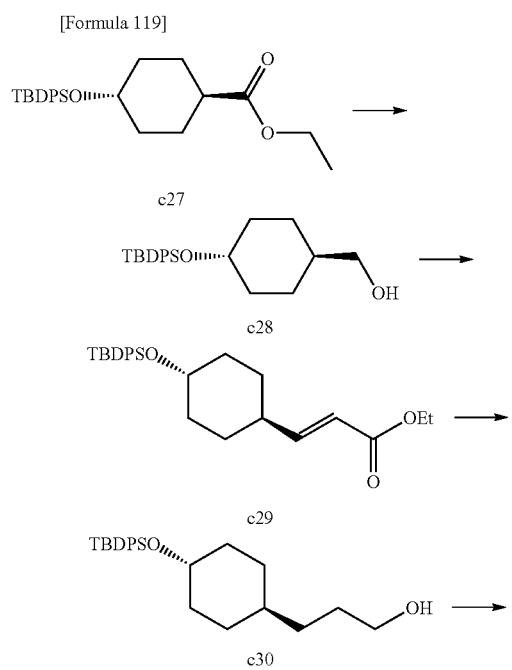

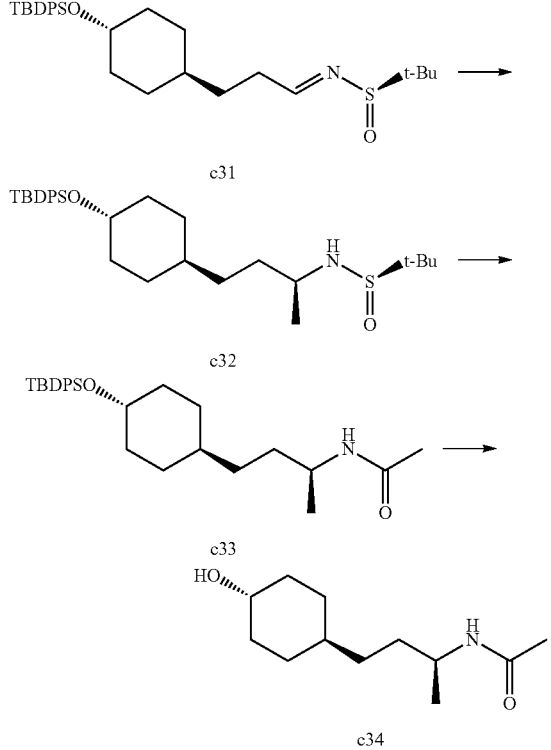

Step 1 Preparation of Compound c28

Compounds c27 (18.9 g, 46 mmol) was dissolved in a mixed solution THF (100 mL) and methanol (20 mL), and sodium borohydride (5.2 g, 138 mmol) was added, and the mixture was stirred at room temperature for 15 hours. The aqueous hydrochloric acid was added to the reaction mixture, and the mixture was extracted with ethyl acetate. The organic layer was washed with saturated brine, and dried over anhydrous magnesium sulfate. The solvent was distilled off under reduced pressure, the obtained residue was purified by silica gel column chromatography (hexane-ethyl acetate) to give compound c28 (8.7 g, 51% yield).

$^1$H-NMR (CDCl$_3$) δ: 0.71-0.92 (m, 3H), 1.05 (s, 9H), 1.17-1.48 (m, 4H), 1.64-1.74 (m, 2H), 1.81-1.91 (m, 2H), 3.34-3.40 (m, 2H), 3.55 (tt, J=10.8, 5.3 Hz, 1H), 7.32-7.45 (m, 6H), 7.62-7.72 (m, 4H).

Step 2 Preparation of Compound c29

Compounds of c28 (5 g, 13.6 mmol) was dissolved in dichloromethane (50 mL) and Des Martin reagent (7.5 g, 17.6 mmol) was added, and stirred for 3 h at 0° C. Sodium hydrogen sulfite and a saturated sodium bicarbonate solution were added to the reaction mixture, and the mixture was extracted with ethyl acetate. The organic layer was washed with water, washed with saturated brine, and dried over anhydrous magnesium sulfate. The solvent was distilled off under reduced pressure to obtain a residue containing the aldehyde.

Sodium hydride (678 mg, 17 mmol) was dissolved in THF (50 mL) and ethyl diethylphosphonoacetate (3.5 mL, 17.6 mmol) was added under ice-cooling, and the mixture was stirred for 30 minutes. The residue obtained above was dissolved in THF (10 mL), it was added to the reaction mixture under ice-cooling. The reaction solution was stirred for 1 hour at 0° C. Saturated aqueous ammonium chloride solution was added to the reaction mixture, and the mixture was extracted with ethyl acetate. The organic layer was washed with water and brine, and dried over anhydrous magnesium sulfate. The solvent was distilled off under reduced pressure, and the obtained residue was purified by silica gel column chromatography (hexane-ethyl acetate) to give compound c29 (4.2 g, 71% yield).

$^1$H-NMR (CDCl$_3$) δ: 0.95-1.07 (m, 2H), 1.05 (s, 9H), 1.26 (t, J=6.5 Hz, 3H), 1.35-1.49 (m, 2H), 1.67-1.76 (m, 2H), 1.81-1.90 (m, 2H), 1.99-2.13 (m, 1H), 3.57 (tt, J=10.5, 4.5 Hz, 1H), 4.15 (q, J=6.5 Hz, 2H), 5.71 (d, J=15.8 Hz, 1H), 6.81 (dd, J=15.8, 7.0 Hz, 1H), 7.31-7.47 (m, 6H), 7.62-7.71 (m, 4H).

Step 3 Preparation of Compound c30

Compound c29 (2.95 g, 6.76 mmol) was dissolved in THF (20 mL) and methanol (3 mL) and sodium borohydride (1.3 g, 33.8 mmol) was added, and the mixture was stirred at room temperature for 4 hours. The aqueous hydrochloric acid was added to the reaction mixture, and the mixture was extracted with ethyl acetate. The organic layer was washed with water and saturated brine, and then dried with anhydrous magnesium sulfate. The solvent was distilled off under reduced pressure, and the obtained residue was purified by silica gel column chromatography (hexane-ethyl acetate) to give compound c30 (2.0 g, 76% yield).

$^1$H-NMR (CDCl$_3$) δ: 0.67-0.81 (m, 2H), 1.04 (s, 9H), 1.10-1.20 (m, 3H), 1.30-1.42 (m, 2H), 1.47-1.54 (m, 2H), 1.61-1.68 (m, 2H), 1.78-1.84 (m, 2H), 3.50-3.61 (m, 3H), 7.33-7.44 (m, 6H), 7.65-7.69 (m, 4H).

Step 4 Preparation of Compound c31

Compound c30 (1.43 g, 3.61 mmol) was dissolved in dichloromethane (4 mL) and des Martin reagent (3.1 g, 7.2 mmol) was added, and the mixture was stirred at room temperature for 2 hours. Water was added to the reaction mixture, and the mixture was extracted with ethyl acetate. The organic layer was washed with a saturated sodium bicarbonate solution and water, and dried over anhydrous magnesium sulfate. The solvent was distilled off under reduced pressure to obtain a residue containing the aldehyde.

The residue was dissolved in toluene (4 mL), (R)-tertiary butyl sulfinamide (524 mg, 4.3 mmol) and titanium tetra-ethoxide (1.07 g, 4.7 mmol) were added, and the mixture was stirred for 1 hour at 80° C. After cooling, water was added to the reaction solution. The precipitated solid was filtered off, and the solvent was evaporated under reduced pressure. The obtained residue was purified by silica gel column chromatography (hexane-ethyl acetate) to give compound c31 (620 mg, 35% yield).

$^1$H-NMR (CDCl$_3$) δ: 0.77 (q, J=12.5 Hz, 2H), 1.04 (s, 9H), 1.18 (s, 9H), 1.34 (q, J=12.5 Hz, 2H), 1.38-1.48 (m, 2H), 1.54-1.61 (m, 1H), 1.63-1.70 (m, 2H), 1.78-1.86 (m, 2H), 2.46 (td, J=7.5, 5.0 Hz, 2H), 3.55 (tt, J=10.5, 5.0 Hz, 1H), 7.33-7.45 (m, 6H), 7.64-7.70 (m, 4H), 8.01 (t, J=5.0 Hz, 1H).

Step 5 Preparation of Compound c32

Compounds c31 (570 mg, 1.15 mmol) was dissolved in toluene (20 mL), methyl magnesium bromide (3 mol/L diethyl ether solution, 1.5 mL, 4.6 mmol) was added and the mixture was stirred at room temperature. Saturated aqueous ammonium chloride solution was added to the reaction mixture, and the mixture was extracted with ethyl acetate. The organic layer was washed with saturated brine, and dried over anhydrous magnesium sulfate. The solvent was distilled off under reduced pressure, the obtained residue was purified by silica gel column chromatography (hexane-ethyl acetate) to give compound c32 (396 mg, 67% yield).

$^1$H-NMR (CDCl$_3$) δ: 0.73-0.76 (m, 2H), 1.04 (s, 9H), 1.08-1.17 (m, 3H), 1.18 (s, 9H), 1.21 (d, J=6.6 Hz, 3H), 1.27-1.39 (m, 3H), 1.39-1.49 (m, 1H), 1.58-1.65 (m, 2H), 1.77-1.84 (m, 2H), 2.82 (d, J=6.7 Hz, 1H), 3.21-3.30 (m, 1H), 3.54 (tt, J=10.4, 5.0 Hz, 1H), 7.33-7.44 (m, 6H), 7.64-7.70 (m, 4H).

Step 6 Preparation of Compound c33

Compound c32 (160 mg, 0.31 mmol) was dissolved in 1,4-dioxane (10 mL) and hydrochloric acid (4 mol/L 1,4-dioxane solution, 0.39 mL, 1.6 mmol) was added, the mixture was stirred at room temperature for 14 hours. The reaction mixture was distilled off under reduced pressure to obtain a residue.

The obtained residue was dissolved in dichloromethane (10 mL), triethylamine (0.43 mL, 3.11 mmol) and acetic anhydride (0.06 mL, 0.62 mmol) were added and the mixture was stirred at room temperature. Water was added to the reaction mixture, and the mixture was extracted with ethyl acetate. The organic layer was washed with saturated brine, and dried over anhydrous magnesium sulfate. The solvent was distilled off under reduced pressure, the obtained residue was purified by silica gel column chromatography (hexane-ethyl acetate) to give compound c33 (125 mg, 89% yield).

$^1$H-NMR (CDCl$_3$) δ: 0.72 (q, J=10.7 Hz, 2H), 1.04 (s, 9H), 1.07 (d, J=6.7 Hz, 3H), 1.08-1.20 (m, 3H), 1.23-1.40 (m, 4H), 1.58-1.65 (m, 2H), 1.76-1.83 (m, 2H), 1.93 (s, 3H), 3.53 (tt, J=10.8, 5.6 Hz, 1H), 3.81-3.95 (m, 1H), 5.12 (d, J=7.3 Hz, 1H), 7.33-7.44 (m, 6H), 7.64-7.69 (m, 4H).

Step 7 Preparation of Compound c34

Compound c33 (168 mg, 0.37) was dissolved in THF (10 mL) and tetrabutylammonium fluoride (1 mol/L THF solution, 0.74 mL, 0.74 mmol) was added. After the reaction mixture was stirred at 50° C. for 4 hours, and then evaporated under reduced pressure. The obtained residue was purified by silica gel column chromatograph (chloroform-methanol) to give Compound c34 (75 mg, 95% yield).

$^1$H-NMR (CDCl$_3$) δ: 0.90-1.00 (m, 2H), 1.11 (d, J=6.7 Hz, 3H), 1.13-1.31 (m, 5H), 1.34-1.49 (m, 2H), 1.70-1.82 (m, 2H), 1.89-2.02 (m, 5H), 3.54 (tt, J=10.9, 4.3 Hz, 1H), 3.87-4.00 (m, 1H), 5.18 (d, J=6.4 Hz, 1H).

Example 19

Preparation of Compound c43

[Formula 120]

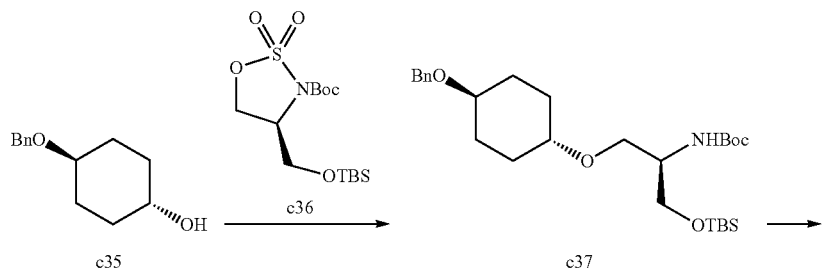

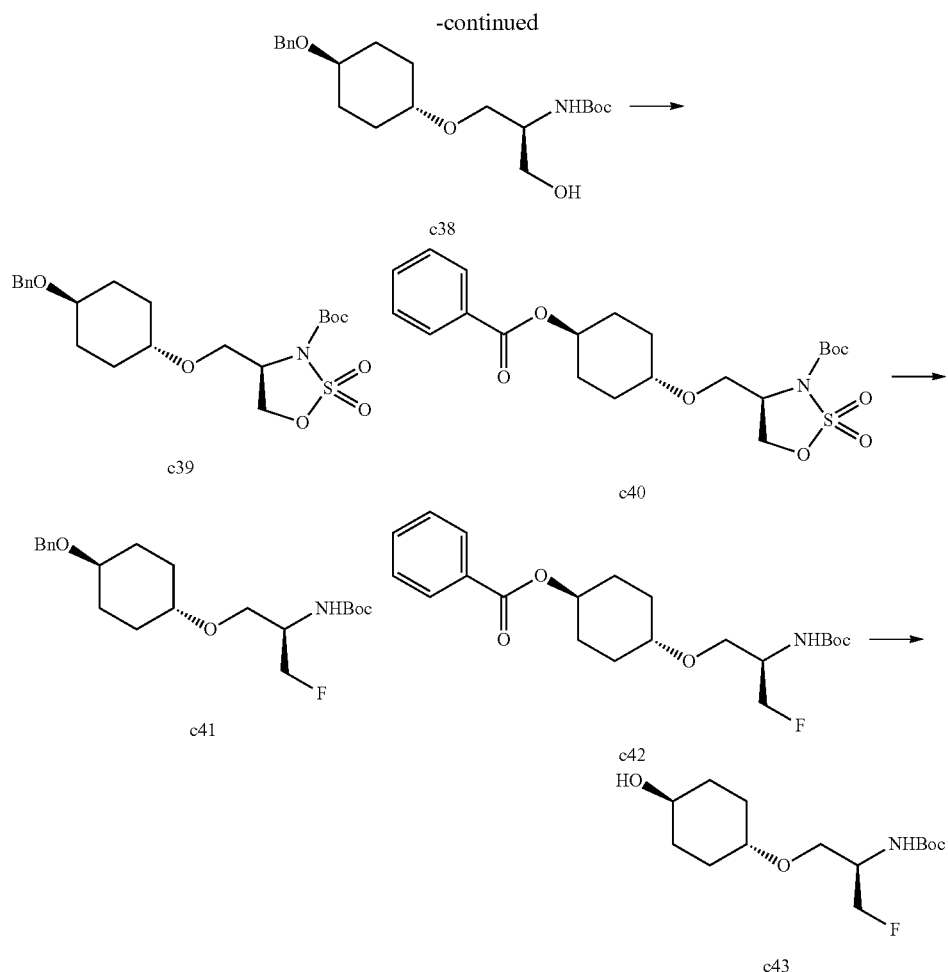

Step 1 Preparation of Compound c37

The DMF (13.5 ml) solution of Compound c35 (1.35 g, 6.55 mmol) was cooled with ice bath, sodium hydride (0.315 g, 7.87 mmol) was added thereto, and the mixture was stirred at same temperature for 30 minutes. Compound c36 (2.65 g, 7.21 mmol) was added thereto, and the reaction mixture was stirred at room temperature for 1 hour. Additionally, Compound c36 (0.482 g, 1.31 mmol) was added thereto, and the reaction mixture was stirred at 60° C. for 1 hour. After cooled to room temperature, 2 mol/L hydrochloric acid (13.1 mL, 26.2 mmol) was added thereto, and the reaction mixture was stirred at room temperature for 1 hour. The reaction mixture was neutralized with sodium carbonate, and then extracted with ethyl acetate. The organic layer was washed with water, and the solvent was concentrated under reduced pressure. The obtained residue was purified by silica gel chromatography (hexane-ethyl acetate) to afford Compound c37 (1.06 g, yield 33%).

[M+H]=494.20, Method Condition 3: retention time 3.35 min

Step 2 Preparation of Compound c38

Compound c37 (400 mg, 0.810 mmol) was dissolved in tetrabutylammonium fluoride (1 mol/L, THF solution, 1 mL, 1.00 mmol). The reaction mixture was stirred at room temperature for 16 hours. The reaction solution was evaporated under reduced pressure, and the obtained residue was purified by silica gel column chromatography (hexane-ethyl acetate) to afford Compound c38 (272 mg, yield 89%).

[M+H]=380.15, Method Condition 3: retention time 2.29 min

Step 3 Preparation of a Mixture of Compound c39 and c40

The dichloromethane solution of imidazole (293 mg, 4.30 mmol) was cooled with ice bath, and thionyl chloride (0.094 mL, 1.29 mmol) was added thereto at room temperature for 1 hour. The reaction mixture was cooled to −15° C., and the dichloromethane (8 ml) solution of Compound c38 (272 mg, 0.717 mmol) was added thereto dropwise. The reaction mixture was stirred at room temperature for 3 hours. 10% citric acid aqueous solution was added to the reaction mixture, and the reaction mixture was extracted. The organic layer was washed with water, and the solvent was concentrated under reduced pressure. The obtained residue was dissolved in dichloromethane (4 mL), sodium meta-periodate (399 mg, 1.86 mol) and ruthenium oxide hydrate (2.4 mg, 0.016 mmol) were added thereto. The reaction mixture was stirred at room temperature for 2 hours. The reaction mixture was diluted with ethyl acetate, and the insoluble matter was filtered off. The filtrate was extracted, and the organic layer was washed with water, and then the solvent was concentrated under reduced pressure. The obtained residue was purified by silica gel column chromatography (hexane-ethyl acetate) to afford a mixture of Compound c39 (148 mg, yield 47%) and Compound c40 (84 mg, yield 26%). Wherein, the ratio of both was calculated based on the area ratio (1.00:0.55) of completely independent two signals at δ4.26 ppm (2H, s, Compound c39) and δ5.00-5.10 ppm (1H, m, Compound c40) in ¹H-NMR.

Step 4 Preparation of a Mixture of Compound c41 and c42

The mixture of Compound c39 (141 mg, 0.320 mmol) and Compound c40 (80 mg, 0.176 mmol) was dissolved in tetrabutylammonium fluoride (1 mol/L, THF solution, 0.991 mL, 0.991 mmol), and stirred at room temperature for 21 hours. 10% citric acid aqueous solution (2 mL) was added to the reaction mixture, and the reaction mixture was stirred at room temperature for 1 hour. The reaction mixture was extracted with ethyl acetate, and the organic layer was concentrated under reduced pressure. The obtained residue was purified by silica gel column chromatography (hexane-ethyl acetate) to afford a mixture of Compound c41 (110 mg, yield 90%) and Compound c42 (63 mg, yield 90%). Wherein, the ration of both was calculated based on the area ratio (1.00:0.55) of completely independent two signals at δ4.78-4.92 ppm (1H, m, Compound c41) and δ5.00-5.10 ppm (1H, m, Compound c42) in ¹H-NMR.

Step 5 Preparation of Compound c43

The mixture of Compound c41 (108 mg, 0.283 mmol) and Compound c42 (62 mg, 0.156 mmol) was dissolved in ethyl acetate (5 mL). 10% palladium-carbon catalyst (wetted with 50% water, 56 mg, 0.013 mmol) was added to the reaction mixture, and the reaction mixture was stirred under hydrogen atmosphere at room temperature for 24 hours. The reaction mixture was filtered, and the filtrate was concentrated under reduced pressure. The obtained crude product of a mixture of Compound a43 and unreacted Compound a42 was dissolved in THF (2 mL) and methanol (2 mL). 2 mol/L sodium hydrate aqueous solution (0.283 mL, 0.566 mmol) was added to the reaction mixture, and the reaction mixture was stirred at room temperature for 4.5 hours. The reaction mixture was concentrated, and extracted with ethyl acetate. After concentrated under reduced pressure, the obtained residue was purified by silica gel column chromatography (hexane-ethyl acetate) to afford Compound a43 (121 mg, yield 95%).

¹H-NMR (CDCl₃) δ: 1.29-1.38 (4H, m), 1.45 (9H, s), 1.91-2.03 (4H, m), 3.27-3.33 (1H, m), 3.48 (1H, ddd, J=9.4, 6.0, 1.8 Hz), 3.59 (1H, ddd, J=9.4, 4.0, 1.3 Hz), 3.67-3.73 (1H, m), 3.88-3.97 (1H, m), 4.40 (1H, ddd, J=47.4, 9.0, 6.0 Hz), 4.39-4.60 (1H, m), 4.82-4.88 (1H, m).

Example 6

Preparation of Compound c45

[Formula 121]

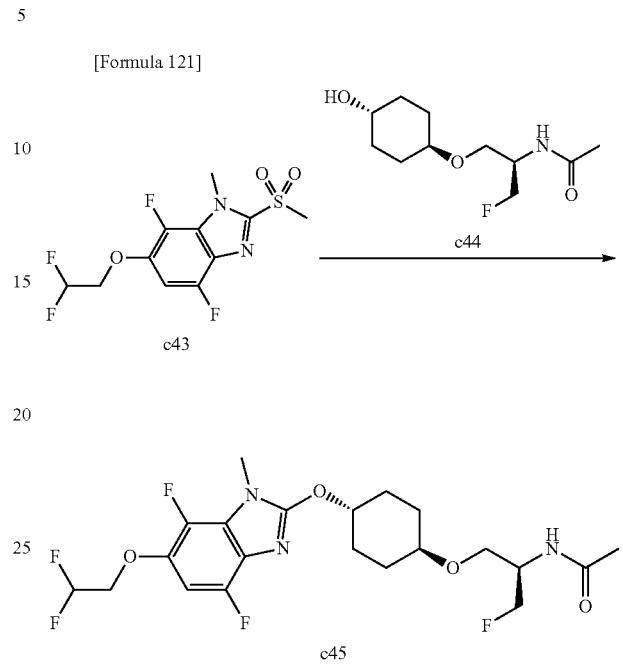

Step 1 Preparation of Compound c45

Compound c44 (17 mg, 0.073 mmol) was dissolved in THF (510 ul), tert-butoxypotassium (20.4 mg, 0.182 mmol) and Compound c43 (35.7 mg, 0.109 mmol) were added to the mixture under ice-cooling, and the mixture was stirred for 2 hours. Saturated aqueous ammonium chloride solution was added to the reaction mixture, and the mixture was extracted with ethyl acetate. The organic layer was washed with brine and dried over anhydrous magnesium sulfate. The solvent was evaporated under reduced pressure, and the obtained residue was purified by silica gel column chromatography (chloroform-methanol) to give the compound c45 (11.9 mg, 0.025 mmol, 34.1%).

¹H-NMR (CDCl₃) δ: 1.57 (2H, m), 1.70 (4H, m), 2.01 (2H, m), 2.03 (3H, s), 2.19 (2H, m), 3.54 (3H, m), 3.70 (3H, s), 4.60-4.19 (5H, m), 5.20 (1H, m), 5.80 (1H, s), 5.80 (1H, s), 6.61 (1H, dd, J=10.6, 6.1 Hz).

[M+Na]=502.2, Method Condition 2: retention time 2.01 minutes

Example 21

Preparation of Compound c56

[Formula 122]

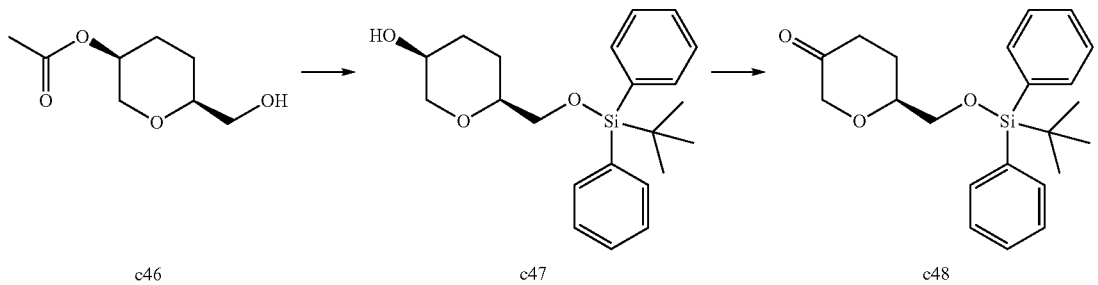

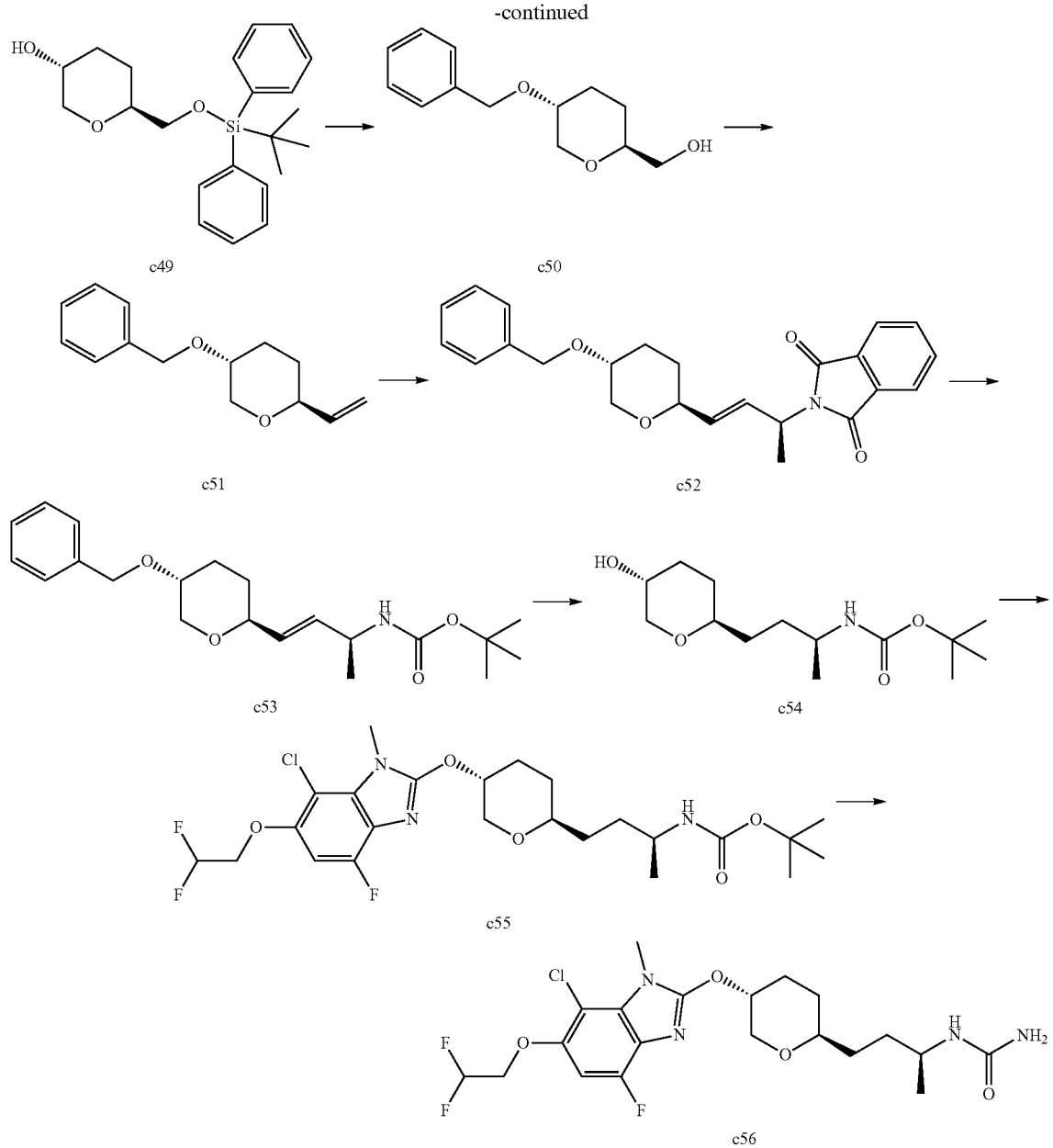

Step 1 Preparation of Compound c47

Compound c46 (11.6 g, 66.4 mmol; J. Org. Chem. 1998, 63, 8133-8144) was dissolved in dichloromethane (116 mL). Tert-buthyldiphenylsilylchoride (20.5 ml, 80 mmol) and imidazole (6.8 g, 100 mmol) were added to the mixture, and the mixture was stirred at room temperature. Water was added to the mixture, and the mixture was extracted with ethyl acetate. The organic layer was washed with 1 mol/L hydrochloric acid and saturated brine, and dried over anhydrous sodium sulfate. The solvent was condensed under reduced pressure to afford a crude product. The afforded crude product was dissolved in THF (116 mL) and methanol (58 mL), and 2 mol/L aqueous sodium hydroxide (100 mL) was added to the mixture. The mixture was stirred at room temperature for two hours. Water was added to the mixture, and the mixture was extracted with ethyl acetate. The organic layer was dried over saturated brine and dried over anhydrous sodium sulfate. The obtained residue was purified by silica gel chromatography (hexane-ethyl acetate) to afford Compound a47 (17.3 g, yield 70%).

$^1$H-NMR (CDCl$_3$) δ: 1.06 (s, 9H), 1.56 (m, 1H), 1.64-1.73 (m, 2H), 1.94 (m, 1H), 2.14 (d, J=8.4 Hz, 1H), 3.45 (m, 1H), 3.57 (d, J=12.0 Hz, 1H), 3.59 (dd, J=5.6, 10.4 Hz, 1H), 3.72 (dd, J=5.6, 10.8 Hz, 1H), 3.75 (m, 1H), 3.85 (ddd, J=2.4, 2.4, 12.0 Hz, 1H), 7.44-7.35 (m, 6H), 7.69-7.65 (m, 4H).

Step 2 Preparation of Compound c48

Oxalyl chloride (2.5 g, 16 mmol) was dissolved in dichloromethane (100 mL), dimethyl sulfoxide (5.4 ml, 76 mmol) was added to the mixture under −78° C. and the mixture was stirred for 1 hour. Methylene chloride solution (20 mL) of Compound c47 (7.0 g, 18.9 mmol) was added to the mixture, then the mixture was stirred 2 hours. Triethylamine (21 ml, 151 mmol) was added to the reaction solution, and the mixture was stirred at room temperature for 1 hour. The saturated sodium bicarbonate water was added to the reaction mixture, and the mixture was extracted with ethyl acetate. The organic layer was washed with water and saturated brine, and then dried over anhydrous sodium sulfate. The obtained residue was purified by silica gel column chromatography (hexane-ethyl acetate) to afford the aldehyde (13.1 g, 94% yield).

$^1$H-NMR (CDCl$_3$) δ: 1.07 (s, 9H), 1.95 (m, 1H), 2.10 (m, 1H), 2.47 (ddd, J=6.8, 10.8, 16.8 Hz, 1H), 2.60 (ddd, J=4.8, 4.8, 16.8 Hz, 1H), 3.69 (m, 1H), 3.79 (m, 1H), 3.81 (m, 1H), 3.94 (d, J=16.8 Hz, 1H), 4.14 (d, J=16.8 Hz, 1H), 7.46-7.36 (m, 6H), 7.69-7.66 (m, 4H).

Step 3 Preparation of Compound c49

Compound c48 (8.0 g, 21.7 mmol) was dissolved in diethyl ether (240 mL), lithium aluminum hydride (0.99 g, 26 mmol) was added, and the mixture was stirred at 0° C. for 0.5 hour. Water (2.97 mL) and 2 mol/L sodium hydroxide (0.99 mL) were added to the reaction solution, and the mixture was stirred at room temperature for 1 hour. An anhydrous sodium sulfate (30 g) was added to the reaction solution and the mixture was filtered. The obtained filtrate was distilled off under reduced pressure, silica gel column chromatography (hexane-ethyl acetate) to give compound c49 (8.0 g, 99.5% yield).

$^1$H-NMR (CDCl$_3$) δ: 1.05 (s, 9H), 1.36-1.42 (m, 2H), 1.83 (m, 1H), 2.13 (m, 1H) 3.09 (dd, J=10.4, 10.4 Hz, 1H), 3.36 (m, 1H), 3.57 (dd, J=5.6, 10.4 Hz, 1H), 3.68 (m, 1H), 3.72 (dd, J=5.6, 10.4 Hz, 1H), 4.00 (ddd, J=2.0, 4.8, 10.4 Hz, 1H), 7.44-7.35 (m, 6H), 7.69-7.64 (m, 4H).

Step 4 Preparation of Compound c50

The compound c49 (12.5 g, 33.7 mmol) was dissolved in DMF (125 mL), benzyl bromide (4.81 ml, 40.5 mmol) and sodium hydride (2.0 g, 50.6 mmol) was added to the mixture at 0° C., and the mixture was stirred at room temperature for 2 hours. Water was added to the reaction mixture, and the mixture was extracted with ethyl acetate. The organic layer was washed with hydrochloric acid and saturated brine, and dried over anhydrous sodium sulfate. The solvent was distilled off under reduced pressure to give the crude product.

The obtained crude product was dissolved in THF (125 mL), 1 mol/L tetrabutylammonium fluoride (50.6 mL, 50.6 mmol) was added, and the mixture was stirred for 1 hour. The reaction solution was distilled off under reduced pressure, and the residue was purified by silica gel column chromatography (hexane-ethyl acetate) to give Compound c50 (6.84 g, 88% yield) and its isomer (0.32 g, yield: 4.1%).

$^1$H-NMR (CDCl$_3$) δ: 1.32-1.53 (m, 2H), 1.64 (m, 1H), 2.23 (m, 1H) 3.22 (dd, J=10.4, 10.4 Hz, 1H), 3.36-3.52 (m, 3H), 3.60 (d, J=11.2 Hz, 1H), 4.11 (ddd, J=2.0, 4.4, 10.8 Hz, 1H), 4.54 (d, J=11.6 Hz, 1H), 4.60 (d, J=11.6 Hz, 1H), 7.37-7.27 (m, 5H).

Step 5 Preparation of Compound c51

Compound c50 (500 mg, 2.25 mmol) was dissolved in methylene chloride (10 mL) and Des Martin reagent (1.43 g, 3.37 mmol) was added under ice-cooling. The reaction mixture was stirred at room temperature for 1 hour. The saturated sodium bicarbonate water was added to the reaction mixture, and the mixture was extracted with ethyl acetate. The organic layer was washed with saturated brine, and then dried over anhydrous sodium sulfate. The solvent was distilled off under reduced pressure, and the obtained residue was purified by silica gel column chromatography (hexane-ethyl acetate) to afford the aldehyde (1.3 g, 67% yield).

To THF solution of methyl triphenylphosphonium bromide (3.18 g, 7.87 mmol), tert-butoxy potassium (757 mg, 6.75 mmol) was added at −78° C., and the mixture was stirred at room temperature for 2 hours. THF solution of the aldehyde (3 mL) was added under −78° C., and the mixture was stirred at room temperature overnight. A saturated aqueous ammonium chloride was added to the mixture, and the mixture was extracted with ethyl acetate. The organic layer was washed with water and saturated brine, and then dried over anhydrous sodium sulfate. The obtained residue was purified by silica gel column chromatography (hexane-ethyl acetate) to give compound c51 (0.47 g, 96% yield).

$^1$H-NMR (CDCl$_3$) δ: 1.37-1.54 (m, 2H), 1.81 (m, 1H), 2.22 (m, 1H) 3.22 (dd, J=10.4, 10.4 Hz, 1H), 3.48 (m, 1H), 3.77 (dd, J=3.6, 9.2 Hz, 1H), 4.14 (m, 1H), 4.54 (d, J=12.0 Hz, 1H), 4.60 (d, J=12.0 Hz, 1H), 5.10 (d, J=10.8 Hz, 1H), 5.24 (d, J=17.6 Hz, 1H), 5.82 (dd, J=5.6, 10.4, 17.6 Hz, 1H), 7.37-7.27 (m, 5H).

Step 6 Preparation of Compound c52

To dichloromethane (5.3 mL) solution of Compound c51 (0.47 g, 2.15 mmol), (S)-2-(3-buten-2-yl) isoindoline-1,3-dione (886 mg, 4.31 mmol) and Grubbs II reagent (55 mg, 0.065 mmol) was added, and the mixture was stirred at 40° C. overnight. The reaction solution was distilled off under reduced pressure, the obtained residue was purified by silica gel column chromatography (hexane-ethyl acetate) to give compound c52 (0.45 g, 53% yield).

[M+H]=392.3, Method Condition 4: retention time 2.52 minutes

Step 7 Preparation of Compound c53

Compound c52 (445 mg, 1.14 mmol) was dissolved in ethanol (4.5 mL), hydrazine (109 mg, 3.41 mmol) was added, and the mixture was stirred at 40° C. for 5 hours. Water was added to the reaction mixture, and the mixture was extracted with dichloromethane. The organic layer was washed with saturated brine, and then dried over anhydrous sodium sulfate. The solvent was evaporated under reduced pressure, and the resulting residue was dissolved in methylene chloride (4.5 mL). Boc$_2$O (396 μl, 1.71 mmol) and triethylamine (315 μl, 2.27 mmol) was added, and the mixture was stirred at room temperature overnight. Water was added to the reaction mixture, and the mixture was extracted with ethyl acetate. The organic layer was washed with saturated brine, and then dried over anhydrous sodium sulfate. The obtained residue was purified by silica gel column chromatography (hexane-ethyl acetate) to give compound c53 (397 mg, 97% yield).

$^1$H-NMR (CDCl$_3$) δ: 1.19 (d, J=8.0 Hz, 3H), 1.37-1.54 (m, 2H), 1.43 (s, 9H), 1.78 (m, 1H), 2.20 (m, 1H) 3.23 (m, 1H), 3.46 (m, 1H), 3.77 (m, 1H), 4.12 (m, 1H), 4.51-4.61 (m, 3H), 5.10 (dd, J=5.6, 15.6 Hz, 1H), 5.67 (m, 1H), 7.37-7.27 (m, 5H).

[M+H]=362.3, Method Condition 4: retention time 2.51 minutes

Step 8 Preparation of Compound c54

Compound c53 (395 mg, 1.095 mmol) was dissolved in a mixed solution of methanol (8 ml) and ethyl acetate (4 ml), palladium hydroxide (40 mg) was added, and the mixture was stirred for 2 hours under a hydrogen atmosphere. The reaction mixture was filtered, and the solvent was evaporated under reduced pressure. The obtained residue was purified by silica gel column chromatography (chloroform-methanol) to give Compound c54 (160 mg, 54% yield).

$^1$H-NMR (CDCl$_3$) δ: 1.11 (d, J=6.8 Hz, 3H), 1.32-1.54 (m, 6H), 1.43 (s, 9H), 1.70 (m, 1H), 2.11 (m, 1H) 3.09 (dd, J=10.8, 10.8 Hz, 1H), 3.21 (m, 1H), 3.68 (m, 2H), 4.00 (m, 1H), 4.33 (m, 1H).

[M+H]=274.3, Method Condition 4: retention time 1.46 minutes

Step 9 Preparation of Compound c55

Compound c18 (41 mg, 0.121 mmol) and the compound c54 (30 mg, 0.110 mmol) were dissolved in THF (0.5 mL), tert-butoxy potassium (31 mg, 0.274 mmol) was added and the mixture was stirred for 1 hour at 0° C. A saturated aqueous ammonium chloride was added to the mixture, and the mixture was extracted with ethyl acetate. The organic layer was washed with saturated brine, and then dried with anhydrous sodium sulfate. The solvent was distilled off under reduced pressure, and the resulting residue was purified by silica gel column chromatography (hexane-ethyl acetate) to give compound c55 (45 mg, 77% yield).

[M+H]=536.4, Method Condition 4: retention time 1.98 minutes

Step 10 Preparation of Compound c56

Compound c55 (27 mg, 0.062 mmol) was dissolved in dichloromethane (0.5 mL) and trifluoroacetic acid (0.05 ml, 0.62 mmol) was added at 0° C., and the mixture was stirred at room temperature for 4 hours. The reaction mixture was evaporated under reduced pressure. The obtained residue was dissolved in THF (0.5 mL), and trichloroacetyl isocyanate (23 mg, 0.124 mmol) and triethylamine (0.034 ml, 0.248 mmol) was added at 0° C. The reaction mixture was stirred for 1 hour at room temperature. The reaction mixture was concentrated under reduced pressure, and the residue was dissolved in methanol (1 ml). Potassium carbonate (34 mg, 0.248 mmol) was added to the reaction mixture and the mixture was stirred for 2 hours. Water was added to the reaction mixture, and the mixture was extracted with dichloromethane. The organic layer was washed with saturated brine, and then dried with anhydrous sodium sulfate. The solvent was distilled off under reduced pressure, the resulting residue was purified by silica gel column chromatography (chloroform-methanol) to give Compound c56 (14 mg, 47% yield).

$^1$H-NMR (CDCl$_3$—CD$_3$OD) δ: 1.14 (d, J=6.4 Hz, 3H), 1.37-1.54 (m, 4H), 1.68 (m, 1H), 1.89-1.80 (m, 2H), 2.40 (m, 1H), 3.30-3.42 (m, 2H), 3.78-3.68 (m, 2H), 3.84 (s, 3H), 4.22 (dt, J=4.0, 13.2 Hz, 1H), 4.28 (m, 1H), 5.10 (m, 1H), 5.18 (d, J=7.6 Hz, 1H), 6.13 (tt, J=4.0, 54.8 Hz, 1H), 6.66 (d, J=10.8 Hz, 1H).

[M+H]=479.3, Method Condition 4: retention time 1.98 minutes

Example 22

Preparation of Compound c62

[Formula 123]

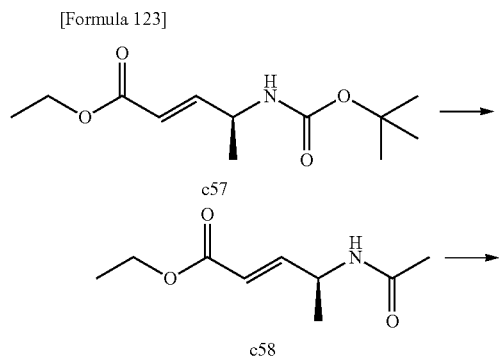

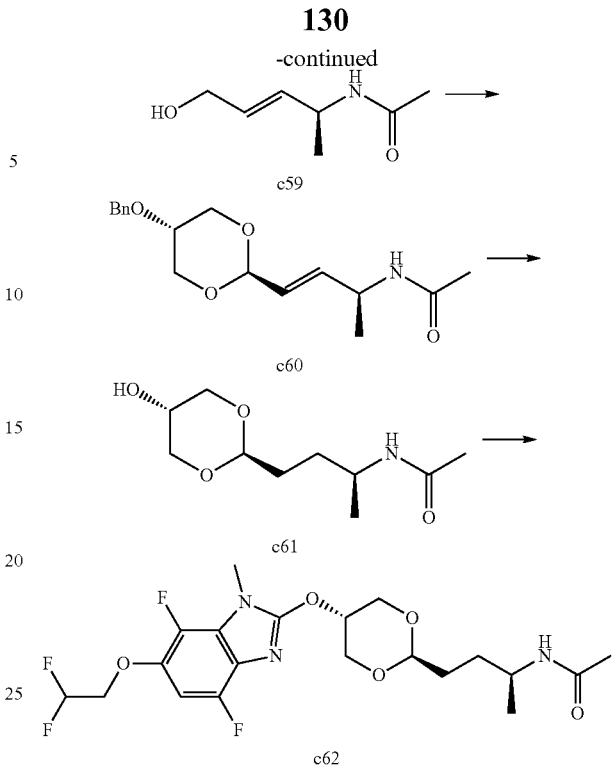

Step 1 Preparation of Compound a58

Compound c57 (131 mg, 0.54 mmol; WO201005562) was dissolved in dichloromethane (2.5 mL), and 1 mol/L diisobutylalminium hydride (2.16 ml, 2.16 mmol) were added thereto at −78° C. It was stirred at room temperature for 1 hour. Ethyl acetate (0.4 ml), saturated Rochelle's salt and ethyl acetate (5 ml) were added the reaction mixture, and the mixture was stirred for 1 hour at room temperature. The reaction mixture was concentrated under reduced pressure, and extracted with dichloromethane. The organic layer was washed with water and brine, and then dried over anhydrous sodium sulfate. The solvent was distilled off under reduced pressure, the resulting residue was purified by silica gel column chromatography (chloroform-methanol) to afford Compound a58 (63 mg, 58% yield).

$^1$H NMR (CDCl$_3$) δ: 1.28 (t, J=7.2 Hz, 3H), 1.29 (d, J=7.2 Hz, 3H), 2.01 (s, 3H), 4.17 (q, J=7.2 Hz, 2H), 4.74 (m, 1H), 5.42 (br.s, 1H), 5.89 (d, J=15.6 Hz, 1H), 6.87 (dd, J=4.8, 15.6 Hz, 1H).

Step 2 Preparation of Compound c59

Compounds a58 (440 mg, 2.04 mmol) was dissolved in dichloromethane (4 mL), and trifluoroacetic acid (1.57 ml, 20.4 mmol) was added at 0° C. The mixture was stirred for 30 minutes. The reaction mixture was concentrated under reduced pressure, and triethylamine (847 μl, 6.11 mmol) and acetic anhydride (385 μl, 4.07 mmol) were added to the dichloromethane solution of the resulting residue (3.0 mL). The reaction mixture was stirred for 1 hour. To the reaction mixture was added water and extracted with dichloromethane. The organic layer was washed with 2 mol/L hydrochloric acid and saturated brine, and dried over anhydrous sodium sulfate. The solvent was distilled off under reduced pressure, the resulting residue was dissolved in THF-H$_2$O (2 ml; 1:1), and 2 mol/L sodium hydroxide was added thereto. The reaction solution was stirred at room temperature for 30 minutes. Water was added to the reaction mixture, and the mixture was extracted with dichloromethane. The organic layer was washed with water and brine, and dried over anhydrous sodium sulfate. The solvent was evaporated under reduced pressure. The obtained residue was purified by silica gel column chromatography (chloroform-methanol) to afford Compound c59 (220 mg, 75% yield).

$^1$H NMR (CDCl$_3$) δ: 1.25 (d, J=6.8 Hz, 3H), 1.40 (s, 1H), 1.99 (s, 3H), 4.55 (br.s, 2H), 4.60 (m, 1H), 5.32 (s, 1H), 5.68 (m, 1H), 5.76 (m, 1H).

Step 3 Preparation of Compound c60

Compounds c59 (40 mg, 0.279 mmol) was dissolved in dichloromethane (2 mL) and manganese dioxide (484 mg, 5.56 mmol) was added thereto, and it was stirred for 1 hour. The reaction mixture was filtered, and the filtrate was concentrated under reduced pressure. The obtained residue was purified by silica gel column chromatography (hexane-ethyl acetate) to give the aldehyde compound (28 mg, 71% yield).

2-(benzyloxy) propane-1,3-diol (54 mg, 0.298 mmol) and pyridinium paratoluene sulfonate (2.5 mg, 9.9 μmol) were added to the toluene (1 ml) solution of the aldehyde, and it was stirred at 90° C. for 6 hours. The reaction solution was concentrated, and the residue was purified by prep HPLC (0.1% formic acid-containing acetonitrile-water) to afford Compound c60 (3.8 mg, 6% yield) and its cis isomer (4.0 mg, 6% yield).

$^1$H NMR (CDCl$_3$) δ: 1.23 (d, J=8.4 Hz, 3H), 1.95 (s, 3H), 3.49 (dd, J=10.8, 10.8 Hz, 2H), 3.67 (m, 1H), 3.49 (dd, J=4.8, 10.8 Hz, 2H), 4.56 (s, 2H), 4.62 (m, 1H), 4.86 (d, J=4.4 Hz, 1H), 5.32 (d, J=8.4 Hz, 1H), 5.59 (ddd, J=1.6, 4.4, 15.6 Hz, 1H) 5.93 (dd, J=5.2, 15.6 Hz, 1H), 7.27-7.37 (m, 5H).

Cis isomer; $^1$H NMR (CDCl$_3$) δ: 1.24 (d, J=6.8 Hz, 3H), 1.96 (s, 3H), 3.25 (s, 1H), 3.87 (d, J=12.0 Hz, 2H), 4.23 (d, J=12.0 Hz, 2H), 4.64 (m, 1H), 4.67 (s, 2H), 5.02 (d, J=4.8 Hz, 1H), 5.36 (d, J=7.2 Hz, 1H), 5.69 (ddd, J=1.6, 4.4, 16.0 Hz, 1H) 5.98 (dd, J=4.8, 16.0 Hz, 1H), 7.27-7.39 (m, 5H).

Step 4 Preparation of Compound c61

Compound c60 (4.0 mg, 0.012 mmol) was dissolved in methanol (1 mL), and palladium hydroxide (1 mg, 0.16 mmol) was added thereto. The reaction mixture was stirred under hydrogen atmosphere for 5 hours. The reaction solution was filtered, and the filtrate was concentrated under reduced pressure to afford Compound c61 (2.6 mg, 100% yield) as a crude product.

$^1$H NMR (CDCl$_3$) δ: 1.13 (d, J=6.8 Hz, 3H), 1.45-1.68 (m, 4H), 1.95 (s, 3H), 3.67 (dd, J=10.8, 10.8 Hz, 2H), 3.67 (m, 1H), 3.88 (m, 1H), 3.97 (m, 1H), 4.16 (dd, J=4.8, 10.8 Hz, 2H), 4.44 (dd, J=4.8, 4.8 Hz, 1H), 5.31 (br.s, 1H).

Step 5 Preparation of Compound c62

Compound c22 (7.5 mg, 0.023 mmol) and Compound c61 (2.6 mg, 0.012 mmol) was dissolved in THF (0.5 mL) and, tert-butoxy potassium (3.2 mg, 0.029 mmol) was added, and the mixture was stirred for 1 hour at 0° C. A saturated aqueous ammonium chloride was added to the reaction mixture, and the mixture was extracted with ethyl acetate. The organic layer was washed with saturated brine, and then dried with anhydrous sodium sulfate. The solvent was distilled off under reduced pressure. The resulting residue was purified by—was purified by (0.1% formic acid-containing acetonitrile-water) with preparative HPLC to give Compound c62 (2.3 mg, 43% yield).

$^1$H-NMR (CDCl$_3$) δ 1.14 (d, J=6.4 Hz, 3H), 1.37-1.54 (m, 4H), 1.96 (s, 3H), 3.62 (dd, J=10.4, 10.4 Hz, 2H), 3.68 (s, 2H), 3.99 (m, 1H), 4.22 (dt, J=4.0, 13.2 Hz, 2H), 4.51 (dd, J=5.6, 11.2 Hz, 2H), 4.57 (dd, J=4.4, 4.4 Hz, 1H), 6.13 (tt, J=4.0, 54.8 Hz, 1H), 6.63 (d, J=6.0, 10.8 Hz, 1H).

[M+H]=0.4, Method Condition 4: retention time 1.87 minutes

Example 23

Preparation of Compound c66

[Formula124]

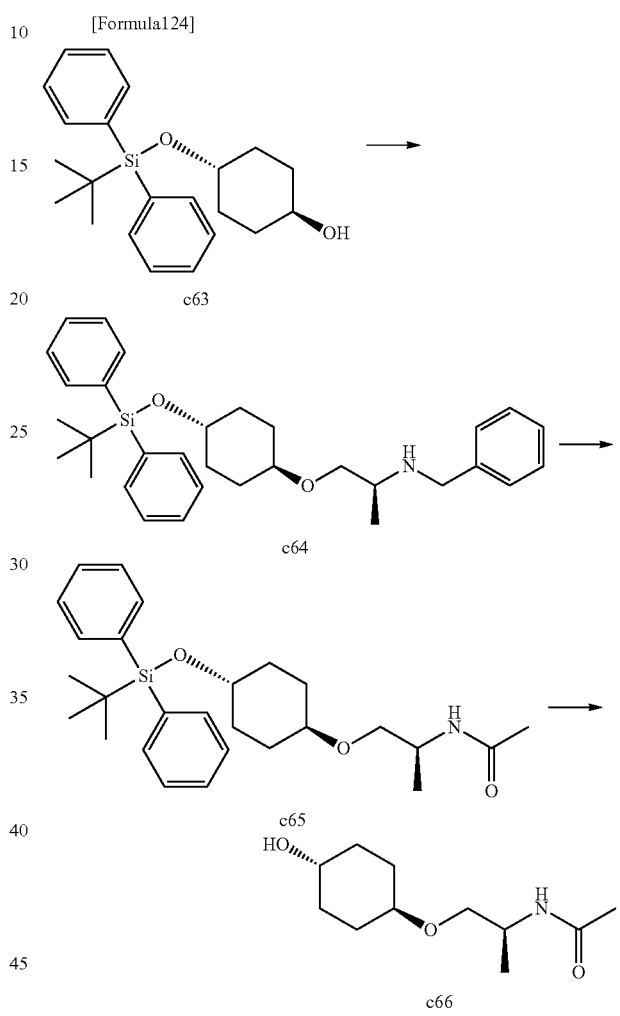

Step 1 Preparation of Compound c64

Compound c63 (3.0 g, 127 mmol) was dissolved in a mixed solution of DMF (30 mL) and THF (30 mL) and sodium hydride (0.51 g, 12.7 mmol) was added under ice-cooling. The reaction mixture was stirred for 30 minutes under ice-cooling. The THF solution (5 mL) of (S)-3-benzyl-4-methyl-1,2,3-oxathiazolidine-2,2-dioxide (2.31 g, 10.15 mmol) was added to the reaction mixture under ice-cooling, and the mixture was stirred for 2 hours at 40° C. 2 mol/L aqueous hydrochloric acid solution (17 mL) was added to the reaction solution under ice-cooling, and the reaction mixture was stirred for 1 hour at room temperature. In addition 2 mol/L sodium hydroxide solution (30 mL) was added to the reaction mixture, and the mixture was extracted with ethyl acetate. The reaction solvent was distilled off under reduced pressure, and the resulting residue was purified by amino silica gel column chromatography—was purified by (chloroform-methanol) to give Compound c64 (3.7 g, 87% yield).

¹H NMR (CDCl₃) δ: 1.01 (d, J=6.0 Hz, 3H), 1.05 (m, 9H), 1.15-1.22 (m, 2H), 1.33-1.41 (m, 2H), 1.74 (m, 2H), 1.88 (m, 2H), 2.85 (m, 1H), 3.25 (m, 2H), 3.35 (dd, J=4.0, 9.2 Hz, 1H), 3.68 (m, 1H), 3.70 (d, J=13.2 Hz, 1H), 3.83 (d, J=13.2 Hz, 1H), 7.20-7.44 (m, 11H), 7.66 (d, J=6.8 Hz, 4H).

Step 2 Preparation of Compound c65

Compound c64 (50.5 g, 101 mmol) was dissolved in ethanol (505 mL), and Pd—C(11.3 g, 5.0 mmol) and ammonium formate (12.7 g, 201 mmol) were added to the mixture. The mixture was stirred at 65° C. for 3 hours. Further ammonium formate (6.35 g, 101 mmol) was added to the mixture, and the mixture was stirred at 65° C. for 2.5 hours. The reaction mixture was filtered, and the filtrate was concentrated under reduced pressure. A saturated aqueous solution of sodium carbonate was added to the residue and the mixture was extracted with ethyl acetate. The organic layer was washed with water and brine, and dried over anhydrous magnesium sulfate. The solvent was distilled off under reduced pressure, and the residue dissolved in dichloromethane (253 mL), triethylamine (13.95 ml, 101 mmol) and acetic anhydride (10.5 ml, 111 mmol) was stirred for 1.5 hours at room temperature was added. Water was added to the reaction mixture, and the mixture was extracted with ethyl acetate. The organic layer was washed with brine and dried over anhydrous magnesium sulfate. The solvent was distilled off under reduced pressure, the resulting residue was purified by silica gel column chromatography—was purified by (chloroform-methanol) to give Compound c65 (37.75 g, 83% yield).

¹H NMR (CDCl₃) δ: 1.05 (m, 9H), 1.12 (d, J=6.8 Hz, 3H), 1.16-1.26 (m, 2H), 1.33-1.43 (m, 2H), 1.75 (m, 2H), 1.89 (m, 2H), 1.93 (s, 3H), 3.28 (m, 1H), 3.32 (m, 1H), 3.38 (dd, J=4.0, 9.2 Hz, 1H), 3.71 (m, 1H), 4.08 (m, 1H), 5.63 (m, 1H), 7.34-7.44 (m, 6H), 7.66 (d, J=6.8 Hz, 4H).

Step 3 Preparation of Compound c66

Compound c65 (30.2 g, 66.6 mmol) was dissolved in THF (100 mL) and 1 mol/L tetrabutylammonium fluoride (100 mL, 100 mmol) was added to the mixture. The mixture was stirred at 70° C. for 7 hours. The reaction solution was distilled off under reduced pressure, the residue was purified by silica gel column chromatography (chloroform-methanol) to give Compound c66 (11.65 g, 81% yield).

¹H NMR (CDCl₃) δ: 1.17 (d, J=6.8 Hz, 3H), 1.23-1.35 (m, 4H), 1.8-1.90 (m, 2H), 1.97 (s, 3H), 3.27 (m, 1H), 3.38 (dd, J=4.0, 9.6 Hz, 1H), 3.44 (dd, J=4.0, 9.6 Hz, 1H), 3.72 (m, 1H), 4.13 (m, 1H), 5.66 (br.s, 1H).

Example 24

Preparation of Compound c69

[Formula 125]

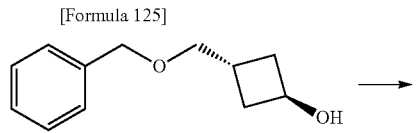
c67

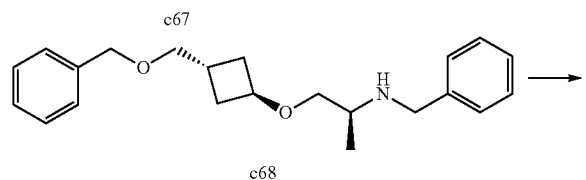
c68

-continued

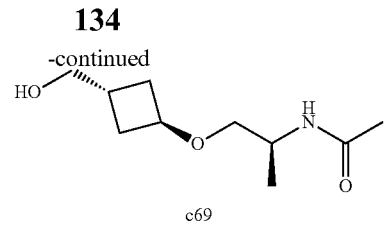
c69

Step 1 Preparation of Compound c68

The compounds of c67 (10 g, 52 mmol) was dissolved in a mixed solution of DMF (100 mL) and THF (50 mL), and sodium hydride (2.5 g, 62.4 mmol) was added to the mixture under ice-cooling. The mixture was stirred for 30 minutes under ice-cooling. THF (40 mL) solution of (S)-3-benzyl-4-methyl-1,2,3-oxathiazolidine-2,2-dioxide (15.4 g, 67.6 mmol) was added to the reaction solution under ice-cooling. The mixture was stirred at room temperature for 2 hours. 2 mol/L hydrochloric acid aqueous solution (100 mL) was added to the reaction solution under ice-cooling, and the mixture was stirred for 1 hour at room temperature. 2 mol/L sodium hydroxide solution (100 mL) was added to the reaction mixture, and the mixture was extracted with ethyl acetate. The organic layer was distilled off under reduced pressure, the residue was purified by amino silica gel column chromatography (chloroform-methanol) to give Compound c68 (13.4 g, 76% yield).

¹H NMR (CDCl₃) δ: 1.05 (d, J=6.4 Hz, 3H), 2.07 (m, 4H), 2.91 (m, 1H), 3.19 (dd, J=7.6, 9.2 Hz, 1H), 3.32 (dd, J=4.4, 9.2 Hz, 1H), 3.45 (m, 2H), 3.73 (d, J=12.8 Hz, 1H), 3.86 (d, J=12.8 Hz, 1H), 4.00 (m, 1H), 4.12 (m, 1H), 4.52 (s, 2H), 7.21-7.37 (m, 10H).

Step 2 Preparation of Compound c69

The compound c68 (1.0 g, 101 mmol) was dissolved in methanol (30 mL), and palladium hydroxide (827 mg, 0.589 mmol) and acetic acid (0.34 ml, 5.89 mmol) were added to the mixture. The mixture was stirred overnight under hydrogen atmosphere. The solvent was evaporated under reduced pressure, and the residue was dissolved in methanol (10 mL), and triethylamine (1.22 ml, 8.84 mmol) and acetic anhydride (0.56 ml, 5.89 mmol) were added to the mixture room temperature for 3 hours. The reaction mixture was concentrated under reduced pressure. A saturated aqueous solution of sodium carbonate was added to the residue and extracted with ethyl acetate. The organic layer was washed with water and brine, and dried over anhydrous sodium sulfate. The solvent was evaporated under reduced pressure, and the residue was purified by silica gel column chromatography (chloroform-methanol) to give Compound c69 (483 mg, 81.5% yield).

¹H NMR (CDCl₃) δ: 1.18 (d, J=6.8 Hz, 3H), 1.46 (br.s, 1H), 1.98 (s, 3H), 2.08 (m, 4H), 2.39 (m, 1H), 3.25 (dd, J=4.0, 9.2 Hz, 1H), 3.32 (dd, J=4.0, 9.2 Hz, 1H), 3.64 (m, 2H), 4.04 (m, 1H), 4.12 (m, 1H), 5.70 (br.s, 1H).

Example 25

Preparation of Compound c81

[Formula 126]

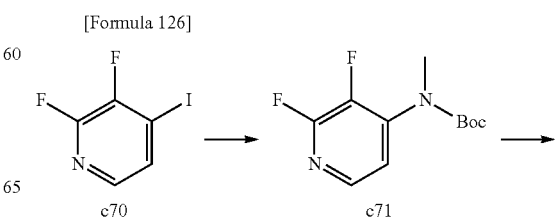
c70          c71

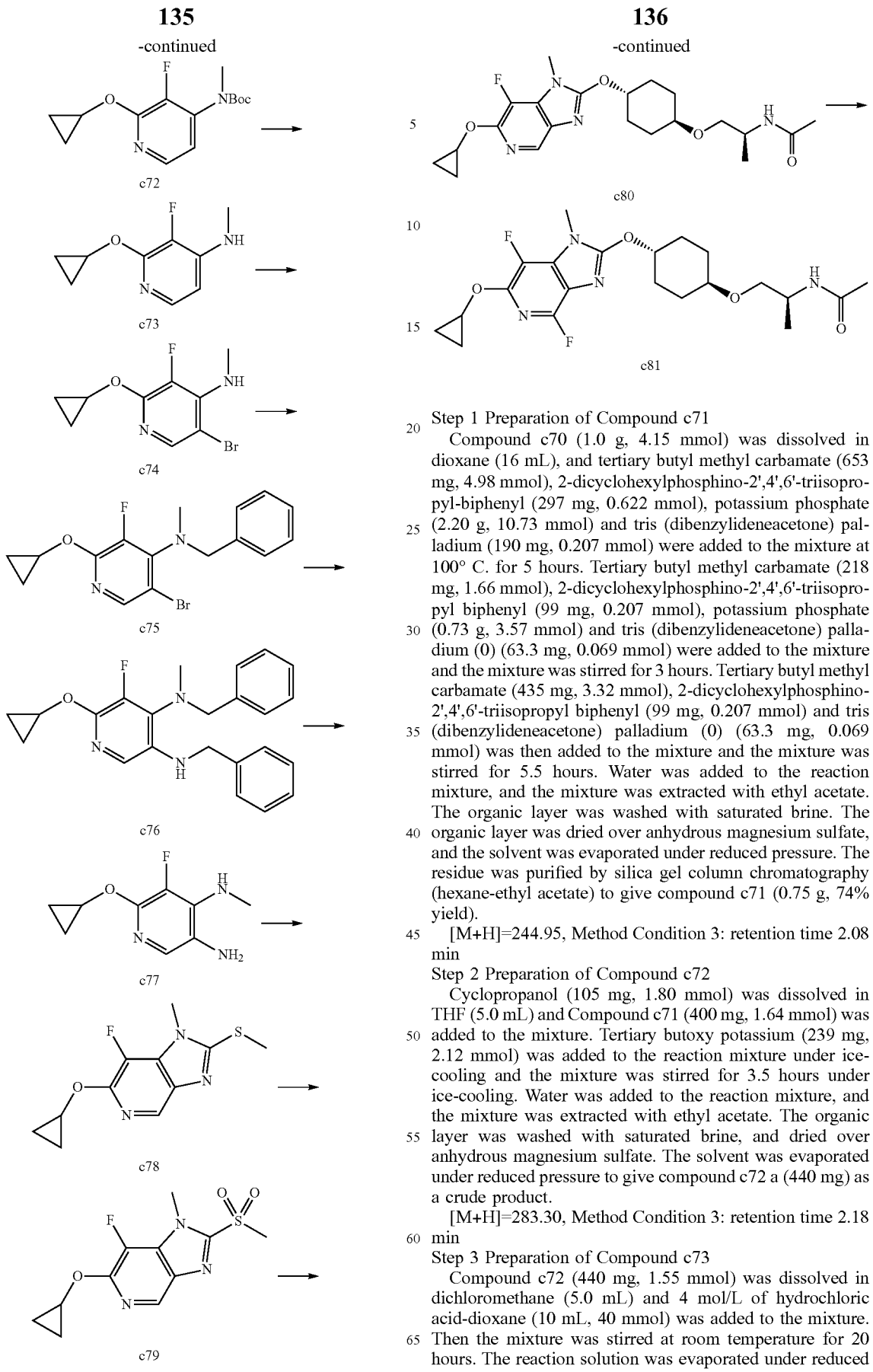

Step 1 Preparation of Compound c71

Compound c70 (1.0 g, 4.15 mmol) was dissolved in dioxane (16 mL), and tertiary butyl methyl carbamate (653 mg, 4.98 mmol), 2-dicyclohexylphosphino-2',4',6'-triisopropyl-biphenyl (297 mg, 0.622 mmol), potassium phosphate (2.20 g, 10.73 mmol) and tris (dibenzylideneacetone) palladium (190 mg, 0.207 mmol) were added to the mixture at 100° C. for 5 hours. Tertiary butyl methyl carbamate (218 mg, 1.66 mmol), 2-dicyclohexylphosphino-2',4',6'-triisopropyl biphenyl (99 mg, 0.207 mmol), potassium phosphate (0.73 g, 3.57 mmol) and tris (dibenzylideneacetone) palladium (0) (63.3 mg, 0.069 mmol) were added to the mixture and the mixture was stirred for 3 hours. Tertiary butyl methyl carbamate (435 mg, 3.32 mmol), 2-dicyclohexylphosphino-2',4',6'-triisopropyl biphenyl (99 mg, 0.207 mmol) and tris (dibenzylideneacetone) palladium (0) (63.3 mg, 0.069 mmol) was then added to the mixture and the mixture was stirred for 5.5 hours. Water was added to the reaction mixture, and the mixture was extracted with ethyl acetate. The organic layer was washed with saturated brine. The organic layer was dried over anhydrous magnesium sulfate, and the solvent was evaporated under reduced pressure. The residue was purified by silica gel column chromatography (hexane-ethyl acetate) to give compound c71 (0.75 g, 74% yield).

[M+H]=244.95, Method Condition 3: retention time 2.08 min

Step 2 Preparation of Compound c72

Cyclopropanol (105 mg, 1.80 mmol) was dissolved in THF (5.0 mL) and Compound c71 (400 mg, 1.64 mmol) was added to the mixture. Tertiary butoxy potassium (239 mg, 2.12 mmol) was added to the reaction mixture under ice-cooling and the mixture was stirred for 3.5 hours under ice-cooling. Water was added to the reaction mixture, and the mixture was extracted with ethyl acetate. The organic layer was washed with saturated brine, and dried over anhydrous magnesium sulfate. The solvent was evaporated under reduced pressure to give compound c72 a (440 mg) as a crude product.

[M+H]=283.30, Method Condition 3: retention time 2.18 min

Step 3 Preparation of Compound c73

Compound c72 (440 mg, 1.55 mmol) was dissolved in dichloromethane (5.0 mL) and 4 mol/L of hydrochloric acid-dioxane (10 mL, 40 mmol) was added to the mixture. Then the mixture was stirred at room temperature for 20 hours. The reaction solution was evaporated under reduced pressure, and 1 mol/L of aqueous sodium carbonate solution was added to the mixture. The mixture was extracted with ethyl acetate. The organic layer was washed with saturated brine, and dried over anhydrous magnesium sulfate. The solvent was evaporated under reduced pressure to give compound c73 a (278 mg) as a crude product.

[M+H]=183.00, Method Condition 3: retention time 0.98 min

Step 4 Preparation of Compound c74

Compound c73 was dissolved in acetonitrile (5.0 mL), and N-bromosuccinimide (312 mg, 1.72 mmol) was added to the mixture. The mixture was stirred for 2 hours at room temperature. After vacuum evaporation of the solvent, the residue was purified by silica gel column chromatography (hexane-ethyl acetate) to give compound c74 (173 mg, 40% yield).

$^1$H-NMR (CDCl$_3$) δ: 0.77-0.82 (m, 4H), 3.17-3.20 (m, 3H), 4.25-4.27 (m, 1H), 4.44 (s, 1H).

[M+H]=262.85, Method Condition 3: retention time 2.09 min

Step 5 Preparation of Compound c75

Compound c74 (173 mg, 0.663 mmol) was dissolved in DMF (3.0 mL) and sodium hydride (34.5 mg, 0.861 mmol) was added to the mixture under ice-cooling, and the mixture was stirred for 5 minutes. Benzyl bromide (0.087 mL, 0.729 mmol) was added to the reaction solution, and the mixture was stirred for 1.5 hours under ice-cooling. Sodium hydride (3.5 mg, 0.086 mmol) and benzyl bromide (0.009 mL, 0.0757 mmol) were added, and the mixture was stirred for 50 minutes. Water was added to the reaction mixture, and the mixture was extracted with ethyl acetate. The organic layer was washed with saturated brine, and the organic layer was dried over anhydrous magnesium sulfate. After vacuum evaporation of the solvent, the residue was purified by silica gel column chromatography-(hexane-ethyl acetate) to give Compound c75 (174 mg, 75% yield).

[M+H]=350.90, Method Condition 3: retention time 2.86 min

Step 6 Preparation of Compound c76

Compound c75 (170 mg, 0.484 mmol) was dissolved in toluene (4.0 mL), tertiary butoxy sodium (93.0 mg, 0.968 mmol), tris (dibenzylideneacetone) palladium (0) (44.3 mg, 0.048 mmol), 2,2'-bis (diphenylphosphino)-1,1'-binaphthyl (60.3 mg, 0.097 mmol) and benzyl amine (0.212 mL, 1.938 mmol) were added to the mixture and the mixture was stirred at 100° C. for 2 hours. Its salt was removed by filtration, and the reaction solution was evaporated under reduced pressure. The residue was purified by silica gel column chromatography (hexane-ethyl acetate) to give compound c76 (140 mg, 76% yield).

[M+H]=378.05, Method Condition 3: retention time 2.83 min

Step 7 Preparation of Compound c77

Compound c76 (140 mg, 0.371 mmol) was dissolved in methanol (3.0 mL), palladium-carbon (96.0 mg, 0.115 mmol) and ammonium formate (234 mg, 0.371 mmol) was added to the mixture. The mixture was stirred at 60° C. for 45 minutes. The reaction mixture was cooled to room temperature and dichloromethane (5.0 mL) was added to the mixture The insoluble was removed by Celite filtration. The solvent was evaporated under reduced pressure to give compound c77 the (69.0 mg) as a crude product.

[M+H]=198.00, Method Condition 3: retention time 1.08 min

Step 8 Preparation of Compound c78

Compound c77 (69.0 mg, 0.349 mmol) was dissolved in THF (3.0 mL) and triethylamine (0.206 mL, 1.484 mmol) and 1,1'-thiocarbonyldiimidazole (74.2 mg, 0.408 mmol) was added to the mixture. The mixture was stirred at room temperature for 2 hours. Triethylamine (0.100 mL, 0.722 mmol) and 1,1'-thiocarbonyldiimidazole (20.0 mg, 0.112 mmol) was added to the mixture, and the mixture was stirred at room temperature for 1 hour. Methyl iodide (0.500 mL, 8.00 mmol) was added to the mixture, and the mixture was stirred for 2 hours at room temperature. The solvent was distilled off under reduced pressure, the residue was purified by silica gel column chromatography-(hexane-ethyl acetate) to give compound c78 (36.0 mg, 38% yield).

[M+H]=253.95, Method Condition 3: retention time 1.87 min

Step 9 Preparation of Compound c79

Compound c79 (36.0 mg, 0.142 mmol) was dissolved in dichloromethane (2.0 mL), and 69 wt % m-chloroperoxybenzoic acid (74.6 mg, 0.298 mmol) was added under ice-cooling, and the mixture was stirred at room temperature for 18 hours. 69 wt % m-chloroperbenzoic acid (25.0 mg, 0.703 mmol) was stirred for 3.5 hours. 69 wt % m-chloroperoxybenzoic acid (10.0 mg, 0.281 mmol) and stirred for 1.5 hours. The reaction solution was purified by silica gel column chromatography (hexane-ethyl acetate) to give the compound c79 (35.0 mg, 86% yield).

[M+H]=285.90, Method Condition 3: retention time 1.77 min

Step 10 Preparation of Compound c80

Compound c66 (32.4 mg, 0.150 mmol) was dissolved in THF (10 mL) and tertiary butoxy potassium (38.9 mg, 0.347 mmol) was added to the mixture while cooling in ice, and the mixture was stirred for 3 minutes. Compound c79 (33.0 mg, 0.116 mmol) was dissolved in THF (2.0 mL) was added to the mixture while cooling in ice. The mixture was stirred for 2 hours under ice cooling. Water was added to the mixture, and the mixture was extracted with ethyl acetate. The organic layer was dried over anhydrous magnesium sulfate, and the solvent was evaporated under reduced pressure. The residue was purified by silica gel column chromatography (hexane-ethyl acetate, then chloroform-methanol) to give the compound c80 (33.3 mg, 68% yield).

$^1$H-NMR (CDCl$_3$) δ: 0.79-0.83 (m, 4H), 1.19 (d, J=6.8 Hz, 3H), 1.50-1.61 (m 2H), 1.64-1.73 (m, 2H), 1.97-2.05 (m, 5H), 2.17-2.25 (m, 2H), 3.44 (tt, J=14.9, 4.8 Hz, 3H), 3.69 (s, 3H), 4.12-4.18 (m, 1H), 4.33-4.38 (m, 1H), 5.10-5.16 (m, 1H), 5.64 (brd, J=7.8 Hz, 1H), 8.17 (s, 1H).

[M+H]=421.20, Method Condition 3: retention time 1.80 min

Step 11 Preparation of Compound c81

Compounds c80 (17.0 mg, 0.040 mmol) was dissolved in acetonitrile (3.4 mL), and N-chlorosuccinimide (13.0 mg, 0.095 mmol) was added to the mixture. Then the mixture was stirred 1.5 hours at 30° C. To the reaction mixture N-chlorosuccinimide (13.0 mg, 0.095 mmol) was added and the mixture was stirred for 1.5 hours. The mixture was allowed to stand at room temperature for 14 hours and stirred for 20 minutes at 40° C. Water was added to the reaction mixture while cooling in ice and the mixture was extracted with ethyl acetate. The organic layer was dried over anhydrous magnesium sulfate, and the solvent was evaporated under reduced pressure. The residue was purified by silica gel column chromatography (chloroform-methanol) to afford Compound c81 (9.0 mg, 49% yield).

¹H-NMR (CDCl₃) δ: 0.79-0.81 (m, 4H), 1.20 (d, J=6.8 Hz, 3H), 1.52-1.73 (m, 4H), 1.95-2.03 (m, 5H), 2.16-2.23 (m, 2H), 3.39-3.48 (m, 3H), 3.68 (s, 3H), 4.11-4.19 (m, 1H), 4.38-4.43 (m, 1H), 5.24-5.30 (m, 1H), 5.66 (brd, J=7.0 Hz, 1H).

[M+H]=455.20, Method Condition 3: retention time 2.12 min

Like the above embodiment, Compound I-001-I-748 were prepared. The chemical structure and chemical data are shown below.

TABLE 1

| Example No. | Structure | Method Condition | Retention time (minute) or NMR | [M + H] |
|---|---|---|---|---|
| I-001 | 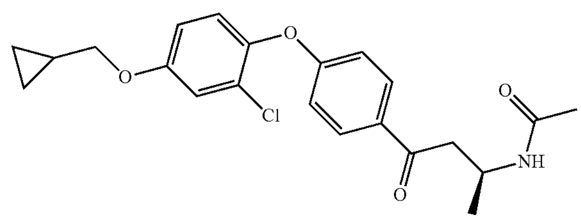 [SMILES: CC(=O)N[C@@H](C)CC(=O)c1ccc(Oc2ccc(OCC3CC3)cc2Cl)cc1] | | 1H-NMR (CDCl3) δ: 0.36 (m, 2H), 0.67 (m, 2H), 1.25 (d, J = 6.7 Hz, 3H), 1.42 (s, 9H), 2.86 (dd, J = 15.1, 6.8 Hz, 1H), 3.16 (dd, J = 15.1, 3.3 Hz, 1H), 3.80 (d, J = 7.0 Hz, 2H), 4.10 (m, 1H), 4.88 (brs, 1H), 6.87 (dd, J = 9.0, 3.0 Hz, 1H), 7.01 (d, J = 3.0 Hz, 1H), 7.22 (d, J = 9.0 Hz, 1H), 7.89 (s, 1H). | |
| I-002 | 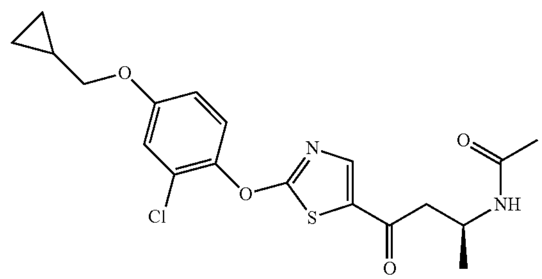 [SMILES: CC(=O)N[C@@H](C)CC(=O)c1cnc(Oc2ccc(OCC3CC3)cc2Cl)s1] | 2 | 2.15 | 409.3 |
| I-003 | 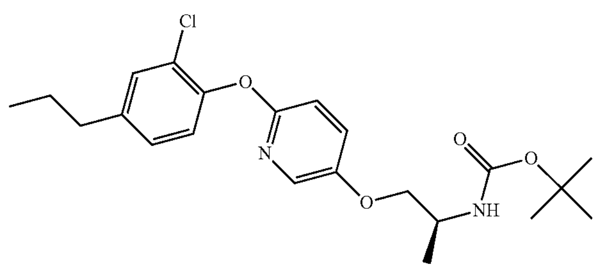 [SMILES: CCCc1ccc(Oc2ccc(OC[C@H](C)NC(=O)OC(C)(C)C)cn2)c(Cl)c1] | 2 | 2.88 | 421.5 |
| I-004 | 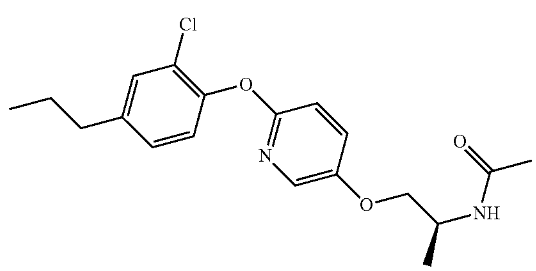 [SMILES: CCCc1ccc(Oc2ccc(OC[C@H](C)NC(C)=O)cn2)c(Cl)c1] | 2 | 2.32 | 363 |
| I-005 | 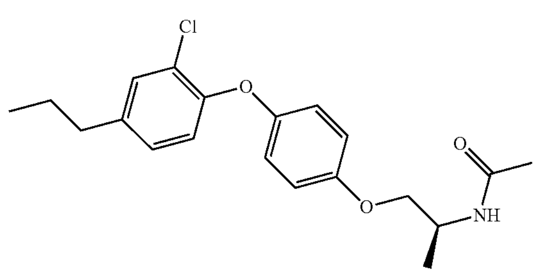 [SMILES: CCCc1ccc(Oc2ccc(OC[C@H](C)NC(C)=O)cc2)c(Cl)c1] | 4 | 2.56 | 362.3 |

TABLE 1-continued
| Example No. | Structure | Method Condition | Retention time (minute) or NMR | [M + H] |
|---|---|---|---|---|
| I-006 | 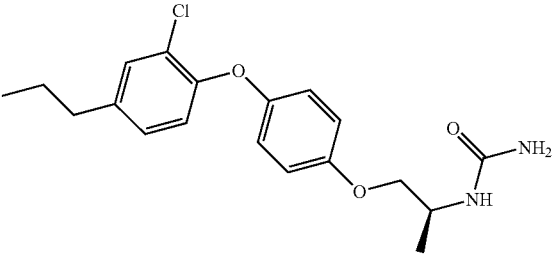 [SMILES: CCCc1ccc(Oc2ccc(OC[C@H](C)NC(N)=O)cc2)c(Cl)c1] | 4 | 2.48 | 363.1 |
TABLE 2
| I-007 | 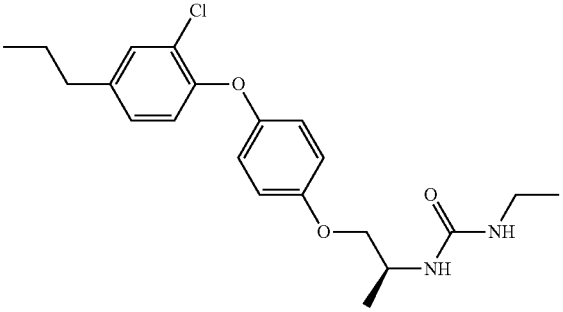 [SMILES: CCCc1ccc(Oc2ccc(OC[C@H](C)NC(=O)NCC)cc2)c(Cl)c1] | 4 | 2.69 | 391 |
| I-008 | 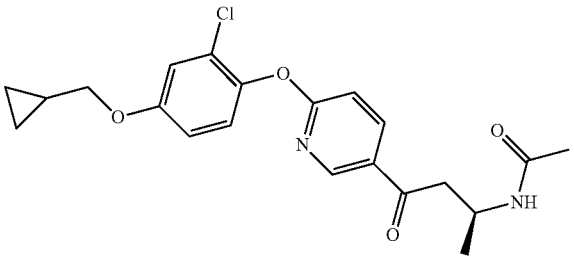 [SMILES: CC(=O)N[C@@H](C)CC(=O)c1ccc(Oc2ccc(OCC3CC3)cc2Cl)nc1] | 2 | 2.14 | 403.3 |
| I-009 | 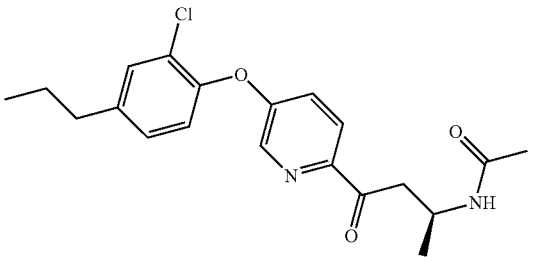 [SMILES: CCCc1ccc(Oc2ccc(C(=O)C[C@H](C)NC(C)=O)nc2)c(Cl)c1] | 2 | 2.44 | 363.4 |
| I-010 | 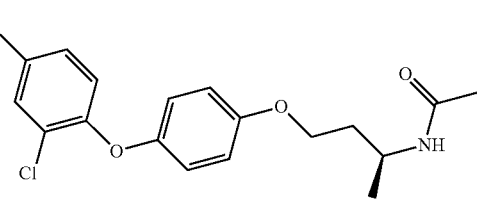 | 2 | 2.61 | 376.3 |

TABLE 2-continued
| | | | | |
|---|---|---|---|---|
| I-011 | 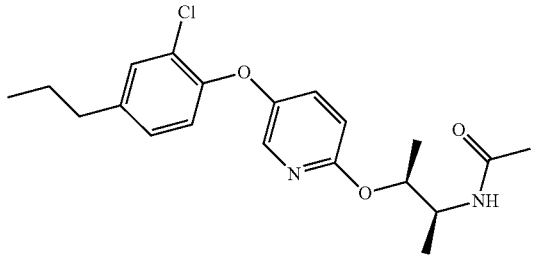 [SMILES: CCCc1ccc(Oc2ccc(O[C@@H](C)[C@H](C)NC(C)=O)nc2)c(Cl)c1] | 4 | 2.6 | 377.4 |
| I-012 | 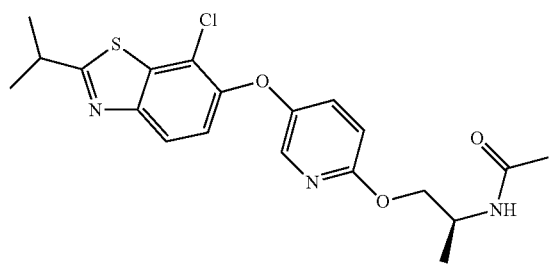 [SMILES: CC(=O)N[C@@H](C)COc1ccc(Oc2ccc3nc(C(C)C)sc3c2Cl)cn1] | 4 | 2.39 | 420.3 |
| I-013 | 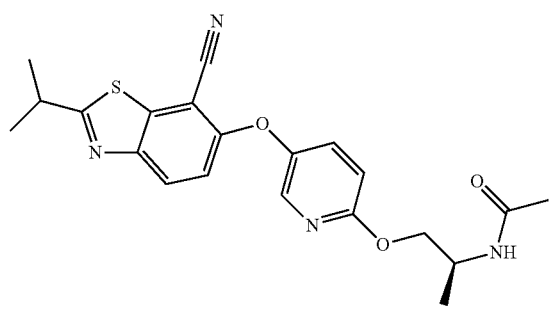 [SMILES: CC(=O)N[C@@H](C)COc1ccc(Oc2ccc3nc(C(C)C)sc3c2C#N)cn1] | 4 | 2.13 | 411.1 |
| I-014 | 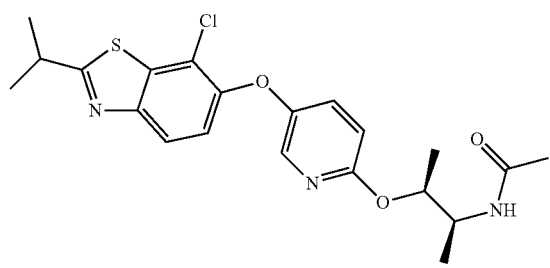 [SMILES: CC(=O)N[C@@H](C)[C@H](C)Oc1ccc(Oc2ccc3nc(C(C)C)sc3c2Cl)cn1] | 4 | 2.54 | 434.3 |
TABLE 3
| | | | | |
|---|---|---|---|---|
| I-015 | 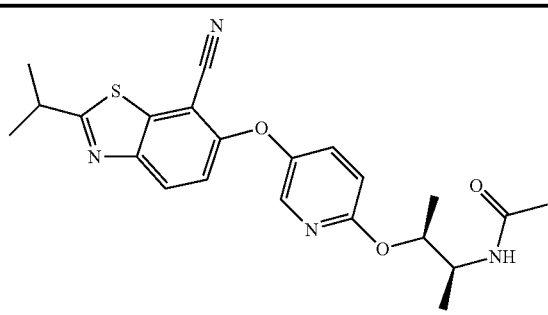 | 4 | 2.26 | 425.1 |

TABLE 3-continued
| | | | | |
|---|---|---|---|---|
| I-016 | 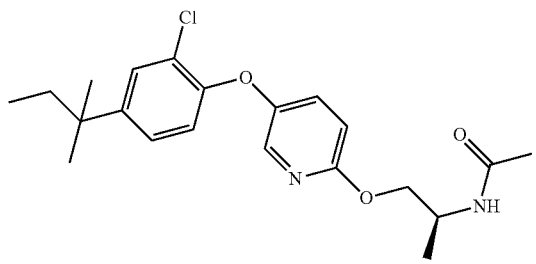 [SMILES: CCC(C)(C)c1ccc(Oc2ccc(OC[C@H](C)NC(C)=O)nc2)c(Cl)c1] | 4 | 2.68 | 393.2 |
| I-017 | 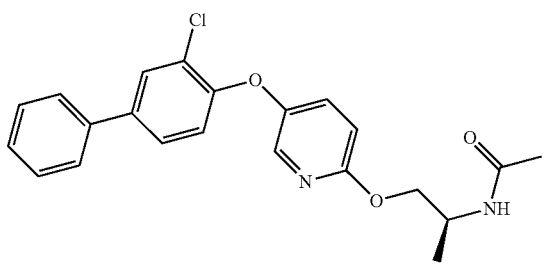 [SMILES: CC(=O)N[C@@H](C)COc1ccc(Oc2ccc(-c3ccccc3)cc2Cl)cn1] | 4 | 2.46 | 398.1 |
| I-018 | 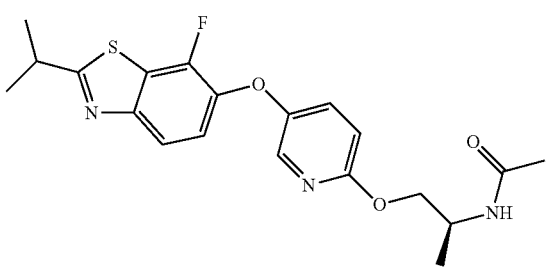 [SMILES: CC(=O)N[C@@H](C)COc1ccc(Oc2ccc3nc(C(C)C)sc3c2F)cn1] | 4 | 2.22 | 404.4 |
| I-019 | 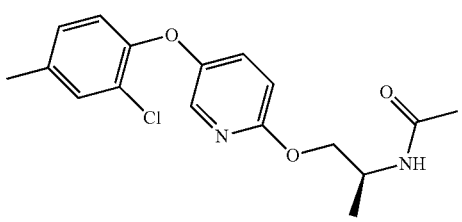 [SMILES: CC(=O)N[C@@H](C)COc1ccc(Oc2ccc(C)cc2Cl)cn1] | 4 | 2.09 | 335.4 |
| I-020 | 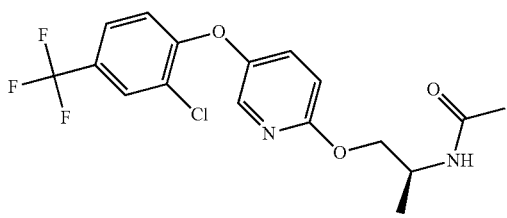 [SMILES: CC(=O)N[C@@H](C)COc1ccc(Oc2ccc(C(F)(F)F)cc2Cl)cn1] | 4 | 2.25 | 389.1 |
| I-021 | 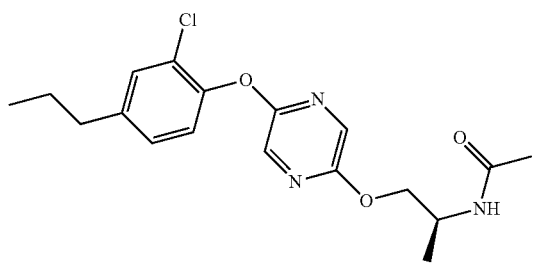 [SMILES: CCCc1ccc(Oc2cnc(OC[C@H](C)NC(C)=O)cn2)c(Cl)c1] | 4 | 2.38 | 364.4 |

TABLE 3-continued

| ID | Structure | | | |
|---|---|---|---|---|
| I-022 | (tert-butyl carbamate tetrahydroisoquinoline with Cl, linked via O-pyridine-O to acetamide with methyl stereocenter) | 4 | 2.38 | 476.5 |

TABLE 4

| ID | Structure | | | |
|---|---|---|---|---|
| I-023 | (5-fluoropyrimidin-2-yl tetrahydroisoquinoline with Cl, linked via O-pyridine-O to acetamide with methyl stereocenter) | 4 | 2.37 | 472.1 |
| I-024 | (2-isopropyl-7-chlorobenzothiazole linked via O-pyridine-O to urea (NH-C(O)-NH₂) with methyl stereocenter) | 4 | 2.2 | 421.4 |
| I-025 | (2-isopropyl-7-chlorobenzothiazole linked via O-pyridine-O to hydroxyacetamide with methyl stereocenter) | 4 | 2.23 | 436.4 |
| I-026 | (2-isopropyl-7-fluorobenzothiazole linked via O-pyrazine-O to acetamide with methyl stereocenter) | 4 | 2.15 | 405.6 |
| I-027 | (2-(2-hydroxypropan-2-yl)-7-chlorobenzothiazole linked via O-pyrazine-O to acetamide with methyl stereocenter) | 4 | 1.69 | 437.5 |

TABLE 4-continued
| I-028 | 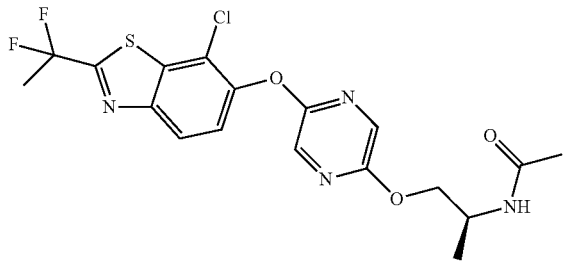 [SMILES: CC(=O)N[C@@H](C)COc1cnc(Oc2ccc3nc(C(C)(F)F)sc3c2Cl)cn1] | 4 | 2.62 | 443.4 |
| I-029 | 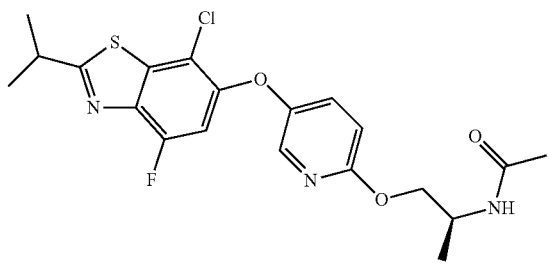 [SMILES: CC(=O)N[C@@H](C)COc1ccc(Oc2cc(F)c3nc(C(C)C)sc3c2Cl)cn1] | 4 | 2.45 | 438.4 |
| I-030 | 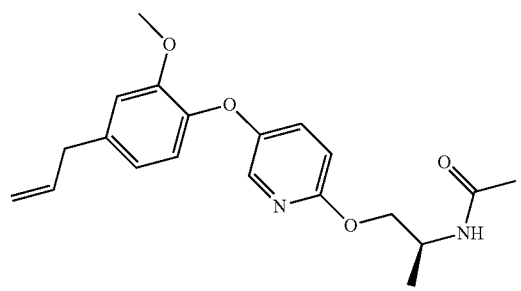 [SMILES: C=CCc1ccc(Oc2ccc(OC[C@H](C)NC(C)=O)nc2)c(OC)c1] | 4 | 2.06 | 357.1 |
TABLE 5
| I-031 | 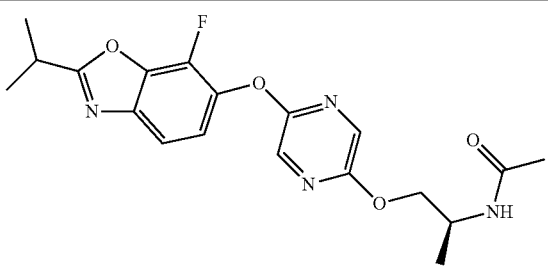 | 4 | 1.97 | 389.2 |
| I-032 | 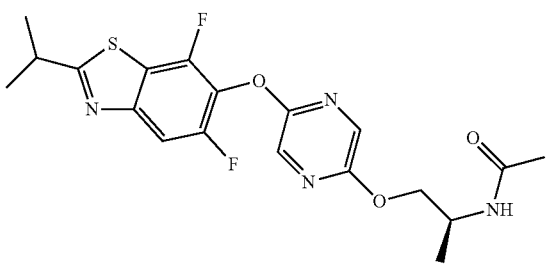 [SMILES: CC(=O)N[C@@H](C)COc1cnc(Oc2c(F)cc3nc(C(C)C)sc3c2F)cn1] | 4 | 2.31 | 423.1 |

TABLE 5-continued

| ID | Structure | | | |
|---|---|---|---|---|
| I-033 | (2-(1,1-difluoropropyl)-7-chlorobenzothiazol-6-yl) structure | 4 | 2.55 | 456.9 |
| I-034 | (2-cyclopropyl-7-fluorobenzothiazol-6-yl) structure | 4 | 2.18 | 403.5 |
| I-035 | (2-(1-methylcyclopropyl)-7-chlorobenzothiazol-6-yl) structure | 4 | 2.57 | 432.8 |
| I-036 | (2-(1,1-difluoroethyl)-7-fluorobenzothiazol-6-yl) structure | 4 | 2.19 | 427.4 |
| I-037 | (2-isopropyl-7-chlorobenzoxazol-6-yl) structure | 4 | 2.31 | 405.1 |
| I-038 | (2-isopropyl-7-chlorobenzothiazol-6-yl) structure | 4 | 2.62 | 421.1 |

TABLE 6

| ID | Structure | | | |
|---|---|---|---|---|
| I-039 | 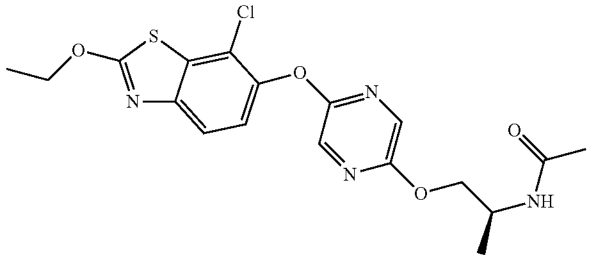 [SMILES: CCOc1nc2ccc(Oc3cnc(OC[C@H](C)NC(C)=O)cn3)c(Cl)c2s1] | 4 | 2.3 | 423.2 |
| I-040 | 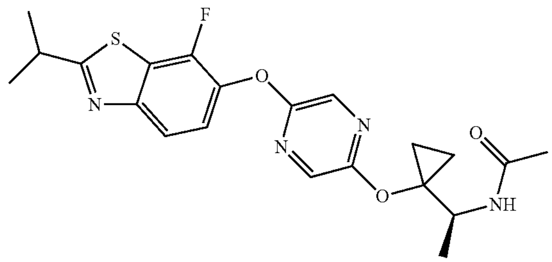 [SMILES: CC(=O)N[C@@H](C)C1(Oc2cnc(Oc3ccc4nc(C(C)C)sc4c3F)cn2)CC1] | 4 | 2.79 | 431.2 |
| I-041 | 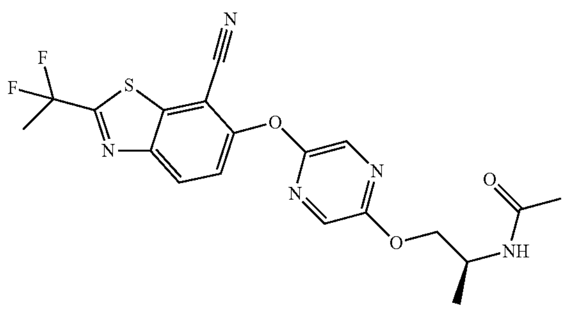 [SMILES: CC(=O)N[C@@H](C)COc1cnc(Oc2ccc3nc(C(C)(F)F)sc3c2C#N)cn1] | 4 | 2.49 | 434.4 |
| I-042 | 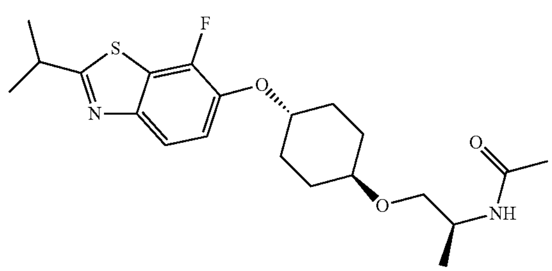 [SMILES: CC(=O)N[C@@H](C)CO[C@H]1CC[C@H](Oc2ccc3nc(C(C)C)sc3c2F)CC1] | 4 | 2.29 | 409.6 |
| I-043 | 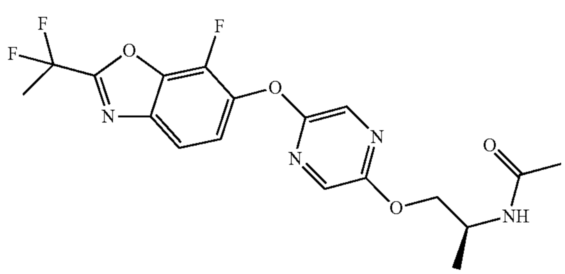 [SMILES: CC(=O)N[C@@H](C)COc1cnc(Oc2ccc3nc(C(C)(F)F)oc3c2F)cn1] | 4 | 1.99 | 411.6 |
| I-044 | 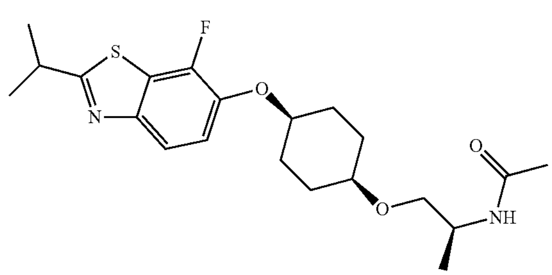 [SMILES: CC(=O)N[C@@H](C)CO[C@H]1CC[C@@H](Oc2ccc3nc(C(C)C)sc3c2F)CC1] | 4 | 2.26 | 408.5 |

TABLE 6-continued
| | | | | |
|---|---|---|---|---|
| I-045 | 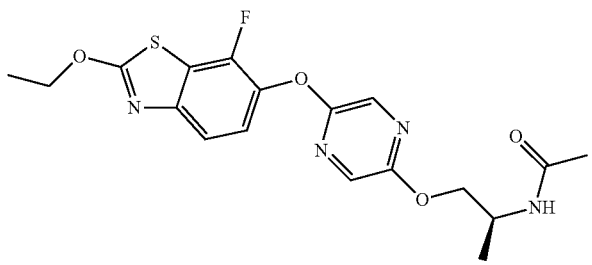 [SMILES: CCOc1nc2ccc(Oc3cnc(OC[C@H](C)NC(C)=O)cn3)c(F)c2s1] | 4 | 2.14 | 407.2 |
| I-046 | 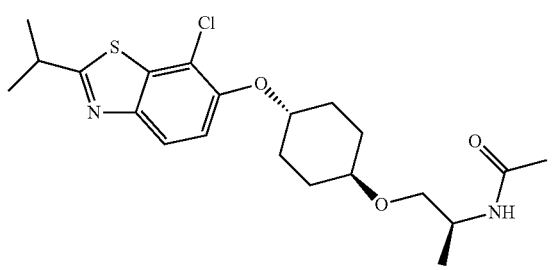 | 4 | 2.47 | 425 |
TABLE 7
| | | | | |
|---|---|---|---|---|
| I-047 | 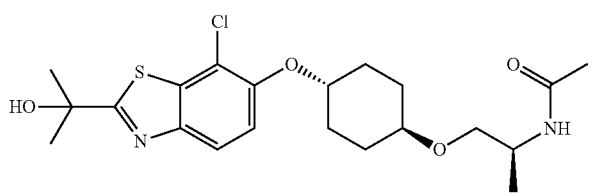 [SMILES: CC(=O)N[C@@H](C)CO[C@H]1CC[C@H](Oc2ccc3nc(C(C)(C)O)sc3c2Cl)CC1] | 4 | 1.79 | 441.2 |
| I-048 | 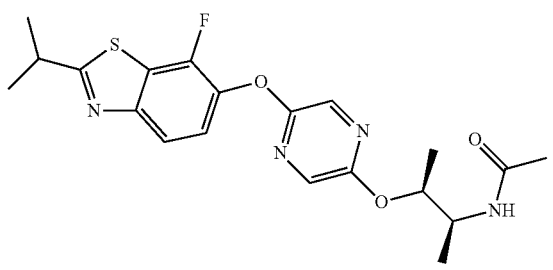 [SMILES: CC(=O)N[C@@H](C)[C@H](C)Oc1cnc(Oc2ccc3nc(C(C)C)sc3c2F)cn1] | 4 | 2.29 | 418.9 |
| I-049 | 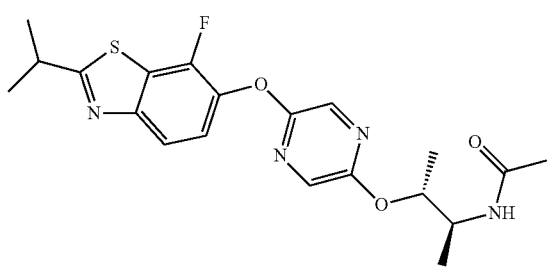 [SMILES: CC(=O)N[C@@H](C)[C@@H](C)Oc1cnc(Oc2ccc3nc(C(C)C)sc3c2F)cn1] | 4 | 2.29 | 419 |

TABLE 7-continued

| ID | Structure | a | b | c |
|---|---|---|---|---|
| I-050 | 2-(1-fluorocyclopropyl)-7-fluorobenzothiazol-6-yl ether linked via pyrazine-O-CH2 to (S)-N-acetyl-2-aminopropyl | 4 | 2.18 | 421.5 |
| I-051 | 2-isopropyl-7-cyanobenzothiazol-6-yl ether linked via trans-cyclohexyl-O-CH2 to (S)-N-acetyl-2-aminopropyl | 2 | 1.96 | 416.1 |
| I-052 | 2-(1,1-difluoroethyl)-7-chlorobenzothiazol-6-yl ether linked via trans-cyclohexyl-O-CH2 to (S)-N-acetyl-2-aminopropyl | 4 | 2.52 | 447.2 |
| I-053 | 2-(difluoromethyl)-7-fluorobenzothiazol-6-yl ether linked via trans-cyclohexyl-O-CH2 to (S)-N-acetyl-2-aminopropyl | 4 | 2.34 | 431 |
| I-054 | 2-ethoxy-7-chlorobenzothiazol-6-yl ether linked via trans-cyclohexyl-O-CH2 to (S)-N-acetyl-2-aminopropyl | 4 | 2.47 | 427.2 |

TABLE 8
| | | | | |
|---|---|---|---|---|
| I-055 | 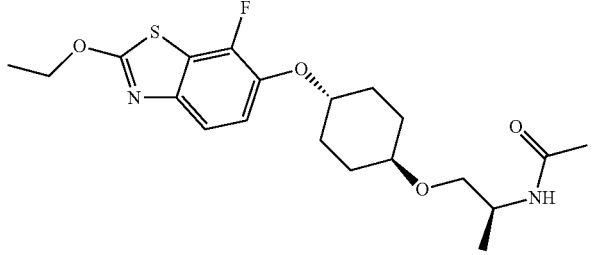 [SMILES: CCOc1nc2ccc(O[C@H]3CC[C@H](OC[C@H](C)NC(C)=O)CC3)c(F)c2s1] | 4 | 2.29 | 411 |
| I-056 | 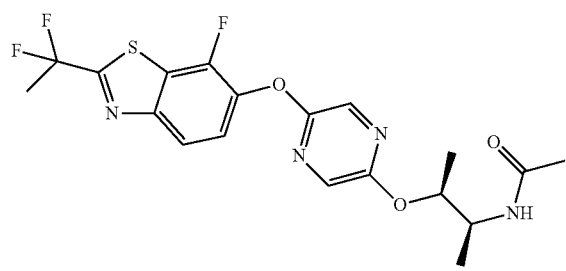 [SMILES: CC(=O)N[C@@H](C)[C@H](C)Oc1cnc(Oc2ccc3nc(C(C)(F)F)sc3c2F)cn1] | 4 | 2.32 | 441.6 |
| I-057 | 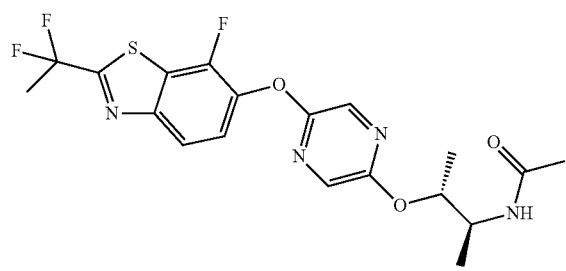 [SMILES: CC(=O)N[C@@H](C)[C@@H](C)Oc1cnc(Oc2ccc3nc(C(C)(F)F)sc3c2F)cn1] | 4 | 2.32 | 441.5 |
| I-058 | 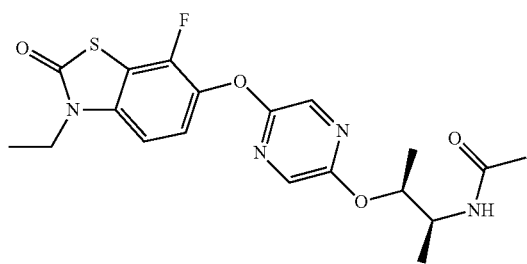 [SMILES: CCn1c(=O)sc2c(F)c(Oc3cnc(O[C@@H](C)[C@H](C)NC(C)=O)cn3)ccc21] | 4 | 1.97 | 420.9 |
| I-059 | 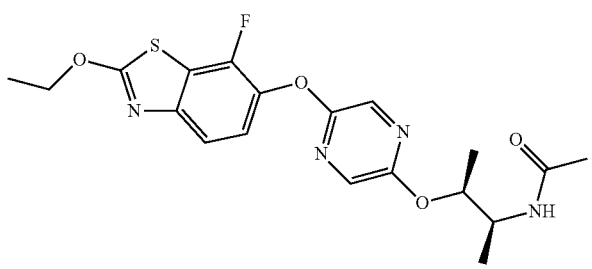 [SMILES: CCOc1nc2ccc(Oc3cnc(O[C@@H](C)[C@H](C)NC(C)=O)cn3)c(F)c2s1] | 4 | 2.29 | 421 |
| I-060 | 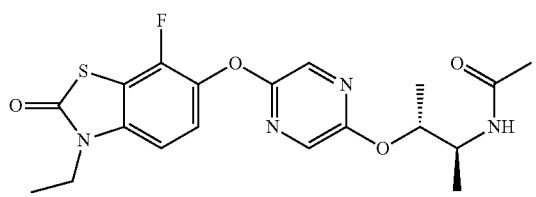 [SMILES: CCn1c(=O)sc2c(F)c(Oc3cnc(O[C@H](C)[C@H](C)NC(C)=O)cn3)ccc21] | 4 | 1.97 | 420.9 |

TABLE 8-continued
| I-061 | 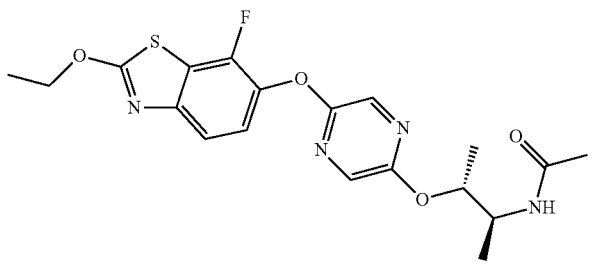 [SMILES: CCOc1nc2ccc(Oc3cnc(O[C@H](C)[C@H](C)NC(C)=O)cn3)c(F)c2s1] | 4 | 2.29 | 421.2 |
| I-062 | 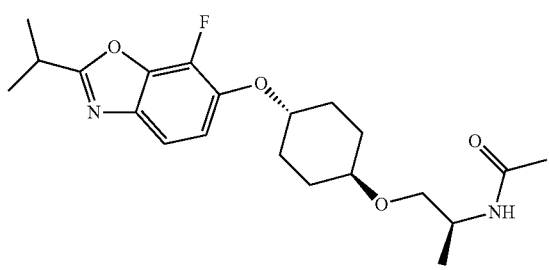 | 4 | 2.1 | 393.1 |
TABLE 9
| I-063 | 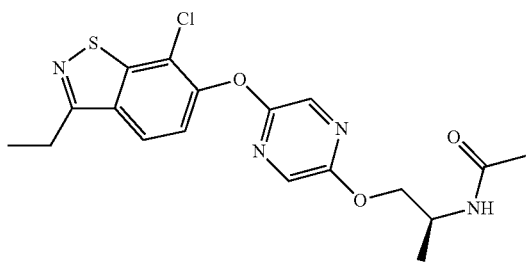 [SMILES: CCc1nsc2c(Cl)c(Oc3cnc(OC[C@H](C)NC(C)=O)cn3)ccc12] | 2 | 2.21 | 407.1 |
| I-064 | 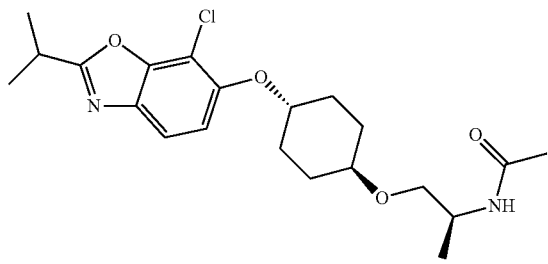 | 4 | 2.27 | 409.2 |
| I-065 | 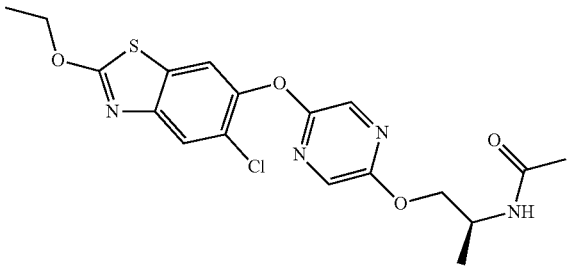 [SMILES: CCOc1nc2cc(Cl)c(Oc3cnc(OC[C@H](C)NC(C)=O)cn3)cc2s1] | 2 | 2.15 | 423.2 |

TABLE 9-continued
| | | | | |
|---|---|---|---|---|
| I-066 | 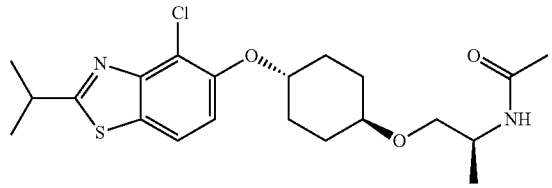 [SMILES: CC(=O)N[C@@H](C)CO[C@H]1CC[C@H](Oc2ccc3sc(C(C)C)nc3c2Cl)CC1] | 4 | 2.36 | 425.2 |
| I-067 | 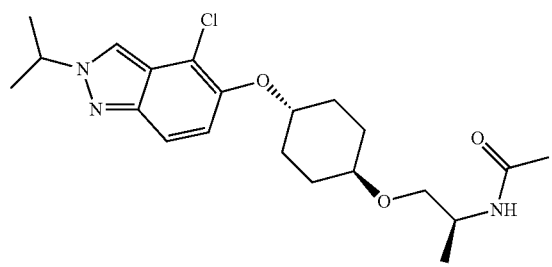 [SMILES: CC(=O)N[C@@H](C)CO[C@H]1CC[C@H](Oc2ccc3nn(C(C)C)cc3c2Cl)CC1] | 4 | 1.96 | 408.3 |
| I-068 | 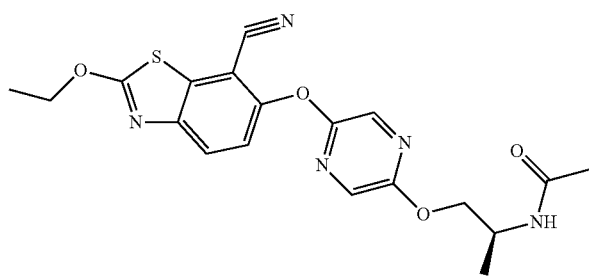 [SMILES: CCOc1nc2ccc(Oc3cnc(OC[C@H](C)NC(C)=O)cn3)c(C#N)c2s1] | 4 | 2.06 | 414.2 |
| I-069 | 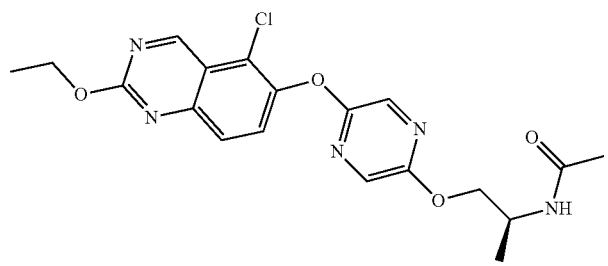 [SMILES: CCOc1ncc2c(Cl)c(Oc3cnc(OC[C@H](C)NC(C)=O)cn3)ccc2n1] | 2 | 1.89 | 418 |
| I-070 | 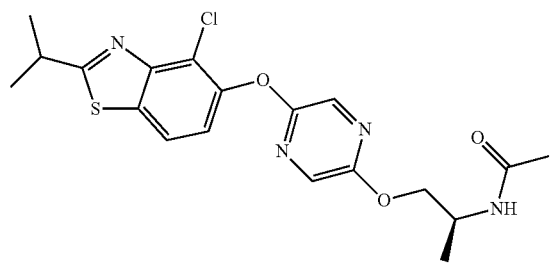 [SMILES: CC(=O)N[C@@H](C)COc1cnc(Oc2ccc3sc(C(C)C)nc3c2Cl)cn1] | 2 | 2.15 | 421.2 |

TABLE 10
| | | | | |
|---|---|---|---|---|
| I-071 | 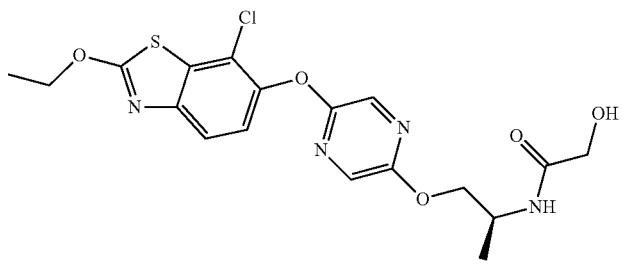 [SMILES: CCOc1nc2ccc(Oc3cnc(OC[C@H](C)NC(=O)CO)cn3)c(Cl)c2s1] | 4 | 2.14 | 439.2 |
| I-072 | 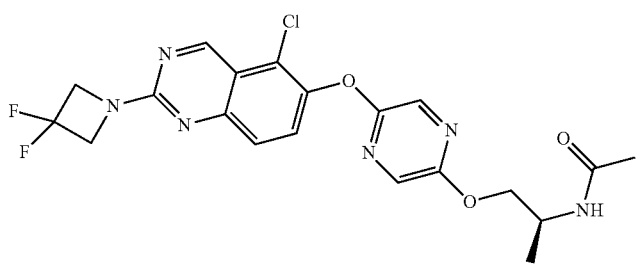 [SMILES: CC(=O)N[C@@H](C)COc1cnc(Oc2ccc3nc(N4CC(F)(F)C4)ncc3c2Cl)cn1] | 2 | 1.97 | 465 |
| I-073 | 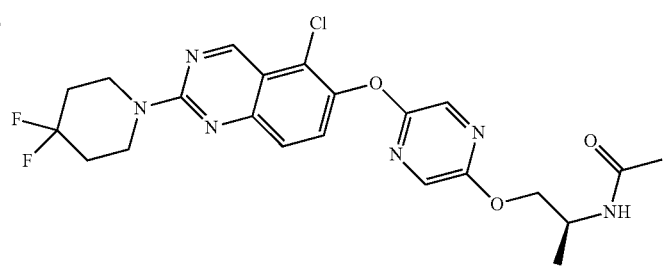 [SMILES: CC(=O)N[C@@H](C)COc1cnc(Oc2ccc3nc(N4CCC(F)(F)CC4)ncc3c2Cl)cn1] | 2 | 2.36 | 493.2 |
| I-074 | 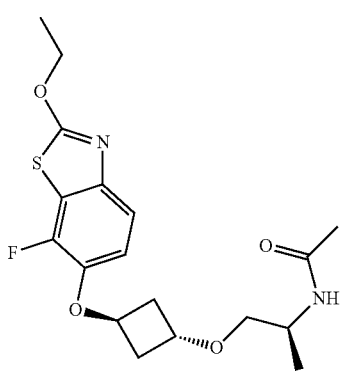 [SMILES: CCOc1nc2ccc(O[C@H]3C[C@H](OC[C@H](C)NC(C)=O)C3)c(F)c2s1] | 4 | 2.12 | 383.6 |
| I-075 | 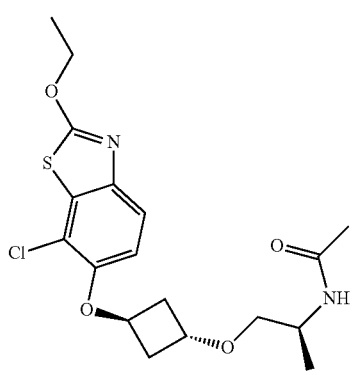 [SMILES: CCOc1nc2ccc(O[C@H]3C[C@H](OC[C@H](C)NC(C)=O)C3)c(Cl)c2s1] | 4 | 2.28 | 399.5 |

TABLE 10-continued
| I-076 | 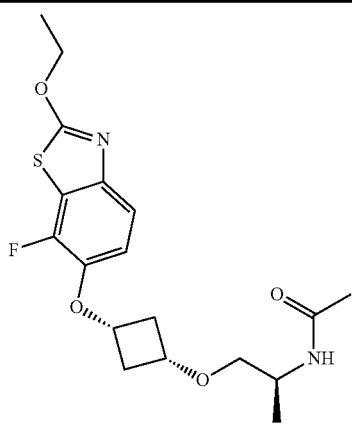 | 3 | 2.07 | 383.2 |
| I-077 | 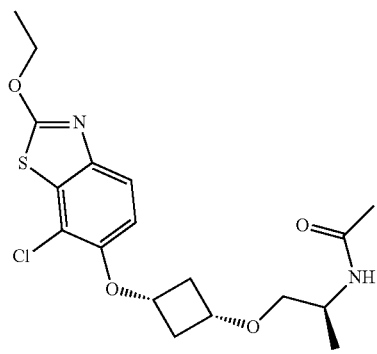 [SMILES: CCOc1nc2ccc(O[C@H]3C[C@@H](OC[C@H](C)NC(C)=O)C3)c(Cl)c2s1] | 3 | 2.21 | 399.5 |
TABLE 11
| I-078 | 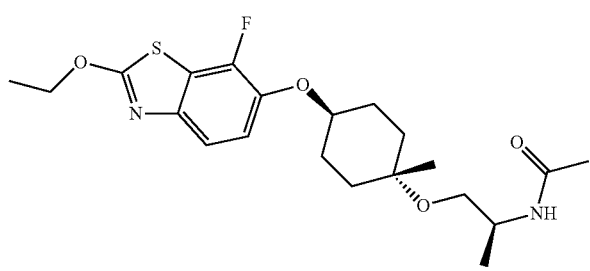 [SMILES: CCOc1nc2ccc(O[C@H]3CC[C@](C)(OC[C@H](C)NC(C)=O)CC3)c(F)c2s1] | 3 | 2.51 | 425.33 |
| I-079 | 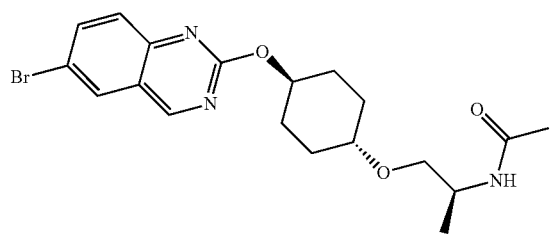 [SMILES: CC(=O)N[C@@H](C)CO[C@H]1CC[C@H](Oc2ncc3cc(Br)ccc3n2)CC1] | 2 | 2.03 | 422.15 |

TABLE 11-continued
I-080 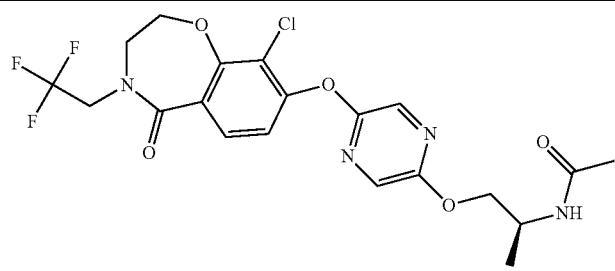 3 1.79 489
I-081 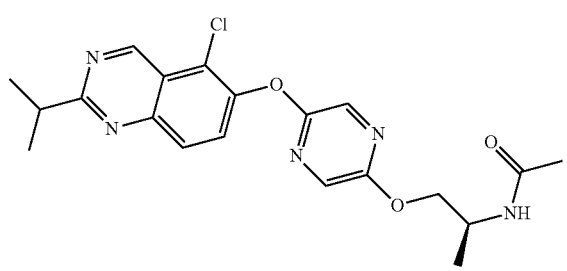 [SMILES: CC(=O)N[C@@H](C)COc1cnc(Oc2ccc3nc(C(C)C)ncc3c2Cl)cn1] 2 2.05 416.2
I-082 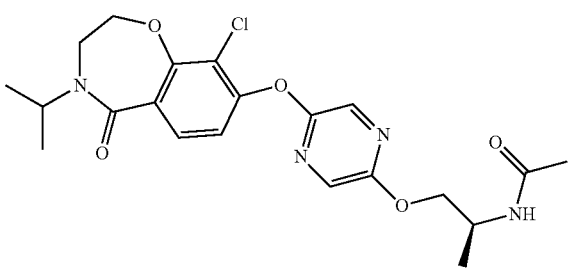 [SMILES: CC(=O)N[C@@H](C)COc1cnc(Oc2ccc3c(c2Cl)OCCN(C(C)C)C3=O)cn1] 3 1.64 449
I-083 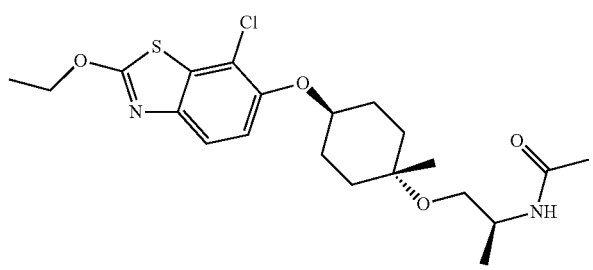 [SMILES: CCOc1nc2ccc(O[C@H]3CC[C@](C)(OC[C@H](C)NC(C)=O)CC3)c(Cl)c2s1] 3 2.72 441.28
I-084 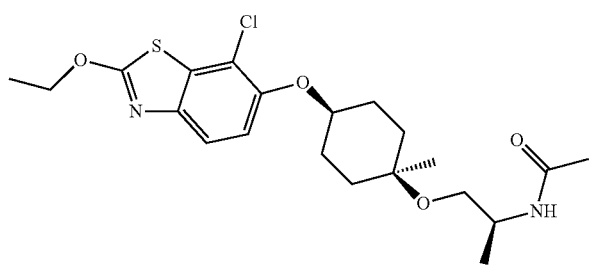 [SMILES: CCOc1nc2ccc(O[C@H]3CC[C@@](C)(OC[C@H](C)NC(C)=O)CC3)c(Cl)c2s1] 3 2.55 441.31

TABLE 11-continued
| I-085 | 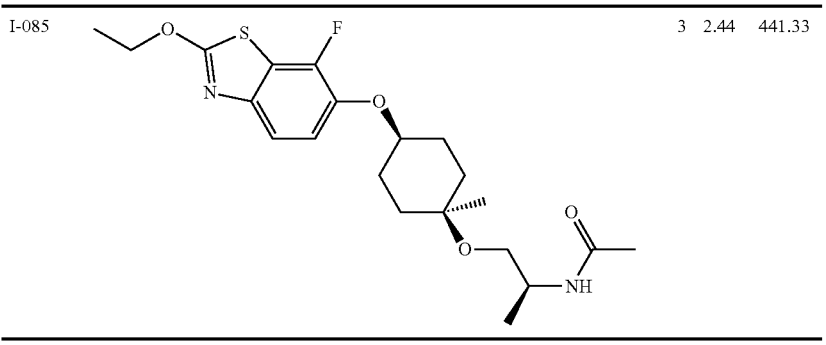 | 3 | 2.44 | 441.33 |
TABLE 12
| I-086 | 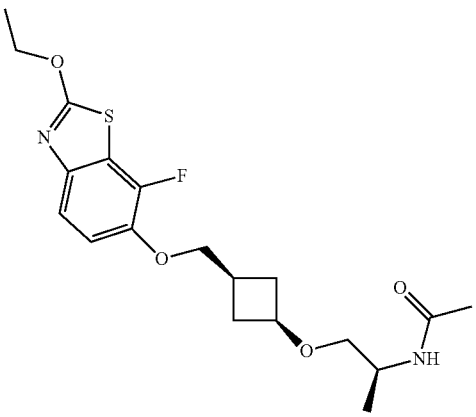 [SMILES: CCOc1nc2ccc(OC[C@H]3C[C@@H](OC[C@H](C)NC(C)=O)C3)c(F)c2s1] | 3 | 2.17 | 397 |
| I-087 | 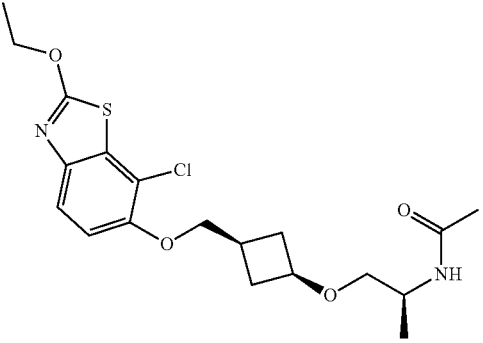 [SMILES: CCOc1nc2ccc(OC[C@H]3C[C@@H](OC[C@H](C)NC(C)=O)C3)c(Cl)c2s1] | 3 | 2.31 | 413 |
| I-088 | 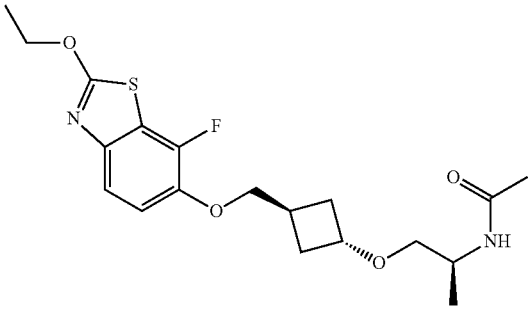 [SMILES: CCOc1nc2ccc(OC[C@H]3C[C@H](OC[C@H](C)NC(C)=O)C3)c(F)c2s1] | 3 | 2.18 | 397.1 |

US 10,150,728 B2
TABLE 12-continued
| I-089 | 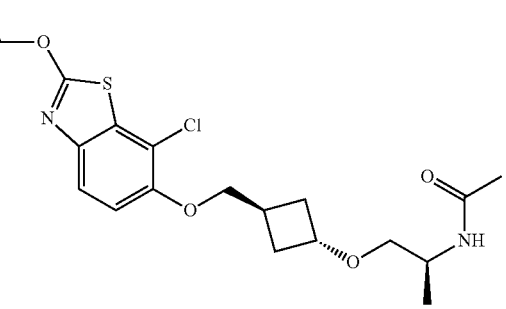 | 3 | 2.32 | 413 |
| I-090 | 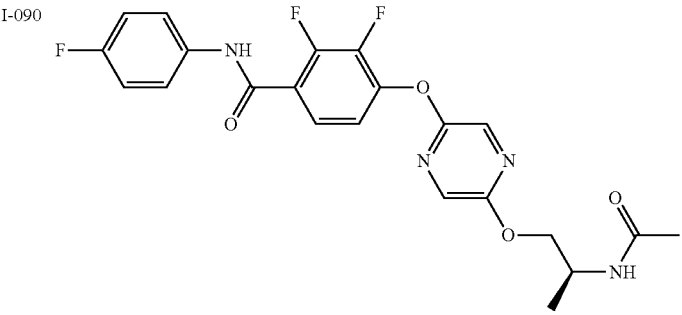 | 2 | 1.93 | 461.05 |
| I-091 | 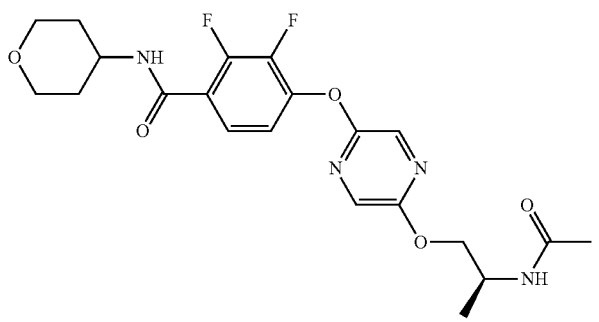 [SMILES: CC(=O)N[C@@H](C)COc1cnc(Oc2ccc(C(=O)NC3CCOCC3)c(F)c2F)cn1] | 2 | 1.45 | 451.1 |
| I-092 | 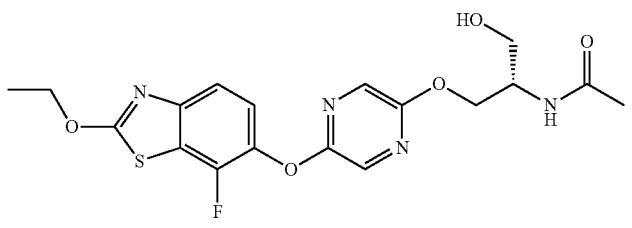 [SMILES: CCOc1nc2ccc(Oc3cnc(OC[C@H](CO)NC(C)=O)cn3)c(F)c2s1] | 2 | 1.83 | 422.95 |
TABLE 13
| I-093 | 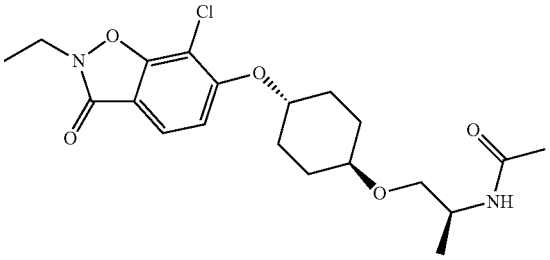 [SMILES: CCn1oc2c(Cl)c(O[C@H]3CC[C@H](OC[C@H](C)NC(C)=O)CC3)ccc2c1=O] | 4 | 1.94 | 411.25 |

TABLE 13-continued
| I-094 | 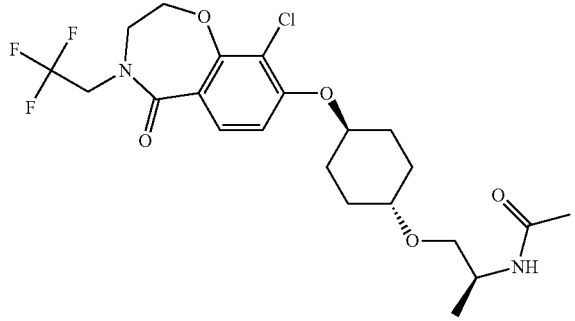 [SMILES: CC(=O)N[C@@H](C)CO[C@H]1CC[C@H](Oc2ccc3c(c2Cl)OCCN(CC(F)(F)F)C3=O)CC1] | 3 | 1.91 | 493 |
| I-095 | 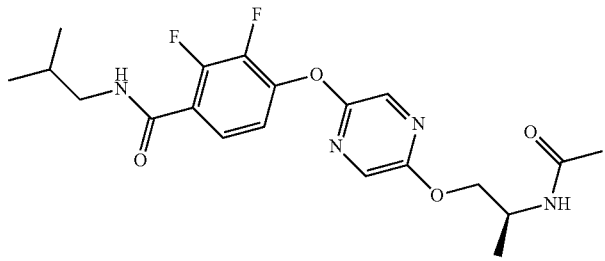 [SMILES: CC(=O)N[C@@H](C)COc1cnc(Oc2ccc(C(=O)NCC(C)C)c(F)c2F)cn1] | 2 | 1.81 | 423.05 |
| I-096 | 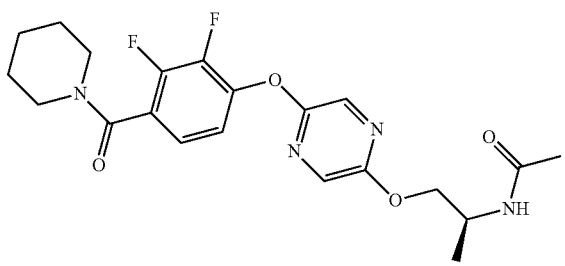 [SMILES: CC(=O)N[C@@H](C)COc1cnc(Oc2ccc(C(=O)N3CCCCC3)c(F)c2F)cn1] | 2 | 1.76 | 435.4 |
| I-097 | 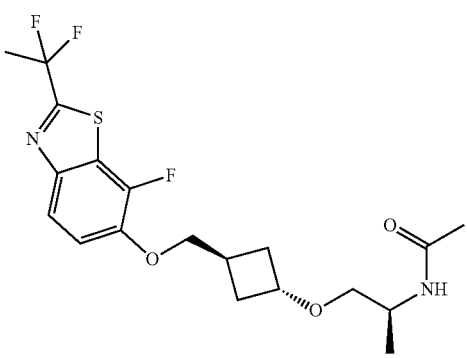 [SMILES: CC(=O)N[C@@H](C)CO[C@H]1C[C@H](COc2ccc3nc(C(C)(F)F)sc3c2F)C1] | 3 | 2.23 | 417 |
| I-098 | 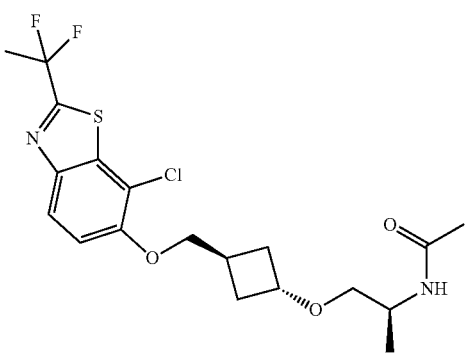 [SMILES: CC(=O)N[C@@H](C)CO[C@H]1C[C@H](COc2ccc3nc(C(C)(F)F)sc3c2Cl)C1] | 3 | 2.36 | 433.3 |

TABLE 13-continued
| I-099 | 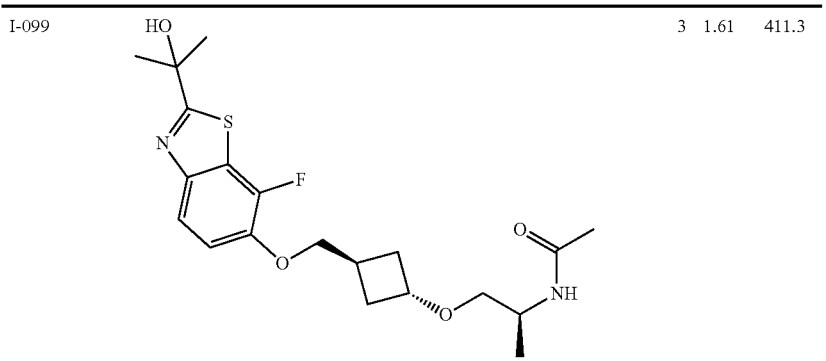 | 3 | 1.61 | 411.3 |
| I-100 | 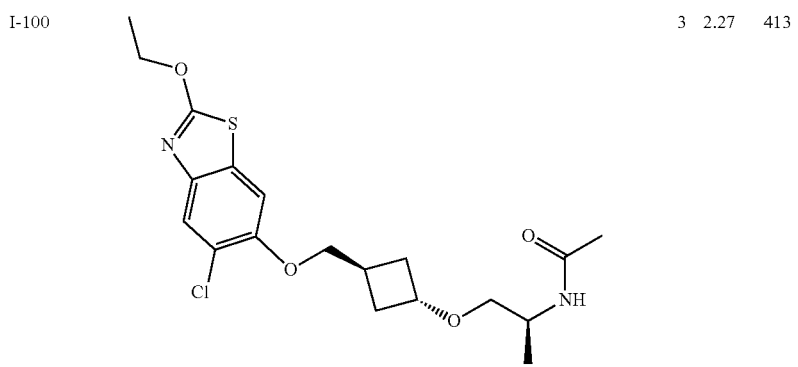 | 3 | 2.27 | 413 |
TABLE 14
| I-101 | 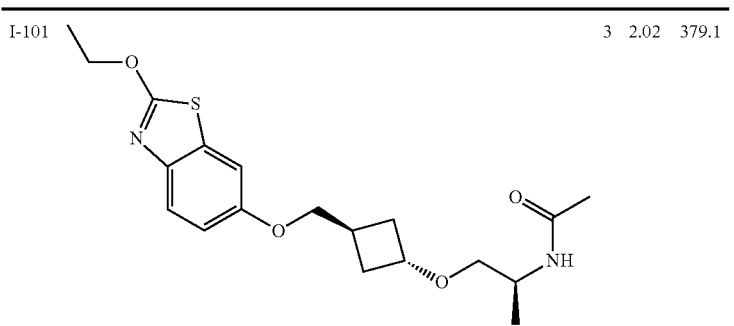 | 3 | 2.02 | 379.1 |
| I-102 | 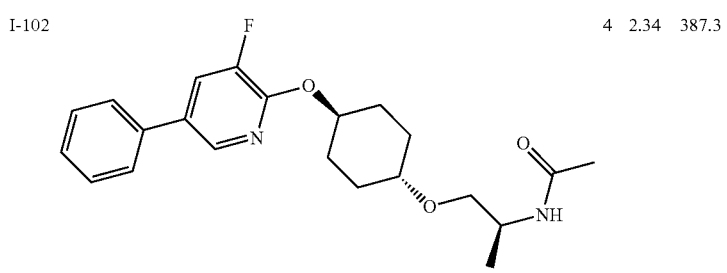 | 4 | 2.34 | 387.3 |

TABLE 14-continued
| | | | | | |
|---|---|---|---|---|---|
| I-103 | 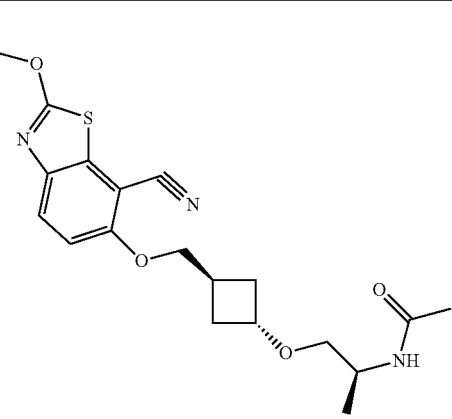 | | 3 | 2.09 | 404 |
| I-104 | 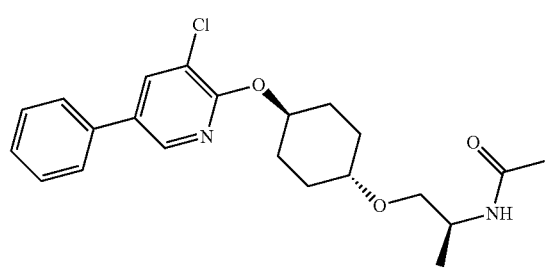 [SMILES: CC(=O)N[C@@H](C)CO[C@H]1CC[C@H](Oc2ncc(-c3ccccc3)cc2Cl)CC1] | | 4 | 2.51 | 403.2 |
| I-105 | 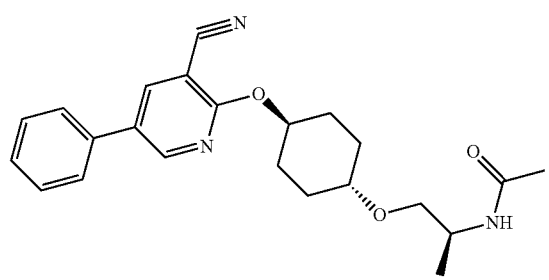 [SMILES: CC(=O)N[C@@H](C)CO[C@H]1CC[C@H](Oc2ncc(-c3ccccc3)cc2C#N)CC1] | | 4 | 2.23 | 394.3 |
TABLE 15
| | | | | | |
|---|---|---|---|---|---|
| I-106 | 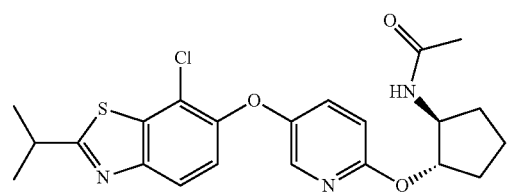 [SMILES: CC(=O)N[C@H]1CCC[C@@H]1Oc1ccc(Oc2ccc3nc(C(C)C)sc3c2Cl)cn1] | | 4 | 2.58 | 446 |

TABLE 16
| | | | | |
|---|---|---|---|---|
| I-107 | 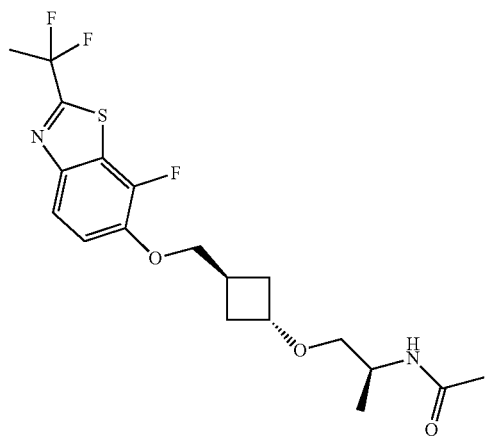 [SMILES: CC(=O)N[C@@H](C)CO[C@H]1C[C@H](COc2ccc3nc(C(C)(F)F)sc3c2F)C1] | 4 | 2.23 | 417.0 |
| I-108 | 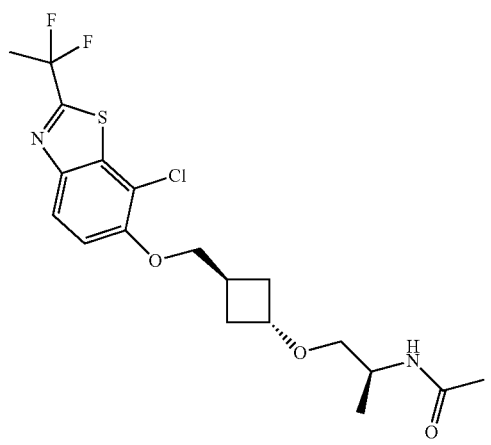 [SMILES: CC(=O)N[C@@H](C)CO[C@H]1C[C@H](COc2ccc3nc(C(C)(F)F)sc3c2Cl)C1] | 4 | 2.36 | 433.3 |
| I-109 | 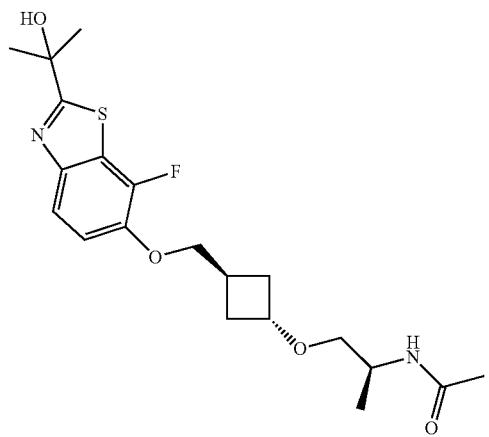 [SMILES: CC(=O)N[C@@H](C)CO[C@H]1C[C@H](COc2ccc3nc(C(C)(C)O)sc3c2F)C1] | 4 | 1.61 | 411.3 |

TABLE 16-continued
| | | | | |
|---|---|---|---|---|
| I-110 | 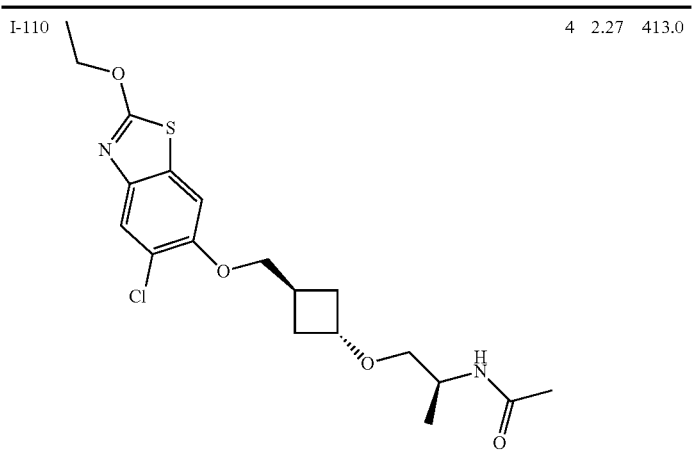 | 4 | 2.27 | 413.0 |
| I-111 | 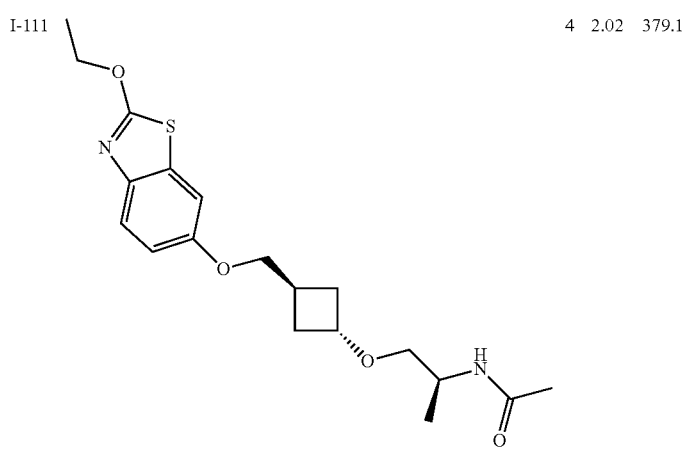 | 4 | 2.02 | 379.1 |
TABLE 17
| | | | | |
|---|---|---|---|---|
| I-112 | 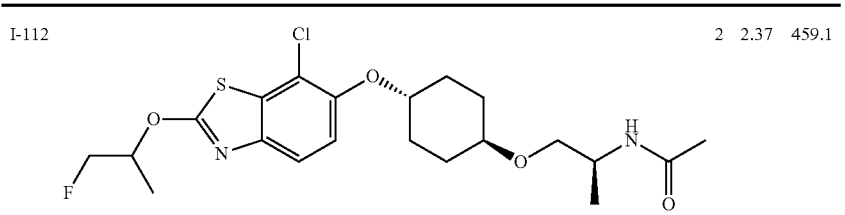 | 2 | 2.37 | 459.1 |
| I-113 | 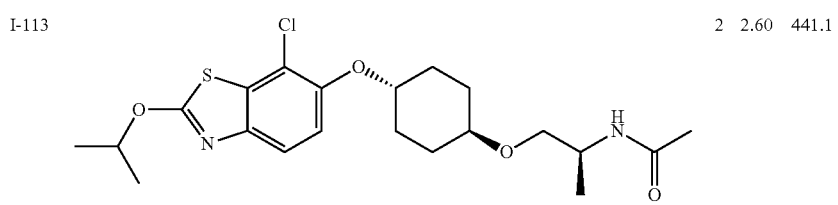 | 2 | 2.60 | 441.1 |
| I-114 | 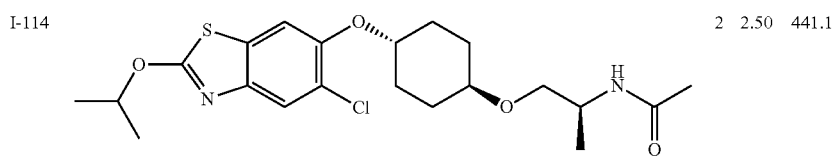 | 2 | 2.50 | 441.1 |

TABLE 17-continued
| | | | | |
|---|---|---|---|---|
| I-115 | 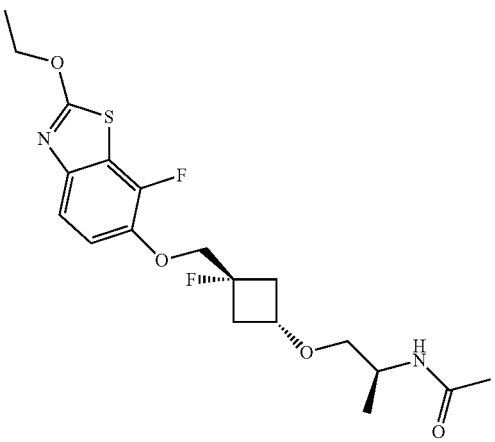 [SMILES: CCOc1nc2ccc(OC[C@]3(F)C[C@@H](OC[C@H](C)NC(C)=O)C3)c(F)c2s1] | 4 | 2.13 | 415.0 |
| I-116 | 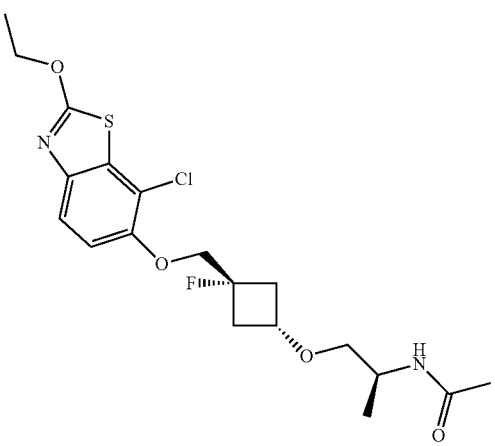 | 4 | 2.25 | 430.9 |
TABLE 18
| | | | | |
|---|---|---|---|---|
| I-117 | 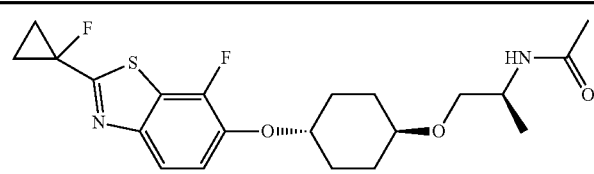 | 2 | 2.31 | 425.2 |
| I-118 | 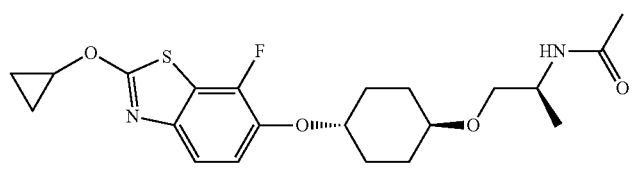 [SMILES: CC(=O)N[C@@H](C)CO[C@H]1CC[C@H](Oc2ccc3nc(OC4CC4)sc3c2F)CC1] | 2 | 2.21 | 423.0 |
| I-119 | 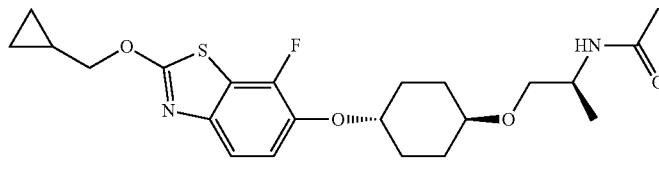 | 2 | 2.46 | 437.1 |

TABLE 18-continued
| | | | | | |
|---|---|---|---|---|---|
| I-120 | 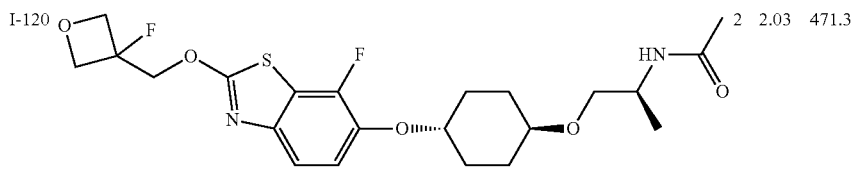 | | 2 | 2.03 | 471.3 |
| I-121 | 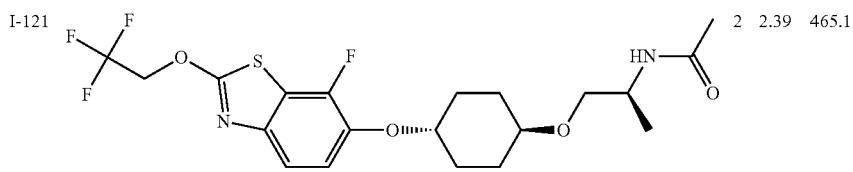 | | 2 | 2.39 | 465.1 |
TABLE 19
| | | | | | |
|---|---|---|---|---|---|
| I-122 | 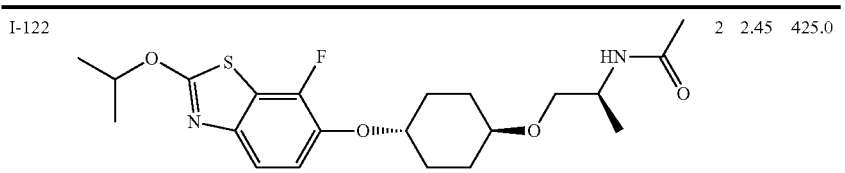 | | 2 | 2.45 | 425.0 |
| I-123 | 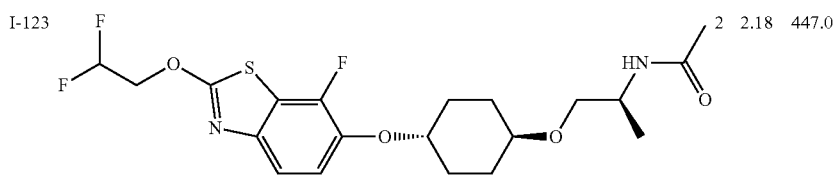 | | 2 | 2.18 | 447.0 |
| I-124 | 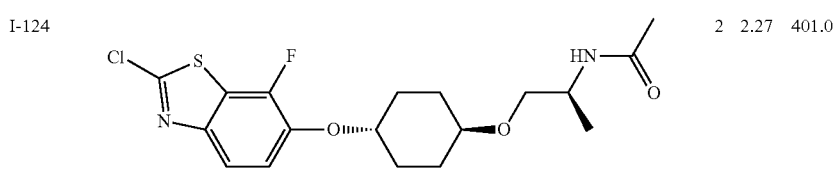 | | 2 | 2.27 | 401.0 |
| I-125 | 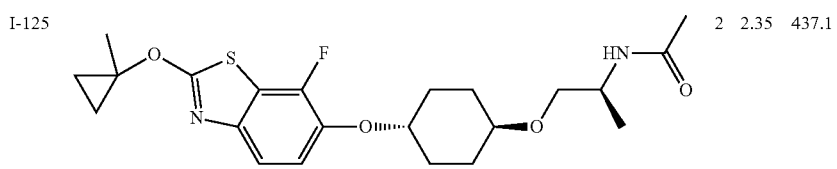 | | 2 | 2.35 | 437.1 |
| I-126 | 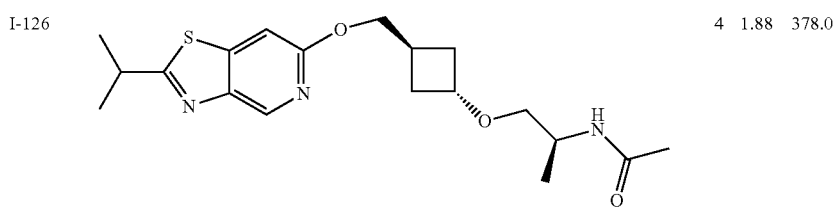 | | 4 | 1.88 | 378.0 |

TABLE 20
| | | | | |
|---|---|---|---|---|
| I-127 | 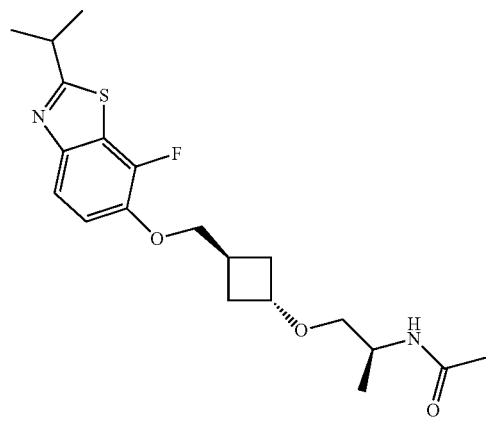 [SMILES: CC(=O)N[C@@H](C)CO[C@H]1C[C@H](COc2ccc3nc(C(C)C)sc3c2F)C1] | 4 | 2.18 | 395.0 |
| I-128 | 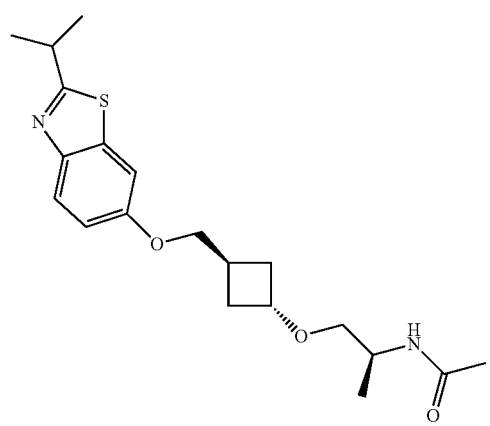 [SMILES: CC(=O)N[C@@H](C)CO[C@H]1C[C@H](COc2ccc3nc(C(C)C)sc3c2)C1] | 4 | 2.02 | 377.0 |
| I-129 | 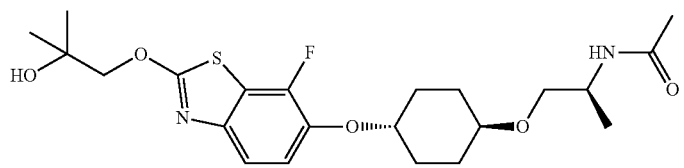 [SMILES: CC(=O)N[C@@H](C)CO[C@H]1CC[C@H](Oc2ccc3nc(OCC(C)(C)O)sc3c2F)CC1] | 2 | 1.87 | 477.3 |
| I-130 | 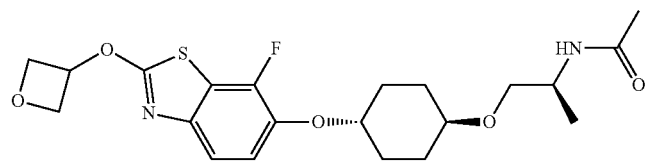 [SMILES: CC(=O)N[C@@H](C)CO[C@H]1CC[C@H](Oc2ccc3nc(OC4COC4)sc3c2F)CC1] | 2 | 1.97 | 439.3 |
| I-131 | 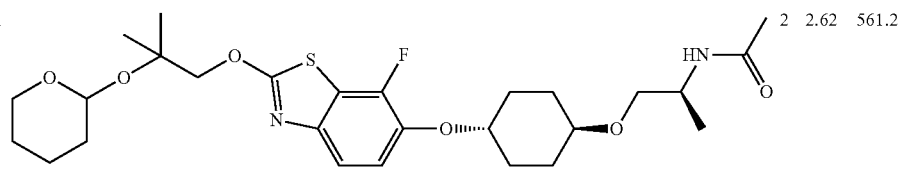 | 2 | 2.62 | 561.2 |

TABLE 21
| | | | | |
|---|---|---|---|---|
| I-132 | 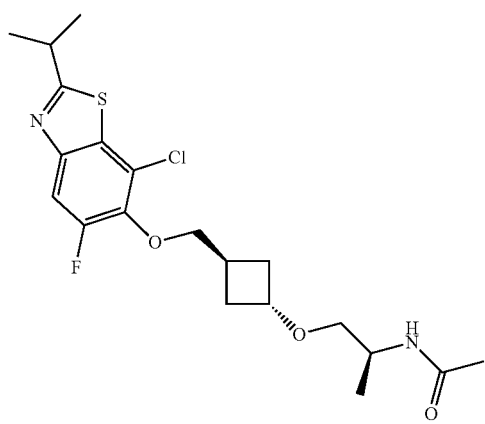 [SMILES: CC(=O)N[C@@H](C)CO[C@H]1C[C@H](COc2c(F)cc3nc(C(C)C)sc3c2Cl)C1] | 4 | 2.58 | 429.6 |
| I-133 | 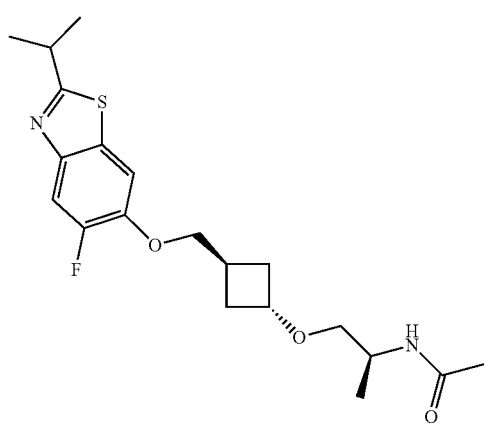 [SMILES: CC(=O)N[C@@H](C)CO[C@H]1C[C@H](COc2cc3sc(C(C)C)nc3cc2F)C1] | 4 | 2.22 | 394.9 |
| I-134 | 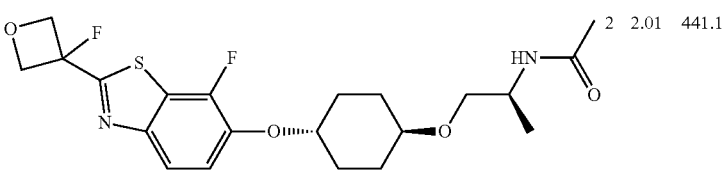 | 2 | 2.01 | 441.1 |
| I-135 | 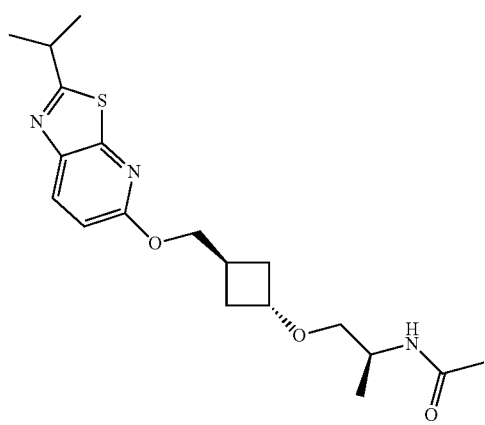 [SMILES: CC(=O)N[C@@H](C)CO[C@H]1C[C@H](COc2ccc3nc(C(C)C)sc3n2)C1] | 4 | 2.01 | 378.4 |

TABLE 21-continued
| | | | | |
|---|---|---|---|---|
| I-136 | 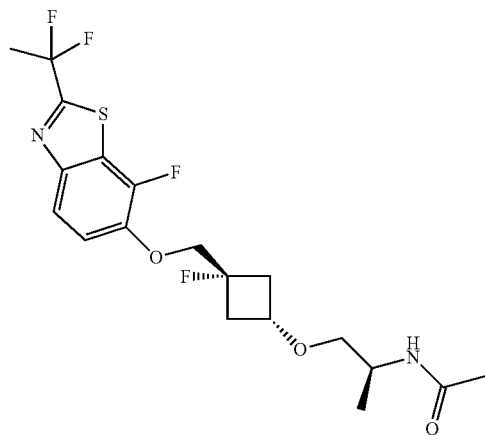 [SMILES: CC(=O)N[C@@H](C)CO[C@H]1C[C@](F)(COc2ccc3nc(C(C)(F)F)sc3c2F)C1] | 4 | 2.18 | 434.9 |
TABLE 22
| | | | | |
|---|---|---|---|---|
| I-137 | 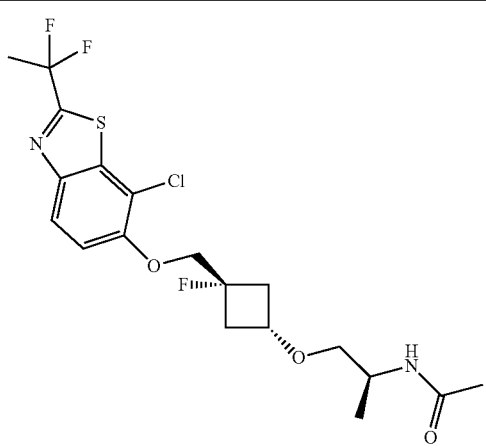 | 4 | 2.30 | 450.9 |
| I-138 | 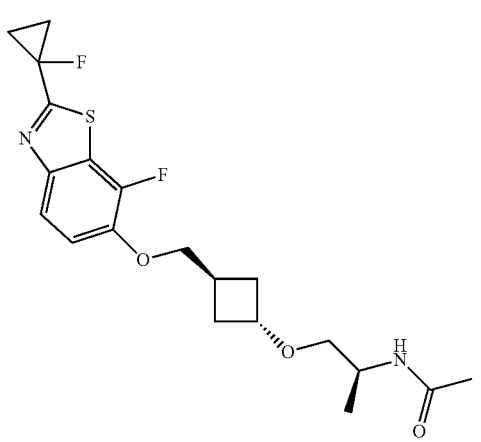 [SMILES: CC(=O)N[C@@H](C)CO[C@H]1C[C@H](COc2ccc3nc(C4(F)CC4)sc3c2F)C1] | 4 | 2.20 | 411.0 |

TABLE 22-continued
| | | | | |
|---|---|---|---|---|
| I-139 | 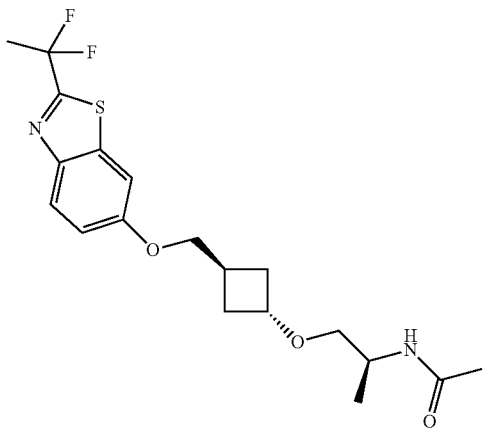 [SMILES: CC(=O)N[C@@H](C)CO[C@H]1C[C@H](COc2ccc3nc(C(C)(F)F)sc3c2)C1] | 4 | 2.09 | 399.0 |
| I-140 | 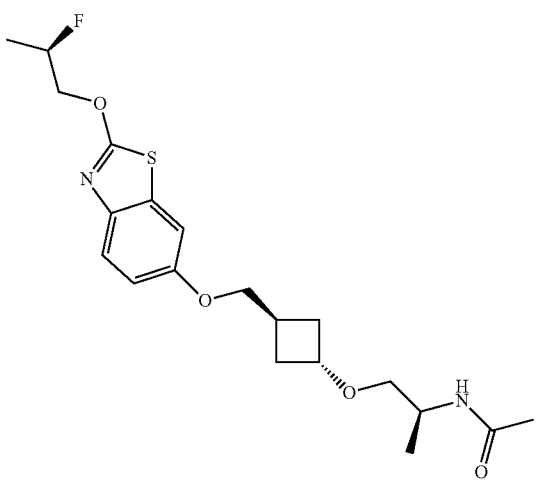 [SMILES: CC(=O)N[C@@H](C)CO[C@H]1C[C@H](COc2ccc3nc(OC[C@@H](C)F)sc3c2)C1] | 4 | 2.01 | 411.0 |
| I-141 | 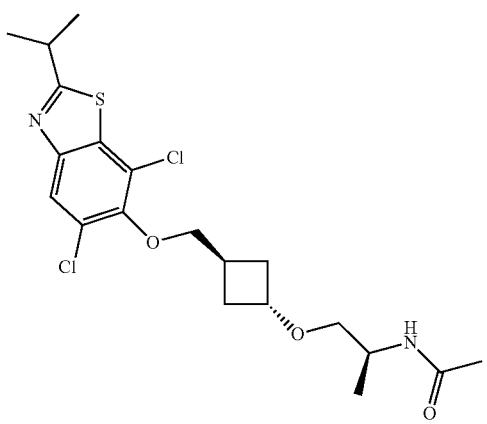 [SMILES: CC(=O)N[C@@H](C)CO[C@H]1C[C@H](COc2c(Cl)cc3nc(C(C)C)sc3c2Cl)C1] | 4 | 2.67 | 445.0 |

TABLE 23

| ID | Structure | a | b | c |
|---|---|---|---|---|
| I-142 | 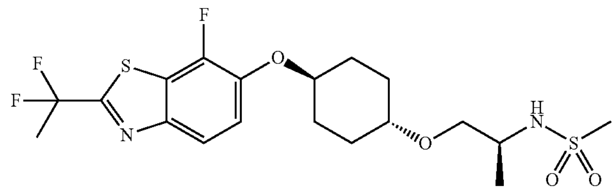 [SMILES: C[C@@H](CO[C@H]1CC[C@H](Oc2ccc3nc(C(C)(F)F)sc3c2F)CC1)NS(C)(=O)=O] | 2 | 2.47 | 467.1 |
| I-143 | 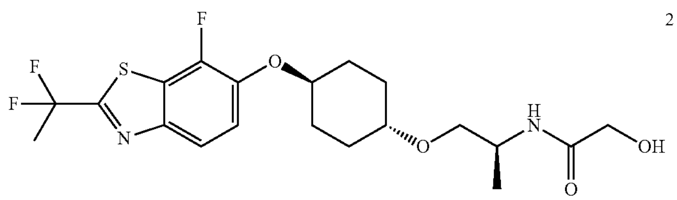 | 2 | 2.19 | 447.3 |
| I-144 | 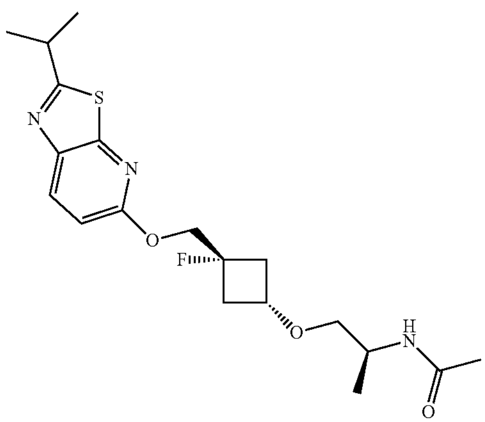 [SMILES: CC(=O)N[C@@H](C)CO[C@H]1C[C@](F)(COc2ccc3nc(C(C)C)sc3n2)C1] | 4 | 1.98 | 395.9 |
| I-145 | 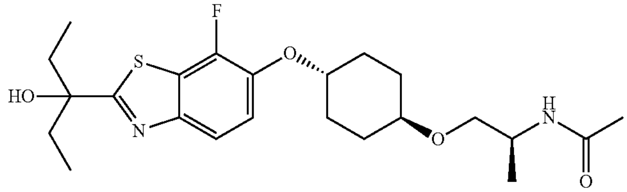 [SMILES: CCC(O)(CC)c1nc2ccc(O[C@H]3CC[C@H](OC[C@H](C)NC(C)=O)CC3)c(F)c2s1] | 4 | 2.00 | 453.6 |
| I-146 | 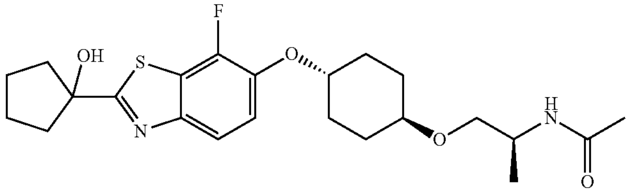 [SMILES: CC(=O)N[C@@H](C)CO[C@H]1CC[C@H](Oc2ccc3nc(C4(O)CCCC4)sc3c2F)CC1] | 4 | 20.10 | 452.2 |

TABLE 24
| | | | | |
|---|---|---|---|---|
| I-147 | 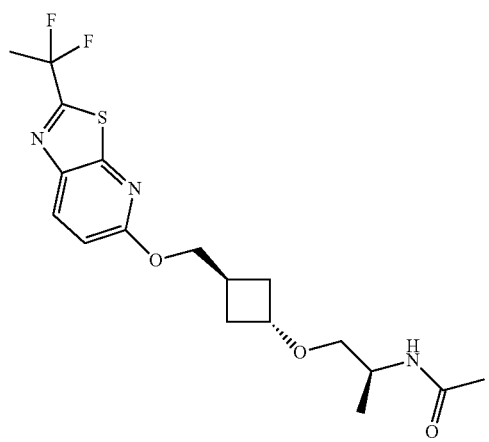 [SMILES: CC(=O)N[C@@H](C)CO[C@H]1C[C@H](COc2ccc3nc(C(C)(F)F)sc3n2)C1] | 4 | 2.16 | 400.0 |
| I-148 | 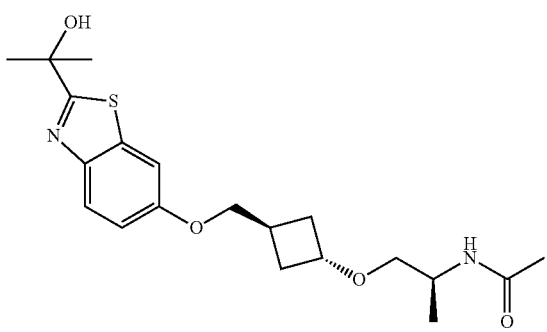 [SMILES: CC(=O)N[C@@H](C)CO[C@H]1C[C@H](COc2ccc3nc(C(C)(C)O)sc3c2)C1] | 2 | 1.54 | 393.1 |
| I-149 | 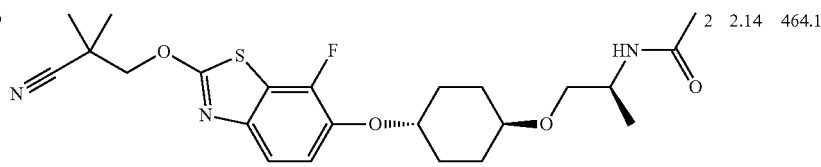 | 2 | 2.14 | 464.1 |
| I-150 | 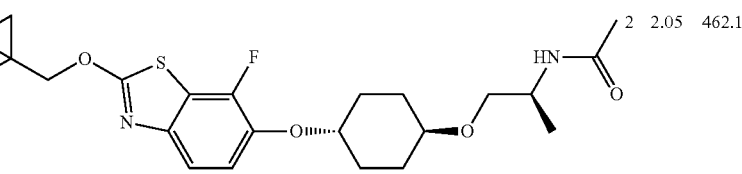 | 2 | 2.05 | 462.1 |
| I-151 | 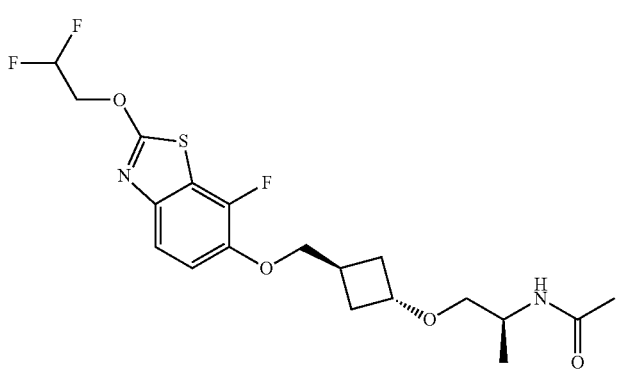 [SMILES: CC(=O)N[C@@H](C)CO[C@H]1C[C@H](COc2ccc3nc(OCC(F)F)sc3c2F)C1] | 4 | 2.17 | 433.0 |

TABLE 25
I-152 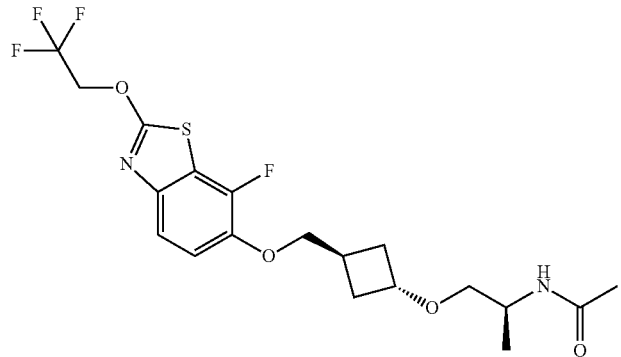 [SMILES: CC(=O)N[C@@H](C)CO[C@H]1C[C@H](COc2ccc3nc(OCC(F)(F)F)sc3c2F)C1] 4 2.38 451.0
I-153 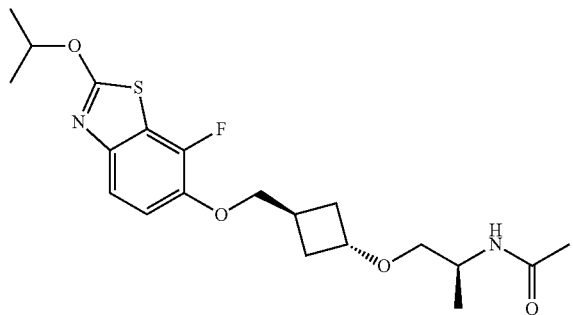 [SMILES: CC(=O)N[C@@H](C)CO[C@H]1C[C@H](COc2ccc3nc(OC(C)C)sc3c2F)C1] 4 2.43 411.0
I-154 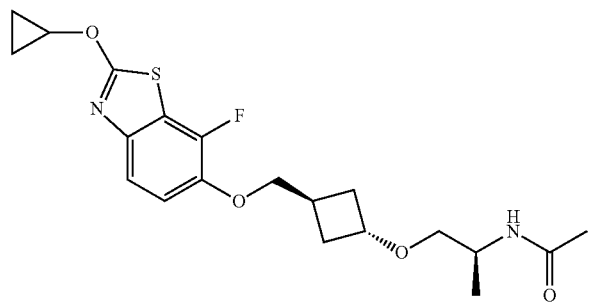 [SMILES: CC(=O)N[C@@H](C)CO[C@H]1C[C@H](COc2ccc3nc(OC4CC4)sc3c2F)C1] 4 2.17 409.0
I-155 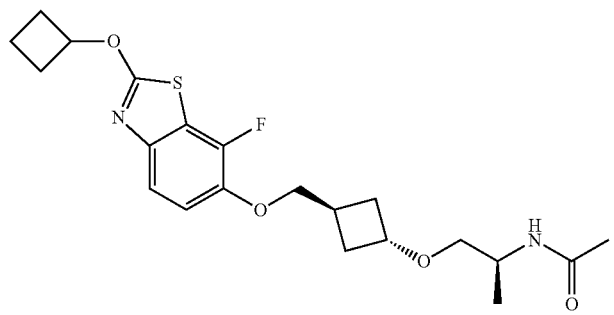 [SMILES: CC(=O)N[C@@H](C)CO[C@H]1C[C@H](COc2ccc3nc(OC4CCC4)sc3c2F)C1] 4 2.54 423.0

TABLE 25-continued

| I-156 | [structure] | 4 | 2.46 | 423.0 |

TABLE 26

| I-157 | [structure] | 4 | 2.02 | 380.0 |
| I-158 | [structure] | 2 | 2.15 | 432.1 |
| I-159 | [structure] | 2 | 1.62 | 411.0 |
| I-160 | [structure] | 4 | 1.64 | 429.0 |

TABLE 26-continued
| I-161 | 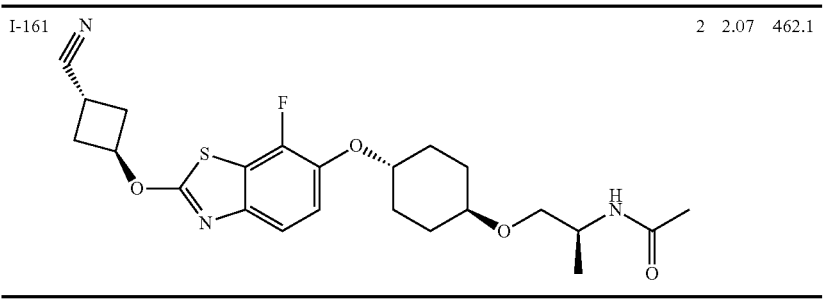 | 2 | 2.07 | 462.1 |
TABLE 27
| I-162 | 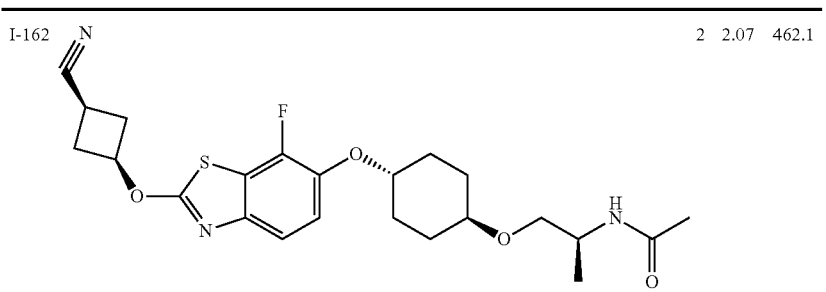 | 2 | 2.07 | 462.1 |
| I-163 | 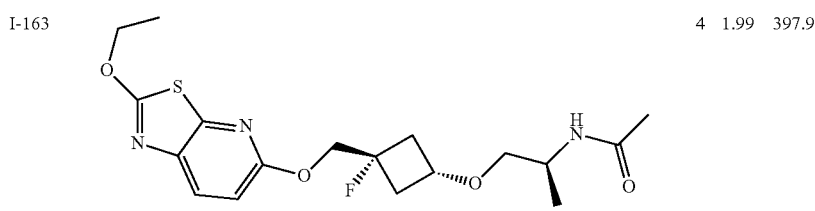 | 4 | 1.99 | 397.9 |
| I-164 | 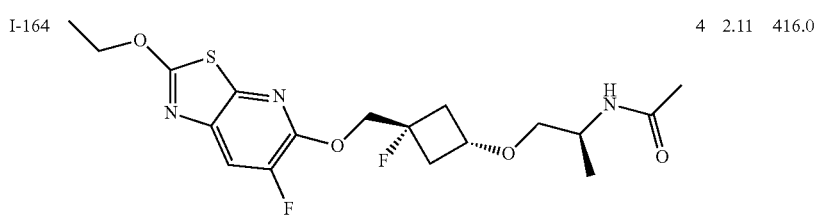 | 4 | 2.11 | 416.0 |
| I-165 | 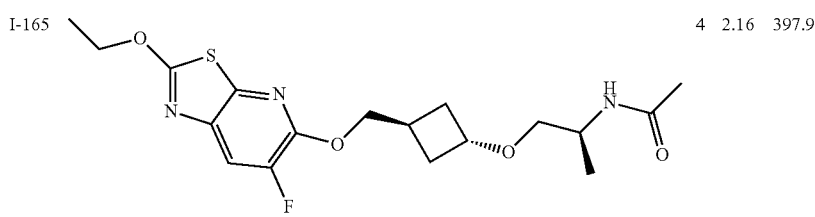 | 4 | 2.16 | 397.9 |

TABLE 27-continued
| | | | | |
|---|---|---|---|---|
| I-166 | 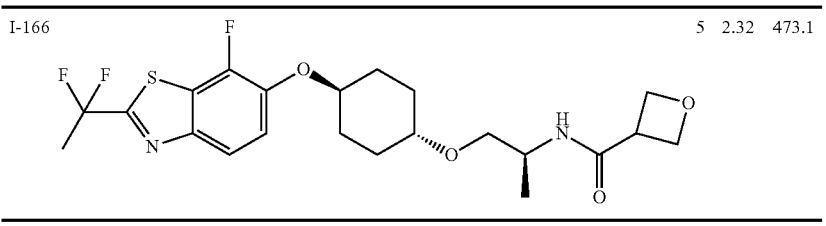 | 5 | 2.32 | 473.1 |
TABLE 28
| | | | | |
|---|---|---|---|---|
| I-167 | 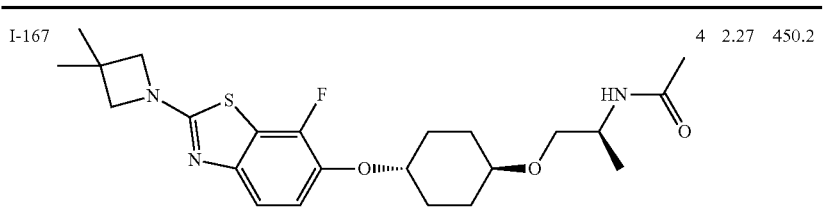 | 4 | 2.27 | 450.2 |
| I-168 | 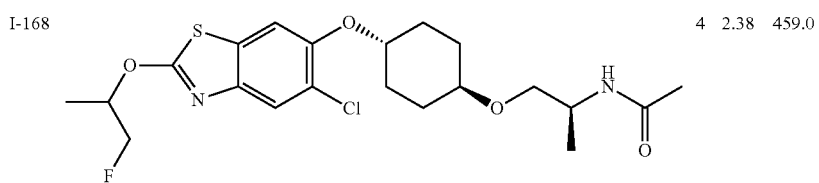 | 4 | 2.38 | 459.0 |
| I-169 | 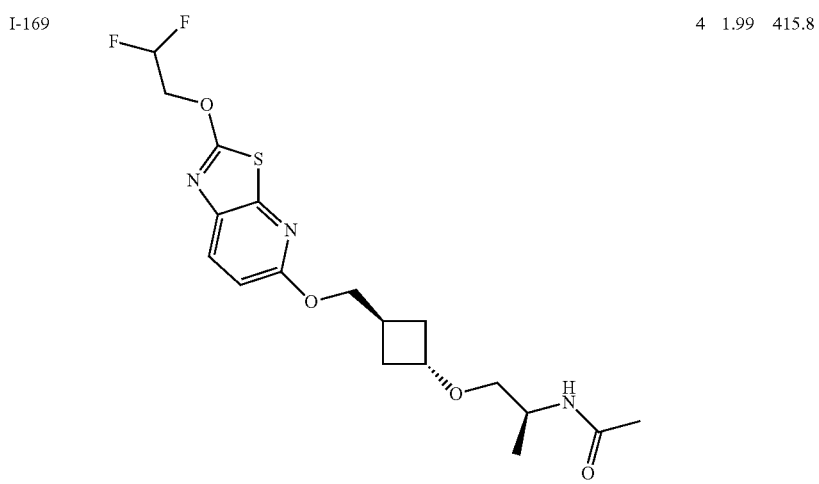 | 4 | 1.99 | 415.8 |

TABLE 28-continued
| | | | | |
|---|---|---|---|---|
| I-170 | 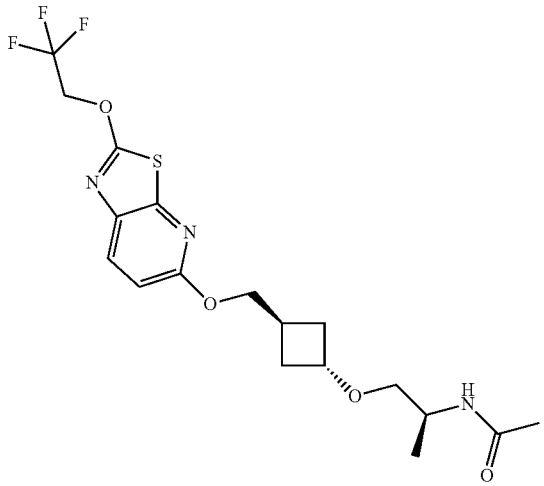 [SMILES: CC(=O)N[C@@H](C)CO[C@H]1C[C@H](COc2ccc3nc(OCC(F)(F)F)sc3n2)C1] | 4 | 2.21 | 433.9 |
| I-171 | 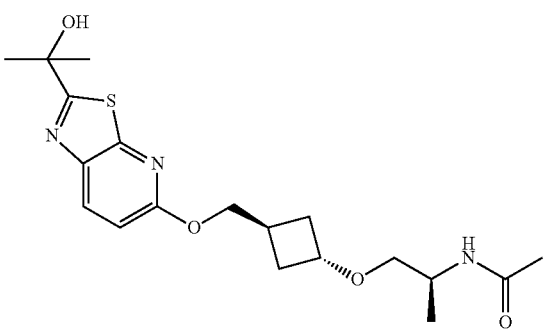 | 2 | 1.52 | 394.1 |
TABLE 29
| | | | | |
|---|---|---|---|---|
| I-172 | 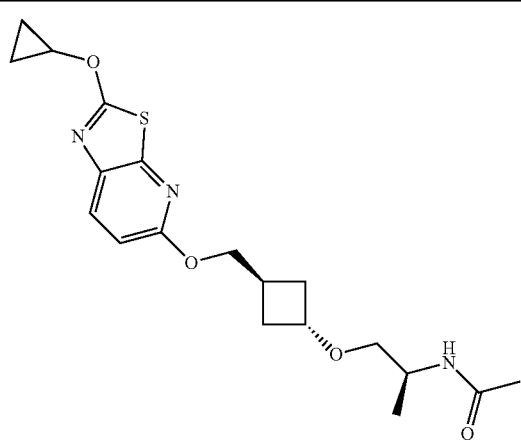 | 4 | 1.95 | 391.9 |

TABLE 29-continued
| | | | | |
|---|---|---|---|---|
| I-173 | 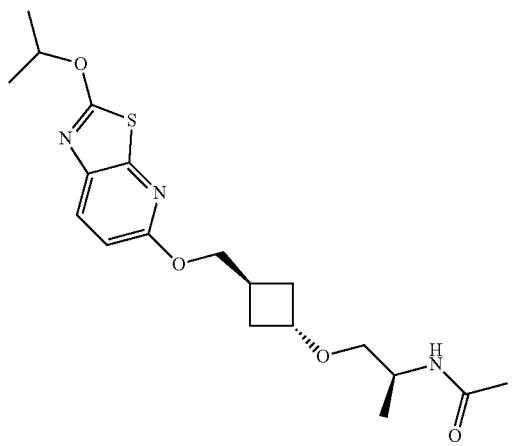 [SMILES: CC(=O)N[C@@H](C)CO[C@H]1C[C@H](COc2ccc3nc(OC(C)C)sc3n2)C1] | 4 | 2.21 | 393.9 |
| I-174 | 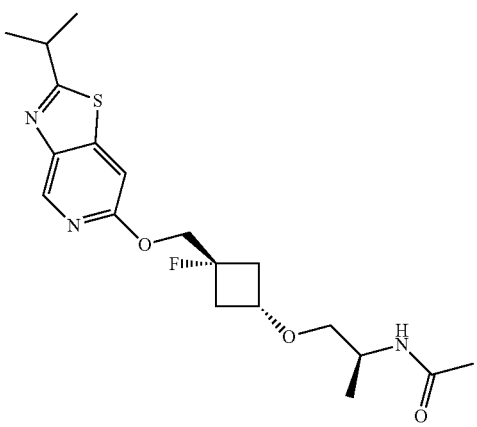 [SMILES: CC(=O)N[C@@H](C)CO[C@H]1C[C@](F)(COc2cc3sc(C(C)C)nc3cn2)C1] | 4 | 1.89 | 396.3 |
| I-175 | 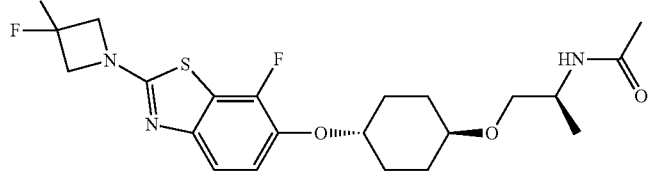 | 2 | 2.02 | 458.1 |
| I-176 | 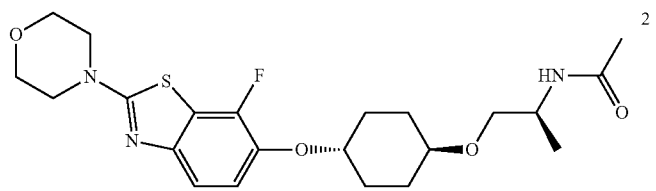 | 2 | 1.85 | 452.1 |
TABLE 30
| | | | | |
|---|---|---|---|---|
| I-177 | 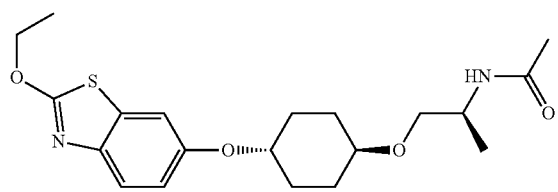 [SMILES: CCOc1nc2ccc(O[C@H]3CC[C@H](OC[C@H](C)NC(C)=O)CC3)cc2s1] | 2 | 2.20 | 393.2 |

TABLE 30-continued
| | | | | |
|---|---|---|---|---|
| I-178 | 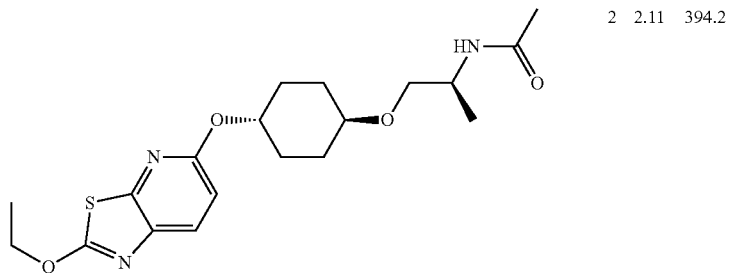 | 2 | 2.11 | 394.2 |
| I-179 | 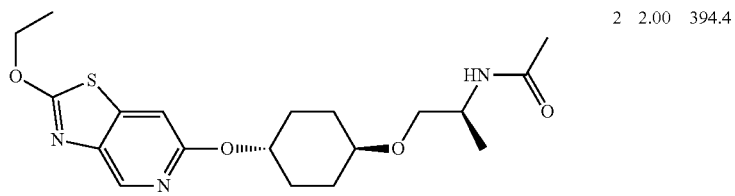 | 2 | 2.00 | 394.4 |
| I-180 | 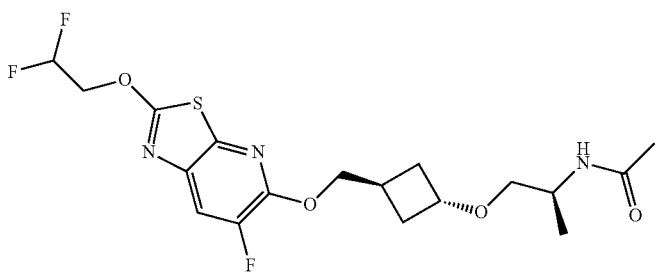 [SMILES: CC(=O)N[C@@H](C)CO[C@H]1C[C@H](COc2nc3sc(OCC(F)F)nc3cc2F)C1] | 4 | 2.09 | 433.9 |
| I-181 | 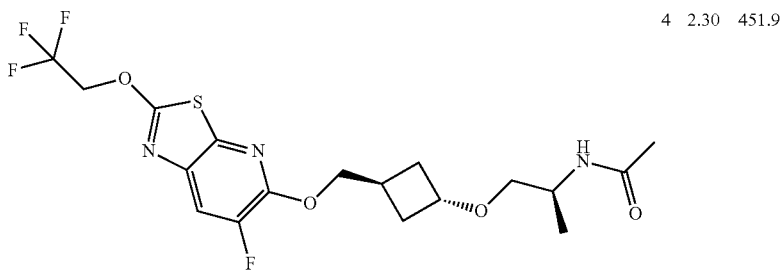 | 4 | 2.30 | 451.9 |
TABLE 31
| | | | | |
|---|---|---|---|---|
| I-182 | 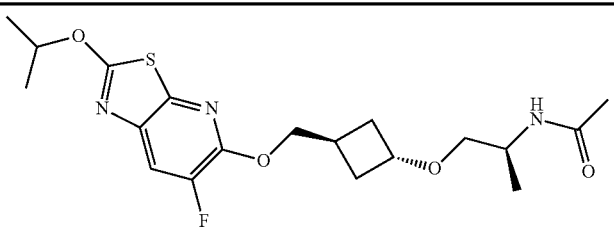 | 4 | 2.35 | 412.0 |
| I-183 | 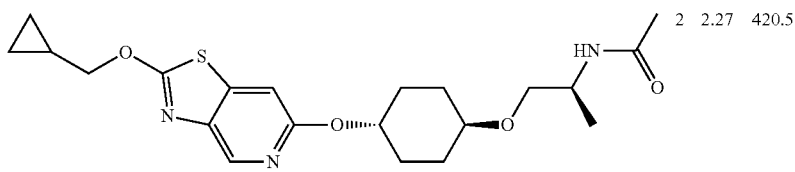 | 2 | 2.27 | 420.5 |

TABLE 31-continued
| | | | | |
|---|---|---|---|---|
| I-184 | 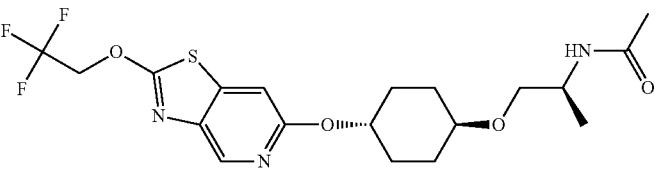 [SMILES: CC(=O)N[C@@H](C)CO[C@H]1CC[C@H](Oc2cc3sc(OCC(F)(F)F)nc3cn2)CC1] | 2 | 2.14 | 448.5 |
| I-185 | 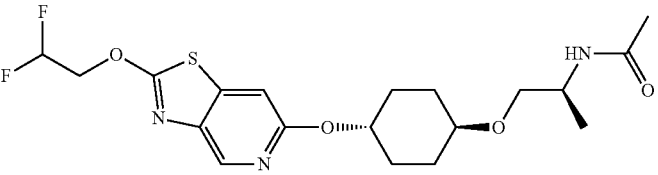 [SMILES: CC(=O)N[C@@H](C)CO[C@H]1CC[C@H](Oc2cc3sc(OCC(F)F)nc3cn2)CC1] | 2 | 1.95 | 430.4 |
| I-186 | 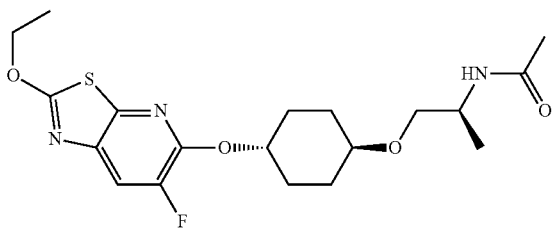 [SMILES: CCOc1nc2cc(F)c(O[C@H]3CC[C@H](OC[C@H](C)NC(C)=O)CC3)nc2s1] | 2 | 2.22 | 412.3 |
TABLE 32
| | | | | |
|---|---|---|---|---|
| I-187 | 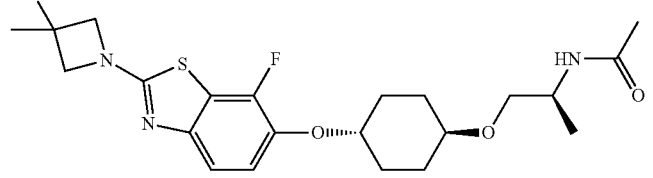 | 4 | 1.62 | 452.1 |
| I-188 | 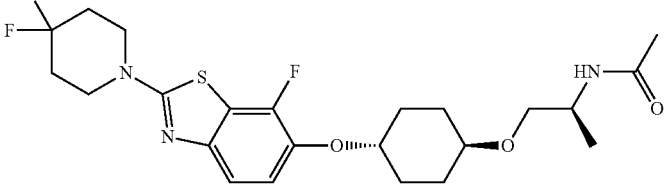 | 4 | 2.23 | 486.1 |
| I-189 | 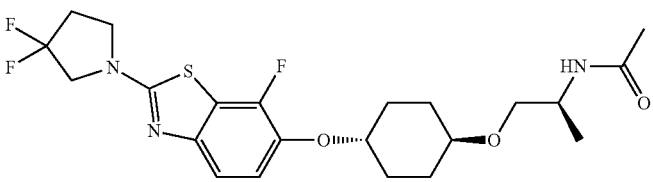 [SMILES: CC(=O)N[C@@H](C)CO[C@H]1CC[C@H](Oc2ccc3nc(N4CCC(F)(F)C4)sc3c2F)CC1] | 4 | 2.08 | 472.1 |
| I-190 | 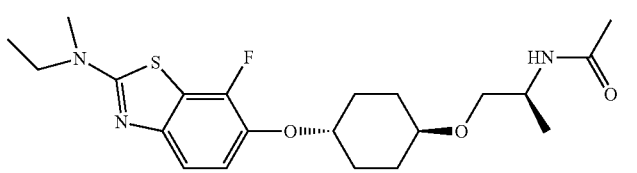 [SMILES: CCN(C)c1nc2ccc(O[C@H]3CC[C@H](OC[C@H](C)NC(C)=O)CC3)c(F)c2s1] | 4 | 2.05 | 424.2 |

TABLE 32-continued
| I-191 | 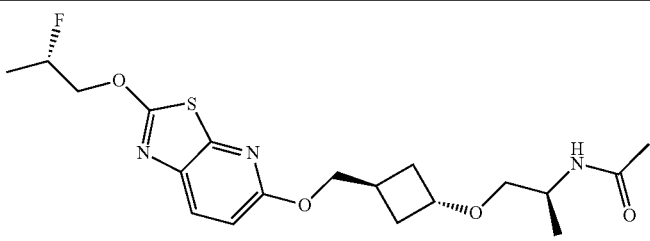 | 4 | 2.00 | 412.0 |
TABLE 33
| I-192 | 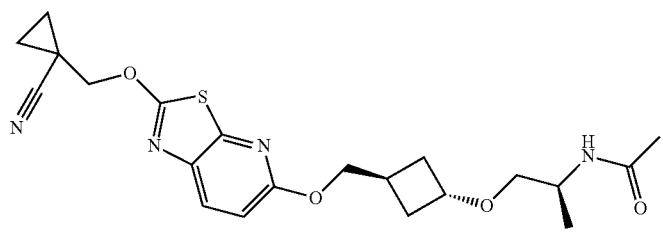 [SMILES: CC(=O)N[C@@H](C)CO[C@H]1C[C@H](COc2ccc3nc(OCC4(C#N)CC4)sc3n2)C1] | 4 | 1.87 | 431.0 |
| I-193 | 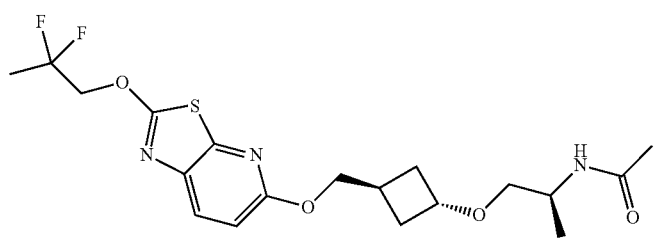 [SMILES: CC(=O)N[C@@H](C)CO[C@H]1C[C@H](COc2ccc3nc(OCC(C)(F)F)sc3n2)C1] | 4 | 2.13 | 429.9 |
| I-194 | 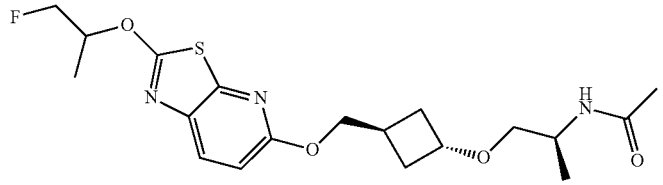 [SMILES: CC(=O)N[C@@H](C)CO[C@H]1C[C@H](COc2ccc3nc(OC(C)CF)sc3n2)C1] | 4 | 2.02 | 412.0 |
| I-195 | 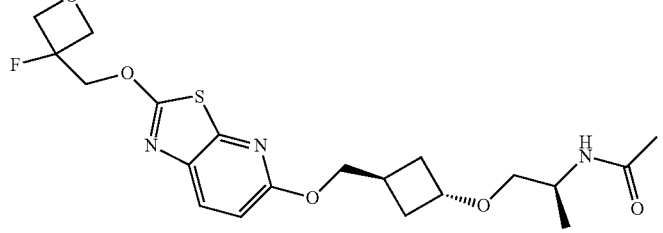 | 4 | 1.80 | 439.9 |
| I-196 | 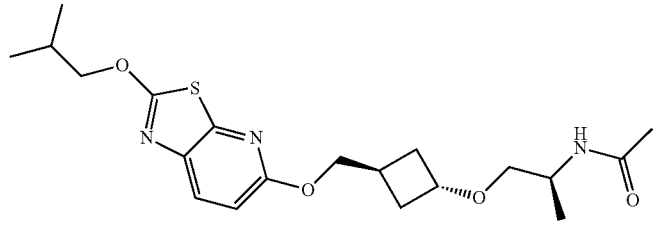 [SMILES: CC(=O)N[C@@H](C)CO[C@H]1C[C@H](COc2ccc3nc(OCC(C)C)sc3n2)C1] | 4 | 2.39 | 408.0 |

TABLE 34

| | | | | |
|---|---|---|---|---|
| I-197 | [structure] | 4 | 2.10 | 442.0 |
| I-198 | [structure] | 4 | 2.38 | 420.0 |
| I-199 | [structure] | 4 | 1.61 | 422.0 |
| I-200 | [structure] | 4 | 2.05 | 406.0 |
| I-201 | [structure] | 4 | 2.14 | 424.0 |

TABLE 35

| | | | | |
|---|---|---|---|---|
| I-202 | [structure] | 4 | 1.93 | 430.0 |

TABLE 35-continued

| ID | Structure | | | |
|---|---|---|---|---|
| I-203 | (structure) | 4 | 2.03 | 448.0 |
| I-204 | (structure) | 4 | 2.18 | 464.0 |
| I-205 | (structure) | 4 | 1.87 | 417.6 |
| I-206 | (structure) | 4 | 1.89 | 432.2 |

TABLE 36

| ID | Structure | | | |
|---|---|---|---|---|
| I-207 | (structure) | 4 | 2.50 | 469.9 |
| I-208 | (structure) | 2 | 1.89 | 441.2 |

TABLE 36-continued
| | | | | |
|---|---|---|---|---|
| I-209 | 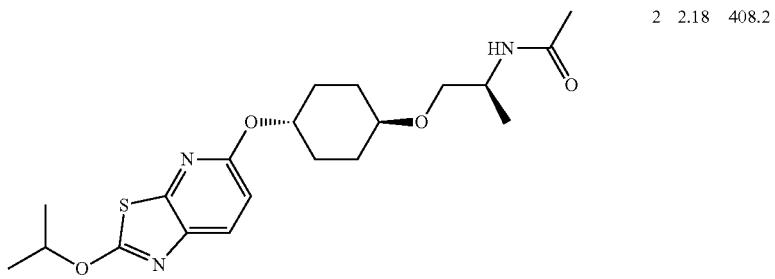 | 2 | 2.18 | 408.2 |
| I-210 | 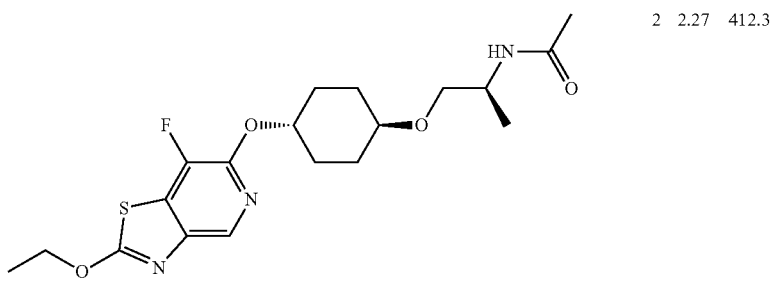 | 2 | 2.27 | 412.3 |
| I-211 | 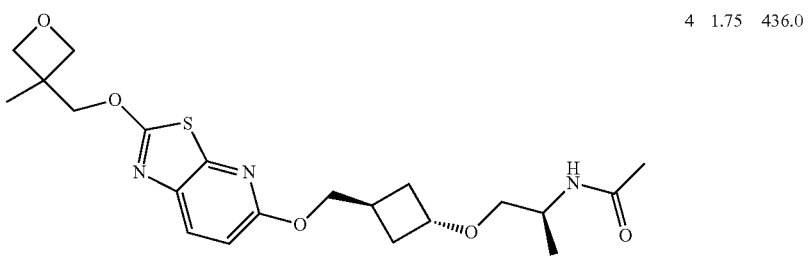 | 4 | 1.75 | 436.0 |
TABLE 37
| | | | | |
|---|---|---|---|---|
| I-212 | 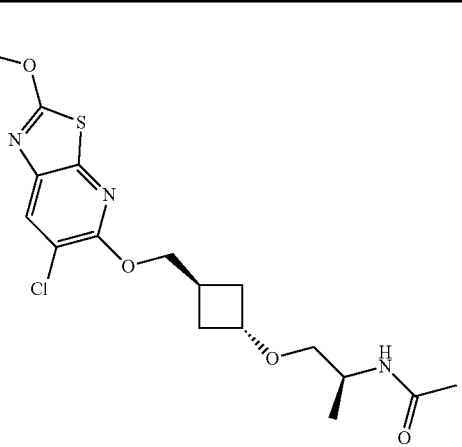 | 4 | 2.36 | 414.0 |

TABLE 37-continued
| I-213 | 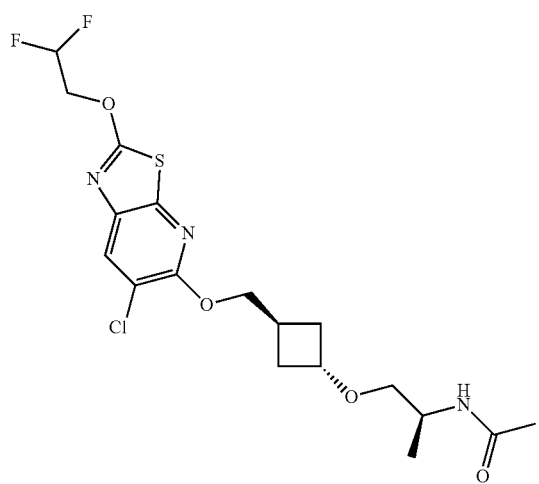 [SMILES: CC(=O)N[C@@H](C)CO[C@H]1C[C@H](COc2nc3sc(OCC(F)F)nc3cc2Cl)C1] | 4 | 2.23 | 449.9 |
| I-214 | 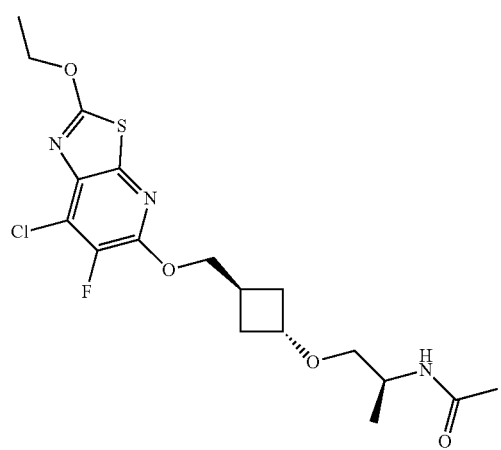 [SMILES: CCOc1nc2c(Cl)c(F)c(OC[C@H]3C[C@H](OC[C@H](C)NC(C)=O)C3)nc2s1] | 4 | 2.38 | 432.0 |
| I-215 | 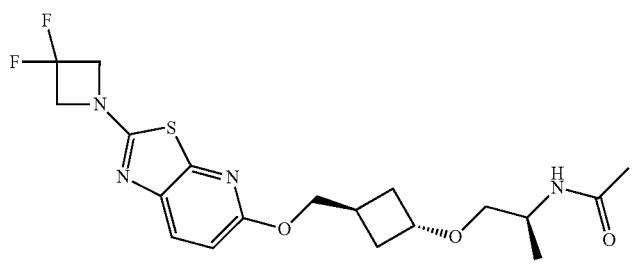 [SMILES: CC(=O)N[C@@H](C)CO[C@H]1C[C@H](COc2ccc3nc(N4CC(F)(F)C4)sc3n2)C1] | 4 | 1.80 | 427.6 |

TABLE 37-continued
| I-216 | 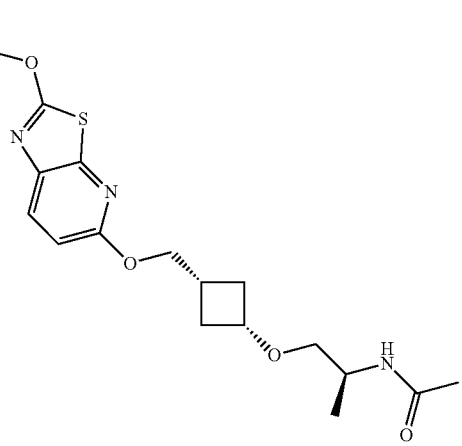 | 4 | 2.00 | 380.0 |
TABLE 38
| I-217 | 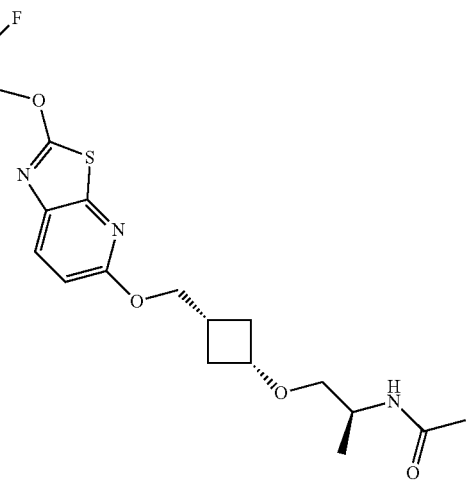 | 4 | 1.98 | 416.0 |
| I-218 | 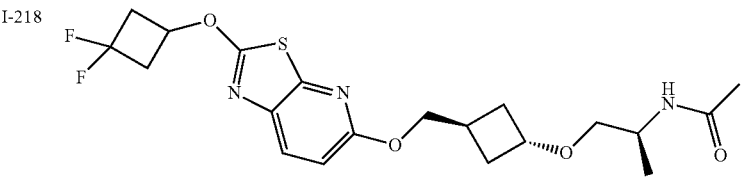 | 4 | 2.20 | 442.0 |
| I-219 | 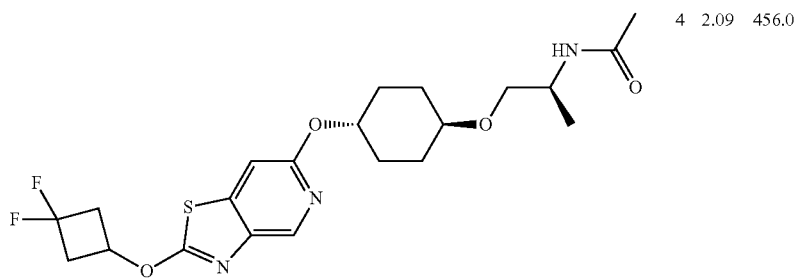 | 4 | 2.09 | 456.0 |

TABLE 38-continued
| | | | | |
|---|---|---|---|---|
| I-220 | 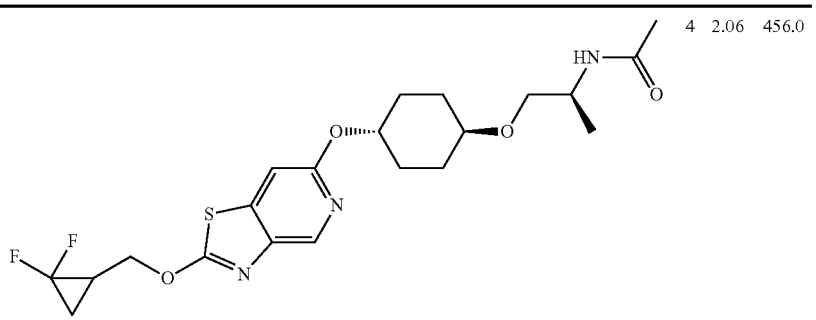 | 4 | 2.06 | 456.0 |
| I-221 | 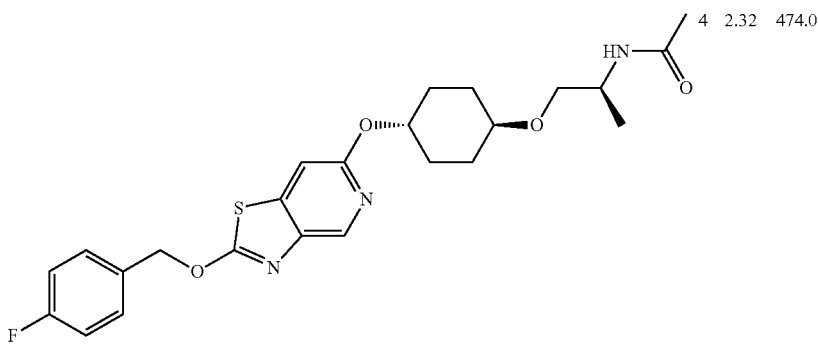 | 4 | 2.32 | 474.0 |
TABLE 39
| | | | | |
|---|---|---|---|---|
| I-222 | 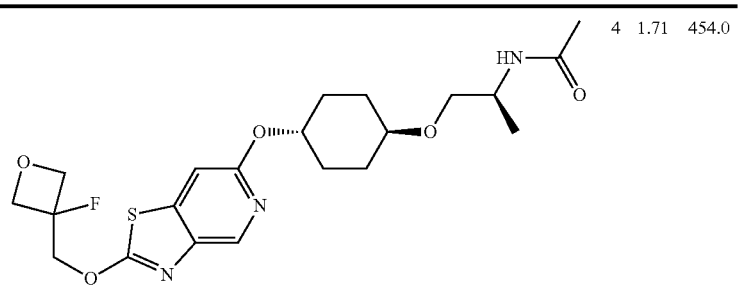 | 4 | 1.71 | 454.0 |
| I-223 | 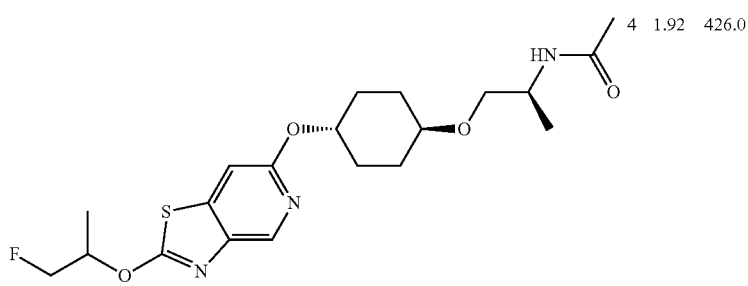 | 4 | 1.92 | 426.0 |
| I-224 | 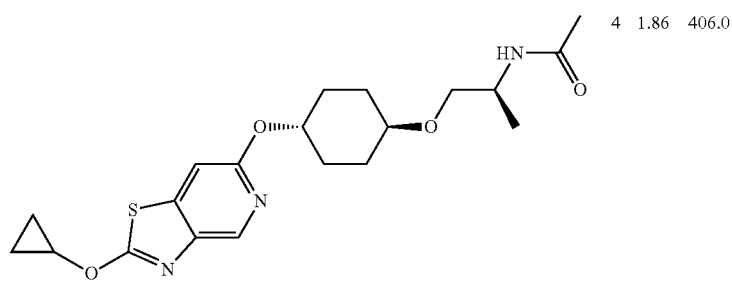 | 4 | 1.86 | 406.0 |

TABLE 39-continued
I-225 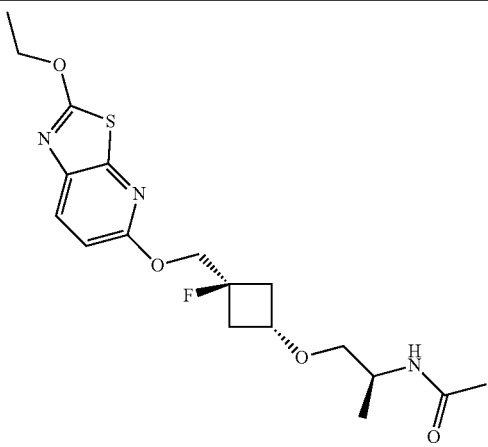 4 1.97 398.0
I-226 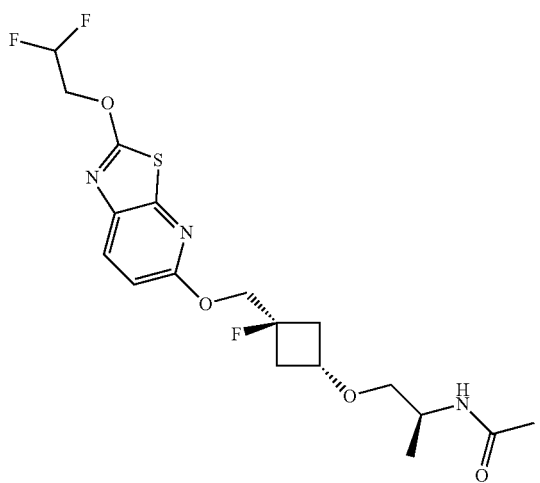 [SMILES: CC(=O)N[C@@H](C)CO[C@H]1C[C@@](F)(COc2ccc3nc(OCC(F)F)sc3n2)C1] 4 1.97 433.9
TABLE 40
I-227 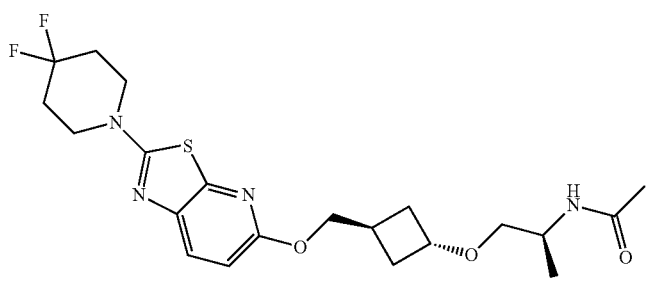 [SMILES: CC(=O)N[C@@H](C)CO[C@H]1C[C@H](COc2ccc3nc(N4CCC(F)(F)CC4)sc3n2)C1] 4 1.95 455.0
I-228 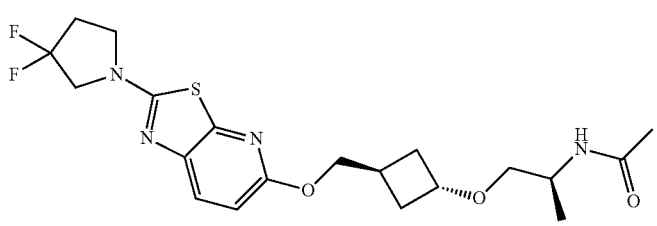 [SMILES: CC(=O)N[C@@H](C)CO[C@H]1C[C@H](COc2ccc3nc(N4CCC(F)(F)C4)sc3n2)C1] 4 1.78 441.0

TABLE 40-continued
| ID | Structure | | | |
|---|---|---|---|---|
| I-229 | 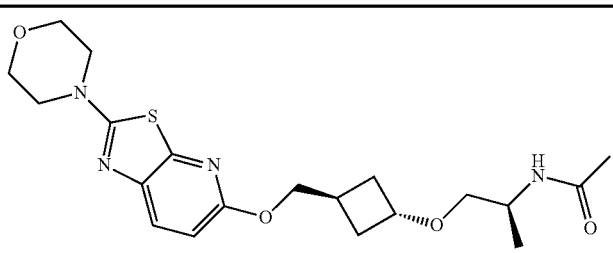 | 4 | 1.52 | 421.0 |
| I-230 | 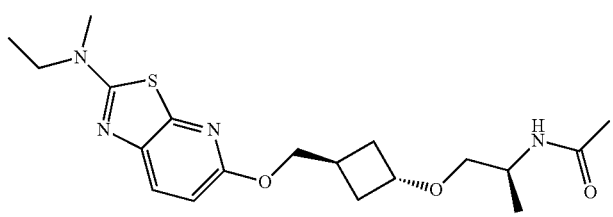 [SMILES: CCN(C)c1nc2ccc(OC[C@H]3C[C@H](OC[C@H](C)NC(C)=O)C3)nc2s1] | 4 | 1.62 | 393.0 |
| I-231 | 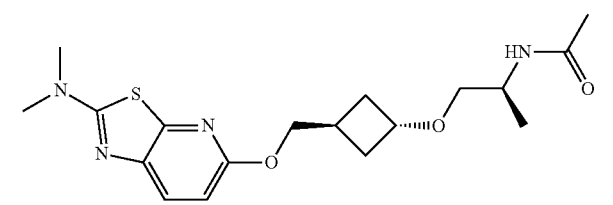 [SMILES: CC(=O)N[C@@H](C)CO[C@H]1C[C@H](COc2ccc3nc(N(C)C)sc3n2)C1] | 4 | 1.45 | 379.0 |
TABLE 41
| ID | Structure | | | |
|---|---|---|---|---|
| I-232 | 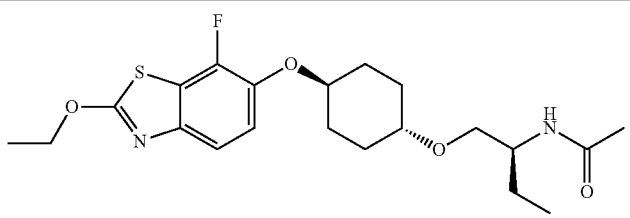 [SMILES: CCOc1nc2ccc(O[C@H]3CC[C@H](OC[C@H](CC)NC(C)=O)CC3)c(F)c2s1] | 4 | 2.35 | 425.3 |
| I-233 | 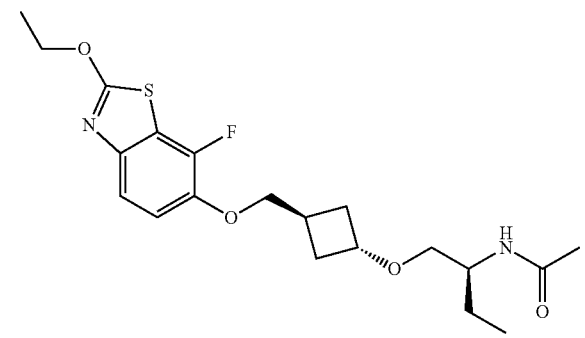 [SMILES: CCOc1nc2ccc(OC[C@H]3C[C@H](OC[C@H](CC)NC(C)=O)C3)c(F)c2s1] | 4 | 2.31 | 412.2 |

TABLE 41-continued
I-234 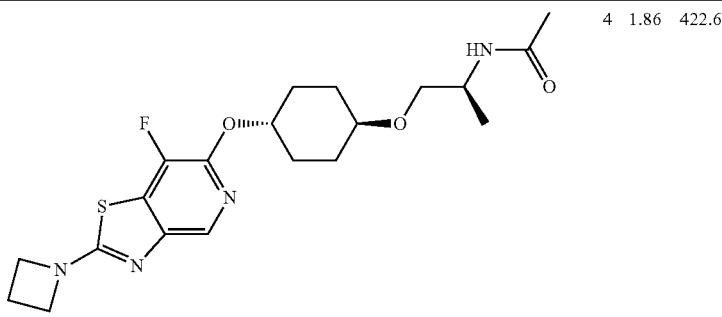 4 1.86 422.6
I-235 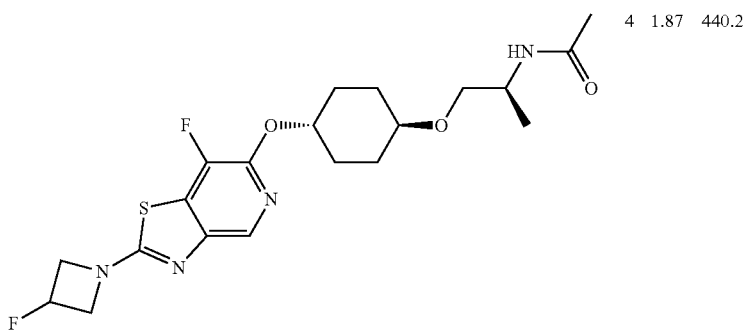 4 1.87 440.2
I-236 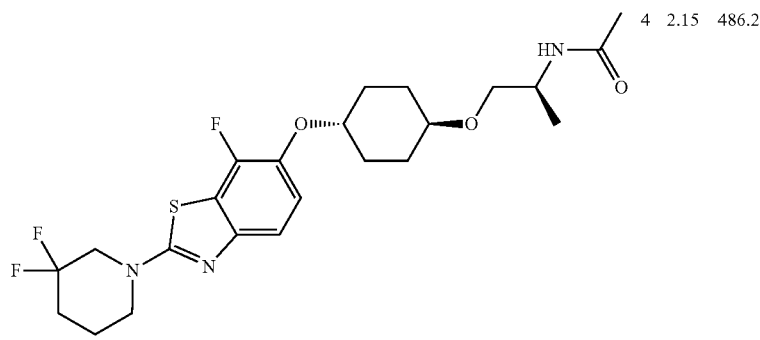 4 2.15 486.2
TABLE 42
I-237 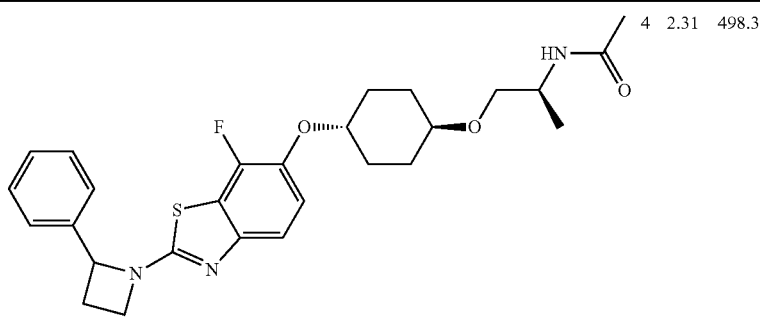 4 2.31 498.3

TABLE 42-continued
| I-238 | 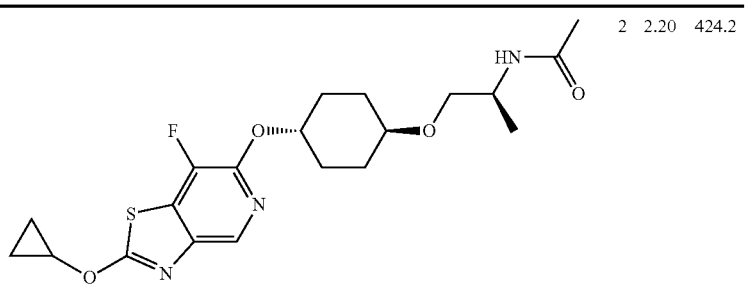 | 2 | 2.20 | 424.2 |
| I-239 | 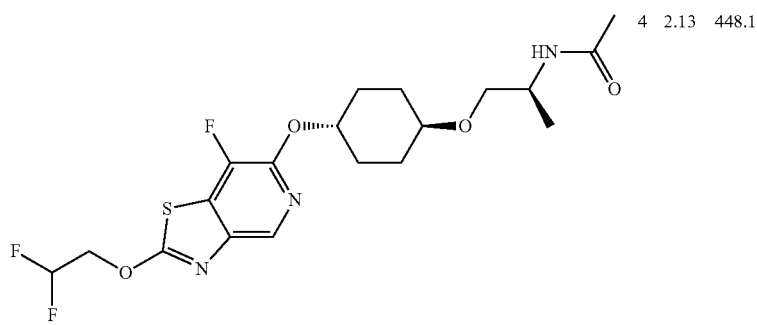 | 4 | 2.13 | 448.1 |
| I-240 | 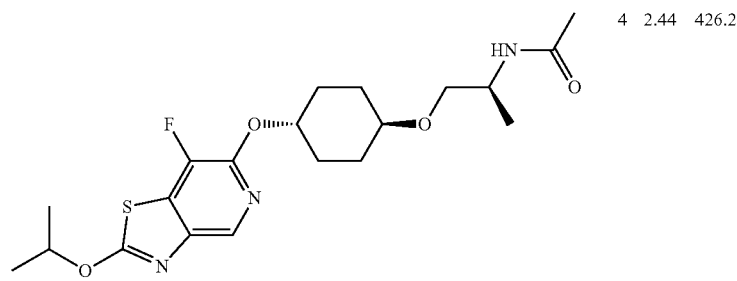 | 4 | 2.44 | 426.2 |
| I-241 | 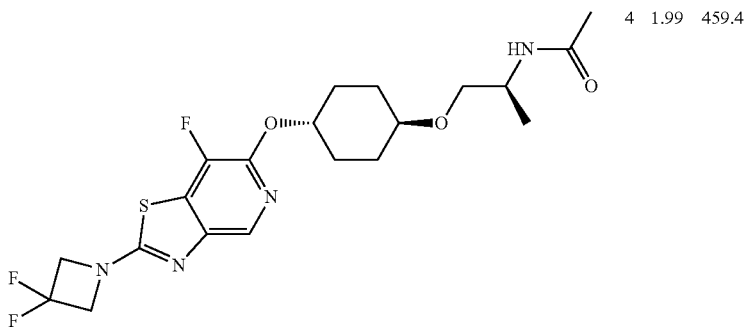 | 4 | 1.99 | 459.4 |
TABLE 43
| I-242 | 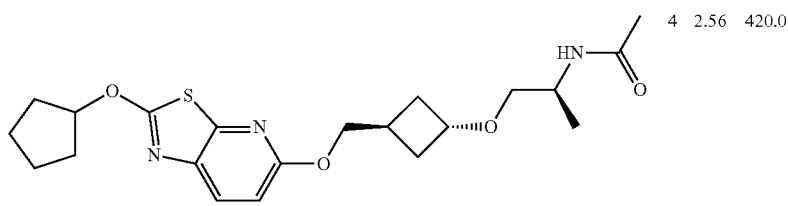 | 4 | 2.56 | 420.0 |

TABLE 43-continued
| | | | | |
|---|---|---|---|---|
| I-243 | 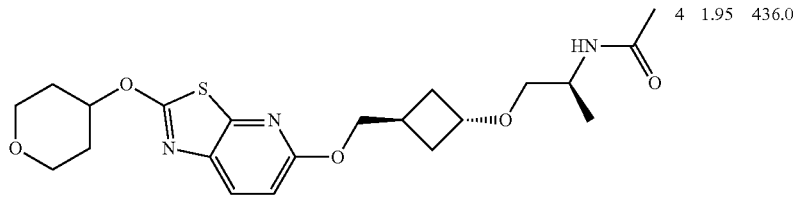 | 4 | 1.95 | 436.0 |
| I-244 | 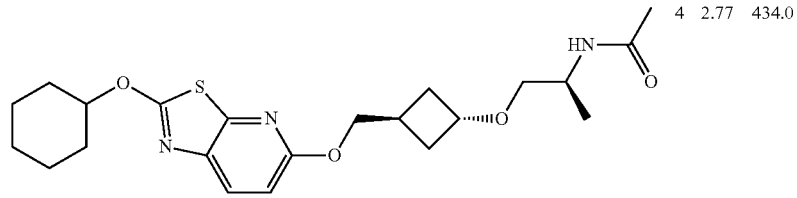 | 4 | 2.77 | 434.0 |
| I-245 | 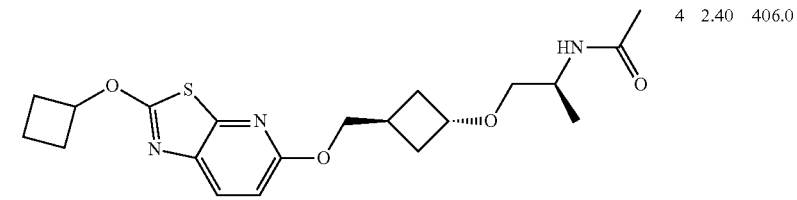 | 4 | 2.40 | 406.0 |
| I-246 | 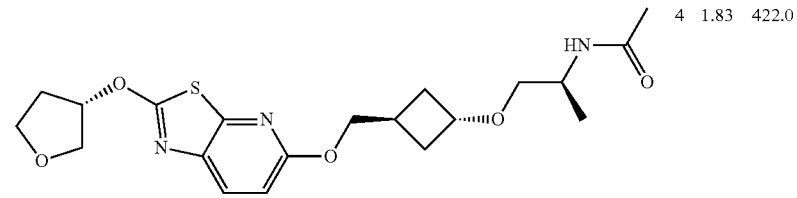 | 4 | 1.83 | 422.0 |
TABLE 44
| | | | | |
|---|---|---|---|---|
| I-247 | 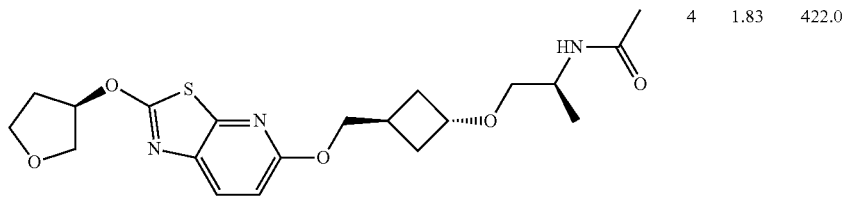 | 4 | 1.83 | 422.0 |
| I-248 | 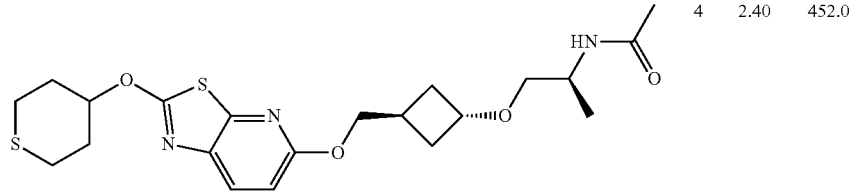 | 4 | 2.40 | 452.0 |
| I-249 | 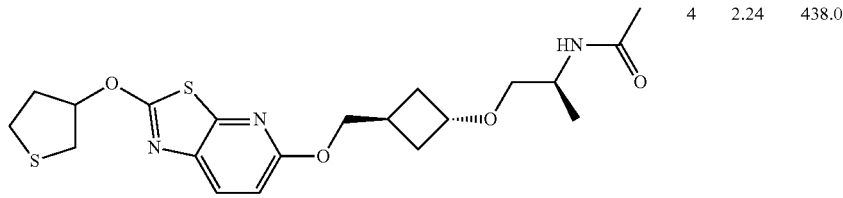 | 4 | 2.24 | 438.0 |

TABLE 44-continued

| ID | Structure | | | |
|---|---|---|---|---|
| I-250 | (structure) | 4 | 1.87 | 366.0 |
| I-251 | (structure) | 4 | 1.77 | 426.9 |

TABLE 45

| ID | Structure | | | |
|---|---|---|---|---|
| I-252 | (structure) | 2 | 2.34 | 474.2 |
| I-253 | (structure) | 2 | 2.31 | 474.2 |
| I-254 | (structure) | 4 | 2.16 | 477.1 |
| I-255 | (structure) | 4 | 1.60 | 391.4 |

TABLE 45-continued

| ID | Structure | a | b | c |
|---|---|---|---|---|
| I-256 | 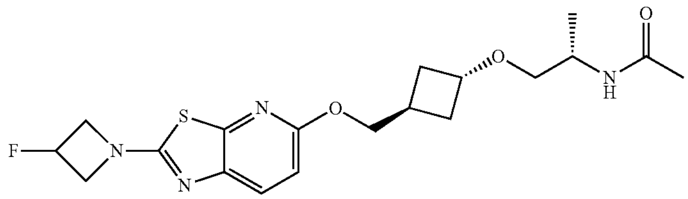 [SMILES: CC(=O)N[C@@H](C)CO[C@H]1C[C@H](COc2ccc3nc(N4CC(F)C4)sc3n2)C1] | 4 | 1.68 | 410.1 |

TABLE 46

| ID | Structure | a | b | c |
|---|---|---|---|---|
| I-257 | 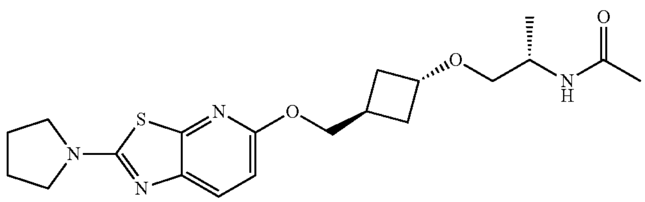 [SMILES: CC(=O)N[C@@H](C)CO[C@H]1C[C@H](COc2ccc3nc(N4CCCC4)sc3n2)C1] | 4 | 1.63 | 405.2 |
| I-258 | 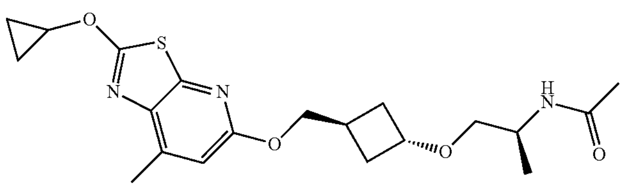 [SMILES: CC(=O)N[C@@H](C)CO[C@H]1C[C@H](COc2cc(C)c3nc(OC4CC4)sc3n2)C1] | 4 | 2.24 | 406.2 |
| I-259 | 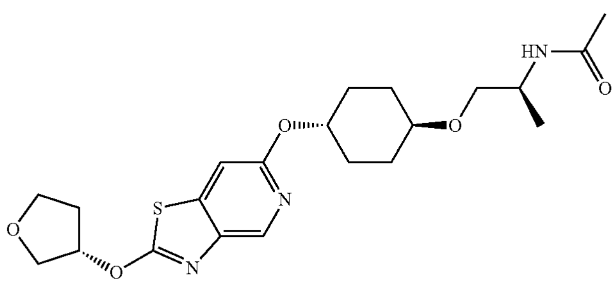 [SMILES: CC(=O)N[C@@H](C)CO[C@H]1CC[C@H](Oc2cc3sc(O[C@H]4CCOC4)nc3cn2)CC1] | 2 | 2.07 | 436.4 |
| I-260 | 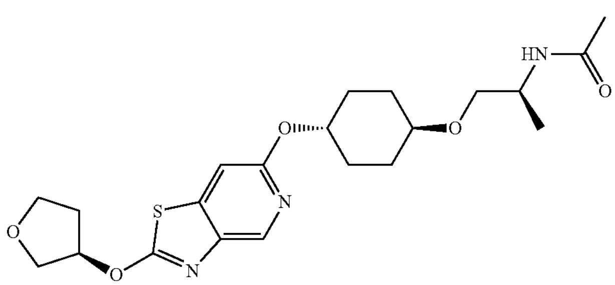 [SMILES: CC(=O)N[C@@H](C)CO[C@H]1CC[C@H](Oc2cc3sc(O[C@@H]4CCOC4)nc3cn2)CC1] | 2 | 2.05 | 436.4 |
| I-261 | 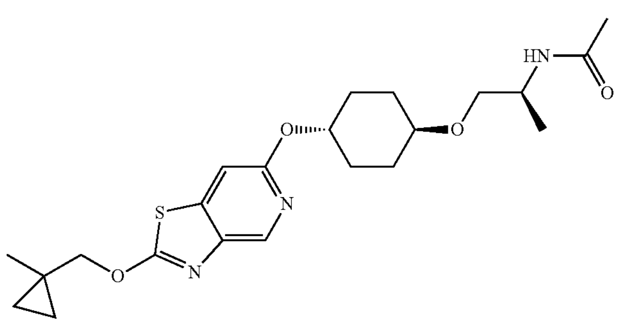 [SMILES: CC(=O)N[C@@H](C)CO[C@H]1CC[C@H](Oc2cc3sc(OCC4(C)CC4)nc3cn2)CC1] | 2 | 2.61 | 434.3 |

TABLE 47
| I-262 | 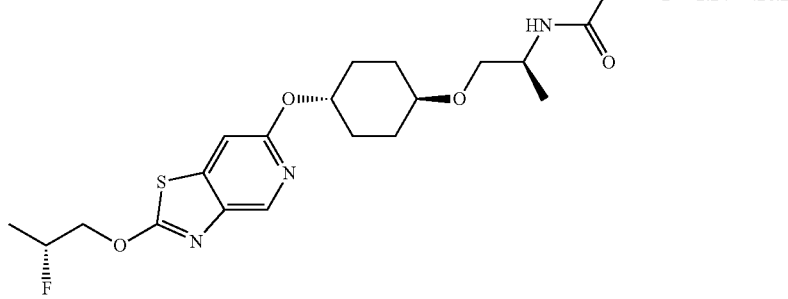 | 2 | 2.24 | 426.2 |
| I-263 | 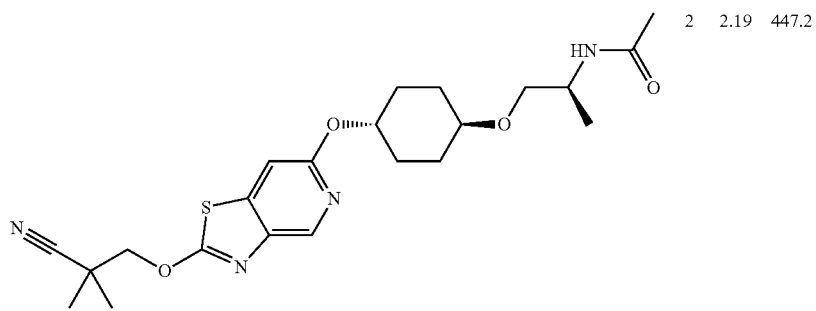 | 2 | 2.19 | 447.2 |
| I-264 | 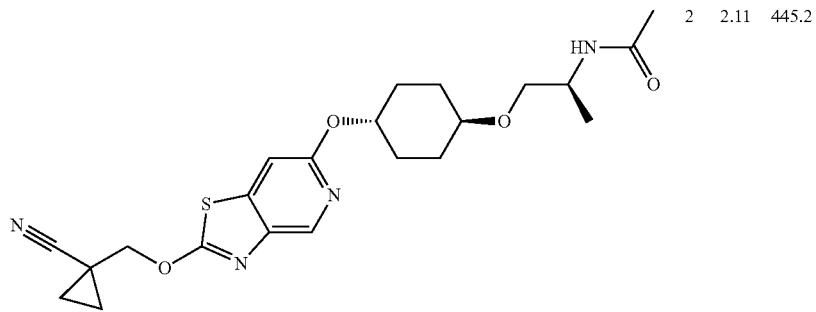 | 2 | 2.11 | 445.2 |
| I-265 | 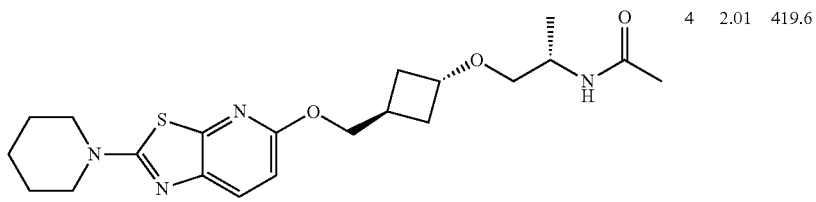 | 4 | 2.01 | 419.6 |
| I-266 | 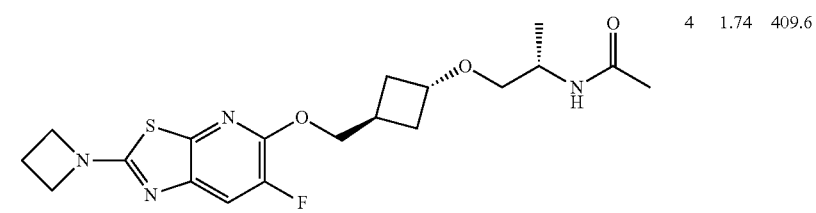 | 4 | 1.74 | 409.6 |

TABLE 48
I-267 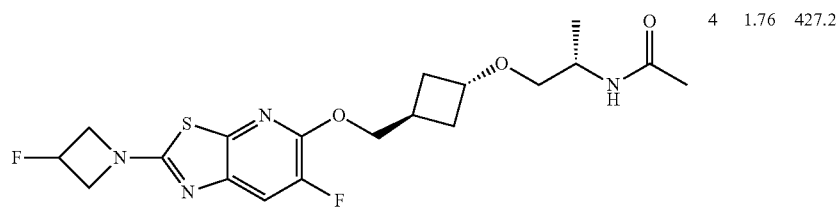 4 1.76 427.2
I-268 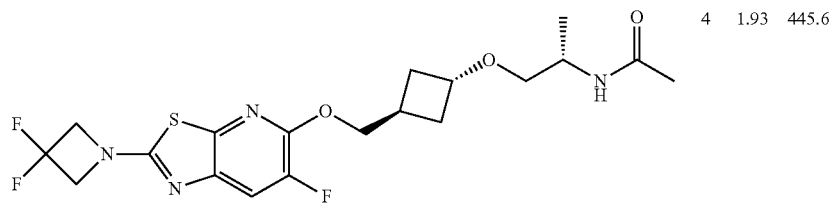 4 1.93 445.6
I-269 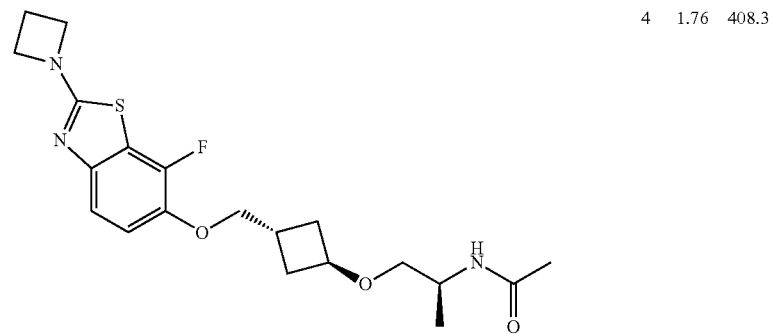 4 1.76 408.3
I-270 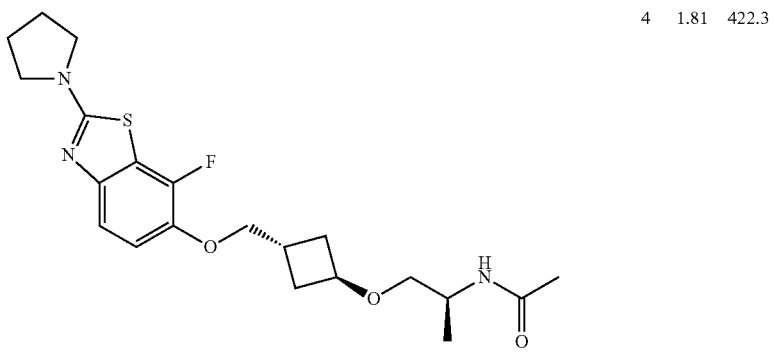 4 1.81 422.3
I-271 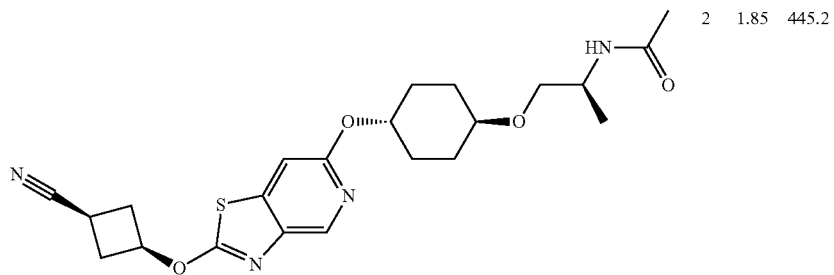 2 1.85 445.2

TABLE 49
| | | | | |
|---|---|---|---|---|
| I-272 | 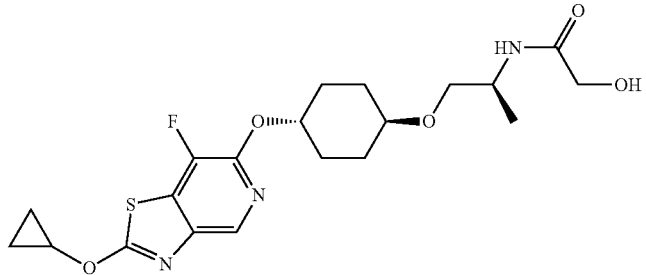 [SMILES: C[C@@H](CO[C@H]1CC[C@H](Oc2ncc3nc(OC4CC4)sc3c2F)CC1)NC(=O)CO] | 2 | 2.15 | 400.0 |
| I-273 | 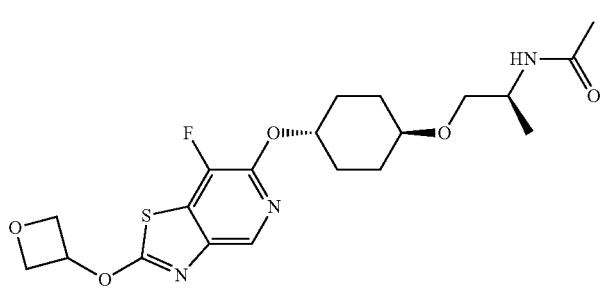 [SMILES: CC(=O)N[C@@H](C)CO[C@H]1CC[C@H](Oc2ncc3nc(OC4COC4)sc3c2F)CC1] | 2 | 1.98 | 440.1 |
| I-274 | 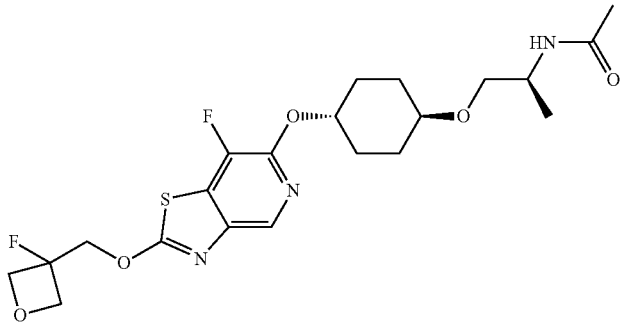 [SMILES: CC(=O)N[C@@H](C)CO[C@H]1CC[C@H](Oc2ncc3nc(OCC4(F)COC4)sc3c2F)CC1] | 2 | 2.07 | 472.2 |
| I-275 | 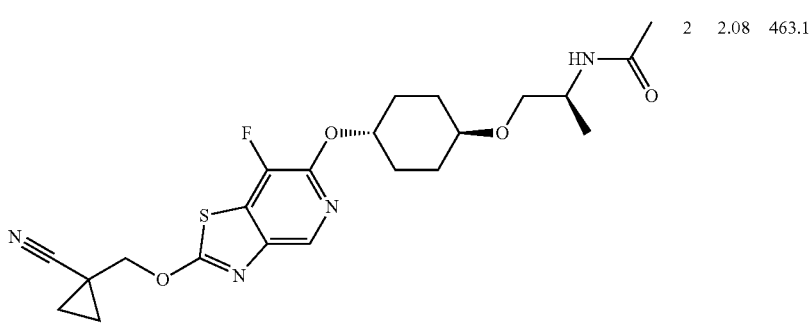 | 2 | 2.08 | 463.1 |
| I-276 | 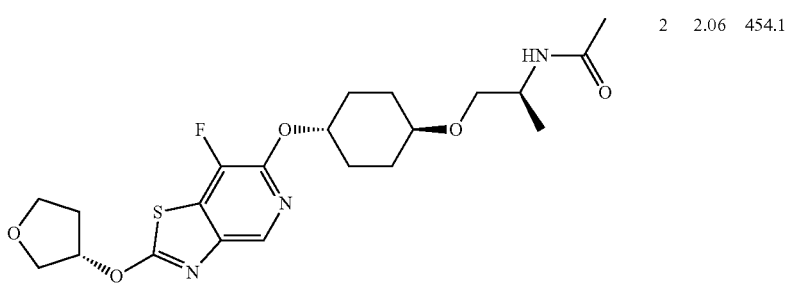 | 2 | 2.06 | 454.1 |

TABLE 50
| | | | | |
|---|---|---|---|---|
| I-277 | 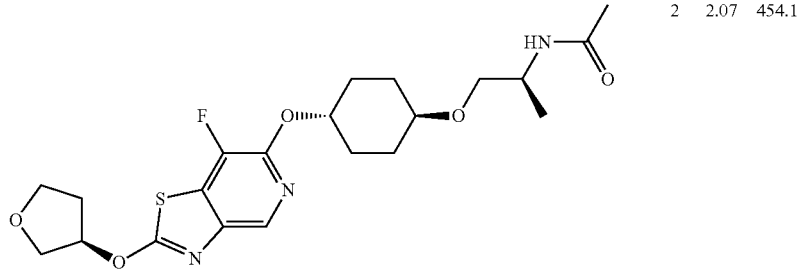 | 2 | 2.07 | 454.1 |
| I-278 | 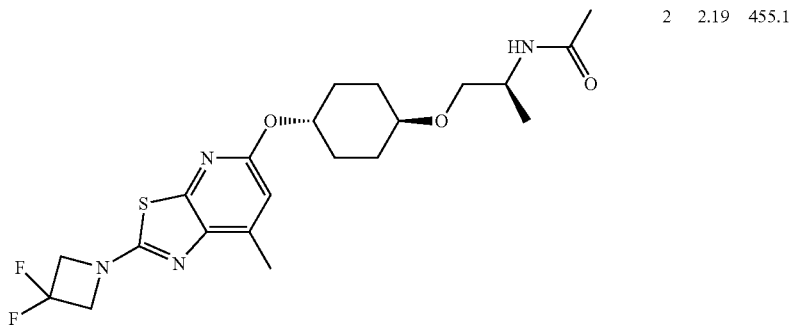 | 2 | 2.19 | 455.1 |
| I-279 | 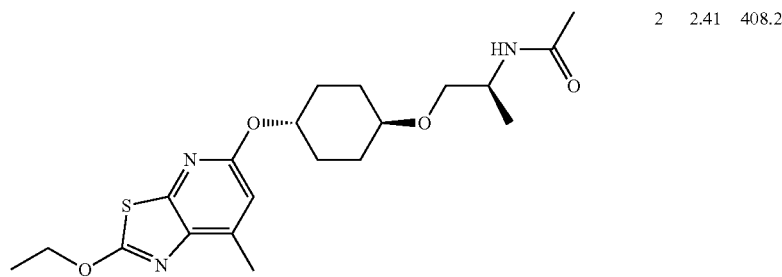 | 2 | 2.41 | 408.2 |
| I-280 | 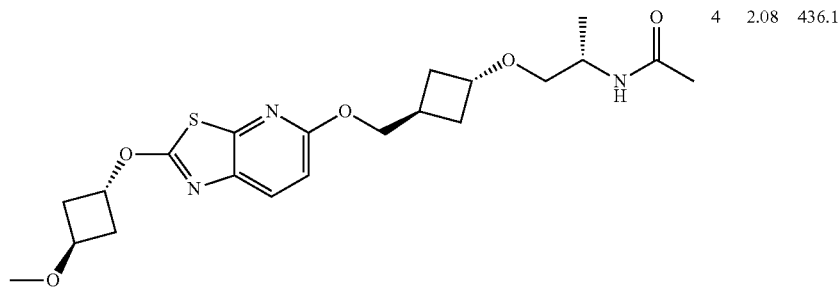 | 4 | 2.08 | 436.1 |
| I-281 | 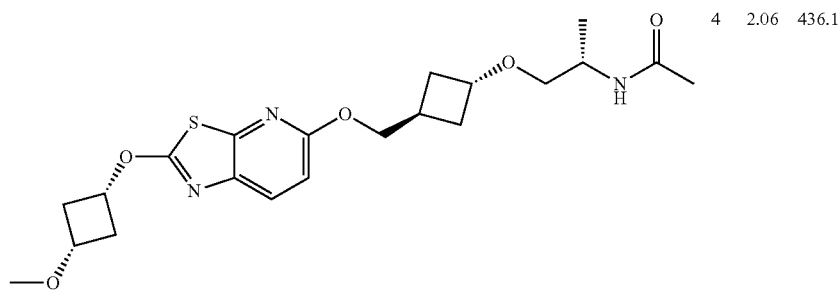 | 4 | 2.06 | 436.1 |

TABLE 51
| I-282 | 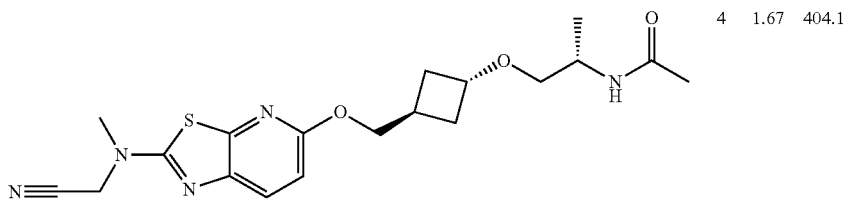 | 4 | 1.67 | 404.1 |
| I-283 | 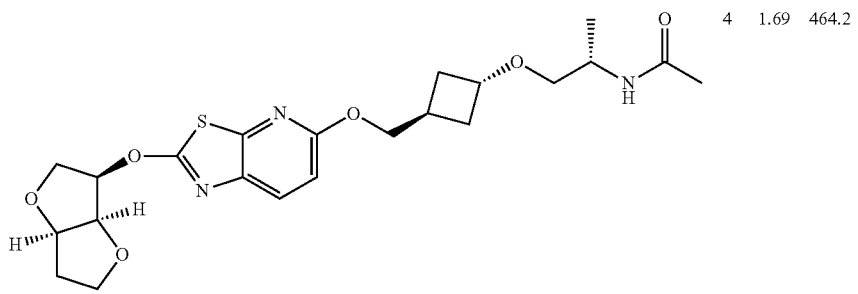 | 4 | 1.69 | 464.2 |
| I-284 | 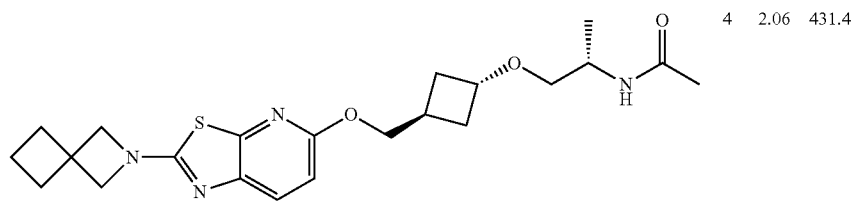 | 4 | 2.06 | 431.4 |
| I-285 | 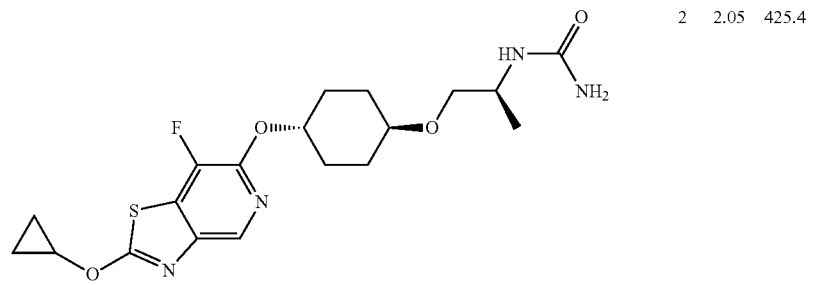 | 2 | 2.05 | 425.4 |
| I-286 | 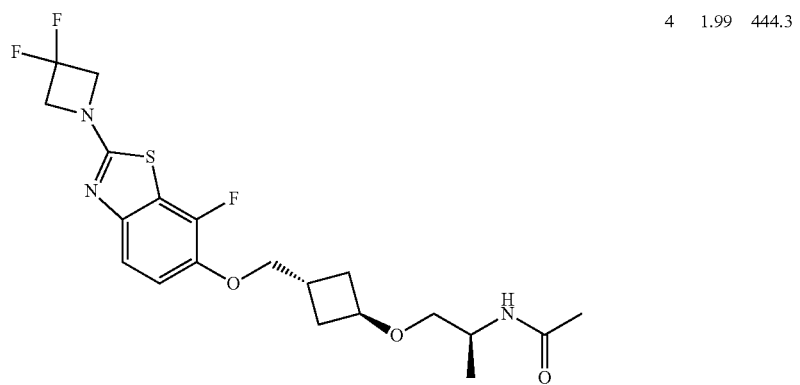 | 4 | 1.99 | 444.3 |

TABLE 52
| | | | | |
|---|---|---|---|---|
| I-287 | 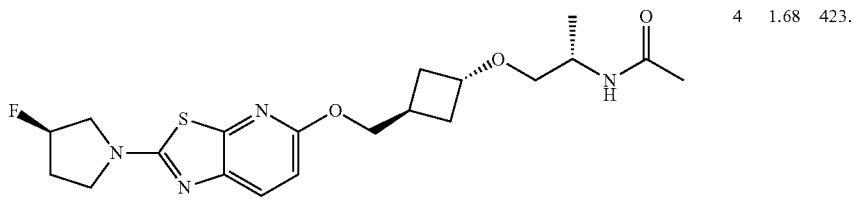 | 4 | 1.68 | 423.1 |
| I-288 | 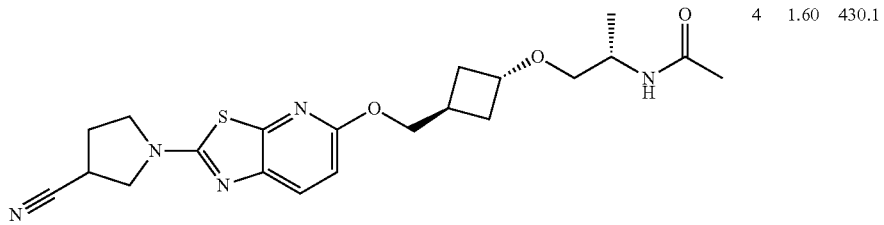 | 4 | 1.60 | 430.1 |
| I-289 | 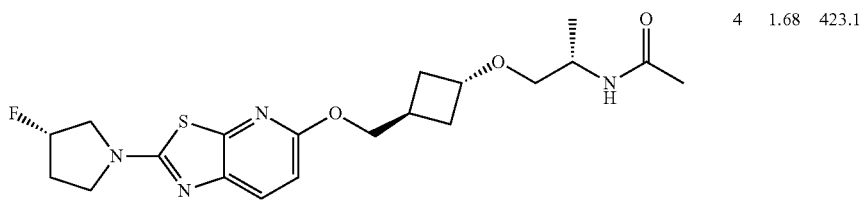 | 4 | 1.68 | 423.1 |
| I-290 | 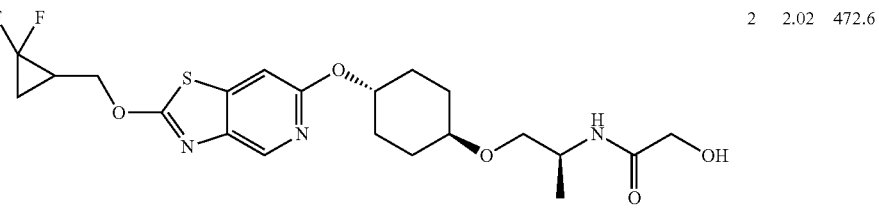 | 2 | 2.02 | 472.6 |
| I-291 | 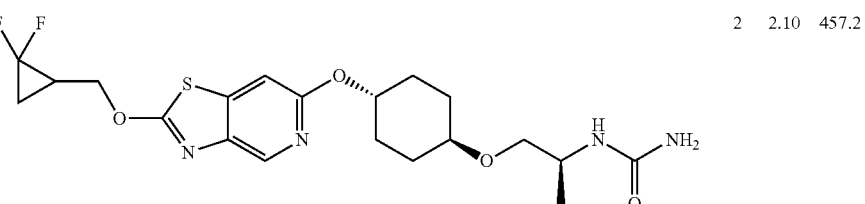 | 2 | 2.10 | 457.2 |
TABLE 53
| | | | | |
|---|---|---|---|---|
| I-292 | 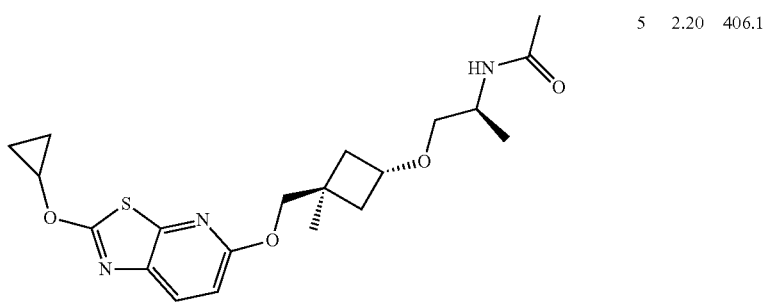 | 5 | 2.20 | 406.1 |

TABLE 53-continued
| I-293 | 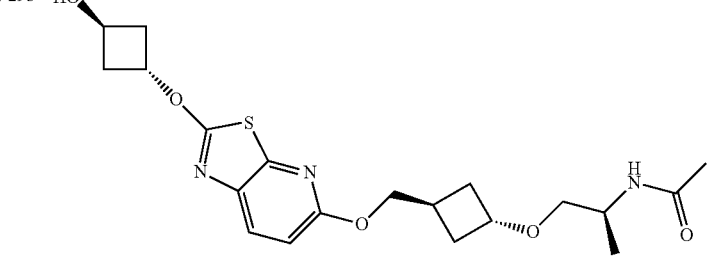 | 4 | 1.53 | 421.9 |
| I-294 | 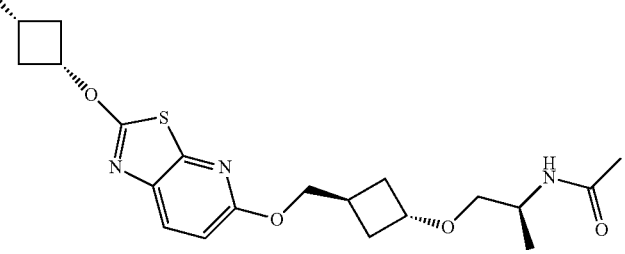 | 4 | 1.52 | 422.0 |
| I-295 | 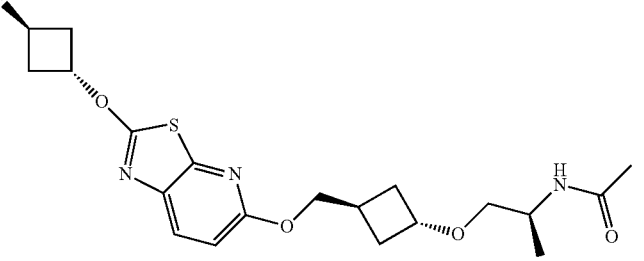 | 4 | 2.10 | 423.9 |
| I-296 | 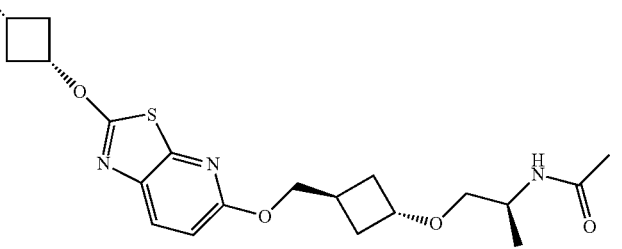 | 4 | 2.10 | 423.9 |
TABLE 54
| I-297 | 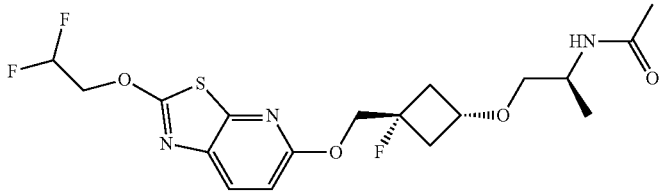 [SMILES: CC(=O)N[C@@H](C)CO[C@H]1C[C@](F)(COc2ccc3nc(OCC(F)F)sc3n2)C1] | 4 | 1.97 | 434.2 |

TABLE 54-continued

| ID | Structure | | | |
|---|---|---|---|---|
| I-298 | 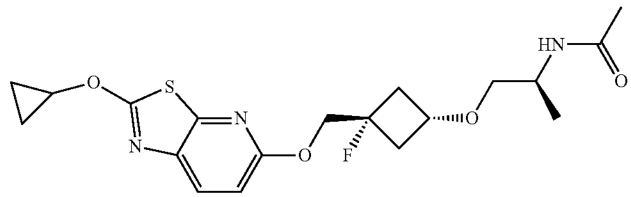 [SMILES: CC(=O)N[C@@H](C)CO[C@H]1C[C@](F)(COc2ccc3nc(OC4CC4)sc3n2)C1] | 4 | 1.86 | 410.0 |
| I-299 | 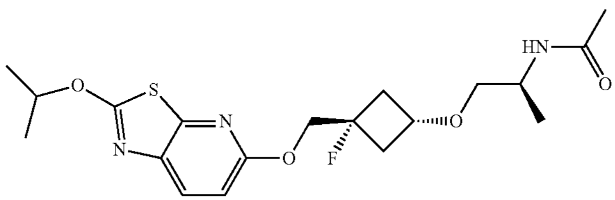 [SMILES: CC(=O)N[C@@H](C)CO[C@H]1C[C@](F)(COc2ccc3nc(OC(C)C)sc3n2)C1] | 4 | 2.11 | 412.0 |
| I-300 | 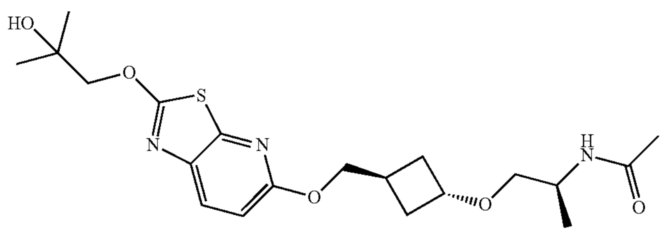 [SMILES: CC(=O)N[C@@H](C)CO[C@H]1C[C@H](COc2ccc3nc(OCC(C)(C)O)sc3n2)C1] | 4 | 1.61 | 424.2 |
| I-301 | 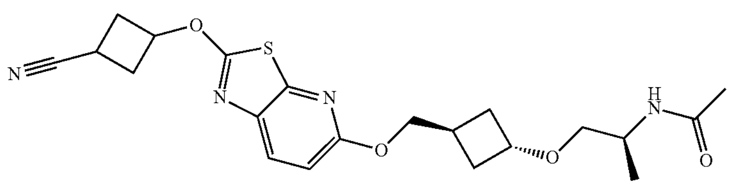 [SMILES: CC(=O)N[C@@H](C)CO[C@H]1C[C@H](COc2ccc3nc(OC4CC(C#N)C4)sc3n2)C1] | 4 | 1.87 | 431.2 |

TABLE 55

| ID | Structure | | | |
|---|---|---|---|---|
| I-302 | 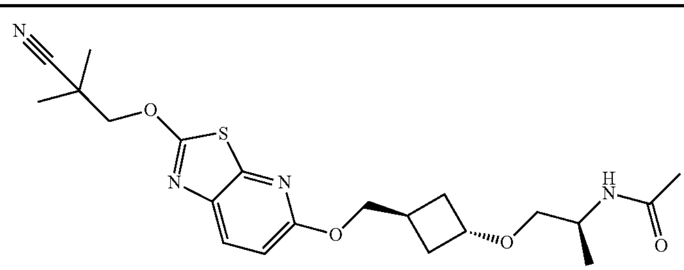 | 4 | 1.97 | 433.0 |
| I-303 | 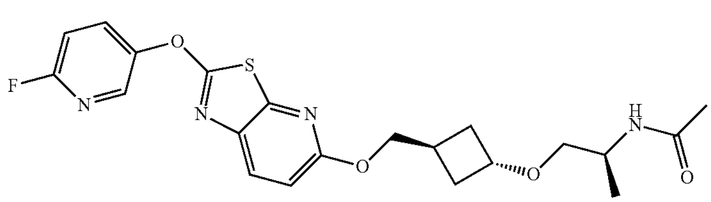 [SMILES: CC(=O)N[C@@H](C)CO[C@H]1C[C@H](COc2ccc3nc(Oc4ccc(F)nc4)sc3n2)C1] | 4 | 2.01 | 447.2 |
| I-304 | 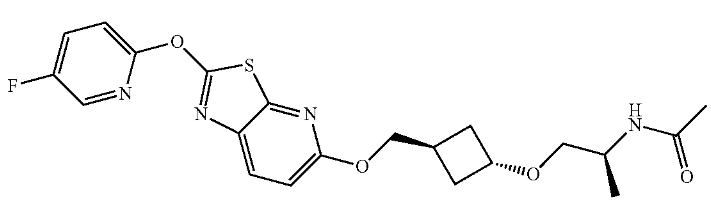 [SMILES: CC(=O)N[C@@H](C)CO[C@H]1C[C@H](COc2ccc3nc(Oc4ccc(F)cn4)sc3n2)C1] | 4 | 1.93 | 441.2 |

TABLE 55-continued

| I-305 | (structure) | 4 | 2.29 | 446.0 |
| I-306 | (structure) | 4 | 2.00 | 411.9 |

TABLE 56

| I-307 | (structure) | 4 | 1.69 | 408.0 |
| I-308 | (structure) | 4 | 2.24 | 406.0 |

TABLE 57

| I-309 | (structure) | 2 | 2.10 | 391.1 |

TABLE 57-continued

| | | | | |
|---|---|---|---|---|
| I-310 | [structure] | 4 | 2.32 | 407.3 |
| I-311 | [structure] | 2 | 1.70 | 393.2 |
| I-312 | [structure] | 2 | 1.96 | 449.0 |
| I-313 | [structure] | 2 | 2.19 | 387.0 |

TABLE 58

| | | | | |
|---|---|---|---|---|
| I-314 | [structure] | 2 | 2.00 | 383.2 |

TABLE 58-continued
| | | | | |
|---|---|---|---|---|
| I-315 | 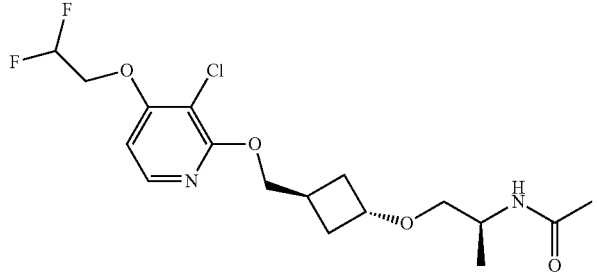 [SMILES: CC(=O)N[C@@H](C)CO[C@H]1C[C@H](COc2nccc(OCC(F)F)c2Cl)C1] | 2 | 1.77 | 393.2 |
| I-316 | 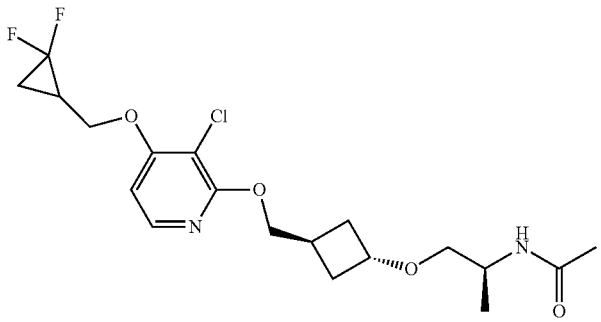 [SMILES: CC(=O)N[C@@H](C)CO[C@H]1C[C@H](COc2nccc(OCC3CC3(F)F)c2Cl)C1] | 2 | 1.90 | 419.0 |
| I-317 | 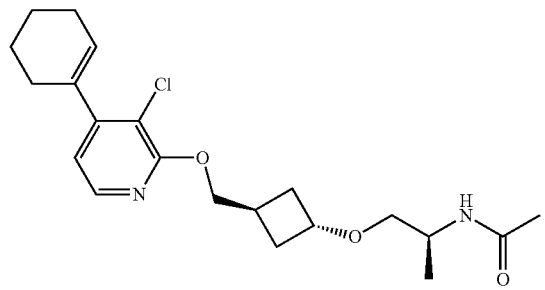 [SMILES: CC(=O)N[C@@H](C)CO[C@H]1C[C@H](COc2nccc(C3=CCCCC3)c2Cl)C1] | 2 | 2.49 | 393.1 |
| I-318 | 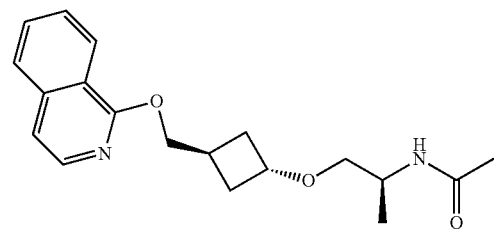 [SMILES: CC(=O)N[C@@H](C)CO[C@H]1C[C@H](COc2nccc3ccccc23)C1] | 2 | 1.87 | 392.5 |
TABLE 59
| | | | | |
|---|---|---|---|---|
| I-319 | 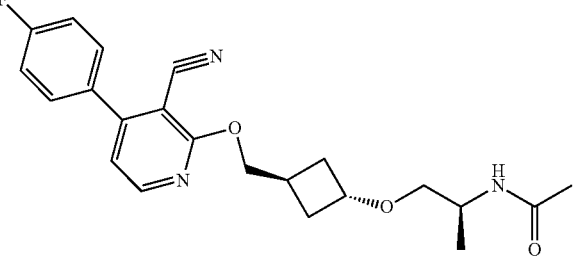 | 2 | 1.95 | 398.1 |

TABLE 59-continued

| ID | Structure | | | |
|---|---|---|---|---|
| I-320 | (4-trifluoromethylphenyl)-chloro-pyridine-O-cyclobutyl-O-CH2-CH(CH3)-NHAc | 4 | 2.63 | 457.0 |
| I-321 | (5-methoxypyrimidin-2-yl)-chloro-pyridine-O-CH2-cyclobutyl-O-CH2-CH(CH3)-NHAc | 2 | 1.64 | 421.1 |
| I-322 | (5-trifluoromethylpyrimidin-2-yl)-chloro-pyridine-O-CH2-cyclobutyl-O-CH2-CH(CH3)-NHAc | 2 | 2.03 | 459.2 |
| I-323 | (3,3-difluoroazetidin-1-yl)-chloro-pyridine-O-CH2-cyclobutyl-O-CH2-CH(CH3)-NHAc | 2 | 1.83 | 404.1 |

TABLE 60

| ID | Structure | | | |
|---|---|---|---|---|
| I-324 | (piperidin-1-yl)-chloro-pyridine-O-CH2-cyclobutyl-O-CH2-CH(CH3)-NHAc | 2 | 2.25 | 396.3 |

TABLE 60-continued
| I-325 | 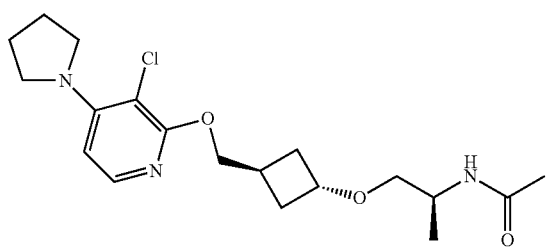 [SMILES: CC(=O)N[C@@H](C)CO[C@H]1C[C@H](COc2nccc(N3CCCC3)c2Cl)C1] | 2 | 1.74 | 382.5 |
| I-326 | 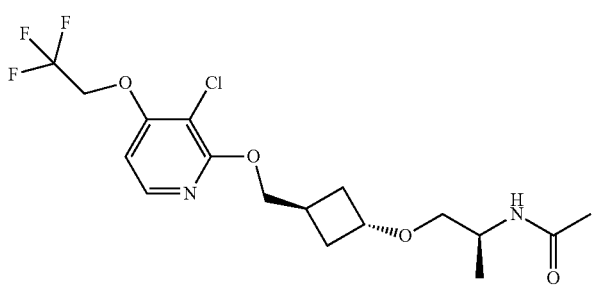 [SMILES: CC(=O)N[C@@H](C)CO[C@H]1C[C@H](COc2nccc(OCC(F)(F)F)c2Cl)C1] | 2 | 1.89 | 411.1 |
| I-327 | 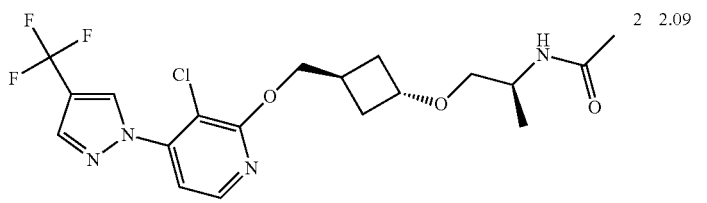 | 2 | 2.09 | 447.0 |
| I-328 | 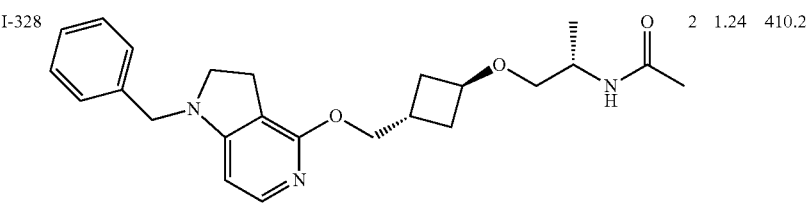 | 2 | 1.24 | 410.2 |
TABLE 61
| I-329 | 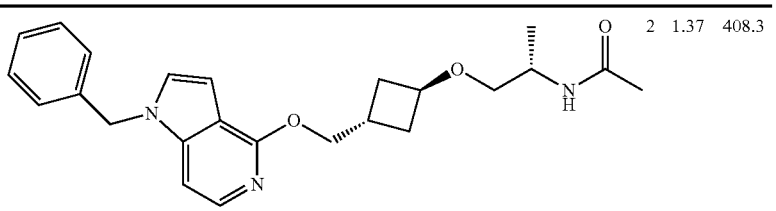 | 2 | 1.37 | 408.3 |
| I-330 | 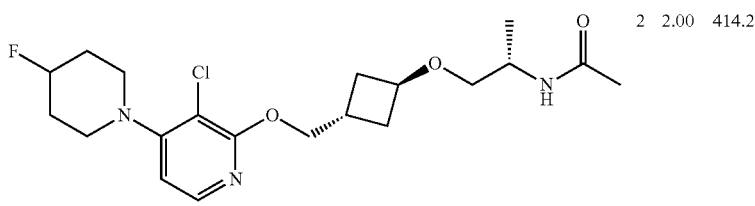 | 2 | 2.00 | 414.2 |

TABLE 61-continued

| | | | | |
|---|---|---|---|---|
| I-331 | | 2 | 0.94 | 376.4 |
| I-332 | | 2 | 2.13 | 408.4 |
| I-333 | | 2 | 1.80 | 390.0 |

TABLE 62

| | | | | |
|---|---|---|---|---|
| I-334 | | 4 | 2.01 | 347.0 |
| I-335 | | 2 | 2.36 | 379.0 |
| I-336 | | 2 | 2.30 | 359.0 |
| I-337 | | 2 | 2.08 | 408.0 |

TABLE 62-continued
I-338 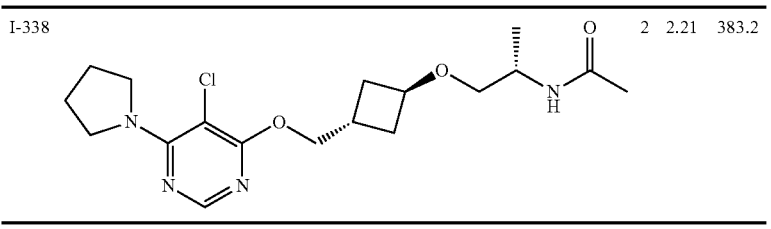 2 2.21 383.2
TABLE 63
I-339 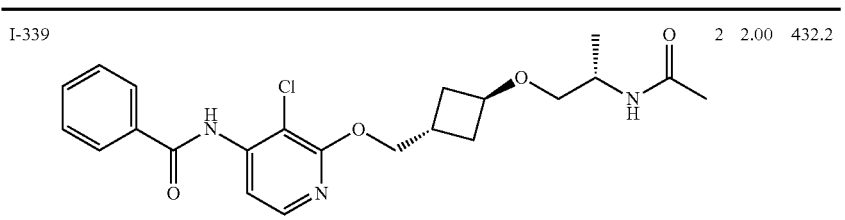 2 2.00 432.2
I-340 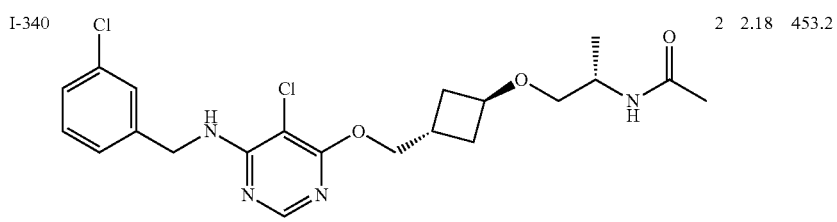 2 2.18 453.2
I-341 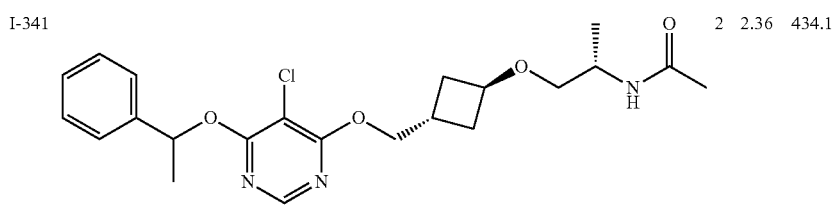 2 2.36 434.1
I-342 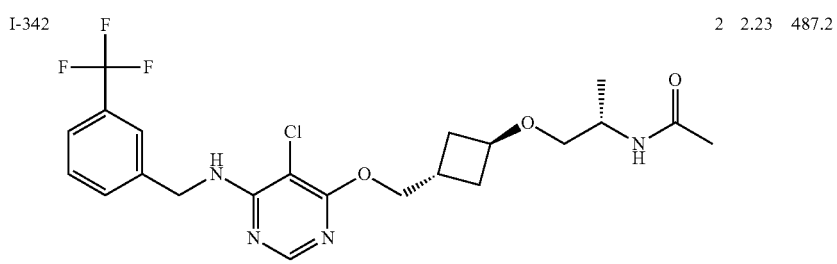 2 2.23 487.2
I-343 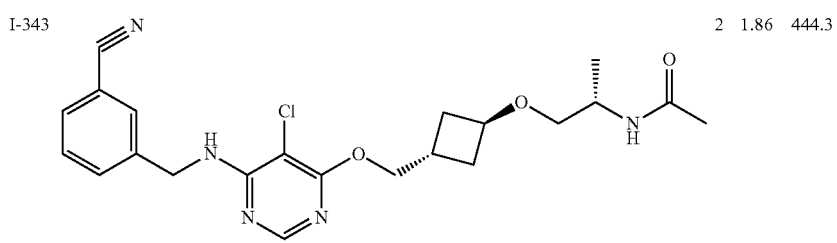 2 1.86 444.3

TABLE 64

| ID | Structure | | | |
|---|---|---|---|---|
| I-344 | (4-chlorobenzyl)amino-chloropyrimidine structure | 2 | 2.20 | 453.2 |
| I-345 | phenethyloxy-chloropyrimidine structure | 2 | 2.33 | 434.4 |
| I-346 | 3-cyanobenzyloxy-chloropyrimidine structure | 2 | 2.06 | 445.2 |
| I-347 | 4-cyanobenzyloxy-chloropyrimidine structure | 2 | 2.04 | 445.2 |
| I-348 | (6-methoxypyridin-3-yl)methoxy-chloropyrimidine structure | 2 | 2.00 | 451.2 |

TABLE 65

| ID | Structure | | | |
|---|---|---|---|---|
| I-349 | 4-(trifluoromethyl)benzyloxy-chloropyrimidine structure | 2 | 2.44 | 488.2 |

TABLE 65-continued

| ID | Structure | a | b | c |
|---|---|---|---|---|
| I-350 | [3-(trifluoromethyl)benzyl ether pyrimidine structure] | 2 | 2.43 | 488.2 |
| I-351 | [6-(trifluoromethyl)pyridin-3-yl methyl ether pyrimidine structure] | 2 | 2.12 | 489.2 |
| I-352 | [1-(cyclopropylmethyl)pyrrolo[3,2-c]pyridine structure] | 2 | 1.18 | 372.2 |
| I-353 | [(5-chloropyrimidin-2-yl)methyl ether pyrimidine structure] | 2 | 1.89 | 456.2 |

TABLE 66

| ID | Structure | a | b | c |
|---|---|---|---|---|
| I-354 | [(5-fluoropyridin-2-yl)methyl ether pyrimidine structure] | 2 | 1.92 | 439.2 |
| I-355 | [cyclopropylmethyl ether pyrimidine structure] | 2 | 2.38 | 384.2 |
| I-356 | [(2,2-difluorocyclopropyl)methyl ether pyrimidine structure] | 3 | 2.09 | 420.1 |

TABLE 66-continued
| I-357 | 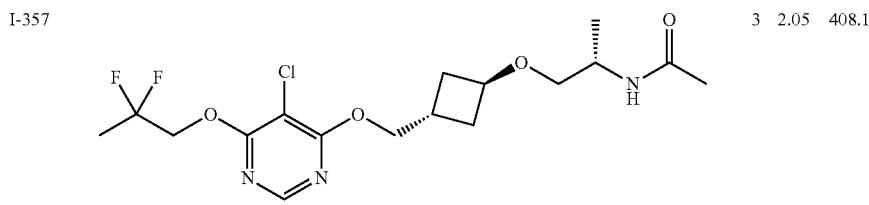 | 3 | 2.05 | 408.1 |
| I-358 | 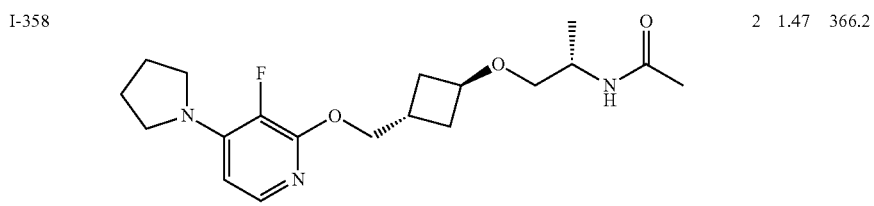 | 2 | 1.47 | 366.2 |
TABLE 67
| I-359 | 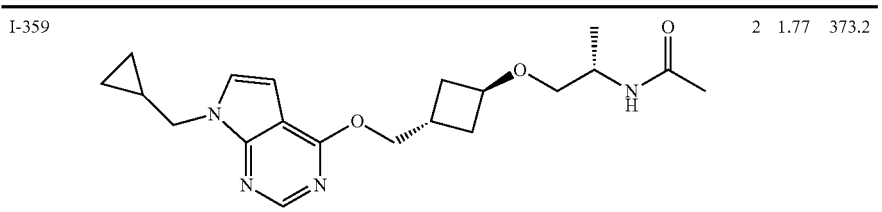 | 2 | 1.77 | 373.2 |
| I-360 | 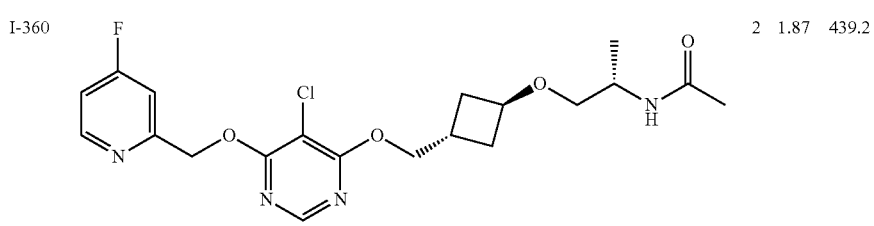 | 2 | 1.87 | 439.2 |
| I-361 | 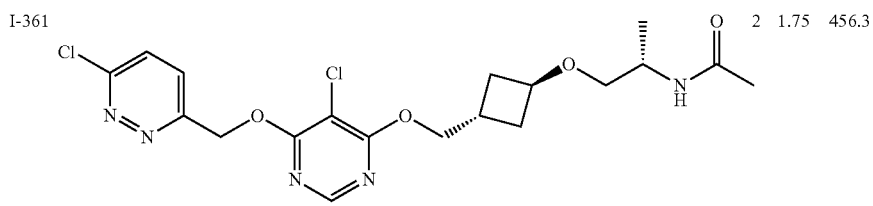 | 2 | 1.75 | 456.3 |
| I-362 | 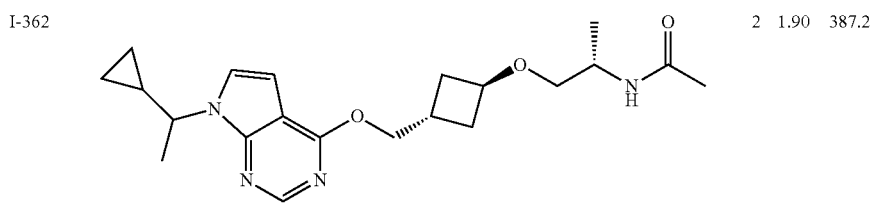 | 2 | 1.90 | 387.2 |
| I-363 | 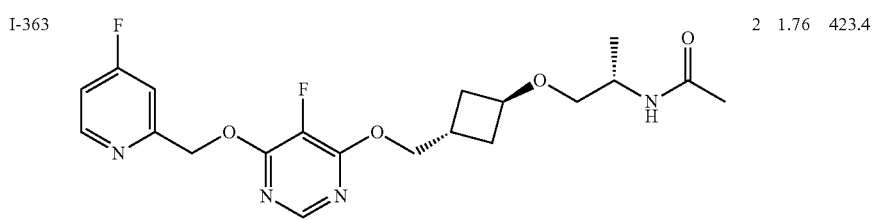 | 2 | 1.76 | 423.4 |

TABLE 68

| ID | Structure | | | |
|---|---|---|---|---|
| I-364 | (3,3-difluoropyrrolidinyl-chloropyridine-O-CH2-cyclobutyl-O-CH2-CH(CH3)-NHAc) | 2 | 1.99 | 418.1 |
| I-365 | (norbornyl-O-chloropyridine-O-CH2-cyclobutyl-O-CH2-CH(CH3)-NHAc) | 2 | 2.41 | 423.0 |
| I-366 | (norbornyl-O-chloropyridine-O-CH2-cyclobutyl-O-CH2-CH(CH3)-NHAc) | 2 | 2.44 | 423.0 |
| I-367 | (cyclobutyl-O-chloropyridine-O-CH2-cyclobutyl-O-CH2-CH(CH3)-NHAc) | 2 | 2.05 | 383.0 |
| I-368 | (cyclohexyl-O-chloropyridine-O-CH2-cyclobutyl-O-CH2-CH(CH3)-NHAc) | 2 | 2.37 | 411.2 |

TABLE 69

| ID | Structure | | | |
|---|---|---|---|---|
| I-369 | (methylcyclopropyl-CH2-O-chloropyridine-O-CH2-cyclobutyl-O-CH2-CH(CH3)-NHAc) | 2 | 2.15 | 397.0 |

TABLE 69-continued

| ID | Structure | | | |
|---|---|---|---|---|
| I-370 | (structure) | 2 | 2.16 | 397.0 |
| I-371 | (structure) | 2 | 1.69 | 408.2 |
| I-372 | (structure) | 2 | 2.37 | 399.2 |
| I-373 | (structure) | 2 | 1.66 | 387.5 |

TABLE 70

| ID | Structure | | | |
|---|---|---|---|---|
| I-374 | (structure) | 2 | 1.55 | 399.2 |
| I-375 | (structure) | 2 | 2.14 | 432.1 |

TABLE 70-continued

| ID | Structure | a | b | c |
|---|---|---|---|---|
| I-376 | 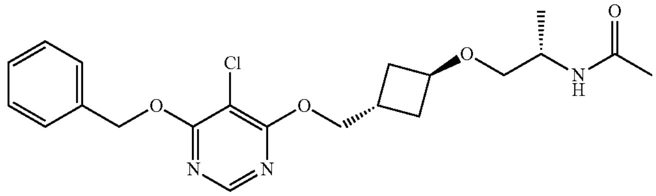 [SMILES: CC(=O)N[C@@H](C)CO[C@H]1C[C@H](COc2ncnc(OCc3ccccc3)c2Cl)C1] | 2 | 2.29 | 420.1 |
| I-377 | 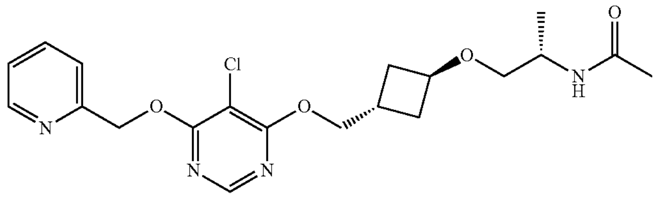 [SMILES: CC(=O)N[C@@H](C)CO[C@H]1C[C@H](COc2ncnc(OCc3ccccn3)c2Cl)C1] | 2 | 1.75 | 421.1 |
| I-378 | 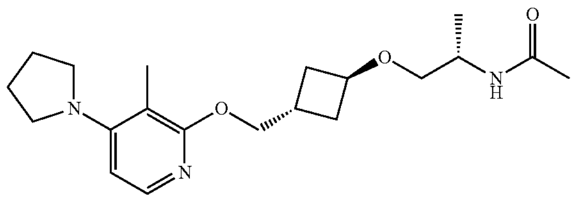 [SMILES: CC(=O)N[C@@H](C)CO[C@H]1C[C@H](COc2nccc(N3CCCC3)c2C)C1] | 2 | 1.09 | 362.2 |

TABLE 71

| ID | Structure | a | b | c |
|---|---|---|---|---|
| I-379 | 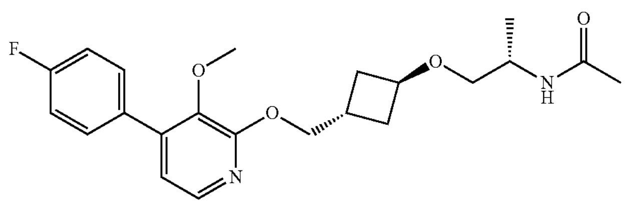 [SMILES: COc1c(-c2ccc(F)cc2)ccnc1OC[C@H]1C[C@H](OC[C@H](C)NC(C)=O)C1] | 2 | 2.15 | 403.2 |
| I-380 | 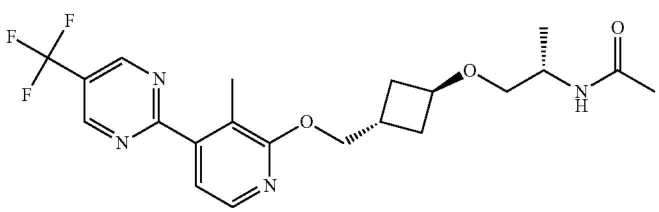 [SMILES: CC(=O)N[C@@H](C)CO[C@H]1C[C@H](COc2nccc(-c3ncc(C(F)(F)F)cn3)c2C)C1] | 3 | 2.12 | 439.1 |
| I-381 | 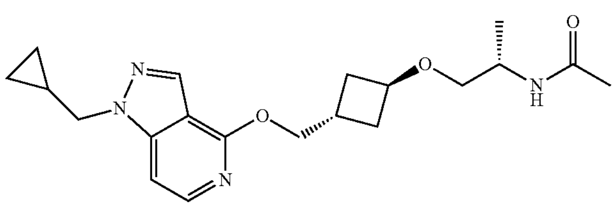 [SMILES: CC(=O)N[C@@H](C)CO[C@H]1C[C@H](COc2nccc3c2cnn3CC2CC2)C1] | 3 | 1.73 | 373.1 |
| I-382 | 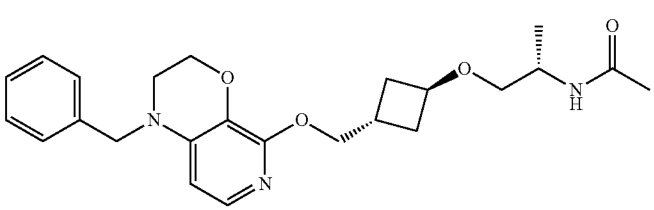 [SMILES: CC(=O)N[C@@H](C)CO[C@H]1C[C@H](COc2nccc3c2OCCN3Cc2ccccc2)C1] | 2 | 1.26 | 426.3 |

TABLE 71-continued

| ID | Structure | a | b | c |
|---|---|---|---|---|
| I-383 | 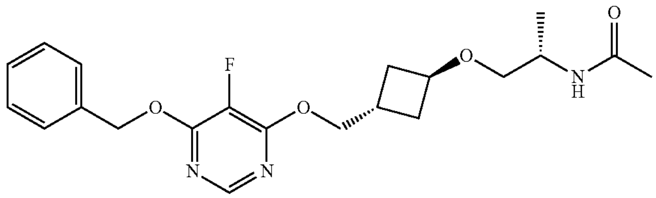 [SMILES: CC(=O)N[C@@H](C)CO[C@H]1C[C@H](COc2ncnc(OCc3ccccc3)c2F)C1] | 3 | 2.18 | 404.1 |
| I-384 | 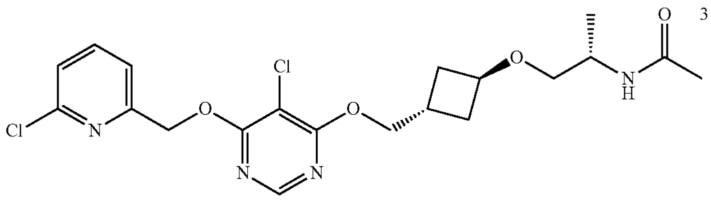 [SMILES: CC(=O)N[C@@H](C)CO[C@H]1C[C@H](COc2ncnc(OCc3cccc(Cl)n3)c2Cl)C1] | 3 | 2.13 | 455.0 |
| I-385 | 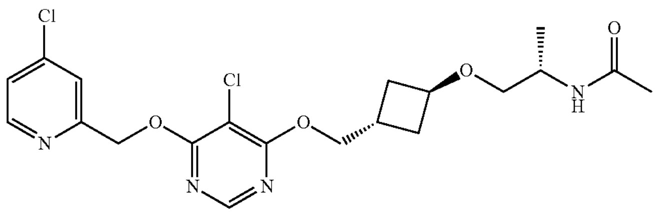 | 3 | 2.09 | 455.0 |
| I-386 | 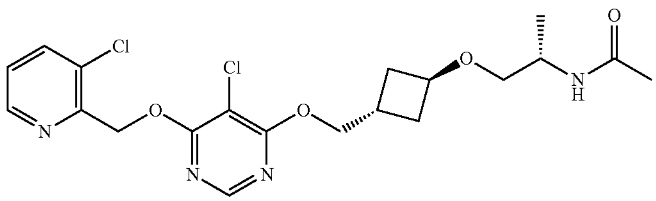 [SMILES: CC(=O)N[C@@H](C)CO[C@H]1C[C@H](COc2ncnc(OCc3ncccc3Cl)c2Cl)C1] | 2 | 1.99 | 455.4 |
| I-387 | 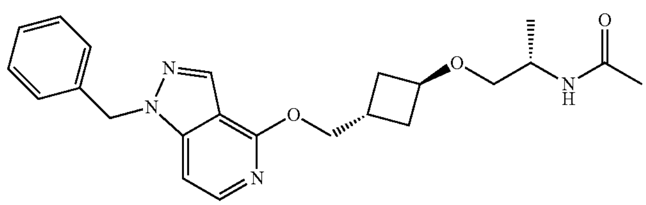 [SMILES: CC(=O)N[C@@H](C)CO[C@H]1C[C@H](COc2nccc3c2cnn3Cc2ccccc2)C1] | 3 | 1.90 | 409.1 |
| I-388 | 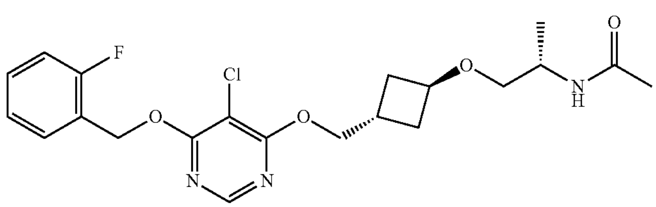 [SMILES: CC(=O)N[C@@H](C)CO[C@H]1C[C@H](COc2ncnc(OCc3ccccc3F)c2Cl)C1] | 3 | 2.29 | 438.0 |

TABLE 73

| ID | Structure | a | b | c |
|---|---|---|---|---|
| I-389 | 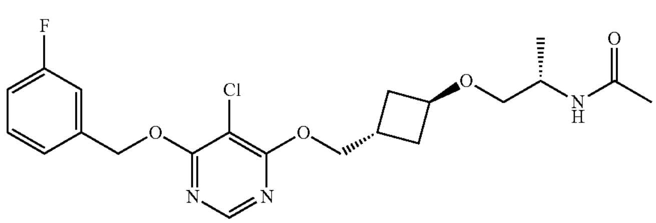 [SMILES: CC(=O)N[C@@H](C)CO[C@H]1C[C@H](COc2ncnc(OCc3cccc(F)c3)c2Cl)C1] | 3 | 2.29 | 438.0 |

TABLE 73-continued

| ID | Structure | | | |
|---|---|---|---|---|
| I-390 | [4-fluorobenzyl-O, Cl-pyrimidine-O-cyclobutyl-O-CH2-CH(CH3)-NHAc] | 3 | 2.28 | 438.0 |
| I-391 | [benzyl-NH, Cl-pyrimidine-O-cyclobutyl-O-CH2-CH(CH3)-NHAc] | 2 | 2.02 | 419.2 |
| I-392 | [pyridin-3-yl-CH2-O, Cl-pyrimidine-O-cyclobutyl-O-CH2-CH(CH3)-NHAc] | 3 | 1.49 | 421.0 |
| I-393 | [pyridin-4-yl-CH2-O, Cl-pyrimidine-O-cyclobutyl-O-CH2-CH(CH3)-NHAc] | 3 | 1.39 | 421.0 |

TABLE 74

| ID | Structure | | | |
|---|---|---|---|---|
| I-394 | [4-fluorophenyl, Cl-pyridine-O-CH2-(Me)cyclobutyl-O-CH2-CH(CH3)-NHAc] | 3 | 2.40 | 421.1 |
| I-395 | [benzyl-O, Cl-pyridine-O-CH2-cyclobutyl-O-CH2-CH(CH3)-NHAc] | 3 | 2.21 | 419.1 |
| I-396 | [5-chloropyridin-2-yl-CH2-O, Cl-pyrimidine-O-CH2-cyclobutyl-O-CH2-CH(CH3)-NHAc] | 3 | 2.14 | 455.0 |

TABLE 74-continued

| I-397 | [structure] | 2 | 2.10 | 447.2 |
| I-398 | [structure] | 2 | 1.78 | 447.1 |

TABLE 75

| I-399 | [structure] | 2 | 2.16 | 463.2 |
| I-400 | [structure] | 2 | 2.34 | 421.3 |
| I-401 | [structure] | 2 | 1.94 | 418.4 |
| I-402 | [structure] | 2 | 2.27 | 433.3 |
| I-403 | [structure] | 2 | 1.69 | 435.2 |

TABLE 76
| | | | | |
|---|---|---|---|---|
| I-404 | 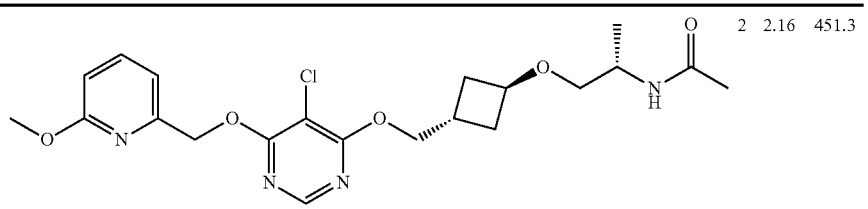 | 2 | 2.16 | 451.3 |
| I-405 | 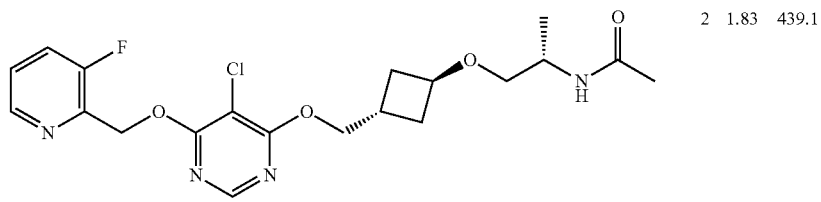 | 2 | 1.83 | 439.1 |
| I-406 | 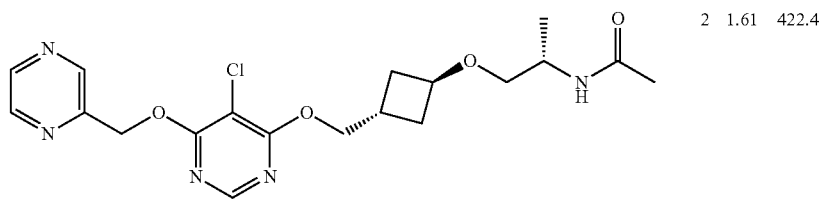 | 2 | 1.61 | 422.4 |
| I-407 | 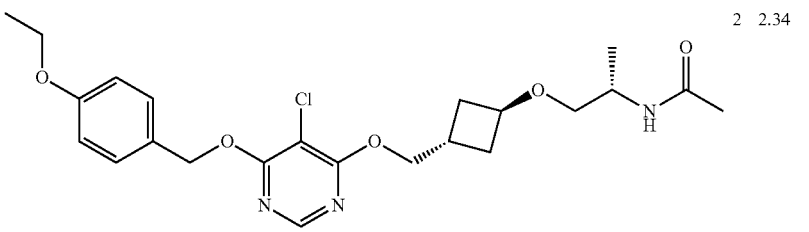 | 2 | 2.34 | 464.2 |
| I-408 | 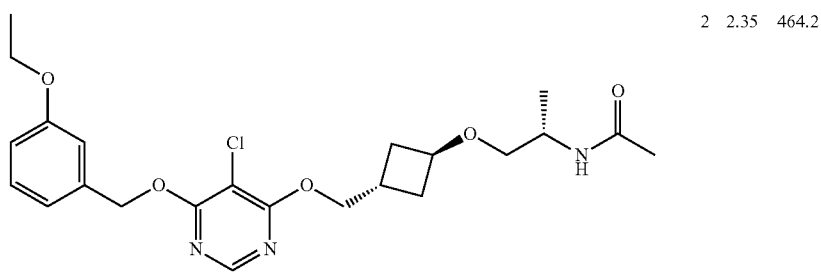 | 2 | 2.35 | 464.2 |
TABLE 77
| | | | | |
|---|---|---|---|---|
| I-409 | 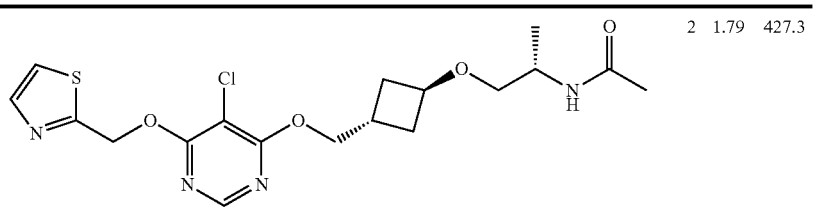 | 2 | 1.79 | 427.3 |

TABLE 77-continued

| ID | Structure | a | b | c |
|---|---|---|---|---|
| I-410 | 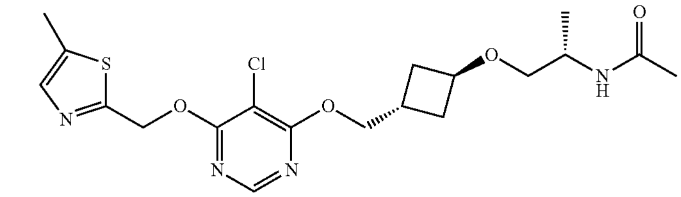 [SMILES: CC(=O)N[C@@H](C)CO[C@H]1C[C@H](COc2ncnc(OCc3ncc(C)s3)c2Cl)C1] | 2 | 1.92 | 441.3 |
| I-411 | 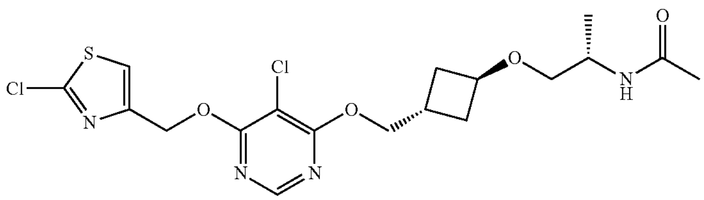 [SMILES: CC(=O)N[C@@H](C)CO[C@H]1C[C@H](COc2ncnc(OCc3csc(Cl)n3)c2Cl)C1] | 2 | 2.09 | 463.0 |
| I-412 | 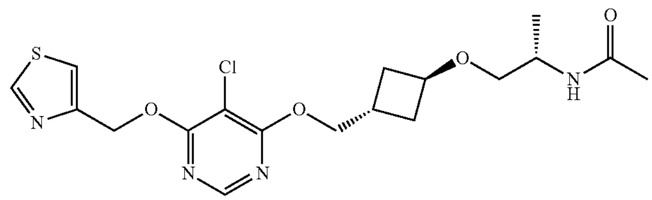 [SMILES: CC(=O)N[C@@H](C)CO[C@H]1C[C@H](COc2ncnc(OCc3cscn3)c2Cl)C1] | 2 | 1.74 | 427.3 |
| I-413 | 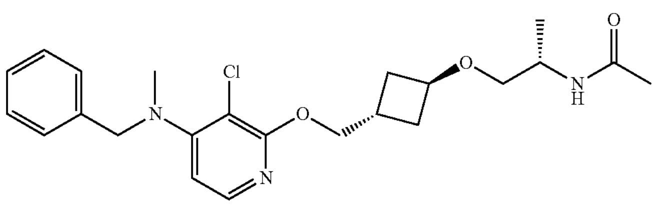 [SMILES: CC(=O)N[C@@H](C)CO[C@H]1C[C@H](COc2nccc(N(C)Cc3ccccc3)c2Cl)C1] | 2 | 2.27 | 432.4 |

TABLE 78

| ID | Structure | a | b | c |
|---|---|---|---|---|
| I-414 | 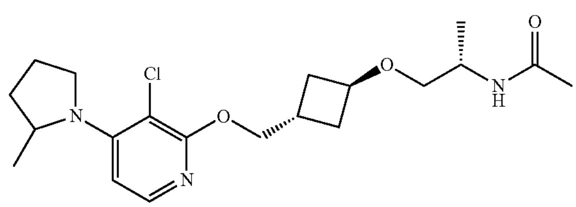 [SMILES: CC(=O)N[C@@H](C)CO[C@H]1C[C@H](COc2nccc(N3CCCC3C)c2Cl)C1] | 2 | 1.97 | 396.2 |
| I-415 | 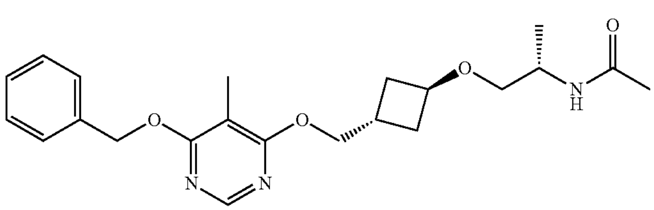 [SMILES: CC(=O)N[C@@H](C)CO[C@H]1C[C@H](COc2ncnc(OCc3ccccc3)c2C)C1] | 3 | 2.28 | 400.1 |
| I-416 | 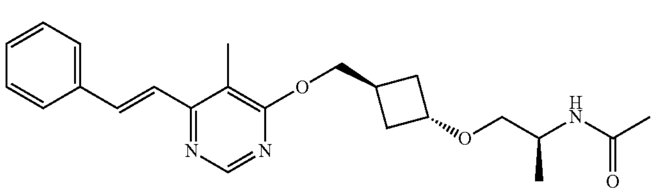 [SMILES: CC(=O)N[C@@H](C)CO[C@H]1C[C@H](COc2ncnc(/C=C/c3ccccc3)c2C)C1] | 2 | 2.07 | 396.0 |

TABLE 78-continued
| | | | | |
|---|---|---|---|---|
| I-417 | 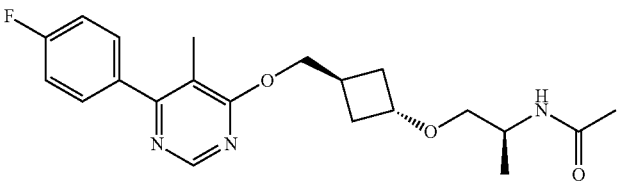 [SMILES: CC(=O)N[C@@H](C)CO[C@H]1C[C@H](COc2ncnc(-c3ccc(F)cc3)c2C)C1] | 2 | 1.84 | 388.0 |
| I-418 | 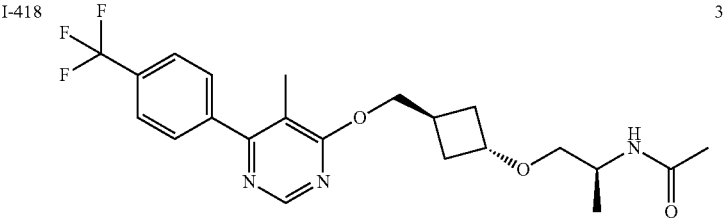 | 3 | 2.28 | 438.0 |
TABLE 79
| | | | | |
|---|---|---|---|---|
| I-419 | 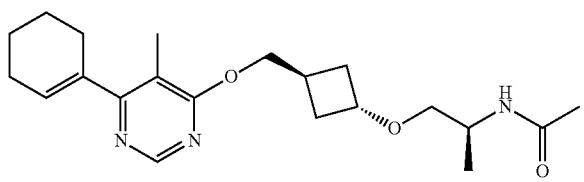 [SMILES: CC(=O)N[C@@H](C)CO[C@H]1C[C@H](COc2ncnc(C3=CCCCC3)c2C)C1] | 3 | 1.90 | 374.0 |
| I-420 | 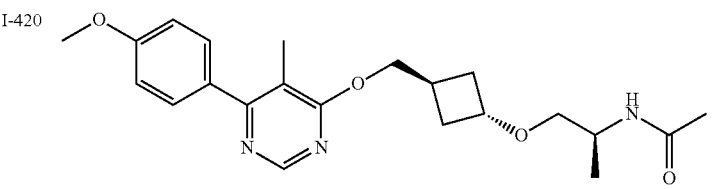 | 3 | 1.81 | 400.0 |
| I-421 | 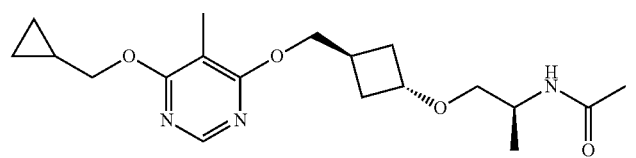 [SMILES: CC(=O)N[C@@H](C)CO[C@H]1C[C@H](COc2ncnc(OCC3CC3)c2C)C1] | 4 | 2.18 | 364.0 |
| I-422 | 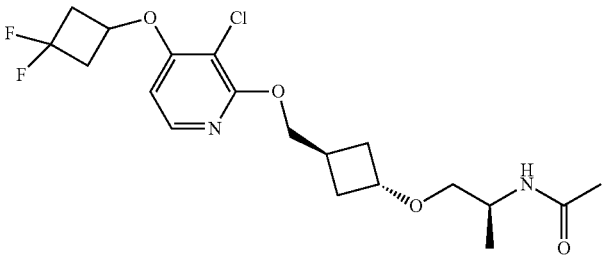 [SMILES: CC(=O)N[C@@H](C)CO[C@H]1C[C@H](COc2nccc(OC3CC(F)(F)C3)c2Cl)C1] | 4 | 2.03 | 419.3 |
| I-423 | 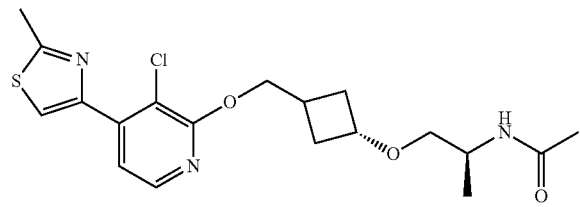 | 2 | 1.94 | 410.0 |

TABLE 80
| | | | | |
|---|---|---|---|---|
| I-424 | 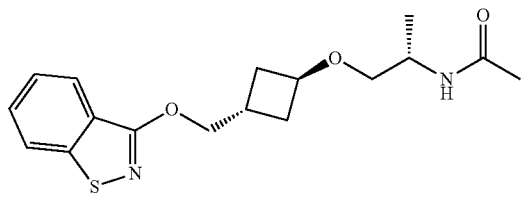 [SMILES: CC(=O)N[C@@H](C)CO[C@H]1C[C@H](COc2nsc3ccccc23)C1] | 2 | 1.96 | 335.1 |
| I-425 | 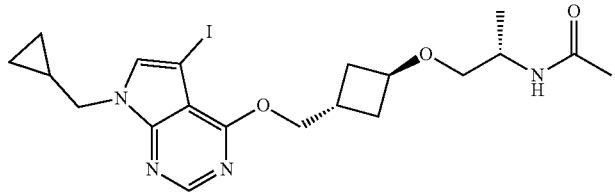 [SMILES: CC(=O)N[C@@H](C)CO[C@H]1C[C@H](COc2ncnc3c2c(I)cn3CC2CC2)C1] | 2 | 2.07 | 499.2 |
| I-426 | 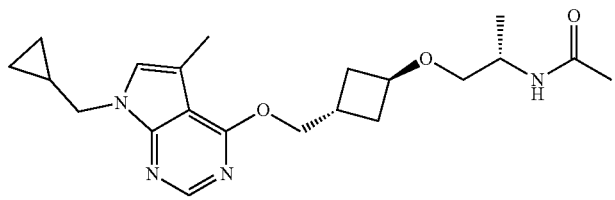 [SMILES: CC(=O)N[C@@H](C)CO[C@H]1C[C@H](COc2ncnc3c2c(C)cn3CC2CC2)C1] | 2 | 1.92 | 387.2 |
| I-427 | 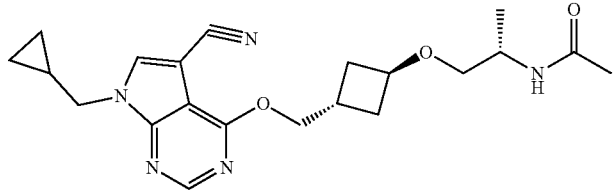 [SMILES: CC(=O)N[C@@H](C)CO[C@H]1C[C@H](COc2ncnc3c2c(C#N)cn3CC2CC2)C1] | 2 | 1.78 | 398.2 |
| I-428 | 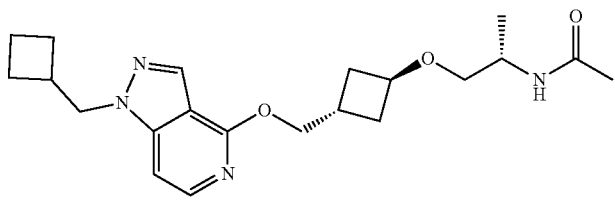 [SMILES: CC(=O)N[C@@H](C)CO[C@H]1C[C@H](COc2nccc3c2cnn3CC2CCC2)C1] | 2 | 1.82 | 387.2 |
TABLE 81
| | | | | |
|---|---|---|---|---|
| I-429 | 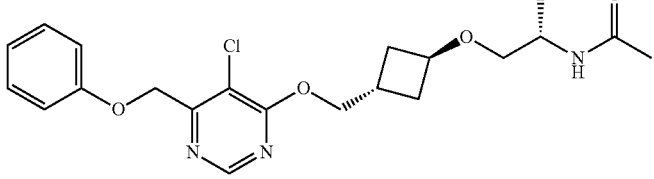 | 2 | 1.98 | 420.2 |
| I-430 | 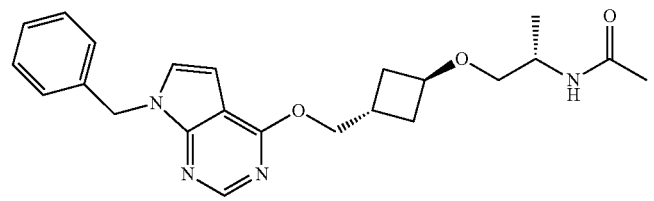 [SMILES: CC(=O)N[C@@H](C)CO[C@H]1C[C@H](COc2ncnc3c2ccn3Cc2ccccc2)C1] | 2 | 1.92 | 409.2 |

TABLE 81-continued
| | | | | |
|---|---|---|---|---|
| I-431 | 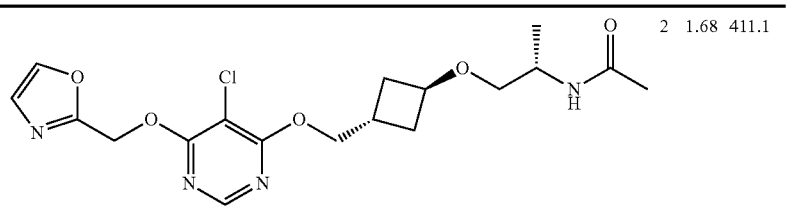 | 2 | 1.68 | 411.1 |
| I-432 | 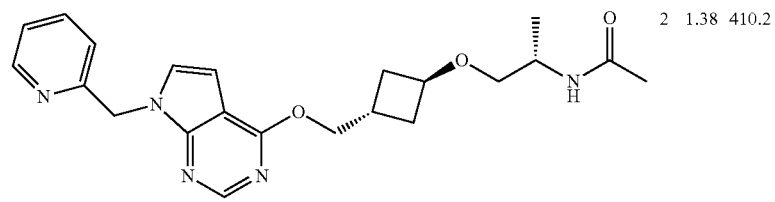 | 2 | 1.38 | 410.2 |
| I-433 | 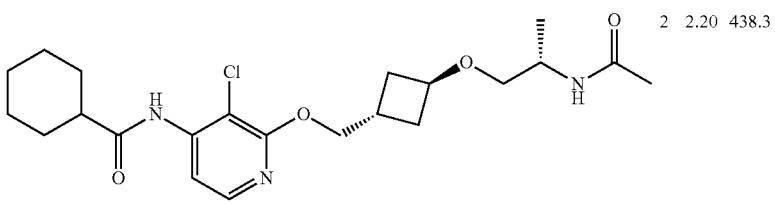 | 2 | 2.20 | 438.3 |
TABLE 82
| | | | | |
|---|---|---|---|---|
| I-434 | 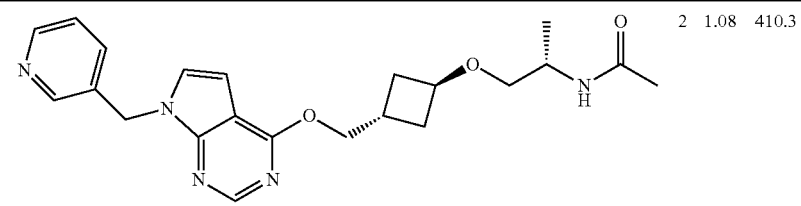 | 2 | 1.08 | 410.3 |
| I-435 | 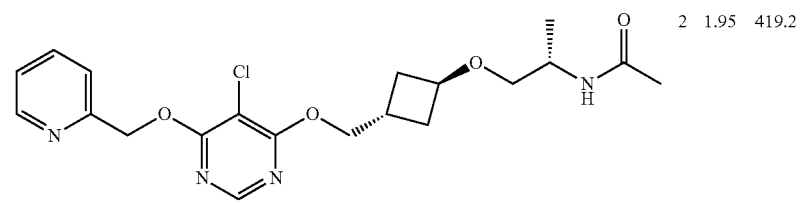 | 2 | 1.95 | 419.2 |
| I-436 | 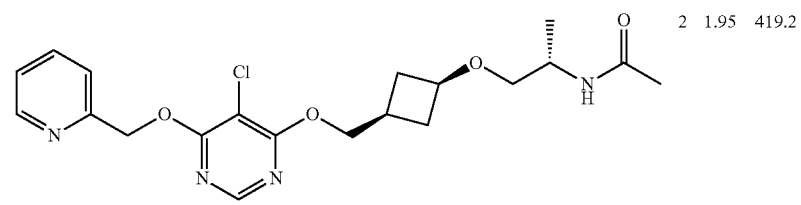 | 2 | 1.95 | 419.2 |
| I-437 | 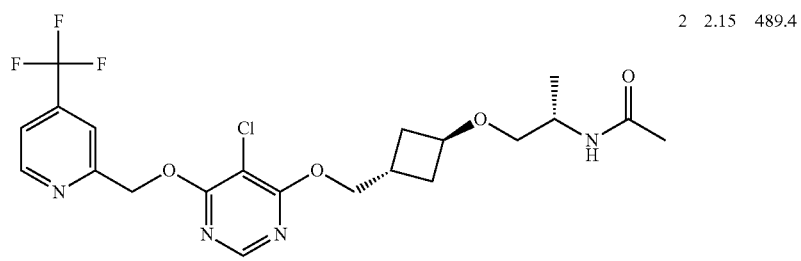 | 2 | 2.15 | 489.4 |

TABLE 82-continued
| I-438 | 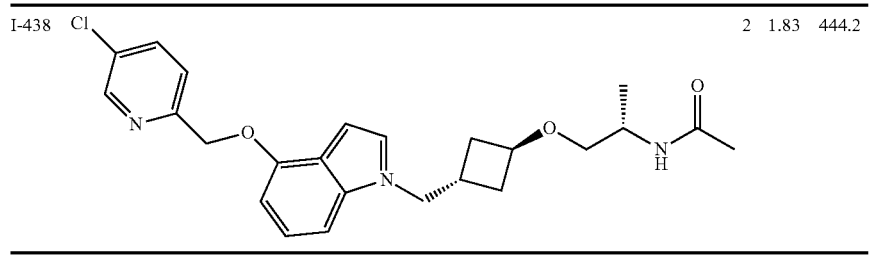 | 2 | 1.83 | 444.2 |
TABLE 83
| I-439 | 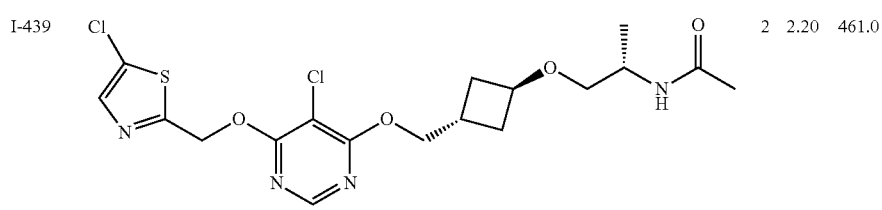 | 2 | 2.20 | 461.0 |
| I-440 | 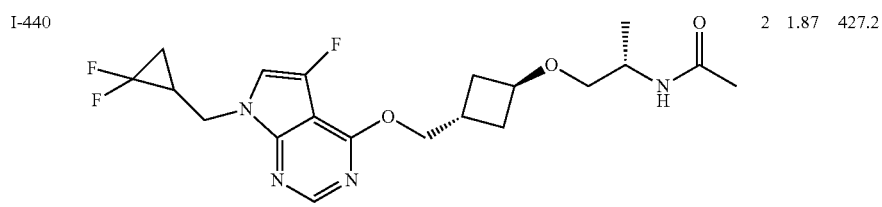 | 2 | 1.87 | 427.2 |
| I-441 | 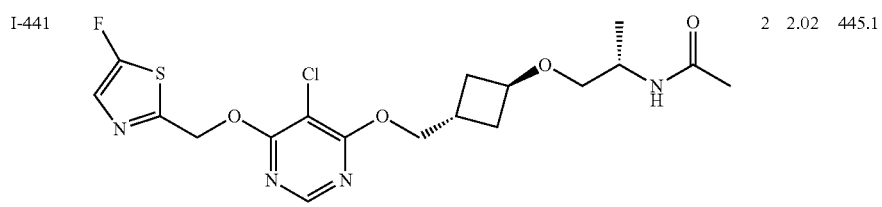 | 2 | 2.02 | 445.1 |
| I-442 | 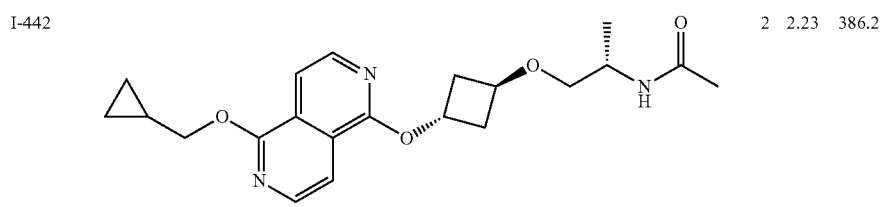 | 2 | 2.23 | 386.2 |
| I-443 | 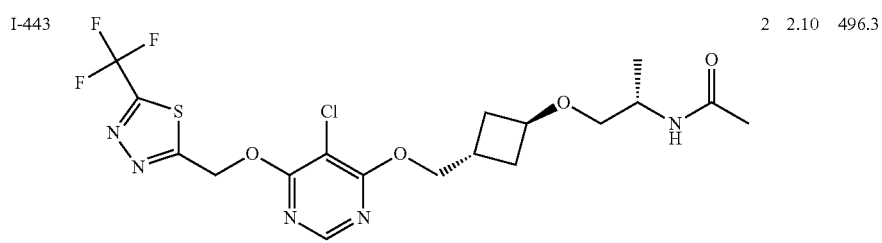 | 2 | 2.10 | 496.3 |

TABLE 84
| | | | | |
|---|---|---|---|---|
| I-444 | 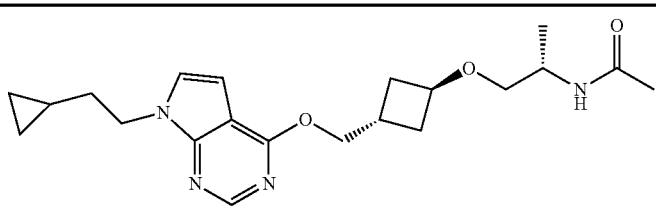 | 2 | 1.86 | 387.0 |
| I-445 | 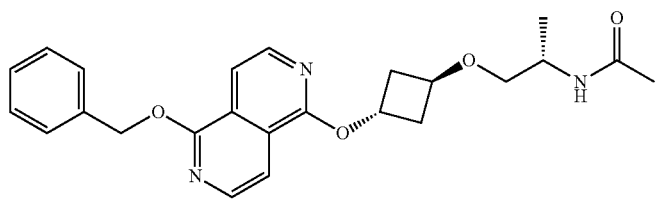 [SMILES: CC(=O)N[C@@H](C)CO[C@H]1C[C@H](Oc2nccc3c(OCc4ccccc4)nccc23)C1] | 2 | 2.36 | 422.2 |
| I-446 | 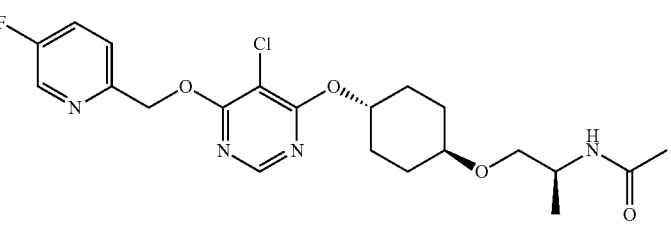 [SMILES: CC(=O)N[C@@H](C)CO[C@H]1CC[C@H](Oc2ncnc(OCc3ccc(F)cn3)c2Cl)CC1] | 2 | 2.04 | 453.2 |
| I-447 | 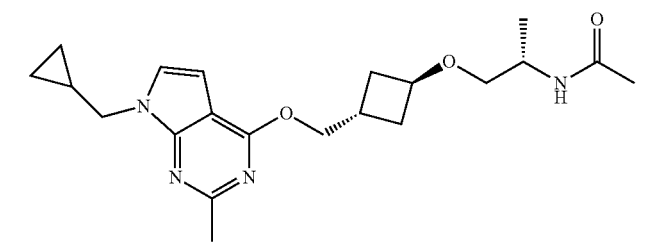 [SMILES: CC(=O)N[C@@H](C)CO[C@H]1C[C@H](COc2nc(C)nc3c2ccn3CC2CC2)C1] | 2 | 1.88 | 387.2 |
| I-448 | 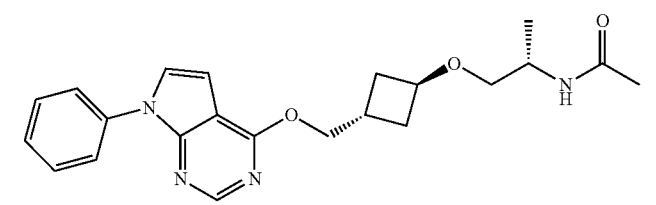 [SMILES: CC(=O)N[C@@H](C)CO[C@H]1C[C@H](COc2ncnc3c2ccn3-c2ccccc2)C1] | 2 | 1.93 | 395.2 |
TABLE 85
| | | | | |
|---|---|---|---|---|
| I-449 | 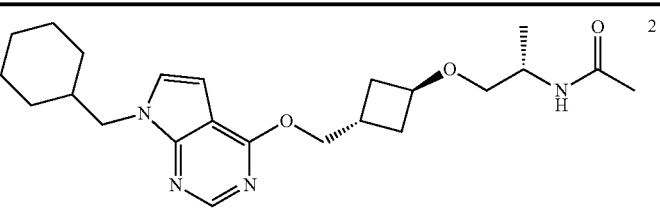 | 2 | 2.25 | 415.3 |
| I-450 | 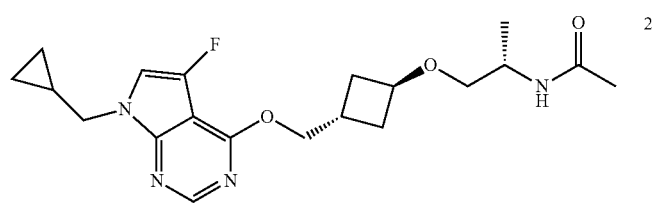 | 2 | 1.88 | 391.2 |

TABLE 85-continued

| ID | Structure | | | |
|---|---|---|---|---|
| I-451 | [structure] | 2 | 2.10 | 401.2 |
| I-452 | [structure] | 2 | 1.61 | 433.2 |
| I-453 | [structure] | 2 | 1.54 | 347.4 |

TABLE 86

| ID | Structure | | | |
|---|---|---|---|---|
| I-454 | [structure] | 2 | 1.88 | 387.4 |
| I-455 | [structure] | 2 | 2.32 | 475.2 |
| I-456 | [structure] | 2 | 1.98 | 396.2 |

TABLE 86-continued

| ID | Structure | | | |
|---|---|---|---|---|
| I-457 | (5-fluoropyridin-2-yl)methyl ether / 5-chloropyrimidine / methylcyclobutyl ether / (S)-N-acetyl propan-2-amine | 2 | 2.04 | 453.2 |
| I-458 | 1-(cyclopropylmethyl)-2,3-dihydro-1H-pyrrolo[3,2-c]pyridine / cyclobutyl ether / (S)-N-acetyl propan-2-amine | 2 | 1.10 | 374.3 |

TABLE 87

| ID | Structure | | | |
|---|---|---|---|---|
| I-459 | (5-fluoropyridin-2-yl)methyl ether / 5-fluoropyrimidine / cyclobutyl ether / (S)-N-acetyl propan-2-amine | 2 | 1.81 | 423.2 |
| I-460 | (4-chloropyridin-2-yl)methyl ether / 5-fluoropyrimidine / cyclobutyl ether / (S)-N-acetyl propan-2-amine | 2 | 1.92 | 439.3 |
| I-461 | (4-fluorobenzyl) ether / 5-fluoropyrimidine / cyclobutyl ether / (S)-N-acetyl propan-2-amine | 2 | 2.14 | 422.2 |
| I-462 | benzoxazol-2-yl / 5-chloropyrimidine / cyclobutyl ether / (S)-N-acetyl propan-2-amine | 2 | 1.90 | 431.3 |
| I-463 | (tetrahydro-2H-pyran-2-yl)methyl ether / 5-chloropyrimidine / cyclobutyl ether / (S)-N-acetyl propan-2-amine | 2 | 2.04 | 428.2 |

TABLE 88
| | | | | |
|---|---|---|---|---|
| I-464 | 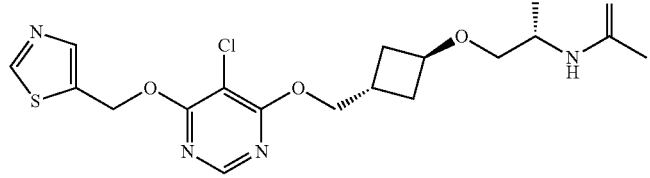 | 2 | 1.73 | 427.1 |
| I-465 | 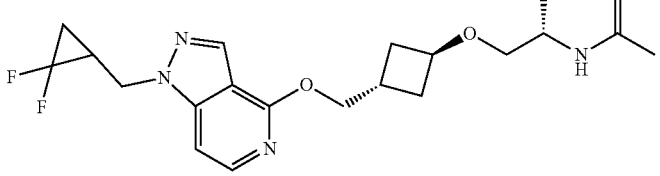 | 2 | 1.64 | 409.2 |
| I-466 | 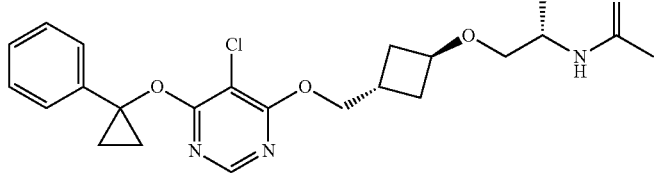 | 2 | 2.30 | 446.4 |
| I-467 | 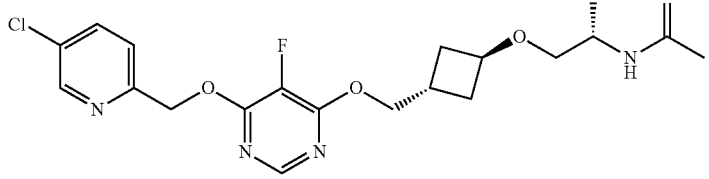 | 2 | 1.97 | 439.2 |
| I-468 | 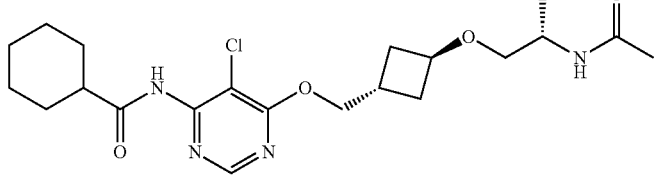 | 4 | 1.83 | 439.0 |
TABLE 89
| | | | | |
|---|---|---|---|---|
| I-469 | 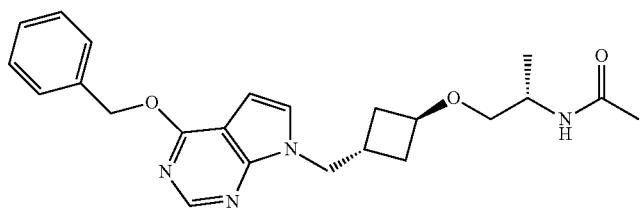 [SMILES: CC(=O)N[C@@H](C)CO[C@H]1C[C@H](Cn2ccc3c(OCc4ccccc4)ncnc32)C1] | 2 | 1.98 | 409.2 |
| I-470 | 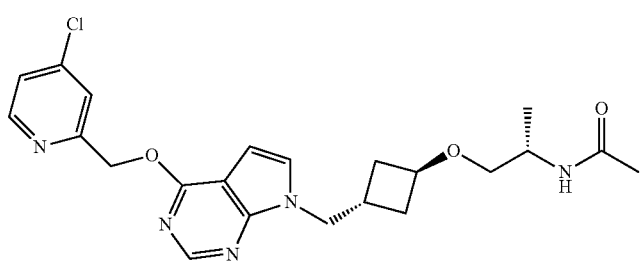 [SMILES: CC(=O)N[C@@H](C)CO[C@H]1C[C@H](Cn2ccc3c(OCc4cc(Cl)ccn4)ncnc32)C1] | 2 | 1.79 | 444.3 |

TABLE 89-continued
| I-471 | 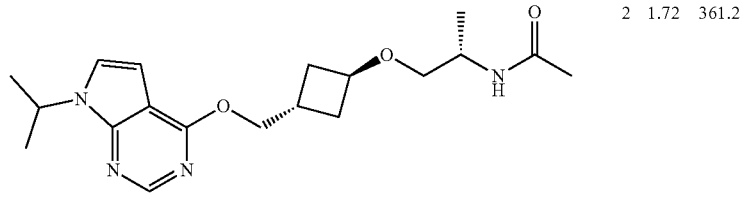 | 2 | 1.72 | 361.2 |
| I-472 | 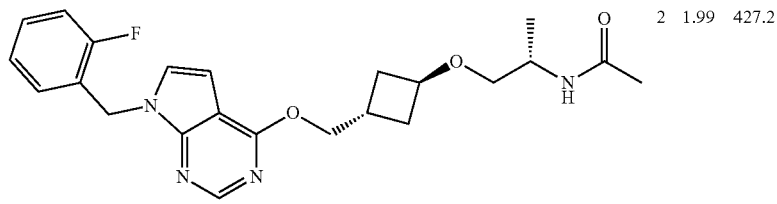 | 2 | 1.99 | 427.2 |
| I-473 | 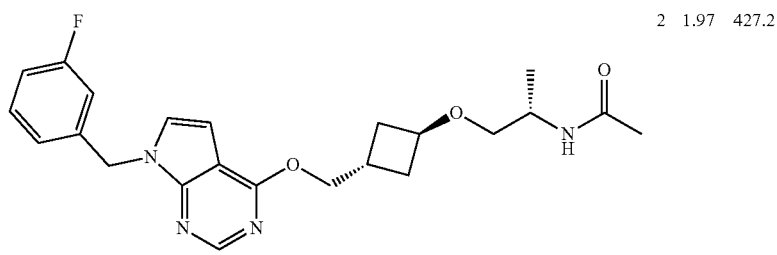 | 2 | 1.97 | 427.2 |
TABLE 90
| I-474 | 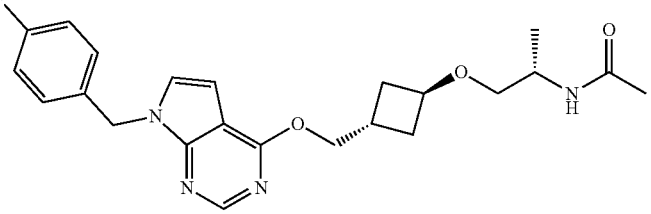 | 2 | 1.97 | 427.2 |
TABLE 91
| I-475 | 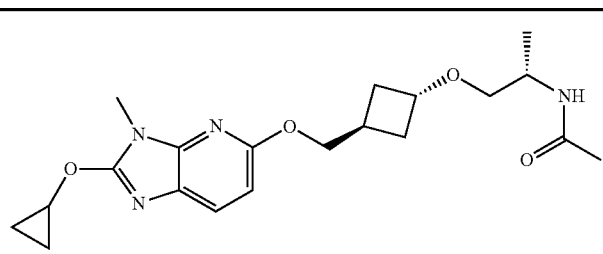 | 4 | 1.60 | 389.2 |
| I-476 | 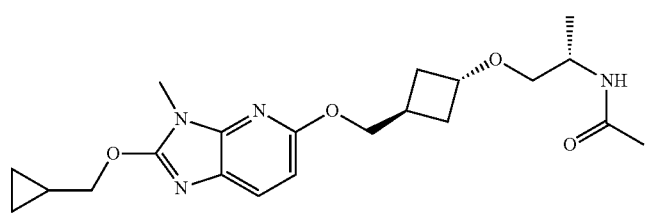 [SMILES: CC(=O)N[C@@H](C)CO[C@H]1C[C@H](COc2ccc3nc(OCC4CC4)n(C)c3n2)C1] | 4 | 1.83 | 403.2 |

TABLE 91-continued

| I-477 | | 4 | 1.90 | 439.4 |
|---|---|---|---|---|
| I-478 | | 4 | 1.92 | 439.4 |
| I-479 | | 4 | 1.72 | 391.1 |

TABLE 92

| I-480 | | 4 | 2.07 | 439.2 |
|---|---|---|---|---|
| I-481 | | 4 | 1.98 | 425.2 |
| I-482 | | 4 | 2.18 | 419.4 |

TABLE 92-continued

| | | | | |
|---|---|---|---|---|
| I-483 | [structure] | 4 | 1.79 | 391.0 |
| I-484 | [structure] | 4 | 1.73 | 413.1 |

TABLE 93

| | | | | |
|---|---|---|---|---|
| I-485 | [structure] | 4 | 1.71 | 409.2 |
| I-486 | [structure] | 4 | 1.89 | 417.7 |
| I-487 | [structure] | 4 | 1.63 | 394.5 |
| I-488 | [structure] | 4 | 1.90 | 411.2 |
| I-489 | [structure] | 4 | 1.50 | 402.3 |

TABLE 94

| | | | | |
|---|---|---|---|---|
| I-490 | (structure) | 4 | 1.79 | 410.3 |
| I-491 | (structure) | 4 | 1.62 | 391.5 |
| I-492 | (structure) | 2 | 1.69 | 479.1 |
| I-493 | (structure) | 2 | 1.81 | 405.6 |
| I-494 | (structure) | 2 | 1.79 | 405.5 |

TABLE 95
I-495 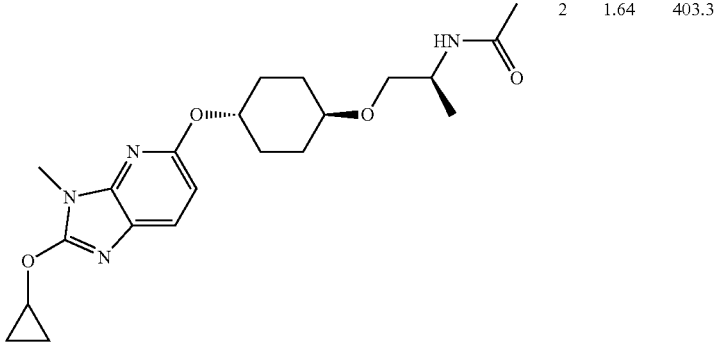 2 1.64 403.3
I-496 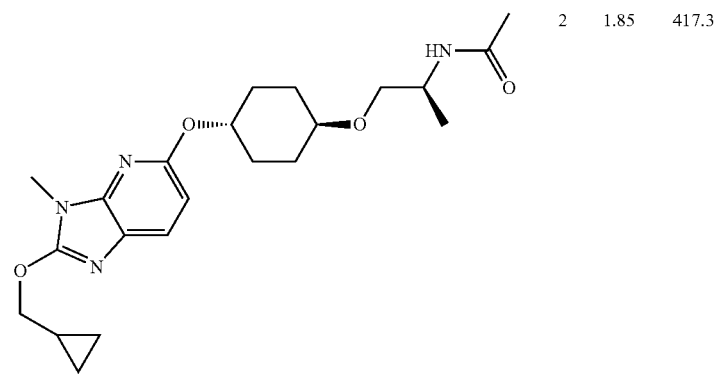 2 1.85 417.3
I-497 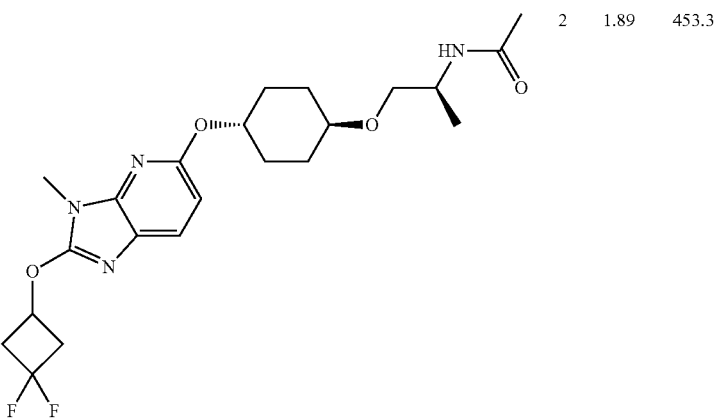 2 1.89 453.3
I-498 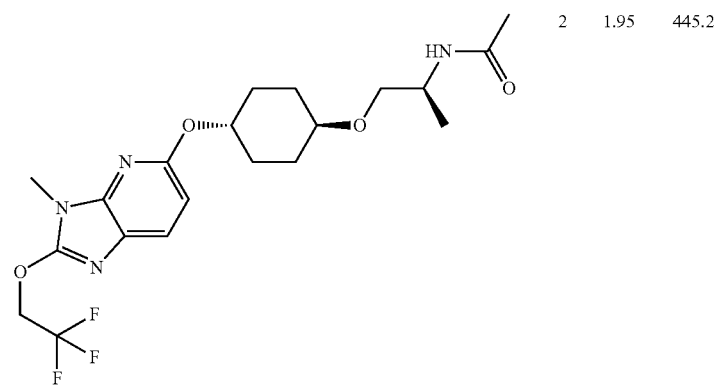 2 1.95 445.2

TABLE 95-continued
| | | | | |
|---|---|---|---|---|
| I-499 | 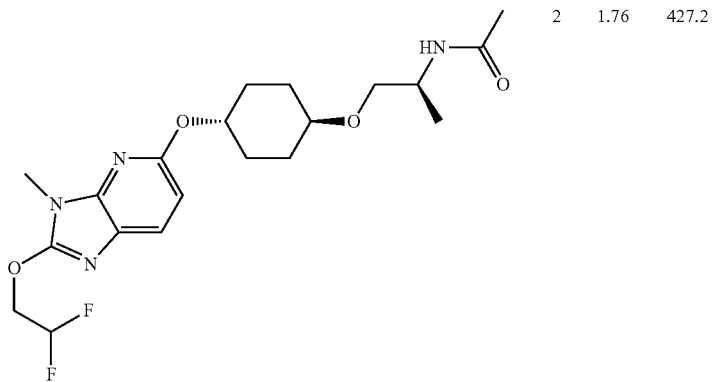 | 2 | 1.76 | 427.2 |
TABLE 96
| | | | | |
|---|---|---|---|---|
| I-500 | 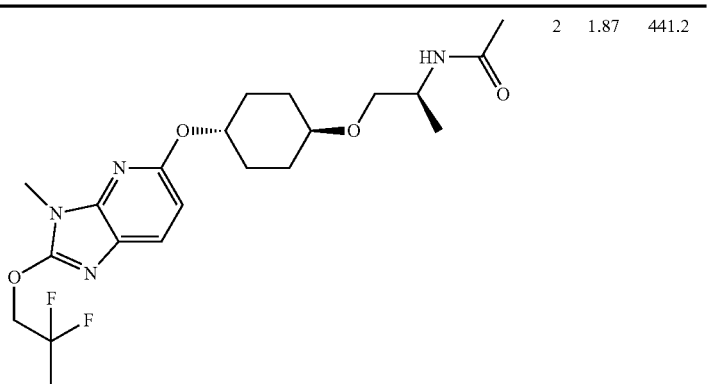 | 2 | 1.87 | 441.2 |
| I-501 | 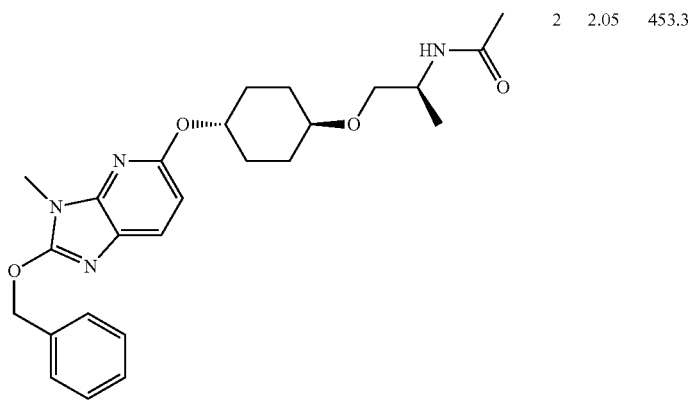 | 2 | 2.05 | 453.3 |
| I-502 | 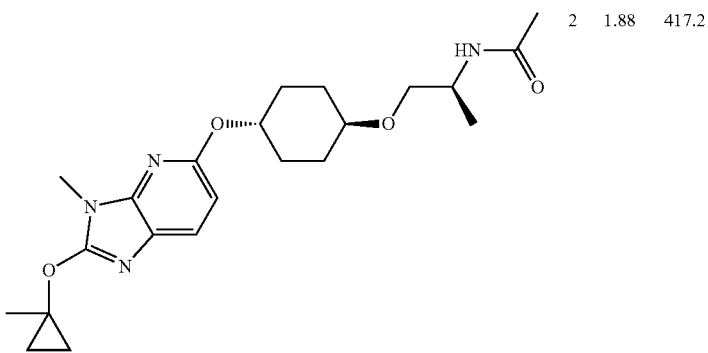 | 2 | 1.88 | 417.2 |

TABLE 96-continued
| I-503 | 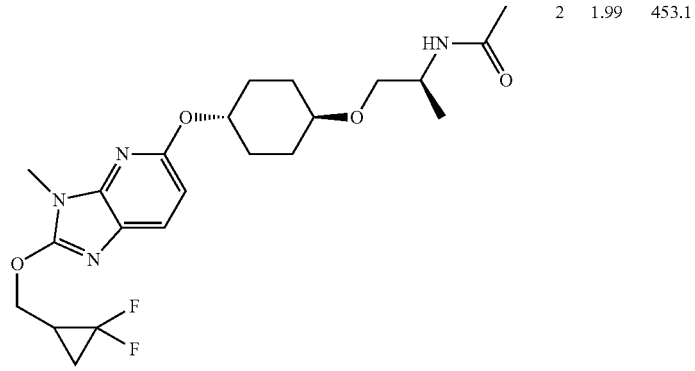 | 2 | 1.99 | 453.1 |
| I-504 | 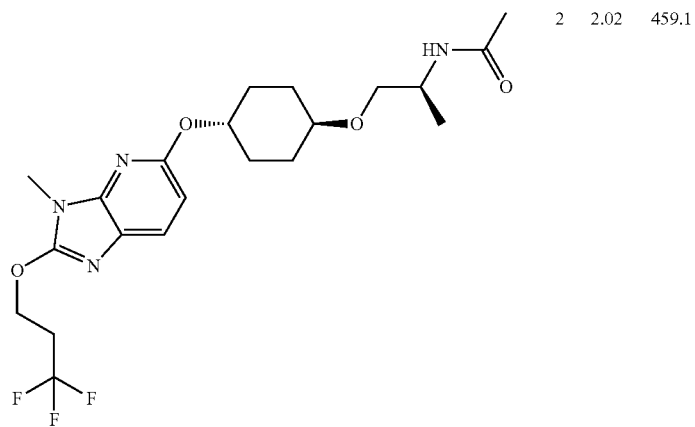 | 2 | 2.02 | 459.1 |
TABLE 97
| I-505 | 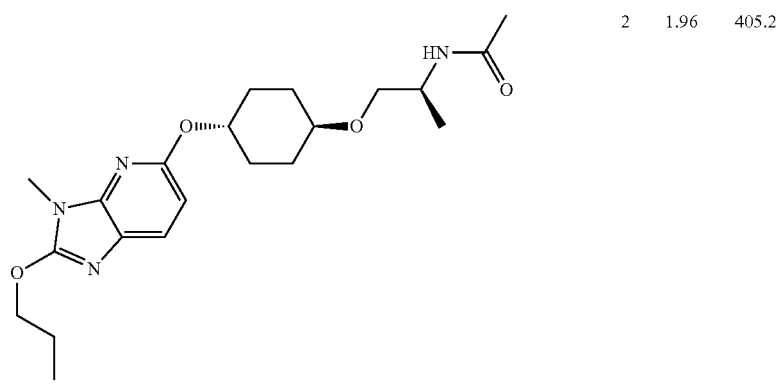 | 2 | 1.96 | 405.2 |
| I-506 | 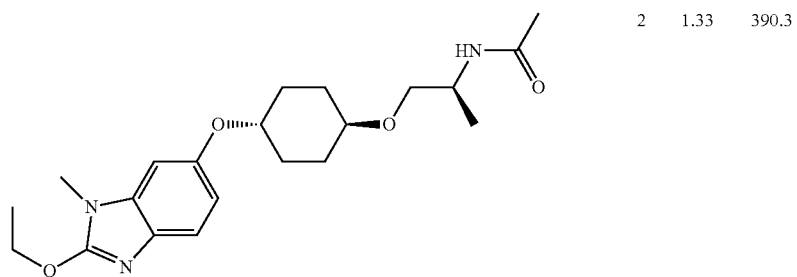 | 2 | 1.33 | 390.3 |

TABLE 97-continued
| | | | | |
|---|---|---|---|---|
| I-507 | 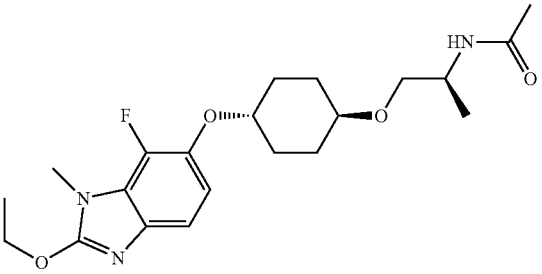 [SMILES: CCOc1nc2ccc(O[C@H]3CC[C@H](OC[C@H](C)NC(C)=O)CC3)c(F)c2n1C] | 2 | 1.88 | 408.1 |
| I-508 | 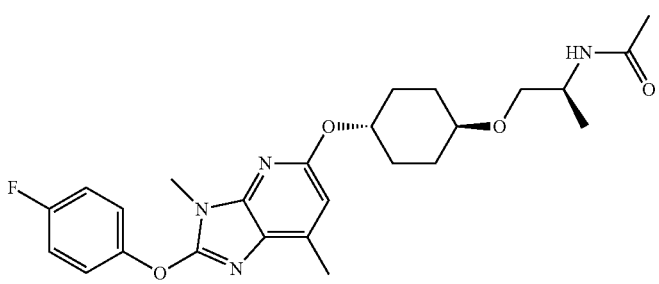 [SMILES: CC(=O)N[C@@H](C)CO[C@H]1CC[C@H](Oc2cc(C)c3nc(Oc4ccc(F)cc4)n(C)c3n2)CC1] | 2 | 2.27 | 471.2 |
| I-509 | 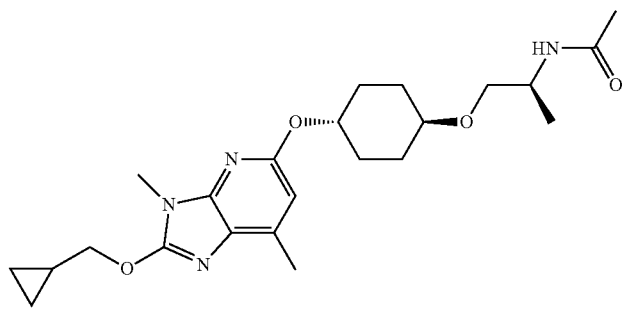 [SMILES: CC(=O)N[C@@H](C)CO[C@H]1CC[C@H](Oc2cc(C)c3nc(OCC4CC4)n(C)c3n2)CC1] | 2 | 1.99 | 431.3 |
TABLE 98
| | | | | |
|---|---|---|---|---|
| I-510 | 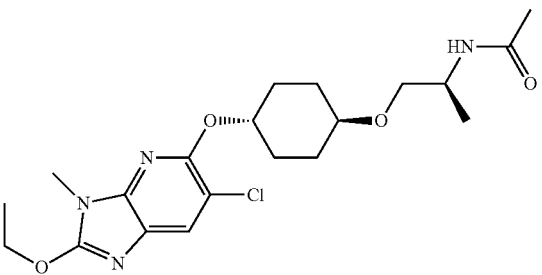 [SMILES: CCOc1nc2cc(Cl)c(O[C@H]3CC[C@H](OC[C@H](C)NC(C)=O)CC3)nc2n1C] | 2 | 2.01 | 425.1 |
| I-511 | 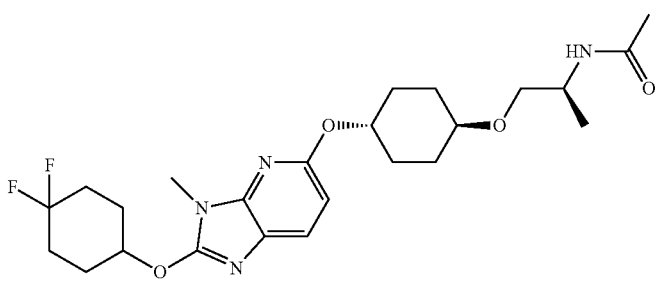 [SMILES: CC(=O)N[C@@H](C)CO[C@H]1CC[C@H](Oc2ccc3nc(OC4CCC(F)(F)CC4)n(C)c3n2)CC1] | 2 | 2.01 | 481.3 |

TABLE 98-continued

| ID | Structure | | | |
|---|---|---|---|---|
| I-512 | (structure) | 2 | 1.12 | 401.3 |
| I-513 | (structure) | 2 | 1.09 | 389.6 |
| I-514 | (structure) | 2 | 1.22 | 415.6 |

TABLE 99

| ID | Structure | | | |
|---|---|---|---|---|
| I-515 | (structure) | 2 | 1.50 | 443.6 |
| I-516 | (structure) | 2 | 1.91 | 409.1 |

TABLE 99-continued
| ID | Structure | | | |
|---|---|---|---|---|
| I-517 | 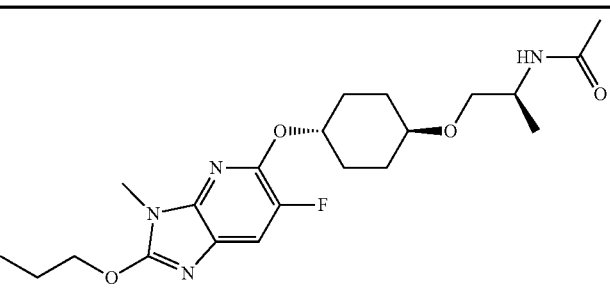 | 2 | 2.02 | 423.4 |
| I-518 | 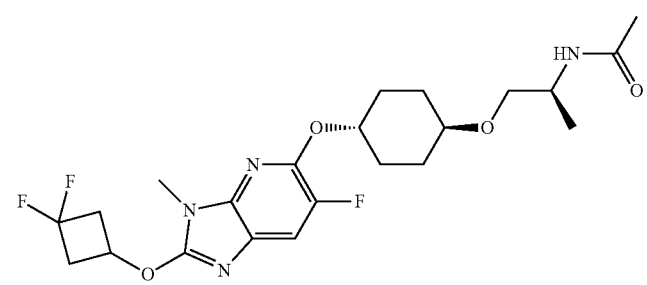 [SMILES: CC(=O)N[C@@H](C)CO[C@H]1CC[C@H](Oc2nc3c(cc2F)nc(OC2CC(F)(F)C2)n3C)CC1] | 2 | 2.04 | 471.5 |
| I-519 | 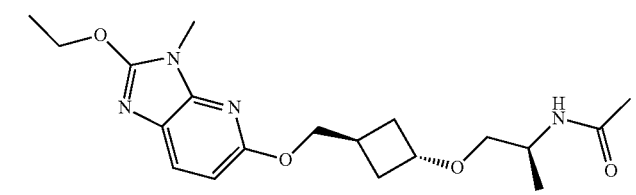 [SMILES: CCOc1nc2ccc(OC[C@H]3C[C@H](OC[C@H](C)NC(C)=O)C3)nc2n1C] | 4 | 1.54 | 377.0 |
TABLE 100
| ID | Structure | | | |
|---|---|---|---|---|
| I-520 | 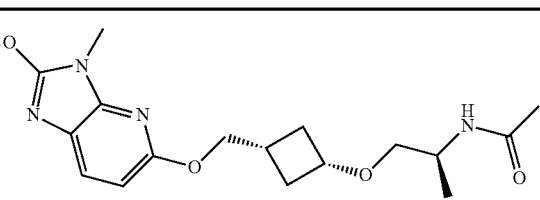 | 4 | 1.58 | 377.2 |
TABLE 101
| ID | Structure | | | |
|---|---|---|---|---|
| I-521 | 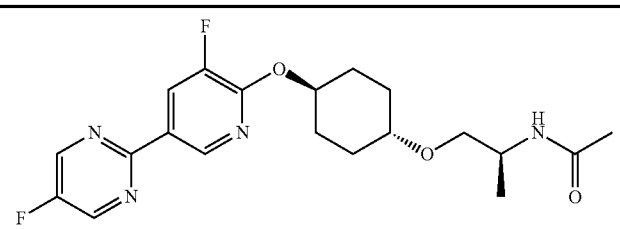 | 2 | 2.04 | 407.2 |
| I-522 | 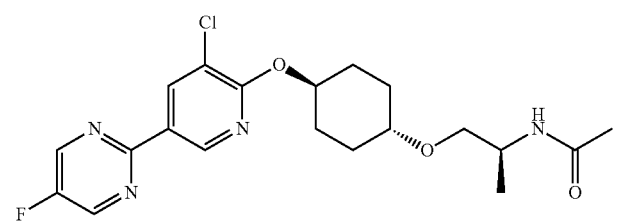 [SMILES: CC(=O)N[C@@H](C)CO[C@H]1CC[C@H](Oc2ncc(-c3ncc(F)cn3)cc2F)CC1] | 3 | 2.32 | 423.2 |

TABLE 101-continued
| | | | | |
|---|---|---|---|---|
| I-523 | 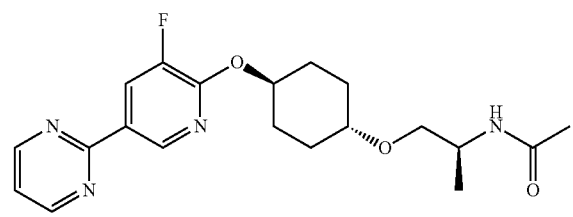 [SMILES: CC(=O)N[C@@H](C)CO[C@H]1CC[C@H](Oc2ncc(-c3ncccn3)cc2F)CC1] | 3 | 1.97 | 389.2 |
| I-524 | 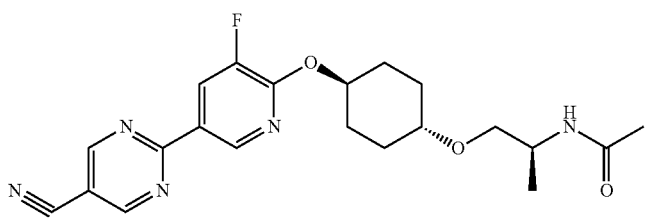 [SMILES: CC(=O)N[C@@H](C)CO[C@H]1CC[C@H](Oc2ncc(-c3ncc(C#N)cn3)cc2F)CC1] | 3 | 2.03 | 414.2 |
| I-525 | 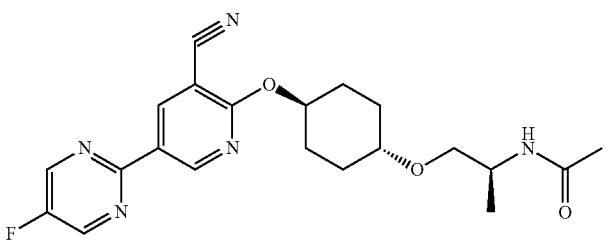 [SMILES: CC(=O)N[C@@H](C)CO[C@H]1CC[C@H](Oc2ncc(-c3ncc(F)cn3)cc2C#N)CC1] | 3 | 2.04 | 414.2 |
TABLE 102
| | | | | |
|---|---|---|---|---|
| I-526 | 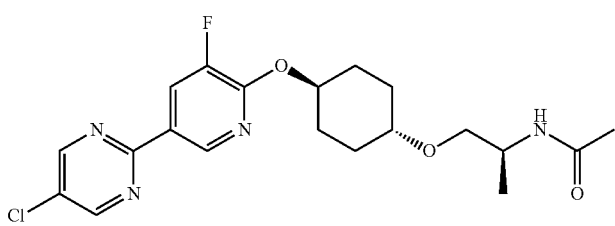 [SMILES: CC(=O)N[C@@H](C)CO[C@H]1CC[C@H](Oc2ncc(-c3ncc(Cl)cn3)cc2F)CC1] | 3 | 2.27 | 423.2 |
| I-527 | 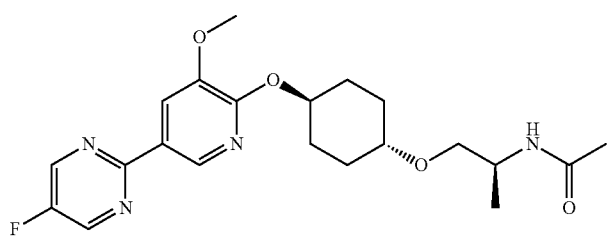 [SMILES: COc1cc(-c2ncc(F)cn2)cnc1O[C@H]1CC[C@H](OC[C@H](C)NC(C)=O)CC1] | 3 | 1.93 | 419.2 |
| I-528 | 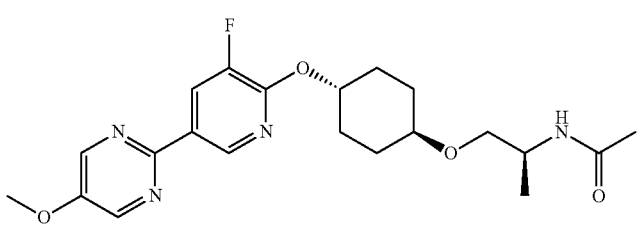 [SMILES: COc1cnc(-c2cnc(O[C@H]3CC[C@H](OC[C@H](C)NC(C)=O)CC3)c(F)c2)nc1] | 3 | 2.07 | 419.2 |

TABLE 102-continued

| ID | Structure | | | |
|---|---|---|---|---|
| I-529 | (structure) | 3 | 2.40 | 431.2 |
| I-530 | (structure) | 3 | 1.85 | 421.2 |

TABLE 103

| ID | Structure | | | |
|---|---|---|---|---|
| I-531 | (structure) | 2 | 1.99 | 414.25 |
| I-532 | (structure) | 3 | 2.20 | 403.2 |
| I-533 | (structure) | 3 | 2.26 | 417.2 |
| I-534 | (structure) | 3 | 2.12 | 403.2 |

TABLE 103-continued

| ID | Structure | | | |
|---|---|---|---|---|
| I-535 | (5-chloropyrimidin-2-yl / cyanopyridine / cyclohexyl-O-CH2-CH(CH3)-NHAc) | 3 | 2.23 | 430.1 |

TABLE 104

| ID | Structure | | | |
|---|---|---|---|---|
| I-536 | (5-cyclopropylpyrimidin-2-yl / 3-fluoropyridine / cyclohexyl-O-CH2-CH(CH3)-NHAc) | 3 | 2.29 | 429.2 |
| I-537 | (5-fluoropyrimidin-2-yl / 3-benzyloxypyridine / cyclohexyl-O-CH2-CH(CH3)-NHAc) | 3 | 2.23 | 495.2 |
| I-538 | (5-fluoropyrimidin-2-yl / 3-fluoropyridine / cyclohexyl-O-CH2-CH(CH3)-NHC(O)NH2) | 2 | 1.89 | 408.6 |
| I-539 | (5-fluoropyrimidin-2-yl / 3-fluoropyridine / cyclohexyl-O-CH2-CH(CH3)-NHC(O)-pyridine-CO2Et) | 2 | 2.32 | 542.2 |
| I-540 | (5-fluoropyrimidin-2-yl / 3-fluoropyridine / cyclohexyl-O-CH2-CH(CH3)-NHSO2Me) | 2 | 2.20 | 443.2 |

TABLE 105

| ID | Structure | | | |
|---|---|---|---|---|
| I-541 | 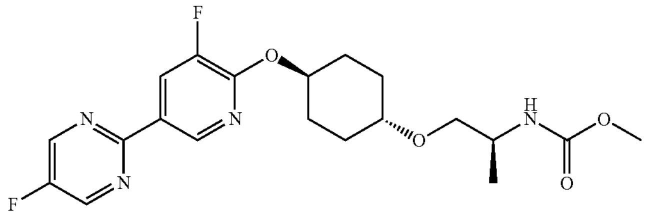 [SMILES: COC(=O)N[C@@H](C)CO[C@H]1CC[C@H](Oc2ncc(-c3ncc(F)cn3)cc2F)CC1] | 2 | 2.34 | 423.2 |
| I-542 | 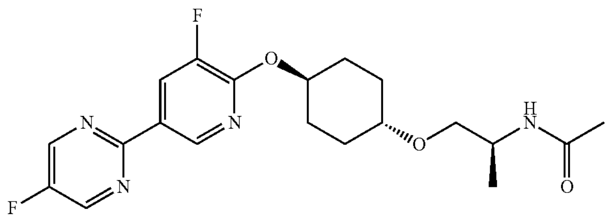 | 2 | 2.40 | 405.3 |
| I-543 | 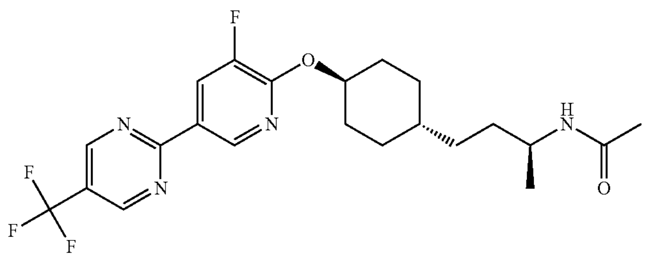 [SMILES: CC(=O)N[C@@H](C)CO[C@H]1CC[C@H](Oc2ncc(-c3ncc(C(F)(F)F)cn3)cc2F)CC1] | 2 | 2.71 | 455.3 |
| I-544 | 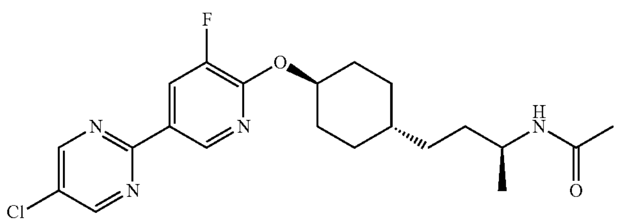 | 2 | 2.67 | 421.3 |
| I-545 | 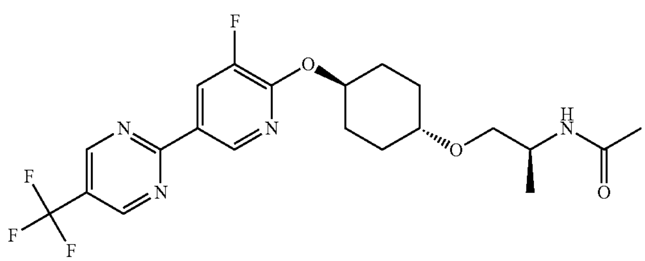 | 4 | 2.37 | 457.2 |

TABLE 106

| ID | Structure | | | |
|---|---|---|---|---|
| I-546 | 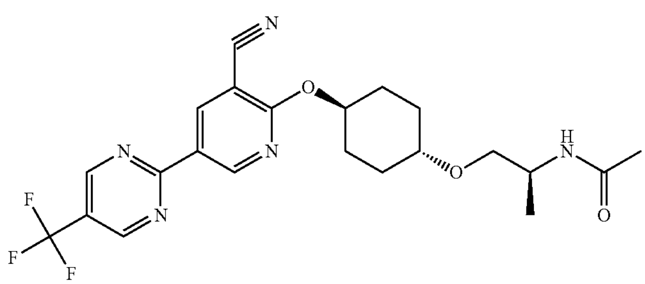 [SMILES: CC(=O)N[C@@H](C)CO[C@H]1CC[C@H](Oc2ncc(-c3ncc(C(F)(F)F)cn3)cc2C#N)CC1] | 4 | 2.25 | 464.2 |

TABLE 107
| | | | | |
|---|---|---|---|---|
| I-547 | 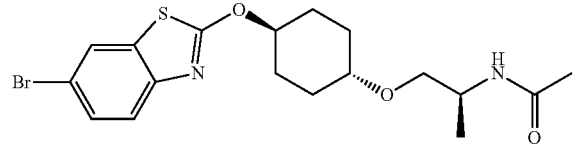 [SMILES: CC(=O)N[C@@H](C)CO[C@H]1CC[C@H](Oc2nc3ccc(Br)cc3s2)CC1] | 2 | 2.43 | 427.2 |
| I-548 | 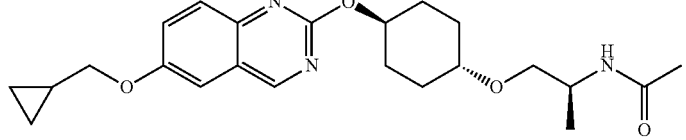 | 3 | 2.08 | 414.3 |
| I-549 | 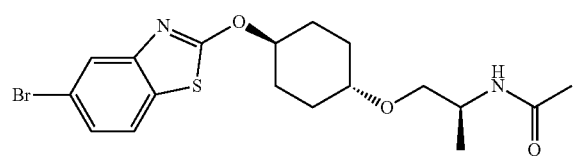 | 3 | 2.39 | 427.2 |
| I-550 | 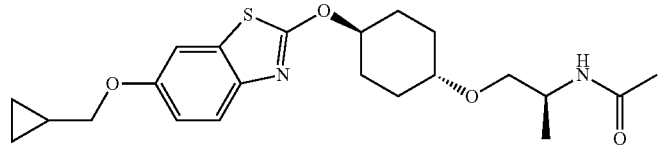 [SMILES: CC(=O)N[C@@H](C)CO[C@H]1CC[C@H](Oc2nc3ccc(OCC4CC4)cc3s2)CC1] | 3 | 2.36 | 419.3 |
| I-551 | 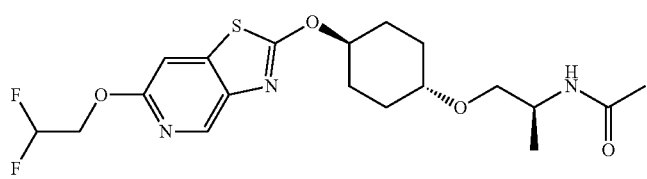 [SMILES: CC(=O)N[C@@H](C)CO[C@H]1CC[C@H](Oc2nc3cnc(OCC(F)F)cc3s2)CC1] | 2 | 2.07 | 430.5 |
TABLE 108
| | | | | |
|---|---|---|---|---|
| I-552 | 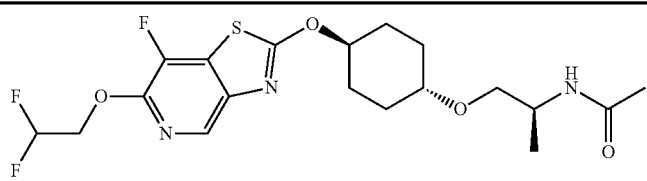 | 2 | 2.22 | 448.3 |
| I-553 | 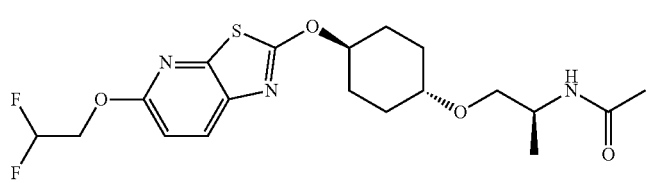 [SMILES: CC(=O)N[C@@H](C)CO[C@H]1CC[C@H](Oc2nc3ccc(OCC(F)F)nc3s2)CC1] | 3 | 2.18 | 430.1 |
| I-554 | 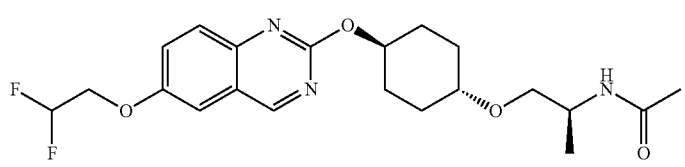 [SMILES: CC(=O)N[C@@H](C)CO[C@H]1CC[C@H](Oc2ncc3cc(OCC(F)F)ccc3n2)CC1] | 3 | 1.84 | 424.0 |

TABLE 108-continued
| I-555 | 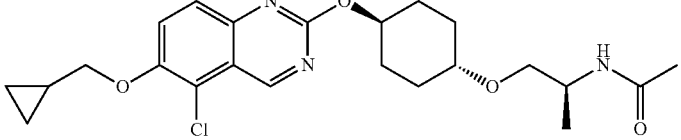 | 3 | 2.26 | 448.1 |
TABLE 109
| 実施例 No. | 構造式 | 測定条件 | 保持時間 (分) | [M + H] |
|---|---|---|---|---|
| I-556 | | 3 | 2.00 | 424.2 |
| I-557 | | 3 | 1.99 | 424.2 |
| I-558 | | 3 | 1.94 | 452.3 |
| I-559 | | 3 | 1.62 | 390.2 |
| I-560 | | 3 | 1.75 | 404.3 |
TABLE 110
| I-561 | 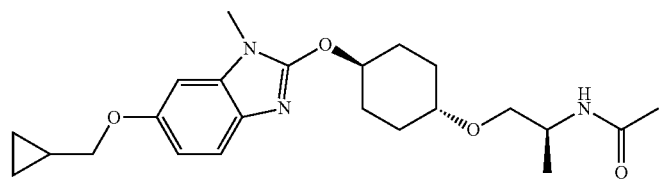 [SMILES: CC(=O)N[C@@H](C)CO[C@H]1CC[C@H](Oc2nc3ccc(OCC4CC4)cc3n2C)CC1] | 3 | 1.67 | 416.1 |

TABLE 110-continued
| | | | | |
|---|---|---|---|---|
| I-562 | 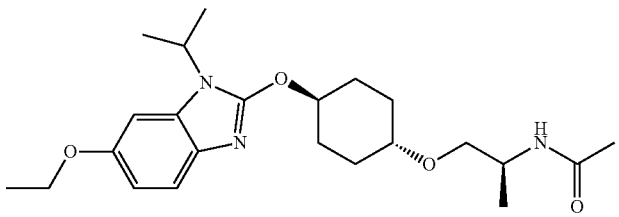 [SMILES: CCOc1ccc2nc(O[C@H]3CC[C@H](OC[C@H](C)NC(C)=O)CC3)n(C(C)C)c2c1] | 3 | 1.88 | 418.3 |
| I-563 | 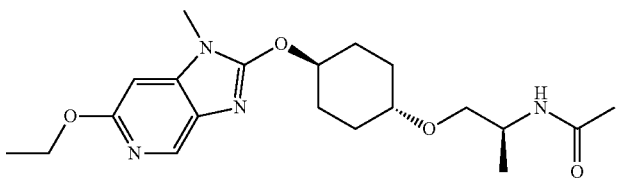 [SMILES: CCOc1cc2c(cn1)nc(O[C@H]1CC[C@H](OC[C@H](C)NC(C)=O)CC1)n2C] | 3 | 1.28 | 391.2 |
| I-564 | 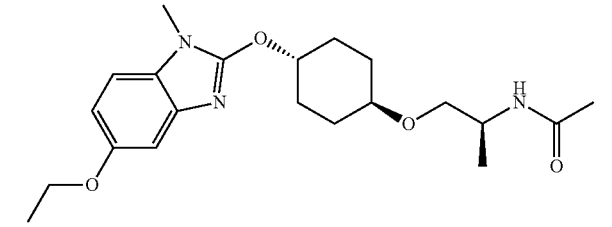 [SMILES: CCOc1ccc2c(c1)nc(O[C@H]1CC[C@H](OC[C@H](C)NC(C)=O)CC1)n2C] | 2 | 1.45 | 390.2 |
| I-565 | 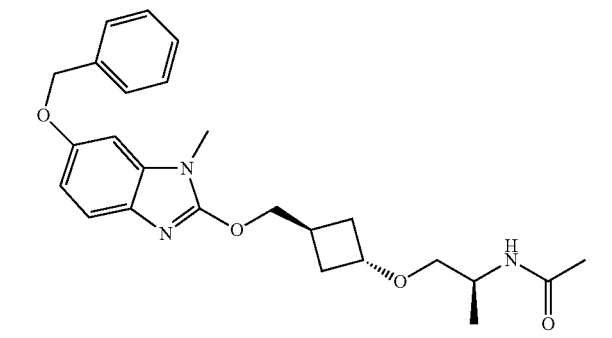 [SMILES: CC(=O)N[C@@H](C)CO[C@H]1C[C@H](COc2nc3ccc(OCc4ccccc4)cc3n2C)C1] | 4 | 1.80 | 438.3 |
TABLE 111
| | | | | |
|---|---|---|---|---|
| I-566 | 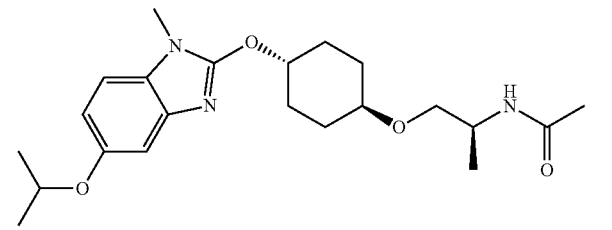 [SMILES: CC(=O)N[C@@H](C)CO[C@H]1CC[C@H](Oc2nc3cc(OC(C)C)ccc3n2C)CC1] | 2 | 1.57 | 404.2 |
| I-567 | 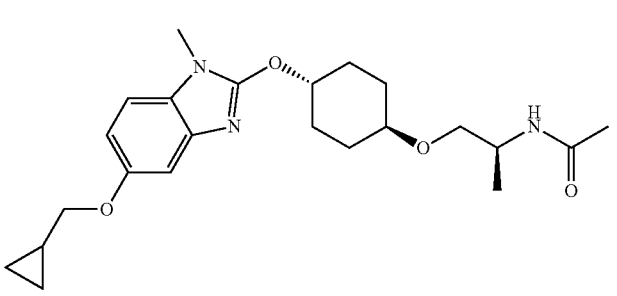 [SMILES: CC(=O)N[C@@H](C)CO[C@H]1CC[C@H](Oc2nc3cc(OCC4CC4)ccc3n2C)CC1] | 2 | 1.59 | 416.5 |

TABLE 111-continued

| ID | Structure | a | b | c |
|---|---|---|---|---|
| I-568 | cyclopropyl-N-benzimidazole with ethoxy, O-cyclohexyl-O-CH2-CH(CH3)-NHAc | 3 | 1.71 | 416.3 |
| I-569 | 1-methyl-benzimidazole with OCH2CHF2, O-cyclohexyl-O-CH2-CH(CH3)-NHAc | 2 | 1.52 | 424.2 |
| I-570 | 1-methyl-benzimidazole with OMe, O-cyclohexyl-O-CH2-CH(CH3)-NHAc | 2 | 1.28 | 376.1 |

TABLE 112

| ID | Structure | a | b | c |
|---|---|---|---|---|
| I-571 | 1-methyl-benzimidazole with OCH2CF3, O-cyclohexyl-O-CH2-CH(CH3)-NHAc | 3 | 1.88 | 444.2 |
| I-572 | 1-methyl-benzimidazole with OCF3, O-cyclohexyl-O-CH2-CH(CH3)-NHAc | 3 | 2.12 | 430.1 |
| I-573 | 1-methyl-benzimidazole with propyl, O-cyclohexyl-O-CH2-CH(CH3)-NHAc | 2 | 1.72 | 388.3 |
| I-574 | 1-methyl-benzimidazole with cyclopropyl, O-cyclohexyl-O-CH2-CH(CH3)-NHAc | 2 | 1.56 | 386.3 |

TABLE 112-continued

| ID | Structure | a | b | c |
|---|---|---|---|---|
| I-575 | (3,3-difluoroazetidinyl-benzimidazole-O-cyclohexyl-O-CH2-CH(CH3)-NHAc) | 2 | 1.45 | 437.3 |

TABLE 113

| ID | Structure | a | b | c |
|---|---|---|---|---|
| I-576 | (cyclopropylmethyl-NH-benzimidazole-O-cyclohexyl-O-CH2-CH(CH3)-NHAc) | 2 | 1.10 | 415.3 |
| I-577 | (ethylthio-benzimidazole-O-cyclohexyl-O-CH2-CH(CH3)-NHAc) | 2 | 1.84 | 406.2 |
| I-578 | (isobutylthio-benzimidazole-O-cyclohexyl-O-CH2-CH(CH3)-NHAc) | 2 | 2.17 | 434.3 |
| I-579 | (ethoxy-N-ethyl-benzimidazole-O-cyclohexyl-O-CH2-CH(CH3)-NHAc) | 2 | 1.57 | 404.3 |
| I-580 | (ethylsulfonyl-benzimidazole-O-cyclohexyl-O-CH2-CH(CH3)-NHAc) | 2 | 1.44 | 438.2 |

TABLE 114

| ID | Structure | a | b | c |
|---|---|---|---|---|
| I-581 | (isobutylsulfonyl-benzimidazole-O-cyclohexyl-O-CH2-CH(CH3)-NHAc) | 3 | 1.87 | 466.2 |

TABLE 114-continued

| ID | Structure | a | b | c |
|---|---|---|---|---|
| I-582 | 1-methyl-6-phenyl-benzimidazole linked via O-cyclohexyl-O-CH2-CH(CH3)-NHAc | 3 | 2.06 | 422.2 |
| I-583 | 1-methyl-6-ethyl-benzimidazole linked via O-cyclohexyl-O-CH2-CH(CH3)-NHAc | 2 | 1.52 | 374.3 |
| I-584 | 1-methyl-6-vinyl-benzimidazole linked via O-cyclohexyl-O-CH2-CH(CH3)-NHAc | 2 | 1.64 | 372.2 |
| I-585 | 1-methyl-6-isopropyl-benzimidazole linked via O-cyclohexyl-O-CH2-CH(CH3)-NHAc | 2 | 1.67 | 388.3 |

TABLE 115

| ID | Structure | a | b | c |
|---|---|---|---|---|
| I-586 | 1-methyl-6-phenoxy-benzimidazole linked via O-cyclohexyl-O-CH2-CH(CH3)-NHAc | 3 | 2.08 | 438.2 |
| I-587 | 1-methyl-5-trifluoromethyl-benzimidazole linked via O-cyclohexyl-O-CH2-CH(CH3)-NHAc | 2 | 1.98 | 414.2 |
| I-588 | 1-methyl-6-trifluoromethyl-benzimidazole linked via O-cyclohexyl-O-CH2-CH(CH3)-NHAc | 2 | 1.98 | 414.5 |

TABLE 115-continued

| ID | Structure | | | |
|---|---|---|---|---|
| I-589 | (1-methyl-6-(pyridin-3-yl)-1H-benzimidazol-2-yl)oxy-cyclohexyl ether with (S)-N-acetyl-propan-2-amine | 2 | 1.08 | 423.2 |
| I-590 | (1-methyl-6-(pyridin-2-yloxy)-1H-benzimidazol-2-yl)oxy-cyclohexyl ether with (S)-N-acetyl-propan-2-amine | 3 | 1.69 | 439.2 |

TABLE 116

| ID | Structure | | | |
|---|---|---|---|---|
| I-591 | 6-cyclopropyl-1-methyl-1H-imidazo[4,5-b]pyridin-2-yl)oxy-cyclohexyl ether with (S)-N-acetyl-propan-2-amine | 2 | 1.15 | 387.3 |
| I-592 | 1-methyl-6-phenoxy-1H-imidazo[4,5-b]pyridin-2-yl)oxy-cyclohexyl ether with (S)-N-acetyl-propan-2-amine | 2 | 1.65 | 439.3 |
| I-593 | 1-methyl-6-(pyridin-3-yloxy)-1H-benzimidazol-2-yl)oxy-cyclohexyl ether with (S)-N-acetyl-propan-2-amine | 3 | 1.48 | 439.2 |
| I-594 | 1-methyl-6-(pyridin-4-yloxy)-1H-benzimidazol-2-yl)oxy-cyclohexyl ether with (S)-N-acetyl-propan-2-amine | 3 | 1.27 | 439.2 |

TABLE 116-continued
| | | | | |
|---|---|---|---|---|
| I-595 | 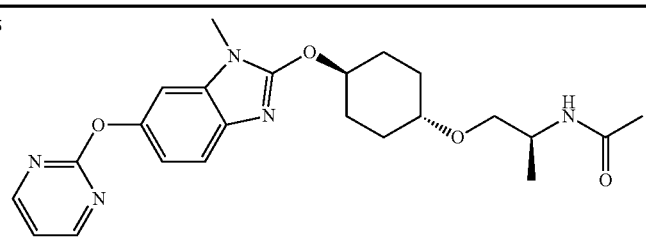 | 3 | 1.45 | 440.2 |
TABLE 117
| | | | | |
|---|---|---|---|---|
| I-596 | 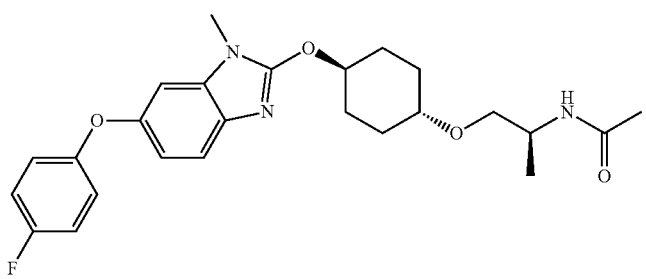 [SMILES: CC(=O)N[C@@H](C)CO[C@H]1CC[C@H](Oc2nc3ccc(Oc4ccc(F)cc4)cc3n2C)CC1] | 3 | 2.09 | 456.1 |
| I-597 | 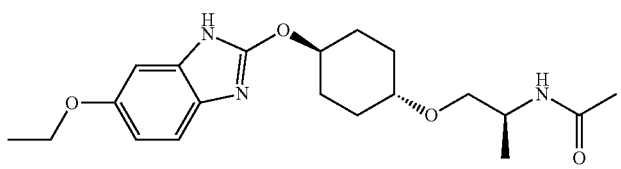 [SMILES: CCOc1ccc2nc(O[C@H]3CC[C@H](OC[C@H](C)NC(C)=O)CC3)[nH]c2c1] | 2 | 1.13 | 376.2 |
| I-598 | 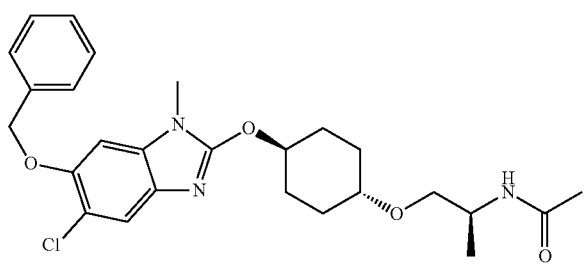 [SMILES: CC(=O)N[C@@H](C)CO[C@H]1CC[C@H](Oc2nc3cc(Cl)c(OCc4ccccc4)cc3n2C)CC1] | 3 | 2.23 | 487.3 |
| I-599 | 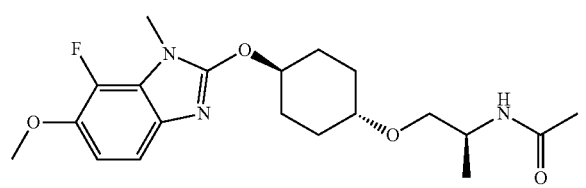 [SMILES: COc1ccc2nc(O[C@H]3CC[C@H](OC[C@H](C)NC(C)=O)CC3)n(C)c2c1F] | 3 | 1.84 | 395.2 |
| I-600 | 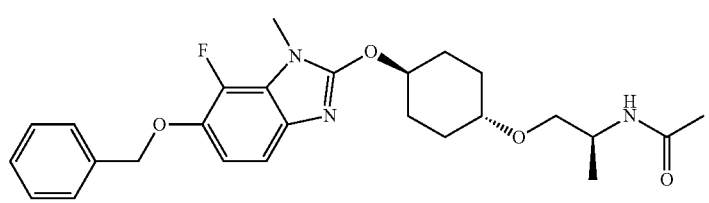 [SMILES: CC(=O)N[C@@H](C)CO[C@H]1CC[C@H](Oc2nc3ccc(OCc4ccccc4)c(F)c3n2C)CC1] | 3 | 2.26 | 470.2 |

TABLE 118

| ID | Structure | | | |
|---|---|---|---|---|
| I-601 | (structure) | 3 | 1.99 | 408.2 |
| I-602 | (structure) | 3 | 2.11 | 422.1 |
| I-603 | (structure) | 2 | 2.33 | 459.2 |
| I-604 | (structure) | 2 | 2.03 | 424.2 |
| I-605 | (structure) | 3 | 2.19 | 469.1 |

TABLE 119

| ID | Structure | | | |
|---|---|---|---|---|
| I-606 | (structure) | 3 | 1.76 | 404.2 |
| I-607 | (structure) | 3 | 1.33 | 405.2 |

TABLE 119-continued

| ID | Structure | a | b | c |
|---|---|---|---|---|
| I-608 | 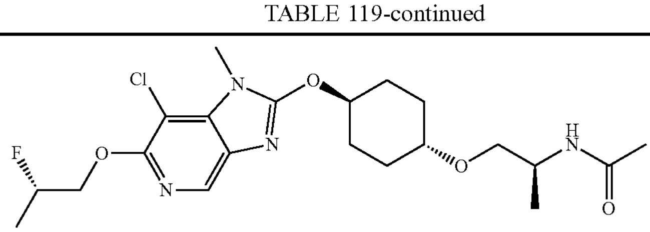 | 3 | 2.07 | 457.1 |
| I-609 | 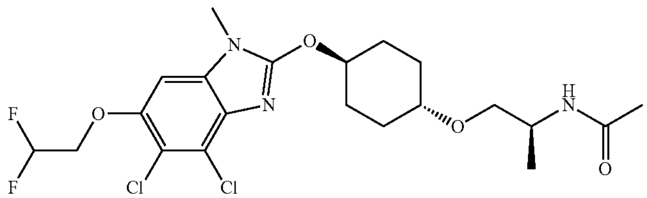 [SMILES: CC(=O)N[C@@H](C)CO[C@H]1CC[C@H](Oc2nc3c(Cl)c(Cl)c(OCC(F)F)cc3n2C)CC1] | 2 | 2.14 | 494.2 |
| I-610 | 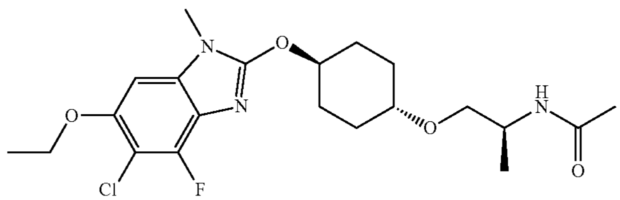 [SMILES: CCOc1cc2c(nc(O[C@H]3CC[C@H](OC[C@H](C)NC(C)=O)CC3)n2C)c(F)c1Cl] | 3 | 2.19 | 442.1 |

TABLE 120

| ID | Structure | a | b | c |
|---|---|---|---|---|
| I-611 | 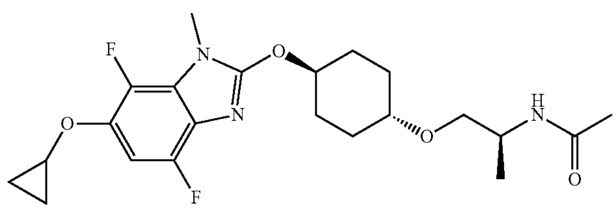 [SMILES: CC(=O)N[C@@H](C)CO[C@H]1CC[C@H](Oc2nc3c(F)cc(OC4CC4)c(F)c3n2C)CC1] | 2 | 2.12 | 438.3 |
| I-612 | 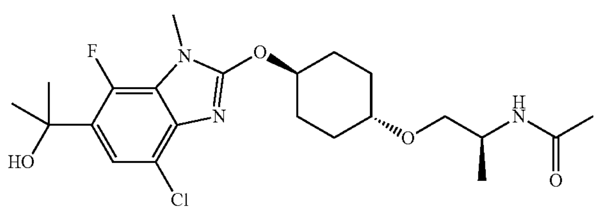 [SMILES: CC(=O)N[C@@H](C)CO[C@H]1CC[C@H](Oc2nc3c(Cl)cc(C(C)(C)O)c(F)c3n2C)CC1] | 2 | 1.85 | 456.2 |
| I-613 | 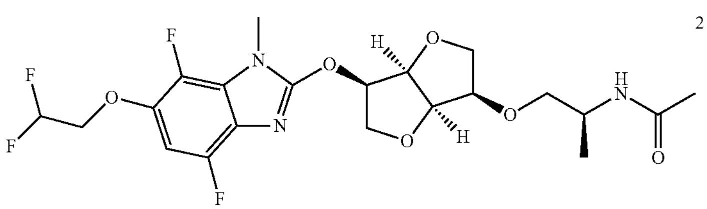 | 2 | 1.62 | 492.2 |
| I-614 | 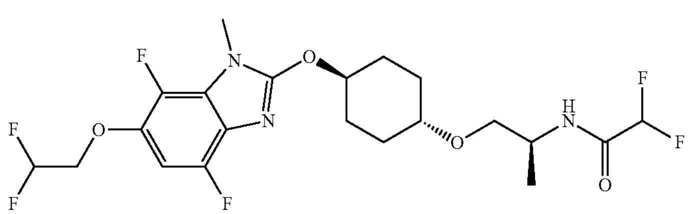 [SMILES: C[C@@H](CO[C@H]1CC[C@H](Oc2nc3c(F)cc(OCC(F)F)c(F)c3n2C)CC1)NC(=O)C(F)F] | 2 | 2.21 | 498.3 |

TABLE 120-continued
| | | | | |
|---|---|---|---|---|
| I-615 | 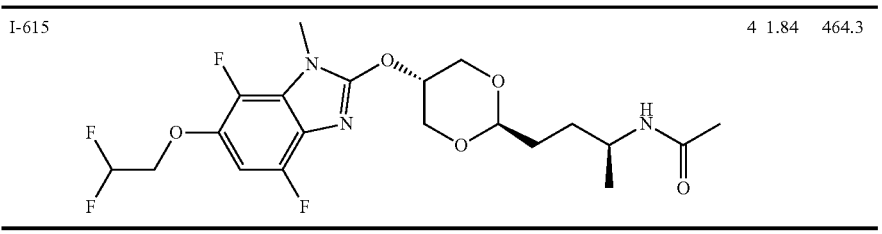 | 4 | 1.84 | 464.3 |
TABLE 121
| | | | | |
|---|---|---|---|---|
| I-616 | 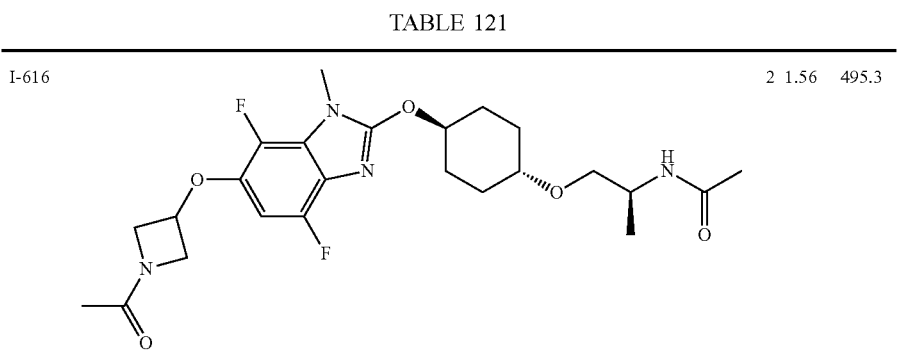 | 2 | 1.56 | 495.3 |
| I-617 | 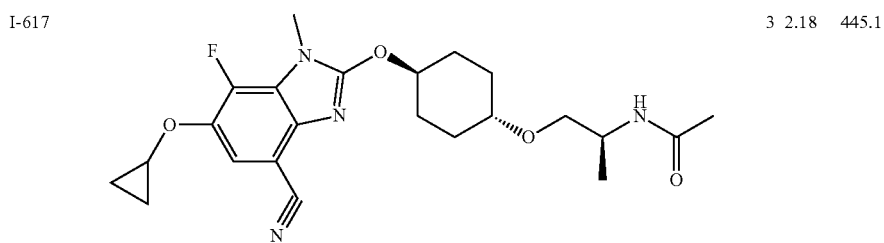 | 3 | 2.18 | 445.1 |
| I-618 | 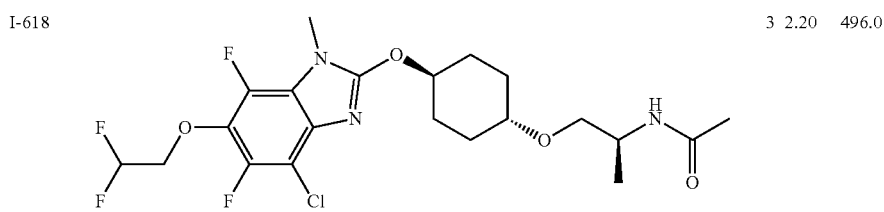 | 3 | 2.20 | 496.0 |
| I-619 | 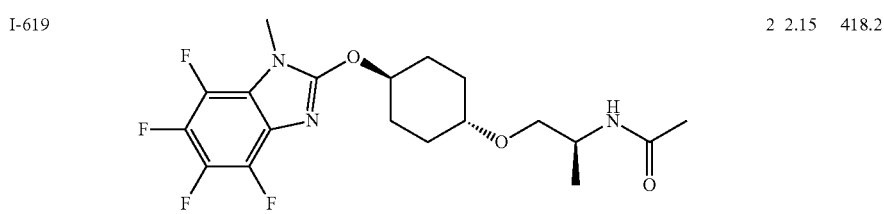 | 2 | 2.15 | 418.2 |
| I-620 | 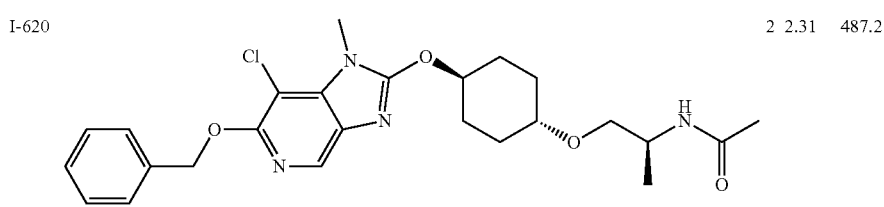 | 2 | 2.31 | 487.2 |

TABLE 122
| | | | |
|---|---|---|---|
| I-621 | 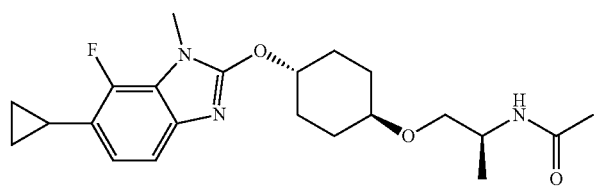 [SMILES: CC(=O)N[C@@H](C)CO[C@H]1CC[C@H](Oc2nc3ccc(C4CC4)c(F)c3n2C)CC1] | 2 2.07 | 404.5 |
| I-622 | 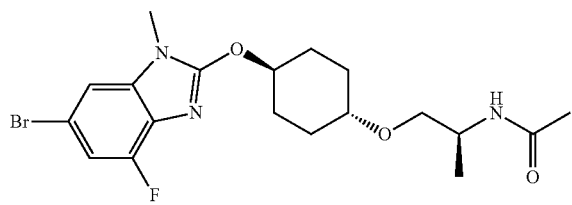 [SMILES: CC(=O)N[C@@H](C)CO[C@H]1CC[C@H](Oc2nc3c(F)cc(Br)cc3n2C)CC1] | 3 2.13 | 443.1 |
| I-623 | 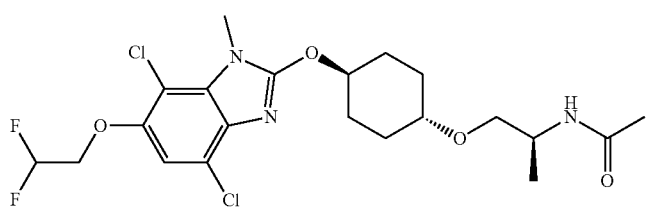 | 2 2.01 | 494.2 |
| I-624 | 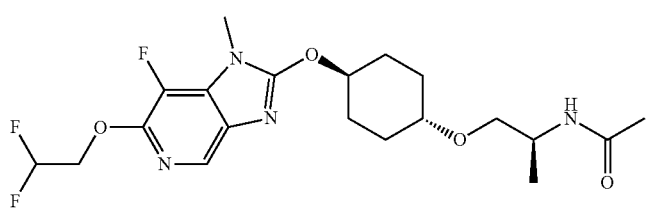 | 3 1.99 | 445.1 |
| I-625 | 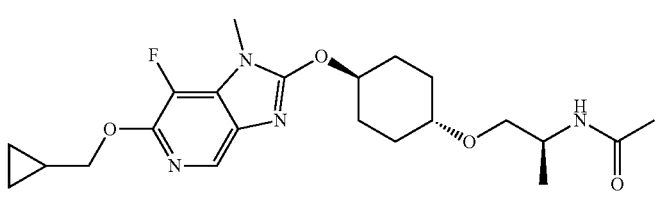 | 2 2.16 | 435.1 |
TABLE 123
| | | | |
|---|---|---|---|
| I-626 | 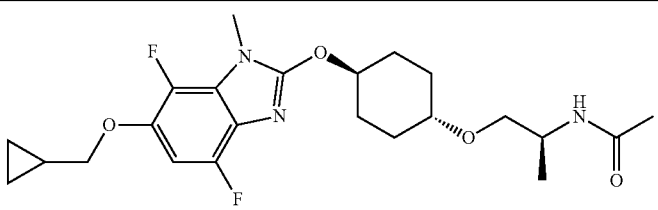 | 2 2.22 | 452.2 |
| I-627 | 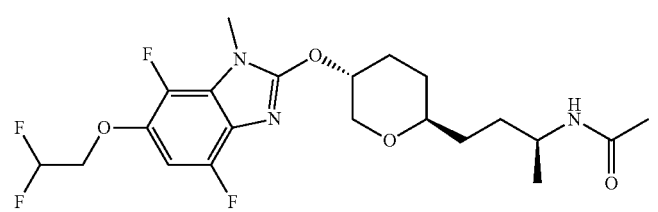 | 4 1.97 | 462.3 |

TABLE 123-continued

| ID | Structure | a | b | c |
|---|---|---|---|---|
| I-628 | 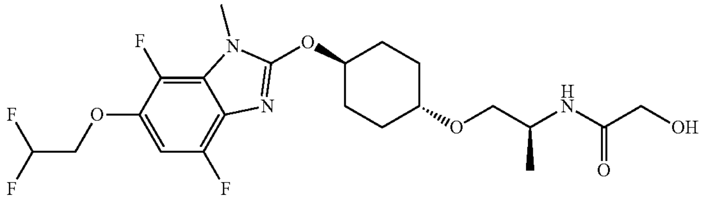 [SMILES: C[C@@H](CO[C@H]1CC[C@H](Oc2nc3c(F)cc(OCC(F)F)c(F)c3n2C)CC1)NC(=O)CO] | 2 | 1.90 | 478.2 |
| I-629 | 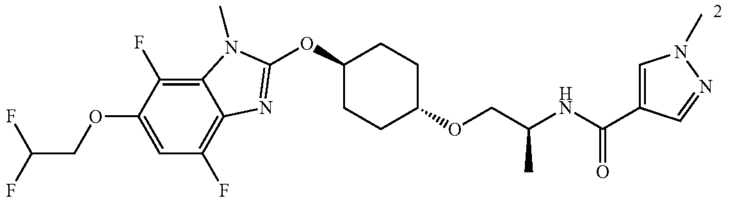 | 2 | 1.99 | 528.2 |
| I-630 | 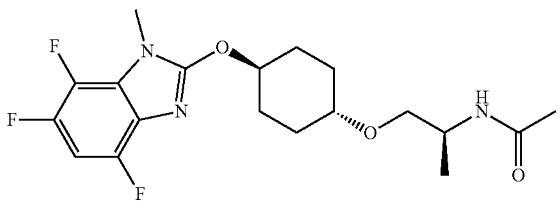 [SMILES: CC(=O)N[C@@H](C)CO[C@H]1CC[C@H](Oc2nc3c(F)cc(F)c(F)c3n2C)CC1] | 2 | 2.03 | 400.2 |

TABLE 124

| ID | Structure | a | b | c |
|---|---|---|---|---|
| I-631 | 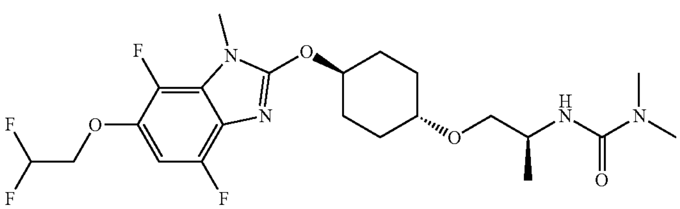 [SMILES: C[C@@H](CO[C@H]1CC[C@H](Oc2nc3c(F)cc(OCC(F)F)c(F)c3n2C)CC1)NC(=O)N(C)C] | 2 | 2.09 | 491.5 |
| I-632 | 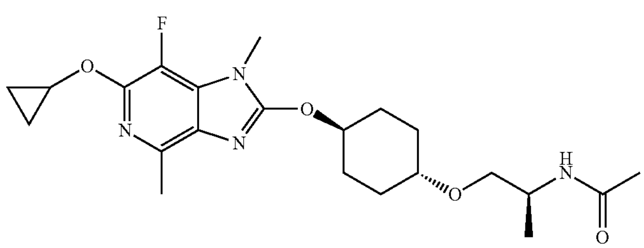 [SMILES: CC(=O)N[C@@H](C)CO[C@H]1CC[C@H](Oc2nc3c(C)nc(OC4CC4)c(F)c3n2C)CC1] | 3 | 2.07 | 435.1 |
| I-633 | 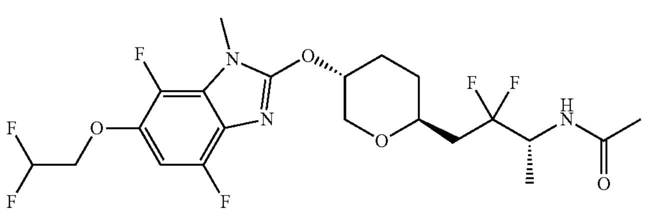 [SMILES: CC(=O)N[C@H](C)C(F)(F)C[C@@H]1CC[C@@H](Oc2nc3c(F)cc(OCC(F)F)c(F)c3n2C)CO1] | 2 | 2.03 | 498.2 |
| I-634 | 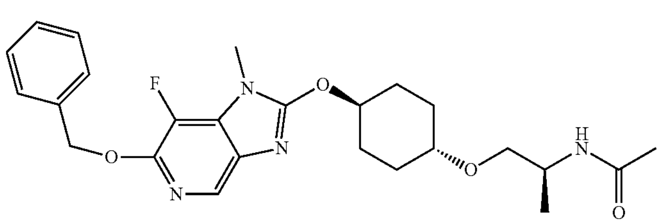 [SMILES: CC(=O)N[C@@H](C)CO[C@H]1CC[C@H](Oc2nc3cnc(OCc4ccccc4)c(F)c3n2C)CC1] | 3 | 2.23 | 471.2 |

TABLE 124-continued
| I-635 | 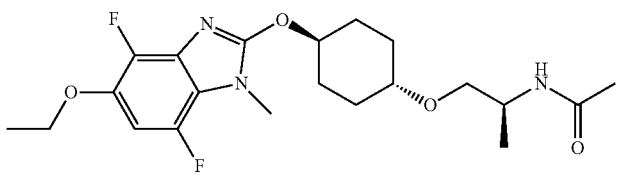 [SMILES: CCOc1cc(F)c2c(nc(O[C@H]3CC[C@H](OC[C@H](C)NC(C)=O)CC3)n2C)c1F] | 2 | 2.05 | 426.3 |
TABLE 125
| I-636 | 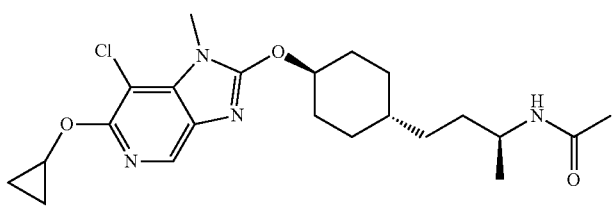 [SMILES: CC(=O)N[C@@H](C)CC[C@H]1CC[C@H](Oc2nc3cnc(OC4CC4)c(Cl)c3n2C)CC1] | 2 | 2.23 | 435.3 |
| I-637 | 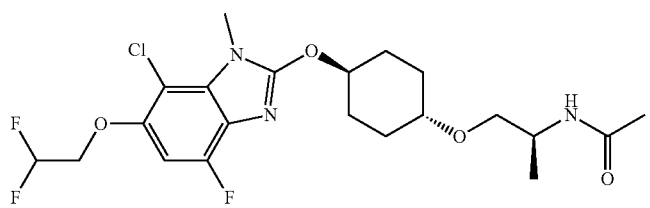 [SMILES: CC(=O)N[C@@H](C)CO[C@H]1CC[C@H](Oc2nc3c(F)cc(OCC(F)F)c(Cl)c3n2C)CC1] | 3 | 2.15 | 478.1 |
| I-638 | 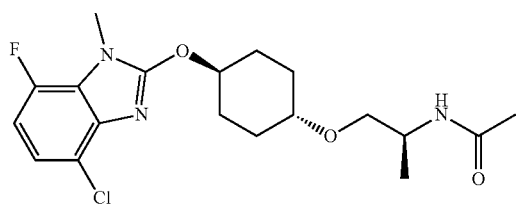 [SMILES: CC(=O)N[C@@H](C)CO[C@H]1CC[C@H](Oc2nc3c(Cl)ccc(F)c3n2C)CC1] | 3 | 2.14 | 398.0 |
| I-639 | 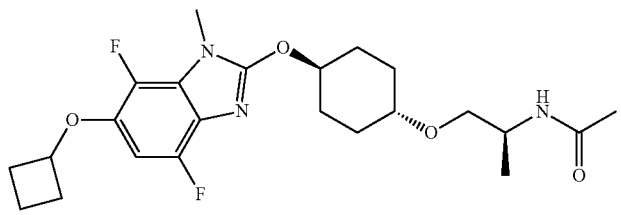 [SMILES: CC(=O)N[C@@H](C)CO[C@H]1CC[C@H](Oc2nc3c(F)cc(OC4CCC4)c(F)c3n2C)CC1] | 2 | 2.30 | 452.3 |
| I-640 | 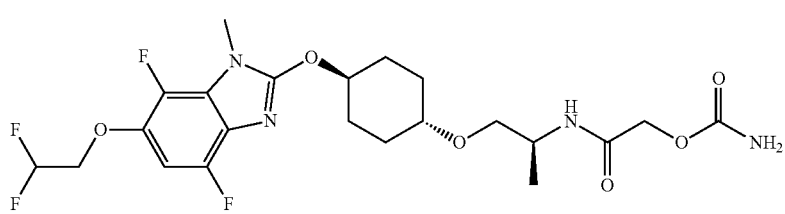 [SMILES: C[C@@H](CO[C@H]1CC[C@H](Oc2nc3c(F)cc(OCC(F)F)c(F)c3n2C)CC1)NC(=O)COC(N)=O] | 2 | 1.92 | 521.2 |

TABLE 126

| ID | Structure | | | |
|---|---|---|---|---|
| I-641 | (structure) | 3 | 1.92 | 409.1 |
| I-642 | (structure) | 4 | 1.96 | 462.3 |
| I-643 | (structure) | 2 | 2.05 | 498.3 |
| I-644 | (structure) | | 2.13 | 475.3 |
| I-645 | (structure) | 2 | 1.91 | 499.5 |

TABLE 127

| ID | Structure | | | |
|---|---|---|---|---|
| I-646 | (structure) | 3 | 2.10 | 425.2 |
| I-647 | (structure) | 3 | 2.23 | 439.2 |

TABLE 127-continued
| | | | | |
|---|---|---|---|---|
| I-648 | 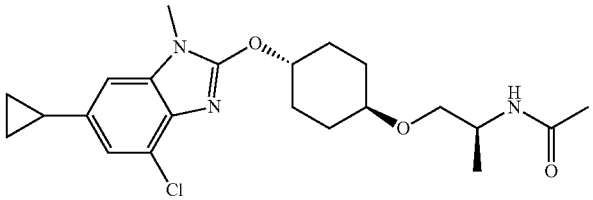 [SMILES: CC(=O)N[C@@H](C)CO[C@H]1CC[C@H](Oc2nc3c(Cl)cc(C4CC4)cc3n2C)CC1] | 2 | 2.14 | 420.2 |
| I-649 | 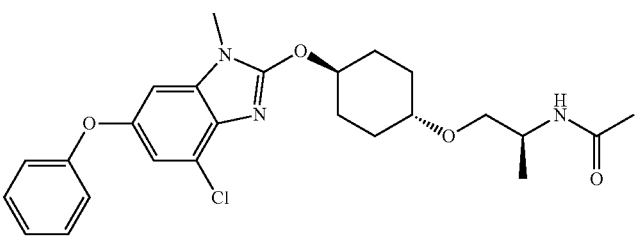 [SMILES: CC(=O)N[C@@H](C)CO[C@H]1CC[C@H](Oc2nc3c(Cl)cc(Oc4ccccc4)cc3n2C)CC1] | 2 | 2.33 | 472.3 |
| I-650 | 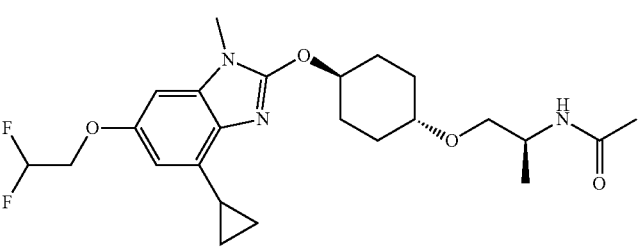 [SMILES: CC(=O)N[C@@H](C)CO[C@H]1CC[C@H](Oc2nc3c(C4CC4)cc(OCC(F)F)cc3n2C)CC1] | 3 | 1.91 | 466.1 |
TABLE 128
| | | | | |
|---|---|---|---|---|
| I-651 | 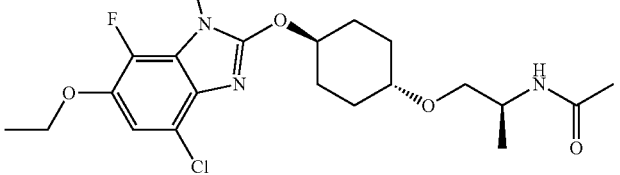 | 2 | 2.15 | 442.2 |
| I-652 | 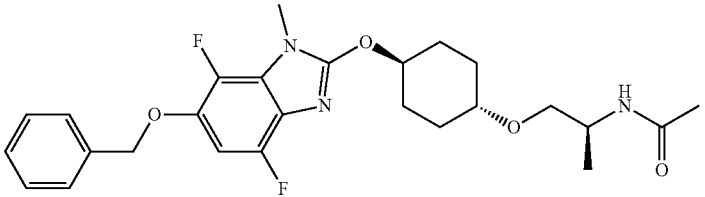 [SMILES: CC(=O)N[C@@H](C)CO[C@H]1CC[C@H](Oc2nc3c(F)cc(OCc4ccccc4)c(F)c3n2C)CC1] | 2 | 2.34 | 488.3 |
| I-653 | 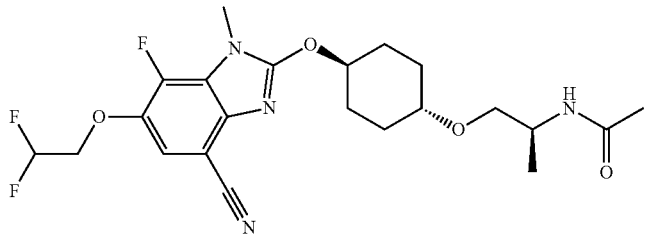 [SMILES: CC(=O)N[C@@H](C)CO[C@H]1CC[C@H](Oc2nc3c(C#N)cc(OCC(F)F)c(F)c3n2C)CC1] | 3 | 2.05 | 469.1 |

TABLE 128-continued

| | | | | |
|---|---|---|---|---|
| I-654 | (structure) | 2 | 2.00 | 513.4 |
| I-655 | (structure) | 2 | 2.28 | 454.2 |

TABLE 129

| | | | | |
|---|---|---|---|---|
| I-656 | (structure) | 2 | 1.90 | 514.2 |
| I-657 | (structure) | 4 | 1.97 | 461.3 |
| I-658 | (structure) | 3 | 2.05 | 462.1 |
| I-659 | (structure) | 2 | 2.13 | 477.1 |
| I-660 | (structure) | 2 | 1.17 | 461.7 |

TABLE 130

| ID | Structure | | | |
|---|---|---|---|---|
| I-661 | (structure) | 3 | 2.13 | 466.2 |
| I-662 | (structure) | 3 | 2.23 | 451.2 |
| I-663 | (structure) | 2 | 2.03 | 411.3 |
| I-664 | (structure) | 3 | 2.18 | 451.2 |
| I-665 | (structure) | 2 | 2.06 | 426.3 |

TABLE 131

| ID | Structure | | | |
|---|---|---|---|---|
| I-666 | (structure) | 3 | 2.02 | 482.2 |

TABLE 131-continued

| ID | Structure | a | b | c |
|---|---|---|---|---|
| I-667 | 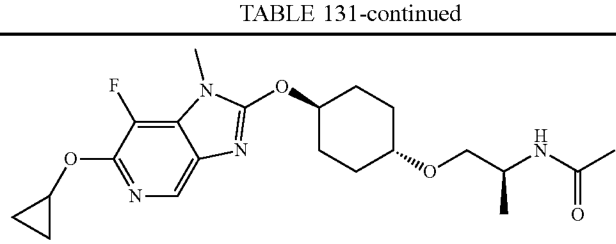 | 3 | 1.91 | 421.1 |
| I-668 | 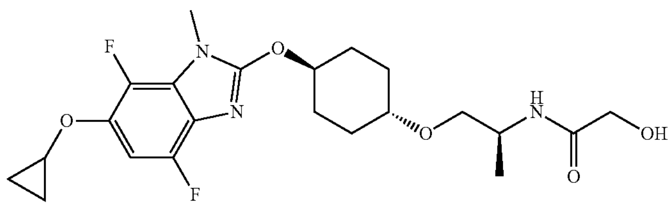 [SMILES: C[C@@H](CO[C@H]1CC[C@H](Oc2nc3c(F)cc(OC4CC4)c(F)c3n2C)CC1)NC(=O)CO] | 2 | 2.02 | 454.4 |
| I-669 | 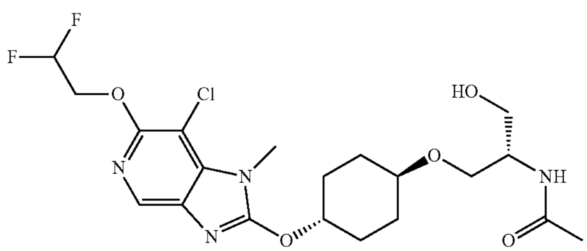 [SMILES: CC(=O)N[C@@H](CO)CO[C@H]1CC[C@H](Oc2nc3cnc(OCC(F)F)c(Cl)c3n2C)CC1] | 2 | 1.77 | 499.2 |
| I-670 | 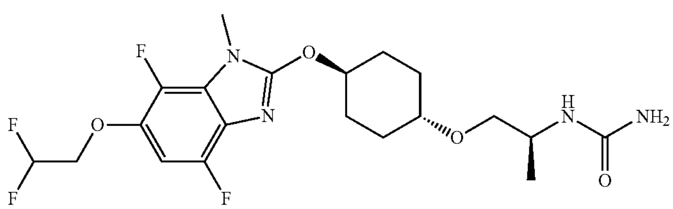 [SMILES: C[C@@H](CO[C@H]1CC[C@H](Oc2nc3c(F)cc(OCC(F)F)c(F)c3n2C)CC1)NC(N)=O] | 2 | 1.88 | 463.2 |

TABLE 132

| ID | Structure | a | b | c |
|---|---|---|---|---|
| I-671 | 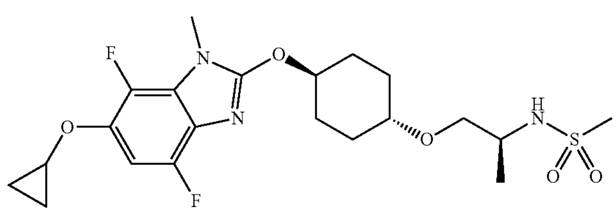 [SMILES: C[C@@H](CO[C@H]1CC[C@H](Oc2nc3c(F)cc(OC4CC4)c(F)c3n2C)CC1)NS(C)(=O)=O] | 2 | 2.28 | 474.2 |
| I-672 | 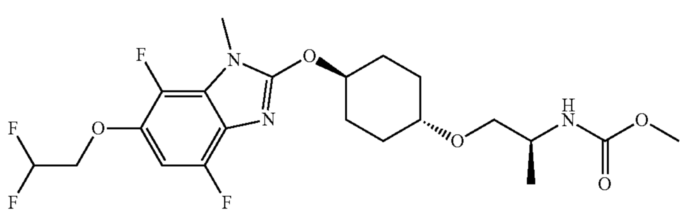 [SMILES: COC(=O)N[C@@H](C)CO[C@H]1CC[C@H](Oc2nc3c(F)cc(OCC(F)F)c(F)c3n2C)CC1] | 2 | 2.23 | 478.5 |

TABLE 132-continued

| | | | | |
|---|---|---|---|---|
| I-673 | (structure) | 3 | 1.96 | 463.1 |
| I-674 | (structure) | 4 | 1.98 | 479.3 |
| I-675 | (structure) | 2 | 2.17 | 475.1 |

TABLE 133

| | | | | |
|---|---|---|---|---|
| I-676 | (structure) | 3 | 2.20 | 480.1 |
| I-677 | (structure) | 3 | 1.97 | 444.2 |
| I-678 | (structure) | 2 | 2.21 | 460.1 |

TABLE 133-continued
| I-679 | 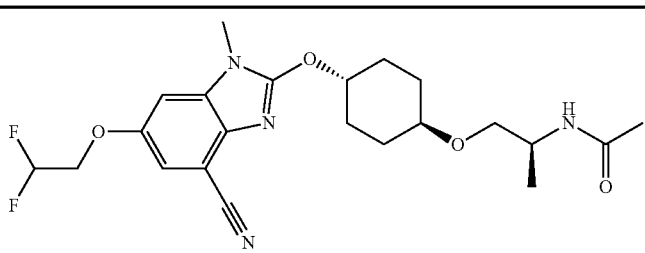 | 2 | 1.87 | 451.4 |
| I-680 | 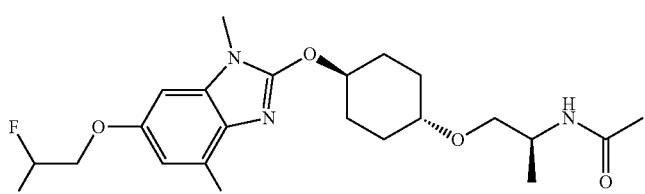 | 2 | 1.98 | 506.2 |
TABLE 134
| I-681 | 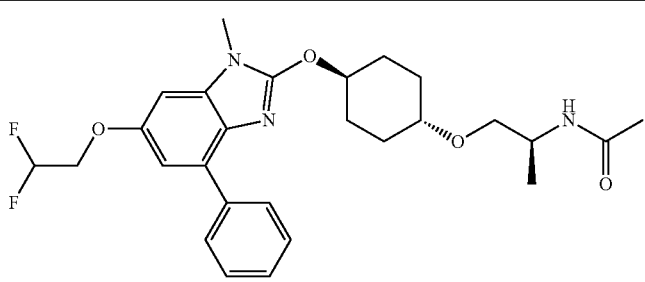 | 3 | 2.29 | 502.1 |
| I-682 | 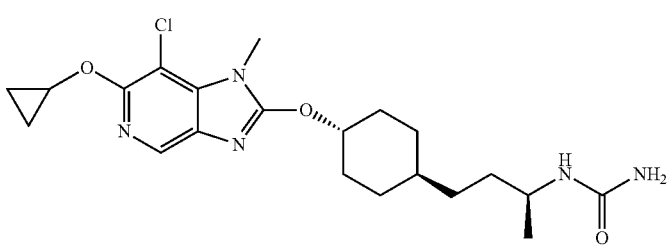 [SMILES: C[C@@H](CC[C@H]1CC[C@H](Oc2nc3cnc(OC4CC4)c(Cl)c3n2C)CC1)NC(N)=O] | 4 | 2.12 | 436.3 |
| I-683 | 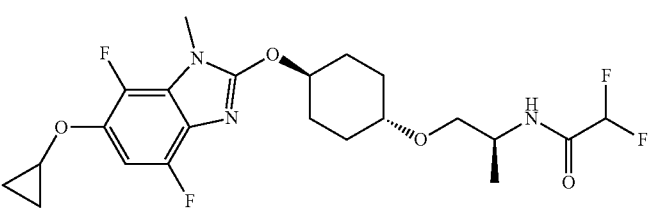 [SMILES: C[C@@H](CO[C@H]1CC[C@H](Oc2nc3c(F)cc(OC4CC4)c(F)c3n2C)CC1)NC(=O)C(F)F] | 2 | 2.35 | 474.2 |
| I-684 | 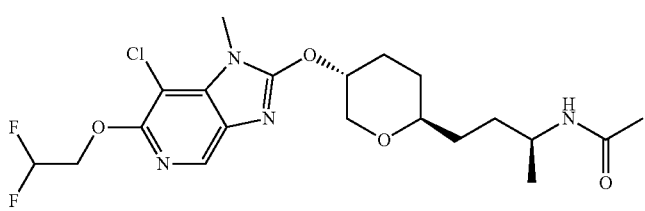 [SMILES: CC(=O)N[C@@H](C)CC[C@@H]1CC[C@@H](Oc2nc3cnc(OCC(F)F)c(Cl)c3n2C)CO1] | 4 | 1.98 | 461.3 |

TABLE 134-continued

| | | | | |
|---|---|---|---|---|
| I-685 | (structure) | 2 | 1.97 | 426.7 |

TABLE 135

| | | | | |
|---|---|---|---|---|
| I-686 | (structure) | 3 | 2.27 | 443.0 |
| I-687 | (structure) | 2 | 1.99 | 479.4 |
| I-688 | (structure) | 4 | 2.09 | 478.3 |
| I-689 | (structure) | 2 | 2.01 | 435.1 |
| I-690 | (structure) | 3 | 1.99 | 477.1 |

TABLE 136

| | | | | |
|---|---|---|---|---|
| I-691 | [structure] | 2 | 2.10 | 444.1 |
| I-692 | [structure] | 2 | 2.00 | 424.4 |
| I-693 | [structure] | 3 | 2.24 | 487.1 |
| I-694 | [structure] | 2 | 1.81 | 409.1 |
| I-695 | [structure] | 2 | 1.38 | 421.2 |

TABLE 137

| | | | | |
|---|---|---|---|---|
| I-696 | [structure] | 4 | 2.59 | 494.1 |
| I-697 | [structure] | 2 | 1.99 | 439.2 |

TABLE 137-continued

| I-698 | (structure) | 2 | 2.04 | 426.7 |
| I-699 | (structure) | 2 | 1.70 | 492.5 |
| I-700 | (structure) | 2 | 2.01 | 502.2 |

TABLE 138

| I-701 | (structure) | 2 | 1.90 | 477.0 |
| I-702 | (structure) | 4 | 2.11 | 476.3 |
| I-703 | (structure) | 3 | 2.11 | 487.1 |

TABLE 138-continued
| I-704 |  | 3 | 1.85 | 454.1 |
| I-705 | 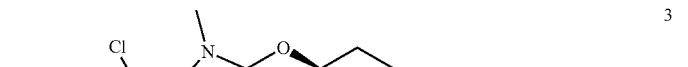 | 3 | 2.08 | 437.1 |
| I-706 | 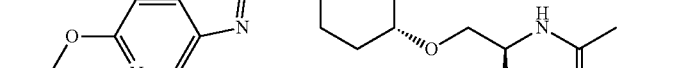 | 2 | 1.94 | 460.2 |
| I-707 |  | 3 | 1.92 | 444.2 |
| I-708 | 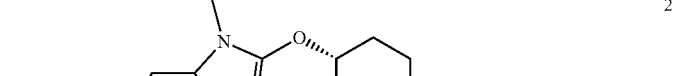 | 3 | 2.18 | 487.1 |
| I-709 | 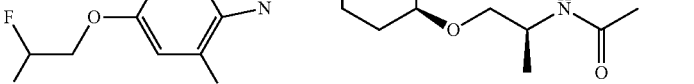 | 2 | 1.57 | 440.3 |
| I-710 |  | 2 | 2.29 | 471.4 |

TABLE 140
| ID | Structure | | | |
|---|---|---|---|---|
| I-711 | 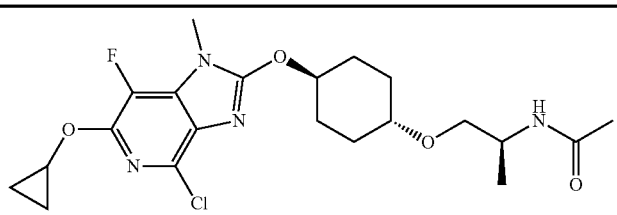 | 2 | 2.12 | 455.2 |
| I-712 | 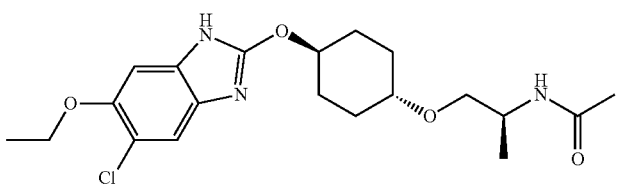 [SMILES: CCOc1cc2[nH]c(O[C@H]3CC[C@H](OC[C@H](C)NC(C)=O)CC3)nc2cc1Cl] | 3 | 1.70 | 410.1 |
| I-713 | 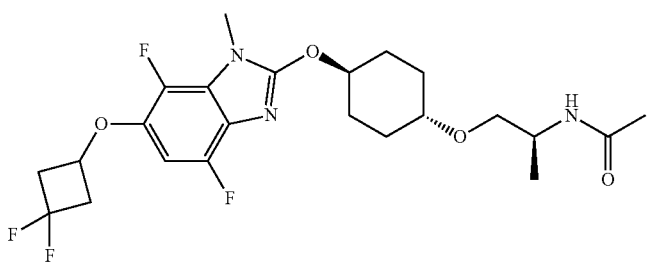 [SMILES: CC(=O)N[C@@H](C)CO[C@H]1CC[C@H](Oc2nc3c(F)cc(OC4CC(F)(F)C4)c(F)c3n2C)CC1] | 2 | 2.19 | 488.2 |
| I-714 | 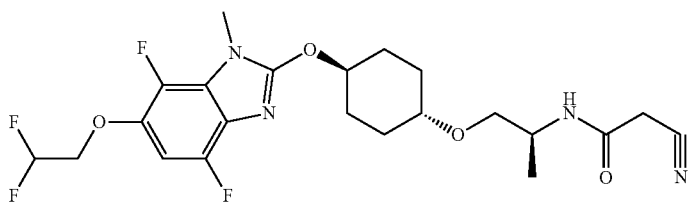 [SMILES: C[C@@H](CO[C@H]1CC[C@H](Oc2nc3c(F)cc(OCC(F)F)c(F)c3n2C)CC1)NC(=O)CC#N] | 2 | 2.06 | 487.2 |
| I-715 | 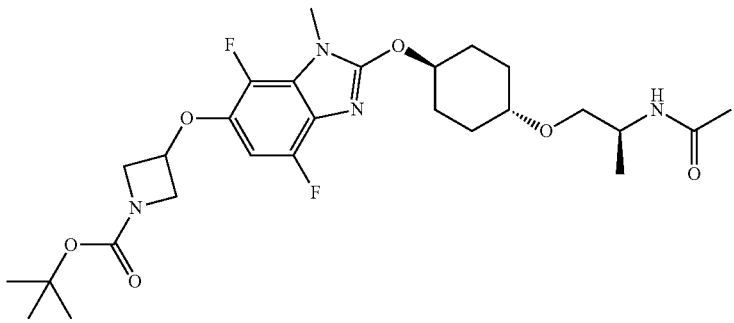 [SMILES: CC(=O)N[C@@H](C)CO[C@H]1CC[C@H](Oc2nc3c(F)cc(OC4CN(C(=O)OC(C)(C)C)C4)c(F)c3n2C)CC1] | 2 | 2.25 | 553.4 |
TABLE 141
| ID | Structure | | | |
|---|---|---|---|---|
| I-716 | 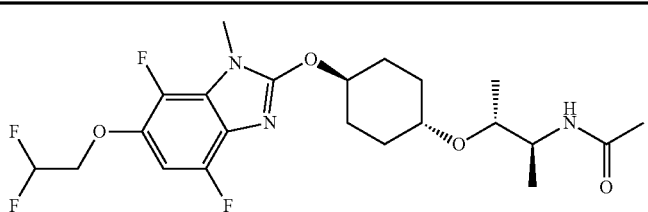 | 2 | 2.08 | 498.2 |

TABLE 141-continued

| | | | | |
|---|---|---|---|---|
| I-717 | | 2 | 2.13 | 476.2 |
| I-718 | | 2 | 1.87 | 457.3 |
| I-719 | | 3 | 1.94 | 407.1 |
| I-720 | | 3 | 1.93 | 415.2 |

TABLE 142

| | | | | |
|---|---|---|---|---|
| I-721 | | 3 | 1.96 | 417.1 |
| I-722 | | 4 | 1.98 | 461.3 |
| I-723 | | 3 | 1.97 | 408.2 |

TABLE 142-continued
| | | | | |
|---|---|---|---|---|
| I-724 | 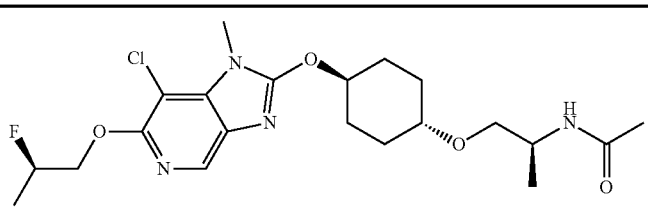 | 3 | 2.07 | 457.1 |
| I-725 | 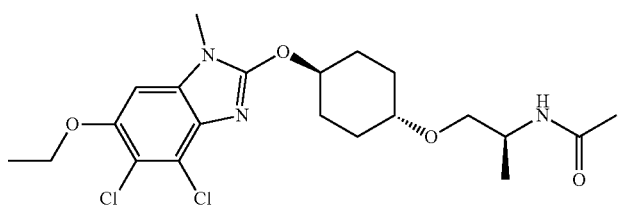 [SMILES: CCOc1cc2c(nc(O[C@H]3CC[C@H](OC[C@H](C)NC(C)=O)CC3)n2C)c(Cl)c1Cl] | 2 | 2.09 | 458.1 |
TABLE 143
| | | | | |
|---|---|---|---|---|
| I-726 | 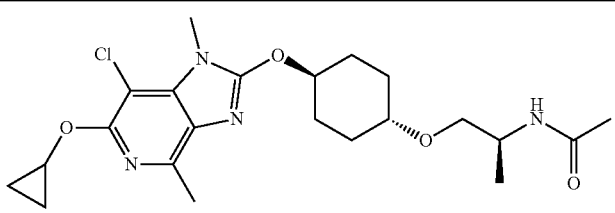 | 2 | 2.20 | 451.3 |
| I-727 | 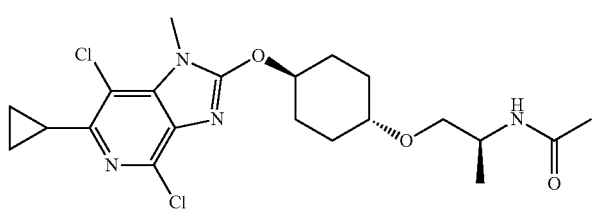 [SMILES: CC(=O)N[C@@H](C)CO[C@H]1CC[C@H](Oc2nc3c(Cl)nc(C4CC4)c(Cl)c3n2C)CC1] | 2 | 2.38 | 455.3 |
| I-728 | 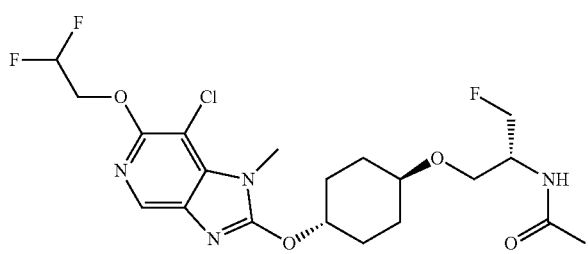 [SMILES: CC(=O)N[C@@H](CF)CO[C@H]1CC[C@H](Oc2nc3cnc(OCC(F)F)c(Cl)c3n2C)CC1] | 2 | 2.03 | 479.2 |
| I-729 | 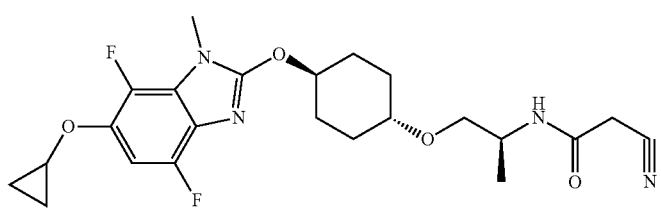 [SMILES: C[C@@H](CO[C@H]1CC[C@H](Oc2nc3c(F)cc(OC4CC4)c(F)c3n2C)CC1)NC(=O)CC#N] | 2 | 2.20 | 463.2 |

TABLE 143-continued
| I-730 | 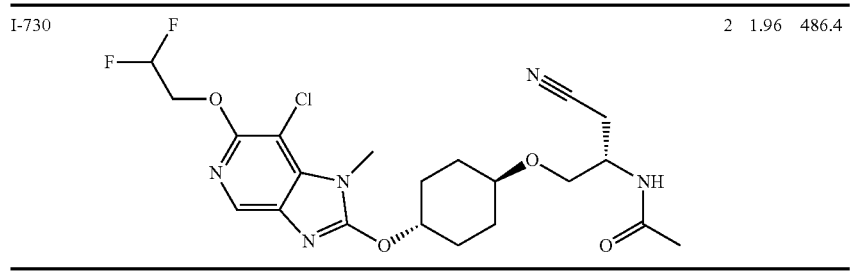 | 2 | 1.96 | 486.4 |
TABLE 144
| I-731 | | 2 | 1.74 | 477.2 |
| I-732 | | 2 | 2.11 | 497.4 |
| I-733 | | 2 | 2.18 | 496.2 |
| I-734 | | 3 | 2.05 | 420.1 |
| I-735 | | 3 | 1.91 | 430.2 |

TABLE 145
| | | | | |
|---|---|---|---|---|
| I-736 | 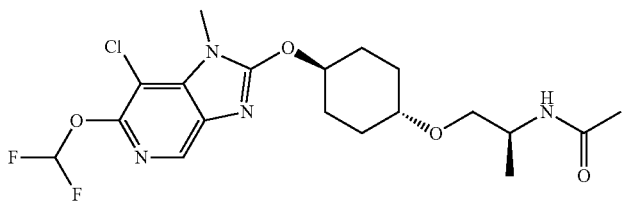 [SMILES: CC(=O)N[C@@H](C)CO[C@H]1CC[C@H](Oc2nc3cnc(OC(F)F)c(Cl)c3n2C)CC1] | 3 | 2.07 | 447.1 |
| I-737 | 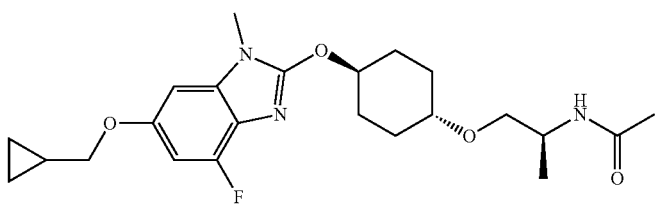 [SMILES: CC(=O)N[C@@H](C)CO[C@H]1CC[C@H](Oc2nc3c(F)cc(OCC4CC4)cc3n2C)CC1] | 3 | 2.10 | 434.2 |
| I-738 | 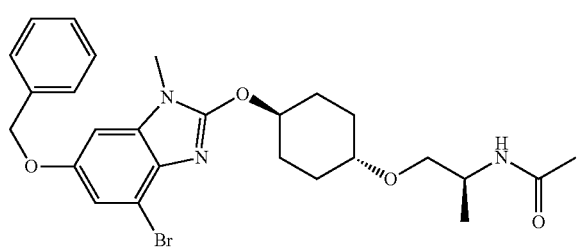 [SMILES: CC(=O)N[C@@H](C)CO[C@H]1CC[C@H](Oc2nc3c(Br)cc(OCc4ccccc4)cc3n2C)CC1] | 3 | 2.37 | 530.1 |
| I-739 | 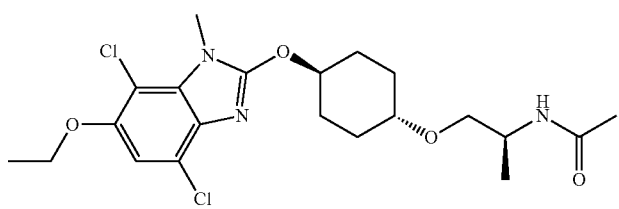 [SMILES: CCOc1cc(Cl)c2nc(O[C@H]3CC[C@H](OC[C@H](C)NC(C)=O)CC3)n(C)c2c1Cl] | 2 | 2.29 | 458.1 |
| I-740 | 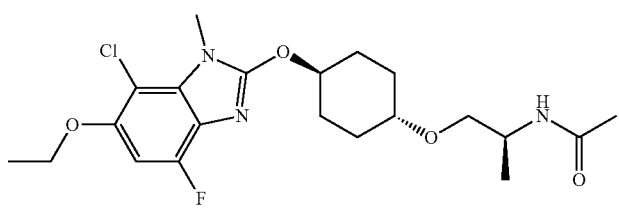 | 3 | 2.32 | 442.1 |
TABLE 146
| | | | | |
|---|---|---|---|---|
| I-741 | 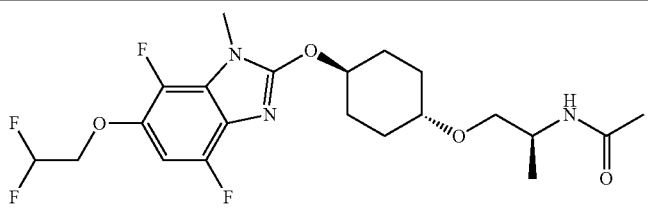 | 5 | 3.85 | 462.5 |
| I-742 | 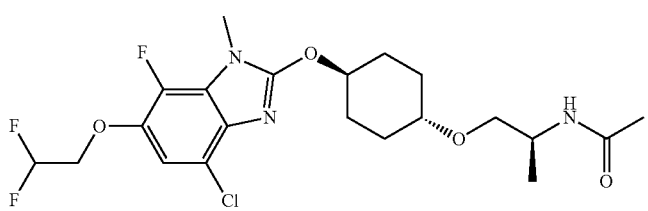 [SMILES: CC(=O)N[C@@H](C)CO[C@H]1CC[C@H](Oc2nc3c(Cl)cc(OCC(F)F)c(F)c3n2C)CC1] | 3 | 2.13 | 478.1 |

TABLE 146-continued

| ID | Structure | | | |
|---|---|---|---|---|
| I-743 | (structure) | 2 | 1.72 | 412.2 |
| I-744 | (structure) | 2 | 1.35 | 461.2 |
| I-745 | (structure) | 2 | 1.73 | 478.3 |

TABLE 147

| ID | Structure | | | |
|---|---|---|---|---|
| I-746 | (structure) | 2 | 1.91 | 435.3 |
| I-747 | (structure) | 2 | 1.98 | 487.5 |
| I-748 | (structure) | 2 | 1.96 | 480.4 |

In the following general formula (I"), the compounds having the following groups can be synthesized in similar methods described in the above working examples.

[Formula 127]

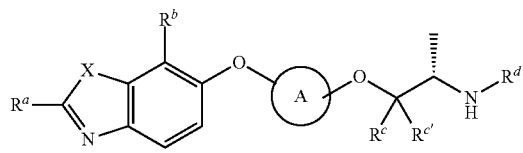

(I")

TABLE 148

| X | |
|---|---|
| $X^1$ | S |
| $X^2$ | O |
| $X^3$ | N(Me) |
| $X^4$ | N(Et) |
| $X^5$ | N(n-Pr) |
| $X^6$ | N(i-Pr) |

TABLE 149

| $R^a$ | |
|---|---|
| $R^{a1}$ | (CF2-) |
| $R^{a2}$ | (EtO-) |
| $R^{a3}$ | (HO-C(CH3)2-) |

TABLE 150

| $R^b$ | |
|---|---|
| $R^{b1}$ | F |
| $R^{b2}$ | Cl |
| $R^{b3}$ | CN |

TABLE 151

| 環A | |
|---|---|
| $A^1$ | cyclobutyl ($L^1$, $L^2$) |
| $A^2$ | cyclopentyl ($L^1$, $L^2$) |

TABLE 151-continued

| 環A | |
|---|---|
| $A^3$ | cyclohexyl ($L^1$, $L^2$) |
| $A^4$ | phenyl ($L^1$, $L^2$) |
| $A^5$ | pyrimidinyl ($L^1$, $L^2$) |

TABLE 152

| $R^c$, $R^{c'}$ | |
|---|---|
| $R^{c1}$ | (CH-O-, with stereochem) |
| $R^{c2}$ | (CH-O-, with stereochem) |
| $R^{c3}$ | (C(CH3)2-O-) |
| $R^{c4}$ | (cyclopropyl-O-) |

TABLE 153

| $R^d$ | |
|---|---|
| $R^{d1}$ | acetyl |
| $R^{d2}$ | -C(O)CH2OH |
| $R^{d3}$ | -C(O)NH2 |

The combination of X, $R^a$, $R^b$, A, $R^c$, and $R^d$, is any one of the following combinations in the above formula (I"):

$(X, R^a, R^b, A, R^c, R^d) = (X^1, R^{a1}, R^{b1}, A^1, R^{c1}, R^{d1}), (X^1, R^{a1}, R^{b1}, A^1, R^{c1}, R^{d2}), (X^1, R^{a1}, R^{b1}, A^1, R^{c1}, R^{d3}), (X^1, R^{a1}, R^{b1}, A^1, R^{c2}, R^{d1}), (X^1, R^{a1}, R^{b1}, A^1, R^{c2}, R^{d2}), (X^1, R^{a1}, R^{b1}, A^1, R^{c2}, R^{d3}), (X^1, R^{a1}, R^{b1}, A^1, R^{c3}, R^{d1}), (X^1, R^{a1}, R^{b1}, A^1, R^{c3}, R^{d2}), (X^1, R^{a1}, R^{b1}, A^1, R^{c3}, R^{d3}), (X^1, R^{a1}, R^{b1}, A^1, R^{c4}, R^{d1}), (X^1, R^{a1}, R^{b1}, A^1, R^{c4}, R^{d2}), (X^1, R^{a1}, R^{b1}, A^1, R^{c4}, R^{d3}), (X^1, R^{a1}, R^{b1}, A^2, R^{c1}, R^{d1}), (X^1, R^{a1}, R^{b1}, A^2, R^{c1}, R^{d2}), (X^1, R^{a1}, R^{b1}, A^2, R^{c1}, R^{d3}), (X^1, R^{a1}, R^{b1}, A^2, R^{c2}, R^{d1}), (X^1, R^{a1}, R^{b1}, A^2, R^{c2}, R^{d2}), (X^1, R^{a1}, R^{b1}, A^2, R^{c2}, R^{d3}), (X^1, R^{a1}, R^{b1}, A^2, R^{c3}, R^{d1}), (X^1, R^{a1}, R^{b1}, A^2, R^{c3}, R^{d2}), (X^1, R^{a1}, R^{b1}, A^2, R^{c3}, R^{d3}), (X^1, R^{a1}, R^{b1}, A^2, R^{c4}, R^{d1}), (X^1, R^{a1}, R^{b1}, A^2, R^{c4}, R^{d2}), (X^1, R^{a1}, R^{b1}, A^2, R^{c4}, R^{d3}), (X^1, R^{a1}, R^{b1}, A^3, R^{c1}, R^{d1}), (X^1, R^{a1}, R^{b1}, A^3, R^{c1}, R^{d2}), (X^1, R^{a1}, R^{b1}, A^3, R^{c1}, R^{d3}), (X^1, R^{a1}, R^{b1}, A^3, R^{c2}, R^{d1}), (X^1, R^{a1}, R^{b1}, A^3, R^{c2}, R^{d2}), (X^1, R^{a1}, R^{b1}, A^3, R^{c2}, R^{d3}), (X^1, R^{a1}, R^{b1}, A^3, R^{c3}, R^{d1}), (X^1, R^{a1}, R^{b1}, A^3, R^{c3}, R^{d2}), (X^1, R^{a1}, R^{b1}, A^3, R^{c3}, R^{d3}), (X^1, R^{a1}, R^{b1}, A^3, R^{c4}, R^{d1}), (X^1, R^{a1}, R^{b1}, A^3, R^{c4}, R^{d2}), (X^1, R^{a1}, R^{b1}, A^3, R^{c4}, R^{d3}), (X^1, R^{a1}, R^{b1}, A^4, R^{c1}, R^{d1}), (X^1, R^{a1}, R^{b1}, A^4, R^{c1}, R^{d2}), (X^1, R^{a1}, R^{b1}, A^4, R^{c1}, R^{d3}), (X^1, R^{a1}, R^{b1}, A^4, R^{c2}, R^{d1}), (X^1, R^{a1}, R^{b1}, A^4, R^{c2}, R^{d2}), (X^1, R^{a1}, R^{b1}, A^4, R^{c2}, R^{d3}), (X^1, R^{a1}, R^{b1}, A^4, R^{c3}, R^{d1}), (X^1, R^{a1}, R^{b1}, A^4, R^{c3}, R^{d2}), (X^1, R^{a1}, R^{b1}, A^4, R^{c3}, R^{d3}), (X^1, R^{a1}, R^{b1}, A^4, R^{c4}, R^{d1}), (X^1, R^{a1}, R^{b1}, A^4, R^{c4}, R^{d2}), (X^1, R^{a1}, R^{b1}, A^4, R^{c4}, R^{d3}), (X^1, R^{a1}, R^{b1}, A^5, R^{c1}, R^{d1}), (X^1, R^{a1}, R^{b1}, A^5, R^{c1}, R^{d2}), (X^1, R^{a1}, R^{b1}, A^5, R^{c1}, R^{d3}), (X^1, R^{a1}, R^{b1}, A^5, R^{c2}, R^{d1}), (X^1, R^{a1}, R^{b1}, A^5, R^{c2}, R^{d2}), (X^1, R^{a1}, R^{b1}, A^5, R^{c2}, R^{d3}), (X^1, R^{a1}, R^{b1}, A^5, R^{c3}, R^{d1}), (X^1, R^{a1}, R^{b1}, A^5, R^{c3}, R^{d2}), (X^1, R^{a1}, R^{b1}, A^5, R^{c3}, R^{d3}), (X^1, R^{a1}, R^{b1}, A^5, R^{c4}, R^{d1}), (X^1, R^{a1}, R^{b1}, A^5, R^{c4}, R^{d2}), (X^1, R^{a1}, R^{b1}, A^5, R^{c4}, R^{d3}), (X^1, R^{a1}, R^{b2}, A^1, R^{c1}, R^{d1}), (X^1, R^{a1}, R^{b2}, A^1, R^{c1}, R^{d2}), (X^1, R^{a1}, R^{b2}, A^1, R^{c1}, R^{d3}), (X^1, R^{a1}, R^{b2}, A^1, R^{c2}, R^{d1}), (X^1, R^{a1}, R^{b2}, A^1, R^{c2}, R^{d2}), (X^1, R^{a1}, R^{b2}, A^1, R^{c2}, R^{d3}), (X^1, R^{a1}, R^{b2}, A^1, R^{c3}, R^{d1}), (X^1, R^{a1}, R^{b2}, A^1, R^{c3}, R^{d2}), (X^1, R^{a1}, R^{b2}, A^1, R^{c3}, R^{d3}), (X^1, R^{a1}, R^{b2}, A^1, R^{c4}, R^{d1}), (X^1, R^{a1}, R^{b2}, A^1, R^{c4}, R^{d2}), (X^1, R^{a1}, R^{b2}, A^1, R^{c4}, R^{d3}), (X^1, R^{a1}, R^{b2}, A^2, R^{c1}, R^{d1}), (X^1, R^{a1}, R^{b2}, A^2, R^{c1}, R^{d2}), (X^1, R^{a1}, R^{b2}, A^2, R^{c1}, R^{d3}), (X^1, R^{a1}, R^{b2}, A^2, R^{c2}, R^{d1}), (X^1, R^{a1}, R^{b2}, A^2, R^{c2}, R^{d2}), (X^1, R^{a1}, R^{b2}, A^2, R^{c2}, R^{d3}), (X^1, R^{a1}, R^{b2}, A^2, R^{c3}, R^{d1}), (X^1, R^{a1}, R^{b2}, A^2, R^{c3}, R^{d2}), (X^1, R^{a1}, R^{b2}, A^2, R^{c3}, R^{d3}), (X^1, R^{a1}, R^{b2}, A^2, R^{c4}, R^{d1}), (X^1, R^{a1}, R^{b2}, A^2, R^{c4}, R^{d2}), (X^1, R^{a1}, R^{b2}, A^2, R^{c4}, R^{d3}), (X^1, R^{a1}, R^{b2}, A^3, R^{c1}, R^{d1}), (X^1, R^{a1}, R^{b2}, A^3, R^{c1}, R^{d2}), (X^1, R^{a1}, R^{b2}, A^3, R^{c1}, R^{d3}), (X^1, R^{a1}, R^{b2}, A^3, R^{c2}, R^{d1}), (X^1, R^{a1}, R^{b2}, A^3, R^{c2}, R^{d2}), (X^1, R^{a1}, R^{b2}, A^3, R^{c2}, R^{d3}), (X^1, R^{a1}, R^{b2}, A^3, R^{c3}, R^{d1}), (X^1, R^{a1}, R^{b2}, A^3, R^{c3}, R^{d2}), (X^1, R^{a1}, R^{b2}, A^3, R^{c3}, R^{d3}), (X^1, R^{a1}, R^{b2}, A^3, R^{c4}, R^{d1}), (X^1, R^{a1}, R^{b2}, A^3, R^{c4}, R^{d2}), (X^1, R^{a1}, R^{b2}, A^3, R^{c4}, R^{d3}), (X^1, R^{a1}, R^{b2}, A^4, R^{c1}, R^{d1}), (X^1, R^{a1}, R^{b2}, A^4, R^{c1}, R^{d2}), (X^1, R^{a1}, R^{b2}, A^4, R^{c1}, R^{d3}), (X^1, R^{a1}, R^{b2}, A^4, R^{c2}, R^{d1}), (X^1, R^{a1}, R^{b2}, A^4, R^{c2}, R^{d2}), (X^1, R^{a1}, R^{b2}, A^4, R^{c2}, R^{d3}), (X^1, R^{a1}, R^{b2}, A^4, R^{c3}, R^{d1}), (X^1, R^{a1}, R^{b2}, A^4, R^{c3}, R^{d2}), (X^1, R^{a1}, R^{b2}, A^4, R^{c3}, R^{d3}), (X^1, R^{a1}, R^{b2}, A^4, R^{c4}, R^{d1}), (X^1, R^{a1}, R^{b2}, A^4, R^{c4}, R^{d2}), (X^1, R^{a1}, R^{b2}, A^4, R^{c4}, R^{d3}), (X^1, R^{a1}, R^{b2}, A^5, R^{c1}, R^{d1}), (X^1, R^{a1}, R^{b2}, A^5, R^{c1}, R^{d2}), (X^1, R^{a1}, R^{b2}, A^5, R^{c1}, R^{d3}), (X^1, R^{a1}, R^{b2}, A^5, R^{c2}, R^{d1}), (X^1, R^{a1}, R^{b2}, A^5, R^{c2}, R^{d2}), (X^1, R^{a1}, R^{b2}, A^5, R^{c2}, R^{d3}), (X^1, R^{a1}, R^{b2}, A^5, R^{c3}, R^{d1}), (X^1, R^{a1}, R^{b2}, A^5, R^{c3}, R^{d2}), (X^1, R^{a1}, R^{b2}, A^5, R^{c3}, R^{d3}), (X^1, R^{a1}, R^{b2}, A^5, R^{c4}, R^{d1}), (X^1, R^{a1}, R^{b2}, A^5, R^{c4}, R^{d2}), (X^1, R^{a1}, R^{b2}, A^5, R^{c4}, R^{d3}), (X^1, R^{a1}, R^{b3}, A^1, R^{c1}, R^{d1}), (X^1, R^{a1}, R^{b3}, A^1, R^{c1}, R^{d2}), (X^1, R^{a1}, R^{b3}, A^1, R^{c1}, R^{d3}), (X^1, R^{a1}, R^{b3}, A^1, R^{c2}, R^{d1}), (X^1, R^{a1}, R^{b3}, A^1, R^{c2}, R^{d2}), (X^1, R^{a1}, R^{b3}, A^1, R^{c2}, R^{d3}), (X^1, R^{a1}, R^{b3}, A^1, R^{c3}, R^{d1}), (X^1, R^{a1}, R^{b3}, A^1, R^{c3}, R^{d2}), (X^1, R^{a1}, R^{b3}, A^1, R^{c3}, R^{d3}), (X^1, R^{a1}, R^{b3}, A^1, R^{c4}, R^{d1}), (X^1, R^{a1}, R^{b3}, A^1, R^{c4}, R^{d2}), (X^1, R^{a1}, R^{b3}, A^1, R^{c4}, R^{d3}), (X^1, R^{a1}, R^{b3}, A^2, R^{c1}, R^{d1}), (X^1, R^{a1}, R^{b3}, A^2, R^{c1}, R^{d2}), (X^1, R^{a1}, R^{b3}, A^2, R^{c1}, R^{d3}), (X^1, R^{a1}, R^{b3}, A^2, R^{c2}, R^{d1}), (X^1, R^{a1}, R^{b3}, A^2, R^{c2}, R^{d2}), (X^1, R^{a1}, R^{b3}, A^2, R^{c2}, R^{d3}), (X^1, R^{a1}, R^{b3}, A^2, R^{c3}, R^{d1}), (X^1, R^{a1}, R^{b3}, A^2, R^{c3}, R^{d2}), (X^1, R^{a1}, R^{b3}, A^2, R^{c3}, R^{d3}), (X^1, R^{a1}, R^{b3}, A^2, R^{c4}, R^{d1}), (X^1, R^{a1}, R^{b3}, A^2, R^{c4}, R^{d2}), (X^1, R^{a1}, R^{b3}, A^2, R^{c4}, R^{d3}), (X^1, R^{a1}, R^{b3}, A^3, R^{c1}, R^{d1}), (X^1, R^{a1}, R^{b3}, A^3, R^{c1}, R^{d2}), (X^1, R^{a1}, R^{b3}, A^3, R^{c1}, R^{d3}), (X^1, R^{a1}, R^{b3}, A^3, R^{c2}, R^{d1}), (X^1, R^{a1}, R^{b3}, A^3, R^{c2}, R^{d2}), (X^1, R^{a1}, R^{b3}, A^3, R^{c2}, R^{d3}), (X^1, R^{a1}, R^{b3}, A^3, R^{c3}, R^{d1}), (X^1, R^{a1}, R^{b3}, A^3, R^{c3}, R^{d2}), (X^1, R^{a1}, R^{b3}, A^3, R^{c3}, R^{d3}), (X^1, R^{a1}, R^{b3}, A^3, R^{c4}, R^{d1}), (X^1, R^{a1}, R^{b3}, A^3, R^{c4}, R^{d2}), (X^1, R^{a1}, R^{b3}, A^3, R^{c4}, R^{d3}), (X^1, R^{a1}, R^{b3}, A^4, R^{c1}, R^{d1}), (X^1, R^{a1}, R^{b3}, A^4, R^{c1}, R^{d2}), (X^1, R^{a1}, R^{b3}, A^4, R^{c1}, R^{d3}), (X^1, R^{a1}, R^{b3}, A^4, R^{c2}, R^{d1}), (X^1, R^{a1}, R^{b3}, A^4, R^{c2}, R^{d2}), (X^1, R^{a1}, R^{b3}, A^4, R^{c2}, R^{d3}), (X^1, R^{a1}, R^{b3}, A^4, R^{c3}, R^{d1}), (X^1, R^{a1}, R^{b3}, A^4, R^{c3}, R^{d2}), (X^1, R^{a1}, R^{b3}, A^4, R^{c3}, R^{d3}), (X^1, R^{a1}, R^{b3}, A^4, R^{c4}, R^{d1}), (X^1, R^{a1}, R^{b3}, A^4, R^{c4}, R^{d2}), (X^1, R^{a1}, R^{b3}, A^4, R^{c4}, R^{d3}), (X^1, R^{a1}, R^{b3}, A^5, R^{c1}, R^{d1}), (X^1, R^{a1}, R^{b3}, A^5, R^{c1}, R^{d2}), (X^1, R^{a1}, R^{b3}, A^5, R^{c1}, R^{d3}), (X^1, R^{a1}, R^{b3}, A^5, R^{c2}, R^{d1}), (X^1, R^{a1}, R^{b3}, A^5, R^{c2}, R^{d2}), (X^1, R^{a1}, R^{b3}, A^5, R^{c2}, R^{d3}), (X^1, R^{a1}, R^{b3}, A^5, R^{c3}, R^{d1}), (X^1, R^{a1}, R^{b3}, A^5, R^{c3}, R^{d2}), (X^1, R^{a1}, R^{b3}, A^5, R^{c3}, R^{d3}), (X^1, R^{a1}, R^{b3}, A^5, R^{c4}, R^{d1}), (X^1, R^{a1}, R^{b3}, A^5, R^{c4}, R^{d2}), (X^1, R^{a1}, R^{b3}, A^5, R^{c4}, R^{d3}), (X^1, R^{a2}, R^{b1}, A^1, R^{c1}, R^{d1}), (X^1, R^{a2}, R^{b1}, A^1, R^{c1}, R^{d2}), (X^1, R^{a2}, R^{b1}, A^1, R^{c1}, R^{d3}), (X^1, R^{a2}, R^{b1}, A^1, R^{c2}, R^{d1}), (X^1, R^{a2}, R^{b1}, A^1, R^{c2}, R^{d2}), (X^1, R^{a2}, R^{b1}, A^1, R^{c2}, R^{d3}), (X^1, R^{a2}, R^{b1}, A^1, R^{c3}, R^{d1}), (X^1, R^{a2}, R^{b1}, A^1, R^{c3}, R^{d2}), (X^1, R^{a2}, R^{b1}, A^1, R^{c3}, R^{d3}), (X^1, R^{a2}, R^{b1}, A^1, R^{c4}, R^{d1}), (X^1, R^{a2}, R^{b1}, A^1, R^{c4}, R^{d2}), (X^1, R^{a2}, R^{b1}, A^1, R^{c4}, R^{d3}), (X^1, R^{a2}, R^{b1}, A^2, R^{c1}, R^{d1}), (X^1, R^{a2}, R^{b1}, A^2, R^{c1}, R^{d2}), (X^1, R^{a2}, R^{b1}, A^2, R^{c1}, R^{d3}), (X^1, R^{a2}, R^{b1}, A^2, R^{c2}, R^{d1}), (X^1, R^{a2}, R^{b1}, A^2, R^{c2}, R^{d2}), (X^1, R^{a2}, R^{b1}, A^2, R^{c2}, R^{d3}), (X^1, R^{a2}, R^{b1}, A^2, R^{c3}, R^{d1}), (X^1, R^{a2}, R^{b1}, A^2, R^{c3}, R^{d2}), (X^1, R^{a2}, R^{b1}, A^2, R^{c3}, R^{d3}), (X^1, R^{a2}, R^{b1}, A^2, R^{c4}, R^{d1}), (X^1, R^{a2}, R^{b1}, A^2, R^{c4}, R^{d2}), (X^1, R^{a2}, R^{b1}, A^2, R^{c4}, R^{d3}), (X^1, R^{a2}, R^{b1}, A^3, R^{c1}, R^{d1}), (X^1, R^{a2}, R^{b1}, A^3, R^{c1}, R^{d2}), (X^1, R^{a2}, R^{b1}, A^3, R^{c1}, R^{d3}), (X^1, R^{a2}, R^{b1}, A^3, R^{c2}, R^{d1}), (X^1, R^{a2}, R^{b1}, A^3, R^{c2}, R^{d2}), (X^1, R^{a2}, R^{b1}, A^3, R^{c2}, R^{d3}), (X^1, R^{a2}, R^{b1}, A^3, R^{c3}, R^{d1}), (X^1, R^{a2}, R^{b1}, A^3, R^{c3}, R^{d2}), (X^1, R^{a2}, R^{b1}, A^3, R^{c3}, R^{d3}), (X^1, R^{a2}, R^{b1}, A^3, R^{c4}, R^{d1}), (X^1, R^{a2}, R^{b1}, A^3, R^{c4}, R^{d2}), (X^1, R^{a2}, R^{b1}, A^3, R^{c4}, R^{d3}), (X^1, R^{a2}, R^{b1}, A^4, R^{c1}, R^{d1}), (X^1, R^{a2}, R^{b1}, A^4, R^{c1}, R^{d2}), (X^1, R^{a2}, R^{b1}, A^4, R^{c1}, R^{d3}), (X^1, R^{a2}, R^{b1}, A^4, R^{c2}, R^{d1}), (X^1, R^{a2}, R^{b1}, A^4, R^{c2}, R^{d2}), (X^1, R^{a2}, R^{b1}, A^4, R^{c2}, R^{d3}), (X^1, R^{a2}, R^{b1}, A^4, R^{c3}, R^{d1}), (X^1, R^{a2}, R^{b1}, A^4, R^{c3}, R^{d2}), (X^1, R^{a2}, R^{b1}, A^4, R^{c3}, R^{d3}), (X^1, R^{a2}, R^{b1}, A^4, R^{c4}, R^{d1}), (X^1, R^{a2}, R^{b1}, A^4, R^{c4}, R^{d2}), (X^1, R^{a2}, R^{b1}, A^4, R^{c4}, R^{d3}), (X^1, R^{a2}, R^{b1}, A^5, R^{c1}, R^{d1}), (X^1, R^{a2}, R^{b1}, A^5, R^{c1}, R^{d2}), (X^1, R^{a2}, R^{b1}, A^5, R^{c1}, R^{d3}), (X^1, R^{a2}, R^{b1}, A^5, R^{c2}, R^{d1}), (X^1, R^{a2}, R^{b1}, A^5, R^{c2}, R^{d2}), (X^1, R^{a2}, R^{b1}, A^5, R^{c2}, R^{d3}), (X^1, R^{a2}, R^{b1}, A^5, R^{c3}, R^{d1}), (X^1, R^{a2}, R^{b1}, A^5, R^{c3}, R^{d2}), (X^1, R^{a2}, R^{b1}, A^5, R^{c3}, R^{d3}), (X^1, R^{a2}, R^{b1}, A^5, R^{c4}, R^{d1}), (X^1, R^{a2}, R^{b1}, A^5, R^{c4}, R^{d2}), (X^1, R^{a2}, R^{b1}, A^5, R^{c4}, R^{d3}), (X^1, R^{a2}, R^{b2}, A^1, R^{c1}, R^{d1}), (X^1, R^{a2}, R^{b2}, A^1, R^{c1}, R^{d2}), (X^1, R^{a2}, R^{b2}, A^1, R^{c1}, R^{d3}), (X^1, R^{a2}, R^{b2}, A^1, R^{c2}, R^{d1}), (X^1, R^{a2}, R^{b2}, A^1, R^{c2}, R^{d2}), (X^1, R^{a2}, R^{b2}, A^1, R^{c2}, R^{d3}), (X^1, R^{a2}, R^{b2}, A^1, R^{c3}, R^{d1}), (X^1, R^{a2}, R^{b2}, A^1, R^{c3}, R^{d2}), (X^1, R^{a2}, R^{b2}, A^1, R^{c3}, R^{d3}), (X^1, R^{a2}, R^{b2}, A^1, R^{c4}, R^{d1}), (X^1, R^{a2}, R^{b2}, A^1, R^{c4}, R^{d2}), (X^1, R^{a2}, R^{b2}, A^1, R^{c4}, R^{d3}), (X^1, R^{a2}, R^{b2}, A^2, R^{c1}, R^{d1}), (X^1, R^{a2}, R^{b2}, A^2, R^{c1}, R^{d2}), (X^1, R^{a2}, R^{b2}, A^2, R^{c1}, R^{d3}), (X^1, R^{a2}, R^{b2}, A^2, R^{c2}, R^{d1}), (X^1, R^{a2}, R^{b2}, A^2, R^{c2}, R^{d2}), (X^1, R^{a2}, R^{b2}, A^2, R^{c2}, R^{d3}), (X^1, R^{a2}, R^{b2}, A^2, R^{c3}, R^{d1}), (X^1, R^{a2}, R^{b2}, A^2, R^{c3}, R^{d2}), (X^1, R^{a2}, R^{b2}, A^2, R^{c3}, R^{d3}), (X^1, R^{a2}, R^{b2}, A^2, R^{c4}, R^{d1}), (X^1, R^{a2}, R^{b2}, A^2, R^{c4}, R^{d2}), (X^1, R^{a2}, R^{b2}, A^2, R^{c4}, R^{d3}), (X^1, R^{a2}, R^{b2}, A^3, R^{c1}, R^{d1}), (X^1, R^{a2}, R^{b2}, A^3, R^{c1}, R^{d2}), (X^1, R^{a2}, R^{b2}, A^3, R^{c1}, R^{d3}), (X^1, R^{a2},$ $R^{b2}, A^3, R^{c2}, R^{d1}), (X^1, R^{a2}, R^{b2}, A^3, R^{c2}, R^{d2}), (X^1, R^{a2},$
$R^{b2}, A^3, R^{c2}, R^{d3}), (X^1, R^{a2}, R^{b2}, A^3, R^{c3}, R^{d1}), (X^1, R^{a2},$
$R^{b2}, A^3, R^{c3}, R^{d2}), (X^1, R^{a2}, R^{b2}, A^3, R^{c3}, R^{d3}), (X^1, R^{a2},$
$R^{b2}, A^3, R^{c4}, R^{d1}), (X^1, R^{a2}, R^{b2}, A^3, R^{c4}, R^{d2}), (X^1, R^{a2},$
$R^{b2}, A^3, R^{c4}, R^{d3}), (X^1, R^{a2}, R^{b2}, A^4, R^{c1}, R^{d1}), (X^1, R^{a2},$
$R^{b2}, A^4, R^{c1}, R^{d2}), (X^1, R^{a2}, R^{b2}, A^4, R^{c1}, R^{d3}), (X^1, R^{a2},$
$R^{b2}, A^4, R^{c2}, R^{d1}), (X^1, R^{a2}, R^{b2}, A^4, R^{c2}, R^{d2}), (X^1, R^{a2},$
$R^{b2}, A^4, R^{c2}, R^{d3}), (X^1, R^{a2}, R^{b2}, A^4, R^{c3}, R^{d1}), (X^1, R^{a2},$
$R^{b2}, A^4, R^{c3}, R^{d2}), (X^1, R^{a2}, R^{b2}, A^4, R^{c3}, R^{d3}), (X^1, R^{a2},$
$R^{b2}, A^4, R^{c4}, R^{d1}), (X^1, R^{a2}, R^{b2}, A^4, R^{c4}, R^{d2}), (X^1, R^{a2},$
$R^{b2}, A^4, R^{c4}, R^{d3}), (X^1, R^{a2}, R^{b2}, A^5, R^{c1}, R^{d1}), (X^1, R^{a2},$
$R^{b2}, A^5, R^{c1}, R^{d2}), (X^1, R^{a2}, R^{b2}, A^5, R^{c1}, R^{d3}), (X^1, R^{a2},$
$R^{b2}, A^5, R^{c2}, R^{d1}), (X^1, R^{a2}, R^{b2}, A^5, R^{c2}, R^{d2}), (X^1, R^{a2},$
$R^{b2}, A^5, R^{c2}, R^{d3}), (X^1, R^{a2}, R^{b2}, A^5, R^{c3}, R^{d1}), (X^1, R^{a2},$
$R^{b2}, A^5, R^{c3}, R^{d2}), (X^1, R^{a2}, R^{b2}, A^5, R^{c3}, R^{d3}), (X^1, R^{a2},$
$R^{b2}, A^5, R^{c4}, R^{d1}), (X^1, R^{a2}, R^{b2}, A^5, R^{c4}, R^{d2}), (X^1, R^{a2},$
$R^{b2}, A^5, R^{c4}, R^{d3}), (X^1, R^{a2}, R^{b3}, A^1, R^{c1}, R^{d1}), (X^1, R^{a2},$
$R^{b3}, A^1, R^{c1}, R^{d2}), (X^1, R^{a2}, R^{b3}, A^1, R^{c1}, R^{d3}), (X^1, R^{a2},$
$R^{b3}, A^1, R^{c2}, R^{d1}), (X^1, R^{a2}, R^{b3}, A^1, R^{c2}, R^{d2}), (X^1, R^{a2},$
$R^{b3}, A^1, R^{c2}, R^{d3}), (X^1, R^{a2}, R^{b3}, A^1, R^{c3}, R^{d1}), (X^1, R^{a2},$
$R^{b3}, A^1, R^{c3}, R^{d2}), (X^1, R^{a2}, R^{b3}, A^1, R^{c3}, R^{d3}), (X^1, R^{a2},$
$R^{b3}, A^1, R^{c4}, R^{d1}), (X^1, R^{a2}, R^{b3}, A^1, R^{c4}, R^{d2}), (X^1, R^{a2},$
$R^{b3}, A^1, R^{c4}, R^{d3}), (X^1, R^{a2}, R^{b3}, A^2, R^{c1}, R^{d1}), (X^1, R^{a2},$
$R^{b3}, A^2, R^{c1}, R^{d2}), (X^1, R^{a2}, R^{b3}, A^2, R^{c1}, R^{d3}), (X^1, R^{a2},$
$R^{b3}, A^2, R^{c2}, R^{d1}), (X^1, R^{a2}, R^{b3}, A^2, R^{c2}, R^{d2}), (X^1, R^{a2},$
$R^{b3}, A^2, R^{c2}, R^{d3}), (X^1, R^{a2}, R^{b3}, A^2, R^{c3}, R^{d1}), (X^1, R^{a2},$
$R^{b3}, A^2, R^{c3}, R^{d2}), (X^1, R^{a2}, R^{b3}, A^2, R^{c3}, R^{d3}), (X^1, R^{a2},$
$R^{b3}, A^2, R^{c4}, R^{d1}), (X^1, R^{a2}, R^{b3}, A^2, R^{c4}, R^{d2}), (X^1, R^{a2},$
$R^{b3}, A^2, R^{c4}, R^{d3}), (X^1, R^{a2}, R^{b3}, A^3, R^{c1}, R^{d1}), (X^1, R^{a2},$
$R^{b3}, A^3, R^{c1}, R^{d2}), (X^1, R^{a2}, R^{b3}, A^3, R^{c1}, R^{d3}), (X^1, R^{a2},$
$R^{b3}, A^3, R^{c2}, R^{d1}), (X^1, R^{a2}, R^{b3}, A^3, R^{c2}, R^{d2}), (X^1, R^{a2},$
$R^{b3}, A^3, R^{c2}, R^{d3}), (X^1, R^{a2}, R^{b3}, A^3, R^{c3}, R^{d1}), (X^1, R^{a2},$
$R^{b3}, A^3, R^{c3}, R^{d2}), (X^1, R^{a2}, R^{b3}, A^3, R^{c3}, R^{d3}), (X^1, R^{a2},$
$R^{b3}, A^3, R^{c4}, R^{d1}), (X^1, R^{a2}, R^{b3}, A^3, R^{c4}, R^{d2}), (X^1, R^{a2},$
$R^{b3}, A^3, R^{c4}, R^{d3}), (X^1, R^{a2}, R^{b3}, A^4, R^{c1}, R^{d1}), (X^1, R^{a2},$
$R^{b3}, A^4, R^{c1}, R^{d2}), (X^1, R^{a2}, R^{b3}, A^4, R^{c1}, R^{d3}), (X^1, R^{a2},$
$R^{b3}, A^4, R^{c2}, R^{d1}), (X^1, R^{a2}, R^{b3}, A^4, R^{c2}, R^{d2}), (X^1, R^{a2},$
$R^{b3}, A^4, R^{c2}, R^{d3}), (X^1, R^{a2}, R^{b3}, A^4, R^{c3}, R^{d1}), (X^1, R^{a2},$
$R^{b3}, A^4, R^{c3}, R^{d2}), (X^1, R^{a2}, R^{b3}, A^4, R^{c3}, R^{d3}), (X^1, R^{a2},$
$R^{b3}, A^4, R^{c4}, R^{d1}), (X^1, R^{a2}, R^{b3}, A^4, R^{c4}, R^{d2}), (X^1, R^{a2},$
$R^{b3}, A^4, R^{c4}, R^{d3}), (X^1, R^{a2}, R^{b3}, A^5, R^{c1}, R^{d1}), (X^1, R^{a2},$
$R^{b3}, A^5, R^{c1}, R^{d2}), (X^1, R^{a2}, R^{b3}, A^5, R^{c1}, R^{d3}), (X^1, R^{a2},$
$R^{b3}, A^5, R^{c2}, R^{d1}), (X^1, R^{a2}, R^{b3}, A^5, R^{c2}, R^{d2}), (X^1, R^{a2},$
$R^{b3}, A^5, R^{c2}, R^{d3}), (X^1, R^{a2}, R^{b3}, A^5, R^{c3}, R^{d1}), (X^1, R^{a2},$
$R^{b3}, A^5, R^{c3}, R^{d2}), (X^1, R^{a2}, R^{b3}, A^5, R^{c3}, R^{d3}), (X^1, R^{a2},$
$R^{b3}, A^5, R^{c4}, R^{d1}), (X^1, R^{a2}, R^{b3}, A^5, R^{c4}, R^{d2}), (X^1, R^{a2},$
$R^{b3}, A^5, R^{c4}, R^{d3}), (X^1, R^{a3}, R^{b1}, A^1, R^{c1}, R^{d1}), (X^1, R^{a3},$
$R^{b1}, A^1, R^{c1}, R^{d2}), (X^1, R^{a3}, R^{b1}, A^1, R^{c1}, R^{d3}), (X^1, R^{a3},$
$R^{b1}, A^1, R^{c2}, R^{d1}), (X^1, R^{a3}, R^{b1}, A^1, R^{c2}, R^{d2}), (X^1, R^{a3},$
$R^{b1}, A^1, R^{c2}, R^{d3}), (X^1, R^{a3}, R^{b1}, A^1, R^{c3}, R^{d1}), (X^1, R^{a3},$
$R^{b1}, A^1, R^{c3}, R^{d2}), (X^1, R^{a3}, R^{b1}, A^1, R^{c3}, R^{d3}), (X^1, R^{a3},$
$R^{b1}, A^1, R^{c4}, R^{d1}), (X^1, R^{a3}, R^{b1}, A^1, R^{c4}, R^{d2}), (X^1, R^{a3},$
$R^{b1}, A^1, R^{c4}, R^{d3}), (X^1, R^{a3}, R^{b1}, A^2, R^{c1}, R^{d1}), (X^1, R^{a3},$
$R^{b1}, A^2, R^{c1}, R^{d2}), (X^1, R^{a3}, R^{b1}, A^2, R^{c1}, R^{d3}), (X^1, R^{a3},$
$R^{b1}, A^2, R^{c2}, R^{d1}), (X^1, R^{a3}, R^{b1}, A^2, R^{c2}, R^{d2}), (X^1, R^{a3},$
$R^{b1}, A^2, R^{c2}, R^{d3}), (X^1, R^{a3}, R^{b1}, A^2, R^{c3}, R^{d1}), (X^1, R^{a3},$
$R^{b1}, A^2, R^{c3}, R^{d2}), (X^1, R^{a3}, R^{b1}, A^2, R^{c3}, R^{d3}), (X^1, R^{a3},$
$R^{b1}, A^2, R^{c4}, R^{d1}), (X^1, R^{a3}, R^{b1}, A^2, R^{c4}, R^{d2}), (X^1, R^{a3},$
$R^{b1}, A^2, R^{c4}, R^{d3}), (X^1, R^{a3}, R^{b1}, A^3, R^{c1}, R^{d1}), (X^1, R^{a3},$
$R^{b1}, A^3, R^{c1}, R^{d2}), (X^1, R^{a3}, R^{b1}, A^3, R^{c1}, R^{d3}), (X^1, R^{a3},$
$R^{b1}, A^3, R^{c2}, R^{d1}), (X^1, R^{a3}, R^{b1}, A^3, R^{c2}, R^{d2}), (X^1, R^{a3},$
$R^{b1}, A^3, R^{c2}, R^{d3}), (X^1, R^{a3}, R^{b1}, A^3, R^{c3}, R^{d1}), (X^1, R^{a3},$
$R^{b1}, A^3, R^{c3}, R^{d2}), (X^1, R^{a3}, R^{b1}, A^3, R^{c3}, R^{d3}), (X^1, R^{a3},$
$R^{b1}, A^3, R^{c4}, R^{d1}), (X^1, R^{a3}, R^{b1}, A^3, R^{c4}, R^{d2}), (X^1, R^{a3},$
$R^{b1}, A^3, R^{c4}, R^{d3}), (X^1, R^{a3}, R^{b1}, A^4, R^{c1}, R^{d1}), (X^1, R^{a3},$
$R^{b1}, A^4, R^{c1}, R^{d2}), (X^1, R^{a3}, R^{b1}, A^4, R^{c1}, R^{d3}), (X^1, R^{a3},$
$R^{b1}, A^4, R^{c2}, R^{d1}), (X^1, R^{a3}, R^{b1}, A^4, R^{c2}, R^{d2}), (X^1, R^{a3},$
$R^{b1}, A^4, R^{c2}, R^{d3}), (X^1, R^{a3}, R^{b1}, A^4, R^{c3}, R^{d1}), (X^1, R^{a3},$
$R^{b1}, A^4, R^{c3}, R^{d2}), (X^1, R^{a3}, R^{b1}, A^4, R^{c3}, R^{d3}), (X^1, R^{a3},$
$R^{b1}, A^4, R^{c4}, R^{d1}), (X^1, R^{a3}, R^{b1}, A^4, R^{c4}, R^{d2}), (X^1, R^{a3},$
$R^{b1}, A^4, R^{c4}, R^{d3}), (X^1, R^{a3}, R^{b1}, A^5, R^{c1}, R^{d1}), (X^1, R^{a3},$
$R^{b1}, A^5, R^{c1}, R^{d2}), (X^1, R^{a3}, R^{b1}, A^5, R^{c1}, R^{d3}), (X^1, R^{a3},$
$R^{b1}, A^5, R^{c2}, R^{d1}), (X^1, R^{a3}, R^{b1}, A^5, R^{c2}, R^{d2}), (X^1, R^{a3},$
$R^{b1}, A^5, R^{c2}, R^{d3}), (X^1, R^{a3}, R^{b1}, A^5, R^{c3}, R^{d1}), (X^1, R^{a3},$
$R^{b1}, A^5, R^{c3}, R^{d2}), (X^1, R^{a3}, R^{b1}, A^5, R^{c3}, R^{d3}), (X^1, R^{a3},$
$R^{b1}, A^5, R^{c4}, R^{d1}), (X^1, R^{a3}, R^{b1}, A^5, R^{c4}, R^{d2}), (X^1, R^{a3},$
$R^{b1}, A^5, R^{c4}, R^{d3}), (X^1, R^{a3}, R^{b2}, A^1, R^{c1}, R^{d1}), (X^1, R^{a3},$
$R^{b2}, A^1, R^{c1}, R^{d2}), (X^1, R^{a3}, R^{b2}, A^1, R^{c1}, R^{d3}), (X^1, R^{a3},$
$R^{b2}, A^1, R^{c2}, R^{d1}), (X^1, R^{a3}, R^{b2}, A^1, R^{c2}, R^{d2}), (X^1, R^{a3},$
$R^{b2}, A^1, R^{c2}, R^{d3}), (X^1, R^{a3}, R^{b2}, A^1, R^{c3}, R^{d1}), (X^1, R^{a3},$
$R^{b2}, A^1, R^{c3}, R^{d2}), (X^1, R^{a3}, R^{b2}, A^1, R^{c3}, R^{d3}), (X^1, R^{a3},$
$R^{b2}, A^1, R^{c4}, R^{d1}), (X^1, R^{a3}, R^{b2}, A^1, R^{c4}, R^{d2}), (X^1, R^{a3},$
$R^{b2}, A^1, R^{c4}, R^{d3}), (X^1, R^{a3}, R^{b2}, A^2, R^{c1}, R^{d1}), (X^1, R^{a3},$
$R^{b2}, A^2, R^{c1}, R^{d2}), (X^1, R^{a3}, R^{b2}, A^2, R^{c1}, R^{d3}), (X^1, R^{a3},$
$R^{b2}, A^2, R^{c2}, R^{d1}), (X^1, R^{a3}, R^{b2}, A^2, R^{c2}, R^{d2}), (X^1, R^{a3},$
$R^{b2}, A^2, R^{c2}, R^{d3}), (X^1, R^{a3}, R^{b2}, A^2, R^{c3}, R^{d1}), (X^1, R^{a3},$
$R^{b2}, A^2, R^{c3}, R^{d2}), (X^1, R^{a3}, R^{b2}, A^2, R^{c3}, R^{d3}), (X^1, R^{a3},$
$R^{b2}, A^2, R^{c4}, R^{d1}), (X^1, R^{a3}, R^{b2}, A^2, R^{c4}, R^{d2}), (X^1, R^{a3},$
$R^{b2}, A^2, R^{c4}, R^{d3}), (X^1, R^{a3}, R^{b2}, A^3, R^{c1}, R^{d1}), (X^1, R^{a3},$
$R^{b2}, A^3, R^{c1}, R^{d2}), (X^1, R^{a3}, R^{b2}, A^3, R^{c1}, R^{d3}), (X^1, R^{a3},$
$R^{b2}, A^3, R^{c2}, R^{d1}), (X^1, R^{a3}, R^{b2}, A^3, R^{c2}, R^{d2}), (X^1, R^{a3},$
$R^{b2}, A^3, R^{c2}, R^{d3}), (X^1, R^{a3}, R^{b2}, A^3, R^{c3}, R^{d1}), (X^1, R^{a3},$
$R^{b2}, A^3, R^{c3}, R^{d2}), (X^1, R^{a3}, R^{b2}, A^3, R^{c3}, R^{d3}), (X^1, R^{a3},$
$R^{b2}, A^3, R^{c4}, R^{d1}), (X^1, R^{a3}, R^{b2}, A^3, R^{c4}, R^{d2}), (X^1, R^{a3},$
$R^{b2}, A^3, R^{c4}, R^{d3}), (X^1, R^{a3}, R^{b2}, A^4, R^{c1}, R^{d1}), (X^1, R^{a3},$
$R^{b2}, A^4, R^{c1}, R^{d2}), (X^1, R^{a3}, R^{b2}, A^4, R^{c1}, R^{d3}), (X^1, R^{a3},$
$R^{b2}, A^4, R^{c2}, R^{d1}), (X^1, R^{a3}, R^{b2}, A^4, R^{c2}, R^{d2}), (X^1, R^{a3},$
$R^{b2}, A^4, R^{c2}, R^{d3}), (X^1, R^{a3}, R^{b2}, A^4, R^{c3}, R^{d1}), (X^1, R^{a3},$
$R^{b2}, A^4, R^{c3}, R^{d2}), (X^1, R^{a3}, R^{b2}, A^4, R^{c3}, R^{d3}), (X^1, R^{a3},$
$R^{b2}, A^4, R^{c4}, R^{d1}), (X^1, R^{a3}, R^{b2}, A^4, R^{c4}, R^{d2}), (X^1, R^{a3},$
$R^{b2}, A^4, R^{c4}, R^{d3}), (X^1, R^{a3}, R^{b2}, A^5, R^{c1}, R^{d1}), (X^1, R^{a3},$
$R^{b2}, A^5, R^{c1}, R^{d2}), (X^1, R^{a3}, R^{b2}, A^5, R^{c1}, R^{d3}), (X^1, R^{a3},$
$R^{b2}, A^5, R^{c2}, R^{d1}), (X^1, R^{a3}, R^{b2}, A^5, R^{c2}, R^{d2}), (X^1, R^{a3},$
$R^{b2}, A^5, R^{c2}, R^{d3}), (X^1, R^{a3}, R^{b2}, A^5, R^{c3}, R^{d1}), (X^1, R^{a3},$
$R^{b2}, A^5, R^{c3}, R^{d2}), (X^1, R^{a3}, R^{b2}, A^5, R^{c3}, R^{d3}), (X^1, R^{a3},$
$R^{b2}, A^5, R^{c4}, R^{d1}), (X^1, R^{a3}, R^{b2}, A^5, R^{c4}, R^{d2}), (X^1, R^{a3},$
$R^{b2}, A^5, R^{c4}, R^{d3}), (X^1, R^{a3}, R^{b3}, A^1, R^{c1}, R^{d1}), (X^1, R^{a3},$
$R^{b3}, A^1, R^{c1}, R^{d2}), (X^1, R^{a3}, R^{b3}, A^1, R^{c1}, R^{d3}), (X^1, R^{a3},$
$R^{b3}, A^1, R^{c2}, R^{d1}), (X^1, R^{a3}, R^{b3}, A^1, R^{c2}, R^{d2}), (X^1, R^{a3},$
$R^{b3}, A^1, R^{c2}, R^{d3}), (X^1, R^{a3}, R^{b3}, A^1, R^{c3}, R^{d1}), (X^1, R^{a3},$
$R^{b3}, A^1, R^{c3}, R^{d2}), (X^1, R^{a3}, R^{b3}, A^1, R^{c3}, R^{d3}), (X^1, R^{a3},$
$R^{b3}, A^1, R^{c4}, R^{d1}), (X^1, R^{a3}, R^{b3}, A^1, R^{c4}, R^{d2}), (X^1, R^{a3},$
$R^{b3}, A^1, R^{c4}, R^{d3}), (X^1, R^{a3}, R^{b3}, A^2, R^{c1}, R^{d1}), (X^1, R^{a3},$
$R^{b3}, A^2, R^{c1}, R^{d2}), (X^1, R^{a3}, R^{b3}, A^2, R^{c1}, R^{d3}), (X^1, R^{a3},$
$R^{b3}, A^2, R^{c2}, R^{d1}), (X^1, R^{a3}, R^{b3}, A^2, R^{c2}, R^{d2}), (X^1, R^{a3},$
$R^{b3}, A^2, R^{c2}, R^{d3}), (X^1, R^{a3}, R^{b3}, A^2, R^{c3}, R^{d1}), (X^1, R^{a3},$
$R^{b3}, A^2, R^{c3}, R^{d2}), (X^1, R^{a3}, R^{b3}, A^2, R^{c3}, R^{d3}), (X^1, R^{a3},$
$R^{b3}, A^2, R^{c4}, R^{d1}), (X^1, R^{a3}, R^{b3}, A^2, R^{c4}, R^{d2}), (X^1, R^{a3},$
$R^{b3}, A^2, R^{c4}, R^{d3}), (X^1, R^{a3}, R^{b3}, A^3, R^{c1}, R^{d1}), (X^1, R^{a3},$
$R^{b3}, A^3, R^{c1}, R^{d2}), (X^1, R^{a3}, R^{b3}, A^3, R^{c1}, R^{d3}), (X^1, R^{a3},$
$R^{b3}, A^3, R^{c2}, R^{d1}), (X^1, R^{a3}, R^{b3}, A^3, R^{c2}, R^{d2}), (X^1, R^{a3},$
$R^{b3}, A^3, R^{c2}, R^{d3}), (X^1, R^{a3}, R^{b3}, A^3, R^{c3}, R^{d1}), (X^1, R^{a3},$
$R^{b3}, A^3, R^{c3}, R^{d2}), (X^1, R^{a3}, R^{b3}, A^3, R^{c3}, R^{d3}), (X^1, R^{a3},$
$R^{b3}, A^3, R^{c4}, R^{d1}), (X^1, R^{a3}, R^{b3}, A^3, R^{c4}, R^{d2}), (X^1, R^{a3},$
$R^{b3}, A^3, R^{c4}, R^{d3}), (X^1, R^{a3}, R^{b3}, A^4, R^{c1}, R^{d1}), (X^1, R^{a3},$
$R^{b3}, A^4, R^{c1}, R^{d2}), (X^1, R^{a3}, R^{b3}, A^4, R^{c1}, R^{d3}), (X^1, R^{a3},$
$R^{b3}, A^4, R^{c2}, R^{d1}), (X^1, R^{a3}, R^{b3}, A^4, R^{c2}, R^{d2}), (X^1, R^{a3},$
$R^{b3}, A^4, R^{c2}, R^{d3}), (X^1, R^{a3}, R^{b3}, A^4, R^{c3}, R^{d1}), (X^1, R^{a3},$
$R^{b3}, A^4, R^{c3}, R^{d2}), (X^1, R^{a3}, R^{b3}, A^4, R^{c3}, R^{d3}), (X^1, R^{a3},$
$R^{b3}, A^4, R^{c4}, R^{d1}), (X^1, R^{a3}, R^{b3}, A^4, R^{c4}, R^{d2}), (X^1, R^{a3},$
$R^{b3}, A^4, R^{c4}, R^{d3}), (X^1, R^{a3}, R^{b3}, A^5, R^{c1}, R^{d1}), (X^1, R^{a3},$
$R^{b3}, A^5, R^{c1}, R^{d2}), (X^1, R^{a3}, R^{b3}, A^5, R^{c1}, R^{d3}), (X^1, R^{a3},$
$R^{b3}, A^5, R^{c2}, R^{d1}), (X^1, R^{a3}, R^{b3}, A^5, R^{c2}, R^{d2}), (X^1, R^{a3},$
$R^{b3}, A^5, R^{c2}, R^{d3}), (X^1, R^{a3}, R^{b3}, A^5, R^{c3}, R^{d1}), (X^1, R^{a3},$ $R^{b3}, A^5, R^{c3}, R^{d2}), (X^1, R^{a3}, R^{b3}, A^5, R^{c3}, R^{d3}), (X^1, R^{a3},$
$R^{b3}, A^5, R^{c4}, R^{d1}), (X^1, R^{a3}, R^{b3}, A^5, R^{c4}, R^{d2}), (X^1, R^{a3},$
$R^{b3}, A^5, R^{c4}, R^{d3}), (X^2, R^{a1}, R^{b1}, A^1, R^{c1}, R^{d3}), (X^2, R^{a1},$
$R^{b1}, A^1, R^{c1}, R^{d2}), (X^2, R^{a1}, R^{b1}, A^1, R^{c2}, R^{d2}), (X^2, R^{a1},$
$R^{b1}, A^1, R^{c2}, R^{d3}), (X^2, R^{a1}, R^{b1}, A^1, R^{c3}, R^{d1}), (X^2, R^{a1},$
$R^{b1}, A^1, R^{c3}, R^{d2}), (X^2, R^{a1}, R^{b1}, A^1, R^{c3}, R^{d3}), (X^2, R^{a1},$
$R^{b1}, A^1, R^{c4}, R^{d1}), (X^2, R^{a1}, R^{b1}, A^1, R^{c4}, R^{d2}), (X^2, R^{a1},$
$R^{b1}, A^1, R^{c4}, R^{d3}), (X^2, R^{a1}, R^{b1}, A^2, R^{c1}, R^{d1}), (X^2, R^{a1},$
$R^{b1}, A^2, R^{c1}, R^{d2}), (X^2, R^{a1}, R^{b1}, A^2, R^{c1}, R^{d3}), (X^2, R^{a1},$
$R^{b1}, A^2, R^{c2}, R^{d1}), (X^2, R^{a1}, R^{b1}, A^2, R^{c2}, R^{d2}), (X^2, R^{a1},$
$R^{b1}, A^2, R^{c2}, R^{d3}), (X^2, R^{a1}, R^{b1}, A^2, R^{c3}, R^{d1}), (X^2, R^{a1},$
$R^{b1}, A^2, R^{c3}, R^{d2}), (X^2, R^{a1}, R^{b1}, A^2, R^{c3}, R^{d3}), (X^2, R^{a1},$
$R^{b1}, A^2, R^{c4}, R^{d1}), (X^2, R^{a1}, R^{b1}, A^2, R^{c4}, R^{d2}), (X^2, R^{a1},$
$R^{b1}, A^2, R^{c4}, R^{d3}), (X^2, R^{a1}, R^{b1}, A^3, R^{c1}, R^{d1}), (X^2, R^{a1},$
$R^{b1}, A^3, R^{c1}, R^{d2}), (X^2, R^{a1}, R^{b1}, A^3, R^{c1}, R^{d3}), (X^2, R^{a1},$
$R^{b1}, A^3, R^{c2}, R^{d1}), (X^2, R^{a1}, R^{b1}, A^3, R^{c2}, R^{d2}), (X^2, R^{a1},$
$R^{b1}, A^3, R^{c2}, R^{d3}), (X^2, R^{a1}, R^{b1}, A^3, R^{c3}, R^{d1}), (X^2, R^{a1},$
$R^{b1}, A^3, R^{c3}, R^{d2}), (X^2, R^{a1}, R^{b1}, A^3, R^{c3}, R^{d3}), (X^2, R^{a1},$
$R^{b1}, A^3, R^{c4}, R^{d1}), (X^2, R^{a1}, R^{b1}, A^3, R^{c4}, R^{d2}), (X^2, R^{a1},$
$R^{b1}, A^3, R^{c4}, R^{d3}), (X^2, R^{a1}, R^{b1}, A^4, R^{c1}, R^{d1}), (X^2, R^{a1},$
$R^{b1}, A^4, R^{c1}, R^{d2}), (X^2, R^{a1}, R^{b1}, A^4, R^{c1}, R^{d3}), (X^2, R^{a1},$
$R^{b1}, A^4, R^{c2}, R^{d1}), (X^2, R^{a1}, R^{b1}, A^4, R^{c2}, R^{d2}), (X^2, R^{a1},$
$R^{b1}, A^4, R^{c2}, R^{d3}), (X^2, R^{a1}, R^{b1}, A^4, R^{c3}, R^{d1}), (X^2, R^{a1},$
$R^{b1}, A^4, R^{c3}, R^{d2}), (X^2, R^{a1}, R^{b1}, A^4, R^{c3}, R^{d3}), (X^2, R^{a1},$
$R^{b1}, A^4, R^{c4}, R^{d1}), (X^2, R^{a1}, R^{b1}, A^4, R^{c4}, R^{d2}), (X^2, R^{a1},$
$R^{b1}, A^4, R^{c4}, R^{d3}), (X^2, R^{a1}, R^{b1}, A^5, R^{c1}, R^{d1}), (X^2, R^{a1},$
$R^{b1}, A^5, R^{c1}, R^{d2}), (X^2, R^{a1}, R^{b1}, A^5, R^{c1}, R^{d3}), (X^2, R^{a1},$
$R^{b1}, A^5, R^{c2}, R^{d1}), (X^2, R^{a1}, R^{b1}, A^5, R^{c2}, R^{d2}), (X^2, R^{a1},$
$R^{b1}, A^5, R^{c2}, R^{d3}), (X^2, R^{a1}, R^{b1}, A^5, R^{c3}, R^{d1}), (X^2, R^{a1},$
$R^{b1}, A^5, R^{c3}, R^{d2}), (X^2, R^{a1}, R^{b1}, A^5, R^{c3}, R^{d3}), (X^2, R^{a1},$
$R^{b1}, A^5, R^{c4}, R^{d1}), (X^2, R^{a1}, R^{b1}, A^5, R^{c4}, R^{d2}), (X^2, R^{a1},$
$R^{b1}, A^5, R^{c4}, R^{d3}), (X^2, R^{a1}, R^{b2}, A^1, R^{c1}, R^{d1}), (X^2, R^{a1},$
$R^{b2}, A^1, R^{c1}, R^{d2}), (X^2, R^{a1}, R^{b2}, A^1, R^{c1}, R^{d3}), (X^2, R^{a1},$
$R^{b2}, A^1, R^{c2}, R^{d1}), (X^2, R^{a1}, R^{b2}, A^1, R^{c2}, R^{d2}), (X^2, R^{a1},$
$R^{b2}, A^1, R^{c2}, R^{d3}), (X^2, R^{a1}, R^{b2}, A^1, R^{c3}, R^{d1}), (X^2, R^{a1},$
$R^{b2}, A^1, R^{c3}, R^{d2}), (X^2, R^{a1}, R^{b2}, A^1, R^{c3}, R^{d3}), (X^2, R^{a1},$
$R^{b2}, A^1, R^{c4}, R^{d1}), (X^2, R^{a1}, R^{b2}, A^1, R^{c4}, R^{d2}), (X^2, R^{a1},$
$R^{b2}, A^1, R^{c4}, R^{d3}), (X^2, R^{a1}, R^{b2}, A^2, R^{c1}, R^{d1}), (X^2, R^{a1},$
$R^{b2}, A^2, R^{c1}, R^{d2}), (X^2, R^{a1}, R^{b2}, A^2, R^{c1}, R^{d3}), (X^2, R^{a1},$
$R^{b2}, A^2, R^{c2}, R^{d1}), (X^2, R^{a1}, R^{b2}, A^2, R^{c2}, R^{d2}), (X^2, R^{a1},$
$R^{b2}, A^2, R^{c2}, R^{d3}), (X^2, R^{a1}, R^{b2}, A^2, R^{c3}, R^{d1}), (X^2, R^{a1},$
$R^{b2}, A^2, R^{c3}, R^{d2}), (X^2, R^{a1}, R^{b2}, A^2, R^{c3}, R^{d3}), (X^2, R^{a1},$
$R^{b2}, A^2, R^{c4}, R^{d1}), (X^2, R^{a1}, R^{b2}, A^2, R^{c4}, R^{d2}), (X^2, R^{a1},$
$R^{b2}, A^2, R^{c4}, R^{d3}), (X^2, R^{a1}, R^{b2}, A^3, R^{c1}, R^{d1}), (X^2, R^{a1},$
$R^{b2}, A^3, R^{c1}, R^{d2}), (X^2, R^{a1}, R^{b2}, A^3, R^{c1}, R^{d3}), (X^2, R^{a1},$
$R^{b2}, A^3, R^{c2}, R^{d1}), (X^2, R^{a1}, R^{b2}, A^3, R^{c2}, R^{d2}), (X^2, R^{a1},$
$R^{b2}, A^3, R^{c2}, R^{d3}), (X^2, R^{a1}, R^{b2}, A^3, R^{c3}, R^{d1}), (X^2, R^{a1},$
$R^{b2}, A^3, R^{c3}, R^{d2}), (X^2, R^{a1}, R^{b2}, A^3, R^{c3}, R^{d3}), (X^2, R^{a1},$
$R^{b2}, A^3, R^{c4}, R^{d1}), (X^2, R^{a1}, R^{b2}, A^3, R^{c4}, R^{d2}), (X^2, R^{a1},$
$R^{b2}, A^3, R^{c4}, R^{d3}), (X^2, R^{a1}, R^{b2}, A^4, R^{c1}, R^{d1}), (X^2, R^{a1},$
$R^{b2}, A^4, R^{c1}, R^{d2}), (X^2, R^{a1}, R^{b2}, A^4, R^{c1}, R^{d3}), (X^2, R^{a1},$
$R^{b2}, A^4, R^{c2}, R^{d1}), (X^2, R^{a1}, R^{b2}, A^4, R^{c2}, R^{d2}), (X^2, R^{a1},$
$R^{b2}, A^4, R^{c2}, R^{d3}), (X^2, R^{a1}, R^{b2}, A^4, R^{c3}, R^{d1}), (X^2, R^{a1},$
$R^{b2}, A^4, R^{c3}, R^{d2}), (X^2, R^{a1}, R^{b2}, A^4, R^{c3}, R^{d3}), (X^2, R^{a1},$
$R^{b2}, A^4, R^{c4}, R^{d1}), (X^2, R^{a1}, R^{b2}, A^4, R^{c4}, R^{d2}), (X^2, R^{a1},$
$R^{b2}, A^4, R^{c4}, R^{d3}), (X^2, R^{a1}, R^{b2}, A^5, R^{c1}, R^{d1}), (X^2, R^{a1},$
$R^{b2}, A^5, R^{c1}, R^{d2}), (X^2, R^{a1}, R^{b2}, A^5, R^{c1}, R^{d3}), (X^2, R^{a1},$
$R^{b2}, A^5, R^{c2}, R^{d1}), (X^2, R^{a1}, R^{b2}, A^5, R^{c2}, R^{d2}), (X^2, R^{a1},$
$R^{b2}, A^5, R^{c2}, R^{d3}), (X^2, R^{a1}, R^{b2}, A^5, R^{c3}, R^{d1}), (X^2, R^{a1},$
$R^{b2}, A^5, R^{c3}, R^{d2}), (X^2, R^{a1}, R^{b2}, A^5, R^{c3}, R^{d3}), (X^2, R^{a1},$
$R^{b2}, A^5, R^{c4}, R^{d1}), (X^2, R^{a1}, R^{b2}, A^5, R^{c4}, R^{d2}), (X^2, R^{a1},$
$R^{b2}, A^5, R^{c4}, R^{d3}), (X^2, R^{a1}, R^{b3}, A^1, R^{c1}, R^{d1}), (X^2, R^{a1},$
$R^{b3}, A^1, R^{c1}, R^{d2}), (X^2, R^{a1}, R^{b3}, A^1, R^{c1}, R^{d3}), (X^2, R^{a1},$
$R^{b3}, A^1, R^{c2}, R^{d1}), (X^2, R^{a1}, R^{b3}, A^1, R^{c2}, R^{d2}), (X^2, R^{a1},$
$R^{b3}, A^1, R^{c2}, R^{d3}), (X^2, R^{a1}, R^{b3}, A^1, R^{c3}, R^{d1}), (X^2, R^{a1},$
$R^{b3}, A^1, R^{c3}, R^{d2}), (X^2, R^{a1}, R^{b3}, A^1, R^{c3}, R^{d3}), (X^2, R^{a1},$ $R^{b3}, A^1, R^{c4}, R^{d1}), (X^2, R^{a1}, R^{b3}, A^1, R^{c4}, R^{d2}), (X^2, R^{a1},$
$R^{b3}, A^1, R^{c4}, R^{d3}), (X^2, R^{a1}, R^{b3}, A^2, R^{c1}, R^{d1}), (X^2, R^{a1},$
$R^{b3}, A^2, R^{c1}, R^{d2}), (X^2, R^{a1}, R^{b3}, A^2, R^{c1}, R^{d3}), (X^2, R^{a1},$
$R^{b3}, A^2, R^{c2}, R^{d1}), (X^2, R^{a1}, R^{b3}, A^2, R^{c2}, R^{d2}), (X^2, R^{a1},$
$R^{b3}, A^2, R^{c2}, R^{d3}), (X^2, R^{a1}, R^{b3}, A^2, R^{c3}, R^{d1}), (X^2, R^{a1},$
$R^{b3}, A^2, R^{c3}, R^{d2}), (X^2, R^{a1}, R^{b3}, A^2, R^{c3}, R^{d3}), (X^2, R^{a1},$
$R^{b3}, A^2, R^{c4}, R^{d1}), (X^2, R^{a1}, R^{b3}, A^2, R^{c4}, R^{d2}), (X^2, R^{a1},$
$R^{b3}, A^2, R^{c4}, R^{d3}), (X^2, R^{a1}, R^{b3}, A^3, R^{c1}, R^{d1}), (X^2, R^{a1},$
$R^{b3}, A^3, R^{c1}, R^{d2}), (X^2, R^{a1}, R^{b3}, A^3, R^{c1}, R^{d3}), (X^2, R^{a1},$
$R^{b3}, A^3, R^{c2}, R^{d1}), (X^2, R^{a1}, R^{b3}, A^3, R^{c2}, R^{d2}), (X^2, R^{a1},$
$R^{b3}, A^3, R^{c2}, R^{d3}), (X^2, R^{a1}, R^{b3}, A^3, R^{c3}, R^{d1}), (X^2, R^{a1},$
$R^{b3}, A^3, R^{c3}, R^{d2}), (X^2, R^{a1}, R^{b3}, A^3, R^{c3}, R^{d3}), (X^2, R^{a1},$
$R^{b3}, A^3, R^{c4}, R^{d1}), (X^2, R^{a1}, R^{b3}, A^3, R^{c4}, R^{d2}), (X^2, R^{a1},$
$R^{b3}, A^3, R^{c4}, R^{d3}), (X^2, R^{a1}, R^{b3}, A^4, R^{c1}, R^{d1}), (X^2, R^{a1},$
$R^{b3}, A^4, R^{c1}, R^{d2}), (X^2, R^{a1}, R^{b3}, A^4, R^{c1}, R^{d3}), (X^2, R^{a1},$
$R^{b3}, A^4, R^{c2}, R^{d1}), (X^2, R^{a1}, R^{b3}, A^4, R^{c2}, R^{d2}), (X^2, R^{a1},$
$R^{b3}, A^4, R^{c2}, R^{d3}), (X^2, R^{a1}, R^{b3}, A^4, R^{c3}, R^{d1}), (X^2, R^{a1},$
$R^{b3}, A^4, R^{c3}, R^{d2}), (X^2, R^{a1}, R^{b3}, A^4, R^{c3}, R^{d3}), (X^2, R^{a1},$
$R^{b3}, A^4, R^{c4}, R^{d1}), (X^2, R^{a1}, R^{b3}, A^4, R^{c4}, R^{d2}), (X^2, R^{a1},$
$R^{b3}, A^4, R^{c4}, R^{d3}), (X^2, R^{a1}, R^{b3}, A^5, R^{c1}, R^{d1}), (X^2, R^{a1},$
$R^{b3}, A^5, R^{c1}, R^{d2}), (X^2, R^{a1}, R^{b3}, A^5, R^{c1}, R^{d3}), (X^2, R^{a1},$
$R^{b3}, A^5, R^{c2}, R^{d1}), (X^2, R^{a1}, R^{b3}, A^5, R^{c2}, R^{d2}), (X^2, R^{a1},$
$R^{b3}, A^5, R^{c3}, R^{d1}), (X^2, R^{a1}, R^{b3}, A^5, R^{c3}, R^{d2}), (X^2, R^{a1},$
$R^{b3}, A^5, R^{c3}, R^{d2}), (X^2, R^{a1}, R^{b3}, A^5, R^{c3}, R^{d3}), (X^2, R^{a1},$
$R^{b3}, A^5, R^{c4}, R^{d1}), (X^2, R^{a1}, R^{b3}, A^5, R^{c4}, R^{d2}), (X^2, R^{a1},$
$R^{b3}, A^5, R^{c4}, R^{d3}), (X^2, R^{a2}, R^{b1}, A^1, R^{c1}, R^{d1}), (X^2, R^{a2},$
$R^{b1}, A^1, R^{c1}, R^{d2}), (X^2, R^{a2}, R^{b1}, A^1, R^{c1}, R^{d3}), (X^2, R^{a2},$
$R^{b1}, A^1, R^{c2}, R^{d1}), (X^2, R^{a2}, R^{b1}, A^1, R^{c2}, R^{d2}), (X^2, R^{a2},$
$R^{b1}, A^1, R^{c2}, R^{d3}), (X^2, R^{a2}, R^{b1}, A^1, R^{c3}, R^{d1}), (X^2, R^{a2},$
$R^{b1}, A^1, R^{c3}, R^{d2}), (X^2, R^{a2}, R^{b1}, A^1, R^{c3}, R^{d3}), (X^2, R^{a2},$
$R^{b1}, A^1, R^{c4}, R^{d1}), (X^2, R^{a2}, R^{b1}, A^1, R^{c4}, R^{d2}), (X^2, R^{a2},$
$R^{b1}, A^1, R^{c4}, R^{d3}), (X^2, R^{a2}, R^{b1}, A^2, R^{c1}, R^{d1}), (X^2, R^{a2},$
$R^{b1}, A^2, R^{c1}, R^{d2}), (X^2, R^{a2}, R^{b1}, A^2, R^{c1}, R^{d3}), (X^2, R^{a2},$
$R^{b1}, A^2, R^{c2}, R^{d1}), (X^2, R^{a2}, R^{b1}, A^2, R^{c2}, R^{d2}), (X^2, R^{a2},$
$R^{b1}, A^2, R^{c2}, R^{d3}), (X^2, R^{a2}, R^{b1}, A^2, R^{c3}, R^{d1}), (X^2, R^{a2},$
$R^{b1}, A^2, R^{c3}, R^{d2}), (X^2, R^{a2}, R^{b1}, A^2, R^{c3}, R^{d3}), (X^2, R^{a2},$
$R^{b1}, A^2, R^{c4}, R^{d1}), (X^2, R^{a2}, R^{b1}, A^2, R^{c4}, R^{d2}), (X^2, R^{a2},$
$R^{b1}, A^2, R^{c4}, R^{d3}), (X^2, R^{a2}, R^{b1}, A^3, R^{c1}, R^{d1}), (X^2, R^{a2},$
$R^{b1}, A^3, R^{c1}, R^{d2}), (X^2, R^{a2}, R^{b1}, A^3, R^{c1}, R^{d3}), (X^2, R^{a2},$
$R^{b1}, A^3, R^{c2}, R^{d1}), (X^2, R^{a2}, R^{b1}, A^3, R^{c2}, R^{d2}), (X^2, R^{a2},$
$R^{b1}, A^3, R^{c2}, R^{d3}), (X^2, R^{a2}, R^{b1}, A^3, R^{c3}, R^{d1}), (X^2, R^{a2},$
$R^{b1}, A^3, R^{c3}, R^{d2}), (X^2, R^{a2}, R^{b1}, A^3, R^{c3}, R^{d3}), (X^2, R^{a2},$
$R^{b1}, A^3, R^{c4}, R^{d1}), (X^2, R^{a2}, R^{b1}, A^3, R^{c4}, R^{d2}), (X^2, R^{a2},$
$R^{b1}, A^3, R^{c4}, R^{d3}), (X^2, R^{a2}, R^{b1}, A^4, R^{c1}, R^{d1}), (X^2, R^{a2},$
$R^{b1}, A^4, R^{c1}, R^{d2}), (X^2, R^{a2}, R^{b1}, A^4, R^{c1}, R^{d3}), (X^2, R^{a2},$
$R^{b1}, A^4, R^{c2}, R^{d1}), (X^2, R^{a2}, R^{b1}, A^4, R^{c2}, R^{d2}), (X^2, R^{a2},$
$R^{b1}, A^4, R^{c2}, R^{d3}), (X^2, R^{a2}, R^{b1}, A^4, R^{c3}, R^{d1}), (X^2, R^{a2},$
$R^{b1}, A^4, R^{c3}, R^{d2}), (X^2, R^{a2}, R^{b1}, A^4, R^{c3}, R^{d3}), (X^2, R^{a2},$
$R^{b1}, A^4, R^{c4}, R^{d1}), (X^2, R^{a2}, R^{b1}, A^4, R^{c4}, R^{d2}), (X^2, R^{a2},$
$R^{b1}, A^4, R^{c4}, R^{d3}), (X^2, R^{a2}, R^{b1}, A^5, R^{c1}, R^{d1}), (X^2, R^{a2},$
$R^{b1}, A^5, R^{c1}, R^{d2}), (X^2, R^{a2}, R^{b1}, A^5, R^{c1}, R^{d3}), (X^2, R^{a2},$
$R^{b1}, A^5, R^{c2}, R^{d1}), (X^2, R^{a2}, R^{b1}, A^5, R^{c2}, R^{d2}), (X^2, R^{a2},$
$R^{b1}, A^5, R^{c2}, R^{d3}), (X^2, R^{a2}, R^{b1}, A^5, R^{c3}, R^{d1}), (X^2, R^{a2},$
$R^{b1}, A^5, R^{c3}, R^{d2}), (X^2, R^{a2}, R^{b1}, A^5, R^{c3}, R^{d3}), (X^2, R^{a2},$
$R^{b1}, A^5, R^{c4}, R^{d1}), (X^2, R^{a2}, R^{b1}, A^5, R^{c4}, R^{d2}), (X^2, R^{a2},$
$R^{b1}, A^5, R^{c4}, R^{d3}), (X^2, R^{a2}, R^{b2}, A^1, R^{c1}, R^{d1}), (X^2, R^{a2},$
$R^{b2}, A^1, R^{c1}, R^{d2}), (X^2, R^{a2}, R^{b2}, A^1, R^{c1}, R^{d3}), (X^2, R^{a2},$
$R^{b2}, A^1, R^{c2}, R^{d1}), (X^2, R^{a2}, R^{b2}, A^1, R^{c2}, R^{d2}), (X^2, R^{a2},$
$R^{b2}, A^1, R^{c2}, R^{d3}), (X^2, R^{a2}, R^{b2}, A^1, R^{c3}, R^{d1}), (X^2, R^{a2},$
$R^{b2}, A^1, R^{c3}, R^{d2}), (X^2, R^{a2}, R^{b2}, A^1, R^{c3}, R^{d3}), (X^2, R^{a2},$
$R^{b2}, A^1, R^{c4}, R^{d1}), (X^2, R^{a2}, R^{b2}, A^1, R^{c4}, R^{d2}), (X^2, R^{a2},$
$R^{b2}, A^2, R^{c1}, R^{d1}), (X^2, R^{a2}, R^{b2}, A^2, R^{c1}, R^{d2}), (X^2, R^{a2},$
$R^{b2}, A^2, R^{c1}, R^{d3}), (X^2, R^{a2}, R^{b2}, A^2, R^{c2}, R^{d1}), (X^2, R^{a2},$
$R^{b2}, A^2, R^{c2}, R^{d2}), (X^2, R^{a2}, R^{b2}, A^2, R^{c2}, R^{d3}), (X^2, R^{a2},$
$R^{b2}, A^2, R^{c3}, R^{d1}), (X^2, R^{a2}, R^{b2}, A^2, R^{c3}, R^{d2}), (X^2, R^{a2},$
$R^{b2}, A^2, R^{c3}, R^{d2}), (X^2, R^{a2}, R^{b2}, A^2, R^{c3}, R^{d3}), (X^2, R^{a2},$
$R^{b2}, A^2, R^{c4}, R^{d1}), (X^2, R^{a2}, R^{b2}, A^2, R^{c4}, R^{d2}), (X^2, R^{a2},$ $R^{b2}$, $A^2$, $R^{c4}$, $R^{d3}$), ($X^2$, $R^{a2}$, $R^{b2}$, $A^3$, $R^{c1}$, $R^{d1}$), ($X^2$, $R^{a2}$, $R^{b2}$, $A^3$, $R^{c1}$, $R^{d2}$), ($X^2$, $R^{a2}$, $R^{b2}$, $A^3$, $R^{c1}$, $R^{d3}$), ($X^2$, $R^{a2}$, $R^{b2}$, $A^3$, $R^{c2}$, $R^{d1}$), ($X^2$, $R^{a2}$, $R^{b2}$, $A^3$, $R^{c2}$, $R^{d2}$), ($X^2$, $R^{a2}$, $R^{b2}$, $A^3$, $R^{c2}$, $R^{d3}$), ($X^2$, $R^{a2}$, $R^{b2}$, $A^3$, $R^{c3}$, $R^{d1}$), ($X^2$, $R^{a2}$, $R^{b2}$, $A^3$, $R^{c3}$, $R^{d2}$), ($X^2$, $R^{a2}$, $R^{b2}$, $A^3$, $R^{c3}$, $R^{d3}$), ($X^2$, $R^{a2}$, $R^{b2}$, $A^3$, $R^{c4}$, $R^{d1}$), ($X^2$, $R^{a2}$, $R^{b2}$, $A^3$, $R^{c4}$, $R^{d2}$), ($X^2$, $R^{a2}$, $R^{b2}$, $A^3$, $R^{c4}$, $R^{d3}$), ($X^2$, $R^{a2}$, $R^{b2}$, $A^4$, $R^{c1}$, $R^{d1}$), ($X^2$, $R^{a2}$, $R^{b2}$, $A^4$, $R^{c1}$, $R^{d2}$), ($X^2$, $R^{a2}$, $R^{b2}$, $A^4$, $R^{c1}$, $R^{d3}$), ($X^2$, $R^{a2}$, $R^{b2}$, $A^4$, $R^{c2}$, $R^{d1}$), ($X^2$, $R^{a2}$, $R^{b2}$, $A^4$, $R^{c2}$, $R^{d2}$), ($X^2$, $R^{a2}$, $R^{b2}$, $A^4$, $R^{c2}$, $R^{d3}$), ($X^2$, $R^{a2}$, $R^{b2}$, $A^4$, $R^{c3}$, $R^{d1}$), ($X^2$, $R^{a2}$, $R^{b2}$, $A^4$, $R^{c3}$, $R^{d2}$), ($X^2$, $R^{a2}$, $R^{b2}$, $A^4$, $R^{c3}$, $R^{d3}$), ($X^2$, $R^{a2}$, $R^{b2}$, $A^4$, $R^{c4}$, $R^{d1}$), ($X^2$, $R^{a2}$, $R^{b2}$, $A^4$, $R^{c4}$, $R^{d2}$), ($X^2$, $R^{a2}$, $R^{b2}$, $A^4$, $R^{c4}$, $R^{d3}$), ($X^2$, $R^{a2}$, $R^{b2}$, $A^5$, $R^{c1}$, $R^{d1}$), ($X^2$, $R^{a2}$, $R^{b2}$, $A^5$, $R^{c1}$, $R^{d2}$), ($X^2$, $R^{a2}$, $R^{b2}$, $A^5$, $R^{c1}$, $R^{d3}$), ($X^2$, $R^{a2}$, $R^{b2}$, $A^5$, $R^{c2}$, $R^{d1}$), ($X^2$, $R^{a2}$, $R^{b2}$, $A^5$, $R^{c2}$, $R^{d2}$), ($X^2$, $R^{a2}$, $R^{b2}$, $A^5$, $R^{c2}$, $R^{d3}$), ($X^2$, $R^{a2}$, $R^{b2}$, $A^5$, $R^{c3}$, $R^{d1}$), ($X^2$, $R^{a2}$, $R^{b2}$, $A^5$, $R^{c3}$, $R^{d2}$), ($X^2$, $R^{a2}$, $R^{b2}$, $A^5$, $R^{c3}$, $R^{d3}$), ($X^2$, $R^{a2}$, $R^{b2}$, $A^5$, $R^{c4}$, $R^{d1}$), ($X^2$, $R^{a2}$, $R^{b2}$, $A^5$, $R^{c4}$, $R^{d2}$), ($X^2$, $R^{a2}$, $R^{b2}$, $A^5$, $R^{c4}$, $R^{d3}$), ($X^2$, $R^{a2}$, $R^{b3}$, $A^1$, $R^{c1}$, $R^{d1}$), ($X^2$, $R^{a2}$, $R^{b3}$, $A^1$, $R^{c1}$, $R^{d2}$), ($X^2$, $R^{a2}$, $R^{b3}$, $A^1$, $R^{c1}$, $R^{d3}$), ($X^2$, $R^{a2}$, $R^{b3}$, $A^1$, $R^{c2}$, $R^{d1}$), ($X^2$, $R^{a2}$, $R^{b3}$, $A^1$, $R^{c2}$, $R^{d2}$), ($X^2$, $R^{a2}$, $R^{b3}$, $A^1$, $R^{c2}$, $R^{d3}$), ($X^2$, $R^{a2}$, $R^{b3}$, $A^1$, $R^{c3}$, $R^{d1}$), ($X^2$, $R^{a2}$, $R^{b3}$, $A^1$, $R^{c3}$, $R^{d2}$), ($X^2$, $R^{a2}$, $R^{b3}$, $A^1$, $R^{c3}$, $R^{d3}$), ($X^2$, $R^{a2}$, $R^{b3}$, $A^1$, $R^{c4}$, $R^{d1}$), ($X^2$, $R^{a2}$, $R^{b3}$, $A^1$, $R^{c4}$, $R^{d2}$), ($X^2$, $R^{a2}$, $R^{b3}$, $A^1$, $R^{c4}$, $R^{d3}$), ($X^2$, $R^{a2}$, $R^{b3}$, $A^2$, $R^{c1}$, $R^{d1}$), ($X^2$, $R^{a2}$, $R^{b3}$, $A^2$, $R^{c1}$, $R^{d2}$), ($X^2$, $R^{a2}$, $R^{b3}$, $A^2$, $R^{c1}$, $R^{d3}$), ($X^2$, $R^{a2}$, $R^{b3}$, $A^2$, $R^{c2}$, $R^{d1}$), ($X^2$, $R^{a2}$, $R^{b3}$, $A^2$, $R^{c2}$, $R^{d2}$), ($X^2$, $R^{a2}$, $R^{b3}$, $A^2$, $R^{c2}$, $R^{d3}$), ($X^2$, $R^{a2}$, $R^{b3}$, $A^2$, $R^{c3}$, $R^{d1}$), ($X^2$, $R^{a2}$, $R^{b3}$, $A^2$, $R^{c3}$, $R^{d2}$), ($X^2$, $R^{a2}$, $R^{b3}$, $A^2$, $R^{c3}$, $R^{d3}$), ($X^2$, $R^{a2}$, $R^{b3}$, $A^2$, $R^{c4}$, $R^{d1}$), ($X^2$, $R^{a2}$, $R^{b3}$, $A^2$, $R^{c4}$, $R^{d2}$), ($X^2$, $R^{a2}$, $R^{b3}$, $A^2$, $R^{c4}$, $R^{d3}$), ($X^2$, $R^{a2}$, $R^{b3}$, $A^3$, $R^{c1}$, $R^{d1}$), ($X^2$, $R^{a2}$, $R^{b3}$, $A^3$, $R^{c1}$, $R^{d2}$), ($X^2$, $R^{a2}$, $R^{b3}$, $A^3$, $R^{c1}$, $R^{d3}$), ($X^2$, $R^{a2}$, $R^{b3}$, $A^3$, $R^{c2}$, $R^{d1}$), ($X^2$, $R^{a2}$, $R^{b3}$, $A^3$, $R^{c2}$, $R^{d2}$), ($X^2$, $R^{a2}$, $R^{b3}$, $A^3$, $R^{c2}$, $R^{d3}$), ($X^2$, $R^{a2}$, $R^{b3}$, $A^3$, $R^{c3}$, $R^{d1}$), ($X^2$, $R^{a2}$, $R^{b3}$, $A^3$, $R^{c3}$, $R^{d2}$), ($X^2$, $R^{a2}$, $R^{b3}$, $A^3$, $R^{c3}$, $R^{d3}$), ($X^2$, $R^{a2}$, $R^{b3}$, $A^3$, $R^{c4}$, $R^{d1}$), ($X^2$, $R^{a2}$, $R^{b3}$, $A^3$, $R^{c4}$, $R^{d2}$), ($X^2$, $R^{a2}$, $R^{b3}$, $A^3$, $R^{c4}$, $R^{d3}$), ($X^2$, $R^{a2}$, $R^{b3}$, $A^4$, $R^{c1}$, $R^{d1}$), ($X^2$, $R^{a2}$, $R^{b3}$, $A^4$, $R^{c1}$, $R^{d2}$), ($X^2$, $R^{a2}$, $R^{b3}$, $A^4$, $R^{c1}$, $R^{d3}$), ($X^2$, $R^{a2}$, $R^{b3}$, $A^4$, $R^{c2}$, $R^{d1}$), ($X^2$, $R^{a2}$, $R^{b3}$, $A^4$, $R^{c2}$, $R^{d2}$), ($X^2$, $R^{a2}$, $R^{b3}$, $A^4$, $R^{c2}$, $R^{d3}$), ($X^2$, $R^{a2}$, $R^{b3}$, $A^4$, $R^{c3}$, $R^{d1}$), ($X^2$, $R^{a2}$, $R^{b3}$, $A^4$, $R^{c3}$, $R^{d2}$), ($X^2$, $R^{a2}$, $R^{b3}$, $A^4$, $R^{c3}$, $R^{d3}$), ($X^2$, $R^{a2}$, $R^{b3}$, $A^4$, $R^{c4}$, $R^{d1}$), ($X^2$, $R^{a2}$, $R^{b3}$, $A^4$, $R^{c4}$, $R^{d2}$), ($X^2$, $R^{a2}$, $R^{b3}$, $A^4$, $R^{c4}$, $R^{d3}$), ($X^2$, $R^{a2}$, $R^{b3}$, $A^5$, $R^{c1}$, $R^{d1}$), ($X^2$, $R^{a2}$, $R^{b3}$, $A^5$, $R^{c1}$, $R^{d2}$), ($X^2$, $R^{a2}$, $R^{b3}$, $A^5$, $R^{c1}$, $R^{d3}$), ($X^2$, $R^{a2}$, $R^{b3}$, $A^5$, $R^{c2}$, $R^{d1}$), ($X^2$, $R^{a2}$, $R^{b3}$, $A^5$, $R^{c2}$, $R^{d2}$), ($X^2$, $R^{a2}$, $R^{b3}$, $A^5$, $R^{c2}$, $R^{d3}$), ($X^2$, $R^{a2}$, $R^{b3}$, $A^5$, $R^{c3}$, $R^{d1}$), ($X^2$, $R^{a2}$, $R^{b3}$, $A^5$, $R^{c3}$, $R^{d2}$), ($X^2$, $R^{a2}$, $R^{b3}$, $A^5$, $R^{c3}$, $R^{d3}$), ($X^2$, $R^{a2}$, $R^{b3}$, $A^5$, $R^{c4}$, $R^{d1}$), ($X^2$, $R^{a2}$, $R^{b3}$, $A^5$, $R^{c4}$, $R^{d2}$), ($X^2$, $R^{a2}$, $R^{b3}$, $A^5$, $R^{c4}$, $R^{d3}$), ($X^2$, $R^{a3}$, $R^{b1}$, $A^1$, $R^{c1}$, $R^{d1}$), ($X^2$, $R^{a3}$, $R^{b1}$, $A^1$, $R^{c1}$, $R^{d2}$), ($X^2$, $R^{a3}$, $R^{b1}$, $A^1$, $R^{c1}$, $R^{d3}$), ($X^2$, $R^{a3}$, $R^{b1}$, $A^1$, $R^{c2}$, $R^{d1}$), ($X^2$, $R^{a3}$, $R^{b1}$, $A^1$, $R^{c2}$, $R^{d2}$), ($X^2$, $R^{a3}$, $R^{b1}$, $A^1$, $R^{c2}$, $R^{d3}$), ($X^2$, $R^{a3}$, $R^{b1}$, $A^1$, $R^{c3}$, $R^{d1}$), ($X^2$, $R^{a3}$, $R^{b1}$, $A^1$, $R^{c3}$, $R^{d2}$), ($X^2$, $R^{a3}$, $R^{b1}$, $A^1$, $R^{c3}$, $R^{d3}$), ($X^2$, $R^{a3}$, $R^{b1}$, $A^1$, $R^{c4}$, $R^{d1}$), ($X^2$, $R^{a3}$, $R^{b1}$, $A^1$, $R^{c4}$, $R^{d2}$), ($X^2$, $R^{a3}$, $R^{b1}$, $A^1$, $R^{c4}$, $R^{d3}$), ($X^2$, $R^{a3}$, $R^{b1}$, $A^2$, $R^{c1}$, $R^{d1}$), ($X^2$, $R^{a3}$, $R^{b1}$, $A^2$, $R^{c1}$, $R^{d2}$), ($X^2$, $R^{a3}$, $R^{b1}$, $A^2$, $R^{c1}$, $R^{d3}$), ($X^2$, $R^{a3}$, $R^{b1}$, $A^2$, $R^{c2}$, $R^{d1}$), ($X^2$, $R^{a3}$, $R^{b1}$, $A^2$, $R^{c2}$, $R^{d2}$), ($X^2$, $R^{a3}$, $R^{b1}$, $A^2$, $R^{c2}$, $R^{d3}$), ($X^2$, $R^{a3}$, $R^{b1}$, $A^2$, $R^{c3}$, $R^{d1}$), ($X^2$, $R^{a3}$, $R^{b1}$, $A^2$, $R^{c3}$, $R^{d2}$), ($X^2$, $R^{a3}$, $R^{b1}$, $A^2$, $R^{c3}$, $R^{d3}$), ($X^2$, $R^{a3}$, $R^{b1}$, $A^2$, $R^{c4}$, $R^{d1}$), ($X^2$, $R^{a3}$, $R^{b1}$, $A^2$, $R^{c4}$, $R^{d2}$), ($X^2$, $R^{a3}$, $R^{b1}$, $A^2$, $R^{c4}$, $R^{d3}$), ($X^2$, $R^{a3}$, $R^{b1}$, $A^3$, $R^{c1}$, $R^{d1}$), ($X^2$, $R^{a3}$, $R^{b1}$, $A^3$, $R^{c1}$, $R^{d2}$), ($X^2$, $R^{a3}$, $R^{b1}$, $A^3$, $R^{c1}$, $R^{d3}$), ($X^2$, $R^{a3}$, $R^{b1}$, $A^3$, $R^{c2}$, $R^{d1}$), ($X^2$, $R^{a3}$, $R^{b1}$, $A^3$, $R^{c2}$, $R^{d2}$), ($X^2$, $R^{a3}$, $R^{b1}$, $A^3$, $R^{c2}$, $R^{d3}$), ($X^2$, $R^{a3}$, $R^{b1}$, $A^3$, $R^{c3}$, $R^{d1}$), ($X^2$, $R^{a3}$, $R^{b1}$, $A^3$, $R^{c3}$, $R^{d2}$), ($X^2$, $R^{a3}$, $R^{b1}$, $A^3$, $R^{c3}$, $R^{d3}$), ($X^2$, $R^{a3}$, $R^{b1}$, $A^3$, $R^{c4}$, $R^{d1}$), ($X^2$, $R^{a3}$, $R^{b1}$, $A^3$, $R^{c4}$, $R^{d2}$), ($X^2$, $R^{a3}$, $R^{b1}$, $A^3$, $R^{c4}$, $R^{d3}$), ($X^2$, $R^{a3}$, $R^{b1}$, $A^4$, $R^{c1}$, $R^{d1}$), ($X^2$, $R^{a3}$, $R^{b1}$, $A^4$, $R^{c1}$, $R^{d2}$), ($X^2$, $R^{a3}$, $R^{b1}$, $A^4$, $R^{c1}$, $R^{d3}$), ($X^2$, $R^{a3}$, $R^{b1}$, $A^4$, $R^{c2}$, $R^{d1}$), ($X^2$, $R^{a3}$, $R^{b1}$, $A^4$, $R^{c2}$, $R^{d2}$), ($X^2$, $R^{a3}$, $R^{b1}$, $A^4$, $R^{c2}$, $R^{d3}$), ($X^2$, $R^{a3}$, $R^{b1}$, $A^4$, $R^{c3}$, $R^{d1}$), ($X^2$, $R^{a3}$, $R^{b1}$, $A^4$, $R^{c3}$, $R^{d2}$), ($X^2$, $R^{a3}$, $R^{b1}$, $A^4$, $R^{c3}$, $R^{d3}$), ($X^2$, $R^{a3}$, $R^{b1}$, $A^4$, $R^{c4}$, $R^{d1}$), ($X^2$, $R^{a3}$, $R^{b1}$, $A^4$, $R^{c4}$, $R^{d2}$), ($X^2$, $R^{a3}$, $R^{b1}$, $A^4$, $R^{c4}$, $R^{d3}$), ($X^2$, $R^{a3}$, $R^{b1}$, $A^5$, $R^{c1}$, $R^{d1}$), ($X^2$, $R^{a3}$, $R^{b1}$, $A^5$, $R^{c1}$, $R^{d2}$), ($X^2$, $R^{a3}$, $R^{b1}$, $A^5$, $R^{c1}$, $R^{d3}$), ($X^2$, $R^{a3}$, $R^{b1}$, $A^5$, $R^{c2}$, $R^{d1}$), ($X^2$, $R^{a3}$, $R^{b1}$, $A^5$, $R^{c2}$, $R^{d2}$), ($X^2$, $R^{a3}$, $R^{b1}$, $A^5$, $R^{c2}$, $R^{d3}$), ($X^2$, $R^{a3}$, $R^{b1}$, $A^5$, $R^{c3}$, $R^{d1}$), ($X^2$, $R^{a3}$, $R^{b1}$, $A^5$, $R^{c3}$, $R^{d2}$), ($X^2$, $R^{a3}$, $R^{b1}$, $A^5$, $R^{c3}$, $R^{d3}$), ($X^2$, $R^{a3}$, $R^{b1}$, $A^5$, $R^{c4}$, $R^{d1}$), ($X^2$, $R^{a3}$, $R^{b1}$, $A^5$, $R^{c4}$, $R^{d2}$), ($X^2$, $R^{a3}$, $R^{b1}$, $A^5$, $R^{c4}$, $R^{d3}$), ($X^2$, $R^{a3}$, $R^{b2}$, $A^1$, $R^{c1}$, $R^{d1}$), ($X^2$, $R^{a3}$, $R^{b2}$, $A^1$, $R^{c1}$, $R^{d2}$), ($X^2$, $R^{a3}$, $R^{b2}$, $A^1$, $R^{c1}$, $R^{d3}$), ($X^2$, $R^{a3}$, $R^{b2}$, $A^1$, $R^{c2}$, $R^{d1}$), ($X^2$, $R^{a3}$, $R^{b2}$, $A^1$, $R^{c2}$, $R^{d2}$), ($X^2$, $R^{a3}$, $R^{b2}$, $A^1$, $R^{c2}$, $R^{d3}$), ($X^2$, $R^{a3}$, $R^{b2}$, $A^1$, $R^{c3}$, $R^{d1}$), ($X^2$, $R^{a3}$, $R^{b2}$, $A^1$, $R^{c3}$, $R^{d2}$), ($X^2$, $R^{a3}$, $R^{b2}$, $A^1$, $R^{c3}$, $R^{d3}$), ($X^2$, $R^{a3}$, $R^{b2}$, $A^1$, $R^{c4}$, $R^{d1}$), ($X^2$, $R^{a3}$, $R^{b2}$, $A^1$, $R^{c4}$, $R^{d2}$), ($X^2$, $R^{a3}$, $R^{b2}$, $A^1$, $R^{c4}$, $R^{d3}$), ($X^2$, $R^{a3}$, $R^{b2}$, $A^2$, $R^{c1}$, $R^{d1}$), ($X^2$, $R^{a3}$, $R^{b2}$, $A^2$, $R^{c1}$, $R^{d2}$), ($X^2$, $R^{a3}$, $R^{b2}$, $A^2$, $R^{c1}$, $R^{d3}$), ($X^2$, $R^{a3}$, $R^{b2}$, $A^2$, $R^{c2}$, $R^{d1}$), ($X^2$, $R^{a3}$, $R^{b2}$, $A^2$, $R^{c2}$, $R^{d2}$), ($X^2$, $R^{a3}$, $R^{b2}$, $A^2$, $R^{c2}$, $R^{d3}$), ($X^2$, $R^{a3}$, $R^{b2}$, $A^2$, $R^{c3}$, $R^{d1}$), ($X^2$, $R^{a3}$, $R^{b2}$, $A^2$, $R^{c3}$, $R^{d2}$), ($X^2$, $R^{a3}$, $R^{b2}$, $A^2$, $R^{c3}$, $R^{d3}$), ($X^2$, $R^{a3}$, $R^{b2}$, $A^2$, $R^{c4}$, $R^{d1}$), ($X^2$, $R^{a3}$, $R^{b2}$, $A^2$, $R^{c4}$, $R^{d2}$), ($X^2$, $R^{a3}$, $R^{b2}$, $A^2$, $R^{c4}$, $R^{d3}$), ($X^2$, $R^{a3}$, $R^{b2}$, $A^3$, $R^{c1}$, $R^{d1}$), ($X^2$, $R^{a3}$, $R^{b2}$, $A^3$, $R^{c1}$, $R^{d2}$), ($X^2$, $R^{a3}$, $R^{b2}$, $A^3$, $R^{c1}$, $R^{d3}$), ($X^2$, $R^{a3}$, $R^{b2}$, $A^3$, $R^{c2}$, $R^{d1}$), ($X^2$, $R^{a3}$, $R^{b2}$, $A^3$, $R^{c2}$, $R^{d2}$), ($X^2$, $R^{a3}$, $R^{b2}$, $A^3$, $R^{c2}$, $R^{d3}$), ($X^2$, $R^{a3}$, $R^{b2}$, $A^3$, $R^{c3}$, $R^{d1}$), ($X^2$, $R^{a3}$, $R^{b2}$, $A^3$, $R^{c3}$, $R^{d2}$), ($X^2$, $R^{a3}$, $R^{b2}$, $A^3$, $R^{c3}$, $R^{d3}$), ($X^2$, $R^{a3}$, $R^{b2}$, $A^3$, $R^{c4}$, $R^{d1}$), ($X^2$, $R^{a3}$, $R^{b2}$, $A^3$, $R^{c4}$, $R^{d2}$), ($X^2$, $R^{a3}$, $R^{b2}$, $A^3$, $R^{c4}$, $R^{d3}$), ($X^2$, $R^{a3}$, $R^{b2}$, $A^4$, $R^{c1}$, $R^{d1}$), ($X^2$, $R^{a3}$, $R^{b2}$, $A^4$, $R^{c1}$, $R^{d2}$), ($X^2$, $R^{a3}$, $R^{b2}$, $A^4$, $R^{c1}$, $R^{d3}$), ($X^2$, $R^{a3}$, $R^{b2}$, $A^4$, $R^{c2}$, $R^{d1}$), ($X^2$, $R^{a3}$, $R^{b2}$, $A^4$, $R^{c2}$, $R^{d2}$), ($X^2$, $R^{a3}$, $R^{b2}$, $A^4$, $R^{c2}$, $R^{d3}$), ($X^2$, $R^{a3}$, $R^{b2}$, $A^4$, $R^{c3}$, $R^{d1}$), ($X^2$, $R^{a3}$, $R^{b2}$, $A^4$, $R^{c3}$, $R^{d2}$), ($X^2$, $R^{a3}$, $R^{b2}$, $A^4$, $R^{c3}$, $R^{d3}$), ($X^2$, $R^{a3}$, $R^{b2}$, $A^4$, $R^{c4}$, $R^{d1}$), ($X^2$, $R^{a3}$, $R^{b2}$, $A^4$, $R^{c4}$, $R^{d2}$), ($X^2$, $R^{a3}$, $R^{b2}$, $A^4$, $R^{c4}$, $R^{d3}$), ($X^2$, $R^{a3}$, $R^{b2}$, $A^5$, $R^{c1}$, $R^{d1}$), ($X^2$, $R^{a3}$, $R^{b2}$, $A^5$, $R^{c1}$, $R^{d2}$), ($X^2$, $R^{a3}$, $R^{b2}$, $A^5$, $R^{c1}$, $R^{d3}$), ($X^2$, $R^{a3}$, $R^{b2}$, $A^5$, $R^{c2}$, $R^{d1}$), ($X^2$, $R^{a3}$, $R^{b2}$, $A^5$, $R^{c2}$, $R^{d2}$), ($X^2$, $R^{a3}$, $R^{b2}$, $A^5$, $R^{c2}$, $R^{d3}$), ($X^2$, $R^{a3}$, $R^{b2}$, $A^5$, $R^{c3}$, $R^{d1}$), ($X^2$, $R^{a3}$, $R^{b2}$, $A^5$, $R^{c3}$, $R^{d2}$), ($X^2$, $R^{a3}$, $R^{b2}$, $A^5$, $R^{c3}$, $R^{d3}$), ($X^2$, $R^{a3}$, $R^{b2}$, $A^5$, $R^{c4}$, $R^{d1}$), ($X^2$, $R^{a3}$, $R^{b2}$, $A^5$, $R^{c4}$, $R^{d2}$), ($X^2$, $R^{a3}$, $R^{b2}$, $A^5$, $R^{c4}$, $R^{d3}$), ($X^2$, $R^{a3}$, $R^{b3}$, $A^1$, $R^{c1}$, $R^{d1}$), ($X^2$, $R^{a3}$, $R^{b3}$, $A^1$, $R^{c1}$, $R^{d2}$), ($X^2$, $R^{a3}$, $R^{b3}$, $A^1$, $R^{c1}$, $R^{d3}$), ($X^2$, $R^{a3}$, $R^{b3}$, $A^1$, $R^{c2}$, $R^{d1}$), ($X^2$, $R^{a3}$, $R^{b3}$, $A^1$, $R^{c2}$, $R^{d2}$), ($X^2$, $R^{a3}$, $R^{b3}$, $A^1$, $R^{c2}$, $R^{d3}$), ($X^2$, $R^{a3}$, $R^{b3}$, $A^1$, $R^{c3}$, $R^{d1}$), ($X^2$, $R^{a3}$, $R^{b3}$, $A^1$, $R^{c3}$, $R^{d2}$), ($X^2$, $R^{a3}$, $R^{b3}$, $A^1$, $R^{c3}$, $R^{d3}$), ($X^2$, $R^{a3}$, $R^{b3}$, $A^1$, $R^{c4}$, $R^{d1}$), ($X^2$, $R^{a3}$, $R^{b3}$, $A^1$, $R^{c4}$, $R^{d2}$), ($X^2$, $R^{a3}$, $R^{b3}$, $A^1$, $R^{c4}$, $R^{d3}$), ($X^2$, $R^{a3}$, $R^{b3}$, $A^2$, $R^{c1}$, $R^{d1}$), ($X^2$, $R^{a3}$, $R^{b3}$, $A^2$, $R^{c1}$, $R^{d2}$), ($X^2$, $R^{a3}$, $R^{b3}$, $A^2$, $R^{c1}$, $R^{d3}$), ($X^2$, $R^{a3}$, $R^{b3}$, $A^2$, $R^{c2}$, $R^{d1}$), ($X^2$, $R^{a3}$, $R^{b3}$, $A^2$, $R^{c2}$, $R^{d2}$), ($X^2$, $R^{a3}$, $R^{b3}$, $A^2$, $R^{c2}$, $R^{d3}$), ($X^2$, $R^{a3}$, $R^{b3}$, $A^2$, $R^{c3}$, $R^{d1}$), ($X^2$, $R^{a3}$, $R^{b3}$, $A^2$, $R^{c3}$, $R^{d2}$), ($X^2$, $R^{a3}$, $R^{b3}$, $A^2$, $R^{c3}$, $R^{d3}$), ($X^2$, $R^{a3}$, $R^{b3}$, $A^2$, $R^{c4}$, $R^{d1}$), ($X^2$, $R^{a3}$, $R^{b3}$, $A^2$, $R^{c4}$, $R^{d2}$), ($X^2$, $R^{a3}$, $R^{b3}$, $A^2$, $R^{c4}$, $R^{d3}$), ($X^2$, $R^{a3}$, $R^{b3}$, $A^3$, $R^{c1}$, $R^{d1}$), ($X^2$, $R^{a3}$, $R^{b3}$, $A^3$, $R^{c1}$, $R^{d2}$), ($X^2$, $R^{a3}$, $R^{b3}$, $A^3$, $R^{c1}$, $R^{d3}$), ($X^2$, $R^{a3}$, $R^{b3}$, $A^3$, $R^{c2}$, $R^{d1}$), ($X^2$, $R^{a3}$, $R^{b3}$, $A^3$, $R^{c2}$, $R^{d2}$), ($X^2$, $R^{a3}$, $R^{b3}$, $A^3$, $R^{c2}$, $R^{d3}$), ($X^2$, $R^{a3}$, $R^{b3}$, $A^3$, $R^{c3}$, $R^{d1}$), ($X^2$, $R^{a3}$, $R^{b3}$, $A^3$, $R^{c3}$, $R^{d2}$), ($X^2$, $R^{a3}$, $R^{b3}$, $A^3$, $R^{c3}$, $R^{d3}$), ($X^2$, $R^{a3}$, $R^{b3}$, $A^3$, $R^{c4}$, $R^{d1}$), ($X^2$, $R^{a3}$, $R^{b3}$, $A^3$, $R^{c4}$, $R^{d2}$), ($X^2$, $R^{a3}$, $R^{b3}$, $A^3$, $R^{c4}$, $R^{d3}$), ($X^2$, $R^{a3}$, $R^{b3}$, $A^4$, $R^{c1}$, $R^{d1}$), ($X^2$, $R^{a3}$, $R^{b3}$, $A^4$, $R^{c1}$, $R^{d2}$), ($X^2$, $R^{a3}$, $R^{b3}$, $A^4$, $R^{c1}$, $R^{d3}$), ($X^2$, $R^{a3}$, $R^{b3}$, $A^4$, $R^{c2}$, $R^{d1}$), ($X^2$, $R^{a3}$, $R^{b3}$, $A^4$, $R^{c2}$, $R^{d2}$), ($X^2$, $R^{a3}$, $R^{b3}$, $A^4$, $R^{c2}$, $R^{d3}$), ($X^2$, $R^{a3}$, $R^{b3}$, $A^4$, $R^{c3}$, $R^{d1}$), ($X^2$, $R^{a3}$, $R^{b3}$, $A^4$, $R^{c3}$, $R^{d2}$), ($X^2$, $R^{a3}$, $R^{b3}$, $A^4$, $R^{c3}$, $R^{d3}$), ($X^2$, $R^{a3}$, $R^{b3}$, $A^4$, $R^{c4}$, $R^{d1}$), ($X^2$, $R^{a3}$, $R^{b3}$, $A^4$, $R^{c4}$, $R^{d2}$), ($X^2$, $R^{a3}$, $R^{b3}$, $A^4$, $R^{c4}$, $R^{d3}$), ($X^2$, $R^{a3}$, $R^{b3}$, $A^5$, $R^{c1}$, $R^{d1}$), ($X^2$, $R^{a3}$, $R^{b3}$, $A^5$, $R^{c1}$, $R^{d2}$), ($X^2$, $R^{a3}$, $R^{b3}$, $A^5$, $R^{c1}$, $R^{d3}$), ($X^2$, $R^{a3}$, $R^{b3}, A^5, R^{c2}, R^{d1}), (X^2, R^{a3}, R^{b3}, A^5, R^{c2}, R^{d3}), (X^2, R^{a3}, R^{b3}, A^5, R^{c3}, R^{d2}), (X^2, R^{a3}, R^{b3}, A^5, R^{c4}, R^{d1}), (X^2, R^{a3}, R^{b3}, A^5, R^{c4}, R^{d3}), (X^3, R^{a1}, R^{b1}, A^1, R^{c1}, R^{d1}), (X^3, R^{a1}, R^{b1}, A^1, R^{c1}, R^{d2}), (X^3, R^{a1}, R^{b1}, A^1, R^{c1}, R^{d3}), (X^3, R^{a1}, R^{b1}, A^1, R^{c2}, R^{d1}), (X^3, R^{a1}, R^{b1}, A^1, R^{c2}, R^{d2}), (X^3, R^{a1}, R^{b1}, A^1, R^{c2}, R^{d3}), (X^3, R^{a1}, R^{b1}, A^1, R^{c3}, R^{d1}), (X^3, R^{a1}, R^{b1}, A^1, R^{c3}, R^{d2}), (X^3, R^{a1}, R^{b1}, A^1, R^{c3}, R^{d3}), (X^3, R^{a1}, R^{b1}, A^1, R^{c4}, R^{d1}), (X^3, R^{a1}, R^{b1}, A^1, R^{c4}, R^{d2}), (X^3, R^{a1}, R^{b1}, A^1, R^{c4}, R^{d3}), (X^3, R^{a1}, R^{b1}, A^2, R^{c1}, R^{d1}), (X^3, R^{a1}, R^{b1}, A^2, R^{c1}, R^{d2}), (X^3, R^{a1}, R^{b1}, A^2, R^{c1}, R^{d3}), (X^3, R^{a1}, R^{b1}, A^2, R^{c2}, R^{d1}), (X^3, R^{a1}, R^{b1}, A^2, R^{c2}, R^{d2}), (X^3, R^{a1}, R^{b1}, A^2, R^{c2}, R^{d3}), (X^3, R^{a1}, R^{b1}, A^2, R^{c3}, R^{d1}), (X^3, R^{a1}, R^{b1}, A^2, R^{c3}, R^{d2}), (X^3, R^{a1}, R^{b1}, A^2, R^{c3}, R^{d3}), (X^3, R^{a1}, R^{b1}, A^2, R^{c4}, R^{d1}), (X^3, R^{a1}, R^{b1}, A^2, R^{c4}, R^{d2}), (X^3, R^{a1}, R^{b1}, A^2, R^{c4}, R^{d3}), (X^3, R^{a1}, R^{b1}, A^3, R^{c1}, R^{d1}), (X^3, R^{a1}, R^{b1}, A^3, R^{c1}, R^{d2}), (X^3, R^{a1}, R^{b1}, A^3, R^{c1}, R^{d3}), (X^3, R^{a1}, R^{b1}, A^3, R^{c2}, R^{d1}), (X^3, R^{a1}, R^{b1}, A^3, R^{c2}, R^{d2}), (X^3, R^{a1}, R^{b1}, A^3, R^{c2}, R^{d3}), (X^3, R^{a1}, R^{b1}, A^3, R^{c3}, R^{d1}), (X^3, R^{a1}, R^{b1}, A^3, R^{c3}, R^{d2}), (X^3, R^{a1}, R^{b1}, A^3, R^{c3}, R^{d3}), (X^3, R^{a1}, R^{b1}, A^3, R^{c4}, R^{d1}), (X^3, R^{a1}, R^{b1}, A^3, R^{c4}, R^{d2}), (X^3, R^{a1}, R^{b1}, A^4, R^{c1}, R^{d1}), (X^3, R^{a1}, R^{b1}, A^4, R^{c1}, R^{d3}), (X^3, R^{a1}, R^{b1}, A^4, R^{c2}, R^{d1}), (X^3, R^{a1}, R^{b1}, A^4, R^{c2}, R^{d2}), (X^3, R^{a1}, R^{b1}, A^4, R^{c3}, R^{d1}), (X^3, R^{a1}, R^{b1}, A^4, R^{c3}, R^{d2}), (X^3, R^{a1}, R^{b1}, A^4, R^{c3}, R^{d3}), (X^3, R^{a1}, R^{b1}, A^4, R^{c4}, R^{d1}), (X^3, R^{a1}, R^{b1}, A^4, R^{c4}, R^{d2}), (X^3, R^{a1}, R^{b1}, A^4, R^{c4}, R^{d3}), (X^3, R^{a1}, R^{b1}, A^5, R^{c1}, R^{d1}), (X^3, R^{a1}, R^{b1}, A^5, R^{c1}, R^{d2}), (X^3, R^{a1}, R^{b1}, A^5, R^{c1}, R^{d3}), (X^3, R^{a1}, R^{b1}, A^5, R^{c2}, R^{d1}), (X^3, R^{a1}, R^{b1}, A^5, R^{c2}, R^{d2}), (X^3, R^{a1}, R^{b1}, A^5, R^{c2}, R^{d3}), (X^3, R^{a1}, R^{b1}, A^5, R^{c3}, R^{d1}), (X^3, R^{a1}, R^{b1}, A^5, R^{c3}, R^{d3}), (X^3, R^{a1}, R^{b1}, A^5, R^{c4}, R^{d1}), (X^3, R^{a1}, R^{b1}, A^5, R^{c4}, R^{d2}), (X^3, R^{a1}, R^{b1}, A^5, R^{c4}, R^{d3}), (X^3, R^{a1}, R^{b2}, A^1, R^{c1}, R^{d1}), (X^3, R^{a1}, R^{b2}, A^1, R^{c1}, R^{d2}), (X^3, R^{a1}, R^{b2}, A^1, R^{c1}, R^{d3}), (X^3, R^{a1}, R^{b2}, A^1, R^{c2}, R^{d1}), (X^3, R^{a1}, R^{b2}, A^1, R^{c2}, R^{d2}), (X^3, R^{a1}, R^{b2}, A^1, R^{c3}, R^{d1}), (X^3, R^{a1}, R^{b2}, A^1, R^{c3}, R^{d3}), (X^3, R^{a1}, R^{b2}, A^1, R^{c4}, R^{d1}), (X^3, R^{a1}, R^{b2}, A^1, R^{c4}, R^{d2}), (X^3, R^{a1}, R^{b2}, A^2, R^{c1}, R^{d1}), (X^3, R^{a1}, R^{b2}, A^2, R^{c1}, R^{d3}), (X^3, R^{a1}, R^{b2}, A^2, R^{c2}, R^{d1}), (X^3, R^{a1}, R^{b2}, A^2, R^{c2}, R^{d2}), (X^3, R^{a1}, R^{b2}, A^2, R^{c2}, R^{d3}), (X^3, R^{a1}, R^{b2}, A^2, R^{c3}, R^{d1}), (X^3, R^{a1}, R^{b2}, A^2, R^{c3}, R^{d3}), (X^3, R^{a1}, R^{b2}, A^2, R^{c4}, R^{d1}), (X^3, R^{a1}, R^{b2}, A^2, R^{c4}, R^{d2}), (X^3, R^{a1}, R^{b2}, A^2, R^{c4}, R^{d3}), (X^3, R^{a1}, R^{b2}, A^3, R^{c1}, R^{d1}), (X^3, R^{a1}, R^{b2}, A^3, R^{c2}, R^{d1}), (X^3, R^{a1}, R^{b2}, A^3, R^{c2}, R^{d2}), (X^3, R^{a1}, R^{b2}, A^3, R^{c3}, R^{d1}), (X^3, R^{a1}, R^{b2}, A^3, R^{c3}, R^{d3}), (X^3, R^{a1}, R^{b2}, A^3, R^{c4}, R^{d1}), (X^3, R^{a1}, R^{b2}, A^3, R^{c4}, R^{d2}), (X^3, R^{a1}, R^{b2}, A^4, R^{c1}, R^{d1}), (X^3, R^{a1}, R^{b2}, A^4, R^{c2}, R^{d1}), (X^3, R^{a1}, R^{b2}, A^4, R^{c2}, R^{d2}), (X^3, R^{a1}, R^{b2}, A^4, R^{c3}, R^{d1}), (X^3, R^{a1}, R^{b2}, A^4, R^{c3}, R^{d3}), (X^3, R^{a1}, R^{b2}, A^4, R^{c4}, R^{d1}), (X^3, R^{a1}, R^{b2}, A^4, R^{c4}, R^{d2}), (X^3, R^{a1}, R^{b2}, A^5, R^{c1}, R^{d1}), (X^3, R^{a1}, R^{b2}, A^5, R^{c1}, R^{d2}), (X^3, R^{a1}, R^{b2}, A^5, R^{c1}, R^{d3}), (X^3, R^{a1}, R^{b2}, A^5, R^{c2}, R^{d1}), (X^3, R^{a1}, R^{b2}, A^5, R^{c2}, R^{d2}), (X^3, R^{a1}, R^{b2}, A^5, R^{c3}, R^{d1}), (X^3, R^{a1}, R^{b2}, A^5, R^{c4}, R^{d1}), (X^3, R^{a1}, R^{b2}, A^5, R^{c4}, R^{d2}), (X^3, R^{a1}, R^{b3}, A^1, R^{c1}, R^{d1}), (X^3, R^{a1}, R^{b3}, A^1, R^{c1}, R^{d2}), (X^3, R^{a1}, R^{b3}, A^1, R^{c1}, R^{d3}), (X^3, R^{a1}, R^{b3}, A^1, R^{c2}, R^{d1}),$ $R^{b3}, A^1, R^{c2}, R^{d3}), (X^3, R^{a1}, R^{b3}, A^1, R^{c3}, R^{d1}), (X^3, R^{a1}, R^{b3}, A^1, R^{c3}, R^{d3}), (X^3, R^{a1}, R^{b3}, A^1, R^{c4}, R^{d2}), (X^3, R^{a1}, R^{b3}, A^1, R^{c4}, R^{d3}), (X^3, R^{a1}, R^{b3}, A^2, R^{c1}, R^{d1}), (X^3, R^{a1}, R^{b3}, A^2, R^{c1}, R^{d2}), (X^3, R^{a1}, R^{b3}, A^2, R^{c1}, R^{d3}), (X^3, R^{a1}, R^{b3}, A^2, R^{c2}, R^{d1}), (X^3, R^{a1}, R^{b3}, A^2, R^{c2}, R^{d2}), (X^3, R^{a1}, R^{b3}, A^2, R^{c2}, R^{d3}), (X^3, R^{a1}, R^{b3}, A^2, R^{c3}, R^{d1}), (X^3, R^{a1}, R^{b3}, A^2, R^{c3}, R^{d3}), (X^3, R^{a1}, R^{b3}, A^2, R^{c4}, R^{d1}), (X^3, R^{a1}, R^{b3}, A^2, R^{c4}, R^{d2}), (X^3, R^{a1}, R^{b3}, A^2, R^{c4}, R^{d3}), (X^3, R^{a1}, R^{b3}, A^3, R^{c1}, R^{d1}), (X^3, R^{a1}, R^{b3}, A^3, R^{c1}, R^{d2}), (X^3, R^{a1}, R^{b3}, A^3, R^{c1}, R^{d3}), (X^3, R^{a1}, R^{b3}, A^3, R^{c2}, R^{d1}), (X^3, R^{a1}, R^{b3}, A^3, R^{c2}, R^{d3}), (X^3, R^{a1}, R^{b3}, A^3, R^{c3}, R^{d1}), (X^3, R^{a1}, R^{b3}, A^3, R^{c3}, R^{d2}), (X^3, R^{a1}, R^{b3}, A^3, R^{c3}, R^{d3}), (X^3, R^{a1}, R^{b3}, A^3, R^{c4}, R^{d1}), (X^3, R^{a1}, R^{b3}, A^3, R^{c4}, R^{d2}), (X^3, R^{a1}, R^{b3}, A^3, R^{c4}, R^{d3}), (X^3, R^{a1}, R^{b3}, A^4, R^{c1}, R^{d1}), (X^3, R^{a1}, R^{b3}, A^4, R^{c1}, R^{d2}), (X^3, R^{a1}, R^{b3}, A^4, R^{c2}, R^{d1}), (X^3, R^{a1}, R^{b3}, A^4, R^{c2}, R^{d2}), (X^3, R^{a1}, R^{b3}, A^4, R^{c3}, R^{d1}), (X^3, R^{a1}, R^{b3}, A^4, R^{c3}, R^{d2}), (X^3, R^{a1}, R^{b3}, A^4, R^{c3}, R^{d3}), (X^3, R^{a1}, R^{b3}, A^4, R^{c4}, R^{d1}), (X^3, R^{a1}, R^{b3}, A^4, R^{c4}, R^{d2}), (X^3, R^{a1}, R^{b3}, A^5, R^{c1}, R^{d1}), (X^3, R^{a1}, R^{b3}, A^5, R^{c1}, R^{d2}), (X^3, R^{a1}, R^{b3}, A^5, R^{c2}, R^{d1}), (X^3, R^{a1}, R^{b3}, A^5, R^{c2}, R^{d2}), (X^3, R^{a1}, R^{b3}, A^5, R^{c2}, R^{d3}), (X^3, R^{a1}, R^{b3}, A^5, R^{c3}, R^{d1}), (X^3, R^{a1}, R^{b3}, A^5, R^{c3}, R^{d3}), (X^3, R^{a1}, R^{b3}, A^5, R^{c4}, R^{d1}), (X^3, R^{a1}, R^{b3}, A^5, R^{c4}, R^{d2}), (X^3, R^{a2}, R^{b1}, A^1, R^{c1}, R^{d1}), (X^3, R^{a2}, R^{b1}, A^1, R^{c1}, R^{d2}), (X^3, R^{a2}, R^{b1}, A^1, R^{c1}, R^{d3}), (X^3, R^{a2}, R^{b1}, A^1, R^{c2}, R^{d1}), (X^3, R^{a2}, R^{b1}, A^1, R^{c2}, R^{d2}), (X^3, R^{a2}, R^{b1}, A^1, R^{c2}, R^{d3}), (X^3, R^{a2}, R^{b1}, A^1, R^{c3}, R^{d1}), (X^3, R^{a2}, R^{b1}, A^1, R^{c3}, R^{d2}), (X^3, R^{a2}, R^{b1}, A^1, R^{c3}, R^{d3}), (X^3, R^{a2}, R^{b1}, A^1, R^{c4}, R^{d1}), (X^3, R^{a2}, R^{b1}, A^1, R^{c4}, R^{d2}), (X^3, R^{a2}, R^{b1}, A^1, R^{c4}, R^{d3}), (X^3, R^{a2}, R^{b1}, A^2, R^{c1}, R^{d1}), (X^3, R^{a2}, R^{b1}, A^2, R^{c1}, R^{d3}), (X^3, R^{a2}, R^{b1}, A^2, R^{c2}, R^{d1}), (X^3, R^{a2}, R^{b1}, A^2, R^{c2}, R^{d2}), (X^3, R^{a2}, R^{b1}, A^2, R^{c2}, R^{d3}), (X^3, R^{a2}, R^{b1}, A^2, R^{c3}, R^{d1}), (X^3, R^{a2}, R^{b1}, A^2, R^{c3}, R^{d2}), (X^3, R^{a2}, R^{b1}, A^2, R^{c3}, R^{d3}), (X^3, R^{a2}, R^{b1}, A^2, R^{c4}, R^{d1}), (X^3, R^{a2}, R^{b1}, A^2, R^{c4}, R^{d2}), (X^3, R^{a2}, R^{b1}, A^2, R^{c4}, R^{d3}), (X^3, R^{a2}, R^{b1}, A^3, R^{c1}, R^{d1}), (X^3, R^{a2}, R^{b1}, A^3, R^{c1}, R^{d2}), (X^3, R^{a2}, R^{b1}, A^3, R^{c1}, R^{d3}), (X^3, R^{a2}, R^{b1}, A^3, R^{c2}, R^{d1}), (X^3, R^{a2}, R^{b1}, A^3, R^{c2}, R^{d2}), (X^3, R^{a2}, R^{b1}, A^3, R^{c3}, R^{d1}), (X^3, R^{a2}, R^{b1}, A^3, R^{c3}, R^{d3}), (X^3, R^{a2}, R^{b1}, A^3, R^{c4}, R^{d1}), (X^3, R^{a2}, R^{b1}, A^3, R^{c4}, R^{d2}), (X^3, R^{a2}, R^{b1}, A^3, R^{c4}, R^{d3}), (X^3, R^{a2}, R^{b1}, A^4, R^{c1}, R^{d1}), (X^3, R^{a2}, R^{b1}, A^4, R^{c1}, R^{d2}), (X^3, R^{a2}, R^{b1}, A^4, R^{c2}, R^{d1}), (X^3, R^{a2}, R^{b1}, A^4, R^{c2}, R^{d2}), (X^3, R^{a2}, R^{b1}, A^4, R^{c2}, R^{d3}), (X^3, R^{a2}, R^{b1}, A^4, R^{c3}, R^{d1}), (X^3, R^{a2}, R^{b1}, A^4, R^{c3}, R^{d2}), (X^3, R^{a2}, R^{b1}, A^4, R^{c3}, R^{d3}), (X^3, R^{a2}, R^{b1}, A^4, R^{c4}, R^{d1}), (X^3, R^{a2}, R^{b1}, A^4, R^{c4}, R^{d2}), (X^3, R^{a2}, R^{b1}, A^5, R^{c1}, R^{d1}), (X^3, R^{a2}, R^{b1}, A^5, R^{c1}, R^{d3}), (X^3, R^{a2}, R^{b1}, A^5, R^{c2}, R^{d1}), (X^3, R^{a1}, R^{b1}, A^5, R^{c2}, R^{d2}), (X^3, R^{a1}, R^{b1}, A^5, R^{c3}, R^{d1}), (X^3, R^{a2}, R^{b1}, A^5, R^{c3}, R^{d3}), (X^3, R^{a2}, R^{b1}, A^5, R^{c4}, R^{d1}), (X^3, R^{a1}, R^{b1}, A^5, R^{c4}, R^{d3}), (X^3, R^{a1}, R^{b2}, A^1, R^{c1}, R^{d1}), (X^3, R^{a2}, R^{b2}, A^1, R^{c1}, R^{d3}), (X^3, R^{a2}, R^{b2}, A^1, R^{c2}, R^{d2}), (X^3, R^{a2}, R^{b2}, A^1, R^{c3}, R^{d1}), (X^3, R^{a2}, R^{b2}, A^1, R^{c4}, R^{d3}), (X^3, R^{a2}, R^{b2}, A^2, R^{c1}, R^{d1}), (X^3, R^{a2}, R^{b2}, A^2, R^{c1}, R^{d3}), (X^3, R^{a2}, R^{b2}, A^2, R^{c2}, R^{d2}), (X^3, R^{a2}, R^{b2}, A^2, R^{c3}, R^{d1}), (X^3, R^{a2},$ $R^{b2}, A^2, R^{c3}, R^{d2})$, $(X^3, R^{a2}, R^{b2}, A^2, R^{c3}, R^{d3})$, $(X^3, R^{a2},$
$R^{b2}, A^2, R^{c4}, R^{d1})$, $(X^3, R^{a2}, R^{b2}, A^2, R^{c4}, R^{d2})$, $(X^3, R^{a2},$
$R^{b2}, A^2, R^{c4}, R^{d3})$, $(X^3, R^{a2}, R^{b2}, A^3, R^{c1}, R^{d3})$, $(X^3, R^{a2},$
$R^{b2}, A^3, R^{c1}, R^{d2})$, $(X^3, R^{a2}, R^{b2}, A^3, R^{c1}, R^{d3})$, $(X^3, R^{a2},$
$R^{b2}, A^3, R^{c2}, R^{d1})$, $(X^3, R^{a2}, R^{b2}, A^3, R^{c2}, R^{d2})$, $(X^3, R^{a2},$
$R^{b2}, A^3, R^{c2}, R^{d3})$, $(X^3, R^{a2}, R^{b2}, A^3, R^{c3}, R^{d1})$, $(X^3, R^{a2},$
$R^{b2}, A^3, R^{c3}, R^{d2})$, $(X^3, R^{a2}, R^{b2}, A^3, R^{c3}, R^{d3})$, $(X^3, R^{a2},$
$R^{b2}, A^3, R^{c4}, R^{d1})$, $(X^3, R^{a2}, R^{b2}, A^3, R^{c4}, R^{d2})$, $(X^3, R^{a2},$
$R^{b2}, A^3, R^{c4}, R^{d3})$, $(X^3, R^{a2}, R^{b2}, A^4, R^{c1}, R^{d1})$, $(X^3, R^{a2},$
$R^{b2}, A^4, R^{c1}, R^{d2})$, $(X^3, R^{a2}, R^{b2}, A^4, R^{c1}, R^{d3})$, $(X^3, R^{a2},$
$R^{b2}, A^4, R^{c2}, R^{d1})$, $(X^3, R^{a2}, R^{b2}, A^4, R^{c2}, R^{d2})$, $(X^3, R^{a2},$
$R^{b2}, A^4, R^{c2}, R^{d3})$, $(X^3, R^{a2}, R^{b2}, A^4, R^{c3}, R^{d1})$, $(X^3, R^{a2},$
$R^{b2}, A^4, R^{c3}, R^{d2})$, $(X^3, R^{a2}, R^{b2}, A^4, R^{c3}, R^{d3})$, $(X^3, R^{a2},$
$R^{b2}, A^4, R^{c4}, R^{d1})$, $(X^3, R^{a2}, R^{b2}, A^4, R^{c4}, R^{d2})$, $(X^3, R^{a2},$
$R^{b2}, A^4, R^{c4}, R^{d3})$, $(X^3, R^{a2}, R^{b2}, A^5, R^{c1}, R^{d1})$, $(X^3, R^{a2},$
$R^{b2}, A^5, R^{c1}, R^{d2})$, $(X^3, R^{a2}, R^{b2}, A^5, R^{c1}, R^{d3})$, $(X^3, R^{a2},$
$R^{b2}, A^5, R^{c2}, R^{d1})$, $(X^3, R^{a2}, R^{b2}, A^5, R^{c2}, R^{d2})$, $(X^3, R^{a1},$
$R^{b2}, A^5, R^{c2}, R^{d3})$, $(X^3, R^{a1}, R^{b2}, A^5, R^{c4}, R^{d1})$, $(X^3, R^{a1},$
$R^{b2}, A^5, R^{c4}, R^{d2})$, $(X^3, R^{a2}, R^{b2}, A^5, R^{c3}, R^{d3})$, $(X^3, R^{a2},$
$R^{b2}, A^5, R^{c4}, R^{d1})$, $(X^3, R^{a2}, R^{b2}, A^5, R^{c4}, R^{d2})$, $(X^3, R^{a2},$
$R^{b2}, A^5, R^{c4}, R^{d3})$, $(X^3, R^{a2}, R^{b3}, A^1, R^{c1}, R^{d1})$, $(X^3, R^{a2},$
$R^{b3}, A^1, R^{c1}, R^{d2})$, $(X^3, R^{a2}, R^{b3}, A^1, R^{c1}, R^{d3})$, $(X^3, R^{a2},$
$R^{b3}, A^1, R^{c2}, R^{d1})$, $(X^3, R^{a2}, R^{b3}, A^1, R^{c2}, R^{d2})$, $(X^3, R^{a2},$
$R^{b3}, A^1, R^{c2}, R^{d3})$, $(X^3, R^{a2}, R^{b3}, A^1, R^{c3}, R^{d1})$, $(X^3, R^{a2},$
$R^{b3}, A^1, R^{c3}, R^{d2})$, $(X^3, R^{a2}, R^{b3}, A^1, R^{c3}, R^{d3})$, $(X^3, R^{a2},$
$R^{b3}, A^1, R^{c4}, R^{d1})$, $(X^3, R^{a2}, R^{b3}, A^1, R^{c4}, R^{d2})$, $(X^3, R^{a2},$
$R^{b3}, A^1, R^{c4}, R^{d3})$, $(X^3, R^{a2}, R^{b3}, A^2, R^{c1}, R^{d1})$, $(X^3, R^{a2},$
$R^{b3}, A^2, R^{c1}, R^{d2})$, $(X^3, R^{a2}, R^{b3}, A^2, R^{c1}, R^{d3})$, $(X^3, R^{a2},$
$R^{b3}, A^2, R^{c2}, R^{d1})$, $(X^3, R^{a2}, R^{b3}, A^2, R^{c2}, R^{d2})$, $(X^3, R^{a2},$
$R^{b3}, A^2, R^{c2}, R^{d3})$, $(X^3, R^{a2}, R^{b3}, A^2, R^{c3}, R^{d1})$, $(X^3, R^{a2},$
$R^{b3}, A^2, R^{c3}, R^{d2})$, $(X^3, R^{a2}, R^{b3}, A^2, R^{c3}, R^{d3})$, $(X^3, R^{a2},$
$R^{b3}, A^2, R^{c4}, R^{d1})$, $(X^3, R^{a2}, R^{b3}, A^2, R^{c4}, R^{d2})$, $(X^3, R^{a2},$
$R^{b3}, A^2, R^{c4}, R^{d3})$, $(X^3, R^{a2}, R^{b3}, A^3, R^{c1}, R^{d1})$, $(X^3, R^{a2},$
$R^{b3}, A^3, R^{c1}, R^{d2})$, $(X^3, R^{a2}, R^{b3}, A^3, R^{c1}, R^{d3})$, $(X^3, R^{a2},$
$R^{b3}, A^3, R^{c2}, R^{d1})$, $(X^3, R^{a2}, R^{b3}, A^3, R^{c2}, R^{d2})$, $(X^3, R^{a2},$
$R^{b3}, A^3, R^{c2}, R^{d3})$, $(X^3, R^{a2}, R^{b3}, A^3, R^{c3}, R^{d1})$, $(X^3, R^{a2},$
$R^{b3}, A^3, R^{c3}, R^{d2})$, $(X^3, R^{a2}, R^{b3}, A^3, R^{c3}, R^{d3})$, $(X^3, R^{a2},$
$R^{b3}, A^3, R^{c4}, R^{d1})$, $(X^3, R^{a2}, R^{b3}, A^3, R^{c4}, R^{d2})$, $(X^3, R^{a2},$
$R^{b3}, A^3, R^{c4}, R^{d3})$, $(X^3, R^{a2}, R^{b3}, A^4, R^{c1}, R^{d1})$, $(X^3, R^{a2},$
$R^{b3}, A^4, R^{c1}, R^{d2})$, $(X^3, R^{a2}, R^{b3}, A^4, R^{c1}, R^{d3})$, $(X^3, R^{a2},$
$R^{b3}, A^4, R^{c2}, R^{d1})$, $(X^3, R^{a2}, R^{b3}, A^4, R^{c2}, R^{d2})$, $(X^3, R^{a2},$
$R^{b3}, A^4, R^{c2}, R^{d3})$, $(X^3, R^{a2}, R^{b3}, A^4, R^{c3}, R^{d1})$, $(X^3, R^{a2},$
$R^{b3}, A^4, R^{c3}, R^{d2})$, $(X^3, R^{a2}, R^{b3}, A^4, R^{c3}, R^{d3})$, $(X^3, R^{a2},$
$R^{b3}, A^4, R^{c4}, R^{d1})$, $(X^3, R^{a2}, R^{b3}, A^4, R^{c4}, R^{d2})$, $(X^3, R^{a2},$
$R^{b3}, A^4, R^{c4}, R^{d3})$, $(X^3, R^{a2}, R^{b3}, A^5, R^{c1}, R^{d1})$, $(X^3, R^{a2},$
$R^{b3}, A^5, R^{c1}, R^{d2})$, $(X^3, R^{a2}, R^{b3}, A^5, R^{c1}, R^{d3})$, $(X^3, R^{a2},$
$R^{b3}, A^5, R^{c2}, R^{d1})$, $(X^3, R^{a2}, R^{b3}, A^5, R^{c2}, R^{d2})$, $(X^3, R^{a2},$
$R^{b3}, A^5, R^{c2}, R^{d3})$, $(X^3, R^{a2}, R^{b3}, A^5, R^{c3}, R^{d1})$, $(X^3, R^{a2},$
$R^{b3}, A^5, R^{c3}, R^{d2})$, $(X^3, R^{a2}, R^{b3}, A^5, R^{c3}, R^{d3})$, $(X^3, R^{a2},$
$R^{b3}, A^5, R^{c4}, R^{d1})$, $(X^3, R^{a2}, R^{b3}, A^5, R^{c4}, R^{d2})$, $(X^3, R^{a2},$
$R^{b3}, A^5, R^{c4}, R^{d3})$, $(X^3, R^{a3}, R^{b1}, A^1, R^{c1}, R^{d1})$, $(X^3, R^{a3},$
$R^{b1}, A^1, R^{c1}, R^{d2})$, $(X^3, R^{a3}, R^{b1}, A^1, R^{c1}, R^{d3})$, $(X^3, R^{a3},$
$R^{b1}, A^1, R^{c2}, R^{d1})$, $(X^3, R^{a3}, R^{b1}, A^1, R^{c2}, R^{d2})$, $(X^3, R^{a3},$
$R^{b1}, A^1, R^{c2}, R^{d3})$, $(X^3, R^{a3}, R^{b1}, A^1, R^{c3}, R^{d1})$, $(X^3, R^{a3},$
$R^{b1}, A^1, R^{c3}, R^{d2})$, $(X^3, R^{a3}, R^{b1}, A^1, R^{c3}, R^{d3})$, $(X^3, R^{a3},$
$R^{b1}, A^1, R^{c4}, R^{d1})$, $(X^3, R^{a3}, R^{b1}, A^1, R^{c4}, R^{d2})$, $(X^3, R^{a3},$
$R^{b1}, A^1, R^{c4}, R^{d3})$, $(X^3, R^{a3}, R^{b1}, A^2, R^{c1}, R^{d1})$, $(X^3, R^{a3},$
$R^{b1}, A^2, R^{c1}, R^{d2})$, $(X^3, R^{a3}, R^{b1}, A^2, R^{c1}, R^{d3})$, $(X^3, R^{a3},$
$R^{b1}, A^2, R^{c2}, R^{d1})$, $(X^3, R^{a3}, R^{b1}, A^2, R^{c2}, R^{d2})$, $(X^3, R^{a3},$
$R^{b1}, A^2, R^{c2}, R^{d3})$, $(X^3, R^{a3}, R^{b1}, A^2, R^{c3}, R^{d1})$, $(X^3, R^{a3},$
$R^{b1}, A^2, R^{c3}, R^{d2})$, $(X^3, R^{a3}, R^{b1}, A^2, R^{c3}, R^{d3})$, $(X^3, R^{a3},$
$R^{b1}, A^2, R^{c4}, R^{d1})$, $(X^3, R^{a3}, R^{b1}, A^2, R^{c4}, R^{d2})$, $(X^3, R^{a3},$
$R^{b1}, A^2, R^{c4}, R^{d3})$, $(X^3, R^{a3}, R^{b1}, A^3, R^{c1}, R^{d1})$, $(X^3, R^{a3},$
$R^{b1}, A^3, R^{c1}, R^{d2})$, $(X^3, R^{a3}, R^{b1}, A^3, R^{c1}, R^{d3})$, $(X^3, R^{a3},$
$R^{b1}, A^3, R^{c2}, R^{d1})$, $(X^3, R^{a3}, R^{b1}, A^3, R^{c2}, R^{d2})$, $(X^3, R^{a3},$
$R^{b1}, A^3, R^{c2}, R^{d3})$, $(X^3, R^{a3}, R^{b1}, A^3, R^{c3}, R^{d1})$, $(X^3, R^{a3},$
$R^{b1}, A^3, R^{c3}, R^{d2})$, $(X^3, R^{a3}, R^{b1}, A^3, R^{c3}, R^{d3})$, $(X^3, R^{a3},$
$R^{b1}, A^3, R^{c4}, R^{d1})$, $(X^3, R^{a3}, R^{b1}, A^3, R^{c4}, R^{d2})$, $(X^3, R^{a3},$
$R^{b1}, A^3, R^{c4}, R^{d3})$, $(X^3, R^{a3}, R^{b1}, A^4, R^{c1}, R^{d1})$, $(X^3, R^{a3},$
$R^{b1}, A^4, R^{c1}, R^{d2})$, $(X^3, R^{a3}, R^{b1}, A^4, R^{c1}, R^{d3})$, $(X^3, R^{a3},$
$R^{b1}, A^4, R^{c2}, R^{d1})$, $(X^3, R^{a3}, R^{b1}, A^4, R^{c2}, R^{d2})$, $(X^3, R^{a3},$
$R^{b1}, A^4, R^{c2}, R^{d3})$, $(X^3, R^{a3}, R^{b1}, A^4, R^{c3}, R^{d1})$, $(X^3, R^{a3},$
$R^{b1}, A^4, R^{c3}, R^{d2})$, $(X^3, R^{a3}, R^{b1}, A^4, R^{c3}, R^{d3})$, $(X^3, R^{a3},$
$R^{b1}, A^4, R^{c4}, R^{d1})$, $(X^3, R^{a3}, R^{b1}, A^4, R^{c4}, R^{d2})$, $(X^3, R^{a3},$
$R^{b1}, A^4, R^{c4}, R^{d3})$, $(X^3, R^{a3}, R^{b1}, A^5, R^{c1}, R^{d1})$, $(X^3, R^{a3},$
$R^{b1}, A^5, R^{c1}, R^{d2})$, $(X^3, R^{a3}, R^{b1}, A^5, R^{c1}, R^{d3})$, $(X^3, R^{a3},$
$R^{b1}, A^5, R^{c2}, R^{d1})$, $(X^3, R^{a3}, R^{b1}, A^5, R^{c2}, R^{d2})$, $(X^3, R^{a3},$
$R^{b1}, A^5, R^{c2}, R^{d3})$, $(X^3, R^{a3}, R^{b1}, A^5, R^{c3}, R^{d1})$, $(X^3, R^{a3},$
$R^{b1}, A^5, R^{c3}, R^{d2})$, $(X^3, R^{a3}, R^{b1}, A^5, R^{c3}, R^{d3})$, $(X^3, R^{a3},$
$R^{b1}, A^5, R^{c4}, R^{d1})$, $(X^3, R^{a3}, R^{b1}, A^5, R^{c4}, R^{d2})$, $(X^3, R^{a3},$
$R^{b1}, A^5, R^{c4}, R^{d3})$, $(X^3, R^{a3}, R^{b2}, A^1, R^{c1}, R^{d1})$, $(X^3, R^{a3},$
$R^{b2}, A^1, R^{c1}, R^{d2})$, $(X^3, R^{a3}, R^{b2}, A^1, R^{c1}, R^{d3})$, $(X^3, R^{a3},$
$R^{b2}, A^1, R^{c2}, R^{d1})$, $(X^3, R^{a3}, R^{b2}, A^1, R^{c2}, R^{d2})$, $(X^3, R^{a3},$
$R^{b2}, A^1, R^{c2}, R^{d3})$, $(X^3, R^{a3}, R^{b2}, A^1, R^{c3}, R^{d1})$, $(X^3, R^{a3},$
$R^{b2}, A^1, R^{c3}, R^{d2})$, $(X^3, R^{a3}, R^{b2}, A^1, R^{c3}, R^{d3})$, $(X^3, R^{a3},$
$R^{b2}, A^1, R^{c4}, R^{d1})$, $(X^3, R^{a3}, R^{b2}, A^1, R^{c4}, R^{d2})$, $(X^3, R^{a3},$
$R^{b2}, A^1, R^{c4}, R^{d3})$, $(X^3, R^{a3}, R^{b2}, A^2, R^{c1}, R^{d1})$, $(X^3, R^{a3},$
$R^{b2}, A^2, R^{c1}, R^{d2})$, $(X^3, R^{a3}, R^{b2}, A^2, R^{c1}, R^{d3})$, $(X^3, R^{a3},$
$R^{b2}, A^2, R^{c2}, R^{d1})$, $(X^3, R^{a3}, R^{b2}, A^2, R^{c2}, R^{d2})$, $(X^3, R^{a3},$
$R^{b2}, A^2, R^{c2}, R^{d3})$, $(X^3, R^{a3}, R^{b2}, A^2, R^{c3}, R^{d1})$, $(X^3, R^{a3},$
$R^{b2}, A^2, R^{c3}, R^{d2})$, $(X^3, R^{a3}, R^{b2}, A^2, R^{c3}, R^{d3})$, $(X^3, R^{a3},$
$R^{b2}, A^2, R^{c4}, R^{d1})$, $(X^3, R^{a3}, R^{b2}, A^2, R^{c4}, R^{d2})$, $(X^3, R^{a3},$
$R^{b2}, A^2, R^{c4}, R^{d3})$, $(X^3, R^{a3}, R^{b2}, A^3, R^{c1}, R^{d1})$, $(X^3, R^{a3},$
$R^{b2}, A^3, R^{c1}, R^{d2})$, $(X^3, R^{a3}, R^{b2}, A^3, R^{c1}, R^{d3})$, $(X^3, R^{a3},$
$R^{b2}, A^3, R^{c2}, R^{d1})$, $(X^3, R^{a3}, R^{b2}, A^3, R^{c2}, R^{d2})$, $(X^3, R^{a3},$
$R^{b2}, A^3, R^{c2}, R^{d3})$, $(X^3, R^{a3}, R^{b2}, A^3, R^{c3}, R^{d1})$, $(X^3, R^{a3},$
$R^{b2}, A^3, R^{c3}, R^{d2})$, $(X^3, R^{a3}, R^{b2}, A^3, R^{c3}, R^{d3})$, $(X^3, R^{a3},$
$R^{b2}, A^3, R^{c4}, R^{d1})$, $(X^3, R^{a3}, R^{b2}, A^3, R^{c4}, R^{d2})$, $(X^3, R^{a3},$
$R^{b2}, A^3, R^{c4}, R^{d3})$, $(X^3, R^{a3}, R^{b2}, A^4, R^{c1}, R^{d1})$, $(X^3, R^{a3},$
$R^{b2}, A^4, R^{c1}, R^{d2})$, $(X^3, R^{a3}, R^{b2}, A^4, R^{c1}, R^{d3})$, $(X^3, R^{a3},$
$R^{b2}, A^4, R^{c2}, R^{d1})$, $(X^3, R^{a3}, R^{b2}, A^4, R^{c2}, R^{d2})$, $(X^3, R^{a3},$
$R^{b2}, A^4, R^{c2}, R^{d3})$, $(X^3, R^{a3}, R^{b2}, A^4, R^{c3}, R^{d1})$, $(X^3, R^{a3},$
$R^{b2}, A^4, R^{c3}, R^{d2})$, $(X^3, R^{a3}, R^{b2}, A^4, R^{c3}, R^{d3})$, $(X^3, R^{a3},$
$R^{b2}, A^4, R^{c4}, R^{d1})$, $(X^3, R^{a3}, R^{b2}, A^4, R^{c4}, R^{d2})$, $(X^3, R^{a3},$
$R^{b2}, A^4, R^{c4}, R^{d3})$, $(X^3, R^{a3}, R^{b2}, A^5, R^{c1}, R^{d1})$, $(X^3, R^{a3},$
$R^{b2}, A^5, R^{c1}, R^{d2})$, $(X^3, R^{a3}, R^{b2}, A^5, R^{c1}, R^{d3})$, $(X^3, R^{a3},$
$R^{b2}, A^5, R^{c2}, R^{d1})$, $(X^3, R^{a3}, R^{b2}, A^5, R^{c2}, R^{d2})$, $(X^3, R^{a3},$
$R^{b2}, A^5, R^{c2}, R^{d3})$, $(X^3, R^{a3}, R^{b2}, A^5, R^{c3}, R^{d1})$, $(X^3, R^{a3},$
$R^{b2}, A^5, R^{c3}, R^{d2})$, $(X^3, R^{a3}, R^{b2}, A^5, R^{c3}, R^{d3})$, $(X^3, R^{a3},$
$R^{b2}, A^5, R^{c4}, R^{d1})$, $(X^3, R^{a3}, R^{b2}, A^5, R^{c4}, R^{d2})$, $(X^3, R^{a3},$
$R^{b2}, A^5, R^{c4}, R^{d3})$, $(X^3, R^{a3}, R^{b3}, A^1, R^{c1}, R^{d1})$, $(X^3, R^{a3},$
$R^{b3}, A^1, R^{c1}, R^{d2})$, $(X^3, R^{a3}, R^{b3}, A^1, R^{c1}, R^{d3})$, $(X^3, R^{a3},$
$R^{b3}, A^1, R^{c2}, R^{d1})$, $(X^3, R^{a3}, R^{b3}, A^1, R^{c2}, R^{d2})$, $(X^3, R^{a3},$
$R^{b3}, A^1, R^{c2}, R^{d3})$, $(X^3, R^{a3}, R^{b3}, A^1, R^{c3}, R^{d1})$, $(X^3, R^{a3},$
$R^{b3}, A^1, R^{c3}, R^{d2})$, $(X^3, R^{a3}, R^{b3}, A^1, R^{c3}, R^{d3})$, $(X^3, R^{a3},$
$R^{b3}, A^1, R^{c4}, R^{d1})$, $(X^3, R^{a3}, R^{b3}, A^1, R^{c4}, R^{d2})$, $(X^3, R^{a3},$
$R^{b3}, A^1, R^{c4}, R^{d3})$, $(X^3, R^{a3}, R^{b3}, A^2, R^{c1}, R^{d1})$, $(X^3, R^{a3},$
$R^{b3}, A^2, R^{c1}, R^{d2})$, $(X^3, R^{a3}, R^{b3}, A^2, R^{c1}, R^{d3})$, $(X^3, R^{a3},$
$R^{b3}, A^2, R^{c2}, R^{d1})$, $(X^3, R^{a3}, R^{b3}, A^2, R^{c2}, R^{d2})$, $(X^3, R^{a3},$
$R^{b3}, A^2, R^{c2}, R^{d3})$, $(X^3, R^{a3}, R^{b3}, A^2, R^{c3}, R^{d1})$, $(X^3, R^{a3},$
$R^{b3}, A^2, R^{c3}, R^{d2})$, $(X^3, R^{a3}, R^{b3}, A^2, R^{c3}, R^{d3})$, $(X^3, R^{a3},$
$R^{b3}, A^2, R^{c4}, R^{d1})$, $(X^3, R^{a3}, R^{b3}, A^2, R^{c4}, R^{d2})$, $(X^3, R^{a3},$
$R^{b3}, A^2, R^{c4}, R^{d3})$, $(X^3, R^{a3}, R^{b3}, A^3, R^{c1}, R^{d1})$, $(X^3, R^{a3},$
$R^{b3}, A^3, R^{c1}, R^{d2})$, $(X^3, R^{a3}, R^{b3}, A^3, R^{c1}, R^{d3})$, $(X^3, R^{a3},$
$R^{b3}, A^3, R^{c2}, R^{d1})$, $(X^3, R^{a3}, R^{b3}, A^3, R^{c2}, R^{d2})$, $(X^3, R^{a3},$
$R^{b3}, A^3, R^{c2}, R^{d3})$, $(X^3, R^{a3}, R^{b3}, A^3, R^{c3}, R^{d1})$, $(X^3, R^{a3},$
$R^{b3}, A^3, R^{c3}, R^{d2})$, $(X^3, R^{a3}, R^{b3}, A^3, R^{c3}, R^{d3})$, $(X^3, R^{a3},$
$R^{b3}, A^3, R^{c4}, R^{d1})$, $(X^3, R^{a3}, R^{b3}, A^3, R^{c4}, R^{d2})$, $(X^3, R^{a3},$
$R^{b3}, A^4, R^{c1}, R^{d2})$, $(X^3, R^{a3}, R^{b3}, A^4, R^{c1}, R^{d1})$, $(X^3, R^{a3},$
$R^{b3}, A^4, R^{c2}, R^{d1})$, $(X^3, R^{a3}, R^{b3}, A^4, R^{c2}, R^{d2})$, $(X^3, R^{a3},$
$R^{b3}, A^4, R^{c2}, R^{d3})$, $(X^3, R^{a3}, R^{b3}, A^4, R^{c3}, R^{d1})$, $(X^3, R^{a3},$
$R^{b3}, A^4, R^{c3}, R^{d2})$, $(X^3, R^{a3}, R^{b3}, A^4, R^{c3}, R^{d3})$, $(X^3, R^{a3},$
$R^{b3}, A^4, R^{c4}, R^{d1})$, $(X^3, R^{a3}, R^{b3}, A^4, R^{c4}, R^{d2})$, $(X^3, R^{a3},$ $R^{b3}, A^4, R^{c4}, R^{d3}), (X^3, R^{a3}, R^{b3}, A^5, R^{c1}, R^{d1}), (X^3, R^{a3},$
$R^{b3}, A^5, R^{c1}, R^{d2}), (X^3, R^{a3}, R^{b3}, A^5, R^{c1}, R^{d3}), (X^3, R^{a3},$
$R^{b3}, A^5, R^{c2}, R^{d1}), (X^3, R^{a3}, R^{b3}, A^5, R^{c2}, R^{d2}), (X^3, R^{a3},$
$R^{b3}, A^5, R^{c2}, R^{d3}), (X^3, R^{a3}, R^{b3}, A^5, R^{c3}, R^{d1}), (X^3, R^{a3},$
$R^{b3}, A^5, R^{c3}, R^{d2}), (X^3, R^{a3}, R^{b3}, A^5, R^{c3}, R^{d3}), (X^3, R^{a3},$
$R^{b3}, A^5, R^{c4}, R^{d1}), (X^3, R^{a3}, R^{b3}, A^5, R^{c4}, R^{d2}), (X^3, R^{a3},$
$R^{b3}, A^5, R^{c4}, R^{d3}), (X^4, R^{a1}, R^{b1}, A^1, R^{c1}, R^{d1}), (X^4, R^{a1},$
$R^{b1}, A^1, R^{c1}, R^{d2}), (X^4, R^{a1}, R^{b1}, A^1, R^{c1}, R^{d3}), (X^4, R^{a1},$
$R^{b1}, A^1, R^{c2}, R^{d1}), (X^4, R^{a1}, R^{b1}, A^1, R^{c2}, R^{d2}), (X^4, R^{a1},$
$R^{b1}, A^1, R^{c2}, R^{d3}), (X^4, R^{a1}, R^{b1}, A^1, R^{c3}, R^{d1}), (X^4, R^{a1},$
$R^{b1}, A^1, R^{c3}, R^{d2}), (X^4, R^{a1}, R^{b1}, A^1, R^{c3}, R^{d3}), (X^4, R^{a1},$
$R^{b1}, A^1, R^{c4}, R^{d1}), (X^4, R^{a1}, R^{b1}, A^1, R^{c4}, R^{d2}), (X^4, R^{a1},$
$R^{b1}, A^1, R^{c4}, R^{d3}), (X^4, R^{a1}, R^{b1}, A^2, R^{c1}, R^{d1}), (X^4, R^{a1},$
$R^{b1}, A^2, R^{c1}, R^{d2}), (X^4, R^{a1}, R^{b1}, A^2, R^{c1}, R^{d3}), (X^4, R^{a1},$
$R^{b1}, A^2, R^{c2}, R^{d1}), (X^4, R^{a1}, R^{b1}, A^2, R^{c2}, R^{d2}), (X^4, R^{a1},$
$R^{b1}, A^2, R^{c2}, R^{d3}), (X^4, R^{a1}, R^{b1}, A^2, R^{c3}, R^{d1}), (X^4, R^{a1},$
$R^{b1}, A^2, R^{c3}, R^{d2}), (X^4, R^{a1}, R^{b1}, A^2, R^{c3}, R^{d3}), (X^4, R^{a1},$
$R^{b1}, A^2, R^{c4}, R^{d1}), (X^4, R^{a1}, R^{b1}, A^2, R^{c4}, R^{d2}), (X^4, R^{a1},$
$R^{b1}, A^2, R^{c4}, R^{d3}), (X^4, R^{a1}, R^{b1}, A^3, R^{c1}, R^{d1}), (X^4, R^{a1},$
$R^{b1}, A^3, R^{c1}, R^{d2}), (X^4, R^{a1}, R^{b1}, A^3, R^{c1}, R^{d3}), (X^4, R^{a1},$
$R^{b1}, A^3, R^{c2}, R^{d1}), (X^4, R^{a1}, R^{b1}, A^3, R^{c2}, R^{d2}), (X^4, R^{a1},$
$R^{b1}, A^3, R^{c2}, R^{d3}), (X^4, R^{a1}, R^{b1}, A^3, R^{c3}, R^{d1}), (X^4, R^{a1},$
$R^{b1}, A^3, R^{c3}, R^{d2}), (X^4, R^{a1}, R^{b1}, A^3, R^{c3}, R^{d3}), (X^4, R^{a1},$
$R^{b1}, A^3, R^{c4}, R^{d1}), (X^4, R^{a1}, R^{b1}, A^3, R^{c4}, R^{d2}), (X^4, R^{a1},$
$R^{b1}, A^3, R^{c4}, R^{d3}), (X^4, R^{a1}, R^{b1}, A^4, R^{c1}, R^{d1}), (X^4, R^{a1},$
$R^{b1}, A^4, R^{c1}, R^{d2}), (X^4, R^{a1}, R^{b1}, A^4, R^{c1}, R^{d3}), (X^4, R^{a1},$
$R^{b1}, A^4, R^{c2}, R^{d1}), (X^4, R^{a1}, R^{b1}, A^4, R^{c2}, R^{d2}), (X^4, R^{a1},$
$R^{b1}, A^4, R^{c2}, R^{d3}), (X^4, R^{a1}, R^{b1}, A^4, R^{c3}, R^{d1}), (X^4, R^{a1},$
$R^{b1}, A^4, R^{c3}, R^{d2}), (X^4, R^{a1}, R^{b1}, A^4, R^{c3}, R^{d3}), (X^4, R^{a1},$
$R^{b1}, A^4, R^{c4}, R^{d1}), (X^4, R^{a1}, R^{b1}, A^4, R^{c4}, R^{d2}), (X^4, R^{a1},$
$R^{b1}, A^4, R^{c4}, R^{d3}), (X^4, R^{a1}, R^{b1}, A^5, R^{c1}, R^{d1}), (X^4, R^{a1},$
$R^{b1}, A^5, R^{c1}, R^{d2}), (X^4, R^{a1}, R^{b1}, A^5, R^{c1}, R^{d3}), (X^4, R^{a1},$
$R^{b1}, A^5, R^{c2}, R^{d1}), (X^4, R^{a1}, R^{b1}, A^5, R^{c2}, R^{d2}), (X^4, R^{a1},$
$R^{b1}, A^5, R^{c2}, R^{d3}), (X^4, R^{a1}, R^{b1}, A^5, R^{c3}, R^{d1}), (X^4, R^{a1},$
$R^{b1}, A^5, R^{c3}, R^{d2}), (X^4, R^{a1}, R^{b1}, A^5, R^{c3}, R^{d3}), (X^4, R^{a1},$
$R^{b1}, A^5, R^{c4}, R^{d1}), (X^4, R^{a1}, R^{b1}, A^5, R^{c4}, R^{d2}), (X^4, R^{a1},$
$R^{b1}, A^5, R^{c4}, R^{d3}), (X^4, R^{a1}, R^{b2}, A^1, R^{c1}, R^{d1}), (X^4, R^{a1},$
$R^{b2}, A^1, R^{c1}, R^{d2}), (X^4, R^{a1}, R^{b2}, A^1, R^{c1}, R^{d3}), (X^4, R^{a1},$
$R^{b2}, A^1, R^{c2}, R^{d1}), (X^4, R^{a1}, R^{b2}, A^1, R^{c2}, R^{d2}), (X^4, R^{a1},$
$R^{b2}, A^1, R^{c2}, R^{d3}), (X^4, R^{a1}, R^{b2}, A^1, R^{c3}, R^{d1}), (X^4, R^{a1},$
$R^{b2}, A^1, R^{c3}, R^{d2}), (X^4, R^{a1}, R^{b2}, A^1, R^{c3}, R^{d3}), (X^4, R^{a1},$
$R^{b2}, A^1, R^{c4}, R^{d1}), (X^4, R^{a1}, R^{b2}, A^1, R^{c4}, R^{d2}), (X^4, R^{a1},$
$R^{b2}, A^1, R^{c4}, R^{d3}), (X^4, R^{a1}, R^{b2}, A^2, R^{c1}, R^{d1}), (X^4, R^{a1},$
$R^{b2}, A^2, R^{c1}, R^{d2}), (X^4, R^{a1}, R^{b2}, A^2, R^{c1}, R^{d3}), (X^4, R^{a1},$
$R^{b2}, A^2, R^{c2}, R^{d1}), (X^4, R^{a1}, R^{b2}, A^2, R^{c2}, R^{d2}), (X^4, R^{a1},$
$R^{b2}, A^2, R^{c2}, R^{d3}), (X^4, R^{a1}, R^{b2}, A^2, R^{c3}, R^{d1}), (X^4, R^{a1},$
$R^{b2}, A^2, R^{c3}, R^{d2}), (X^4, R^{a1}, R^{b2}, A^2, R^{c3}, R^{d3}), (X^4, R^{a1},$
$R^{b2}, A^2, R^{c4}, R^{d1}), (X^4, R^{a1}, R^{b2}, A^2, R^{c4}, R^{d2}), (X^4, R^{a1},$
$R^{b2}, A^2, R^{c4}, R^{d3}), (X^4, R^{a1}, R^{b2}, A^3, R^{c1}, R^{d1}), (X^4, R^{a1},$
$R^{b2}, A^3, R^{c1}, R^{d2}), (X^4, R^{a1}, R^{b2}, A^3, R^{c1}, R^{d3}), (X^4, R^{a1},$
$R^{b2}, A^3, R^{c2}, R^{d1}), (X^4, R^{a1}, R^{b2}, A^3, R^{c2}, R^{d2}), (X^4, R^{a1},$
$R^{b2}, A^3, R^{c2}, R^{d3}), (X^4, R^{a1}, R^{b2}, A^3, R^{c3}, R^{d1}), (X^4, R^{a1},$
$R^{b2}, A^3, R^{c3}, R^{d2}), (X^4, R^{a1}, R^{b2}, A^3, R^{c3}, R^{d3}), (X^4, R^{a1},$
$R^{b2}, A^3, R^{c4}, R^{d1}), (X^4, R^{a1}, R^{b2}, A^3, R^{c4}, R^{d2}), (X^4, R^{a1},$
$R^{b2}, A^3, R^{c4}, R^{d3}), (X^4, R^{a1}, R^{b2}, A^4, R^{c1}, R^{d1}), (X^4, R^{a1},$
$R^{b2}, A^4, R^{c1}, R^{d2}), (X^4, R^{a1}, R^{b2}, A^4, R^{c1}, R^{d3}), (X^4, R^{a1},$
$R^{b2}, A^4, R^{c2}, R^{d1}), (X^4, R^{a1}, R^{b2}, A^4, R^{c2}, R^{d2}), (X^4, R^{a1},$
$R^{b2}, A^4, R^{c2}, R^{d3}), (X^4, R^{a1}, R^{b2}, A^4, R^{c3}, R^{d1}), (X^4, R^{a1},$
$R^{b2}, A^4, R^{c3}, R^{d2}), (X^4, R^{a1}, R^{b2}, A^4, R^{c3}, R^{d3}), (X^4, R^{a1},$
$R^{b2}, A^4, R^{c4}, R^{d1}), (X^4, R^{a1}, R^{b2}, A^4, R^{c4}, R^{d2}), (X^4, R^{a1},$
$R^{b2}, A^4, R^{c4}, R^{d3}), (X^4, R^{a1}, R^{b2}, A^5, R^{c1}, R^{d1}), (X^4, R^{a1},$
$R^{b2}, A^5, R^{c1}, R^{d2}), (X^4, R^{a1}, R^{b2}, A^5, R^{c1}, R^{d3}), (X^4, R^{a1},$
$R^{b2}, A^5, R^{c2}, R^{d1}), (X^4, R^{a1}, R^{b2}, A^5, R^{c2}, R^{d2}), (X^4, R^{a1},$
$R^{b2}, A^5, R^{c2}, R^{d3}), (X^4, R^{a1}, R^{b2}, A^5, R^{c3}, R^{d1}), (X^4, R^{a1},$
$R^{b2}, A^5, R^{c3}, R^{d2}), (X^4, R^{a1}, R^{b2}, A^5, R^{c3}, R^{d3}), (X^4, R^{a1},$
$R^{b2}, A^5, R^{c4}, R^{d1}), (X^4, R^{a1}, R^{b2}, A^5, R^{c4}, R^{d2}), (X^4, R^{a1},$
$R^{b2}, A^5, R^{c4}, R^{d3}), (X^4, R^{a1}, R^{b3}, A^1, R^{c1}, R^{d1}), (X^4, R^{a1},$ $R^{b3}, A^1, R^{c1}, R^{d2}), (X^4, R^{a1}, R^{b3}, A^1, R^{c1}, R^{d3}), (X^4, R^{a1},$
$R^{b3}, A^1, R^{c2}, R^{d1}), (X^4, R^{a1}, R^{b3}, A^1, R^{c2}, R^{d2}), (X^4, R^{a1},$
$R^{b3}, A^1, R^{c2}, R^{d3}), (X^4, R^{a1}, R^{b3}, A^1, R^{c3}, R^{d1}), (X^4, R^{a1},$
$R^{b3}, A^1, R^{c3}, R^{d2}), (X^4, R^{a1}, R^{b3}, A^1, R^{c3}, R^{d3}), (X^4, R^{a1},$
$R^{b3}, A^1, R^{c4}, R^{d1}), (X^4, R^{a1}, R^{b3}, A^1, R^{c4}, R^{d2}), (X^4, R^{a1},$
$R^{b3}, A^1, R^{c4}, R^{d3}), (X^4, R^{a1}, R^{b3}, A^2, R^{c1}, R^{d1}), (X^4, R^{a1},$
$R^{b3}, A^2, R^{c1}, R^{d2}), (X^4, R^{a1}, R^{b3}, A^2, R^{c1}, R^{d3}), (X^4, R^{a1},$
$R^{b3}, A^2, R^{c2}, R^{d1}), (X^4, R^{a1}, R^{b3}, A^2, R^{c2}, R^{d2}), (X^4, R^{a1},$
$R^{b3}, A^2, R^{c2}, R^{d3}), (X^4, R^{a1}, R^{b3}, A^2, R^{c3}, R^{d1}), (X^4, R^{a1},$
$R^{b3}, A^2, R^{c3}, R^{d2}), (X^4, R^{a1}, R^{b3}, A^2, R^{c3}, R^{d3}), (X^4, R^{a1},$
$R^{b3}, A^2, R^{c4}, R^{d1}), (X^4, R^{a1}, R^{b3}, A^2, R^{c4}, R^{d2}), (X^4, R^{a1},$
$R^{b3}, A^2, R^{c4}, R^{d3}), (X^4, R^{a1}, R^{b3}, A^3, R^{c1}, R^{d1}), (X^4, R^{a1},$
$R^{b3}, A^3, R^{c1}, R^{d2}), (X^4, R^{a1}, R^{b3}, A^3, R^{c1}, R^{d3}), (X^4, R^{a1},$
$R^{b3}, A^3, R^{c2}, R^{d1}), (X^4, R^{a1}, R^{b3}, A^3, R^{c2}, R^{d2}), (X^4, R^{a1},$
$R^{b3}, A^3, R^{c2}, R^{d3}), (X^4, R^{a1}, R^{b3}, A^3, R^{c3}, R^{d1}), (X^4, R^{a1},$
$R^{b3}, A^3, R^{c3}, R^{d2}), (X^4, R^{a1}, R^{b3}, A^3, R^{c3}, R^{d3}), (X^4, R^{a1},$
$R^{b3}, A^3, R^{c4}, R^{d1}), (X^4, R^{a1}, R^{b3}, A^3, R^{c4}, R^{d2}), (X^4, R^{a1},$
$R^{b3}, A^3, R^{c4}, R^{d3}), (X^4, R^{a1}, R^{b3}, A^4, R^{c1}, R^{d1}), (X^4, R^{a1},$
$R^{b3}, A^4, R^{c1}, R^{d2}), (X^4, R^{a1}, R^{b3}, A^4, R^{c1}, R^{d3}), (X^4, R^{a1},$
$R^{b3}, A^4, R^{c2}, R^{d1}), (X^4, R^{a1}, R^{b3}, A^4, R^{c2}, R^{d2}), (X^4, R^{a1},$
$R^{b3}, A^4, R^{c2}, R^{d3}), (X^4, R^{a1}, R^{b3}, A^4, R^{c3}, R^{d1}), (X^4, R^{a1},$
$R^{b3}, A^4, R^{c3}, R^{d2}), (X^4, R^{a1}, R^{b3}, A^4, R^{c3}, R^{d3}), (X^4, R^{a1},$
$R^{b3}, A^4, R^{c4}, R^{d1}), (X^4, R^{a1}, R^{b3}, A^4, R^{c4}, R^{d2}), (X^4, R^{a1},$
$R^{b3}, A^4, R^{c4}, R^{d3}), (X^4, R^{a1}, R^{b3}, A^5, R^{c1}, R^{d1}), (X^4, R^{a1},$
$R^{b3}, A^5, R^{c1}, R^{d2}), (X^4, R^{a1}, R^{b3}, A^5, R^{c1}, R^{d3}), (X^4, R^{a1},$
$R^{b3}, A^5, R^{c2}, R^{d1}), (X^4, R^{a1}, R^{b3}, A^5, R^{c2}, R^{d2}), (X^4, R^{a1},$
$R^{b3}, A^5, R^{c2}, R^{d3}), (X^4, R^{a1}, R^{b3}, A^5, R^{c3}, R^{d1}), (X^4, R^{a1},$
$R^{b3}, A^5, R^{c3}, R^{d2}), (X^4, R^{a1}, R^{b3}, A^5, R^{c3}, R^{d3}), (X^4, R^{a1},$
$R^{b3}, A^5, R^{c4}, R^{d1}), (X^4, R^{a1}, R^{b3}, A^5, R^{c4}, R^{d2}), (X^4, R^{a1},$
$R^{b3}, A^5, R^{c4}, R^{d3}), (X^4, R^{a2}, R^{b1}, A^1, R^{c1}, R^{d1}), (X^4, R^{a2},$
$R^{b1}, A^1, R^{c1}, R^{d2}), (X^4, R^{a2}, R^{b1}, A^1, R^{c1}, R^{d3}), (X^4, R^{a2},$
$R^{b1}, A^1, R^{c2}, R^{d1}), (X^4, R^{a2}, R^{b1}, A^1, R^{c2}, R^{d2}), (X^4, R^{a2},$
$R^{b1}, A^1, R^{c2}, R^{d3}), (X^4, R^{a2}, R^{b1}, A^1, R^{c3}, R^{d1}), (X^4, R^{a2},$
$R^{b1}, A^1, R^{c3}, R^{d2}), (X^4, R^{a2}, R^{b1}, A^1, R^{c3}, R^{d3}), (X^4, R^{a2},$
$R^{b1}, A^1, R^{c4}, R^{d1}), (X^4, R^{a2}, R^{b1}, A^1, R^{c4}, R^{d2}), (X^4, R^{a2},$
$R^{b1}, A^1, R^{c4}, R^{d3}), (X^4, R^{a2}, R^{b1}, A^2, R^{c1}, R^{d1}), (X^4, R^{a2},$
$R^{b1}, A^2, R^{c1}, R^{d2}), (X^4, R^{a2}, R^{b1}, A^2, R^{c1}, R^{d3}), (X^4, R^{a2},$
$R^{b1}, A^2, R^{c2}, R^{d1}), (X^4, R^{a2}, R^{b1}, A^2, R^{c2}, R^{d2}), (X^4, R^{a2},$
$R^{b1}, A^2, R^{c2}, R^{d3}), (X^4, R^{a2}, R^{b1}, A^2, R^{c3}, R^{d1}), (X^4, R^{a2},$
$R^{b1}, A^2, R^{c3}, R^{d2}), (X^4, R^{a2}, R^{b1}, A^2, R^{c3}, R^{d3}), (X^4, R^{a2},$
$R^{b1}, A^2, R^{c4}, R^{d1}), (X^4, R^{a2}, R^{b1}, A^2, R^{c4}, R^{d2}), (X^4, R^{a2},$
$R^{b1}, A^2, R^{c4}, R^{d3}), (X^4, R^{a2}, R^{b1}, A^3, R^{c1}, R^{d1}), (X^4, R^{a2},$
$R^{b1}, A^3, R^{c1}, R^{d2}), (X^4, R^{a2}, R^{b1}, A^3, R^{c1}, R^{d3}), (X^4, R^{a2},$
$R^{b1}, A^3, R^{c2}, R^{d1}), (X^4, R^{a2}, R^{b1}, A^3, R^{c2}, R^{d2}), (X^4, R^{a2},$
$R^{b1}, A^3, R^{c2}, R^{d3}), (X^4, R^{a2}, R^{b1}, A^3, R^{c3}, R^{d1}), (X^4, R^{a2},$
$R^{b1}, A^3, R^{c3}, R^{d2}), (X^4, R^{a2}, R^{b1}, A^3, R^{c3}, R^{d3}), (X^4, R^{a2},$
$R^{b1}, A^3, R^{c4}, R^{d1}), (X^4, R^{a2}, R^{b1}, A^3, R^{c4}, R^{d2}), (X^4, R^{a2},$
$R^{b1}, A^3, R^{c4}, R^{d3}), (X^4, R^{a2}, R^{b1}, A^4, R^{c1}, R^{d1}), (X^4, R^{a2},$
$R^{b1}, A^4, R^{c1}, R^{d2}), (X^4, R^{a2}, R^{b1}, A^4, R^{c1}, R^{d3}), (X^4, R^{a2},$
$R^{b1}, A^4, R^{c2}, R^{d1}), (X^4, R^{a2}, R^{b1}, A^4, R^{c2}, R^{d2}), (X^4, R^{a2},$
$R^{b1}, A^4, R^{c2}, R^{d3}), (X^4, R^{a2}, R^{b1}, A^4, R^{c3}, R^{d1}), (X^4, R^{a2},$
$R^{b1}, A^4, R^{c3}, R^{d2}), (X^4, R^{a2}, R^{b1}, A^4, R^{c3}, R^{d3}), (X^4, R^{a2},$
$R^{b1}, A^4, R^{c4}, R^{d1}), (X^4, R^{a2}, R^{b1}, A^4, R^{c4}, R^{d2}), (X^4, R^{a2},$
$R^{b1}, A^4, R^{c4}, R^{d3}), (X^4, R^{a2}, R^{b1}, A^5, R^{c1}, R^{d1}), (X^4, R^{a2},$
$R^{b1}, A^5, R^{c1}, R^{d2}), (X^4, R^{a2}, R^{b1}, A^5, R^{c1}, R^{d3}), (X^4, R^{a2},$
$R^{b1}, A^5, R^{c2}, R^{d1}), (X^4, R^{a2}, R^{b1}, A^5, R^{c2}, R^{d2}), (X^4, R^{a2},$
$R^{b1}, A^5, R^{c2}, R^{d3}), (X^4, R^{a2}, R^{b1}, A^5, R^{c3}, R^{d1}), (X^4, R^{a2},$
$R^{b1}, A^5, R^{c3}, R^{d2}), (X^4, R^{a2}, R^{b1}, A^5, R^{c3}, R^{d3}), (X^4, R^{a2},$
$R^{b1}, A^5, R^{c4}, R^{d1}), (X^4, R^{a2}, R^{b1}, A^5, R^{c4}, R^{d2}), (X^4, R^{a2},$
$R^{b1}, A^5, R^{c4}, R^{d3}), (X^4, R^{a2}, R^{b2}, A^1, R^{c1}, R^{d1}), (X^4, R^{a2},$
$R^{b2}, A^1, R^{c1}, R^{d2}), (X^4, R^{a2}, R^{b2}, A^1, R^{c1}, R^{d3}), (X^4, R^{a2},$
$R^{b2}, A^1, R^{c2}, R^{d1}), (X^4, R^{a2}, R^{b2}, A^1, R^{c2}, R^{d2}), (X^4, R^{a2},$
$R^{b2}, A^1, R^{c2}, R^{d3}), (X^4, R^{a2}, R^{b2}, A^1, R^{c3}, R^{d1}), (X^4, R^{a2},$
$R^{b2}, A^1, R^{c3}, R^{d2}), (X^4, R^{a2}, R^{b2}, A^1, R^{c3}, R^{d3}), (X^4, R^{a2},$
$R^{b2}, A^1, R^{c4}, R^{d1}), (X^4, R^{a2}, R^{b2}, A^1, R^{c4}, R^{d2}), (X^4, R^{a2},$
$R^{b2}, A^1, R^{c4}, R^{d3}), (X^4, R^{a2}, R^{b2}, A^2, R^{c1}, R^{d1}), (X^4, R^{a2},$
$R^{b2}, A^2, R^{c1}, R^{d2}), (X^4, R^{a2}, R^{b2}, A^2, R^{c1}, R^{d3}), (X^4, R^{a2},$
$R^{b2}, A^2, R^{c2}, R^{d1}), (X^4, R^{a2}, R^{b2}, A^2, R^{c2}, R^{d2}), (X^4, R^{a2},$
$R^{b2}, A^2, R^{c2}, R^{d2}), (X^4, R^{a2}, R^{b2}, A^2, R^{c2}, R^{d3}), (X^4, R^{a2},$ $R^{b2}, A^2, R^{c3}, R^{d1}$), ($X^4, R^{a2}, R^{b2}, A^2, R^{c3}, R^{d2}$), ($X^4, R^{a2}, R^{b2}, A^2, R^{c3}, R^{d3}$), ($X^4, R^{a2}, R^{b2}, A^2, R^{c4}, R^{d1}$), ($X^4, R^{a2}, R^{b2}, A^2, R^{c4}, R^{d2}$), ($X^4, R^{a2}, R^{b2}, A^2, R^{c4}, R^{d3}$), ($X^4, R^{a2}, R^{b2}, A^3, R^{c1}, R^{d1}$), ($X^4, R^{a2}, R^{b2}, A^3, R^{c1}, R^{d2}$), ($X^4, R^{a2}, R^{b2}, A^3, R^{c1}, R^{d3}$), ($X^4, R^{a2}, R^{b2}, A^3, R^{c2}, R^{d1}$), ($X^4, R^{a2}, R^{b2}, A^3, R^{c2}, R^{d2}$), ($X^4, R^{a2}, R^{b2}, A^3, R^{c2}, R^{d3}$), ($X^4, R^{a2}, R^{b2}, A^3, R^{c3}, R^{d1}$), ($X^4, R^{a2}, R^{b2}, A^3, R^{c3}, R^{d2}$), ($X^4, R^{a2}, R^{b2}, A^3, R^{c3}, R^{d3}$), ($X^4, R^{a2}, R^{b2}, A^3, R^{c4}, R^{d1}$), ($X^4, R^{a2}, R^{b2}, A^3, R^{c4}, R^{d2}$), ($X^4, R^{a2}, R^{b2}, A^3, R^{c4}, R^{d3}$), ($X^4, R^{a2}, R^{b2}, A^4, R^{c1}, R^{d1}$), ($X^4, R^{a2}, R^{b2}, A^4, R^{c1}, R^{d2}$), ($X^4, R^{a2}, R^{b2}, A^4, R^{c1}, R^{d3}$), ($X^4, R^{a2}, R^{b2}, A^4, R^{c2}, R^{d1}$), ($X^4, R^{a2}, R^{b2}, A^4, R^{c2}, R^{d2}$), ($X^4, R^{a2}, R^{b2}, A^4, R^{c2}, R^{d3}$), ($X^4, R^{a2}, R^{b2}, A^4, R^{c3}, R^{d1}$), ($X^4, R^{a2}, R^{b2}, A^4, R^{c3}, R^{d2}$), ($X^4, R^{a2}, R^{b2}, A^4, R^{c3}, R^{d3}$), ($X^4, R^{a2}, R^{b2}, A^4, R^{c4}, R^{d1}$), ($X^4, R^{a2}, R^{b2}, A^4, R^{c4}, R^{d2}$), ($X^4, R^{a2}, R^{b2}, A^4, R^{c4}, R^{d3}$), ($X^4, R^{a2}, R^{b2}, A^5, R^{c1}, R^{d1}$), ($X^4, R^{a2}, R^{b2}, A^5, R^{c1}, R^{d2}$), ($X^4, R^{a2}, R^{b2}, A^5, R^{c1}, R^{d3}$), ($X^4, R^{a2}, R^{b2}, A^5, R^{c2}, R^{d1}$), ($X^4, R^{a2}, R^{b2}, A^5, R^{c2}, R^{d2}$), ($X^4, R^{a2}, R^{b2}, A^5, R^{c2}, R^{d3}$), ($X^4, R^{a2}, R^{b2}, A^5, R^{c3}, R^{d1}$), ($X^4, R^{a2}, R^{b2}, A^5, R^{c3}, R^{d2}$), ($X^4, R^{a2}, R^{b2}, A^5, R^{c3}, R^{d3}$), ($X^4, R^{a2}, R^{b2}, A^5, R^{c4}, R^{d1}$), ($X^4, R^{a2}, R^{b2}, A^5, R^{c4}, R^{d2}$), ($X^4, R^{a2}, R^{b2}, A^5, R^{c4}, R^{d3}$), ($X^4, R^{a2}, R^{b3}, A^1, R^{c1}, R^{d1}$), ($X^4, R^{a2}, R^{b3}, A^1, R^{c1}, R^{d2}$), ($X^4, R^{a2}, R^{b3}, A^1, R^{c1}, R^{d3}$), ($X^4, R^{a2}, R^{b3}, A^1, R^{c2}, R^{d1}$), ($X^4, R^{a2}, R^{b3}, A^1, R^{c2}, R^{d2}$), ($X^4, R^{a2}, R^{b3}, A^1, R^{c2}, R^{d3}$), ($X^4, R^{a2}, R^{b3}, A^1, R^{c3}, R^{d1}$), ($X^4, R^{a2}, R^{b3}, A^1, R^{c3}, R^{d2}$), ($X^4, R^{a2}, R^{b3}, A^1, R^{c3}, R^{d3}$), ($X^4, R^{a2}, R^{b3}, A^1, R^{c4}, R^{d1}$), ($X^4, R^{a2}, R^{b3}, A^1, R^{c4}, R^{d2}$), ($X^4, R^{a2}, R^{b3}, A^1, R^{c4}, R^{d3}$), ($X^4, R^{a2}, R^{b3}, A^2, R^{c1}, R^{d1}$), ($X^4, R^{a2}, R^{b3}, A^2, R^{c1}, R^{d2}$), ($X^4, R^{a2}, R^{b3}, A^2, R^{c1}, R^{d3}$), ($X^4, R^{a2}, R^{b3}, A^2, R^{c2}, R^{d1}$), ($X^4, R^{a2}, R^{b3}, A^2, R^{c2}, R^{d2}$), ($X^4, R^{a2}, R^{b3}, A^2, R^{c2}, R^{d3}$), ($X^4, R^{a2}, R^{b3}, A^2, R^{c3}, R^{d1}$), ($X^4, R^{a2}, R^{b3}, A^2, R^{c3}, R^{d2}$), ($X^4, R^{a2}, R^{b3}, A^2, R^{c3}, R^{d3}$), ($X^4, R^{a2}, R^{b3}, A^2, R^{c4}, R^{d1}$), ($X^4, R^{a2}, R^{b3}, A^2, R^{c4}, R^{d2}$), ($X^4, R^{a2}, R^{b3}, A^2, R^{c4}, R^{d3}$), ($X^4, R^{a2}, R^{b3}, A^3, R^{c1}, R^{d1}$), ($X^4, R^{a2}, R^{b3}, A^3, R^{c1}, R^{d2}$), ($X^4, R^{a2}, R^{b3}, A^3, R^{c1}, R^{d3}$), ($X^4, R^{a2}, R^{b3}, A^3, R^{c2}, R^{d1}$), ($X^4, R^{a2}, R^{b3}, A^3, R^{c2}, R^{d2}$), ($X^4, R^{a2}, R^{b3}, A^3, R^{c2}, R^{d3}$), ($X^4, R^{a2}, R^{b3}, A^3, R^{c3}, R^{d1}$), ($X^4, R^{a2}, R^{b3}, A^3, R^{c3}, R^{d2}$), ($X^4, R^{a1}, R^{b3}, A^3, R^{c3}, R^{d3}$), ($X^4, R^{a2}, R^{b3}, A^3, R^{c4}, R^{d1}$), ($X^4, R^{a2}, R^{b3}, A^3, R^{c4}, R^{d2}$), ($X^4, R^{a2}, R^{b3}, A^3, R^{c4}, R^{d3}$), ($X^4, R^{a2}, R^{b3}, A^4, R^{c1}, R^{d1}$), ($X^4, R^{a2}, R^{b3}, A^4, R^{c1}, R^{d2}$), ($X^4, R^{a2}, R^{b3}, A^4, R^{c1}, R^{d3}$), ($X^4, R^{a2}, R^{b3}, A^4, R^{c2}, R^{d1}$), ($X^4, R^{a2}, R^{b3}, A^4, R^{c2}, R^{d2}$), ($X^4, R^{a2}, R^{b3}, A^4, R^{c2}, R^{d3}$), ($X^4, R^{a2}, R^{b3}, A^4, R^{c3}, R^{d1}$), ($X^4, R^{a2}, R^{b3}, A^4, R^{c3}, R^{d2}$), ($X^4, R^{a2}, R^{b3}, A^4, R^{c3}, R^{d3}$), ($X^4, R^{a2}, R^{b3}, A^4, R^{c4}, R^{d1}$), ($X^4, R^{a2}, R^{b3}, A^4, R^{c4}, R^{d2}$), ($X^4, R^{a2}, R^{b3}, A^4, R^{c4}, R^{d3}$), ($X^4, R^{a2}, R^{b3}, A^5, R^{c1}, R^{d1}$), ($X^4, R^{a2}, R^{b3}, A^5, R^{c1}, R^{d2}$), ($X^4, R^{a2}, R^{b3}, A^5, R^{c1}, R^{d3}$), ($X^4, R^{a2}, R^{b3}, A^5, R^{c2}, R^{d1}$), ($X^4, R^{a2}, R^{b3}, A^5, R^{c2}, R^{d2}$), ($X^4, R^{a2}, R^{b3}, A^5, R^{c2}, R^{d3}$), ($X^4, R^{a2}, R^{b3}, A^5, R^{c3}, R^{d1}$), ($X^4, R^{a2}, R^{b3}, A^5, R^{c3}, R^{d2}$), ($X^4, R^{a2}, R^{b3}, A^5, R^{c3}, R^{d3}$), ($X^4, R^{a2}, R^{b3}, A^5, R^{c4}, R^{d1}$), ($X^4, R^{a2}, R^{b3}, A^5, R^{c4}, R^{d2}$), ($X^4, R^{a2}, R^{b3}, A^5, R^{c4}, R^{d3}$), ($X^4, R^{a3}, R^{b1}, A^1, R^{c1}, R^{d1}$), ($X^4, R^{a3}, R^{b1}, A^1, R^{c1}, R^{d2}$), ($X^4, R^{a3}, R^{b1}, A^1, R^{c1}, R^{d3}$), ($X^4, R^{a3}, R^{b1}, A^1, R^{c2}, R^{d1}$), ($X^4, R^{a3}, R^{b1}, A^1, R^{c2}, R^{d2}$), ($X^4, R^{a3}, R^{b1}, A^1, R^{c2}, R^{d3}$), ($X^4, R^{a3}, R^{b1}, A^1, R^{c3}, R^{d1}$), ($X^4, R^{a3}, R^{b1}, A^1, R^{c3}, R^{d2}$), ($X^4, R^{a3}, R^{b1}, A^1, R^{c3}, R^{d3}$), ($X^4, R^{a3}, R^{b1}, A^1, R^{c4}, R^{d1}$), ($X^4, R^{a3}, R^{b1}, A^1, R^{c4}, R^{d2}$), ($X^4, R^{a3}, R^{b1}, A^1, R^{c4}, R^{d3}$), ($X^4, R^{a3}, R^{b1}, A^2, R^{c1}, R^{d1}$), ($X^4, R^{a3}, R^{b1}, A^2, R^{c1}, R^{d2}$), ($X^4, R^{a3}, R^{b1}, A^2, R^{c1}, R^{d3}$), ($X^4, R^{a3}, R^{b1}, A^2, R^{c2}, R^{d1}$), ($X^4, R^{a3}, R^{b1}, A^2, R^{c2}, R^{d2}$), ($X^4, R^{a3}, R^{b1}, A^2, R^{c2}, R^{d3}$), ($X^4, R^{a3}, R^{b1}, A^2, R^{c3}, R^{d1}$), ($X^4, R^{a3}, R^{b1}, A^2, R^{c3}, R^{d2}$), ($X^4, R^{a3}, R^{b1}, A^2, R^{c3}, R^{d3}$), ($X^4, R^{a3}, R^{b1}, A^2, R^{c4}, R^{d1}$), ($X^4, R^{a3}, R^{b1}, A^2, R^{c4}, R^{d2}$), ($X^4, R^{a3}, R^{b1}, A^2, R^{c4}, R^{d3}$), ($X^4, R^{a3}, R^{b1}, A^3, R^{c1}, R^{d1}$), ($X^4, R^{a3}, R^{b1}, A^3, R^{c1}, R^{d2}$), ($X^4, R^{a3}, R^{b1}, A^3, R^{c1}, R^{d3}$), ($X^4, R^{a3}, R^{b1}, A^3, R^{c2}, R^{d1}$), ($X^4, R^{a3}, R^{b1}, A^3, R^{c2}, R^{d2}$), ($X^4, R^{a3}, R^{b1}, A^3, R^{c2}, R^{d3}$), ($X^4, R^{a3}, R^{b1}, A^3, R^{c3}, R^{d1}$), ($X^4, R^{a3}, R^{b1}, A^3, R^{c3}, R^{d2}$), ($X^4, R^{a3}, R^{b1}, A^3, R^{c3}, R^{d3}$), ($X^4, R^{a3}, R^{b1}, A^3, R^{c4}, R^{d1}$), ($X^4, R^{a3}, R^{b1}, A^3, R^{c4}, R^{d2}$), ($X^4, R^{a3}, R^{b1}, A^3, R^{c4}, R^{d3}$), ($X^4, R^{a3}, R^{b1}, A^4, R^{c1}, R^{d1}$), ($X^4, R^{a3}, R^{b1}, A^4, R^{c1}, R^{d2}$), ($X^4, R^{a3}, R^{b1}, A^4, R^{c1}, R^{d3}$), ($X^4, R^{a3}, R^{b1}, A^4, R^{c2}, R^{d1}$), ($X^4, R^{a3}, R^{b1}, A^4, R^{c2}, R^{d2}$), ($X^4, R^{a3}, R^{b1}, A^4, R^{c2}, R^{d3}$), ($X^4, R^{a3}, R^{b1}, A^4, R^{c3}, R^{d1}$), ($X^4, R^{a3}, R^{b1}, A^4, R^{c3}, R^{d2}$), ($X^4, R^{a3}, R^{b1}, A^4, R^{c3}, R^{d3}$), ($X^4, R^{a3}, R^{b1}, A^4, R^{c4}, R^{d1}$), ($X^4, R^{a3}, R^{b1}, A^4, R^{c4}, R^{d2}$), ($X^4, R^{a3}, R^{b1}, A^4, R^{c4}, R^{d3}$), ($X^4, R^{a3}, R^{b1}, A^5, R^{c1}, R^{d1}$), ($X^4, R^{a3}, R^{b1}, A^5, R^{c1}, R^{d2}$), ($X^4, R^{a3}, R^{b1}, A^5, R^{c1}, R^{d3}$), ($X^4, R^{a3}, R^{b1}, A^5, R^{c2}, R^{d1}$), ($X^4, R^{a3}, R^{b1}, A^5, R^{c2}, R^{d2}$), ($X^4, R^{a3}, R^{b1}, A^5, R^{c2}, R^{d3}$), ($X^4, R^{a3}, R^{b1}, A^5, R^{c3}, R^{d1}$), ($X^4, R^{a3}, R^{b1}, A^5, R^{c3}, R^{d2}$), ($X^4, R^{a3}, R^{b1}, A^5, R^{c3}, R^{d3}$), ($X^4, R^{a3}, R^{b1}, A^5, R^{c4}, R^{d1}$), ($X^4, R^{a3}, R^{b1}, A^5, R^{c4}, R^{d2}$), ($X^4, R^{a3}, R^{b1}, A^5, R^{c4}, R^{d3}$), ($X^4, R^{a3}, R^{b2}, A^1, R^{c1}, R^{d1}$), ($X^4, R^{a3}, R^{b2}, A^1, R^{c1}, R^{d2}$), ($X^4, R^{a3}, R^{b2}, A^1, R^{c1}, R^{d3}$), ($X^4, R^{a3}, R^{b2}, A^1, R^{c2}, R^{d1}$), ($X^4, R^{a3}, R^{b2}, A^1, R^{c2}, R^{d2}$), ($X^4, R^{a3}, R^{b2}, A^1, R^{c2}, R^{d3}$), ($X^4, R^{a3}, R^{b2}, A^1, R^{c3}, R^{d1}$), ($X^4, R^{a3}, R^{b2}, A^1, R^{c3}, R^{d2}$), ($X^4, R^{a3}, R^{b2}, A^1, R^{c3}, R^{d3}$), ($X^4, R^{a3}, R^{b2}, A^1, R^{c4}, R^{d1}$), ($X^4, R^{a3}, R^{b2}, A^1, R^{c4}, R^{d2}$), ($X^4, R^{a3}, R^{b2}, A^1, R^{c4}, R^{d3}$), ($X^4, R^{a3}, R^{b2}, A^2, R^{c1}, R^{d1}$), ($X^4, R^{a3}, R^{b2}, A^2, R^{c1}, R^{d2}$), ($X^4, R^{a3}, R^{b2}, A^2, R^{c1}, R^{d3}$), ($X^4, R^{a3}, R^{b2}, A^2, R^{c2}, R^{d1}$), ($X^4, R^{a3}, R^{b2}, A^2, R^{c2}, R^{d2}$), ($X^4, R^{a3}, R^{b2}, A^2, R^{c2}, R^{d3}$), ($X^4, R^{a3}, R^{b2}, A^2, R^{c3}, R^{d1}$), ($X^4, R^{a3}, R^{b2}, A^2, R^{c3}, R^{d2}$), ($X^4, R^{a3}, R^{b2}, A^2, R^{c3}, R^{d3}$), ($X^4, R^{a3}, R^{b2}, A^2, R^{c4}, R^{d1}$), ($X^4, R^{a3}, R^{b2}, A^2, R^{c4}, R^{d2}$), ($X^4, R^{a3}, R^{b2}, A^2, R^{c4}, R^{d3}$), ($X^4, R^{a3}, R^{b2}, A^3, R^{c1}, R^{d1}$), ($X^4, R^{a3}, R^{b2}, A^3, R^{c1}, R^{d2}$), ($X^4, R^{a3}, R^{b2}, A^3, R^{c1}, R^{d3}$), ($X^4, R^{a3}, R^{b2}, A^3, R^{c2}, R^{d1}$), ($X^4, R^{a3}, R^{b2}, A^3, R^{c2}, R^{d2}$), ($X^4, R^{a3}, R^{b2}, A^3, R^{c2}, R^{d3}$), ($X^4, R^{a3}, R^{b2}, A^3, R^{c3}, R^{d1}$), ($X^4, R^{a3}, R^{b2}, A^3, R^{c3}, R^{d2}$), ($X^4, R^{a3}, R^{b2}, A^3, R^{c3}, R^{d3}$), ($X^4, R^{a3}, R^{b2}, A^3, R^{c4}, R^{d1}$), ($X^4, R^{a3}, R^{b2}, A^3, R^{c4}, R^{d2}$), ($X^4, R^{a3}, R^{b2}, A^3, R^{c4}, R^{d3}$), ($X^4, R^{a3}, R^{b2}, A^4, R^{c1}, R^{d1}$), ($X^4, R^{a3}, R^{b2}, A^4, R^{c1}, R^{d2}$), ($X^4, R^{a3}, R^{b2}, A^4, R^{c1}, R^{d3}$), ($X^4, R^{a3}, R^{b2}, A^4, R^{c2}, R^{d1}$), ($X^4, R^{a3}, R^{b2}, A^4, R^{c2}, R^{d2}$), ($X^4, R^{a3}, R^{b2}, A^4, R^{c2}, R^{d3}$), ($X^4, R^{a3}, R^{b2}, A^4, R^{c3}, R^{d1}$), ($X^4, R^{a3}, R^{b2}, A^4, R^{c3}, R^{d2}$), ($X^4, R^{a3}, R^{b2}, A^4, R^{c3}, R^{d3}$), ($X^4, R^{a3}, R^{b2}, A^4, R^{c4}, R^{d1}$), ($X^4, R^{a3}, R^{b2}, A^4, R^{c4}, R^{d2}$), ($X^4, R^{a3}, R^{b2}, A^4, R^{c4}, R^{d3}$), ($X^4, R^{a3}, R^{b2}, A^5, R^{c1}, R^{d1}$), ($X^4, R^{a3}, R^{b2}, A^5, R^{c1}, R^{d2}$), ($X^4, R^{a3}, R^{b2}, A^5, R^{c1}, R^{d3}$), ($X^4, R^{a3}, R^{b2}, A^5, R^{c2}, R^{d1}$), ($X^4, R^{a3}, R^{b2}, A^5, R^{c2}, R^{d2}$), ($X^4, R^{a3}, R^{b2}, A^5, R^{c2}, R^{d3}$), ($X^4, R^{a3}, R^{b2}, A^5, R^{c3}, R^{d1}$), ($X^4, R^{a3}, R^{b2}, A^5, R^{c3}, R^{d2}$), ($X^4, R^{a3}, R^{b2}, A^5, R^{c3}, R^{d3}$), ($X^4, R^{a3}, R^{b2}, A^5, R^{c4}, R^{d1}$), ($X^4, R^{a3}, R^{b2}, A^5, R^{c4}, R^{d2}$), ($X^4, R^{a3}, R^{b2}, A^5, R^{c4}, R^{d3}$), ($X^4, R^{a3}, R^{b3}, A^1, R^{c1}, R^{d1}$), ($X^4, R^{a3}, R^{b3}, A^1, R^{c1}, R^{d2}$), ($X^4, R^{a3}, R^{b3}, A^1, R^{c1}, R^{d3}$), ($X^4, R^{a3}, R^{b3}, A^1, R^{c2}, R^{d1}$), ($X^4, R^{a3}, R^{b3}, A^1, R^{c2}, R^{d2}$), ($X^4, R^{a3}, R^{b3}, A^1, R^{c2}, R^{d3}$), ($X^4, R^{a3}, R^{b3}, A^1, R^{c3}, R^{d1}$), ($X^4, R^{a3}, R^{b3}, A^1, R^{c3}, R^{d2}$), ($X^4, R^{a3}, R^{b3}, A^1, R^{c3}, R^{d3}$), ($X^4, R^{a3}, R^{b3}, A^1, R^{c4}, R^{d1}$), ($X^4, R^{a3}, R^{b3}, A^1, R^{c4}, R^{d2}$), ($X^4, R^{a3}, R^{b3}, A^1, R^{c4}, R^{d3}$), ($X^4, R^{a3}, R^{b3}, A^2, R^{c1}, R^{d1}$), ($X^4, R^{a3}, R^{b3}, A^2, R^{c1}, R^{d2}$), ($X^4, R^{a3}, R^{b3}, A^2, R^{c1}, R^{d3}$), ($X^4, R^{a3}, R^{b3}, A^2, R^{c2}, R^{d1}$), ($X^4, R^{a3}, R^{b3}, A^2, R^{c2}, R^{d2}$), ($X^4, R^{a3}, R^{b3}, A^2, R^{c2}, R^{d3}$), ($X^4, R^{a3}, R^{b3}, A^2, R^{c3}, R^{d1}$), ($X^4, R^{a3}, R^{b3}, A^2, R^{c3}, R^{d2}$), ($X^4, R^{a3}, R^{b3}, A^2, R^{c3}, R^{d3}$), ($X^4, R^{a3}, R^{b3}, A^2, R^{c4}, R^{d1}$), ($X^4, R^{a3}, R^{b3}, A^2, R^{c4}, R^{d2}$), ($X^4, R^{a3}, R^{b3}, A^2, R^{c4}, R^{d3}$), ($X^4, R^{a3}, R^{b3}, A^3, R^{c1}, R^{d1}$), ($X^4, R^{a3}, R^{b3}, A^3, R^{c1}, R^{d2}$), ($X^4, R^{a3}, R^{b3}, A^3, R^{c1}, R^{d3}$), ($X^4, R^{a3}, R^{b3}, A^3, R^{c2}, R^{d1}$), ($X^4, R^{a3}, R^{b3}, A^3, R^{c2}, R^{d2}$), ($X^4, R^{a3}, R^{b3}, A^3, R^{c2}, R^{d3}$), ($X^4, R^{a3}, R^{b3}, A^3, R^{c3}, R^{d1}$), ($X^4, R^{a3}, R^{b3}, A^3, R^{c3}, R^{d2}$), ($X^4, R^{a3}, R^{b3}, A^3, R^{c3}, R^{d3}$), ($X^4, R^{a3}, R^{b3}, A^3, R^{c4}, R^{d1}$), ($X^4, R^{a3}, R^{b3}, A^4, R^{c1}, R^{d1}$), ($X^4, R^{a3}, R^{b3}, A^4, R^{c1}, R^{d2}$), ($X^4, R^{a3}, R^{b3}, A^4, R^{c1}, R^{d3}$), ($X^4, R^{a3}, R^{b3}, A^4, R^{c2}, R^{d1}$), ($X^4, R^{a3}, R^{b3}, A^4, R^{c2}, R^{d2}$), ($X^4, R^{a3}, R^{b3}, A^4, R^{c2}, R^{d3}$), ($X^4, R^{a3}, R^{b3}, A^4, R^{c3}, R^{d1}$), ($X^4, R^{a3}, R^{b3}, A^4, R^{c3}, R^{d2}$), ($X^4, R^{a3}, R^{b3}, A^4, R^{c3}, R^{d3}$), ($X^4, R^{a3}, R^{b3}, A^4, R^{c4}, R^{d1}$), ($X^4, R^{a3},

421

$R^{b3}, A^4, R^{c4}, R^{d2}), (X^4, R^{a3}, R^{b3}, A^4, R^{c4}, R^{d3}), (X^4, R^{a3},$
$R^{b3}, A^5, R^{c1}, R^{d1}), (X^4, R^{a3}, R^{b3}, A^5, R^{c1}, R^{d2}), (X^4, R^{a3},$
$R^{b3}, A^5, R^{c1}, R^{d3}), (X^4, R^{a3}, R^{b3}, A^5, R^{c2}, R^{d1}), (X^4, R^{a3},$
$R^{b3}, A^5, R^{c2}, R^{d2}), (X^4, R^{a3}, R^{b3}, A^5, R^{c2}, R^{d3}), (X^4, R^{a3},$
$R^{b3}, A^5, R^{c3}, R^{d1}), (X^4, R^{a3}, R^{b3}, A^5, R^{c3}, R^{d2}), (X^4, R^{a3},$
$R^{b3}, A^5, R^{c3}, R^{d3}), (X^4, R^{a3}, R^{b3}, A^5, R^{c4}, R^{d1}), (X^4, R^{a3},$
$R^{b3}, A^5, R^{c4}, R^{d2}), (X^4, R^{a3}, R^{b3}, A^5, R^{c4}, R^{d3}), (X^5, R^{a1},$
$R^{b1}, A^1, R^{c1}, R^{d1}), (X^5, R^{a1}, R^{b1}, A^1, R^{c1}, R^{d2}), (X^5, R^{a1},$
$R^{b1}, A^1, R^{c1}, R^{d3}), (X^5, R^{a1}, R^{b1}, A^1, R^{c2}, R^{d1}), (X^5, R^{a1},$
$R^{b1}, A^1, R^{c2}, R^{d2}), (X^5, R^{a1}, R^{b1}, A^1, R^{c2}, R^{d3}), (X^5, R^{a1},$
$R^{b1}, A^1, R^{c3}, R^{d1}), (X^5, R^{a1}, R^{b1}, A^1, R^{c3}, R^{d2}), (X^5, R^{a1},$
$R^{b1}, A^1, R^{c3}, R^{d3}), (X^5, R^{a1}, R^{b1}, A^1, R^{c4}, R^{d1}), (X^5, R^{a1},$
$R^{b1}, A^1, R^{c4}, R^{d2}), (X^5, R^{a1}, R^{b1}, A^1, R^{c4}, R^{d3}), (X^5, R^{a1},$
$R^{b1}, A^2, R^{c1}, R^{d1}), (X^5, R^{a1}, R^{b1}, A^2, R^{c1}, R^{d2}), (X^5, R^{a1},$
$R^{b1}, A^2, R^{c1}, R^{d3}), (X^5, R^{a1}, R^{b1}, A^2, R^{c2}, R^{d1}), (X^5, R^{a1},$
$R^{b1}, A^2, R^{c2}, R^{d2}), (X^5, R^{a1}, R^{b1}, A^2, R^{c2}, R^{d3}), (X^5, R^{a1},$
$R^{b1}, A^2, R^{c3}, R^{d1}), (X^5, R^{a1}, R^{b1}, A^2, R^{c3}, R^{d2}), (X^5, R^{a1},$
$R^{b1}, A^2, R^{c3}, R^{d3}), (X^5, R^{a1}, R^{b1}, A^2, R^{c4}, R^{d1}), (X^5, R^{a1},$
$R^{b1}, A^2, R^{c4}, R^{d2}), (X^5, R^{a1}, R^{b1}, A^2, R^{c4}, R^{d3}), (X^5, R^{a1},$
$R^{b1}, A^3, R^{c1}, R^{d1}), (X^5, R^{a1}, R^{b1}, A^3, R^{c1}, R^{d2}), (X^5, R^{a1},$
$R^{b1}, A^3, R^{c1}, R^{d3}), (X^5, R^{a1}, R^{b1}, A^3, R^{c2}, R^{d1}), (X^5, R^{a1},$
$R^{b1}, A^3, R^{c2}, R^{d2}), (X^5, R^{a1}, R^{b1}, A^3, R^{c2}, R^{d3}), (X^5, R^{a1},$
$R^{b1}, A^3, R^{c3}, R^{d1}), (X^5, R^{a1}, R^{b1}, A^3, R^{c3}, R^{d2}), (X^5, R^{a1},$
$R^{b1}, A^3, R^{c3}, R^{d3}), (X^5, R^{a1}, R^{b1}, A^3, R^{c4}, R^{d1}), (X^5, R^{a1},$
$R^{b1}, A^3, R^{c4}, R^{d2}), (X^5, R^{a1}, R^{b1}, A^3, R^{c4}, R^{d3}), (X^5, R^{a1},$
$R^{b1}, A^4, R^{c1}, R^{d1}), (X^5, R^{a1}, R^{b1}, A^4, R^{c1}, R^{d2}), (X^5, R^{a1},$
$R^{b1}, A^4, R^{c1}, R^{d3}), (X^5, R^{a1}, R^{b1}, A^4, R^{c2}, R^{d1}), (X^5, R^{a1},$
$R^{b1}, A^4, R^{c2}, R^{d2}), (X^5, R^{a1}, R^{b1}, A^4, R^{c2}, R^{d3}), (X^5, R^{a1},$
$R^{b1}, A^4, R^{c3}, R^{d1}), (X^5, R^{a1}, R^{b1}, A^4, R^{c3}, R^{d2}), (X^5, R^{a1},$
$R^{b1}, A^4, R^{c3}, R^{d3}), (X^5, R^{a1}, R^{b1}, A^4, R^{c4}, R^{d1}), (X^5, R^{a1},$
$R^{b1}, A^4, R^{c4}, R^{d2}), (X^5, R^{a1}, R^{b1}, A^4, R^{c4}, R^{d3}), (X^5, R^{a1},$
$R^{b1}, A^5, R^{c1}, R^{d1}), (X^5, R^{a1}, R^{b1}, A^5, R^{c1}, R^{d2}), (X^5, R^{a1},$
$R^{b1}, A^5, R^{c1}, R^{d3}), (X^5, R^{a1}, R^{b1}, A^5, R^{c2}, R^{d1}), (X^5, R^{a1},$
$R^{b1}, A^5, R^{c2}, R^{d2}), (X^5, R^{a1}, R^{b1}, A^5, R^{c2}, R^{d3}), (X^5, R^{a1},$
$R^{b1}, A^5, R^{c3}, R^{d1}), (X^5, R^{a1}, R^{b1}, A^5, R^{c3}, R^{d2}), (X^5, R^{a1},$
$R^{b1}, A^5, R^{c3}, R^{d3}), (X^5, R^{a1}, R^{b1}, A^5, R^{c4}, R^{d1}), (X^5, R^{a1},$
$R^{b1}, A^5, R^{c4}, R^{d2}), (X^5, R^{a1}, R^{b1}, A^5, R^{c4}, R^{d3}), (X^5, R^{a1},$
$R^{b2}, A^1, R^{c1}, R^{d1}), (X^5, R^{a1}, R^{b2}, A^1, R^{c1}, R^{d2}), (X^5, R^{a1},$
$R^{b2}, A^1, R^{c1}, R^{d3}), (X^5, R^{a1}, R^{b2}, A^1, R^{c2}, R^{d1}), (X^5, R^{a1},$
$R^{b2}, A^1, R^{c2}, R^{d2}), (X^5, R^{a1}, R^{b2}, A^1, R^{c2}, R^{d3}), (X^5, R^{a1},$
$R^{b2}, A^1, R^{c3}, R^{d1}), (X^5, R^{a1}, R^{b2}, A^1, R^{c3}, R^{d2}), (X^5, R^{a1},$
$R^{b2}, A^1, R^{c3}, R^{d3}), (X^5, R^{a1}, R^{b2}, A^1, R^{c4}, R^{d1}), (X^5, R^{a1},$
$R^{b2}, A^1, R^{c4}, R^{d2}), (X^5, R^{a1}, R^{b2}, A^1, R^{c4}, R^{d3}), (X^5, R^{a1},$
$R^{b2}, A^2, R^{c1}, R^{d1}), (X^5, R^{a1}, R^{b2}, A^2, R^{c1}, R^{d2}), (X^5, R^{a1},$
$R^{b2}, A^2, R^{c1}, R^{d3}), (X^5, R^{a1}, R^{b2}, A^2, R^{c2}, R^{d1}), (X^5, R^{a1},$
$R^{b2}, A^2, R^{c2}, R^{d2}), (X^5, R^{a1}, R^{b2}, A^2, R^{c2}, R^{d3}), (X^5, R^{a1},$
$R^{b2}, A^2, R^{c3}, R^{d1}), (X^5, R^{a1}, R^{b2}, A^2, R^{c3}, R^{d2}), (X^5, R^{a1},$
$R^{b2}, A^2, R^{c3}, R^{d3}), (X^5, R^{a1}, R^{b2}, A^2, R^{c4}, R^{d1}), (X^5, R^{a1},$
$R^{b2}, A^2, R^{c4}, R^{d2}), (X^5, R^{a1}, R^{b2}, A^2, R^{c4}, R^{d3}), (X^5, R^{a1},$
$R^{b2}, A^3, R^{c1}, R^{d1}), (X^5, R^{a1}, R^{b2}, A^3, R^{c1}, R^{d2}), (X^5, R^{a1},$
$R^{b2}, A^3, R^{c1}, R^{d3}), (X^5, R^{a1}, R^{b2}, A^3, R^{c2}, R^{d1}), (X^5, R^{a1},$
$R^{b2}, A^3, R^{c2}, R^{d2}), (X^5, R^{a1}, R^{b2}, A^3, R^{c2}, R^{d3}), (X^5, R^{a1},$
$R^{b2}, A^3, R^{c3}, R^{d1}), (X^5, R^{a1}, R^{b2}, A^3, R^{c3}, R^{d2}), (X^5, R^{a1},$
$R^{b2}, A^3, R^{c3}, R^{d3}), (X^5, R^{a1}, R^{b2}, A^3, R^{c4}, R^{d1}), (X^5, R^{a1},$
$R^{b2}, A^3, R^{c4}, R^{d2}), (X^5, R^{a1}, R^{b2}, A^3, R^{c4}, R^{d3}), (X^5, R^{a1},$
$R^{b2}, A^4, R^{c1}, R^{d1}), (X^5, R^{a1}, R^{b2}, A^4, R^{c1}, R^{d2}), (X^5, R^{a1},$
$R^{b2}, A^4, R^{c1}, R^{d3}), (X^5, R^{a1}, R^{b2}, A^4, R^{c2}, R^{d1}), (X^5, R^{a1},$
$R^{b2}, A^4, R^{c2}, R^{d2}), (X^5, R^{a1}, R^{b2}, A^4, R^{c2}, R^{d3}), (X^5, R^{a1},$
$R^{b2}, A^4, R^{c3}, R^{d1}), (X^5, R^{a1}, R^{b2}, A^4, R^{c3}, R^{d2}), (X^5, R^{a1},$
$R^{b2}, A^4, R^{c3}, R^{d3}), (X^5, R^{a1}, R^{b2}, A^4, R^{c4}, R^{d1}), (X^5, R^{a1},$
$R^{b2}, A^4, R^{c4}, R^{d2}), (X^5, R^{a1}, R^{b2}, A^4, R^{c4}, R^{d3}), (X^5, R^{a1},$
$R^{b2}, A^5, R^{c1}, R^{d1}), (X^5, R^{a1}, R^{b2}, A^5, R^{c1}, R^{d2}), (X^5, R^{a1},$
$R^{b2}, A^5, R^{c1}, R^{d3}), (X^5, R^{a1}, R^{b2}, A^5, R^{c2}, R^{d1}), (X^5, R^{a1},$
$R^{b2}, A^5, R^{c2}, R^{d2}), (X^5, R^{a1}, R^{b2}, A^5, R^{c2}, R^{d3}), (X^5, R^{a1},$
$R^{b2}, A^5, R^{c3}, R^{d1}), (X^5, R^{a1}, R^{b2}, A^5, R^{c3}, R^{d2}), (X^5, R^{a1},$
$R^{b2}, A^5, R^{c3}, R^{d3}), (X^5, R^{a1}, R^{b2}, A^5, R^{c4}, R^{d1}), (X^5, R^{a1},$
$R^{b2}, A^5, R^{c4}, R^{d2}), (X^5, R^{a1}, R^{b2}, A^5, R^{c4}, R^{d3}), (X^5, R^{a1},$

422

$R^{b3}, A^1, R^{c1}, R^{d1}), (X^5, R^{a1}, R^{b3}, A^1, R^{c1}, R^{d2}), (X^5, R^{a1},$
$R^{b3}, A^1, R^{c1}, R^{d3}), (X^5, R^{a1}, R^{b3}, A^1, R^{c2}, R^{d1}), (X^5, R^{a1},$
$R^{b3}, A^1, R^{c2}, R^{d2}), (X^5, R^{a1}, R^{b3}, A^1, R^{c2}, R^{d3}), (X^5, R^{a1},$
$R^{b3}, A^1, R^{c3}, R^{d1}), (X^5, R^{a1}, R^{b3}, A^1, R^{c3}, R^{d2}), (X^5, R^{a1},$
$R^{b3}, A^1, R^{c3}, R^{d3}), (X^5, R^{a1}, R^{b3}, A^1, R^{c4}, R^{d1}), (X^5, R^{a1},$
$R^{b3}, A^1, R^{c4}, R^{d2}), (X^5, R^{a1}, R^{b3}, A^1, R^{c4}, R^{d3}), (X^5, R^{a1},$
$R^{b3}, A^2, R^{c1}, R^{d1}), (X^5, R^{a1}, R^{b3}, A^2, R^{c1}, R^{d2}), (X^5, R^{a1},$
$R^{b3}, A^2, R^{c1}, R^{d3}), (X^5, R^{a1}, R^{b3}, A^2, R^{c2}, R^{d1}), (X^5, R^{a1},$
$R^{b3}, A^2, R^{c2}, R^{d2}), (X^5, R^{a1}, R^{b3}, A^2, R^{c2}, R^{d3}), (X^5, R^{a1},$
$R^{b3}, A^2, R^{c3}, R^{d1}), (X^5, R^{a1}, R^{b3}, A^2, R^{c3}, R^{d2}), (X^5, R^{a1},$
$R^{b3}, A^2, R^{c3}, R^{d3}), (X^5, R^{a1}, R^{b3}, A^2, R^{c4}, R^{d1}), (X^5, R^{a1},$
$R^{b3}, A^2, R^{c4}, R^{d2}), (X^5, R^{a1}, R^{b3}, A^2, R^{c4}, R^{d3}), (X^5, R^{a1},$
$R^{b3}, A^3, R^{c1}, R^{d1}), (X^5, R^{a1}, R^{b3}, A^3, R^{c1}, R^{d2}), (X^5, R^{a1},$
$R^{b3}, A^3, R^{c1}, R^{d3}), (X^5, R^{a1}, R^{b3}, A^3, R^{c2}, R^{d1}), (X^5, R^{a1},$
$R^{b3}, A^3, R^{c2}, R^{d2}), (X^5, R^{a1}, R^{b3}, A^3, R^{c2}, R^{d3}), (X^5, R^{a1},$
$R^{b3}, A^3, R^{c3}, R^{d1}), (X^5, R^{a1}, R^{b3}, A^3, R^{c3}, R^{d2}), (X^5, R^{a1},$
$R^{b3}, A^3, R^{c3}, R^{d3}), (X^5, R^{a1}, R^{b3}, A^3, R^{c4}, R^{d1}), (X^5, R^{a1},$
$R^{b3}, A^3, R^{c4}, R^{d2}), (X^5, R^{a1}, R^{b3}, A^3, R^{c4}, R^{d3}), (X^5, R^{a1},$
$R^{b3}, A^4, R^{c1}, R^{d1}), (X^5, R^{a1}, R^{b3}, A^4, R^{c1}, R^{d2}), (X^5, R^{a1},$
$R^{b3}, A^4, R^{c1}, R^{d3}), (X^5, R^{a1}, R^{b3}, A^4, R^{c2}, R^{d1}), (X^5, R^{a1},$
$R^{b3}, A^4, R^{c2}, R^{d2}), (X^5, R^{a1}, R^{b3}, A^4, R^{c2}, R^{d3}), (X^5, R^{a1},$
$R^{b3}, A^4, R^{c3}, R^{d1}), (X^5, R^{a1}, R^{b3}, A^4, R^{c3}, R^{d2}), (X^5, R^{a1},$
$R^{b3}, A^4, R^{c3}, R^{d3}), (X^5, R^{a1}, R^{b3}, A^4, R^{c4}, R^{d1}), (X^5, R^{a1},$
$R^{b3}, A^4, R^{c4}, R^{d2}), (X^5, R^{a1}, R^{b3}, A^4, R^{c4}, R^{d3}), (X^5, R^{a1},$
$R^{b3}, A^5, R^{c1}, R^{d1}), (X^5, R^{a1}, R^{b3}, A^5, R^{c1}, R^{d2}), (X^5, R^{a1},$
$R^{b3}, A^5, R^{c1}, R^{d3}), (X^5, R^{a1}, R^{b3}, A^5, R^{c2}, R^{d1}), (X^5, R^{a1},$
$R^{b3}, A^5, R^{c2}, R^{d2}), (X^5, R^{a1}, R^{b3}, A^5, R^{c2}, R^{d3}), (X^5, R^{a1},$
$R^{b3}, A^5, R^{c3}, R^{d1}), (X^5, R^{a1}, R^{b3}, A^5, R^{c3}, R^{d2}), (X^5, R^{a1},$
$R^{b3}, A^5, R^{c3}, R^{d3}), (X^5, R^{a1}, R^{b3}, A^5, R^{c4}, R^{d1}), (X^5, R^{a1},$
$R^{b3}, A^5, R^{c4}, R^{d2}), (X^5, R^{a1}, R^{b3}, A^5, R^{c4}, R^{d3}), (X^5, R^{a2},$
$R^{b1}, A^1, R^{c1}, R^{d1}), (X^5, R^{a2}, R^{b1}, A^1, R^{c1}, R^{d2}), (X^5, R^{a2},$
$R^{b1}, A^1, R^{c1}, R^{d3}), (X^5, R^{a2}, R^{b1}, A^1, R^{c2}, R^{d1}), (X^5, R^{a2},$
$R^{b1}, A^1, R^{c2}, R^{d2}), (X^5, R^{a2}, R^{b1}, A^1, R^{c2}, R^{d3}), (X^5, R^{a2},$
$R^{b1}, A^1, R^{c3}, R^{d1}), (X^5, R^{a2}, R^{b1}, A^1, R^{c3}, R^{d2}), (X^5, R^{a2},$
$R^{b1}, A^1, R^{c3}, R^{d3}), (X^5, R^{a2}, R^{b1}, A^1, R^{c4}, R^{d1}), (X^5, R^{a2},$
$R^{b1}, A^1, R^{c4}, R^{d2}), (X^5, R^{a2}, R^{b1}, A^1, R^{c4}, R^{d3}), (X^5, R^{a2},$
$R^{b1}, A^2, R^{c1}, R^{d1}), (X^5, R^{a2}, R^{b1}, A^2, R^{c1}, R^{d2}), (X^5, R^{a2},$
$R^{b1}, A^2, R^{c1}, R^{d3}), (X^5, R^{a2}, R^{b1}, A^2, R^{c2}, R^{d1}), (X^5, R^{a2},$
$R^{b1}, A^2, R^{c2}, R^{d2}), (X^5, R^{a2}, R^{b1}, A^2, R^{c2}, R^{d3}), (X^5, R^{a2},$
$R^{b1}, A^2, R^{c3}, R^{d1}), (X^5, R^{a2}, R^{b1}, A^2, R^{c3}, R^{d2}), (X^5, R^{a2},$
$R^{b1}, A^2, R^{c3}, R^{d3}), (X^5, R^{a2}, R^{b1}, A^2, R^{c4}, R^{d1}), (X^5, R^{a2},$
$R^{b1}, A^2, R^{c4}, R^{d2}), (X^5, R^{a2}, R^{b1}, A^2, R^{c4}, R^{d3}), (X^5, R^{a2},$
$R^{b1}, A^3, R^{c1}, R^{d1}), (X^5, R^{a2}, R^{b1}, A^3, R^{c1}, R^{d2}), (X^5, R^{a2},$
$R^{b1}, A^3, R^{c1}, R^{d3}), (X^5, R^{a2}, R^{b1}, A^3, R^{c2}, R^{d1}), (X^5, R^{a2},$
$R^{b1}, A^3, R^{c2}, R^{d2}), (X^5, R^{a2}, R^{b1}, A^3, R^{c2}, R^{d3}), (X^5, R^{a2},$
$R^{b1}, A^3, R^{c3}, R^{d1}), (X^5, R^{a2}, R^{b1}, A^3, R^{c3}, R^{d2}), (X^5, R^{a2},$
$R^{b1}, A^3, R^{c3}, R^{d3}), (X^5, R^{a2}, R^{b1}, A^3, R^{c4}, R^{d1}), (X^5, R^{a2},$
$R^{b1}, A^3, R^{c4}, R^{d2}), (X^5, R^{a2}, R^{b1}, A^3, R^{c4}, R^{d3}), (X^5, R^{a2},$
$R^{b1}, A^4, R^{c1}, R^{d1}), (X^5, R^{a2}, R^{b1}, A^4, R^{c1}, R^{d2}), (X^5, R^{a2},$
$R^{b1}, A^4, R^{c1}, R^{d3}), (X^5, R^{a2}, R^{b1}, A^4, R^{c2}, R^{d1}), (X^5, R^{a2},$
$R^{b1}, A^4, R^{c2}, R^{d2}), (X^5, R^{a2}, R^{b1}, A^4, R^{c2}, R^{d3}), (X^5, R^{a2},$
$R^{b1}, A^4, R^{c3}, R^{d1}), (X^5, R^{a2}, R^{b1}, A^4, R^{c3}, R^{d2}), (X^5, R^{a2},$
$R^{b1}, A^4, R^{c3}, R^{d3}), (X^5, R^{a2}, R^{b1}, A^4, R^{c4}, R^{d1}), (X^5, R^{a2},$
$R^{b1}, A^4, R^{c4}, R^{d2}), (X^5, R^{a2}, R^{b1}, A^4, R^{c4}, R^{d3}), (X^5, R^{a2},$
$R^{b1}, A^5, R^{c1}, R^{d1}), (X^5, R^{a2}, R^{b1}, A^5, R^{c1}, R^{d2}), (X^5, R^{a2},$
$R^{b1}, A^5, R^{c1}, R^{d3}), (X^5, R^{a2}, R^{b1}, A^5, R^{c2}, R^{d1}), (X^5, R^{a2},$
$R^{b1}, A^5, R^{c2}, R^{d2}), (X^5, R^{a1}, R^{b1}, A^5, R^{c2}, R^{d3}), (X^5, R^{a1},$
$R^{b1}, A^5, R^{c4}, R^{d1}), (X^5, R^{a1}, R^{b1}, A^5, R^{c4}, R^{d2}), (X^5, R^{a2},$
$R^{b1}, A^5, R^{c3}, R^{d3}), (X^5, R^{a2}, R^{b1}, A^5, R^{c4}, R^{d1}), (X^5, R^{a2},$
$R^{b1}, A^5, R^{c4}, R^{d2}), (X^5, R^{a1}, R^{b1}, A^5, R^{c4}, R^{d3}), (X^5, R^{a1},$
$R^{b2}, A^1, R^{c1}, R^{d1}), (X^5, R^{a1}, R^{b2}, A^1, R^{c1}, R^{d2}), (X^5, R^{a2},$
$R^{b2}, A^1, R^{c1}, R^{d3}), (X^5, R^{a2}, R^{b2}, A^1, R^{c2}, R^{d1}), (X^5, R^{a2},$
$R^{b2}, A^1, R^{c2}, R^{d2}), (X^5, R^{a2}, R^{b2}, A^1, R^{c2}, R^{d3}), (X^5, R^{a2},$
$R^{b2}, A^1, R^{c3}, R^{d1}), (X^5, R^{a2}, R^{b2}, A^1, R^{c3}, R^{d2}), (X^5, R^{a2},$
$R^{b2}, A^1, R^{c3}, R^{d3}), (X^5, R^{a2}, R^{b2}, A^1, R^{c4}, R^{d1}), (X^5, R^{a2},$
$R^{b2}, A^1, R^{c4}, R^{d2}), (X^5, R^{a2}, R^{b2}, A^1, R^{c4}, R^{d3}), (X^5, R^{a2},$
$R^{b2}, A^2, R^{c1}, R^{d1}), (X^5, R^{a2}, R^{b2}, A^2, R^{c1}, R^{d2}), (X^5, R^{a2},$ $R^{b2}$, $A^2$, $R^{c1}$, $R^{d3}$), ($X^5$, $R^{a2}$, $R^{b2}$, $A^2$, $R^{c2}$, $R^{d1}$), ($X^5$, $R^{a2}$,
$R^{b2}$, $A^2$, $R^{c2}$, $R^{d2}$), ($X^5$, $R^{a2}$, $R^{b2}$, $A^2$, $R^{c2}$, $R^{d3}$), ($X^5$, $R^{a2}$,
$R^{b2}$, $A^2$, $R^{c3}$, $R^{d1}$), ($X^5$, $R^{a2}$, $R^{b2}$, $A^2$, $R^{c3}$, $R^{d2}$), ($X^5$, $R^{a2}$,
$R^{b2}$, $A^2$, $R^{c3}$, $R^{d3}$), ($X^5$, $R^{a2}$, $R^{b2}$, $A^2$, $R^{c4}$, $R^{d1}$), ($X^5$, $R^{a2}$,
$R^{b2}$, $A^2$, $R^{c4}$, $R^{d2}$), ($X^5$, $R^{a2}$, $R^{b2}$, $A^2$, $R^{c4}$, $R^{d3}$), ($X^5$, $R^{a2}$,
$R^{b2}$, $A^3$, $R^{c1}$, $R^{d1}$), ($X^5$, $R^{a2}$, $R^{b2}$, $A^3$, $R^{c1}$, $R^{d2}$), ($X^5$, $R^{a2}$,
$R^{b2}$, $A^3$, $R^{c1}$, $R^{d3}$), ($X^5$, $R^{a2}$, $R^{b2}$, $A^3$, $R^{c2}$, $R^{d1}$), ($X^5$, $R^{a2}$,
$R^{b2}$, $A^3$, $R^{c2}$, $R^{d2}$), ($X^5$, $R^{a1}$, $R^{b2}$, $A^3$, $R^{c2}$, $R^{d3}$), ($X^5$, $R^{a1}$,
$R^{b2}$, $A^3$, $R^{c3}$, $R^{d1}$), ($X^5$, $R^{a1}$, $R^{b2}$, $A^3$, $R^{c3}$, $R^{d2}$), ($X^5$, $R^{a2}$,
$R^{b2}$, $A^3$, $R^{c3}$, $R^{d3}$), ($X^5$, $R^{a2}$, $R^{b2}$, $A^3$, $R^{c4}$, $R^{d1}$), ($X^5$, $R^{a2}$,
$R^{b2}$, $A^3$, $R^{c4}$, $R^{d2}$), ($X^5$, $R^{a2}$, $R^{b2}$, $A^3$, $R^{c4}$, $R^{d3}$), ($X^5$, $R^{a2}$,
$R^{b2}$, $A^4$, $R^{c1}$, $R^{d1}$), ($X^5$, $R^{a2}$, $R^{b2}$, $A^4$, $R^{c1}$, $R^{d2}$), ($X^5$, $R^{a2}$,
$R^{b2}$, $A^4$, $R^{c1}$, $R^{d3}$), ($X^5$, $R^{a2}$, $R^{b2}$, $A^4$, $R^{c2}$, $R^{d1}$), ($X^5$, $R^{a2}$,
$R^{b2}$, $A^4$, $R^{c2}$, $R^{d2}$), ($X^5$, $R^{a2}$, $R^{b2}$, $A^4$, $R^{c2}$, $R^{d3}$), ($X^5$, $R^{a2}$,
$R^{b2}$, $A^4$, $R^{c3}$, $R^{d1}$), ($X^5$, $R^{a2}$, $R^{b2}$, $A^4$, $R^{c3}$, $R^{d2}$), ($X^5$, $R^{a2}$,
$R^{b2}$, $A^4$, $R^{c3}$, $R^{d3}$), ($X^5$, $R^{a2}$, $R^{b2}$, $A^4$, $R^{c4}$, $R^{d1}$), ($X^5$, $R^{a2}$,
$R^{b2}$, $A^4$, $R^{c4}$, $R^{d2}$), ($X^5$, $R^{a2}$, $R^{b2}$, $A^4$, $R^{c4}$, $R^{d3}$), ($X^5$, $R^{a2}$,
$R^{b2}$, $A^5$, $R^{c1}$, $R^{d1}$), ($X^5$, $R^{a2}$, $R^{b2}$, $A^5$, $R^{c1}$, $R^{d2}$), ($X^5$, $R^{a2}$,
$R^{b2}$, $A^5$, $R^{c1}$, $R^{d3}$), ($X^5$, $R^{a2}$, $R^{b2}$, $A^5$, $R^{c2}$, $R^{d1}$), ($X^5$, $R^{a2}$,
$R^{b2}$, $A^5$, $R^{c2}$, $R^{d2}$), ($X^5$, $R^{a1}$, $R^{b2}$, $A^5$, $R^{c2}$, $R^{d3}$), ($X^5$, $R^{a1}$,
$R^{b2}$, $A^5$, $R^{c4}$, $R^{d1}$), ($X^5$, $R^{a1}$, $R^{b2}$, $A^5$, $R^{c4}$, $R^{d2}$), ($X^5$, $R^{a2}$,
$R^{b2}$, $A^5$, $R^{c3}$, $R^{d3}$), ($X^5$, $R^{a2}$, $R^{b2}$, $A^5$, $R^{c4}$, $R^{d1}$), ($X^5$, $R^{a1}$,
$R^{b2}$, $A^5$, $R^{c4}$, $R^{d2}$), ($X^5$, $R^{a2}$, $R^{b2}$, $A^5$, $R^{c4}$, $R^{d3}$), ($X^5$, $R^{a1}$,
$R^{b3}$, $A^1$, $R^{c1}$, $R^{d1}$), ($X^5$, $R^{a1}$, $R^{b3}$, $A^1$, $R^{c1}$, $R^{d2}$), ($X^5$, $R^{a2}$,
$R^{b3}$, $A^1$, $R^{c1}$, $R^{d3}$), ($X^5$, $R^{a2}$, $R^{b3}$, $A^1$, $R^{c2}$, $R^{d1}$), ($X^5$, $R^{a2}$,
$R^{b3}$, $A^1$, $R^{c2}$, $R^{d2}$), ($X^5$, $R^{a1}$, $R^{b3}$, $A^1$, $R^{c2}$, $R^{d3}$), ($X^5$, $R^{a1}$,
$R^{b3}$, $A^1$, $R^{c4}$, $R^{d1}$), ($X^5$, $R^{a2}$, $R^{b3}$, $A^1$, $R^{c4}$, $R^{d2}$), ($X^5$, $R^{a2}$,
$R^{b3}$, $A^1$, $R^{c3}$, $R^{d3}$), ($X^5$, $R^{a2}$, $R^{b3}$, $A^1$, $R^{c4}$, $R^{d1}$), ($X^5$, $R^{a2}$,
$R^{b3}$, $A^1$, $R^{c4}$, $R^{d2}$), ($X^5$, $R^{a1}$, $R^{b3}$, $A^1$, $R^{c4}$, $R^{d3}$), ($X^5$, $R^{a1}$,
$R^{b3}$, $A^2$, $R^{c1}$, $R^{d1}$), ($X^5$, $R^{a1}$, $R^{b3}$, $A^2$, $R^{c1}$, $R^{d2}$), ($X^5$, $R^{a2}$,
$R^{b3}$, $A^2$, $R^{c1}$, $R^{d3}$), ($X^5$, $R^{a2}$, $R^{b3}$, $A^2$, $R^{c2}$, $R^{d1}$), ($X^5$, $R^{a2}$,
$R^{b3}$, $A^2$, $R^{c2}$, $R^{d2}$), ($X^5$, $R^{a1}$, $R^{b3}$, $A^2$, $R^{c2}$, $R^{d3}$), ($X^5$, $R^{a1}$,
$R^{b3}$, $A^2$, $R^{c4}$, $R^{d1}$), ($X^5$, $R^{a2}$, $R^{b3}$, $A^2$, $R^{c4}$, $R^{d2}$), ($X^5$, $R^{a2}$,
$R^{b3}$, $A^2$, $R^{c3}$, $R^{d3}$), ($X^5$, $R^{a2}$, $R^{b3}$, $A^2$, $R^{c4}$, $R^{d1}$), ($X^5$, $R^{a2}$,
$R^{b3}$, $A^2$, $R^{c4}$, $R^{d2}$), ($X^5$, $R^{a2}$, $R^{b3}$, $A^2$, $R^{c4}$, $R^{d3}$), ($X^5$, $R^{a2}$,
$R^{b3}$, $A^3$, $R^{c1}$, $R^{d1}$), ($X^5$, $R^{a2}$, $R^{b3}$, $A^3$, $R^{c1}$, $R^{d2}$), ($X^5$, $R^{a2}$,
$R^{b3}$, $A^3$, $R^{c1}$, $R^{d3}$), ($X^5$, $R^{a2}$, $R^{b3}$, $A^3$, $R^{c2}$, $R^{d1}$), ($X^5$, $R^{a2}$,
$R^{b3}$, $A^3$, $R^{c2}$, $R^{d2}$), ($X^5$, $R^{a2}$, $R^{b3}$, $A^3$, $R^{c2}$, $R^{d3}$), ($X^5$, $R^{a2}$,
$R^{b3}$, $A^3$, $R^{c3}$, $R^{d1}$), ($X^5$, $R^{a2}$, $R^{b3}$, $A^3$, $R^{c3}$, $R^{d2}$), ($X^5$, $R^{a2}$,
$R^{b3}$, $A^3$, $R^{c3}$, $R^{d3}$), ($X^5$, $R^{a2}$, $R^{b3}$, $A^3$, $R^{c4}$, $R^{d1}$), ($X^5$, $R^{a2}$,
$R^{b3}$, $A^3$, $R^{c4}$, $R^{d2}$), ($X^5$, $R^{a2}$, $R^{b3}$, $A^3$, $R^{c4}$, $R^{d3}$), ($X^5$, $R^{a2}$,
$R^{b3}$, $A^4$, $R^{c1}$, $R^{d1}$), ($X^5$, $R^{a2}$, $R^{b3}$, $A^4$, $R^{c1}$, $R^{d2}$), ($X^5$, $R^{a2}$,
$R^{b3}$, $A^4$, $R^{c1}$, $R^{d3}$), ($X^5$, $R^{a2}$, $R^{b3}$, $A^4$, $R^{c2}$, $R^{d1}$), ($X^5$, $R^{a2}$,
$R^{b3}$, $A^4$, $R^{c2}$, $R^{d2}$), ($X^5$, $R^{a2}$, $R^{b3}$, $A^4$, $R^{c2}$, $R^{d3}$), ($X^5$, $R^{a2}$,
$R^{b3}$, $A^4$, $R^{c3}$, $R^{d1}$), ($X^5$, $R^{a2}$, $R^{b3}$, $A^4$, $R^{c3}$, $R^{d2}$), ($X^5$, $R^{a2}$,
$R^{b3}$, $A^4$, $R^{c3}$, $R^{d3}$), ($X^5$, $R^{a2}$, $R^{b3}$, $A^4$, $R^{c4}$, $R^{d1}$), ($X^5$, $R^{a2}$,
$R^{b3}$, $A^4$, $R^{c4}$, $R^{d2}$), ($X^5$, $R^{a2}$, $R^{b3}$, $A^4$, $R^{c4}$, $R^{d3}$), ($X^5$, $R^{a2}$,
$R^{b3}$, $A^5$, $R^{c1}$, $R^{d1}$), ($X^5$, $R^{a2}$, $R^{b3}$, $A^5$, $R^{c1}$, $R^{d2}$), ($X^5$, $R^{a2}$,
$R^{b3}$, $A^5$, $R^{c1}$, $R^{d3}$), ($X^5$, $R^{a2}$, $R^{b3}$, $A^5$, $R^{c2}$, $R^{d1}$), ($X^5$, $R^{a2}$,
$R^{b3}$, $A^5$, $R^{c2}$, $R^{d2}$), ($X^5$, $R^{a2}$, $R^{b3}$, $A^5$, $R^{c2}$, $R^{d3}$), ($X^5$, $R^{a2}$,
$R^{b3}$, $A^5$, $R^{c3}$, $R^{d1}$), ($X^5$, $R^{a2}$, $R^{b3}$, $A^5$, $R^{c3}$, $R^{d2}$), ($X^5$, $R^{a2}$,
$R^{b3}$, $A^5$, $R^{c3}$, $R^{d3}$), ($X^5$, $R^{a2}$, $R^{b3}$, $A^5$, $R^{c4}$, $R^{d1}$), ($X^5$, $R^{a2}$,
$R^{b3}$, $A^5$, $R^{c4}$, $R^{d2}$), ($X^5$, $R^{a2}$, $R^{b3}$, $A^5$, $R^{c4}$, $R^{d3}$), ($X^5$, $R^{a3}$,
$R^{b1}$, $A^1$, $R^{c1}$, $R^{d1}$), ($X^5$, $R^{a3}$, $R^{b1}$, $A^1$, $R^{c1}$, $R^{d2}$), ($X^5$, $R^{a3}$,
$R^{b1}$, $A^1$, $R^{c1}$, $R^{d3}$), ($X^5$, $R^{a3}$, $R^{b1}$, $A^1$, $R^{c2}$, $R^{d1}$), ($X^5$, $R^{a3}$,
$R^{b1}$, $A^1$, $R^{c2}$, $R^{d2}$), ($X^5$, $R^{a3}$, $R^{b1}$, $A^1$, $R^{c2}$, $R^{d3}$), ($X^5$, $R^{a3}$,
$R^{b1}$, $A^1$, $R^{c3}$, $R^{d1}$), ($X^5$, $R^{a3}$, $R^{b1}$, $A^1$, $R^{c3}$, $R^{d2}$), ($X^5$, $R^{a3}$,
$R^{b1}$, $A^1$, $R^{c3}$, $R^{d3}$), ($X^5$, $R^{a3}$, $R^{b1}$, $A^1$, $R^{c4}$, $R^{d1}$), ($X^5$, $R^{a3}$,
$R^{b1}$, $A^1$, $R^{c4}$, $R^{d2}$), ($X^5$, $R^{a3}$, $R^{b1}$, $A^1$, $R^{c4}$, $R^{d3}$), ($X^5$, $R^{a3}$,
$R^{b1}$, $A^2$, $R^{c1}$, $R^{d1}$), ($X^5$, $R^{a3}$, $R^{b1}$, $A^2$, $R^{c1}$, $R^{d2}$), ($X^5$, $R^{a3}$,
$R^{b1}$, $A^2$, $R^{c1}$, $R^{d3}$), ($X^5$, $R^{a3}$, $R^{b1}$, $A^2$, $R^{c2}$, $R^{d1}$), ($X^5$, $R^{a3}$,
$R^{b1}$, $A^2$, $R^{c2}$, $R^{d2}$), ($X^5$, $R^{a3}$, $R^{b1}$, $A^2$, $R^{c2}$, $R^{d3}$), ($X^5$, $R^{a3}$,
$R^{b1}$, $A^2$, $R^{c3}$, $R^{d1}$), ($X^5$, $R^{a3}$, $R^{b1}$, $A^2$, $R^{c3}$, $R^{d2}$), ($X^5$, $R^{a3}$,
$R^{b1}$, $A^2$, $R^{c3}$, $R^{d3}$), ($X^5$, $R^{a3}$, $R^{b1}$, $A^2$, $R^{c4}$, $R^{d1}$), ($X^5$, $R^{a3}$,
$R^{b1}$, $A^2$, $R^{c4}$, $R^{d2}$), ($X^5$, $R^{a3}$, $R^{b1}$, $A^2$, $R^{c4}$, $R^{d3}$), ($X^5$, $R^{a3}$,
$R^{b1}$, $A^3$, $R^{c1}$, $R^{d1}$), ($X^5$, $R^{a3}$, $R^{b1}$, $A^3$, $R^{c1}$, $R^{d2}$), ($X^5$, $R^{a3}$,
$R^{b1}$, $A^3$, $R^{c2}$, $R^{d2}$), ($X^5$, $R^{a3}$, $R^{b1}$, $A^3$, $R^{c2}$, $R^{d3}$), ($X^5$, $R^{a3}$,
$R^{b1}$, $A^3$, $R^{c3}$, $R^{d1}$), ($X^5$, $R^{a3}$, $R^{b1}$, $A^3$, $R^{c3}$, $R^{d2}$), ($X^5$, $R^{a3}$,
$R^{b1}$, $A^3$, $R^{c3}$, $R^{d3}$), ($X^5$, $R^{a3}$, $R^{b1}$, $A^3$, $R^{c4}$, $R^{d2}$), ($X^5$, $R^{a3}$,
$R^{b1}$, $A^3$, $R^{c4}$, $R^{d2}$), ($X^5$, $R^{a3}$, $R^{b1}$, $A^3$, $R^{c4}$, $R^{d3}$), ($X^5$, $R^{a3}$,
$R^{b1}$, $A^4$, $R^{c1}$, $R^{d1}$), ($X^5$, $R^{a3}$, $R^{b1}$, $A^4$, $R^{c1}$, $R^{d2}$), ($X^5$, $R^{a3}$,
$R^{b1}$, $A^4$, $R^{c1}$, $R^{d3}$), ($X^5$, $R^{a3}$, $R^{b1}$, $A^4$, $R^{c2}$, $R^{d1}$), ($X^5$, $R^{a3}$,
$R^{b1}$, $A^4$, $R^{c2}$, $R^{d2}$), ($X^5$, $R^{a3}$, $R^{b1}$, $A^4$, $R^{c2}$, $R^{d3}$), ($X^5$, $R^{a3}$,
$R^{b1}$, $A^4$, $R^{c3}$, $R^{d1}$), ($X^5$, $R^{a3}$, $R^{b1}$, $A^4$, $R^{c3}$, $R^{d2}$), ($X^5$, $R^{a3}$,
$R^{b1}$, $A^4$, $R^{c3}$, $R^{d3}$), ($X^5$, $R^{a3}$, $R^{b1}$, $A^4$, $R^{c4}$, $R^{d1}$), ($X^5$, $R^{a3}$,
$R^{b1}$, $A^4$, $R^{c4}$, $R^{d2}$), ($X^5$, $R^{a3}$, $R^{b1}$, $A^4$, $R^{c4}$, $R^{d3}$), ($X^5$, $R^{a3}$,
$R^{b1}$, $A^5$, $R^{c1}$, $R^{d1}$), ($X^5$, $R^{a3}$, $R^{b1}$, $A^5$, $R^{c1}$, $R^{d2}$), ($X^5$, $R^{a3}$,
$R^{b1}$, $A^5$, $R^{c1}$, $R^{d3}$), ($X^5$, $R^{a3}$, $R^{b1}$, $A^5$, $R^{c2}$, $R^{d1}$), ($X^5$, $R^{a3}$,
$R^{b1}$, $A^5$, $R^{c2}$, $R^{d2}$), ($X^5$, $R^{a3}$, $R^{b1}$, $A^5$, $R^{c2}$, $R^{d3}$), ($X^5$, $R^{a3}$,
$R^{b1}$, $A^5$, $R^{c3}$, $R^{d1}$), ($X^5$, $R^{a3}$, $R^{b1}$, $A^5$, $R^{c3}$, $R^{d2}$), ($X^5$, $R^{a3}$,
$R^{b1}$, $A^5$, $R^{c3}$, $R^{d3}$), ($X^5$, $R^{a3}$, $R^{b1}$, $A^5$, $R^{c4}$, $R^{d1}$), ($X^5$, $R^{a3}$,
$R^{b1}$, $A^5$, $R^{c4}$, $R^{d2}$), ($X^5$, $R^{a3}$, $R^{b1}$, $A^5$, $R^{c4}$, $R^{d3}$), ($X^5$, $R^{a3}$,
$R^{b2}$, $A^1$, $R^{c1}$, $R^{d1}$), ($X^5$, $R^{a3}$, $R^{b2}$, $A^1$, $R^{c1}$, $R^{d2}$), ($X^5$, $R^{a3}$,
$R^{b2}$, $A^1$, $R^{c1}$, $R^{d3}$), ($X^5$, $R^{a3}$, $R^{b2}$, $A^1$, $R^{c2}$, $R^{d1}$), ($X^5$, $R^{a3}$,
$R^{b2}$, $A^1$, $R^{c2}$, $R^{d2}$), ($X^5$, $R^{a3}$, $R^{b2}$, $A^1$, $R^{c2}$, $R^{d3}$), ($X^5$, $R^{a3}$,
$R^{b2}$, $A^1$, $R^{c3}$, $R^{d1}$), ($X^5$, $R^{a3}$, $R^{b2}$, $A^1$, $R^{c3}$, $R^{d2}$), ($X^5$, $R^{a3}$,
$R^{b2}$, $A^1$, $R^{c3}$, $R^{d3}$), ($X^5$, $R^{a3}$, $R^{b2}$, $A^1$, $R^{c4}$, $R^{d1}$), ($X^5$, $R^{a3}$,
$R^{b2}$, $A^1$, $R^{c4}$, $R^{d2}$), ($X^5$, $R^{a3}$, $R^{b2}$, $A^1$, $R^{c4}$, $R^{d3}$), ($X^5$, $R^{a3}$,
$R^{b2}$, $A^2$, $R^{c1}$, $R^{d1}$), ($X^5$, $R^{a3}$, $R^{b2}$, $A^2$, $R^{c1}$, $R^{d2}$), ($X^5$, $R^{a3}$,
$R^{b2}$, $A^2$, $R^{c1}$, $R^{d3}$), ($X^5$, $R^{a3}$, $R^{b2}$, $A^2$, $R^{c2}$, $R^{d1}$), ($X^5$, $R^{a3}$,
$R^{b2}$, $A^2$, $R^{c2}$, $R^{d2}$), ($X^5$, $R^{a3}$, $R^{b2}$, $A^2$, $R^{c2}$, $R^{d3}$), ($X^5$, $R^{a3}$,
$R^{b2}$, $A^2$, $R^{c3}$, $R^{d1}$), ($X^5$, $R^{a3}$, $R^{b2}$, $A^2$, $R^{c3}$, $R^{d2}$), ($X^5$, $R^{a3}$,
$R^{b2}$, $A^2$, $R^{c3}$, $R^{d3}$), ($X^5$, $R^{a3}$, $R^{b2}$, $A^2$, $R^{c4}$, $R^{d1}$), ($X^5$, $R^{a3}$,
$R^{b2}$, $A^2$, $R^{c4}$, $R^{d2}$), ($X^5$, $R^{a3}$, $R^{b2}$, $A^2$, $R^{c4}$, $R^{d3}$), ($X^5$, $R^{a3}$,
$R^{b2}$, $A^3$, $R^{c1}$, $R^{d1}$), ($X^5$, $R^{a3}$, $R^{b2}$, $A^3$, $R^{c1}$, $R^{d2}$), ($X^5$, $R^{a3}$,
$R^{b2}$, $A^3$, $R^{c1}$, $R^{d3}$), ($X^5$, $R^{a3}$, $R^{b2}$, $A^3$, $R^{c2}$, $R^{d1}$), ($X^5$, $R^{a3}$,
$R^{b2}$, $A^3$, $R^{c2}$, $R^{d2}$), ($X^5$, $R^{a3}$, $R^{b2}$, $A^3$, $R^{c2}$, $R^{d3}$), ($X^5$, $R^{a3}$,
$R^{b2}$, $A^3$, $R^{c3}$, $R^{d1}$), ($X^5$, $R^{a3}$, $R^{b2}$, $A^3$, $R^{c3}$, $R^{d2}$), ($X^5$, $R^{a3}$,
$R^{b2}$, $A^3$, $R^{c3}$, $R^{d3}$), ($X^5$, $R^{a3}$, $R^{b2}$, $A^3$, $R^{c4}$, $R^{d1}$), ($X^5$, $R^{a3}$,
$R^{b2}$, $A^3$, $R^{c4}$, $R^{d2}$), ($X^5$, $R^{a3}$, $R^{b2}$, $A^3$, $R^{c4}$, $R^{d3}$), ($X^5$, $R^{a3}$,
$R^{b2}$, $A^4$, $R^{c1}$, $R^{d1}$), ($X^5$, $R^{a3}$, $R^{b2}$, $A^4$, $R^{c1}$, $R^{d2}$), ($X^5$, $R^{a3}$,
$R^{b2}$, $A^4$, $R^{c1}$, $R^{d3}$), ($X^5$, $R^{a3}$, $R^{b2}$, $A^4$, $R^{c2}$, $R^{d1}$), ($X^5$, $R^{a3}$,
$R^{b2}$, $A^4$, $R^{c2}$, $R^{d2}$), ($X^5$, $R^{a3}$, $R^{b2}$, $A^4$, $R^{c2}$, $R^{d3}$), ($X^5$, $R^{a3}$,
$R^{b2}$, $A^4$, $R^{c3}$, $R^{d1}$), ($X^5$, $R^{a3}$, $R^{b2}$, $A^4$, $R^{c3}$, $R^{d2}$), ($X^5$, $R^{a3}$,
$R^{b2}$, $A^4$, $R^{c3}$, $R^{d3}$), ($X^5$, $R^{a3}$, $R^{b2}$, $A^4$, $R^{c4}$, $R^{d1}$), ($X^5$, $R^{a3}$,
$R^{b2}$, $A^4$, $R^{c4}$, $R^{d2}$), ($X^5$, $R^{a3}$, $R^{b2}$, $A^4$, $R^{c4}$, $R^{d3}$), ($X^5$, $R^{a3}$,
$R^{b2}$, $A^5$, $R^{c1}$, $R^{d1}$), ($X^5$, $R^{a3}$, $R^{b2}$, $A^5$, $R^{c1}$, $R^{d2}$), ($X^5$, $R^{a3}$,
$R^{b2}$, $A^5$, $R^{c1}$, $R^{d3}$), ($X^5$, $R^{a3}$, $R^{b2}$, $A^5$, $R^{c2}$, $R^{d1}$), ($X^5$, $R^{a3}$,
$R^{b2}$, $A^5$, $R^{c2}$, $R^{d2}$), ($X^5$, $R^{a3}$, $R^{b2}$, $A^5$, $R^{c2}$, $R^{d3}$), ($X^5$, $R^{a3}$,
$R^{b2}$, $A^5$, $R^{c3}$, $R^{d1}$), ($X^5$, $R^{a3}$, $R^{b2}$, $A^5$, $R^{c3}$, $R^{d2}$), ($X^5$, $R^{a3}$,
$R^{b2}$, $A^5$, $R^{c3}$, $R^{d3}$), ($X^5$, $R^{a3}$, $R^{b2}$, $A^5$, $R^{c4}$, $R^{d1}$), ($X^5$, $R^{a3}$,
$R^{b2}$, $A^5$, $R^{c4}$, $R^{d2}$), ($X^5$, $R^{a3}$, $R^{b2}$, $A^5$, $R^{c4}$, $R^{d3}$), ($X^5$, $R^{a3}$,
$R^{b3}$, $A^1$, $R^{c1}$, $R^{d1}$), ($X^5$, $R^{a3}$, $R^{b3}$, $A^1$, $R^{c1}$, $R^{d2}$), ($X^5$, $R^{a3}$,
$R^{b3}$, $A^1$, $R^{c1}$, $R^{d3}$), ($X^5$, $R^{a3}$, $R^{b3}$, $A^1$, $R^{c2}$, $R^{d1}$), ($X^5$, $R^{a3}$,
$R^{b3}$, $A^1$, $R^{c2}$, $R^{d2}$), ($X^5$, $R^{a3}$, $R^{b3}$, $A^1$, $R^{c2}$, $R^{d3}$), ($X^5$, $R^{a3}$,
$R^{b3}$, $A^1$, $R^{c3}$, $R^{d1}$), ($X^5$, $R^{a3}$, $R^{b3}$, $A^1$, $R^{c3}$, $R^{d2}$), ($X^5$, $R^{a3}$,
$R^{b3}$, $A^1$, $R^{c3}$, $R^{d3}$), ($X^5$, $R^{a3}$, $R^{b3}$, $A^1$, $R^{c4}$, $R^{d1}$), ($X^5$, $R^{a3}$,
$R^{b3}$, $A^1$, $R^{c4}$, $R^{d2}$), ($X^5$, $R^{a3}$, $R^{b3}$, $A^1$, $R^{c4}$, $R^{d3}$), ($X^5$, $R^{a3}$,
$R^{b3}$, $A^2$, $R^{c1}$, $R^{d1}$), ($X^5$, $R^{a3}$, $R^{b3}$, $A^2$, $R^{c1}$, $R^{d2}$), ($X^5$, $R^{a3}$,
$R^{b3}$, $A^2$, $R^{c1}$, $R^{d3}$), ($X^5$, $R^{a3}$, $R^{b3}$, $A^2$, $R^{c2}$, $R^{d1}$), ($X^5$, $R^{a3}$,
$R^{b3}$, $A^2$, $R^{c2}$, $R^{d2}$), ($X^5$, $R^{a3}$, $R^{b3}$, $A^2$, $R^{c2}$, $R^{d3}$), ($X^5$, $R^{a3}$,
$R^{b3}$, $A^2$, $R^{c3}$, $R^{d1}$), ($X^5$, $R^{a3}$, $R^{b3}$, $A^2$, $R^{c3}$, $R^{d2}$), ($X^5$, $R^{a3}$,
$R^{b3}$, $A^2$, $R^{c3}$, $R^{d3}$), ($X^5$, $R^{a3}$, $R^{b3}$, $A^2$, $R^{c4}$, $R^{d1}$), ($X^5$, $R^{a3}$,
$R^{b3}$, $A^2$, $R^{c4}$, $R^{d2}$), ($X^5$, $R^{a3}$, $R^{b3}$, $A^2$, $R^{c4}$, $R^{d3}$), ($X^5$, $R^{a3}$,
$R^{b3}$, $A^3$, $R^{c1}$, $R^{d1}$), ($X^5$, $R^{a3}$, $R^{b3}$, $A^3$, $R^{c1}$, $R^{d2}$), ($X^5$, $R^{a3}$,
$R^{b3}$, $A^3$, $R^{c1}$, $R^{d3}$), ($X^5$, $R^{a3}$, $R^{b3}$, $A^3$, $R^{c2}$, $R^{d1}$), ($X^5$, $R^{a3}$,
$R^{b3}$, $A^3$, $R^{c2}$, $R^{d2}$), ($X^5$, $R^{a3}$, $R^{b3}$, $A^3$, $R^{c2}$, $R^{d3}$), ($X^5$, $R^{a3}$,
$R^{b3}$, $A^3$, $R^{c3}$, $R^{d1}$), ($X^5$, $R^{a3}$, $R^{b3}$, $A^3$, $R^{c3}$, $R^{d2}$), ($X^5$, $R^{a3}$,
$R^{b3}$, $A^3$, $R^{c3}$, $R^{d3}$), ($X^5$, $R^{a3}$, $R^{b3}$, $A^3$, $R^{c4}$, $R^{d1}$), ($X^5$, $R^{a3}$,
$R^{b3}$, $A^3$, $R^{c4}$, $R^{d2}$), ($X^5$, $R^{a3}$, $R^{b3}$, $A^3$, $R^{c4}$, $R^{d3}$), ($X^5$, $R^{a3}$,
$R^{b3}$, $A^4$, $R^{c1}$, $R^{d1}$), ($X^5$, $R^{a3}$, $R^{b3}$, $A^4$, $R^{c1}$, $R^{d2}$), ($X^5$, $R^{a3}$,
$R^{b3}$, $A^4$, $R^{c1}$, $R^{d3}$), ($X^5$, $R^{a3}$, $R^{b3}$, $A^4$, $R^{c2}$, $R^{d1}$), ($X^5$, $R^{a3}$,
$R^{b3}$, $A^4$, $R^{c2}$, $R^{d2}$), ($X^5$, $R^{a3}$, $R^{b3}$, $A^4$, $R^{c2}$, $R^{d3}$), ($X^5$, $R^{a3}$, $(R^{b3}, A^4, R^{c3}, R^{d1})$, $(X^5, R^{a3}, R^{b3}, A^4, R^{c3}, R^{d2})$, $(X^5, R^{a3}, R^{b3}, A^4, R^{c3}, R^{d3})$, $(X^5, R^{a3}, R^{b3}, A^4, R^{c4}, R^{d1})$, $(X^5, R^{a3}, R^{b3}, A^4, R^{c4}, R^{d2})$, $(X^5, R^{a3}, R^{b3}, A^4, R^{c4}, R^{d3})$, $(X^5, R^{a3}, R^{b3}, A^5, R^{c1}, R^{d1})$, $(X^5, R^{a3}, R^{b3}, A^5, R^{c1}, R^{d2})$, $(X^5, R^{a3}, R^{b3}, A^5, R^{c1}, R^{d3})$, $(X^5, R^{a3}, R^{b3}, A^5, R^{c2}, R^{d1})$, $(X^5, R^{a3}, R^{b3}, A^5, R^{c2}, R^{d2})$, $(X^5, R^{a3}, R^{b3}, A^5, R^{c2}, R^{d3})$, $(X^5, R^{a3}, R^{b3}, A^5, R^{c3}, R^{d1})$, $(X^5, R^{a3}, R^{b3}, A^5, R^{c3}, R^{d2})$, $(X^5, R^{a3}, R^{b3}, A^5, R^{c3}, R^{d3})$, $(X^5, R^{a3}, R^{b3}, A^5, R^{c4}, R^{d1})$, $(X^5, R^{a3}, R^{b3}, A^5, R^{c4}, R^{d2})$, $(X^5, R^{a3}, R^{b3}, A^5, R^{c4}, R^{d3})$, $(X^6, R^{a1}, R^{b1}, A^1, R^{c1}, R^{d1})$, $(X^6, R^{a1}, R^{b1}, A^1, R^{c1}, R^{d2})$, $(X^6, R^{a1}, R^{b1}, A^1, R^{c1}, R^{d3})$, $(X^6, R^{a1}, R^{b1}, A^1, R^{c2}, R^{d1})$, $(X^6, R^{a1}, R^{b1}, A^1, R^{c2}, R^{d2})$, $(X^6, R^{a1}, R^{b1}, A^1, R^{c2}, R^{d3})$, $(X^6, R^{a1}, R^{b1}, A^1, R^{c3}, R^{d1})$, $(X^6, R^{a1}, R^{b1}, A^1, R^{c3}, R^{d2})$, $(X^6, R^{a1}, R^{b1}, A^1, R^{c3}, R^{d3})$, $(X^6, R^{a1}, R^{b1}, A^1, R^{c4}, R^{d1})$, $(X^6, R^{a1}, R^{b1}, A^1, R^{c4}, R^{d2})$, $(X^6, R^{a1}, R^{b1}, A^1, R^{c4}, R^{d3})$, $(X^6, R^{a1}, R^{b1}, A^2, R^{c1}, R^{d1})$, $(X^6, R^{a1}, R^{b1}, A^2, R^{c1}, R^{d2})$, $(X^6, R^{a1}, R^{b1}, A^2, R^{c1}, R^{d3})$, $(X^6, R^{a1}, R^{b1}, A^2, R^{c2}, R^{d1})$, $(X^6, R^{a1}, R^{b1}, A^2, R^{c2}, R^{d2})$, $(X^6, R^{a1}, R^{b1}, A^2, R^{c2}, R^{d3})$, $(X^6, R^{a1}, R^{b1}, A^2, R^{c3}, R^{d1})$, $(X^6, R^{a1}, R^{b1}, A^2, R^{c3}, R^{d2})$, $(X^6, R^{a1}, R^{b1}, A^2, R^{c3}, R^{d3})$, $(X^6, R^{a1}, R^{b1}, A^2, R^{c4}, R^{d1})$, $(X^6, R^{a1}, R^{b1}, A^2, R^{c4}, R^{d2})$, $(X^6, R^{a1}, R^{b1}, A^2, R^{c4}, R^{d3})$, $(X^6, R^{a1}, R^{b1}, A^3, R^{c1}, R^{d1})$, $(X^6, R^{a1}, R^{b1}, A^3, R^{c1}, R^{d2})$, $(X^6, R^{a1}, R^{b1}, A^3, R^{c1}, R^{d3})$, $(X^6, R^{a1}, R^{b1}, A^3, R^{c2}, R^{d1})$, $(X^6, R^{a1}, R^{b1}, A^3, R^{c2}, R^{d2})$, $(X^6, R^{a1}, R^{b1}, A^3, R^{c2}, R^{d3})$, $(X^6, R^{a1}, R^{b1}, A^3, R^{c3}, R^{d1})$, $(X^6, R^{a1}, R^{b1}, A^3, R^{c3}, R^{d2})$, $(X^6, R^{a1}, R^{b1}, A^3, R^{c3}, R^{d3})$, $(X^6, R^{a1}, R^{b1}, A^3, R^{c4}, R^{d1})$, $(X^6, R^{a1}, R^{b1}, A^3, R^{c4}, R^{d2})$, $(X^6, R^{a1}, R^{b1}, A^3, R^{c4}, R^{d3})$, $(X^6, R^{a1}, R^{b1}, A^4, R^{c1}, R^{d1})$, $(X^6, R^{a1}, R^{b1}, A^4, R^{c1}, R^{d2})$, $(X^6, R^{a1}, R^{b1}, A^4, R^{c1}, R^{d3})$, $(X^6, R^{a1}, R^{b1}, A^4, R^{c2}, R^{d1})$, $(X^6, R^{a1}, R^{b1}, A^4, R^{c2}, R^{d2})$, $(X^6, R^{a1}, R^{b1}, A^4, R^{c2}, R^{d3})$, $(X^6, R^{a1}, R^{b1}, A^4, R^{c3}, R^{d1})$, $(X^6, R^{a1}, R^{b1}, A^4, R^{c3}, R^{d2})$, $(X^6, R^{a1}, R^{b1}, A^4, R^{c3}, R^{d3})$, $(X^6, R^{a1}, R^{b1}, A^4, R^{c4}, R^{d1})$, $(X^6, R^{a1}, R^{b1}, A^4, R^{c4}, R^{d2})$, $(X^6, R^{a1}, R^{b1}, A^4, R^{c4}, R^{d3})$, $(X^6, R^{a1}, R^{b1}, A^5, R^{c1}, R^{d1})$, $(X^6, R^{a1}, R^{b1}, A^5, R^{c1}, R^{d2})$, $(X^6, R^{a1}, R^{b1}, A^5, R^{c1}, R^{d3})$, $(X^6, R^{a1}, R^{b1}, A^5, R^{c2}, R^{d1})$, $(X^6, R^{a1}, R^{b1}, A^5, R^{c2}, R^{d2})$, $(X^6, R^{a1}, R^{b1}, A^5, R^{c2}, R^{d3})$, $(X^6, R^{a1}, R^{b1}, A^5, R^{c3}, R^{d1})$, $(X^6, R^{a1}, R^{b1}, A^5, R^{c3}, R^{d2})$, $(X^6, R^{a1}, R^{b1}, A^5, R^{c3}, R^{d3})$, $(X^6, R^{a1}, R^{b1}, A^5, R^{c4}, R^{d1})$, $(X^6, R^{a1}, R^{b1}, A^5, R^{c4}, R^{d2})$, $(X^6, R^{a1}, R^{b1}, A^5, R^{c4}, R^{d3})$, $(X^6, R^{a1}, R^{b2}, A^1, R^{c1}, R^{d1})$, $(X^6, R^{a1}, R^{b2}, A^1, R^{c1}, R^{d2})$, $(X^6, R^{a1}, R^{b2}, A^1, R^{c1}, R^{d3})$, $(X^6, R^{a1}, R^{b2}, A^1, R^{c2}, R^{d1})$, $(X^6, R^{a1}, R^{b2}, A^1, R^{c2}, R^{d2})$, $(X^6, R^{a1}, R^{b2}, A^1, R^{c2}, R^{d3})$, $(X^6, R^{a1}, R^{b2}, A^1, R^{c3}, R^{d1})$, $(X^6, R^{a1}, R^{b2}, A^1, R^{c3}, R^{d2})$, $(X^6, R^{a1}, R^{b2}, A^1, R^{c3}, R^{d3})$, $(X^6, R^{a1}, R^{b2}, A^1, R^{c4}, R^{d1})$, $(X^6, R^{a1}, R^{b2}, A^1, R^{c4}, R^{d2})$, $(X^6, R^{a1}, R^{b2}, A^1, R^{c4}, R^{d3})$, $(X^6, R^{a1}, R^{b2}, A^2, R^{c1}, R^{d1})$, $(X^6, R^{a1}, R^{b2}, A^2, R^{c1}, R^{d2})$, $(X^6, R^{a1}, R^{b2}, A^2, R^{c1}, R^{d3})$, $(X^6, R^{a1}, R^{b2}, A^2, R^{c2}, R^{d1})$, $(X^6, R^{a1}, R^{b2}, A^2, R^{c2}, R^{d2})$, $(X^6, R^{a1}, R^{b2}, A^2, R^{c2}, R^{d3})$, $(X^6, R^{a1}, R^{b2}, A^2, R^{c3}, R^{d1})$, $(X^6, R^{a1}, R^{b2}, A^2, R^{c3}, R^{d2})$, $(X^6, R^{a1}, R^{b2}, A^2, R^{c3}, R^{d3})$, $(X^6, R^{a1}, R^{b2}, A^2, R^{c4}, R^{d1})$, $(X^6, R^{a1}, R^{b2}, A^2, R^{c4}, R^{d2})$, $(X^6, R^{a1}, R^{b2}, A^2, R^{c4}, R^{d3})$, $(X^6, R^{a1}, R^{b2}, A^3, R^{c1}, R^{d1})$, $(X^6, R^{a1}, R^{b2}, A^3, R^{c1}, R^{d2})$, $(X^6, R^{a1}, R^{b2}, A^3, R^{c1}, R^{d3})$, $(X^6, R^{a1}, R^{b2}, A^3, R^{c2}, R^{d1})$, $(X^6, R^{a1}, R^{b2}, A^3, R^{c2}, R^{d2})$, $(X^6, R^{a1}, R^{b2}, A^3, R^{c2}, R^{d3})$, $(X^6, R^{a1}, R^{b2}, A^3, R^{c3}, R^{d1})$, $(X^6, R^{a1}, R^{b2}, A^3, R^{c3}, R^{d2})$, $(X^6, R^{a1}, R^{b2}, A^3, R^{c3}, R^{d3})$, $(X^6, R^{a1}, R^{b2}, A^3, R^{c4}, R^{d1})$, $(X^6, R^{a1}, R^{b2}, A^3, R^{c4}, R^{d2})$, $(X^6, R^{a1}, R^{b2}, A^3, R^{c4}, R^{d3})$, $(X^6, R^{a1}, R^{b2}, A^4, R^{c1}, R^{d1})$, $(X^6, R^{a1}, R^{b2}, A^4, R^{c1}, R^{d2})$, $(X^6, R^{a1}, R^{b2}, A^4, R^{c1}, R^{d3})$, $(X^6, R^{a1}, R^{b2}, A^4, R^{c2}, R^{d1})$, $(X^6, R^{a1}, R^{b2}, A^4, R^{c2}, R^{d2})$, $(X^6, R^{a1}, R^{b2}, A^4, R^{c2}, R^{d3})$, $(X^6, R^{a1}, R^{b2}, A^4, R^{c3}, R^{d1})$, $(X^6, R^{a1}, R^{b2}, A^4, R^{c3}, R^{d2})$, $(X^6, R^{a1}, R^{b2}, A^4, R^{c3}, R^{d3})$, $(X^6, R^{a1}, R^{b2}, A^4, R^{c4}, R^{d1})$, $(X^6, R^{a1}, R^{b2}, A^4, R^{c4}, R^{d2})$, $(X^6, R^{a1}, R^{b2}, A^4, R^{c4}, R^{d3})$, $(X^6, R^{a1}, R^{b2}, A^5, R^{c1}, R^{d1})$, $(X^6, R^{a1}, R^{b2}, A^5, R^{c1}, R^{d2})$, $(X^6, R^{a1}, R^{b2}, A^5, R^{c1}, R^{d3})$, $(X^6, R^{a1}, R^{b2}, A^5, R^{c2}, R^{d1})$, $(X^6, R^{a1}, R^{b2}, A^5, R^{c2}, R^{d2})$, $(X^6, R^{a1}, R^{b2}, A^5, R^{c2}, R^{d3})$, $(X^6, R^{a1}, R^{b2}, A^5, R^{c3}, R^{d1})$, $(X^6, R^{a1}, R^{b2}, A^5, R^{c3}, R^{d2})$, $(X^6, R^{a1}, R^{b2}, A^5, R^{c3}, R^{d3})$, $(X^6, R^{a1}, R^{b2}, A^5, R^{c4}, R^{d1})$, $(X^6, R^{a1}, R^{b2}, A^5, R^{c4}, R^{d2})$, $(X^6, R^{a1}, R^{b2}, A^5, R^{c4}, R^{d3})$, $(X^6, R^{a1}, R^{b3}, A^1, R^{c1}, R^{d1})$, $(X^6, R^{a1}, R^{b3}, A^1, R^{c1}, R^{d2})$, $(X^6, R^{a1}, R^{b3}, A^1, R^{c1}, R^{d3})$, $(X^6, R^{a1}, R^{b3}, A^1, R^{c2}, R^{d1})$, $(X^6, R^{a1}, R^{b3}, A^1, R^{c2}, R^{d2})$, $(X^6, R^{a1}, R^{b3}, A^1, R^{c2}, R^{d3})$, $(X^6, R^{a1}, R^{b3}, A^1, R^{c3}, R^{d1})$, $(X^6, R^{a1}, R^{b3}, A^1, R^{c3}, R^{d2})$, $(X^6, R^{a1}, R^{b3}, A^1, R^{c3}, R^{d3})$, $(X^6, R^{a1}, R^{b3}, A^1, R^{c4}, R^{d1})$, $(X^6, R^{a1}, R^{b3}, A^1, R^{c4}, R^{d2})$, $(X^6, R^{a1}, R^{b3}, A^1, R^{c4}, R^{d3})$, $(X^6, R^{a1}, R^{b3}, A^2, R^{c1}, R^{d1})$, $(X^6, R^{a1}, R^{b3}, A^2, R^{c1}, R^{d2})$, $(X^6, R^{a1}, R^{b3}, A^2, R^{c1}, R^{d3})$, $(X^6, R^{a1}, R^{b3}, A^2, R^{c2}, R^{d1})$, $(X^6, R^{a1}, R^{b3}, A^2, R^{c2}, R^{d2})$, $(X^6, R^{a1}, R^{b3}, A^2, R^{c2}, R^{d3})$, $(X^6, R^{a1}, R^{b3}, A^2, R^{c3}, R^{d1})$, $(X^6, R^{a1}, R^{b3}, A^2, R^{c3}, R^{d2})$, $(X^6, R^{a1}, R^{b3}, A^2, R^{c3}, R^{d3})$, $(X^6, R^{a1}, R^{b3}, A^2, R^{c4}, R^{d1})$, $(X^6, R^{a1}, R^{b3}, A^2, R^{c4}, R^{d2})$, $(X^6, R^{a1}, R^{b3}, A^2, R^{c4}, R^{d3})$, $(X^6, R^{a1}, R^{b3}, A^3, R^{c1}, R^{d1})$, $(X^6, R^{a1}, R^{b3}, A^3, R^{c1}, R^{d2})$, $(X^6, R^{a1}, R^{b3}, A^3, R^{c1}, R^{d3})$, $(X^6, R^{a1}, R^{b3}, A^3, R^{c2}, R^{d1})$, $(X^6, R^{a1}, R^{b3}, A^3, R^{c2}, R^{d2})$, $(X^6, R^{a1}, R^{b3}, A^3, R^{c2}, R^{d3})$, $(X^6, R^{a1}, R^{b3}, A^3, R^{c3}, R^{d1})$, $(X^6, R^{a1}, R^{b3}, A^3, R^{c3}, R^{d2})$, $(X^6, R^{a1}, R^{b3}, A^3, R^{c3}, R^{d3})$, $(X^6, R^{a1}, R^{b3}, A^3, R^{c4}, R^{d1})$, $(X^6, R^{a1}, R^{b3}, A^3, R^{c4}, R^{d2})$, $(X^6, R^{a1}, R^{b3}, A^3, R^{c4}, R^{d3})$, $(X^6, R^{a1}, R^{b3}, A^4, R^{c1}, R^{d1})$, $(X^6, R^{a1}, R^{b3}, A^4, R^{c1}, R^{d2})$, $(X^6, R^{a1}, R^{b3}, A^4, R^{c1}, R^{d3})$, $(X^6, R^{a1}, R^{b3}, A^4, R^{c2}, R^{d1})$, $(X^6, R^{a1}, R^{b3}, A^4, R^{c2}, R^{d2})$, $(X^6, R^{a1}, R^{b3}, A^4, R^{c2}, R^{d3})$, $(X^6, R^{a1}, R^{b3}, A^4, R^{c3}, R^{d1})$, $(X^6, R^{a1}, R^{b3}, A^4, R^{c3}, R^{d2})$, $(X^6, R^{a1}, R^{b3}, A^4, R^{c3}, R^{d3})$, $(X^6, R^{a1}, R^{b3}, A^4, R^{c4}, R^{d1})$, $(X^6, R^{a1}, R^{b3}, A^4, R^{c4}, R^{d2})$, $(X^6, R^{a1}, R^{b3}, A^4, R^{c4}, R^{d3})$, $(X^6, R^{a1}, R^{b3}, A^5, R^{c1}, R^{d1})$, $(X^6, R^{a1}, R^{b3}, A^5, R^{c1}, R^{d2})$, $(X^6, R^{a1}, R^{b3}, A^5, R^{c1}, R^{d3})$, $(X^6, R^{a1}, R^{b3}, A^5, R^{c2}, R^{d1})$, $(X^6, R^{a1}, R^{b3}, A^5, R^{c2}, R^{d2})$, $(X^6, R^{a1}, R^{b3}, A^5, R^{c2}, R^{d3})$, $(X^6, R^{a1}, R^{b3}, A^5, R^{c3}, R^{d1})$, $(X^6, R^{a1}, R^{b3}, A^5, R^{c3}, R^{d2})$, $(X^6, R^{a1}, R^{b3}, A^5, R^{c3}, R^{d3})$, $(X^6, R^{a1}, R^{b3}, A^5, R^{c4}, R^{d1})$, $(X^6, R^{a1}, R^{b3}, A^5, R^{c4}, R^{d2})$, $(X^6, R^{a1}, R^{b3}, A^5, R^{c4}, R^{d3})$, $(X^6, R^{a2}, R^{b1}, A^1, R^{c1}, R^{d1})$, $(X^6, R^{a2}, R^{b1}, A^1, R^{c1}, R^{d2})$, $(X^6, R^{a2}, R^{b1}, A^1, R^{c1}, R^{d3})$, $(X^6, R^{a2}, R^{b1}, A^1, R^{c2}, R^{d1})$, $(X^6, R^{a2}, R^{b1}, A^1, R^{c2}, R^{d2})$, $(X^6, R^{a2}, R^{b1}, A^1, R^{c2}, R^{d3})$, $(X^6, R^{a2}, R^{b1}, A^1, R^{c3}, R^{d1})$, $(X^6, R^{a2}, R^{b1}, A^1, R^{c3}, R^{d2})$, $(X^6, R^{a2}, R^{b1}, A^1, R^{c3}, R^{d3})$, $(X^6, R^{a2}, R^{b1}, A^1, R^{c4}, R^{d1})$, $(X^6, R^{a2}, R^{b1}, A^1, R^{c4}, R^{d2})$, $(X^6, R^{a2}, R^{b1}, A^1, R^{c4}, R^{d3})$, $(X^6, R^{a2}, R^{b1}, A^2, R^{c1}, R^{d1})$, $(X^6, R^{a2}, R^{b1}, A^2, R^{c1}, R^{d2})$, $(X^6, R^{a2}, R^{b1}, A^2, R^{c1}, R^{d3})$, $(X^6, R^{a2}, R^{b1}, A^2, R^{c2}, R^{d1})$, $(X^6, R^{a2}, R^{b1}, A^2, R^{c2}, R^{d2})$, $(X^6, R^{a2}, R^{b1}, A^2, R^{c2}, R^{d3})$, $(X^6, R^{a2}, R^{b1}, A^2, R^{c3}, R^{d1})$, $(X^6, R^{a2}, R^{b1}, A^2, R^{c3}, R^{d2})$, $(X^6, R^{a2}, R^{b1}, A^2, R^{c3}, R^{d3})$, $(X^6, R^{a2}, R^{b1}, A^2, R^{c4}, R^{d1})$, $(X^6, R^{a2}, R^{b1}, A^2, R^{c4}, R^{d2})$, $(X^6, R^{a2}, R^{b1}, A^2, R^{c4}, R^{d3})$, $(X^6, R^{a2}, R^{b1}, A^3, R^{c1}, R^{d1})$, $(X^6, R^{a2}, R^{b1}, A^3, R^{c1}, R^{d2})$, $(X^6, R^{a2}, R^{b1}, A^3, R^{c1}, R^{d3})$, $(X^6, R^{a2}, R^{b1}, A^3, R^{c2}, R^{d1})$, $(X^6, R^{a2}, R^{b1}, A^3, R^{c2}, R^{d2})$, $(X^6, R^{a2}, R^{b1}, A^3, R^{c2}, R^{d3})$, $(X^6, R^{a2}, R^{b1}, A^3, R^{c3}, R^{d1})$, $(X^6, R^{a2}, R^{b1}, A^3, R^{c3}, R^{d2})$, $(X^6, R^{a2}, R^{b1}, A^3, R^{c3}, R^{d3})$, $(X^6, R^{a2}, R^{b1}, A^3, R^{c4}, R^{d1})$, $(X^6, R^{a2}, R^{b1}, A^3, R^{c4}, R^{d2})$, $(X^6, R^{a2}, R^{b1}, A^3, R^{c4}, R^{d3})$, $(X^6, R^{a2}, R^{b1}, A^4, R^{c1}, R^{d1})$, $(X^6, R^{a2}, R^{b1}, A^4, R^{c1}, R^{d2})$, $(X^6, R^{a2}, R^{b1}, A^4, R^{c1}, R^{d3})$, $(X^6, R^{a2}, R^{b1}, A^4, R^{c2}, R^{d1})$, $(X^6, R^{a2}, R^{b1}, A^4, R^{c2}, R^{d2})$, $(X^6, R^{a2}, R^{b1}, A^4, R^{c2}, R^{d3})$, $(X^6, R^{a2}, R^{b1}, A^4, R^{c3}, R^{d1})$, $(X^6, R^{a2}, R^{b1}, A^4, R^{c3}, R^{d2})$, $(X^6, R^{a2}, R^{b1}, A^4, R^{c3}, R^{d3})$, $(X^6, R^{a2}, R^{b1}, A^4, R^{c4}, R^{d1})$, $(X^6, R^{a2}, R^{b1}, A^4, R^{c4}, R^{d2})$, $(X^6, R^{a2}, R^{b1}, A^4, R^{c4}, R^{d3})$, $(X^6, R^{a2}, R^{b1}, A^5, R^{c1}, R^{d1})$, $(X^6, R^{a2}, R^{b1}, A^5, R^{c1}, R^{d2})$, $(X^6, R^{a2}, R^{b1}, A^5, R^{c1}, R^{d3})$, $(X^6, R^{a2}, R^{b1}, A^5, R^{c2}, R^{d1})$, $(X^6, R^{a2}, R^{b1}, A^5, R^{c2}, R^{d2})$, $(X^6, R^{a2}, R^{b1}, A^5, R^{c2}, R^{d3})$, $(X^6, R^{a2}, R^{b1}, A^5, R^{c3}, R^{d1})$, $(X^6, R^{a2}, R^{b1}, A^5, R^{c3}, R^{d2})$, $(X^6, R^{a2}, R^{b1}, A^5, R^{c3}, R^{d3})$, $(X^6, R^{a2}, R^{b1}, A^5, R^{c4}, R^{d1})$, $(X^6, R^{a2}, R^{b1}, A^5, R^{c4}, R^{d2})$, $(X^6, R^{a2}, R^{b1}, A^5, R^{c4}, R^{d3})$, $(X^6, R^{a2}, R^{b2}, A^1, R^{c1}, R^{d1})$, $(X^6, R^{a2}, R^{b2}, A^1, R^{c1}, R^{d2})$, $(X^6, R^{a2}, R^{b2}, A^1, R^{c1}, R^{d3})$, $(X^6, R^{a2}, R^{b2}, A^1, R^{c2}, R^{d1})$, $(X^6, R^{a2}, R^{b2}, A^1, R^{c2}, R^{d2})$, $(X^6, R^{a2}, R^{b2}, A^1, R^{c2}, R^{d3})$, $(X^6, R^{a2}, R^{b2}, A^1, R^{c3}, R^{d1})$, $(X^6, R^{a2}, R^{b2}, A^1, R^{c3}, R^{d2})$, $(X^6, R^{a2}, R^{b2}, A^1, R^{c3}, R^{d3})$, $(X^6, R^{a2}, R^{b2}, A^1, R^{c4}, R^{d1})$, $(X^6, R^{a2}, $R^{b2}, A^1, R^{c4}, R^{d2}), (X^6, R^{a2}, R^{b2}, A^1, R^{c4}, R^{d3}), (X^6, R^{a2},$
$R^{b2}, A^2, R^{c1}, R^{d1}), (X^6, R^{a2}, R^{b2}, A^2, R^{c1}, R^{d2}), (X^6, R^{a2},$
$R^{b2}, A^2, R^{c1}, R^{d3}), (X^6, R^{a2}, R^{b2}, A^2, R^{c2}, R^{d1}), (X^6, R^{a2},$
$R^{b2}, A^2, R^{c2}, R^{d2}), (X^6, R^{a2}, R^{b2}, A^2, R^{c2}, R^{d3}), (X^6, R^{a2},$
$R^{b2}, A^2, R^{c3}, R^{d1}), (X^6, R^{a2}, R^{b2}, A^2, R^{c3}, R^{d2}), (X^6, R^{a2},$
$R^{b2}, A^2, R^{c3}, R^{d3}), (X^6, R^{a2}, R^{b2}, A^2, R^{c4}, R^{d1}), (X^6, R^{a2},$
$R^{b2}, A^2, R^{c4}, R^{d2}), (X^6, R^{a2}, R^{b2}, A^2, R^{c4}, R^{d3}), (X^6, R^{a2},$
$R^{b2}, A^3, R^{c1}, R^{d1}), (X^6, R^{a2}, R^{b2}, A^3, R^{c1}, R^{d2}), (X^6, R^{a2},$
$R^{b2}, A^3, R^{c1}, R^{d3}), (X^6, R^{a2}, R^{b2}, A^3, R^{c2}, R^{d1}), (X^6, R^{a2},$
$R^{b2}, A^3, R^{c2}, R^{d2}), (X^6, R^{a2}, R^{b2}, A^3, R^{c2}, R^{d3}), (X^6, R^{a2},$
$R^{b2}, A^3, R^{c3}, R^{d1}), (X^6, R^{a2}, R^{b2}, A^3, R^{c3}, R^{d2}), (X^6, R^{a2},$
$R^{b2}, A^3, R^{c3}, R^{d3}), (X^6, R^{a2}, R^{b2}, A^3, R^{c4}, R^{d1}), (X^6, R^{a2},$
$R^{b2}, A^3, R^{c4}, R^{d2}), (X^6, R^{a2}, R^{b2}, A^3, R^{c4}, R^{d3}), (X^6, R^{a2},$
$R^{b2}, A^4, R^{c1}, R^{d1}), (X^6, R^{a2}, R^{b2}, A^4, R^{c1}, R^{d2}), (X^6, R^{a2},$
$R^{b2}, A^4, R^{c1}, R^{d3}), (X^6, R^{a2}, R^{b2}, A^4, R^{c2}, R^{d1}), (X^6, R^{a2},$
$R^{b2}, A^4, R^{c2}, R^{d2}), (X^6, R^{a2}, R^{b2}, A^4, R^{c2}, R^{d3}), (X^6, R^{a2},$
$R^{b2}, A^4, R^{c3}, R^{d1}), (X^6, R^{a2}, R^{b2}, A^4, R^{c3}, R^{d2}), (X^6, R^{a2},$
$R^{b2}, A^4, R^{c3}, R^{d3}), (X^6, R^{a2}, R^{b2}, A^4, R^{c4}, R^{d1}), (X^6, R^{a2},$
$R^{b2}, A^4, R^{c4}, R^{d2}), (X^6, R^{a2}, R^{b2}, A^4, R^{c4}, R^{d3}), (X^6, R^{a2},$
$R^{b2}, A^5, R^{c1}, R^{d1}), (X^6, R^{a2}, R^{b2}, A^5, R^{c1}, R^{d2}), (X^6, R^{a2},$
$R^{b2}, A^5, R^{c1}, R^{d3}), (X^6, R^{a2}, R^{b2}, A^5, R^{c2}, R^{d1}), (X^6, R^{a2},$
$R^{b2}, A^5, R^{c2}, R^{d2}), (X^6, R^{a2}, R^{b2}, A^5, R^{c2}, R^{d3}), (X^6, R^{a2},$
$R^{b2}, A^5, R^{c3}, R^{d1}), (X^6, R^{a2}, R^{b2}, A^5, R^{c3}, R^{d2}), (X^6, R^{a2},$
$R^{b2}, A^5, R^{c3}, R^{d3}), (X^6, R^{a2}, R^{b2}, A^5, R^{c4}, R^{d1}), (X^6, R^{a2},$
$R^{b2}, A^5, R^{c4}, R^{d2}), (X^6, R^{a2}, R^{b2}, A^5, R^{c4}, R^{d3}), (X^6, R^{a2},$
$R^{b3}, A^1, R^{c1}, R^{d1}), (X^6, R^{a2}, R^{b3}, A^1, R^{c1}, R^{d2}), (X^6, R^{a2},$
$R^{b3}, A^1, R^{c1}, R^{d3}), (X^6, R^{a2}, R^{b3}, A^1, R^{c2}, R^{d1}), (X^6, R^{a2},$
$R^{b3}, A^1, R^{c2}, R^{d2}), (X^6, R^{a2}, R^{b3}, A^1, R^{c2}, R^{d3}), (X^6, R^{a2},$
$R^{b3}, A^1, R^{c3}, R^{d1}), (X^6, R^{a2}, R^{b3}, A^1, R^{c3}, R^{d2}), (X^6, R^{a2},$
$R^{b3}, A^1, R^{c3}, R^{d3}), (X^6, R^{a2}, R^{b3}, A^1, R^{c4}, R^{d1}), (X^6, R^{a2},$
$R^{b3}, A^1, R^{c4}, R^{d2}), (X^6, R^{a2}, R^{b3}, A^1, R^{c4}, R^{d3}), (X^6, R^{a2},$
$R^{b3}, A^2, R^{c1}, R^{d1}), (X^6, R^{a2}, R^{b3}, A^2, R^{c1}, R^{d2}), (X^6, R^{a2},$
$R^{b3}, A^2, R^{c1}, R^{d3}), (X^6, R^{a2}, R^{b3}, A^2, R^{c2}, R^{d1}), (X^6, R^{a2},$
$R^{b3}, A^2, R^{c2}, R^{d2}), (X^6, R^{a2}, R^{b3}, A^2, R^{c2}, R^{d3}), (X^6, R^{a2},$
$R^{b3}, A^2, R^{c3}, R^{d1}), (X^6, R^{a2}, R^{b3}, A^2, R^{c3}, R^{d2}), (X^6, R^{a2},$
$R^{b3}, A^2, R^{c3}, R^{d3}), (X^6, R^{a2}, R^{b3}, A^2, R^{c4}, R^{d1}), (X^6, R^{a2},$
$R^{b3}, A^2, R^{c4}, R^{d2}), (X^6, R^{a2}, R^{b3}, A^2, R^{c4}, R^{d3}), (X^6, R^{a2},$
$R^{b3}, A^3, R^{c1}, R^{d1}), (X^6, R^{a2}, R^{b3}, A^3, R^{c1}, R^{d2}), (X^6, R^{a2},$
$R^{b3}, A^3, R^{c1}, R^{d3}), (X^6, R^{a2}, R^{b3}, A^3, R^{c2}, R^{d1}), (X^6, R^{a2},$
$R^{b3}, A^3, R^{c2}, R^{d2}), (X^6, R^{a2}, R^{b3}, A^3, R^{c2}, R^{d3}), (X^6, R^{a2},$
$R^{b3}, A^3, R^{c3}, R^{d1}), (X^6, R^{a2}, R^{b3}, A^3, R^{c3}, R^{d2}), (X^6, R^{a2},$
$R^{b3}, A^3, R^{c3}, R^{d3}), (X^6, R^{a2}, R^{b3}, A^3, R^{c4}, R^{d1}), (X^6, R^{a2},$
$R^{b3}, A^3, R^{c4}, R^{d2}), (X^6, R^{a2}, R^{b3}, A^3, R^{c4}, R^{d3}), (X^6, R^{a2},$
$R^{b3}, A^4, R^{c1}, R^{d1}), (X^6, R^{a2}, R^{b3}, A^4, R^{c1}, R^{d2}), (X^6, R^{a2},$
$R^{b3}, A^4, R^{c1}, R^{d3}), (X^6, R^{a2}, R^{b3}, A^4, R^{c2}, R^{d1}), (X^6, R^{a2},$
$R^{b3}, A^4, R^{c2}, R^{d2}), (X^6, R^{a2}, R^{b3}, A^4, R^{c2}, R^{d3}), (X^6, R^{a2},$
$R^{b3}, A^4, R^{c3}, R^{d1}), (X^6, R^{a2}, R^{b3}, A^4, R^{c3}, R^{d2}), (X^6, R^{a2},$
$R^{b3}, A^4, R^{c3}, R^{d3}), (X^6, R^{a2}, R^{b3}, A^4, R^{c4}, R^{d1}), (X^6, R^{a2},$
$R^{b3}, A^4, R^{c4}, R^{d2}), (X^6, R^{a2}, R^{b3}, A^4, R^{c4}, R^{d3}), (X^6, R^{a2},$
$R^{b3}, A^5, R^{c1}, R^{d1}), (X^6, R^{a2}, R^{b3}, A^5, R^{c1}, R^{d2}), (X^6, R^{a2},$
$R^{b3}, A^5, R^{c1}, R^{d3}), (X^6, R^{a2}, R^{b3}, A^5, R^{c2}, R^{d1}), (X^6, R^{a2},$
$R^{b3}, A^5, R^{c2}, R^{d2}), (X^6, R^{a2}, R^{b3}, A^5, R^{c2}, R^{d3}), (X^6, R^{a2},$
$R^{b3}, A^5, R^{c3}, R^{d1}), (X^6, R^{a2}, R^{b3}, A^5, R^{c3}, R^{d2}), (X^6, R^{a2},$
$R^{b3}, A^5, R^{c3}, R^{d3}), (X^6, R^{a2}, R^{b3}, A^5, R^{c4}, R^{d1}), (X^6, R^{a2},$
$R^{b3}, A^5, R^{c4}, R^{d2}), (X^6, R^{a2}, R^{b3}, A^5, R^{c4}, R^{d3}), (X^6, R^{a2},$
$R^{b1}, A^1, R^{c1}, R^{d1}), (X^6, R^{a3}, R^{b1}, A^1, R^{c1}, R^{d2}), (X^6, R^{a3},$
$R^{b1}, A^1, R^{c1}, R^{d3}), (X^6, R^{a3}, R^{b1}, A^1, R^{c2}, R^{d1}), (X^6, R^{a3},$
$R^{b1}, A^1, R^{c2}, R^{d2}), (X^6, R^{a3}, R^{b1}, A^1, R^{c2}, R^{d3}), (X^6, R^{a3},$
$R^{b1}, A^1, R^{c3}, R^{d1}), (X^6, R^{a3}, R^{b1}, A^1, R^{c3}, R^{d2}), (X^6, R^{a3},$
$R^{b1}, A^1, R^{c3}, R^{d3}), (X^6, R^{a3}, R^{b1}, A^1, R^{c4}, R^{d1}), (X^6, R^{a3},$
$R^{b1}, A^1, R^{c4}, R^{d2}), (X^6, R^{a3}, R^{b1}, A^1, R^{c4}, R^{d3}), (X^6, R^{a3},$
$R^{b1}, A^2, R^{c1}, R^{d1}), (X^6, R^{a3}, R^{b1}, A^2, R^{c1}, R^{d2}), (X^6, R^{a3},$
$R^{b1}, A^2, R^{c1}, R^{d3}), (X^6, R^{a3}, R^{b1}, A^2, R^{c2}, R^{d1}), (X^6, R^{a3},$
$R^{b1}, A^2, R^{c2}, R^{d2}), (X^6, R^{a3}, R^{b1}, A^2, R^{c2}, R^{d3}), (X^6, R^{a3},$
$R^{b1}, A^2, R^{c3}, R^{d1}), (X^6, R^{a3}, R^{b1}, A^2, R^{c3}, R^{d2}), (X^6, R^{a3},$
$R^{b1}, A^2, R^{c3}, R^{d3}), (X^6, R^{a3}, R^{b1}, A^2, R^{c4}, R^{d1}), (X^6, R^{a3},$
$R^{b1}, A^2, R^{c4}, R^{d2}), (X^6, R^{a3}, R^{b1}, A^2, R^{c4}, R^{d3}), (X^6, R^{a3},$
$R^{b1}, A^3, R^{c1}, R^{d1}), (X^6, R^{a3}, R^{b1}, A^3, R^{c1}, R^{d2}), (X^6, R^{a3},$
$R^{b1}, A^3, R^{c1}, R^{d3}), (X^6, R^{a3}, R^{b1}, A^3, R^{c2}, R^{d1}), (X^6, R^{a3},$
$R^{b1}, A^3, R^{c2}, R^{d2}), (X^6, R^{a3}, R^{b1}, A^3, R^{c2}, R^{d3}), (X^6, R^{a3},$
$R^{b1}, A^3, R^{c3}, R^{d1}), (X^6, R^{a3}, R^{b1}, A^3, R^{c3}, R^{d2}), (X^6, R^{a3},$
$R^{b1}, A^3, R^{c3}, R^{d3}), (X^6, R^{a3}, R^{b1}, A^3, R^{c4}, R^{d1}), (X^6, R^{a3},$
$R^{b1}, A^3, R^{c4}, R^{d2}), (X^6, R^{a3}, R^{b1}, A^3, R^{c4}, R^{d3}), (X^6, R^{a3},$
$R^{b1}, A^4, R^{c1}, R^{d1}), (X^6, R^{a3}, R^{b1}, A^4, R^{c1}, R^{d2}), (X^6, R^{a3},$
$R^{b1}, A^4, R^{c1}, R^{d3}), (X^6, R^{a3}, R^{b1}, A^4, R^{c2}, R^{d1}), (X^6, R^{a3},$
$R^{b1}, A^4, R^{c2}, R^{d2}), (X^6, R^{a3}, R^{b1}, A^4, R^{c2}, R^{d3}), (X^6, R^{a3},$
$R^{b1}, A^4, R^{c3}, R^{d1}), (X^6, R^{a3}, R^{b1}, A^4, R^{c3}, R^{d2}), (X^6, R^{a3},$
$R^{b1}, A^4, R^{c3}, R^{d3}), (X^6, R^{a3}, R^{b1}, A^4, R^{c4}, R^{d1}), (X^6, R^{a3},$
$R^{b1}, A^4, R^{c4}, R^{d2}), (X^6, R^{a3}, R^{b1}, A^4, R^{c4}, R^{d3}), (X^6, R^{a3},$
$R^{b1}, A^5, R^{c1}, R^{d1}), (X^6, R^{a3}, R^{b1}, A^5, R^{c1}, R^{d2}), (X^6, R^{a3},$
$R^{b1}, A^5, R^{c1}, R^{d3}), (X^6, R^{a3}, R^{b1}, A^5, R^{c2}, R^{d1}), (X^6, R^{a3},$
$R^{b1}, A^5, R^{c2}, R^{d2}), (X^6, R^{a3}, R^{b1}, A^5, R^{c2}, R^{d3}), (X^6, R^{a3},$
$R^{b1}, A^5, R^{c3}, R^{d1}), (X^6, R^{a3}, R^{b1}, A^5, R^{c3}, R^{d2}), (X^6, R^{a3},$
$R^{b1}, A^5, R^{c3}, R^{d3}), (X^6, R^{a3}, R^{b1}, A^5, R^{c4}, R^{d1}), (X^6, R^{a3},$
$R^{b1}, A^5, R^{c4}, R^{d2}), (X^6, R^{a3}, R^{b1}, A^5, R^{c4}, R^{d3}), (X^6, R^{a3},$
$R^{b2}, A^1, R^{c1}, R^{d1}), (X^6, R^{a3}, R^{b2}, A^1, R^{c1}, R^{d2}), (X^6, R^{a3},$
$R^{b2}, A^1, R^{c1}, R^{d3}), (X^6, R^{a3}, R^{b2}, A^1, R^{c2}, R^{d1}), (X^6, R^{a3},$
$R^{b2}, A^1, R^{c2}, R^{d2}), (X^6, R^{a3}, R^{b2}, A^1, R^{c2}, R^{d3}), (X^6, R^{a3},$
$R^{b2}, A^1, R^{c3}, R^{d1}), (X^6, R^{a3}, R^{b2}, A^1, R^{c3}, R^{d2}), (X^6, R^{a3},$
$R^{b2}, A^1, R^{c3}, R^{d3}), (X^6, R^{a3}, R^{b2}, A^1, R^{c4}, R^{d1}), (X^6, R^{a3},$
$R^{b2}, A^1, R^{c4}, R^{d2}), (X^6, R^{a3}, R^{b2}, A^1, R^{c4}, R^{d3}), (X^6, R^{a3},$
$R^{b2}, A^2, R^{c1}, R^{d1}), (X^6, R^{a3}, R^{b2}, A^2, R^{c1}, R^{d2}), (X^6, R^{a3},$
$R^{b2}, A^2, R^{c1}, R^{d3}), (X^6, R^{a3}, R^{b2}, A^2, R^{c2}, R^{d1}), (X^6, R^{a3},$
$R^{b2}, A^2, R^{c2}, R^{d2}), (X^6, R^{a3}, R^{b2}, A^2, R^{c2}, R^{d3}), (X^6, R^{a3},$
$R^{b2}, A^2, R^{c3}, R^{d1}), (X^6, R^{a3}, R^{b2}, A^2, R^{c3}, R^{d2}), (X^6, R^{a3},$
$R^{b2}, A^2, R^{c3}, R^{d3}), (X^6, R^{a3}, R^{b2}, A^2, R^{c4}, R^{d1}), (X^6, R^{a3},$
$R^{b2}, A^2, R^{c4}, R^{d2}), (X^6, R^{a3}, R^{b2}, A^2, R^{c4}, R^{d3}), (X^6, R^{a3},$
$R^{b2}, A^3, R^{c1}, R^{d1}), (X^6, R^{a3}, R^{b2}, A^3, R^{c1}, R^{d2}), (X^6, R^{a3},$
$R^{b2}, A^3, R^{c1}, R^{d3}), (X^6, R^{a3}, R^{b2}, A^3, R^{c2}, R^{d1}), (X^6, R^{a3},$
$R^{b2}, A^3, R^{c2}, R^{d2}), (X^6, R^{a3}, R^{b2}, A^3, R^{c2}, R^{d3}), (X^6, R^{a3},$
$R^{b2}, A^3, R^{c3}, R^{d1}), (X^6, R^{a3}, R^{b2}, A^3, R^{c3}, R^{d2}), (X^6, R^{a3},$
$R^{b2}, A^3, R^{c3}, R^{d3}), (X^6, R^{a3}, R^{b2}, A^3, R^{c4}, R^{d1}), (X^6, R^{a3},$
$R^{b2}, A^3, R^{c4}, R^{d2}), (X^6, R^{a3}, R^{b2}, A^3, R^{c4}, R^{d3}), (X^6, R^{a3},$
$R^{b2}, A^4, R^{c1}, R^{d1}), (X^6, R^{a3}, R^{b2}, A^4, R^{c1}, R^{d2}), (X^6, R^{a3},$
$R^{b2}, A^4, R^{c1}, R^{d3}), (X^6, R^{a3}, R^{b2}, A^4, R^{c2}, R^{d1}), (X^6, R^{a3},$
$R^{b2}, A^4, R^{c2}, R^{d2}), (X^6, R^{a3}, R^{b2}, A^4, R^{c2}, R^{d3}), (X^6, R^{a3},$
$R^{b2}, A^4, R^{c3}, R^{d1}), (X^6, R^{a3}, R^{b2}, A^4, R^{c3}, R^{d2}), (X^6, R^{a3},$
$R^{b2}, A^4, R^{c3}, R^{d3}), (X^6, R^{a3}, R^{b2}, A^4, R^{c4}, R^{d1}), (X^6, R^{a3},$
$R^{b2}, A^4, R^{c4}, R^{d2}), (X^6, R^{a3}, R^{b2}, A^4, R^{c4}, R^{d3}), (X^6, R^{a3},$
$R^{b2}, A^5, R^{c1}, R^{d1}), (X^6, R^{a3}, R^{b2}, A^5, R^{c1}, R^{d2}), (X^6, R^{a3},$
$R^{b2}, A^5, R^{c1}, R^{d3}), (X^6, R^{a3}, R^{b2}, A^5, R^{c2}, R^{d1}), (X^6, R^{a3},$
$R^{b2}, A^5, R^{c2}, R^{d2}), (X^6, R^{a3}, R^{b2}, A^5, R^{c2}, R^{d3}), (X^6, R^{a3},$
$R^{b2}, A^5, R^{c3}, R^{d1}), (X^6, R^{a3}, R^{b2}, A^5, R^{c3}, R^{d2}), (X^6, R^{a3},$
$R^{b2}, A^5, R^{c3}, R^{d3}), (X^6, R^{a3}, R^{b2}, A^5, R^{c4}, R^{d1}), (X^6, R^{a3},$
$R^{b2}, A^5, R^{c4}, R^{d2}), (X^6, R^{a3}, R^{b2}, A^5, R^{c4}, R^{d3}), (X^6, R^{a3},$
$R^{b3}, A^1, R^{c1}, R^{d1}), (X^6, R^{a3}, R^{b3}, A^1, R^{c1}, R^{d2}), (X^6, R^{a3},$
$R^{b3}, A^1, R^{c1}, R^{d3}), (X^6, R^{a3}, R^{b3}, A^1, R^{c2}, R^{d1}), (X^6, R^{a3},$
$R^{b3}, A^1, R^{c2}, R^{d2}), (X^6, R^{a3}, R^{b3}, A^1, R^{c2}, R^{d3}), (X^6, R^{a3},$
$R^{b3}, A^1, R^{c3}, R^{d1}), (X^6, R^{a3}, R^{b3}, A^1, R^{c3}, R^{d2}), (X^6, R^{a3},$
$R^{b3}, A^1, R^{c3}, R^{d3}), (X^6, R^{a3}, R^{b3}, A^1, R^{c4}, R^{d1}), (X^6, R^{a3},$
$R^{b3}, A^1, R^{c4}, R^{d2}), (X^6, R^{a3}, R^{b3}, A^1, R^{c4}, R^{d3}), (X^6, R^{a3},$
$R^{b3}, A^2, R^{c1}, R^{d1}), (X^6, R^{a3}, R^{b3}, A^2, R^{c1}, R^{d2}), (X^6, R^{a3},$
$R^{b3}, A^2, R^{c1}, R^{d3}), (X^6, R^{a3}, R^{b3}, A^2, R^{c2}, R^{d1}), (X^6, R^{a3},$
$R^{b3}, A^2, R^{c2}, R^{d2}), (X^6, R^{a3}, R^{b3}, A^2, R^{c2}, R^{d3}), (X^6, R^{a3},$
$R^{b3}, A^2, R^{c3}, R^{d1}), (X^6, R^{a3}, R^{b3}, A^2, R^{c3}, R^{d2}), (X^6, R^{a3},$
$R^{b3}, A^2, R^{c3}, R^{d3}), (X^6, R^{a3}, R^{b3}, A^2, R^{c4}, R^{d1}), (X^6, R^{a3},$
$R^{b3}, A^2, R^{c4}, R^{d2}), (X^6, R^{a3}, R^{b3}, A^2, R^{c4}, R^{d3}), (X^6, R^{a3},$
$R^{b3}, A^3, R^{c1}, R^{d1}), (X^6, R^{a3}, R^{b3}, A^3, R^{c1}, R^{d2}), (X^6, R^{a3},$
$R^{b3}, A^3, R^{c1}, R^{d3}), (X^6, R^{a3}, R^{b3}, A^3, R^{c2}, R^{d1}), (X^6, R^{a3},$
$R^{b3}, A^3, R^{c2}, R^{d2}), (X^6, R^{a3}, R^{b3}, A^3, R^{c2}, R^{d3}), (X^6, R^{a3},$
$R^{b3}, A^3, R^{c3}, R^{d1}), (X^6, R^{a3}, R^{b3}, A^3, R^{c3}, R^{d2}), (X^6, R^{a3},$
$R^{b3}, A^3, R^{c3}, R^{d3}), (X^6, R^{a3}, R^{b3}, A^3, R^{c4}, R^{d1}), (X^6, R^{a3},$
$R^{b3}, A^3, R^{c4}, R^{d2}), (X^6, R^{a3}, R^{b3}, A^3, R^{c4}, R^{d3}), (X^6, R^{a3},$
$R^{b3}, A^4, R^{c1}, R^{d1}), (X^6, R^{a3}, R^{b3}, A^4, R^{c1}, R^{d2}), (X^6, R^{a3},$ $R^{b3}$, $A^4$, $R^{c1}$, $R^{d3}$), ($X^6$, $R^{a3}$, $R^{b3}$, $A^4$, $R^{c2}$, $R^{d1}$), ($X^6$, $R^{a3}$, $R^{b3}$, $A^4$, $R^{c2}$, $R^{d2}$), ($X^6$, $R^{a3}$, $R^{b3}$, $A^4$, $R^{c2}$, $R^{d3}$), ($X^6$, $R^{a3}$, $R^{b3}$, $A^4$, $R^{c3}$, $R^{d1}$), ($X^6$, $R^{a3}$, $R^{b3}$, $A^4$, $R^{c3}$, $R^{d2}$), ($X^6$, $R^{a3}$, $R^{b3}$, $A^4$, $R^{c3}$, $R^{d3}$), ($X^6$, $R^{a3}$, $R^{b3}$, $A^4$, $R^{c4}$, $R^{d1}$), ($X^6$, $R^{a3}$, $R^{b3}$, $A^4$, $R^{c4}$, $R^{d2}$), ($X^6$, $R^{a3}$, $R^{b3}$, $A^4$, $R^{c4}$, $R^{d3}$), ($X^6$, $R^{a3}$, $R^{b3}$, $A^5$, $R^{c1}$, $R^{d1}$), ($X^6$, $R^{a3}$, $R^{b3}$, $A^5$, $R^{c1}$, $R^{d2}$), ($X^6$, $R^{a3}$, $R^{b3}$, $A^5$, $R^{c1}$, $R^{d3}$), ($X^6$, $R^{a3}$, $R^{b3}$, $A^5$, $R^{c2}$, $R^{d1}$), ($X^6$, $R^{a3}$, $R^{b3}$, $A^5$, $R^{c2}$, $R^{d2}$), ($X^6$, $R^{a3}$, $R^{b3}$, $A^5$, $R^{c2}$, $R^{d3}$), ($X^6$, $R^{a3}$, $R^{b3}$, $A^5$, $R^{c3}$, $R^{d1}$), ($X^6$, $R^{a3}$, $R^{b3}$, $A^5$, $R^{c3}$, $R^{d2}$), ($X^6$, $R^{a3}$, $R^{b3}$, $A^5$, $R^{c3}$, $R^{d3}$), ($X^6$, $R^{a3}$, $R^{b3}$, $A^5$, $R^{c4}$, $R^{d1}$), ($X^6$, $R^{a3}$, $R^{b3}$, $A^5$, $R^{c4}$, $R^{d2}$), ($X^6$, $R^{a3}$, $R^{b3}$, $A^5$, $R^{c4}$, $R^{d3}$).

The Biological Test Examples of the present invention are described as follows.

Preparation 1: Preparation of Recombinant Human ACC2

After a cDNA encoding human ACC2 (27 amino acid residue to 2458 amino acid residues from the N-terminus) was cloned from human kidney cDNA library (Clontech), human ACC2 gene containing His-tag sequence at 5' terminus was inserted into pFastBac1 (Invitrogen). Recombinant baculovirus was generated using Bac-to-Bac baculovirus expression system (Invitrogen) according to the manufacturer's protocol. To express human ACC2, Sf-9 cells were infected with recombinant baculovirus. After infected cells were disrupted, the filtrated lysate was subjected to Ni-affinity chromatography and anion-exchange chromatography. The fractions containing human ACC2 protein were pooled as recombinant human ACC2 solution.

Preparation 2: Preparation of Recombinant Human ACC1

After a cDNA encoding human ACC1 (1 amino acid residue to 2346 amino acid residues from the N-terminus) was cloned from human liver cDNA library (BioChain), human ACC1 gene containing myc-tag and His-tag sequence at 3' terminus was inserted into pIEXBAC3 (Novagen). Recombinant baculovirus was generated using FlashBACGOLD system (Oxford Expression Technologies) according to the manufacturer's protocol. To express human ACC1, Sf-9 cells were infected with recombinant baculovirus. After infected cells were disrupted, the filtrated lysate was subjected to Ni-affinity chromatography and anion-exchange chromatography. The fractions containing human ACC1 protein were pooled as recombinant human ACC1 solution.

Test Example 1

The Measurement of Inhibitory Activity on Human ACC1 and the ACC2

Recombinant human ACC1 and recombinant human ACC2, which were prepared by the method mentioned above, were preincubated with assay buffer solution (50 mM HEPES-KOH (pH 7.4), 10 mM magnesium chloride, 6-10 mM potassium citrate, 4 mM reduced form of glutathione, 1.5 mg/ml bovine serum albumin) for one hour. Then, 0.2 µL of each this invention compound solution (in DMSO) were dispensed to 384-well microplate, 5 µL of the preincubated enzyme solution and 5 µL of substrate solution (50 mM HEPES-KOH (pH 7.4), 1 mM ATP, 0.8 mM acetyl CoA and 25-50 mM potassium bicarbonate) were added to microplate. After centrifugation and shaking, the reaction mixtures were incubated in a humidified box at room temperature for 1 to 3 hours. After the incubation, the enzyme reactions were stopped by the addition of EDTA. Then, after the samples were cocrystallized with CHCA (α-cyano-4-hydroxy cinnamic acid) matrices on MALDI target plate, by using the matrix assist laser deionization time-of-flight mass spectrometer (MALDI-TOF MS), samples were measured in reflector negative mode. Deprotonated ions of acetyl CoA (AcCoA) of substrate and malonyl CoA (MalCoA) of the reaction product were detected, then, the conversion rates of acetyl CoA to malonyl CoA was calculated by the intensity of [MalCoA-H]−/(Intensity of [MalCoA-H]−+Intensity of [AcCoA-H]−) using each signal strength. The 50% inhibitory concentration (IC50) was calculated from the inhibition rate of the enzymatic reaction at each concentration of the compounds. In addition, potassium citrate concentrations in assay buffer solution, potassium hydrogen carbonate concentrations in substrate solution and incubation time were adjusted by each lot of enzyme.

The 50% inhibitory concentration (IC50) on human ACC1 of Compound I-001, I-002, I-003, I-037, I-058, I-067, I-079, I-081, I-091, I-098, I-103 and I-106 were measured, that of these compounds was more than 100 µM.

The inhibitory activity on human ACC2 of the each present compound is described in the following tables 154-159.

TABLE 154

| Example No. | IC50 (uM) |
|---|---|
| I-001 | 0.071 |
| I-002 | 0.770 |
| I-004 | 3.730 |
| I-005 | 0.184 |
| I-006 | 0.348 |
| I-007 | 1.390 |
| I-008 | 0.220 |
| I-009 | 1.060 |
| I-010 | 1.010 |
| I-011 | 0.120 |
| I-012 | 0.064 |
| I-013 | 0.395 |
| I-014 | 0.759 |
| I-016 | 0.400 |
| I-018 | 0.075 |
| I-021 | 0.502 |
| I-022 | 1.250 |
| I-023 | 0.038 |
| I-024 | 0.133 |
| I-025 | 0.652 |
| I-026 | 0.020 |
| I-027 | 0.378 |
| I-028 | 0.028 |
| I-029 | 0.068 |
| I-031 | 0.052 |
| I-032 | 0.052 |
| I-033 | 0.050 |
| I-034 | 0.049 |
| I-035 | 0.102 |
| I-036 | 0.015 |
| I-037 | 0.167 |
| I-038 | 0.072 |
| I-039 | 0.016 |
| I-041 | 0.102 |
| I-042 | 0.015 |
| I-043 | 0.093 |
| I-044 | 0.756 |
| I-045 | 0.008 |
| I-046 | 0.213 |
| I-047 | 0.336 |
| I-048 | 0.083 |
| I-049 | 0.134 |
| I-050 | 0.010 |
| I-051 | 0.084 |
| I-052 | 0.265 |
| I-053 | 0.012 |
| I-054 | 0.015 |
| I-055 | 0.013 |
| I-056 | 0.057 |
| I-057 | 0.166 |
| I-059 | 0.029 |

TABLE 154-continued

| Example No. | IC50 (uM) |
|---|---|
| I-061 | 0.115 |
| I-062 | 0.024 |
| I-063 | 0.128 |
| I-064 | 1.120 |
| I-065 | 0.089 |
| I-066 | 1.300 |
| I-067 | 0.933 |
| I-068 | 0.025 |
| I-069 | 1.400 |
| I-070 | 0.469 |
| I-071 | 0.054 |
| I-072 | 0.154 |
| I-073 | 0.221 |
| I-074 | 0.085 |
| I-075 | 0.020 |
| I-076 | 0.102 |
| I-077 | 0.168 |
| I-078 | 0.189 |
| I-079 | 1.760 |
| I-080 | 1.290 |
| I-081 | 0.344 |
| I-082 | 3.800 |
| I-083 | 0.351 |
| I-086 | 0.042 |
| I-087 | 0.065 |
| I-088 | 0.015 |
| I-089 | 0.062 |
| I-090 | 0.045 |
| I-092 | 0.089 |
| I-094 | 0.187 |
| I-095 | 1.050 |
| I-096 | 0.775 |
| I-097 | 0.097 |
| I-098 | 0.792 |
| I-099 | 0.148 |
| I-100 | 0.027 |
| I-101 | 0.026 |
| I-102 | 0.044 |
| I-103 | 4.500 |
| I-104 | 0.012 |
| I-105 | 0.182 |
| I-106 | 0.091 |

TABLE 155

| Eample No. | IC50 (μM) |
|---|---|
| I-107 | 0.097 |
| I-108 | 0.792 |
| I-109 | 0.148 |
| I-110 | 0.027 |
| I-111 | 0.026 |
| I-112 | 0.031 |
| I-113 | 0.010 |
| I-114 | 0.193 |
| I-115 | 0.012 |
| I-116 | 0.041 |
| I-117 | 0.007 |
| I-118 | 0.010 |
| I-119 | 0.004 |
| I-120 | 0.022 |
| I-121 | 0.009 |
| I-122 | 0.012 |
| I-123 | 0.015 |
| I-124 | 0.037 |
| I-125 | 0.029 |
| I-126 | 0.398 |
| I-127 | 0.084 |
| I-128 | 0.050 |
| I-129 | 0.139 |
| I-130 | 0.057 |
| I-131 | 0.334 |
| I-132 | 0.048 |

TABLE 155-continued

| Eample No. | IC50 (μM) |
|---|---|
| I-133 | 0.077 |
| I-134 | 0.023 |
| I-135 | 0.016 |
| I-136 | 0.087 |
| I-137 | 0.403 |
| I-138 | 0.091 |
| I-139 | 0.090 |
| I-140 | 0.144 |
| I-141 | 0.080 |
| I-142 | 0.181 |
| I-143 | 0.120 |
| I-144 | 0.127 |
| I-145 | 0.190 |
| I-146 | 0.044 |
| I-147 | 0.012 |
| I-148 | 0.404 |
| I-149 | 0.063 |
| I-150 | 0.036 |
| I-151 | 0.075 |
| I-152 | 0.064 |
| I-153 | 0.043 |
| I-154 | 0.017 |
| I-155 | 0.025 |
| I-156 | 0.012 |
| I-157 | 0.003 |
| I-158 | 0.048 |
| I-159 | 0.641 |
| I-160 | 0.809 |
| I-161 | 0.146 |
| I-162 | 0.074 |
| I-163 | 0.039 |
| I-164 | 0.039 |
| I-165 | 0.007 |
| I-166 | 0.030 |
| I-167 | 0.059 |
| I-168 | 0.095 |
| I-169 | 0.010 |
| I-170 | 0.006 |
| I-171 | 0.152 |
| I-172 | 0.013 |
| I-173 | 0.005 |
| I-174 | 0.931 |
| I-175 | 0.011 |
| I-176 | 0.042 |
| I-177 | 0.006 |
| I-178 | 0.003 |
| I-179 | 0.028 |
| I-180 | 0.021 |
| I-181 | 0.014 |
| I-182 | 0.012 |
| I-183 | 0.014 |
| I-184 | 0.054 |
| I-185 | 0.044 |
| I-186 | 0.005 |
| I-187 | 0.234 |
| I-188 | 0.041 |
| I-189 | 0.027 |
| I-190 | 0.073 |
| I-191 | 0.012 |
| I-192 | 0.061 |
| I-193 | 0.012 |
| I-194 | 0.012 |
| I-195 | 0.028 |
| I-196 | 0.012 |
| I-197 | 0.015 |
| I-198 | 0.005 |
| I-199 | 0.121 |
| I-200 | 0.030 |
| I-201 | 0.017 |
| I-202 | 0.066 |
| I-203 | 0.048 |
| I-204 | 0.113 |
| I-205 | 0.025 |
| I-206 | 0.079 |
| I-207 | 0.011 |
| I-208 | 0.008 |
| I-209 | 0.012 |

TABLE 155-continued

| Example No. | IC50 (μM) |
|---|---|
| I-210 | 0.006 |
| I-211 | 0.097 |
| I-212 | 0.017 |
| I-213 | 0.028 |
| I-214 | 0.039 |
| I-215 | 0.021 |
| I-216 | 0.008 |
| I-217 | 0.008 |
| I-218 | 0.008 |
| I-219 | 0.004 |
| I-220 | 0.009 |
| I-221 | 0.172 |
| I-222 | 0.246 |
| I-223 | 0.048 |
| I-224 | 0.034 |
| I-225 | 0.048 |
| I-226 | 0.103 |
| I-227 | 0.036 |
| I-228 | 0.027 |
| I-229 | 0.113 |
| I-230 | 0.054 |
| I-231 | 0.183 |
| I-232 | 0.021 |
| I-233 | 0.084 |
| I-234 | 0.008 |
| I-235 | 0.022 |
| I-236 | 0.102 |
| I-237 | 0.891 |
| I-238 | 0.004 |
| I-239 | 0.008 |
| I-240 | 0.007 |
| I-241 | 0.173 |
| I-242 | 0.007 |
| I-243 | 0.028 |
| I-244 | 0.007 |
| I-245 | 0.004 |
| I-246 | 0.047 |
| I-247 | 0.017 |
| I-248 | 0.009 |
| I-249 | 0.008 |
| I-250 | 0.031 |
| I-251 | 0.022 |
| I-252 | 0.008 |
| I-253 | 0.011 |
| I-254 | 0.020 |
| I-255 | 0.024 |
| I-256 | 0.039 |

TABLE 156

| Example No. | IC50 (μM) |
|---|---|
| I-257 | 0.014 |
| I-258 | 0.099 |
| I-259 | 0.086 |
| I-260 | 0.102 |
| I-261 | 0.017 |
| I-262 | 0.053 |
| I-263 | 0.862 |
| I-264 | 0.372 |
| I-265 | 0.016 |
| I-266 | 0.036 |
| I-267 | 0.058 |
| I-268 | 0.042 |
| I-269 | 0.125 |
| I-270 | 0.116 |
| I-271 | 0.083 |
| I-272 | 0.123 |
| I-273 | 0.035 |
| I-274 | 0.090 |
| I-275 | 0.156 |
| I-276 | 0.013 |
| I-277 | 0.032 |
| I-278 | 0.087 |
| I-279 | 0.008 |
| I-280 | 0.079 |
| I-281 | 0.041 |
| I-282 | 0.892 |
| I-283 | 0.984 |
| I-284 | 0.017 |
| I-285 | 0.038 |
| I-286 | 0.125 |
| I-287 | 0.051 |
| I-288 | 0.759 |
| I-289 | 0.110 |
| I-290 | 0.082 |
| I-291 | 0.032 |
| I-292 | 0.052 |
| I-293 | 0.171 |
| I-294 | 0.300 |
| I-295 | 0.012 |
| I-296 | 0.006 |
| I-297 | 0.042 |
| I-298 | 0.052 |
| I-299 | 0.026 |
| I-300 | 0.165 |
| I-301 | 0.037 |
| I-302 | 0.052 |
| I-303 | 0.068 |
| I-304 | 0.242 |
| I-305 | 0.022 |
| I-306 | 0.015 |
| I-307 | 0.043 |
| I-308 | 0.006 |
| I-309 | 0.024 |
| I-310 | 0.034 |
| I-311 | 0.106 |
| I-312 | 0.401 |
| I-313 | 0.072 |
| I-314 | 0.025 |
| I-315 | 0.503 |
| I-316 | 0.074 |
| I-317 | 0.014 |
| I-318 | 0.049 |
| I-319 | 0.281 |
| I-320 | 0.067 |
| I-321 | 0.167 |
| I-322 | 0.063 |
| I-323 | 0.345 |
| I-324 | 0.051 |
| I-325 | 0.037 |
| I-326 | 0.280 |
| I-327 | 0.080 |
| I-328 | 0.018 |
| I-329 | 0.014 |
| I-330 | 0.105 |
| I-331 | 0.470 |
| I-332 | 0.056 |
| I-333 | 0.203 |
| I-334 | 0.179 |
| I-335 | 0.018 |
| I-336 | 0.025 |
| I-337 | 0.007 |
| I-338 | 0.026 |
| I-339 | 0.035 |
| I-340 | 0.021 |
| I-341 | 0.119 |
| I-342 | 0.108 |
| I-343 | 0.118 |
| I-344 | 0.013 |
| I-345 | 0.038 |
| I-346 | 0.019 |
| I-347 | 0.055 |
| I-348 | 0.057 |
| I-349 | 0.039 |
| I-350 | 0.049 |
| I-351 | 0.087 |
| I-352 | 0.022 |
| I-353 | 0.011 |
| I-354 | 0.011 |
| I-355 | 0.018 |
| I-356 | 0.066 |
| I-357 | 0.103 |
| I-358 | 0.019 |
| I-359 | 0.021 |
| I-360 | 0.017 |

TABLE 156-continued

| | |
|---|---|
| I-361 | 0.570 |
| I-362 | 0.130 |
| I-363 | 0.032 |
| I-364 | 0.044 |
| I-365 | 0.100 |
| I-366 | 0.031 |
| I-367 | 0.113 |
| I-368 | 0.048 |
| I-369 | 0.019 |
| I-370 | 0.013 |
| I-371 | 0.198 |
| I-372 | 0.013 |
| I-373 | 0.894 |
| I-374 | 0.637 |
| I-375 | 0.102 |
| I-376 | 0.007 |
| I-377 | 0.039 |
| I-378 | 0.144 |
| I-379 | 0.258 |
| I-380 | 0.059 |
| I-381 | 0.155 |
| I-382 | 0.176 |
| I-383 | 0.008 |
| I-384 | 0.364 |
| I-385 | 0.004 |
| I-386 | 0.070 |
| I-387 | 0.392 |
| I-388 | 0.014 |
| I-389 | 0.008 |
| I-390 | 0.007 |
| I-391 | 0.021 |
| I-392 | 0.069 |
| I-393 | 0.155 |
| I-394 | 0.018 |
| I-395 | 0.007 |
| I-396 | 0.008 |
| I-397 | 0.031 |
| I-398 | 0.115 |
| I-399 | 0.040 |
| I-400 | 0.017 |
| I-401 | 0.023 |
| I-402 | 0.083 |
| I-403 | 0.043 |
| I-404 | 0.676 |
| I-405 | 0.062 |
| I-406 | 0.131 |

TABLE 157

| | |
|---|---|
| I-407 | 0.533 |
| I-408 | 0.465 |
| I-409 | 0.074 |
| I-410 | 0.015 |
| I-411 | 0.937 |
| I-412 | 0.042 |
| I-413 | 0.084 |
| I-414 | 0.059 |
| I-415 | 0.018 |
| I-416 | 0.090 |
| I-417 | 0.451 |
| I-418 | 0.733 |
| I-419 | 0.109 |
| I-420 | 0.447 |
| I-421 | 0.024 |
| I-422 | 0.358 |
| I-423 | 0.072 |
| I-424 | 0.122 |
| I-425 | 0.170 |
| I-426 | 0.057 |
| I-427 | 0.270 |
| I-428 | 0.053 |
| I-429 | 0.026 |
| I-430 | 0.012 |
| I-431 | 0.809 |
| I-432 | 0.588 |
| I-433 | 0.011 |
| I-434 | 0.653 |

TABLE 157-continued

| | |
|---|---|
| I-435 | 0.007 |
| I-436 | 0.004 |
| I-437 | 0.019 |
| I-438 | 0.540 |
| I-439 | 0.004 |
| I-440 | 0.019 |
| I-441 | 0.012 |
| I-442 | 0.035 |
| I-443 | 0.240 |
| I-444 | 0.051 |
| I-445 | 0.014 |
| I-446 | 0.077 |
| I-447 | 0.076 |
| I-448 | 0.400 |
| I-449 | 0.051 |
| I-450 | 0.014 |
| I-451 | 0.040 |
| I-452 | 0.109 |
| I-453 | 0.610 |
| I-454 | 0.087 |
| I-455 | 0.050 |
| I-456 | 0.280 |
| I-457 | 0.019 |
| I-458 | 0.032 |
| I-459 | 0.016 |
| I-460 | 0.004 |
| I-461 | 0.004 |
| I-462 | 0.090 |
| I-463 | 0.017 |
| I-464 | 0.036 |
| I-465 | 0.160 |
| I-466 | 0.179 |
| I-467 | 0.007 |
| I-468 | 0.368 |
| I-469 | 0.596 |
| I-470 | 0.426 |
| I-471 | 0.159 |
| I-472 | 0.026 |
| I-473 | 0.028 |
| I-474 | 0.016 |
| I-475 | 0.540 |
| I-476 | 0.074 |
| I-477 | 0.247 |
| I-478 | 0.116 |
| I-479 | 0.563 |
| I-480 | 0.041 |
| I-481 | 0.298 |
| I-482 | 0.087 |
| I-483 | 0.081 |
| I-484 | 0.204 |
| I-485 | 0.180 |
| I-486 | 0.724 |
| I-487 | 0.363 |
| I-488 | 0.314 |
| I-489 | 0.843 |
| I-490 | 0.480 |
| I-491 | 0.051 |
| I-493 | 0.070 |
| I-494 | 0.046 |
| I-495 | 0.074 |
| I-496 | 0.024 |
| I-497 | 0.015 |
| I-498 | 0.013 |
| I-499 | 0.040 |
| I-500 | 0.021 |
| I-501 | 0.009 |
| I-502 | 0.062 |
| I-503 | 0.024 |
| I-504 | 0.018 |
| I-505 | 0.012 |
| I-506 | 0.249 |
| I-507 | 0.132 |
| I-508 | 0.081 |
| I-509 | 0.225 |
| I-510 | 0.028 |
| I-511 | 0.022 |
| I-512 | 0.110 |
| I-513 | 0.260 |
| I-514 | 0.032 |
| I-515 | 0.041 |

TABLE 157-continued

| | |
|---|---|
| I-516 | 0.027 |
| I-517 | 0.014 |
| I-518 | 0.013 |
| I-519 | 0.170 |
| I-520 | 0.315 |
| I-521 | 0.020 |
| I-522 | 0.008 |
| I-523 | 0.105 |
| I-524 | 0.064 |
| I-525 | 0.041 |
| I-526 | 0.013 |
| I-527 | 0.158 |
| I-528 | 0.061 |
| I-529 | 0.172 |
| I-530 | 0.196 |
| I-531 | 0.481 |
| I-532 | 0.006 |
| I-533 | 0.102 |
| I-534 | 0.067 |
| I-535 | 0.030 |
| I-536 | 0.028 |
| I-537 | 0.975 |
| I-538 | 0.071 |
| I-539 | 0.092 |
| I-540 | 0.323 |
| I-541 | 0.130 |
| I-542 | 0.006 |
| I-543 | 0.014 |
| I-544 | 0.004 |
| I-545 | 0.046 |
| I-546 | 0.066 |
| I-547 | 0.104 |
| I-548 | 0.124 |
| I-549 | 0.037 |
| I-550 | 0.021 |
| I-551 | 0.015 |
| I-552 | 0.013 |
| I-553 | 0.196 |
| I-554 | 0.620 |
| I-555 | 0.034 |
| I-556 | 0.105 |
| I-557 | 0.216 |

TABLE 158

| | |
|---|---|
| I-558 | 0.043 |
| I-559 | 0.043 |
| I-560 | 0.101 |
| I-561 | 0.104 |
| I-562 | 0.350 |
| I-563 | 0.101 |
| I-564 | 0.385 |
| I-566 | 0.304 |
| I-567 | 0.167 |
| I-568 | 0.225 |
| I-569 | 0.086 |
| I-570 | 0.935 |
| I-571 | 0.166 |
| I-572 | 0.227 |
| I-573 | 0.068 |
| I-574 | 0.129 |
| I-577 | 0.062 |
| I-578 | 0.110 |
| I-579 | 0.334 |
| I-582 | 0.168 |
| I-583 | 0.071 |
| I-585 | 0.077 |
| I-586 | 0.009 |
| I-587 | 0.087 |
| I-590 | 0.584 |
| I-592 | 0.110 |
| I-593 | 0.080 |
| I-594 | 0.383 |
| I-596 | 0.010 |
| I-599 | 0.023 |
| I-600 | 0.013 |
| I-601 | 0.008 |

TABLE 158-continued

| | |
|---|---|
| I-602 | 0.012 |
| I-603 | 0.007 |
| I-604 | 0.006 |
| I-605 | 0.013 |
| I-606 | 0.074 |
| I-607 | 0.110 |
| I-608 | 0.011 |
| I-609 | 0.525 |
| I-610 | 0.085 |
| I-611 | 0.003 |
| I-614 | 0.011 |
| I-615 | 0.027 |
| I-616 | 0.240 |
| I-617 | 0.009 |
| I-618 | 0.017 |
| I-619 | 0.009 |
| I-620 | 0.028 |
| I-621 | 0.008 |
| I-622 | 0.072 |
| I-623 | 0.017 |
| I-624 | 0.009 |
| I-625 | 0.005 |
| I-626 | 0.006 |
| I-627 | 0.005 |
| I-628 | 0.059 |
| I-629 | 0.098 |
| I-630 | 0.025 |
| I-631 | 0.010 |
| I-632 | 0.019 |
| I-634 | 0.034 |
| I-635 | 0.104 |
| I-636 | 0.004 |
| I-637 | 0.004 |
| I-638 | 0.140 |
| I-639 | 0.002 |
| I-640 | 0.110 |
| I-641 | 0.073 |
| I-642 | 0.007 |
| I-643 | 0.250 |
| I-644 | 0.026 |
| I-646 | 0.015 |
| I-647 | 0.006 |
| I-648 | 0.110 |
| I-649 | 0.009 |
| I-650 | 0.375 |
| I-651 | 0.004 |
| I-652 | 0.007 |
| I-653 | 0.065 |
| I-655 | 0.002 |
| I-656 | 0.039 |
| I-657 | 0.014 |
| I-658 | 0.004 |
| I-659 | 0.023 |
| I-661 | 0.457 |
| I-662 | 0.005 |
| I-663 | 0.700 |
| I-664 | 0.011 |
| I-665 | 0.004 |
| I-666 | 0.298 |
| I-667 | 0.008 |
| I-668 | 0.007 |
| I-669 | 0.620 |
| I-670 | 0.011 |
| I-671 | 0.011 |
| I-672 | 0.030 |
| I-673 | 0.650 |
| I-674 | 0.007 |
| I-675 | 0.018 |
| I-677 | 0.013 |
| I-678 | 0.123 |
| I-679 | 0.625 |
| I-680 | 0.140 |
| I-682 | 0.005 |
| I-683 | 0.003 |
| I-684 | 0.006 |
| I-685 | 0.170 |
| I-686 | 0.005 |
| I-687 | 0.014 |
| I-688 | 0.004 |
| I-689 | 0.025 |

TABLE 158-continued

| | |
|---|---|
| I-691 | 0.025 |
| I-692 | 0.034 |
| I-693 | 0.008 |
| I-694 | 0.013 |
| I-695 | 0.096 |
| I-696 | 0.497 |
| I-697 | 0.004 |
| I-698 | 0.003 |
| I-700 | 0.009 |
| I-701 | 0.023 |
| I-702 | 0.015 |
| I-703 | 0.030 |
| I-705 | 0.009 |
| I-706 | 0.048 |
| I-707 | 0.084 |
| I-708 | 0.005 |
| I-709 | 0.133 |
| I-710 | 0.006 |
| I-711 | 0.007 |
| I-713 | 0.003 |
| I-714 | 0.044 |
| I-716 | 0.170 |
| I-717 | 0.015 |
| I-720 | 0.775 |
| I-722 | 0.009 |
| I-723 | 0.041 |
| I-724 | 0.009 |
| I-725 | 0.101 |
| I-726 | 0.009 |
| I-727 | 0.194 |
| I-728 | 0.008 |
| I-729 | 0.004 |
| I-730 | 0.910 |
| I-732 | 0.260 |
| I-733 | 0.009 |
| I-734 | 0.004 |
| I-735 | 0.677 |
| I-736 | 0.087 |

TABLE 159

| | |
|---|---|
| I-737 | 0.033 |
| I-738 | 0.035 |
| I-739 | 0.007 |
| I-740 | 0.003 |
| I-741 | 0.007 |
| I-742 | 0.013 |
| I-744 | 0.740 |
| I-745 | 0.490 |
| I-746 | 0.350 |
| I-747 | 0.044 |
| I-748 | 0.005 |

Test Example 2

CYP Inhibition Test

Using commercially available human hepatic microsome, and employing, as markers, 7-ethoxyresorufin O-deethylation (CYP1A2), tolbutamide methyl-hydroxylation (CYP2C9), mephenytoin 4'-hydroxylation (CYP2C19), dextromethorphan 0-demethylation (CYP2D6), and terfenedine hydroxylation atypical substrate metabolism reactions of human main five CYP enzyme forms (CYP1A2, 2C9, 2C19, 2D6, 3A4), an inhibitory degree of each metabolite production amount by a test compound was assessed.

The reaction conditions were as follows: substrate, 0.5 µmol/L ethoxyresorufin (CYP1A2), 100 µmol/L tolbutamide (CYP2C9), 50 µmol/L S-mephenitoin (CYP2C19), 5 mmol/L dextromethorphan (CYP2D6), 1 µmol/L terfenedine (CYP3A4); reaction time, 15 minutes; reaction temperature, 37° C.; enzyme, pooled human hepatic microsome 0.2 mg protein/mL; test drug concentration, 1, 5, 10, 20 µmol/L (four points).

Each five kinds of substrates, human hepatic microsome, or a test drug in 50 mM Hepes buffer as a reaction solution was added to a 96-well plate at the composition as described above, NADPH, as a cofactor was added to initiate metabolism reactions as markers and, after the incubation at 37° C. for 15 minutes, a methanol/acetonitrile=1/1 (v/v) solution was added to stop the reaction. After the centrifugation at 3000 rpm for 15 minutes, resorufin (CYP1A2 metabolite) in the supernatant was quantified by a fluorescent multilabel counter and tributamide hydroxide (CYP2CP metabolite), mephenytoin 4' hydroxide (CYP2C19 metabolite), dextromethorphan (CYP2D6 metabolite), and terfenadine alcohol (CYP3A4 metabolite) are quantified by LC/MS/MS.

Addition of only DMSO being a solvent dissolving a drug to a reaction system was adopted as a control (100%), remaining activity (%) was calculated at each concentration of a test drug added as the solution and IC50 was calculated by reverse presumption by a logistic model using a concentration and an inhibition rate.

Test Example 3

BA Test

An experimental material and a method for examining oral absorbability
(1) Animals used: SD rats or mice were used
(2) Breeding condition: chow and sterilized tap water were allowed to be taken in freely.
(3) Setting of a dosage and grouping: a predetermined dosage was administered orally or intravenously. Groups were formed as shown below. (A dosage varied depending on each compound)
Oral administration 1-30 mg/kg (n=2 to 3)
Intravenous administration 0.5-10 mg/kg (n=2 to 3)
(4) Preparation of administered liquid: In oral administration, a solution or suspension was administered. In intravenous administration, after solubilization, the administration was performed.
(5) Method of Administration: In oral administration, compulsory administration to the stomach was conducted using an oral probe.
In intravenous administration, administration from the caudal vein was conducted using a syringe with an injection needle.
(6) Evaluation item: Blood was chronologically collected, and then the concentration of a compound of the present invention in blood plasma was measured using a LC/MS/MS.
(7) Statistical analysis: With regard to a shift in plasma concentration, the plasma concentration-time area under the curve (AUC) was calculated using a nonlinear least-squares program WinNonlin® Bioavailability (BA) was calculated from the AUCs of the oral administration group and the intravenous administration group, respectively.

Test Example 4

Metabolism Stability Test

Using commercially available pooled human hepatic microsomes, a test compound was reacted for a constant time, a remaining rate was calculated by comparing a reacted sample and an unreacted sample, thereby, a degree of metabolism in liver was assessed.

A reaction was performed (oxidative reaction) at 37° C. for 0 minute or 30 minutes in the presence of 1 mmol/L NADPH in 0.2 mL of a buffer (50 mmol/L Tris-HCl pH 7.4, 150 mmol/L potassium chloride, 10 mol/L magnesium chloride) containing 0.5 mg protein/mL of human liver microsomes. After the reaction, 50 μL of the reaction solution was added to 100 μL of a methanol/acetonitrile=1/1 (v/v), mixed and centrifuged at 3000 rpm for 15 minutes. The test compound in the supernatant was quantified by LC/MS/MS, and a remaining amount of the test compound after the reaction was calculated, letting a compound amount at 0 minute reaction time to be 100%. Hydrolysis reaction was performed in the absence of NADPH and glucuronidation reaction was in the presence of 5 mM UDP-glucuronic acid in place of NADPH, followed by similar operations.

Test Example 5

CYP3A4 Fluorescent MBI Test

The CYP3A4 fluorescent MBI test is a test of investigating enhancement of CYP3A4 inhibition of a compound by a metabolism reaction, and the test was performed using, a reaction in which 7-benzyloxytrifluoromethylcoumarin (7-BFC) was debenzylated by the CYP3A4 enzyme to produce a metabolite, 7-hydroxytrifluoromethylcoumarin (HFC) emitting fluorescent light.

The reaction conditions were as follows: substrate, 5.6 μmol/L 7-BFC; pre-reaction time, 0 or 30 minutes; reaction time, 15 minutes; reaction temperature, 25° C. (room temperature); CYP3A4 content (expressed in *Escherichia coli*), at pre-reaction 62.5 pmol/mL, at reaction 6.25 pmol/mL (at 10-fold dilution); test drug concentration, 0.625, 1.25, 2.5, 5, 10, 20 μmol/L (six points).

An enzyme in a K-Pi buffer (pH 7.4) and a test drug solution as a pre-reaction solution were added to a 96-well plate at the composition of the pre-reaction, a part of it was transferred to another 96-well plate so that it was 1/10 diluted by a substrate in a K-Pi buffer, NADPH as a co-factor was added to initiate a reaction as an index (without preincubation) and, after a predetermined time of a reaction, acetonitrile/0.5 mol/L Tris (trishydroxyaminomethane)=4/1 was added to stop the reaction. In addition, NADPH was added to a remaining preincubation solution to initiate a preincubation (with preincubation) and, after a predetermined time of a preincubation, a part was transferred to another plate so that it was 1/10 diluted with a substrate and a K-Pi buffer to initiate a reaction as an index. After a predetermined time of a reaction, acetonitrile/0.5 mol/L Tris (trishydroxyaminomethane)=4/1 was added to stop the reaction. For the plate on which each index reaction had been performed, a fluorescent value of 7-HFC which is a metabolite was measured with a fluorescent plate reader. (Ex=420 nm, Em=535 nm).

Addition of only DMSO which was a solvent dissolving a drug to a reaction system was adopted as a control (100%), remaining activity (%) was calculated at each concentration of a test drug added as the solution, and IC50 was calculated by reverse-presumption by a logistic model using a concentration and an inhibition rate. When a difference between IC50 values was 5 μM or more, this was defined as (+) and, when the difference was 3 μM or less, this was defined as (−).

Test Example 6

Fluctuation Ames Test

The compounds of the present invention are assessed for mutagenic property.

20 μL of freezing-stored rat typhoid bacillus (*Salmonella typhimurium* TA98 strain, TA100 strain) is inoculated on 10 mL of a liquid nutrient medium (2.5% Oxoid nutrient broth No. 2), and this is cultured before shaking at 37° C. for 10 hours. 9 mL of a bacterial solution of the TA98 strain is centrifuged (2000 g, 10 minutes) to remove a culturing solution, the bacteria is suspended in 9 mL of a Micro F buffer (K2HPO4: 3.5 g/L, KH2PO4: 1 g/L, (NH4)2SO4: 1 g/L, trisodium citrate dehydrate: 0.25 g/L, MgSO4.7H2O: 0.1 g/L), the suspension is added to 110 mL of an Exposure medium (Micro F buffer containing Biotin: 8 μg/mL, histidine: 0.2 μg/mL, glucose: 8 mg/mL), and the TA100 strain is added to 120 mL of the Exposure medium relative to 3.16 mL of the bacterial solution to prepare a test bacterial solution. Each 12 mL of a test substance DMSO solution (8 stage dilution from maximum dose 50 mg/mL at 2-fold ratio), DMSO as a negative control, 50 μg/mL of 4-nitroquinoline-1-oxide DMSO solution for the TA98 strain, 0.25 μg/mL of 2-(2-furyl)-3-(5-nitro-2-furyl)acrylamide DMSO solution for the TA100 strain under the non-metabolism activating condition, 40 μg/mL of 2-aminoanthracene DMSO solution for the TA98 strain, 20 μg/mL of 2-aminoanthracene DMSO solution for the TA100 strain under the metabolism activating condition as a positive control, and 588 μL of the test bacterial solution (a mixed solution of 498 μl of the test bacterial solution and 90 μL of S9 mix under the metabolism activating condition) are mixed, and this is shaking-cultured at 37° C. for 90 minutes. 460 μL of the bacterial solution exposed to the test substance is mixed with 2300 μL of an Indicator medium (Micro F buffer containing biotin: 8 μg/mL, histidine: 0.2 μg/mL, glucose: 8 μg/mL, Bromo Cresol Purple: 37.5 μg/mL), each 50 μL is dispensed into microplate 48 wells/dose, and this is subjected to stationary culturing at 37° C. for 3 days. Since a well containing a bacterium which has obtained the proliferation ability by mutation of an amino acid (histidine) synthesizing enzyme gene turns from purple to yellow due to a pH change, the bacterium proliferation well which has turned to yellow in 48 wells per dose is counted, and is assessed by comparing with a negative control group. 0 means that mutagenicity is negative and (+) is positive.

Test Example 7 hERG Test

For the purpose of assessing risk of an electrocardiogram QT interval prolongation, effects on delayed rectifier K+ current (IKr), which plays an important role in the ventricular repolarization process of the compound of the present invention, was studied using HEK293 cells expressing human ether-a-go-go related gene (hERG) channel.

After a cell was retained at a membrane potential of −80 mV by whole cell patch clamp method using an automated patch clamp system (PatchXpress 7000A, Axon Instruments Inc.), IKr induced by depolarization pulse stimulation at +40 mV for 2 seconds and, further, repolarization pulse stimulation at −50 mV for 2 seconds is recorded. After the generated current was stabilized, extracellular solution (NaCl: 135 mmol/L, KCl: 5.4 mmol/L, NaH$_2$PO$_4$: 0.3 mmol/L, CaCl$_2$.2H2O: 1.8 mmol/L, MgCl$_2$. 6H2O: 1 mmol/

L, glucose: 10 mmol/L, HEPES (4-(2-hydroxyethyl)-1-piperazineethanesulfonic acid): 10 mmol/L, pH=7.4) in which the test compound has been dissolved at an objective concentration is applied to the cell under the room temperature condition for 10 minutes. From the recording IKr, an absolute value of the tail peak current was measured based on the current value at the resting membrane potential using an analysis software (DataXpress ver. 1, Molecular Devices Corporation). Further, the % inhibition relative to the tail peak current before application of the test substance was calculated, and compared with the vehicle-applied group (0.1% dimethyl sulfoxide solution) to assess influence of the test substance on IKr.

Test Example 8

Solubility Test

The solubility of the compounds of the present invention was determined in 1% DMSO addition condition. The 10 mmol/L compound solution was prepared in DMSO, To the pH6.8 artificial intestinal fluid (To 0.2 mol/L potassium dihydrogen phosphate reagent 250 mL and 0.2 mol/L NaOH reagent solution, water was added until it become 1000 mL solution) 594 µL, the compound of the present invention solution 6 µL was added. After stood at 25° C. for 16 hours, the mixture was filtered while suctioning. The filtrate was diluted two-fold with methanol/water=1/1(V/V), and its concentration into the filtrate was measured by the absolute calibration curve method using HPLC or LC/MS/MS.

Test Example 9

Powder Solubility Test

Appropriate amounts of the test substances were put into appropriate containers. To the respective containers were added 200 µL of JP-1 fluid (sodium chloride 2.0 g, hydrochloric acid 7.0 mL and water to reach 1000 mL), 200 µL of JP-2 fluid (phosphate buffer (pH6.8) 500 mL and water 500 mL), and 200 µL of 20 mmol/L TCA (sodium taurocholate)/JP-2 fluid (TCA 1.08 g and water to reach 100 mL). In the case that the test compound was dissolved after the addition of the test fluid, the bulk powder was added as appropriate. The containers were sealed, and shaken for 1 hour at 37° C. The mixtures are filtered, and 100 µL of methanol was added to each of the filtrate (100 µL) so that the filtrates were two-fold diluted. The dilution ratio was changed if necessary. The dilutions were observed for bubbles and precipitates, and then the containers were sealed and shaken. Quantification was performed by HPLC with an absolute calibration method.

Formulation Example

The following Formulation Examples are only exemplified and not intended to limit the scope of this invention.

Formulation Example 1

Tablets

| The compound of the present invention | 15 mg |
|---|---|
| Lactose | 15 mg |
| Calcium stearate | 3 mg |

The components other than calcium stearate are homogeneously mixed and dried by crushing granulation, and appropriate size granules. Then the tablets are compression-molded by the addition of calcium stearate.

Formulation Example 2

Capsules

| The compound of the present invention | 10 mg |
|---|---|
| Magnesium sterate | 10 mg |
| Lactose | 80 mg |

They are uniformly mixed to produce a powder medicine as a powder or fine granules. The capsule are made by filling them into a capsule container Formulation Example 3

Granules

| The compound of the present invention | 30 g |
|---|---|
| Lactose | 265 g |
| Magnesium stearate | 5 g |

After the above ingredients are mixed uniformly, the mixture is compressed, crushed, granulated and sieved to obtain a suitable size of granules.

INDUSTRIAL APPLICABILITY

The compounds of this invention have an ACC2 inhibitory activity, and are very useful for treatment or prevention of a disease associated with ACC2.

The invention claimed is:
1. A compound of Formula (I):

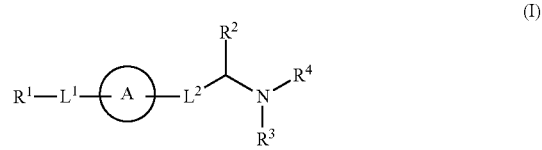

or its pharmaceutically acceptable salt,
wherein
$R^1$ is substituted or unsubstituted benzoxazole, substituted or unsubstituted benzothiazole, substituted or unsubstituted phenyl, substituted or unsubstituted 1H-imidazo[4,5-c]pyridine, substituted or unsubstituted benzimidazole, substituted or unsubstituted quinazoline, substituted or unsubstituted indazole, substituted or unsubstituted 1H-imidazo[4,5-b]pyridine, substituted or unsubstituted thiazolo[4,5-c]pyridine, substituted or unsubstituted oxazolo[4,5-c]pyridine, substituted or unsubstituted 2,6-naphthyridine, or substituted or unsubstituted thiazolo[5,4-b]pyridine, ring A is substituted or unsubstituted cyclohexane, substituted or unsubstituted cyclobutane, substituted or unsubstituted tetrahydropyran, or substituted or unsubstituted 1,3-dioxane, -$L^1$- is —O—$(CR^6R^7)$m-, -$L^2$- is —O—$(CR^6R^7)$n-, —$(CR^6R^7)$n- or —C(=O)—$(CR^6R^7)$n-, each $R^6$ is independently hydrogen, halogen, cyano, substituted or unsubstituted alkyl, substituted or unsubstituted alkenyl or substituted or unsubstituted alkynyl, each $R^7$ is independently hydrogen, halogen, cyano, substituted or unsubstituted alkyl, substituted or unsubstituted alkenyl or substituted or unsubstituted alkynyl, or $R^6$ and $R^7$ on the same carbon atom may be taken together with the carbon atom to form a ring, or $R^2$ is taken together with either $R^6$ or $R^7$ to form a ring, each m is independently an integer of 0, 1, 2 or 3, each n is independently an integer of 1, 2 or 3, $R^2$ is substituted or unsubstituted alkyl, $R^3$ is hydrogen or substituted or unsubstituted alkyl, and $R^4$ is substituted or unsubstituted alkylcarbonyl, substituted or unsubstituted alkenylcarbonyl, substituted or unsubstituted alkynylcarbonyl, substituted or unsubstituted alkyloxycarbonyl, substituted or unsubstituted alkenyloxycarbonyl, substituted or unsubstituted alkynyloxycarbonyl, or substituted or unsubstituted carbamoyl.

2. The compound or its pharmaceutically acceptable salt according to claim 1, wherein ring A is substituted or unsubstituted cyclobutane, substituted or unsubstituted cyclohexane, or substituted or unsubstituted 1,3-dioxane.

3. The compound or its pharmaceutically acceptable salt according to claim 1, wherein $R^1$ is substituted or unsubstituted benzoxazole, or substituted or unsubstituted benzothiazole.

4. The compound or its pharmaceutically acceptable salt according to claim 1, wherein $R^1$ is substituted or unsubstituted benzothiazole, substituted or unsubstituted benzoxazole, substituted or unsubstituted benzoimidazole, substituted or unsubstituted indazole, or substituted or unsubstituted quinazoline.

5. The compound or its pharmaceutically acceptable salt according to claim 1, wherein $R^4$ is substituted or unsubstituted alkylcarbonyl.

6. The compound or its pharmaceutically acceptable salt according to claim 5, wherein $R^4$ is methylcarbonyl.

7. The compound or its pharmaceutically acceptable salt according to claim 1, wherein $R^4$ is substituted or unsubstituted carbamoyl.

8. The compound or its pharmaceutically acceptable salt according to claim 1, wherein m is 0.

9. The compound or its pharmaceutically acceptable salt according to claim 1, wherein -$L^2$- is —O—$(CR^6R^7)$n-.

10. The compound or its pharmaceutically acceptable salt according to claim 1, wherein n is 1.

11. The compound or its pharmaceutically acceptable salt according to claim 1, wherein -$L^2$- is —O—$(CR^{67})$—, and $R^2$ is taken together with either $R^6$ or $R^7$ to form ring.

12. The compound or its pharmaceutically acceptable salt according to claim 1, wherein -$L^1$- is —O—$(CR^6R^7)$m-, and -$L^2$- is —O—$(CR^6R^7)$n- or —$(CR^6R^7)$n-.

13. A pharmaceutical composition, which comprises the compound or its pharmaceutically acceptable salt according to claim 1, and a pharmaceutically acceptable additive.

14. A method for treatment of obesity and/or diabetes comprising administering an effective amount of the compound or its pharmaceutically acceptable salt according to claim 1 to a patient in need thereof.

15. The compound or its pharmaceutically acceptable salt according to claim 1, wherein ring A is substituted or unsubstituted 1,3-dioxane.

16. The compound or its pharmaceutically acceptable salt according to claim 1, wherein $R^1$ is substituted or unsubstituted benzimidazole.

17. The compound or its pharmaceutically acceptable salt according to claim 1, wherein $R^1$ is substituted or unsubstituted benzimidazole; ring A is substituted or unsubstituted 1,3-dioxane; and m is 0.

18. The compound or its pharmaceutically acceptable salt according to claim 1, wherein $R^1$ is substituted benzimidazole.

19. The compound or its pharmaceutically acceptable salt according to claim 1, wherein $R^6$ and $R^7$ are hydrogen.

* * * * *